US006830900B2

(12) United States Patent
Yan et al.

(10) Patent No.: US 6,830,900 B2
(45) Date of Patent: Dec. 14, 2004

(54) ISOLATED HUMAN GLUTAMATE RECEPTOR DNA

(75) Inventors: Chunhua Yan, Boyds, MD (US); Ming-Hui Wei, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 324 days.

(21) Appl. No.: 09/820,007

(22) Filed: Mar. 29, 2001

(65) Prior Publication Data

US 2004/0229304 A1 Nov. 18, 2004

(51) Int. Cl.[7] ........................ C12N 15/12; C12N 15/63; C12N 5/10

(52) U.S. Cl. ................... 435/69.1; 435/320.1; 435/325; 536/23.5

(58) Field of Search ............................. 435/69.1, 320.1, 435/325; 536/23.5

(56) References Cited

FOREIGN PATENT DOCUMENTS

EP 568384 * 11/1993

* cited by examiner

*Primary Examiner*—Michael Pak
(74) *Attorney, Agent, or Firm*—Celera Genomics; Lin Sun-Hoffman

(57) ABSTRACT

The present invention provides amino acid sequences of peptides that are encoded by genes within the human genome, the transporter peptides of the present invention. The present invention specifically provides isolated peptide and nucleic acid molecules, methods of identifying orthologs and paralogs of the transporter peptides, and methods of identifying modulators of the transporter peptides.

9 Claims, 126 Drawing Sheets

```
   1 TGCAGTTTAA GTGTTCGGAT TCCAAGGGAA ACAGACAAAC CTCACGAAAG
  51 GAAGGAAGCA AGCAAGCAAG GAAGGAACTG CAGGAGGAAA AGAACAGGCA
 101 GAACAGCGAG AAGAATAAAG GGAAAGGGGG GGAAACACCA AATCTATGAT
 151 TGGACCTGGG CTTCTTTTTC GCCAATGCAA AAAGGAATAT GCAGCACATT
 201 TTTGCCTTCT TCTGCACCGG TTTCCTAGGC GCGGTAGTAG GTGCCAATTT
 251 CCCCAACAAT ATCCAGATCG GGGGATTATT TCCAAACCAG CAGTCACAGG
 301 AACATGCTGC TTTTAGATTT GCTTTGTCGC AACTCACAGA GCCCCCGAAG
 351 CTGCTCCCCC AGATTGATAT TGTGAACATC AGCGACAGCT TTGAGATGAC
 401 CTATAGATTC TGTTCCCAGT TCTCCAAAGG AGTCTATGCC ATCTTTGGGT
 451 TTTATGAACG TAGGACTGTC AACATGCTGA CCTCCTTTTG TGGGGCCCTC
 501 CACGTCTGCT TCATTACGCC GAGCTTTCCC GTTGATACAT CCAATCAGTT
 551 TGTCCTTCAG CTGCGCCCTG AACTGCAGGA TGCCCTCATC AGCATCATTG
 601 ACCATTACAA GTGGCAGAAA TTTGTCTACA TTTATGATGC CGACCGGGGC
 651 TTATCCGTCC TGCAGAAAGT CCTGGATACA GCTGCTGAGA AGAACTGGCA
 701 GGTGACAGCA GTCAACATTT TGACAACCAC AGAGGAGGGA TACCGGATGC
 751 TCTTTCAGGA CCTGGAGAAG AAAAAGGAGC GGCTGGTGGT GGTGGACTGT
 801 GAATCAGAAC GCCTCAATGC TATCTTGGGC CAGATTATAA AGCTAGAGAA
 851 GAATGGCATC GGCTACCACT ACATTCTTGC AAATCTGGGC TTCATGGACA
 901 TTGACTTAAA CAAATTCAAG GAGAGTGGCG CCAATGTGAC AGGTTTCCAG
 951 CTGGTGAACT ACACAGACAC TATTCCGGCC AAGATCATGC AGCAGTGGAA
1001 GAATAGTGAT GCTCGAGACC ACACACGGGT GGACTGGAAG AGACCCAAGT
1051 ACACCTCTGC GCTCACCTAC GATGGGGTGA AGGTGATGGC TGAGGCTTTC
1101 CAGAGCCTGC GGAGGCAGAG AATTGATATA TCTCGCCGGG GGAATGCTGG
1151 GGATTGTCTG GCTAACCCAG CTGTTCCCTG GGGCCAAGGG ATCGACATCC
1201 AGAGAGCTCT GCAGCAGGTG CGATTTGAAG GTTTAACAGG AAACGTGCAG
1251 TTTAATGAGA AAGGACGCCG GACCAACTAC ACGCTCCACG TGATTGAAAT
1301 GAAACATGAC GGCATCCGAA AGATTGGTTA CTGGAATGAA GATGATAAGT
1351 TTGTCCCTGC AGCCACCGAT GCCCAAGCTG GGGGCGATAA TTCAAGTGTT
1401 CAGAACAGAA CATACATCGT CACAACAATC CTAGAAGATC CTTATGTGAT
1451 GCTCAAGAAG AACGCCAATC AGTTTGAGGG CAATGACCGT TACGAGGGCT
1501 ACTGTGTAGA GCTGGCGGCA GAGATTGCCA AGCACGTGGG CTACTCCTAC
1551 CGTCTGGAGA TTGTCAGTGA TGGAAAATAC GGAGCCCGAG ACCCTGACAC
1601 GAAGGCCTGG AATGGCATGG TGGGAGAGCT GGTCTATGGA GTAAGTTCAC
1651 TGCAGGGTGG GAAATTAGAG GGCGGAGGCA GAGGGTTTGA CAGCAAATCA
1701 TTTGGTGGTT GGGTGGCCCT GCCCACAGAT GTCTATGAAA CCCTGTAATT
1751 GAGTGTTGTT GCTGCTGAAC AGATGAGTCA TCCAAAATCC AATTTCTTCA
1801 GACACTCTTT GTTCAGGTTA CTGGTCCCAG GTCCCTCAAT CCCACTCAGA
1851 GTCTTGTGAC GTCAGTTGAT TGTCGTCCAA CACAGGTGAC AGCATAGCTC
1901 CAAGATCAAT TTTCTTGAGG CAGACTGCTG AGTTGTCTAT ACAAAGTCAC
1951 TTGTGGCTCT CTCAGTATCA GTTTCTTCTC TGATATTAAA TGCATCTGGA
2001 GCCAACCTAA CTTTCTAGTT ACTTGCCTCT CTAGTTTCAT GCTCTCTCAT
2051 GAAATTTCCA ATTCAGTCAA ATGCCCCTTA ATTACTCTGT TCCCTAGAGT
2101 GCTCCCTTCC ACTCTCCACC CCTAAGATAC TACTCCTTCA AAACCTATAT
2151 CAAATAATAC TTTTTTCAGG GTGTGTTTCT TTCTTTCTTC TCATAATAGG
2201 TATGAATGTG CCTTTTAATT GTTCTCGCCT TCCCCTATAG AATTTAGTTG
2251 CTGGTTTTTT TTAATGGTTT ACCCTGCCTT ATATAACGGT TACCTGTGTA
2301 ACAGGGGTAG GACTATTCTA TCTTTATAGT GCTCACCACA CTTGAAATAA
2351 CTCCATGCAC AATTGCTATA AAATCTTCAA TAAATTACAG CAGTTTTGAA
2401 AAAAAAAAAA AAAAAAAAAA AAAAAAAAAA AAAA
  (SEQ ID NO: 1)
```

FEATURES:

```
5'UTR:        1 - 188
Start Codon:  189
Stop Codon:   1746
3'UTR:        1749
```

FIGURE 1, page 1 of 2

HOMOLOGOUS PROTEINS:

Top BLAST Hits:

| Sequences producing significant alignments: | Score (bits) | E Value |
|---|---|---|
| CRA\|18000004891320 /altid=gi\|106114 /def=pir\|\|A41273 glutamate ... | 998 | 0.0 |
| CRA\|18000004924128 /altid=gi\|183281 /def=gb\|AAA58613.1\| (M64752... | 998 | 0.0 |
| CRA\|18000004904030 /altid=gi\|478699 /def=pir\|\|S25852 glutamate ... | 996 | 0.0 |
| CRA\|18000004891322 /altid=gi\|4504113 /def=ref\|NP_000818.1\| glut... | 996 | 0.0 |
| CRA\|18000004904031 /altid=gi\|481504 /def=pir\|\|S38723 glutamate ... | 990 | 0.0 |
| CRA\|18000004938820 /altid=gi\|6680087 /def=ref\|NP_032191.1\| glut... | 984 | 0.0 |
| CRA\|18000004967647 /altid=gi\|227246 /def=prf\|\|1617121A Glu rece... | 984 | 0.0 |
| CRA\|18000005162807 /altid=gi\|3402257 /def=emb\|CAA35050.1\| (X171... | 982 | 0.0 |
| CRA\|18000004967543 /altid=gi\|279674 /def=pir\|\|ACRTK1 glutamate ... | 979 | 0.0 |
| CRA\|18000004936319 /altid=gi\|202868 /def=gb\|AAA63479.1\| (M38060... | 979 | 0.0 |

EST:

| Sequences producing significant alignments: | Score (bits) | E Value |
|---|---|---|
| gi\|12445102 /dataset=dbest /taxon=96... | 1023 | 0.0 |
| gi\|8061803 /dataset=dbest /taxon=960... | 690 | 0.0 |
| gi\|12066444 /dataset=dbest /taxon=96... | 373 | e-100 |

EXPRESSION INFORMATION FOR MODULATORY USE:

gi|12445102 placenta
gi|8061803 /nervous
gi|12066444 brain

Tissue Expression:

hippocampus

FIGURE 1, page 2 of 2

```
  1 MQHIFAFFCT GFLGAVVGAN FPNNIQIGGL FPNQQSQEHA AFRFALSQLT
 51 EPPKLLPQID IVNISDSFEM TYRFCSQFSK GVYAIFGFYE RRTVNMLTSF
101 CGALHVCFIT PSFPVDTSNQ FVLQLRPELQ DALISIIDHY KWQKFVYIYD
151 ADRGLSVLQK VLDTAAEKNW QVTAVNILTT TEEGYRMLFQ DLEKKKERLV
201 VVDCESERLN AILGQIIKLE KNGIGYHYIL ANLGFMDIDL NKFKESGANV
251 TGFQLVNYTD TIPAKIMQQW KNSDARDHTR VDWKRPKYTS ALTYDGVKVM
301 AEAFQSLRRQ RIDISRRGNA GDCLANPAVP WGQGIDIQRA LQQVRFEGLT
351 GNVQFNEKGR RTNYTLHVIE MKHDGIRKIG YWNEDDKFVP AATDAQAGGD
401 NSSVQNRTYI VTTILEDPYV MLKKNANQFE GNDRYEGYCV ELAAEIAKHV
451 GYSYRLEIVS DGKYGARDPD TKAWNGMVGE LVYGVSSLQG GKLEGGGRGF
501 DRKSFGGWVA LPTDVYETL
 (SEQ ID NO: 2)
```

FEATURES:
Functional domains and key regions:
[1] PDOC00001 PS00001 ASN_GLYCOSYLATION
N-glycosylation site Number of matches: 6

| | | |
|---|---|---|
| 1 | 63-66 | NISD |
| 2 | 249-252 | NVTG |
| 3 | 257-260 | NYTD |
| 4 | 363-366 | NYTL |
| 5 | 401-404 | NSSV |
| 6 | 406-409 | NRTY |

---

[2] PDOC00005 PS00005 PKC_PHOSPHO_SITE
Protein kinase C phosphorylation site

Number of matches: 5

| | | |
|---|---|---|
| 1 | 71-73 | TYR |
| 2 | 206-208 | SER |
| 3 | 306-308 | SLR |
| 4 | 315-317 | SRR |
| 5 | 453-455 | SYR |

---

[3] PDOC00006 PS00006 CK2_PHOSPHO_SITE
Casein kinase II phosphorylation site

Number of matches: 6

| | | |
|---|---|---|
| 1 | 135-138 | SIID |
| 2 | 164-167 | TAAE |
| 3 | 179-182 | TTTE |
| 4 | 180-183 | TTEE |
| 5 | 279-282 | TRVD |
| 6 | 413-416 | TILE |

---

[4] PDOC00008 PS00008 MYRISTYL
N-myristoylation site

Number of matches: 7

| | | |
|---|---|---|
| 1 | 14-19 | GAVVGA |
| 2 | 29-34 | GLFPNQ |
| 3 | 247-252 | GANVTG |
| 4 | 348-353 | GLTGNV |
| 5 | 398-403 | GGDNSS |
| 6 | 495-500 | GGGRGF |
| 7 | 506-511 | GGWVAL |

---

[5] PDOC00009 PS00009 AMIDATION
Amidation site 358-361 KGRR

Membrane spanning structure and domains:

| Helix | Begin | End | Score | Certainity |
|---|---|---|---|---|
| 1 | 3 | 23 | 1.803 | Certain |
| 2 | 95 | 115 | 1.636 | Certain |

FIGURE 2, page 1 of 2

BLAST Alignment to Top Hit:

```
>CRA|18000004891320 /altid=gi|106114 /def=pir||A41273 glutamate
           receptor precursor - human (fragment) /org=human
           /taxon=9606 /dataset=nraa /length=896
         Length = 896

 Score =  998 bits (2553), Expect = 0.0
 Identities = 484/484 (100%), Positives = 484/484 (100%)
 Frame = +3

Query: 189  MQHIFAFFCTGFLGAVVGANFPNNIQIGGLFPNQQSQEHAAFRFALSQLTEPPKLLPQID 368
             MQHIFAFFCTGFLGAVVGANFPNNIQIGGLFPNQQSQEHAAFRFALSQLTEPPKLLPQID
Sbjct: 1    MQHIFAFFCTGFLGAVVGANFPNNIQIGGLFPNQQSQEHAAFRFALSQLTEPPKLLPQID 60

Query: 369  IVNISDSFEMTYRFCSQFSKGVYAIFGFYERRTVNMLTSFCGALHVCFITPSFPVDTSNQ 548
             IVNISDSFEMTYRFCSQFSKGVYAIFGFYERRTVNMLTSFCGALHVCFITPSFPVDTSNQ
Sbjct: 61   IVNISDSFEMTYRFCSQFSKGVYAIFGFYERRTVNMLTSFCGALHVCFITPSFPVDTSNQ 120

Query: 549  FVLQLRPELQDALISIIDHYKWQKFVYIYDADRGLSVLQKVLDTAAEKNWQVTAVNILTT 728
             FVLQLRPELQDALISIIDHYKWQKFVYIYDADRGLSVLQKVLDTAAEKNWQVTAVNILTT
Sbjct: 121  FVLQLRPELQDALISIIDHYKWQKFVYIYDADRGLSVLQKVLDTAAEKNWQVTAVNILTT 180

Query: 729  TEEGYRMLFQDLEKKKERLVVVDCESERLNAILGQIIKLEKNGIGYHYILANLGFMDIDL 908
             TEEGYRMLFQDLEKKKERLVVVDCESERLNAILGQIIKLEKNGIGYHYILANLGFMDIDL
Sbjct: 181  TEEGYRMLFQDLEKKKERLVVVDCESERLNAILGQIIKLEKNGIGYHYILANLGFMDIDL 240

Query: 909  NKFKESGANVTGFQLVNYTDTIPAKIMQQWKNSDARDHTRVDWKRPKYTSALTYDGVKVM 1088
             NKFKESGANVTGFQLVNYTDTIPAKIMQQWKNSDARDHTRVDWKRPKYTSALTYDGVKVM
Sbjct: 241  NKFKESGANVTGFQLVNYTDTIPAKIMQQWKNSDARDHTRVDWKRPKYTSALTYDGVKVM 300

Query: 1089 AEAFQSLRRQRIDISRRGNAGDCLANPAVPWGQGIDIQRALQQVRFEGLTGNVQFNEKGR 1268
             AEAFQSLRRQRIDISRRGNAGDCLANPAVPWGQGIDIQRALQQVRFEGLTGNVQFNEKGR
Sbjct: 301  AEAFQSLRRQRIDISRRGNAGDCLANPAVPWGQGIDIQRALQQVRFEGLTGNVQFNEKGR 360

Query: 1269 RTNYTLHVIEMKHDGIRKIGYWNEDDKFVPAATDAQAGGDNSSVQNRTYIVTTILEDPYV 1448
             RTNYTLHVIEMKHDGIRKIGYWNEDDKFVPAATDAQAGGDNSSVQNRTYIVTTILEDPYV
Sbjct: 361  RTNYTLHVIEMKHDGIRKIGYWNEDDKFVPAATDAQAGGDNSSVQNRTYIVTTILEDPYV 420

Query: 1449 MLKKNANQFEGNDRYEGYCVELAAEIAKHVGYSYRLEIVSDGKYGARDPDTKAWNGMVGE 1628
             MLKKNANQFEGNDRYEGYCVELAAEIAKHVGYSYRLEIVSDGKYGARDPDTKAWNGMVGE
Sbjct: 421  MLKKNANQFEGNDRYEGYCVELAAEIAKHVGYSYRLEIVSDGKYGARDPDTKAWNGMVGE 480

Query: 1629 LVYG 1640
             LVYG
Sbjct: 481  LVYG 484 (SEQ ID NO : 4)
```

Hmmer search results (Pfam):

```
Scores for sequence family classification (score includes all domains):
Model     Description                                    Score    E-value  N
--------  -----------                                    -----    -------  ---
CE00269   CE00269 kainate_receptor                       646.8   1.1e-190   1
PF01094   Receptor family ligand binding region          101.4    1.4e-27   1
CE00294   E00294 glutamate_receptor_6                     47.5    5.9e-14   1

Parsed for domains:
Model     Domain  seq-f seq-t    hmm-f hmm-t      score  E-value
--------  ------- ----- -----    ----- -----      -----  -------
PF01094    1/1      55   391 ..    56   464 .]   101.4  1.4e-27
CE00294    1/1     347   479 ..   376   507 ..    47.5  5.9e-14
CE00269    1/1      21   484 ..    42   544 ..   646.8 1.1e-190
```

FIGURE 2, page 2 of 2

```
   1 TTCAAAGTAG TAAGATACAA AAACTGAAAA TGGAGAAATT AAAAGATGGA
  51 ATCATTAAAT CAGAGACTCT TAATGTTGGC AGAGACCTTA GAAGTGATCT
 101 TTCCTGATTC TGTTCTCTCA TCTTCCTATG CTGATGCTTA TTCTTCCTTT
 151 AGAAGGTTCC TACCCAGTGC TTGCTGTTAT TAGAGCCTAA GAGTTAAGAG
 201 CTGGGGCCTG ATGGTGGCAT TTACTGTGTT TAAATGCCCA ATCTCTTTCA
 251 TTAGCAGTGA AAACTTGGGG TGAGTTTTTA GACCTCTGTT TCTTCATCTA
 301 TAAAATGGGC ATGAGGCTAC CTACACAGGT ATTGTACAAA TAAATGATGC
 351 AGGTGCATTT CTTAGCATGG TACCTGGCAC ATTCAAAATA CTGAATAAAC
 401 ATTAGCCTTA AAAATTATTT TAGCTAATTA ATTAATATAT GTGAAAGTGC
 451 ATAGGAAATC ACAAAGCATT TGACCTCCAA GTTGTTCCTA TTTTGGGGCT
 501 TCATTGTACA TGGTCAGATA TTTTTTACAA ATCCCAGTCC TTGTAGCTGT
 551 CACTCAAGTC CACATGATAT ACAGTCCTGG TGAGGGAAGT GAAGAGTCTG
 601 TGGATAAAAT GGCCTATTCA TATGGCAAAG CAAAATGGAG TCCAAAGTCT
 651 ATTATTTCTT TCTTACTAAA GACAAAGTTG ACTTTCCTTT TCCTGGATCA
 701 TCTCCTGTTG GACAGGAGTC CTGGCCAGGG CAGTAAGTCA ACTGCTAACG
 751 GCCAAAGCAC TCAAGTTTGT AGGTTGTACT GTACATCTTA GTAGGTCTGT
 801 GTCTTTATGA CTTAATCCCA GAAGTCTTAT CTTTTTCATC TGTAAAACAG
 851 GGCTCATGGC CACTTTACAG GTTTGGAGTG AAGATAGATG GATAAAAATC
 901 TGTAAAGTTC CTTCAAAAAC TGTATTCTGT GGCGGCTAGT GGCTGCTGCT
 951 TTGCATTTAA CACTACTATC CTGAACACAG CTGATCTCTC TACAGGTTAT
1001 TTCAGCAGAA GCCCTGGTCT AGGAGAGTCT ATGAAGTTCC AGCTTACACC
1051 AGACATGACC AGCATCCAGA AAGACCTGAA AGAAGCTTGA ATCCCTCTCAC
1101 TAGAATCCCT GCAAAATGAC TCATGTAATT GCTCTGTGTA AGTATCCTTA
1151 GTCTTTATTG TACACCCACA CGATTCTGAT GCTATAGACT CCTCTGGAAT
1201 GCAGGGAAAG AGAGAAGGGG GCCCATTTTA AATGCCTAGG ATTGAAAAGA
1251 GACCACCGTT TCACTTGTAA AGGTAGACAG GGACTGTCAA ATACCTGGTC
1301 AAAATACCTG CCAGTCACTC CAGATCCTCC CTTGTTTGTC TATCTGTCAT
1351 TCCTTCCATT AGGAGAGAGA AAGCTTTTTT TTTTTTTTCC TTTAAATTTC
1401 CTAGGAGGGA TTTCTAGGGT CTTTCCCTCA GGAATTAGTT GTAGGAATAA
1451 TTGGGCCAGT GGAGTGCAGG AGATATATCC AGCGCAGCCC ATGCACTCCT
1501 AGAAAAAGTG ACCTAGATCA AGCAGCTGGT GGATTGAGGA CTATTGTGGG
1551 GACCCCCTGC CACCTACTGA CTTACAGCTG AACCCACATT CCCAGCAGCT
1601 TCAGCCTGGG GGCTGGGGGA GCGGGCAGAC CGAGCTCAGA AAGGCAGGGG
1651 AGGGTAAAGA GGACTGTGGG GTTGCCCCTT TCAGGACCAA GTGCCACGTG
1701 TCACACACCC CCACCTCCAC CTTTCTGCAC ACACAGAAAG GAGGATAAGG
1751 TGAGGATGGG AGGAAGGGGG AACAGGTAGG GAGGTCGGCT GTGGAACTCC
1801 AAGCTAGCTC GGTGGGTATT AGCATAGAGC TTGCTGCCTG TGTGAGTGTG
1851 AGGGGGAGAG CGAGAGAGAG CAAGGGAGGG AGAGAGAGGC AGGCTGCGAG
1901 GGGAGAGGAG AGGGAGTGGG GGAGCCAGCG CTCCAGCTAG CATGAGGACG
1951 GGCTTCTTTT CCCGTGCTCA GTTAATCTGG CTGTCAGTTG GTGTTAACGC
2001 TGCAGTTTAA GTGTTCGGAT TCCAAGGGAA ACAGACAAAC CTCACGAAAG
2051 GAAGGAAGCA AGCAAGCAAG GAAGGAACTG CAGGAGGAAA AGAACAGGCA
2101 GAACAGCGAG AAGAATAAAG GGAAAGGGGG GGAAACACCA AATCTATGAT
2151 TGGACCTGGG CTTCTTTTTC GCCAATGCAA AAAGGAATAT GCAGCACATT
2201 TTTGCCTTCT TCTGCACCGG TTTCCTAGGC GCGGTAGTAG GTGCCAATTT
2251 CCCCAACAAT ATCCAGATCG GTGAGTGAGG GGGCAGCCTG GGGAGGGACT
2301 TTCTGGGTCT GGCCAGGGAT TTTTTTGGGG ATAGGGGTTG TGTACCCCCT
2351 CCCCGGTACT GACTGTTTTG CTTGGCTCCC TAAAGCTGTG CTGCGGTAAC
2401 AGAAGGGAGA CTTGGGCTTA CAGCCAGAGG AGGGGGCTTC TCCTGATCGG
2451 ATGAGGGGCA GAGGGGAAGT GTTCACACAC GCACACATAC CCTACTCGCA
2501 CTCCAGGCAA GAGCATGTGA AATGGAGGAA CCATCGCTTT GGAGGAAAAA
2551 AAAAATCAGG CTGGAAAGGG TGGTGGGTGT TTAAGGAGTT AACTCTATTG
2601 CTTGGTAGAT GGTGCTTGAT TCCATTTTTA ATGTAAGTAT GTATGGTGTG
2651 TGTGTTTTCA CGTGTGTGAT TATATATTAC ATATGCACAT ATATATGTAA
2701 TTGAAGGAGG CAGTGCTTTC TCTGCTGGGG GACAGAAAAG AGACCCTCGA
2751 GAAGAAGGAG TGAGGGGTGC TGGGTATATT GCAGCCACTG AAATAATGCC
2801 AGAAGGCCCC CACTCCAAGG CGGGTAGGCT CCCTCTCCTG TTCTGGACTC
2851 CTCCAGCTGC CTTCTCTTTG CTGTCTGCCA TGCTGCGCTG GTGGTCTCCA
2901 CTCCCCCGAT CCTGGAACTT CCTCGCCTGC CTTTTCTCCG TTCCTTCCTT
2951 GCCCCCTCCT CTTAGATTTC CTATCCACAG AGGTCTACCT TTTACACACA
3001 CAAACACACA CACGTACACA TGCTCCTTTC TCCTCCTGTT GGCTCTCCAT
3051 TATCCTTGTT ACTGGGCTCC ATCCTCTCAA CTTGGAGGCA GGTTTCAACA
3101 TGCTGCATGC TTTTTTTGTT CCCCATTTCC CCTTCTTAGT TGTTACACTT
3151 CTCAAAGGCC CCGCCACCCT CCCTGTATTT CTGAGGGGAC TGACAGATAT
3201 TGCTACTCCT GATAATCATG AGGGAAAGCA AAACAAACAG AAGCAATAAC
3251 ACCAATCACA AAGCATGTCC ACAAGGGCTT GGGGCTTCCG TGTGACCAGC
3301 ATGTCAGTGT CGTTTGTGTC CCGGAATGAA GCAAGCTGCT GTGTTTGGAA
3351 GCATCTTCGT TGGTTTGGTT TCTAGTCTCT CTCCCCTGGT AGGGAGATAG
3401 CTCCACTAGG GAAAGTTCGC ATTGCTGGGA GTTTGTGCTC TTTTGTGAGT
3451 GTGTGTTTGA GGGGGGATGT GGTGCAATTG ATATTTTGTC GGGCATACAT
3501 GTGCTGCAGT ACCCATCTCT TTCAGCCTCT CCAGCTAGCT GGCGGCTTGG
```

FIGURE 3, page 1 of 122

```
3551 AGTGGCCATG GAGTAACTTG CTTTGTTTCC TGACACCTGT TAAGCTACAT
3601 CCTGAAGTGT GTACGTATCT GTGTGTTAGT GCCTAACACG CAAAACTTCC
3651 TGCCTTCAGG GGAGACACTT CCCTTGTAGC CCAGCCCGTA GCCTTCTACT
3701 CCTCAACCTC CCATCCTTTC TCTTTCATTC ATTGCAGAGG AGGAGAAAGG
3751 GGACAGGGAA GTGTTTGGGG TGTGGTCATC TGGGGGGAAG GGGGAGCATC
3801 ATAATCAAGA ATTTTTTTTG TTTTCATTCT TTAAAATGGG AGCACTTGTA
3851 CATGTGGAAA TCACTGGCTC TTACATGTGG CATTGTTTAC ATTTGTGCTT
3901 ATATACTACC TATCCTTTGT GGCTTGGAAG TGTTTGTCTA GTATATTTGT
3951 GTATATAGTA AATGGTATAA ATGCATGAGG ATGTTTCATG TATGTGCTAT
4001 GTTTTCTCAT GTATCTCTGC ATATTTTTAA AATTATATTT AGCCCTAACT
4051 TGGTTGTTCA ACTGATAAAG CCATTGCTAC TGTTTTCAAA AAAAAAAGAG
4101 ATTGAAGCAT TAAATTGTAG AACAAAATGC TGAAAATATC ACTGCCATCA
4151 GGTAGTACTT GATTCTATTT GTGTGATCTG TAACAAAAGG CTTGCAATCC
4201 ATTTATTGGT TCTTAAAAAC AGACACCCAC TCTACAAGAA GTTAGAAGTG
4251 CATTATGTTT GGACTGTGAT TACTGTCAGA TTTGAGATAA ACTTCTATGT
4301 AAACATCATT ATAGTTCAGT CTCTAGAAAT GGCTGATTTT AATTCACAGA
4351 AATGTAATTG ATTTACATGT TGACAGTAAA TACAAAGGTA AGCCATGGAC
4401 TCTTGTTTCT CGGAACAGGC ATCCCATCAG GCACCTTTAC TATACCTTTT
4451 ACTAGAATAG AATGTTTGTA TCCTCTTGAG ATGCCTAAGA TCCCACATCT
4501 TTGAAGCACA AGGTTCCACC ATGCAAACAC ACAATGGCAA TCCCTTATGT
4551 AACAAGTCAT TCCTAGGTAA CTGGGATCAT GTGTGGTGAA AGAGTAAGCA
4601 AAACATTGTT TGCAGAAAAG CAAGAGTTTT TAGAGAAAAT GAATAATAAA
4651 CCTTAGGGGC AATAGAATAG TTAAATTGCA TGCAGGTCTT GCTAGGCCAA
4701 AGACTAAAAA CTGTCCATGT AAACAGTTAT AGTAGTGGAG AAGCCCACAG
4751 GGTCCCAGAG CTAGATTTCA ATCACCCTGC AGCACTGATT AGTACCTACT
4801 TCCCGTAAGG CTCTCTGGTG AGAGATGAGG CTGATGTAAG AAAAATTACA
4851 CATGACTAGA GGGTGAGGGG GCTTATGTGT ATGTTTATAT AAGAGAATAG
4901 CAGCTCCTAG GTGGTTTGCA CAAGGGAGGA AGAAGAGAAA TGGCACAAGT
4951 CTCCTGTTTT CTCTGACTTT AGCTGAGTTG AGGGGTACAC AATCAAATGT
5001 TTGAGCAAAG TAATAGATAT TAGAGGCCCA TGTCACAAAA AAGCTCATCT
5051 GTAGGAGTTT AAGTTTCAGT GTCCAGTTAA GCCTATTTGA ACTCTCATCT
5101 CTACCACTCA AGGCTACAGC TAGTGAGTTT GGCATGGGGA GAAGAAAAGG
5151 ACTCATCTGG AGTGAGTCGT GAGGAACTAA AACCTGTCTC TAGCCCATAT
5201 ACCATGTTGC ATTTTCTTTT CTCATAGGGG GATTATTTCC AAACCAGCAG
5251 TCACAGGAAC ATGCTGCTTT TAGATTTGCT TTGTCGCAAC TCACAGAGCC
5301 CCCGAAGCTG CTCCCCCAGA TTGATATTGT GAACATCAGC GACAGCTTTG
5351 AGATGACCTA TAGATGTAAG TAATTGCTTC TATTTCTGAG ATGTCTTTCT
5401 GCGCTAGACC AATGAAAGGA GGGCCTGTGG GTAGGTGGTG GTGTTGCAAA
5451 AATGACTTCA GTTGCCATTC GTCTTTGTAA GAGAAAGCCC TCCAAGAAAA
5501 ATTTCTAGAG CCTTCTGAGT GATTCCAGCA GTTGGCATTT TAGCCCCTGC
5551 AATGCTTCAT GTAATGGATT TGCTTTTTCA CTGTCAGCTA ACTTTAATGC
5601 CAGCACGATG GGTGCTTGGG TTGACTGCAT CTTCCCTACC TTGCAGAGGT
5651 TTTCTGGCAC AGCTGAGAGA GTTTTACACA TACGAATCTT CTGAGAGGCA
5701 TAGAATTAAG GGTCCTGAGT TTGTGAAAAT GTGGTTTAAA GTGCTTAAGG
5751 CATTTCCTAT CTACATGTTA AATGGACAGA ATGTAGCTTG ATAAGAAATA
5801 ATAGCTGAGA AGTTGTACAC ATCTGGTTCT TCATTTTCGG AAGTGACCAA
5851 TAATTAAAAC TTGGTGCCTT GGTCATTTTA AAAATAGCTT GAGGAAATTG
5901 GTTGTTTAAG GCACAGTTTG TAGGATGGTC ATTGAGCATC AAACAGAACA
5951 AAGGTGGCCT CAAGAAGAAG GGATAGATAA ATCTCTGACA TCTGAATTGA
6001 ATGCATTGTA AAATGTGGGC AACAAACACC ATTCTGAGTT TTCCTGGCAA
6051 CTAGGAATGA AAAGGAAGCC TGTGCTCACA TGATTGGCTT TTCATGACAG
6101 ATGAAAGCAT AAAAATTAAT CAGGAAACAT ATTTTCCCTT CAGGGATTAA
6151 GCTCAAGTAA AAATTTATGG CAGGGAAATG TGAGCTGAAT TCACAAGAAC
6201 AATTTGAGAC CCCAAACTGG ATTGAATTGG CACGATAGTC TTGGTGTGTC
6251 ACTATTGACT TGGTGACTTC TGCTGAGCTG TCTCTGGTGG AAGTCATGGA
6301 CCATATTTCC TTTGTGTCTT TCTCATAGTC CCACTGGTGA GTTCTCAATG
6351 ATTTGAATAG GCTATGCTTT GAAGTCTCAA AATGAGAAGT CAGAATTCTT
6401 TCTATCCCAA AGACCACTCC TAAAATAATG TTGTTACAAA TTCCAAGAAC
6451 TATAATTATA GCAGATTTCA TTTATTGAGA ACTTACTGTG CATCAGAACT
6501 ATGATAAATA CTTTATAGTC ATTTATAGTC ACATTCATTA CCATGTATTA
6551 AGCACTGACT ACAGCCCATG TAATGCACTA ATTGCTTTTT ATCTGTTAGC
6601 TCATTTAATC CTCACAGGAG CTTTGCAGAG TACTAGACAT TATCTTCCTT
6651 TTAGAGATGA GAAAACTGAG GCTACAACAG ATTATATAAC TTGCCCAAGG
6701 TTACTCAGGA AGCAAATGGT GGTTTTGAGA CCTGAAGGTC CATGTTCCTG
6751 GATACTGTGA CAGATACACT GATTCTTATG GTACCCTAAT CAACTAGTGG
6801 GATTACCCAA GAAATGAAAG GGAATTTTCA GGGTCTTGTA AGGCAGAGGT
6851 CTAATAAAGT ACCTAAGGAG AAAAACTTAC AGTGTTTCAA ACTGTAGCTA
6901 TGATTTGCAC AGGACTGGTC CATTGAATAA ATAAAATAGC AATTCTTCAT
6951 TTTGGTAATG CTGAGGTTGA AAATCTTATC TACTGTGTTA CTCACTACCC
7001 TTAAAAAAAT AGCTGAAGTT TAATTGCTGA ATTTTAGTTC TATGAAACTA
7051 TCTTTCTGGG AATCTAGAAT AATACTGAGT AGCTATTTTG CTATTAGATA
```

FIGURE 3, page 2 of 122

```
 7101 ACCTTTCTTT ACTTTTTAAT GTGGCTTTGA TTAGGGTCTT TGGAAGGGGC
 7151 ATTTGGTTGG GGGCATCAGT GTACCTATAA ATGTTTAAAC GCATATACAT
 7201 GTGCTAATTT ATTTCCTGGA GCAGGGCTCC ATAGCTTTTG TCATACTTTA
 7251 TAGCTTTTGT ATTACTTGCA TAGAGAATCA AGAATAAATA GCTGGTGTGT
 7301 GTATTCACTC ATGCTGCTGA GAAATATCTA CAGCAGGTTT TGGTTGAAAG
 7351 AGATGTGAAC TGCTCTCCTA GTAGTGTCAA GATGTTGACT GGCACAGCAA
 7401 GAAAATAAAA GACAAAAATA GGAGAAAAGG TTCTAAGGCA AAAGGTGGTG
 7451 CTTCTGTCTT GTTATCTCAG CAACCTAAGA CTTGATCTCT AATAGGGTTA
 7501 ATGACTGTTT ATTAGGGAGA CAGAAATATG ATACAGACAA TGTTGTTCAT
 7551 TTTGGTCAAC AGGCCTGGAG TGGATGAATC TGAGTTCTTG AACTTGATGC
 7601 TGCCATCCAT GAACTAGTGT ACAGGTTTCC ATGAATTCCT GTCTTGTTCG
 7651 TTCAGTTAAT TCTTTAAGTG TTTCTTCAAA GCTATAAACT GAAATAGATA
 7701 TTGGAAATAC AGAGATGATA AAATGCCCTT GCTCTCAGGT AGCTTACAGT
 7751 CTAGTGGGAA ACATTGTTAT GGGGATTATC TGAGAAGCAA TAATCTTATT
 7801 TTGTGCTTAG ACTTTGTGTT TCTTTTCTTT AGCTCCCAGA TCCCAAAGGG
 7851 GGTACTGGGC AAGTTAGGTG GAAATGGTGG CCTGGCTGGA GGAGCCTCTC
 7901 TTAAATTTCA TGTAAGGCTA GGAATACTTT AGGGCTGTGT TCACTGTGGT
 7951 CCATTGGTTT GGGAAAACTT TACATCTGTC CCAATTTTAA TTGAGTAAAA
 8001 AATGTCAGTG GGAGCAAAGC AGTTTTAGGA AGAATGTACT CATTACTGAT
 8051 ACATGGAAAA GCAAGAAAAG CATCTTATTC AGACTAATTT TCTGTGCTGT
 8101 GTTTTTTGAA ATCTGAATTA GTAGTTGCCT TAAATTAACT GCCCAATAAG
 8151 TCTTAGATCT AGAAAATGAC CAAATTTTAT TTGTTTTTTT TTCATAATTT
 8201 TTGCTGTCAT TTGATTTTTT CCCTTTGCAT TTTGCTATTC ATTGTCCCTC
 8251 CACCAGAGGG TGGAGAAGGG AAGGGAGAGG AAGTGTAATG GGACCTGTTC
 8301 ATGCTAGACA TGTTAGCAGC AGGGGACTAA AAATGAGGAG AGGTGGTTAT
 8351 ATGGTAGGGA AGGTGGGGAA GATAGAAGAG GACTATGGCT ACTACTACTG
 8401 GCCAAGGTGA GAGTTTGGTG CCTTCTTCGT GTTCAATCTT TCTTGCTTCC
 8451 CTGGTCTGCC ATTGTTAAAG AGTAAAGCCA TTGAATCAGC AACCCAATGC
 8501 CTTGGGATCT CCTTTAAGCA CTTTTCCAAG CTTACAGGGG TAGAGTTTGG
 8551 GGAGATTGTG CATAGAGAAG ATATTTACTG ATCAGCTACC CAGCTTATTT
 8601 TGGTGCCTTT GTGGTAAGTG TAAATAAAGG AATAAATGAA ATGCTGATTG
 8651 AGATTATTAC TATTAGAGGT CTGAGTAGCA TAGTTGCAGC TTAATTCTTA
 8701 CCTTTTAATT TATTCACCTA TTTATTCATT CATTCATTCA GCAAGTATAT
 8751 ACTGAATGCC TACTTCATGC CAAACACTGG GCCAGACGCT AGGAATATAG
 8801 GGGCCAGGAA AGAAGGCACA GCCTCTTTCC TTGTGGAGCT AACAGTTTAG
 8851 CCCAGAGGTT CACAAACTTC AGTGCACTTA AAATTCACTC AGGGAGCTTG
 8901 TTTAAAGCAA GACTCATGAT GAACTTTTTA CTTCTTGAAT CAAGATATTC
 8951 AAGAGTAGGC CCTGGAGGAA TTCTATAGCA ATTATTATGG GGATTACACT
 9001 TTAAGAATCT CTTTAATCTA AAAAGTCTTC CATCCCTTTA GTAAGCATTT
 9051 TTGAGCCCTC AACCAAACCT AGGCATGACA TAAAGTGCTA CAAATGCAGA
 9101 CAACAGTAAG TTGCATTCCC CACCCTGGAG TACTTTATCC ATAGTAAGAC
 9151 ATTTTCTATC CTGTAAAGAG AAAATTAAAA TGTAATGTTG TAAGTGCTAT
 9201 AGCAGCAATT TGTATGGAGT ATTGAAGATT CCTTGAAGAG TGGAGTTTTT
 9251 CTCTAGGAGG TGGTGATTGA ATTGAGCCTC AACGATAAAT AGGGTTATCT
 9301 ATCTGCAGAA GGGGTCACCA AATATAGCCA TCCACAAGCC AGTTCCAGCA
 9351 CAGAGACTGA GTTCTGGGCC CATACACTGT GTAAGAACCA TGGAATTTCA
 9401 CATTAGAACT TGGACATCTT GTCTTGACTA ATATTTTTAA ATATTAAAAT
 9451 ATCTGGCAAC ACTAGGGCCC AGGTCTATGC AGCCTCAATT TGCTGAGATG
 9501 GGACAGAGTA AACCCCATCT ACATGGCCTC TTTCCCAATC AGCCCATTCT
 9551 TCCCATTTTC TTTACCTGCT GGCTTTGGCA AGCATTGAGT TTGCAAGCCC
 9601 TGATTGATAG CACTGCAATG TTGTCTGTGT TGTGTCTTTA TAGGTTAGCT
 9651 TCACCACCAG AATATAAACT GCTGTCAGAA AGACCATGTA TATCTATAGT
 9701 TTAGTGTTGA GAACACTTGG AAATGCCTCT AATACAAATG AATAAATGTC
 9751 TGTAGGAGTC AGGGAATTAC ACAGCATAAA AATGTTCAGA GCCTCAATGA
 9801 CAATAGGTGA AAGGTAGCAA CCCTAACTAC AGTGGGATGC CCTCTGTCAT
 9851 GGACCTACTG GGGAAGCCCA GGGGCTTCCT AACAAGACAT TAGGCACTGG
 9901 CAACAGAGAG ATGGCCTTAG CTCTTGCCTG AACATGGCTC ATCAACTTCA
 9951 GAGTTGCAAC ACAGATTTGT TTTTCTTGAC CTACACAATG CTTTTTCATA
10001 TTTGGCATAA AAATCCAGAT TTCTGGCATC TTTAAAAAAA AAACTTAGGG
10051 CATTAAGCAA CCCTAGGCCC ACATTCCTGC TTAACTTCTA TTTTCTAGAG
10101 CTGAGAAGTG CTGCCCTTTT TAAATACATA AACTCCCAAG TTAACCAAAG
10151 TTTCCATTAC TTCCTGTTTG ATTGCTAGAG TAATCAAATT ATGTTGTTTG
10201 GGCAGGCCTG TAAGTAGGCC AATCTACTCA TACCTGATTT ATATCGTCAG
10251 CATTCATCAT TTTATTATTT TGTTCTAATA ATATCTATTA CTTACCCTGT
10301 CAAAAATAAT AAAAGACACA AAAGATGTAT AACTCCTACT CTCAAAAAAA
10351 GTAGTGTGTA TACAGTAATG AAGAGAATGG TGGCTGATGG TGGGATAAAC
10401 AAGAATTATT TTGAAGACCT ACTATGTGCC AAATACTTTG CAGGTGTTGT
10451 CTTAAGTTTT ATAACTGTCT TGAAAGGTGA TTATCCCCAT TTCATTGATG
10501 ATGGTACTGA GACTGAGAGA GATTGTGTCT TCTTTATATT ATGCAACAAA
10551 TAAAAACCTA AGCTAGTATT TAAAGCCAGT TTGGGGGGCT CCAAAACTCA
10601 ATGAGCATTC TCCTTTTAAA GATCTATGAA TATGGCCAGG GGCAGTGGCT
```

FIGURE 3, page 3 of 122

```
10651 CACACTTGTA ATCCCAGCAC TTTGGAAGGC CGAGGTGGGC AGATCATGAG
10701 GTCAGGAGAT TGACACCATC CTGGCTAATA CAGTGAAACC CCATCTCTAC
10751 TAAAAATACA AAAACTTAGC TGGGCGTGGT GGCACGCACC TGTAGTCCCA
10801 GCTACTCAGG AGGCTGAGGC AGGAGAATTG CTTGAACTCA GGAGGCAGAG
10851 GTTGCATTGA GCCAAGATCA CGCCACTGCA CTCCAGCCTG GCAACAGAGC
10901 GAGAATTTGT CTCAAAAAAA AAAAAAAAAA AAAAAAAAAA CCTATGAATA
10951 TATGGACAGA GAAAAGTACC ATAGCAGTGA AATAGCCCAA CGGTAGAAGT
11001 GTCACAGTGG AATTTATGAT TCAAGCTTAA GAGCTAAGTC TTCCAAGGCA
11051 GAAGCTATGA CTGTGGATGA TGAAAACTTC TTGGGGAAGG TGGAACTTTA
11101 GCAGGCATTA AAGGGTGGAG CAGATTTTGG TTGTGGAGTG GGAGGAGGGT
11151 ATTTTGAGTG GGTAAAGTCA CAATATTCCT CCTCGCCTCC CCTCAACCAC
11201 TGCTGCATAT GCTTGTTACC ATGTGGTGGA GATTTGGGAG TTTGCCTCCT
11251 GCACCACACT ATGTTCTCAG CTCCATGGCA GATGTCTACA TTTCTCTGGT
11301 TAATGTTACA GTCTGAAGTT GGCTCCTCAA TCTTCACCCG TGCCCTTACA
11351 TTAAGGCACA CAAGTGTTGA CATTTGTCTG TGGTTGACTC TTGGCTCTTA
11401 TTATAATATT GATAATCATC AGCTTTTATG GATAGAAAAA TCCTTGTAAA
11451 CATTTCTTTC CCTGACTAGT TTGAAGATCC TGCTGGGATG AGTGAGCTTA
11501 CTGCTCTCCT CTCAGCCACT CAGGATAAAG TGATCATATA GCACATTTGG
11551 AAAACTGGTA AGCTTCATGT ATTTGTTCAT TCATTCATTC ATCCGAAACC
11601 CTTTTATTAT CACCTTCTAT GGGGATATGT ACTGTCACTG CCCCACTCCA
11651 TACCTTTGTA GACAGCATTA GTTGATTACA GAATTTTTTC CCACTGAATC
11701 TACACGTGGC CTCAAATTGG TGACAGCTGA TGCAAGAGAT GAAATCCATT
11751 TTTCATTACA AGGCATTGCA CTAGAAATTG AGAAAAATAA AATGCATTAG
11801 GCATTGATTT TCCTCTTAAG GGGCTCAGGT TCTTATAAAG GAAATAGGCA
11851 TAAACCAAAT CTGCCTCTCT TTCTCTCTCT CTCTCTCTCT CTCTCTCCCC
11901 CTCTTACATA CACACACACA CACACACACA CACACACACA CACACACACA
11951 CATTCAGAGG AAGGAAGGAA AACCTTTAGT TGGAGGGATT TAGGTTTCAT
12001 AAAACAAGGA CATTTGAGTT GAATTTGGAA AGATAGGTAG GATGTAGATG
12051 GGAAAATATA TATGTATATA TTTGTATACA CACACACACA CCCCACACAC
12101 CTTCCTGTAA TGGCAGGTTT GATGCAGTAA ATAGCATACT GAGTTGAGAT
12151 TTGAAGACAT GGATTCAAAT GCTGGACTAC CTTCTTGAAT CGTTTAGGTA
12201 TAACCTTGGA GAAACATCCC CTCCCCCAAG CTTATTTATA AAATGAAGCT
12251 CATGGTCTCT GAGAGTCCTT CTGGGGCTGT ATTTCTATGC TGGCAGCATA
12301 TGGAAAACAC CAGAGATATA TGATTAATAG AAGTTCTCTA CCTTTGGCTA
12351 GCAAGAGGAT CCCTAAACAA GCTAAGTGTC TAAGGAAAGC TCTAGACTTC
12401 CCTTCCACCA ACTTGCACAT TCAGGGCGCA TTCTGTATGC AAATGCTGAA
12451 GCATTATGCC TACTTTGGGG CCTCAGATGA ATTCATTCAA TATTTAACAA
12501 ATATTTATGG AGTGCTTACT ATTGTGAACA AAACTAGAAA GCAGCCCTGT
12551 GCTCATGGAG CTCACCAGCT AATAAAGGAG GCTGCCATTA GATGATCACA
12601 TGAATGAGTG TATAGGTTGT AATAAACAAT CTGAAAGAAA GGGCCATGAT
12651 TCTATGAAAG CATATACAAA GGAACCAGCT CGTGCAGGAG GATGAATAGG
12701 TGCTTGAGCT GAGGACTGAA GGCTTTGGTG ATGCAGTGAT GGGAACAGGA
12751 GGAGTGTTTG AGAAGCTTCC TGGGCAGAGG CCTGGCCAGG CCTTGTAGGC
12801 TCTGTTATGG ATTTTGATCT TTAGCTCAAA CACTAAAGAA CCCATGGAAG
12851 GGTTTTAAGC AGAGAAGTGC CGTGTTTAGA TTTCTGTTTT CTCATCAGAA
12901 ATCAGATGCT TGATAGTACT TTGCCAAATT CACATTTGCT GAAGACGTCT
12951 GGCTTGTGTT TCAATGGCCT TGTTTCTTTA CTTCCATCTC CAGTTTGGGA
13001 TGGAGTCTGG CAGATGGGCA GGAGGATGGG GACAGAGGCC AGGGGAAAGG
13051 GAAGCTGATG ACTTGGTTTA GGGGTGCGTT GTCATGGTAT GTGGCTCTCT
13101 GTGTGCCCAT GGGCATTCCT GGAGATTGGA GGCTGATCCA GTGCAGTGCC
13151 TGGAGAACTG GTGAGGCTGT GTGGAGGCAG GGATTCATTC AGAGTCCTCA
13201 TTTATTTTAA CAAGGAAGAC ATACATAGCA CTGAAGCTCA GCCTCTGTTC
13251 CAATCAGACA ACTCAGTGGT CTTCAAATTC ACACTGCCAT TTCCTTCACT
13301 TACACTTACA AACTGCTCCT TCCATACTGC TCTGCTGAAA TTCTGTCCTT
13351 CTGGTCAGCC CTAGCTCTTA TTTTACCTTC TTCACTGAGC CTTTTTTCTC
13401 TTTCATATTC ACATGCTCTT CTGCCCTTCA GCTGTTTTTA CCATCTCCCT
13451 AGCAATGGTC ACGCTTATCC CCAGGTTTTA CTCACCTTGT CACTTGAACA
13501 CGTGTCTTAC CTGCCCAACT GGACTAAGCA ATGTGAGGTC AATGACCTTG
13551 TTTACTTTAG CTTCCCATCA CAGTCTCCAC CACAGTATAG TGTTCAGTGG
13601 TGCTAGATGA ATGAAAGAAT AGATGGCAGT GACAAGAATA AGCCTGAATC
13651 ATTGCTGCTT AGGGTAATGC TTTTGATATT ATGAGTTTTG AGAGTTCCAA
13701 CAGGCTGTGC TGTAAATACC TATGGATGGT TATTACTGTG TAGCTCCAAA
13751 GTTATGGGGG TGAAAATCAG GTGTAAGTCC AATTGAAAGC TCATTTTAGC
13801 TCCCGCTGGA CTATTGTCAT GAGGGGTCCT AAATAAGGTA TAAGGTTCCA
13851 TCTTCTAAAT AAAGAATTTC TGATTCAAGC CCTGGGTTTG CCATTGATGT
13901 ATGAGCCTTG TATGCATCTT ACGACTTTGG TGTGTCCCAG CCTGCTGTCC
13951 AGAAAGCACA GGGGAGCCCA GGGCCATGGG AGGTCCAGGT TGAGGAGGCA
14001 GGCAAAACTG GGGCAAATGA GGCAGTTGGA GGCTAATGAA ATTGATACCC
14051 TATGGTTAGG CGTGTTTCCA TGTGTTCATT GTTTGGAACC TCTAGGATGA
14101 AAATAAAGTT TGAGAATAGC CTTTAGTTTG TCTACAAAAG TAATATATAC
14151 ATTACAGAAA GCTATAGGAA CAGAGACAGC AAACACAATA AAACTTGTAT
```

FIGURE 3, page 4 of 122

14201 AATTATAGTA CTAAGGATAC ATTTTCCATC CTTTTTTGAA CCTAACAATT
14251 TAAACATTAA TAGATTTATC TTACTGTCTT ATAACATGAT TTTTTGCATA
14301 TTACAACCTT TAGGCTACTT TTATTATTGC ACATTCATTT TTAATGGTTT
14351 CATAAAAGCC CACTGTACAT ATGTACCCTA ATTTATTTAA GCTGTCTCCT
14401 TTTATGGGAT ATCTAGTTTA TTTCCCTTTT TTTCTTAAAA ACAGTGCTGT
14451 GATATTTCTC TCAATAAAAT TTTAATCATT TGTACATATT TTGTTGTGAT
14501 TTTAAGGGAA CTATAAACCC AGTAGAACAA TTTCCAATGA AATTGAATAA
14551 AATTTCTAGT ATGTGCAGAA CTTGAGATAA CTTGTTTAAT GTGAGTTCTG
14601 ACATTGACTT GCTGTGTAAC CTTGAAAAGC TTTTATATCC AGTTTAGTTT
14651 CCAGATGTAT AATATGGGGT GCTAATACCT GATTCTCAAA CTTATTAGAA
14701 CAGGCAAGTG CCATTATTTG TATGAAAGAG CTTTGAAAAA TCAAACATGC
14751 TAGGCAAACG CAGGGTAATA TAATTAACCA GGCTTCTTAT CTATTAGCAT
14801 AAATGCACAT AAGTAAAATG TAACTAATTA ATTTTTAGTG TTTTCCTAGG
14851 AAGGTGTTCA TTACCCATAA ATGAATCTAT TTTATGGATA GGGAAAATTG
14901 AAATCTTAAG GCTAAGTTTA TCCAAGATCT AAATATATAG CTATGCTAAG
14951 TCTGAAAGCA TTTCTTTTCA TTTATGATTC AATCCATGAA AATGGACGAA
15001 ATATGTGGAT CATAAGAGTT TCTTTGGCTT AAGAAATTAT TGTTTATAGA
15051 AATAAGGGGG AAAGCCCATT TGAGCAGTAA GCAGTCAGGA CTGTTTGTGG
15101 CAAGTGACAG AAACCCAACT AACTGGATAG TTTTAACTTC AGGTATAGCC
15151 AAATTCAAGG GCTTGATTGA TGTCATCAGG ACTGAGACAT GCCCTCTAGA
15201 TTTTTATGCT TAGCTTTTCT CTAAACTGGC TTTACTCTCA GGCATAGATA
15251 TGTCATATAT CAGATCCCAG CACTGGCAGC CTTCACCTGC CCAGCTACAA
15301 GTCCAGTGGA AAGGAAACTT CTCTTTTCTC ATCAGTTCCA CAAAAGTCCT
15351 GGGCCTGATG TCATTGGATA AAACTTAGGA CACATGCTCA TTTCTGAATA
15401 TGACACAGTG GCCAGGATAT TGTAGTCTTT TGCTTGACAT GGGCCTAGTG
15451 AAATCATCAT TTTTAGAGCT TGGGGTAGTG AGAAGAACCA AAAGATTGTG
15501 GATTTAAGCC AGCCCACCAA AACCATACGG ACATGGGGGA GGAATAATTC
15551 CCTCAAAGGG AATCAGGATG CTATTACCAA AAGAATGGAG ATTGAATGCT
15601 TGAGAGGCAA AATAGATATA TATATATATT TTTGTCTATT AAGCATATAT
15651 ATATATACAC TATCTATATA TAGATGTAAA TGTATTTATT GTCTATTTTA
15701 TGTATTTATT GTAAATAAAT ACATTTACTC TCTCTATATA TATATTCTAT
15751 CTATATATAG ATGTCCCCCA TTGCACATCT TTTCAGAAAA GAAAATTCAG
15801 ACAGGCTGGA GCTGAACCAA TGCAGACAAA AAGTCAACAT GCTAAAGTCA
15851 GAAGAGCCAC CAATGAGACA AGCACATACA AGGGATTCTG GTGGGTAAGT
15901 CAAGATCAGA AGTCAGGACA GGCAAAAGGT CTGAAATTCA GGCTTCTCAG
15951 TTAATCAAAG CTGTAGGGGT CTTTGGTAAT CCTTGTCCAG CCACGAGCAA
16001 ACCTGTGTTC ACAGAACAGT TAGAAAGTGC TAGCCATTCA CCCACATAGA
16051 AGCGACTGGG AGGTGGTCTC TCCAGGCCAC TCTGATAATA AGTTGAGGTT
16101 GTCGGCTGTA AAATGTTTGG TGATCCTGAG GCACCAATAC TCTGTCCCAG
16151 TGACCAGGAC ATTTCCTGCT CTACTCAAAC ACTCAAGCTA TTGTGCACAA
16201 ACTCTTTAAC AGTCCCAGTT GGAATCTTGG CTGCAAATCT GATGAGCCCA
16251 CACCACCAGA TGGTAGGTTC TCCTAATTGG TTCCATCCCC TCTAGTTTTT
16301 CGCAGGAACG AAACCTTCCC TATACCTGAA GAGGGGACAG GGAGAGCCAG
16351 GATCAAATGA AGGAGGCTTT AACCTCTGTT AAACAAGCAG AGATCTCAAG
16401 CTGGCTCCTG TCCAAGGCAA ACAGGGCAGT ATGGTTCTTT TACATAGGTC
16451 ATGGATTTAC AGGGGACTGA TATCCTAAGA CTAACACTGA TGAGGCACAA
16501 GACTGTAATG ATTGAAAAGT GGTTTAGCTA CAAAGGTCAA CTGATTTGGG
16551 GGAAGGTGCA CTTGTTTATT CAATAATTGA TATTTGTGGA GCATCGTGGT
16601 AGATGAGATT ATTATTTGGC AATTATTTCT CTCTCCCTCA AACTCCTTGG
16651 GAAAAAAATA TAACTTCCTG CTTCATTAAT GTCACATTTG GTCATTTGAC
16701 ATGCTCTGGC AACTTAGATA TTAGTAGATA TGTTTGAAGC AGAGATTATG
16751 AGAAGAACAT GCCCCAGAGA GCCTGCTCGT CTCATAGGAA AGGTAAATAC
16801 AGTAAGTAGA AGTGTCCCAG TCAACCCACA GCCCACAGAC TAAAGTTTGA
16851 AGCAGAGCTA TCCCAGCTGA CCTGAAAATC TGTGAGCATT GTAGGAAATG
16901 CTCAATGTTA TATACCACTG AAATTGGAAA TGGTTTGTTT TGCAGCAATA
16951 GCTGGCCAAT AGAAGCAACC AGCGTGTGTT CCACACTTTG CTAGGCACTG
17001 AGGGAACATT GGAAATGACA GACATAGTCC TGGTCTCCAT GGAGCACTAT
17051 TGTAGCTAGG AAGATAGACA ATGAATACAT TTACAAATAA AATATATATA
17101 GAGAGATCAT TACTAGGGTC ATAAAGAAAA TAGGATGTAG TGACATCACC
17151 ACTATGGTAG AGAAGAACAC CTTTAAAGTA AGTGGTCAAA GAAGGCATTT
17201 CAAAGGAGGT GACTTCTGAG CTCAGATATA AAAGTTGGAA GAGAGCCAAA
17251 TGAGAGTAAA TTCCCCTGTG GAATGTCGAA ATCCAGCCCC ATGGGCAACT
17301 TGGATTGAGA ATCTTGGTCT AGGCAGAGGA GAATGAGGTG CCCTGGAAAA
17351 ATCTCCTGCA AACTAGGTCA CTCACTTGTC TTAGGGCAGA TACTAGCTTC
17401 TCTCTACCAC ATCACATGTG CAAGTCAAGG GCTGGCAGAT CACTTGCTGC
17451 CAAGACTAGA TGGTCTCAGG CATTGGAAGC CACTGAGCAT AGCAAGGCAG
17501 AGAGGGGGAG GTATGCTAGG GCATTCCTAA CCATGAGGTG ATGGAATTGG
17551 CTATACTTCT TGGCTTGGCT CCAGAATACT CAAGAGTTGT TGCTTATTAG
17601 GATGGCAAGA AGGGGTGTGT GTGTGTGTGT GTGTGTGTGT GTGTGTGTGT
17651 GTGTGTTCAT ACATATATTC ATTCTTTCAC AGAGGAGGAA AATGAACTAG
17701 ATGGCTTCTA GATCCCTTTC CAAGTGTGTG ATTATAAAAA GGATGCTGAG

FIGURE 3, page 5 of 122

17751 ATTTAAATTA TGTGTGAAGG AAATGTTAAA TTGAAGAACT TCATCTTAGC
17801 TCTGTGCCAA GCTCCATTTG TTAATTGAGG TGGTTAATTA GAAAGGAGTC
17851 TCCCTTGAGC AAGCAGGATA AGCTCCAGCA TCCCTAATCT ATCTGGTAAA
17901 GGCTATAGAG GTGTCACACC TACAAGGGAG AACAAAGAAC ATCTAATGCA
17951 AGCCCTCTGT TTAATCTTCA CTCCAGACAC TGAAAAGCAA GAATGTTGGG
18001 GGACAGGAAG CTCACAGCGC CCGCATGGAA TTTAGACTCC AAGTAGTTTA
18051 TTAGCTTTGG GAAAATTATT TAACTTACAC TGCACTTACT AGCTCTTCTT
18101 CCTTACTCCA AGATCACTCT GAATACTTTA AAATATGGTT GGACATGGTG
18151 GCTCACACCT GTAATCCCAG CACTTTGGGA GGCCAAGGCG GGCAGATCAC
18201 TTGAGGCCAG GAGTTCGAGA TCAGTCGGGC CAACATGGCA AAACCCTGCC
18251 TCTACTAAAA AATACAAAAA ATAGCTGGCA TGGTGGCACA CACCTGGAAT
18301 CTCAGCTACT TGGGAGGCTG AGGCACGAGA ATTACTTGAA TATGGGAGGT
18351 GGAGGTTGCA GTGAGCCAAG ATCAAGCCAC TGCACTCCAG CCTGGGAGAA
18401 AGAGTGAGAC TCCTTCTCAA AAAATAATAA TAATAAATAA ATAAAAGATG
18451 GTTTCTATGT TGATGTAATG AACCAAGTAT TCTAGGGTTA TGGAAGAATT
18501 TCTCATCAGC AAATCCAGCT ACTTATGTCT TTGTTTCTTG CAGCCTAGGG
18551 CTGATGGAAG TCTTCACACC CCTTCCAAGA ACCCCCACAA ACATTCCACC
18601 ACCCCCACAT ACCCCTGCAA GAATGAAGCT TTCTGGGGCT ATGTTCTCCT
18651 CAACACCACC ACAGGGGTCC TCTCTCACTC CTTCTGCTCC TTTTTTCTCA
18701 CTAGCGTCTA CCCTTTCCCC AGGATTCCAG CCTATACATT CTGAGTTCAA
18751 CATATCAAAA CCAGAACTTG GCATCCTTCC TGCCAAACTC ATTGCTCTTT
18801 TCTCACTTTA TTTCTGTTCA ATCATTCAGC CTTAAAATGT GGGTGTCTGG
18851 TTTCAACTTC TCCATATAAT CAATATTATG TGTTGATTTC ACCACCACTA
18901 TGACTCGAGT CTATCCCCAT TTTCTTCTTT TCCCACTGGA TTATGGCTTT
18951 TGCCTTCTGA CTGTCATCTT CATGATATAA TCCACTTACA GGTGGCGGAT
19001 CAATTTATTG AAGACTATTT CTGATCATCA AGCTTCTTGT CTCAAAAAAA
19051 TATCAGTGGC TTCCCATCTT ATTTTAAGTT CAAACTCAGA CTAAAATATG
19101 AGTCTCTCCA TAATGGGTCT CTGCCTGCCT TCCTTTTGAG ACTTACCTAA
19151 ACCCTACACT CTATGTTCCA GCCAAACTAG ACTACCTAGT GTTGCCACAA
19201 ACATGCCTCT CAGTCTTTCA CTGCTTTGGT CATACTACTG ATTCCATCTG
19251 AAATAGTCTC TACCACATTG AGCACCCACT CTCTACTAAA CCCTGGAGAT
19301 ACCGCAGAAA ACAAAACCAG CAAACTCCCT GTACCCTTGG GGTTTACGTC
19351 CTGGGAAACA AATACATATA ATGATTTCAA ATACTAGTTA AATGATACAA
19401 ACATAGCCAA ATAGAGTCAT GGGACAGAGA GTGAGCTGTA GTGCTACATT
19451 AGATGGGTGG TCAGGGAGGA CAGGCATCAC CTGAAGAGAT GATATTTTAA
19501 CTGAGCCTTG TTGCAATCCA TAGAACTTTC TGCAGTGTTG GGAGACATTC
19551 TATATCTGTG CTGTCTAATA TGTAGGCACT AGCAACATCT GCCCCTATTA
19601 CACATTAGAA ATGTAGTGAG CATGACTGAG GAACCAAATC TTTCATGTAA
19651 TTTAATTTTT ATTAATTGTA ATTTAAAAAG TCACATGTGG CTAGTGACTG
19701 TCATATTAGA CAGTGCTAAT CTAGATTCTA GAATATTTCA GACAAGAAAA
19751 AAAAAACAGT AAGCATAAAG GCTTTAAATG AGAGTGAGTG TATATTCAAA
19801 GAACAGAAAG AAGGCCAGTG GAGCTAAAGC ATGCTGAGGA AAGAGACAGG
19851 GTATTTTGTA AGTCATGATA AGGAATTGAC ATGGAGTTTA AATGCAATAA
19901 AATCACTAAT GGATTTTAAG CTTGGGAGTG TAGTGATCTG ATTTAATTTT
19951 CAAAAGATTA CTGTGGCTCC TCTGTGGAGG AAGGAGAAGT GATAAATTGA
20001 CATGAAAACA GTATGTGTCA GTCAGTTTTT GCTGCATAAC AAATAACATC
20051 AAAATCTCAG TGGTTTATAA CAAAAGCTTT TTTAAAAAAC AATCACATCT
20101 GCAGGTTGCA GGCTGCAGTC TGTAGGTCAA CCATGATTCT GATTACACTG
20151 TAGGATAGGT TAGGCTAAAC TCCAGGAGGG TTCAGGTCTG CCCGATGTGT
20201 CTTTGTTTGG GTATTGAGGG TCAAGGGGCA GCAGCTACAA AAAGACCTGC
20251 TCTCCTTTTC CAGGAGCACA AGAGGCTAAG CTTTATCATG CAAATATATT
20301 TAAAGCTTCT GCTCATGTCA TGTTCTCTAA TATTCCATTG GTTCAAGCAA
20351 GGTATGCAGC TAAACCTAAT GCTCATGGGG CAGAAAACAC ACTCTGTCTT
20401 CTAAAAGGAA TTACAAAGTC ATATGACAAA AGGCATAGAT GTGTAATTTT
20451 ATAACAATAT CCAATGTAAC ACAGAGGGGA CTGGGGAGGT TCCTACAATA
20501 GTCTGGATGA CAGATGGTGG TGGCTTGGAA AAGGTGTTAG TAGAAGAGAT
20551 GAAAGAGGTA AGATTCATAA AGTATTTTGA AGAAAGTATG CACAGGATTT
20601 AGTGAGAGAA TGAAAGTAAA GTATGGGGTA AAGAAAACAG ACCATTTTCC
20651 AAAGTGCTTC TCAGATGCTA CCACAGCCCT GTGAAGCTGC TTCTCCCTCC
20701 CTCAATTGCA GCTGATTTCC TTTTCTCTTA TCTCACTGGC TCTCTTTTTT
20751 GTGCTGCTTT TATTGGCCCA TTTCAACTTT CTACCTTCTG TTCTTGAGAG
20801 GTTTTATCTA TTGTTAAGAC TCTGAGGTTT TGAGGGCAAG AGAATAAAAT
20851 TATTTGTATT TGCAACCCAA CTGCCTAGGG AATAGGCTCA ATAAATATTT
20901 CCAGGGCAAT ACAATGGTTA AGAGCAAGGA CTTTGGAGAT ATCATCCTCA
20951 TTTTGGATCT TGTGTGATCT TTATAATTGA CTTAACCTCT CAAAGCCTTG
21001 GTTTTTATTT ATAAAGTGGC AGTAATCATA CACTCCTTTT ACAGTTGTGC
21051 AGATTGAAGG AGATCAACTT GGAAAGTGCT TAGCATAAGG CCTGGCATAG
21101 AGTAAGTACC CGATAAATGA GAGCTATTAT TGTTTGTTCA ATTTAATTGT
21151 TTGTGATGAC AAGCTTCTTT GGAAATGCCC TCCAGAGTCT TCATCAGAAA
21201 ATTCAATGTT CTTGTTGAAA TGAGGGGCAC AGAGAATAAA AACACTCTGG
21251 ATGGGATTTT GTAATTTAGT AAGGAGATCT CTAGATCTAA AGTCTCTTTG

FIGURE 3, page 6 of 122

```
21301 ATCTGAAAAT GACAGCAACA ACAAAACCCC AAAATAGAGC CACTTTGCTA
21351 CTTGTTTCCT TTTACCATCT GCCAAGATGG TTCTTTTTAG TTCTCGAGGT
21401 CTTGCTTGGA GTCAGCTGCC TTAAAATAAT AAAATAAAAT TTAAATCTGG
21451 TCCTGCACTT ATTTGGGAGC GAGAAGACAA ACTGCTTTAA CTAAATATAT
21501 AGCTAGTTGC TGCTGGAGTG AAATATAGGG CAATGTTGAC TAAAGTGTTT
21551 GAGGAATGAA CTGCTCTGGG AAAGTGAATT TTAGGATAAA ACTGAGGATT
21601 AATCAGAACC TGACTTTTTT TTTGGTAACA TTTGTAATTG AGACAGTTTC
21651 CGACATGTAC TTTTCAAGCT TTCTTGCCTT AGTGAGATGA CTTTGTTGAT
21701 CCTAGTTTAA AGTTGCCTTG ATCATAAGTA TCCTGTAAAT CCAGCGGGCA
21751 TTGTGAACAG AGATTGTCTG CGATTGCAGA TGAGAACAGA AAGGTTGGGG
21801 GTGAAATCGC TGAAAAAGAG TGCATGAAAG AGGTGAAAAG TTAACATGAT
21851 GAGTTTGGAT ATCTGCAGGA GGGTTTCTCC GGAGCTCTGC AAGATACATT
21901 TGGAAAAATA GGCTGGGTTC AGACTAGAGA AGGCTTTGAA GGTCAGGAAT
21951 AAGTATTTGA GAGACAAAAT AATATGTTTA AGTTGCATTG TTGATATTCC
22001 AAAGGTCTTG TTTATAAGCA AATAAAGGAT GATTTTATTT AGCAAGTACT
22051 AGAATAATCC TCAGCAAACA TAAAGTTACC TGACATCAAA TGATGCAGAA
22101 TATCCACATT TCTACACAAT GAACTCTACA GGGTTCATTT TTAAAGTGTT
22151 TTAGGAGCTC ATTTAGTCAG TGCTTCCCAT TAGAACTGTG ATGTTCTGAG
22201 GATATTAATA GGTTATTTGG GGAGCATTGG GGGTGATGAG GGAAGGTTGC
22251 ATGGTTATAA ATTTAGTCAT GCTGATTAAG CAAAGTATAA GGGGTGCTGT
22301 GTTTTAGGAT TTTGAAGACC CTTTAAAATG CTAATGTGTC TTGTTAATTT
22351 CTAAAAAAGA GGATACAGTA TGTATTTTCC AAACTTAGTC CCTCTGTAGC
22401 CCACAGAACA GGCGGGTCTG ATTGCTTGGT GAGTGACAGA TCAATGACCA
22451 CAACCAAGGA GTATTTTAAA AAGGGATTTT ATTACTTGCA ACAAGTAAGG
22501 ATGGCTGACA CTGAGCATAG TTCCCAAAGC AGTGCCTCCC CAAATAAAGG
22551 TGAACCCAGG GCTTTTATTG ACCTGGTTGG CTGAATCATT GTATGTAGAG
22601 GTGAAGTAAA GGCAGTGCAG GTGCAGGTGC AGTCACAGAT CATGCTTTTA
22651 TACTTGTGGC ATGTATAGGA AATGTTGAAT AAGCTCATCT CTCCATGGGG
22701 ATTTTAGTAC GTTAATAAAG GGAGTTCACC AAAGTTCATC TCCAACTCAG
22751 GCATCTCAAC CAGTTTTTGT TTTTTGGGCT TCTTCCTGGA ATTTTTTTTG
22801 AAACAAGAAC TCAAGGTGCA ACAGTTACAA GTGTGTAATT TCTCATTGTG
22851 TGTACCCAAC AATCTGGGGA CCCTGAGTTA TAACTCTTTT TGCTGAATTT
22901 GTGAATAATG TCTTGTGATG TTTAATCCTG TTTTACATAT GGTGAAACTA
22951 AGGCTGAGAG CATACACAGG GATTTATCTG CAGTCAGGTA GCAGCCAGGT
23001 CACGATGCTA ACACAGAACT TTTGACCGTC ACCCAAGGCC TCCTACTCTT
23051 CCAGGCTCCC TGTCAATTTT TGGAGCCAGT CCTCTAAACA GTTTTACCCA
23101 GAACAAGGAA TTGCCGGTGA TTTCAGAAAG AACTGGCAGA CTCGGGGGAG
23151 GCACTTGCCA AATTGGCTCA GGCTGGCCTT GCTGCCATGC TTCTTTTCCT
23201 CGTTCCTGCA AAGCCAGTTC TAGGTAACCT ACCTGCAGAT GTCTACCCTG
23251 AAATAACACC CAGCCTCTGT TACACTGCTG TTACACACAA ACAAACAAAG
23301 CAAATCTGCT GCAAAAAGAG GCAGGTTGAA ATAAATTATT TTTAGTGCAA
23351 CATATAACGT CAATGTCAAA AATACGAAAG AGGCAGGTTG CATAGGGAGG
23401 CTGAGGAGGA GATGCTGAGA TTCACTCTCG AAGGTGACAA GATAAGAGGA
23451 GGAAAGTTTG CCCTGGCCCT GAGGCAGCAA AATTAATTTT GCCCCAGGCC
23501 TTTAACTGAG GGAACCAAAT CTATTTATTA CAGAAATTAT AAAGAGATTT
23551 GGTGACTGAC CCCACTTTAC CTTGAGTGAT TGGACTTTAC ACGCAGGTAA
23601 TAGGAATAAT AGTGTCATAT TTATAGAGCA TGTTCAGGTG GTTGAGGATA
23651 TGGAAAGCCT TTCCAGTAAG GAATGGTTGG AGGCTCTGAG AAGGAAAAAC
23701 TTAGGCTTGG ATTTCATCAT CAAACTTCTA AACAAACATA TTTGGAAAGG
23751 TACTGCATTT TCTATGGCCC AAGAGGCCAA AACACAGACA AAGTGAGTAC
23801 AACATTTGGT CTGGCAGATT TTGACTCCAC ACGACAGAGC CCATTCTAAG
23851 TGTGTGGACT GGCTAGCAGT GGCGAGGGTT CCCTTTCTCT AGTCTGCAAA
23901 CCTCCCAATC AACATGGCTG TTAGAAACCT GGTCCTTTTG CAGAATTGCT
23951 TTACCACTTC TACCTTGATG ACCCAGTGCC TGTGATACCA CCGTTAGAAA
24001 GTCATCTAAT TGCGTTTAAA CTTGTTCTCT CCAGCATCCG TTGAATAGCA
24051 AAGACAAATC CTTCTGACCA TAGTTCTAAT TCTGTGGGCT GGCACTATGG
24101 ATTTAATTGT GCCCTCCCAA AATCCGTTTG TTAAAGCCCT AACCTCCAGC
24151 ATGATGGTAG TGGGTTTACC TCTCGTCATG AGGATGTCAT CCTCATAATG
24201 GATTAATACT CTATAAGAGA CACCAGAATA CTTGCTCTTT CTCTTTTTCT
24251 GTGCACATGC ACCAAAGTAA GGTCATGAGA ACACACAGCA AGATGGCGGC
24301 CATTGGCAAG TCAGGAAGAG AACCTCACCA TAGTGGCACC ATGATCTCGC
24351 ACTTCCAGTT TCCAGAACTG TGAAAAAAGA AATTTTTGTT GTTTAAGTCA
24401 CCATTCCATA GTATTTGGTT ATGGCATCCT GAGCTGACTA ACACCACTGG
24451 TAATTAAGGT GTTTCTTCCA TGAAAAATGA AATGATGGTC AATAGGAAGC
24501 AAACAGAAGC TTAAGCAGAA GGGCAGAAAG GAGTGCATTT GGGAACCAGA
24551 GGGAGTCCTA TAGAGACTAG ACCTGGGATT TTGACAGTTC TGCTGAGGGC
24601 TGGCCCTGTG CCCAGCCTCC TTCCACTTCT CTTCATCTCA CTAGACCAAG
24651 AAAATATGCA CATCTGTTAT CCACAAATAC TCTGAATTCC CCCGCCAACG
24701 CAGATCCCCG GGAAAACCTA ACACAAGCAG AACAGTGGAG GAGATGCACG
24751 GGGTATTTGG TGTTTCTCAG GAAAAAGGCT TGATTTTTTG ACACCCTCTA
24801 TCTTGGTCTC TTAATTTGTC CTGAGTCAGT GAGCCACAGT GAAGTCCAGA
```

24851 GAAAAAAATG GAAATAGGAG AATCGGGCTT AAACCTCAGT TTTGTCGCTG
24901 ATTAACCTGT GATCTTGGGC AACCCACTGA TCTGTTCTTT GTTTCAGTTT
24951 CCCTCCATGA CCCTGAGTAC TTTAATAGCC TCTATTCTCC CATGTATCTC
25001 TGTTGAACAG ATCATAAAGA GTAGTGATTA TGAATCCAGA CTTTACTGTT
25051 ACTGTCAAAT ATCACATTAA TTTCCTCAGC CACTTTACAC CTGTGCAACC
25101 TGAGGCAAAA TTTTGTAATA TCTCTGTTTC AGTTTTTATA GCTGTCAAAT
25151 GGGGTTAATA ACAATCCCTA TCACAAGCAG TCTTTACAGG CATGGAATGA
25201 AAAATTGCTT GTGAAATGCT GAGTGTAAGG CCTATTATAT TCAGTAACTA
25251 TTACCTCTAT TTTGGTTCAA CACCATTTTG CAGTCTCCCC CAAACACCCT
25301 GCTGCAACAC ACCTCTAAGC CTTGGCTATG CTGGCCTAAA AAACTTCTAG
25351 ACACCCTTGA TGACCCAAAT GAAAATCTTC TGAACCCAAG GAATGCTTTC
25401 CTGGCTGTGT AGGTGGCAAG CATCACACTC TCAAGGGAGT AAAACTGTGC
25451 CTTTCTGCAA CCATTATTGC CCATAACCCA TCATGTTGTG ATGCGTTTTT
25501 TACAAGATTG TCTTTTGTTG TCTATGCTTT TGGGGTTATA TGCAAGAAAT
25551 CATTATCCAG ACCAATGTCA CATGGTTTTT CCCCTATGTT TTTCTCCAGT
25601 CGTTTTACAA TTTCAGGACT TACATTTAAG TATTTAATTC ATTTTGAGTT
25651 GATTCTTGTG TAAGGGATGA GAAAACGGTC CAATTCAATT CTTCTGCATG
25701 TGAATAGCCA GCTTTTCCGG CACCATTTAT TGAAGAGACT ATCCTTTTCC
25751 CCTTGTGTGC TCTTGGCACC TTTGTAGAAA ATCAGTTGAT CATAGACTTG
25801 TAGGTTTATT TCTCAGCTGT CTATCCTATT CCATTGGTCT ACATATCTGC
25851 TTTTATGCTA GTACCATGCT GTTTTGATTA GTATAGCTTT GCAATATATT
25901 TTGAAATCAG ATCATGTGAT GCCTGCAGCT TTGTTTTTGC TTAAAATTGC
25951 TTTGGCTGTT TGGGATTTTT TTGTAGTTCC ATACAAATTT TGGGATTTTT
26001 TTCTATTTCT GTGAAGAATG ATGTTGGAAT TTTGACAGAG ATTGCATTTA
26051 ACAAGAAAAT TAATAACCCT ATTAAAAATG GGCAAAAGAC TTGAATGGAC
26101 ATTCCTCAAA AGAAAGCATA CAATAATGGA CAACAGATAT ATAAAAAAAT
26151 GTTCCACATC ATTAATCATC AGGAAAATGC AAATTAAAAC CACAGCATAA
26201 TATCACCTCA GACCTCTTAG AATGGTATTA TCAAAAAGAT GAAAAAAAGC
26251 AAATGCTGGT AAGGATGTGA AAAGAAAAGG AAACCCTTGT ATACTGTTGG
26301 AAATCATGTA AATTATTGCC CTCAGTTTAC AAAACAATAT GAAGGTTTCT
26351 CAAAAAATTA AAAGCAGAAT TATCATGATT CAACCAATTG AATCATGGTA
26401 AACATCTAAA GTTCTGGGTA TATATCTAAA GAAATTGAAA TAAATATGTC
26451 AAAGAAATAT CTGCACTCTC ATGTTCATTG CAGCATTATT TACAATAGTT
26501 AAGATATGGA AACAACCTAA ATGCCCATCA ACAGATGCTA GGATAAAAAA
26551 ATGTGGTATT GCTACATAAT GAAATACTAC TGAGACTTTA AAAAAAGAAG
26601 AAAATTCTGT TATCTGTGAC AACATGAATA TAACTAGAGG ACATCATGCT
26651 AAGTTAAATA ATCCAACCAC AGAATGACAA ATATTGCATG ATCTCATTCA
26701 TATGTGAAAT CTAAAAGCAT CAAACTCGTA GAAGTAAAGA GTAGAATGGT
26751 GGTTGCAGAG GCTGGGGACT TGGGGCATAT GTTGGTCAAA GGGCACAAGG
26801 TTTCAGTTAG ACAGAAGGAA TAAGTTCTGG TGAGATATTG CACAACAAAG
26851 TGACTGTAGT TAATAATATA TTATGTATTT CAAAATTTCT AAAAGACTGG
26901 ATTTTAAATG TTCTCACCAC AAAGAAATGA CAAGTATGTG AGGTTATGAA
26951 TACGTTAATT AGCCTGATTT GTTCATGCCA CAATGTATAT GTCTATCAAA
27001 AGATCACACT GTAACACAGA AATAGATATT ATTTGTCAAT TAAAAACAAA
27051 TTTTTTAAAA AGGCTATTTT TCTTGCTGAA TCCCACATGT CTCTGGGGCT
27101 AGGGTAGATG TCTTTTTTAA CCAGATTGTG TCCAGCTTAG TCCGGTGTTC
27151 AATAAGCATT AAGTGTCTGA AGGGTGGTCA ATGGACAAAC AGATGAAGGG
27201 TTGCATAGAT TAATAGAAGT CTACCATATC TAGGCTGGGA GTGGTGGCTC
27251 ACACCTGTAA TCCCAGCACT TTGGGAGGCC AAGGTGGGCG GATCATGAGG
27301 TCAGGAGATT GAGACCATCC TGGCTAACAC GGTGAAACCC TGTCTCTACT
27351 AAAAATACAA AAAATCAGCC TGACGTGGTG GCGGGCGCCT GTAATCCCAG
27401 CTGCTCAGAA GGCTAAGGCA GGAGAATCAC TTGAACCTGG GAGGCAGAGA
27451 TTTCAGTGAG CCAAGATCAC ACCACTGCAC TCCAGCCTGG GCAACCGAGT
27501 GAGACTCTGT CTCAAAAAAA TAAAAATAAG AAATCTACCA TATCTACTTC
27551 TCAGGCATAA ATATGATAAC TATTTCCTTT AATTTCCCAT TGGATAAATA
27601 ACTGTTTATA AACATCTAGT TGCCAGACCC ATGCTTGGAG TCTCAGGGCT
27651 AAAAGAAATG CTCCCCATTT GCTCTATGTG CTAGTCACAT CAATCCCACT
27701 TGATCCCCAC AGCACCCTTT GGGGGAAAGA GAGTAGTTGA TAATCTGATT
27751 TTACCAATGA ACAAAGGCTC AGAAAAGACT AGTTGATCCT AAAAACACCA
27801 CACAGCATTC TAATGTTGTA AAAATACCTG GATTTGAGTC CCCTGTACAC
27851 TGATGCCTTG TGGTGTGGCA TTGGCTCAGA TGCTTCCCTC CTCTGGGATG
27901 TGGACTGGCC TCTGAGGTCT CTTTAACCTC TGGAATCATG TGAGCTGGAG
27951 CACCTGTTGG CTGGGGAGAC AAAAGGCTGC TGCGTCCAGA TCTCCCTTCA
28001 CGAGGAAGAA ATGTGTCTGC ACTTTTCATA TCAAAGCACT TGGGCAGCAT
28051 GGGGGCGTAT TGTGATGAGG CTGATGGATC CTCCCTGAAC TGGTGCCTCA
28101 GCGTTCCCAT GCCAACTGAG GGAAGGAAAA GAAAAAAAGG AAAAACAAAA
28151 ATCAAACACG AAAACTGAGC TTGATCTAGA GCTGAAGAAA AATATTCTAC
28201 TGATGGCAAC ATTCATGGCC GTATTATGAA GAAAAACAAA TTCATAAAAA
28251 CCTCAGCTTG GCCTTAATGG TTGGATCTTA AGATGAGTGA CAAATGACGA
28301 AATATTGGGT ATGAGAGAGA GGCAGGAGGT GGGAGGAGAG CAGGCCCTGC
28351 AATCAGAATC ACTTATTTGT AACATCCATT CACGAATACA TTGCCCTCAG

FIGURE 3, page 8 of 122

28401 CCACGCAGGA AACCCACACA GGCCTAGAGG ATGCTCTCTG CTTTTTTCGT
28451 GGTCCTGCCA TTCCCACCAG TACCCAGAGG CCCGAACCAG CGAGGAGAAA
28501 ACATTCACTC TTTCTCTGAA TATTCAATTG AACTTGTTTT CAGTTTCCTG
28551 ACAGCATCCA GATCCCCAGA GTGCCTGCAT GGCTTTATTT TTTCATCCAC
28601 CGCCTGCTGA CTGGTCCCTC TCTTAATACC CCTCCTCCCC CAGGGCTTGC
28651 TTCTTCCTGT TTTGTGGGGA GCAGAACATT TGAGCTTCCA GGGGTAGTAA
28701 CCACTAGTGC TGGTAAGCAC AGCTTTGGAA ATCAGGGGAG GGACCCTCAA
28751 AGAACCATGG AAAGTCCCCT GGGCCCTCAG AAAGGGAGGG ATCAAATTAA
28801 GTAAGGGAAA CAGACATGAG ATATGGGCAG ATGGGAAGCT AAGTAGCTGT
28851 GGCAGCTCCT TATAAAGAGA TCACAGCTGG AGATGCGTTC ACTAATCCCA
28901 CAGAATAATC CTCTGTTTCT CTTTCCTGAA CCCCCACATC TAGTTCATCA
28951 GCAAGTCTGT CAGTGCTAGT TACAAAATAT ATTTTGAATC CACACACTTT
29001 TTTCAAAAAA AATCTCTACC ATAACCCCGT ATCCCTCACA CTGTGATCTT
29051 TTTCCCATAT CACTACATTA ACCTCCTAAC CTGTCTTCTT GCCTCCTTCC
29101 AGACAATGTT CCACCTGGAG GCTAAAGTGA CTTTTTAAAC CTATTGAGCT
29151 GAACATTCCA TTCCTCTGCT TAAGTAAATG TAGACTCCCT TCCTTGGCCT
29201 ACAAGGCCCT CCATGAACCT GTCCCTCCCT AACCTTACCT CTTGCCCCTC
29251 TCTCATGTAA CTGGATTTCA GCCTTCCAGG CCTTCCTTCA GTTCCTTAAA
29301 CAGGCCAAGC TGCCAGGGCC TTTGCACTGG CTGTTCCCTT TGCCTGGGAT
29351 GCCGTTAAAT CTCATCATGG CTGGCTCTAG TTCACTATTC AGGTCCCAAT
29401 TCCCACGTTA CTTTCTCAGA GAGTGTTCCC TGAACACTTA ATCTAAAGTA
29451 AATTTCTAAT TGCCCTCTCT TCCAGCACTT CAACATCCTT CAAAGCATTT
29501 TTTTTAAATA GCCCACAGGT GCTACTAAAC TTTGAAGCTT TTTTTTTATA
29551 ATTAGTACCC ATTTTGCCTA CTTACTTGTA TTATCTGATG TCTTTTTTTA
29601 CCTGCTCAGT GTAAGCGCCA CAAGAAAAGG ATCTGCTTCT TGTTCCTTGT
29651 ATCCTGTGTC TAGTCTGGGG TTAGCACAGA CTAAGTGCTT AGTAGACATT
29701 TATCAAGTAA CCACATAAAT GAATGAATTT CTGAAGTGGC TATTTCTTTC
29751 TACCTGGATT TGAGCTCAGC CCTGGGGATA CAGACATGAA AAATACACAG
29801 CCACTACTCT GAAGCTGCTC ATGGCCTAAT GAGGGAAACT GAGAAGTCAG
29851 TAGTTTCAGG ATTAAAAGCC AGTAGTTTCA GGATTAAAAG TATGATAATG
29901 TATATTATTA ATCATGTGTA TACATGTACA ATAATAGTAA TAGTGGCCAA
29951 ACTTGAGCCA TTATGTGCTC AGCACTGTAC AAATATTATG CAAGTATTTT
30001 TTTTCATATA ATTGCCACAA TAAACTTATG AGTTAGTATT ATCACATTTA
30051 AACTACATAA AAATGCATTT GGCAGATGCA GAAATGGAGA TACTGCGAGG
30101 TTCAAATAAC TGGGCCATGG GGACAGTTAG TAAGTGGCTG AGTGAATTCA
30151 GCCTGGCATC GTGCTCCATG TCAGAGCCAG TGCTCTGAAG CACTAGATCA
30201 GTGATTCTCA AAAGATGACC GTCCTGGACT GGTAGAGTCA GCATCACATG
30251 GCAGCCTGTT AGAAATGCCA GTTCAAGGCC AGGCACGGTG GCTTACGCCT
30301 GTAATCCCAG CACTTTGGGA GGCCGAGGTG GGCAGATCAC AAGGTCAGGA
30351 GATCGAGACC ATCCTGGCTA ACACCGTGAA ACCCCGTCTC TACCAAAAAT
30401 ACAAAAAATT AGCCGGGCAT GATGGCACGC ACCTGTAGTC CAGCTCCTCA
30451 GGAGGCTGAG GCAGGAGAAT CGCTGGAATC GGGAGGTGGC AGCTGCAGTG
30501 AGCCAAGATC ACGCCACTGC ACTCCAGCCT GGACGACAGA GCGAGACTCC
30551 ATCTCAAAAA AAAAGGAAAG AAAAGAAATG CCAATTCGAG GGTCTCAGGC
30601 CGGACCTCCT GAATCAGAAA CTTTGGAGTT GGGGCTCAGC ACTCTGTTTT
30651 AACAGGCCCC GCAGATGATT CTGAAGATGC TCACCAAAGT TTGACAACCA
30701 CTACCTATTG AATGACTTAA TTTTATGGGA TACTAGATCA GACTAGATCA
30751 GAGTCTGAAG TTTTTCTGTA ACTCAGTTCT CATCTTAACG CTGTGAGTGT
30801 AGATTGCTCT CAATCCACGG CTGAAGAAGC CAGATTGTGA CTGAATAAAG
30851 CCAGTTACCC TGCCTGACCC TGGCTCCAGG ACCTGCAGCA TGTAAAACAT
30901 CATCCAGGAG TGCAGCCCCT GTGAAGACAG CTGACCTGAA GGGCATGGAG
30951 TCTGTGACCC CATCCACCTT GAGAAGCATG CTTCAACCAG CAAAGGAAAG
31001 ACAGTCCTAG ACAAGGAAAC ATCATCAAGT CTCTCTGTAG GAATACTTCA
31051 TATCAGACCA TATTCCCATG TGTTGAAGAT TATTATATAA TGATAATAAT
31101 TAGTACAATA GTAATACCAT ACATTTTGAT TACATTTTTG ACATTTTCAA
31151 GGCATGTTTA TATTCTAATA ATCTATTTTC CCTCTTGATA ATTTTATTTT
31201 CTCCCTTAAA AATCTCTCCA GTTACACAAA GTAGAGTAGG AGTGAAAGGA
31251 TTGTTAATCT GTTAATCTGC CTGTCCAGGG GAGAGGCAAA GTAAAGAGAT
31301 GTATCTGTGA TTTCATGGCC TGTTAGGTTC GTAGTAACAA TAGCTAATGT
31351 GTGTTAGGGA GCTTAAGTGG GCCAGGCTCT TTGCTAGATA TGTCAGTGCT
31401 TATTAATTTA ATAAAACCTC TAGATCCAAG GCTTCCAGAC TCCCAACTGG
31451 TCTCCTTCAG CAAGCAGCGT TTCTTTTCTT TCACCTCACT CTGAATTCTT
31501 CAGACTCTCT AGTCATTCAT TTATTTTATT CATTCAACTT TTATTTAGCT
31551 TATACATCCT ACAGAGAAGG TGAAGGGCAC AGAGGTGAAT GTGCTGGCCC
31601 ACAAATTGCT AGCTCTCTCA GGGGAATCCA GAACAATGCA GTGCCACCCA
31651 CAGTGGAGCC TTGAAGGACA AAGGCAAATT ATTTACCAAA TCAAAAGTTG
31701 CCAGATTCAA GATTCTCTGC AGTTCTTTGA GGTTTGAGCT TGGTGCATAA
31751 GAAGAAAGGG GGATTTTGTT CTAATGAAAG ACAGGACACA AGGGCCTACC
31801 TACAAAAATT GCTGCAATAA ATGAGGACAT CATTAAAATT GTCTTTGTGG
31851 GGGCCCATGG ATATGGAAGT GAGTAGGGAA GATGTATACA AGCAATGGAA
31901 GGAATAAAAG ACAGAAGACT TCCTAGATCT AGTGCTAGAG GCTCCATAGT

FIGURE 3, page 9 of 122

31951 TCTGTTCCTT ACAAATGCTG TAACTTTGGG CCAGCCTCCC AACCTATTCA
32001 ACCTTCTGCT TCCTTCTCCA TGAAATAAGA ACCTGGATTT CTTACTCACC
32051 TGATTCACAG GGAACCTCTG AAAATCAAAC GTAAGAATTA GTAATAGTAA
32101 TAATAACAAT ATAAATAGCT AACATCTATT GAGCAATTAT ATTTCTTACT
32151 TTCACTGGCT TATTTCATTT AATCATGAAA GCATTTCCAT GAAGCAGATA
32201 ATGTTTTAGG CCCCAGTTTA TAGATTATAA AAACAGAGGT TTAGTAAATT
32251 ACTAAGTTCA CCCACCCTTA ACAAGCAGTG GAACAAGGAT TTGAATTCAG
32301 ATCTGTCTGA TCTTTGAACC TATTACTATT AAATCACTAC CCCAGAATTC
32351 AAAAACAAAT GAGGAAAACT CTGCGAGTCA TGCTGATGAA ATGAGCGGAA
32401 TCAAAAGAGG GAACAAAAGT GAGGGCCTGG GGTCAGAGGC TGTTAGCTTG
32451 GCATGAAGGA TGGAAAGCAT TTCCAGATAC CATGTCCTGA GTGAGCACAA
32501 TGCTTAGGCT ATGCAGCAGA CCCTGGACAG TGGACCAAGG TTTAAGAGTC
32551 AGTGTGAACT TTCAGGAAGA AGAGTTTATG CAGAGTAACA CATGCCATAA
32601 ACAGAAGAAA GTATCAGGGA CCAGAGAAAC AGAGTAAGAG GCAGAGCTGG
32651 AGTCAGGCAG CTGCAGATTC CAATGGCCTC TGACTTTCTG CTGTAGCTGC
32701 AAAGGTACAT TTTATTTAAC TCCATGCCCA GCCCTGTGGC AGTCTGGGAG
32751 CCCTTTGACA GAACTACAGC TTCCACATCT GGCTCAGTGG GGAAGGAGAA
32801 ATAGATCTTC CCGGGCAAAA AGAAGCAGCT CAGTCTTGCT GCCTTCCCTT
32851 GAGTCTGGAC AGAACCATCC TCGGTGGTGA GCTTCCCAGA GCCTTTTGGG
32901 AGTGGCTCAG GGGACCAATT TGCTTCCTTG AAGAATTTTG AATAGCTTCA
32951 GATGTAGCTC TGGTGGTTGA AGCTAAGGAC AATAATGAAA ATAATATGAT
33001 AGCTGACATT CATTGAACTC TAATCAGGGG CTTGTTTTAA GGCATATTTT
33051 AGGCTCTATG CACTGTTGTG TGTCTTGCTG CTCTCATTAC ACCAAAGATA
33101 TTATAGCACA CCCACATCTC ACATTGAATC TGATTTATGT GTGAGTTGAG
33151 TGGCATTGCT GCACACTAGT TGGTGCAATG ACATGTTTTA TAGATATTTA
33201 AATATTTATT AATTTGATTT TACAGTTTGC TTTTAATATT TCAGAGTCAA
33251 TATATTTATT TTTCTGGTCA GACATACTTT TTAGGCCCAC CCTTCAAAAG
33301 ACTGTAGGAC CCAGACACTG AGTTTTCTCA TGCCACCTGG AGAAAGTGAT
33351 CCTGTAATTA TTGTGTTGGG AGCTGAGTGC TCCCACACAT TGCCTGTGGA
33401 TAAGTGTAAG ACTCTGGAAT TAAACTGCCT TAGGTTTGAA TCCTGAACCC
33451 ACTACTTTCT AGCTGTGTAA TCTTTGGCAA GTGCCATATC CTATTTGTGC
33501 CTCAGTTTTC TCATTTGCAA GATGGTTATT GTAAGGACTG AATCAGAGAA
33551 CACATAAACA GTTTAAAATA CTACCTGTAA CCTGTATCAT GGCATGTAAA
33601 GTTGTTATTA TTGATATTTA AAATGTCCCA GTGAGGTAGC CACTATAGTT
33651 ATTCCCATTT TGAAAATGAA GTCAATTTGA TGAATGGTGG AGAGGGACAT
33701 TGAACTCAGG TGGTCTGACC GTAGAGCTCA TATTCATAAT GAGTAAGAGT
33751 TTGTATCAGT CAAGTTAGGC CAGGTTATAC CACAGTAACA AATGACCCCC
33801 AAACTTCCAT GGGCTAATAT AACATGAGTT TATTTCTTGG TCATGCTGCA
33851 AGTCCAACAC AAAATGGTGG GGGAGTGGGG AGAGGCATTG CTCCTCATGC
33901 TTCCTTAGGG ACCCAAGCTG AAAGAGGGAC CATCCTAACA TGATCACAGT
33951 GTCAAAGGAA CTTATGTAAT AAGCCACACC CTGGCTCTAA AGCCTTATTC
34001 CCAAGGTCAC GGACATCATT TCCACACACA GTTCATTGGA TCAAGCAAGT
34051 TGATGGCCAG GCTTAACTTT AAAGGAGGTA GAAAAGTGAA ATCTTACCAT
34101 GTAACTGCAA AATTGGGAAT AGCCAAATGT TATCTCAGAG GAAGGTTTTG
34151 AGGATCAAAT TAATTAATCT ATGAAATTAT CAAAAATAGG GCCTAGAACA
34201 TAGAAAAATC TTCTTTAATG TTAGGTATGA ATTCTTATTA ATTAATGAAT
34251 TGCCTCTTGT AGCAGCTCTC CTGTATAAAT ATCTTCCACC TGATTCTCTT
34301 GTTCCTGATA TCTCTCTCTC TCTCTCTCTC TCTCTCTCTC TCAATGATCC
34351 ATCTTGCAGA CCTGATCCAT TTTATTATTA GACCTCTCTC TTATCATGTC
34401 ATCTCTCTTG TTCTCCCTTG TCTGATTGGG TAAGTTCAGA GTCCTAAGCA
34451 AGATATCTGA GGGCAATCCG TAATTCACTT CTAACCTACT CTGGAATTTT
34501 TTCTCCCACT TTTCTCTAAG GCTGTGTTCT AACTGGAAGG ACTCATTCAC
34551 TGTTCCCAAA TTAGACTGGC ACATTCCTAC CCCATCCCTT GATATTCTTC
34601 ATTCTTATTG TATAATCTCC CTTCTCAAAT GCCTCTTGCC TTTCTGCAAT
34651 TTTATATCCC TCATTATGCA GTTTACCACT TCCTCCAAGA AGCCTCATTT
34701 TTCACCACAG CCTGAAATGA TTTCATTCAG GGCTGAACTT CCACAGTACT
34751 ACTCATTTGG CTGAACTTTA CTACTCATTT GACCCTGAAC TCAGACTGCT
34801 TTGAACATTT TTTTTTTTAT TTATGCTTAT GTTGTTACTG TTGTGGAAAG
34851 AACACAGAGC ACAGCATCAG ACTCATATTG ATCTAAATTT CAGGTCTGTC
34901 ATTGACTGGC CTTGACACCC TGTGCAGGTC AGCCATGTTC TCGAGCTCCT
34951 TGCCCCTTTC CTGTGACATG AAAGTGATTA TACCTATTTC ATAAGAATGC
35001 TGCCAGGATA GAATTGAAAA CAAGTTATAG TGACCTACAT ATAGGAGATG
35051 ACTGTCCTCA TCATAGCTGT GTCCCTAGTA TCAAGAACAG TACCTGGCAA
35101 ATAATAGTCA GCTCAATGAC TATTTGTTGA CTGAATGAAT TATTAGTAAT
35151 CACCAGCCAC TCTTACTGCA TGCTAGTTTT CTCCAAAAGC TGTAAGTTCC
35201 TTGAAGACAG CTTTGAAAAG TAAAGTTCTT TGGAGTCTTA GGCAACGGTT
35251 CTCAAGCTTA ATTATACAGG AGAAGCAAGG AATGTTATTG AAATGCTAGT
35301 AGTTGGAATC TGGATGTACT GAATCAGAAT TCCTGGCACA GGGCCAGGCG
35351 CAGTGGCTCA CGCCTGTAAT CCCAGCACTT TGGGACGCTG AGGCAGGCAG
35401 ATCACAAGGT CAAGACATAG AGATCAGCCT GACCAACATG GTGAAATCCC
35451 TGTCTCCACT AAAAATACAA AAATTAGCTG GGCGTGGTGG GGCTCACCTG

FIGURE 3, page 10 of 122

35501 TAGTCCCAGC TACTCAGGAG GCTGAGGCAG GAGAATTGCT TGAACCTTGG
35551 AGGCGGAGGT TGCAGTGAGC CAAGGTCACG CCACTGCACT CCAGCCTGGA
35601 AACAGAGTGA GACTCAGTTT AAAAAAACAA AAAGAATTCT TGGCACAGAG
35651 TCTAAACATC TGTATGATAA CAAACTTCCC AAATGATAGA GTCTGAAGAT
35701 TATGCTTTGA GAAATCTTAT TTTGGAAGAG CTCCTCTTGA CTGGATACAA
35751 ATCTTTTCCT GGTAGGGCTT TGTAAGACAA CTCATCTATA AGGATGAATA
35801 AACTTTCTAT CCTTCTGGAC TAGCTTTCCT GCATAGCTAA CTCATTTAAT
35851 TCCAGGCTAG ATCACTTCTA AAAAATCAAT GCATTAGAAT TGAATTAATT
35901 TGTGTTCACT TAATTGATAT AGTGTGTGCT TTTCTAAATG GCACTAGGTT
35951 TGAAAGTGAA GCTGGTCACA CTTTTTTACA GTAGGCTTCT CTAATAACAC
36001 TTGATTCTGT CTTTGTACCC AGTGTCTTCT GTATAGTATT AGCTCAGGGA
36051 TTTGTACGTT GTTGGCCAAC AAACTTTGTT GATGCATTGA AAAATACAGT
36101 TTCCTAATTG CAACTCCAGT GAACCTGTAA TATAGTAAGA TCCTACAGGT
36151 CTCTGTAGGA AATATTGCTA CTGAAAGTCA AAGATCACTC ATTAAGTCCA
36201 TCTCATAGTT GATTGTAGTC CAGTGGAAAT ATTTGCTATA TTTGGCAGAA
36251 CTGTCTTTGT ATAAATAGTG AACAGATACA TTCCATCTTA GCACTGCCAG
36301 CTTAGGATCT CTTAAGGATT CGACTATTTA CTTAACTGAG GTACAGCCCA
36351 TGGGACACAC ATCACCTATT GAATTCCAGG TCTTAGCAGT TTATTAGAAC
36401 TGTAAACAAT GCTTCCATTC AAAAAAGTCA ACTCATCCAA TTGTTAAGAC
36451 GATTTATCTT TTTTCTTTCA TTTCAGCCTA GTGCAGTGAT TCTCAGCTGG
36501 GAGTGATTTT GCCCCTTTCC CTTCCTGGGG GACATGTGGC AATGTCTGGA
36551 GACACTTTTA AGTGTCACAA CTCAGGACTG GAGAACTACT ATTGACATTT
36601 AGGTAAAAGC AATGGATGTG CTAACCATCC TGTAATGCAC AGAACAAACC
36651 CCTACAACAA ATAATTATCT GGGCTAAAAT GTCAATAATG CTGAGGTTAA
36701 GAAACCTCAT TCTATTTTTT GTACTCATTA ACTATCCCCC TCAAAACATC
36751 TCATGTACCC CATAAATATA TATACCTACT ATGTACCACA AAATTAAAAA
36801 TAAAAAAGAG TATAAAATTA AAAAAAAAAA CCACCTAGTC TAGTTCTTTT
36851 TTTGGCCAAG TGCTGGGCAC TGGTTCCCTC TGCTATTTCA TTGTGTGGAA
36901 CCTGGATGGG CTACTCAGAG TGTTCCTTGT TCAGAATCAA CTTCAGCTGG
36951 CTTACTCTTA GTGGGAAGGC AAAACTTGGG AGATAAGGGT CATCTCAATT
37001 TCTCCTTTCT TTAAGCACTA GTGGTTAGCC CTGTAGCTGG AATACAAACC
37051 ACAACCCTCT CTCCTGATTC ACTATAAGAA CCTGGCTTGG ACTTCTCAAG
37101 ATAGTTTTCC CTCCTCATTT CCCTGGCTTG GTTGGAACAC ACTCCACTCA
37151 GTAAGTTGGA GAGTCTCTGT GGGTATACAA CTGGCACTTT GATTGCCGCA
37201 ACTTTGTTAT CTGTGATCAT GGTATATAAT AATCAGGATG AAAGTCAAGT
37251 TTCCTATTAG TAATTTAGCA ACAGTCACTC AACACTGTAA AAGAAAACTA
37301 CTCCTGTGGA AATTAAACAG AGTCATTTTC TTGTGGTGAA AAGGTCCTGG
37351 GTTTGCCTCA GTGGGTCTAG ATTTCAGCCT TGGCTACTAA ACTTGCTCAT
37401 GGGCCTCTGT TTCTTTATCT GTATGATGGG AATAATAATT TCTGCCCTGA
37451 TTACATTAAT GATGGAGAGG ATCTATAAGA TGGCTCCTAA GTTCTGTAAA
37501 ATGTACCGCA GTTGCTCCCC AAAAGTGAAA CTTGGGATTG GGAAAACTTC
37551 TACACAATCC CAGTCTATGA ATTAACACTT AGGAATCACT GCATTATTAT
37601 TTGAAGAAGT ATATTTATAA CTGCAGCATA TCAGCAAAAT GAGGCCAATA
37651 TAGTAAAGCA AAATGTATAT TTTAAAGGAC TCATATTCTA AGCTTATACT
37701 CTTTTTTTGT TCAAATACCT TTTCTATTAT GCAATGTTAT GGTGATAGAT
37751 TGCAGAATGT TTGGTTGTGT TTTAAAACAA CTTACATGAA AATATCAAAC
37801 ATTAACAACC TGTATCAGTC CCAGAAATGT CTTTAAATAT TTTTCTGATC
37851 TTTGAAACTG AATCCAAAGG AACTCTGCAA AGTCTCCTCA GCAGGAATGT
37901 TATCATGGAT GATACATTGT GAATAAAGTT GTGTGAATGT AAACTGGATC
37951 CATTTGGTAT GTTAAAAATA CTGTTCACAT GCTTTATTAA TTCATGCACA
38001 ATCATCTGCA GGAGGCAGAT CCTATTTGCC CGGGATCACA CTGAAACACA
38051 AAGAGGGTGA ATATGTGCAC AGGGCAGCAA AGCAAAAAGA TCAGCAGCTT
38101 TGGACTCAGG CAAAGCTGAT GTCCCTGCTG AGCTCAGCCA CTTATCAGCT
38151 TCATGACTCT ATGCTAAATT TTAAGAGCCT CAGTTTCTTC ATCTGCAAAA
38201 ATGGAAATAG TAATACTACC CCACAGGGTT GTTTGTGTGA CTAAGTGAGC
38251 CAATATAGGG AAGAGGCTAG ATAGAGAGAC TAGCACTTGG TGGGTGCTCA
38301 GGGTTGTTTG TTTCATTCAT TTAAATTATT TCCAGTATCC CCTAGTGTGT
38351 AAATAGTGAA TCTGTGACAT GGAGGCTCTT CCAAATTTAA TCCAGTGCCA
38401 TATGCCTTCG TGATGCTCAT CATAATCTTG AGAACACAAT CCTGAACTCC
38451 GCAATCTTGA ATACTGAAAT CGCAAAAATT CAAAATCCCT AAAGTCTAAA
38501 ATTTCCAATA GCTAAATTCC TGAAAAACAC AATTTTGAAA GATTAAAATT
38551 GCAAATCTTG AAATCTTGCA AATCAAATCC TGGGGAAGGG ATTAGTGTAT
38601 TTTTGGTTGT ACACAGGATA GGTGCATCGT GTTAGTTACA TCATATTAGG
38651 CACAACTCTT ATCCTGTTAT TGTCTTCATT TGGAAATTAA TTATGGTTTA
38701 AGGAGATGCA TATTGGAGCT GACAAGGGGC AGACATGTGG GCTTAATTTT
38751 AGGTGTACAC TTGACTGGAT TAAGGAATAT CTAAAACCTG GTAAAACATT
38801 ACTTTTGGTG TGTCTGTGAG TGTGTTTCCA GAGGAGTGTG TGACCTAAGT
38851 GGATTAGGCG GGGAAGATCT GCCCTCAGTG GTGGCAGGCA CCCTTCAATC
38901 AGCAGAGGGC ACAGGAAGAA CAAATACAGA AGTCAAATTG GTCTCTCTGG
38951 CAGCTGGCTG GCTTTTCTTC TACTGCACTG GACATCAGAA ATATTCCAAA
39001 AAGTGTAGTT TCACAATGTT CACTTTCTCC ATAAGCATCA TGTGTGTACA

FIGURE 3, page 11 of 122

39051 TGAAAACATG GAAACTTCCT TAATAAATGT AGAGATGTCT TTTTGTATAT
39101 CTTCGTTGGT GAAATGGAAC ATTTCTTGAG ATCTCAGTTC TGTGAGCAAT
39151 TGCAAGTGTG GTGATGACCC ATTGCAGTTC TTGATCAATT TCGTCAAAAG
39201 ATTTAGGTTG TCCATCATGT ATTTCAGATG ATTGCAGTAG TAAAGCTTAG
39251 TGCACACAAT TACCAACCAT AGTTATATAC ATTTGTAAAT TTTACTTTTT
39301 GACTTATTAC TTTATGAGTA CAGTTCATTT GCACATCTTT GTTGTAACCA
39351 TGAAACTGCC ATTAGTACAC CTGAGTGTTT ATGCTTGCGA AAATGTGTAT
39401 GTTATTATTG AATATTTTAT TGTATAGAGT GGACTATGTG TGTTCTTTGC
39451 ATTTTTATTT TTCTCAAAAC ATATAGACAT TATTTTATGT TTCTCAAATA
39501 AAAGAAACAT TGCCCTTTTA AAATGTGAAT AAATGTCTTT TAAATTTTCT
39551 TTTTATTATT TTTTCCAGAA TATGTTTTTG GGTTTTTGAT CTTTTGAGAT
39601 TTCAACATTT GGGATTATGG TGTTTGGGAT TGTGTCTTTC AGGATTATAG
39651 CCAAACCCAT TTCTTCTCTG CCTCTGAACA TCTGCAAACC CACTATTCTA
39701 GTCCTCACTT TTAAGGGTAC AGGCTCAGAG GACTAAACTG AGGTTCTCAA
39751 GCTTTTATGT GCATCAGACT CACCTGGAAA ACTTGTTAAA ACACAGCTTG
39801 CAAGGCCAAC CCCAGAATTT CTGATTTGGG AGGTCTGGTG TGAGGACAAG
39851 AATTTACATT TCTACCAAGT TCCAGGTGAT GCTGATGCTG CTGGTCCAGG
39901 GACCACCTTT TGAGAATCAC TGAGCTAAAT GTTTCTTTCT CTTTTCAGCA
39951 ACATTTCACT CCTGTGGTTC CTGACTGTTG TTGGCAGTTT TCCCACAATT
40001 TTCCAAAACT GGTCTTCATC CAGTGTCTCC TCTCATAGTA GACATCACAT
40051 TCATCCAGAA AATAAGGCAT TCTCCTATAT GCCTTCTTCT CTCTTCCTCC
40101 ACGTTCCTTC TGTCTTCAGG CATTGTCTCA CTGGTCCCTG GCCCAGTCTG
40151 TCAATCAGCT GACATCACTG CCCCCACTTG CTTTGAATCA TGCCTCCTCC
40201 CTTAATGTCT ATGTGTCCTT GCATAGGTTG GTTACCAGAG TAGATATACA
40251 AAGAATGAAT GAGTCTCCCC ATCTTTCCGA CCTCAAGAAC TTGATTAGTG
40301 GTATCCTGAC TGGAACAATG GAATATGGCC TTTTGTCTGC AAACAGAAAC
40351 AATTATAGCA GGTTTTCTCA CTAGGGTCAT GTTTGCCTAT TTTATGTTAA
40401 TAAGAGCTGT TGTATTGACT TAGCTGTCTT TATTCTAGTC ACTTCTGCTT
40451 CACAATAAGA GGCTATCTGT GCTTGCGTTC CAGGGGGTGA GTTACTGTCT
40501 TATATTGTCT GACAGGGCTG TCCCTTGAGG AATATCTTTC CCCAATGCCA
40551 GTTCTTGTAG AGGGGCCAGG AGGTCAGAAC TTAAGCTAAC AAATGATTAT
40601 CTTTCTCAGC AGAATTACCA GAGGACCTCA GACTCCTGGG TTCCTCCTTA
40651 AGGGACTCAG GTTCAGATCT TTGGCCCAGA ACACACTGTA ACCTCTGAGT
40701 TCAGGCTTTA GATGAGGCAC CTGTCAATTC CTATGGGACC TCAACCCAGT
40751 CTCAAATACT TGGTCAAAAG GTGAGTTGAA ACTTAAAACA GTACCAGCCC
40801 CTGGACAGTA TAAGTTGGTC TCATCACATC GAAGTATTCA TGATGAGCAT
40851 CATAAAATCT TCTGAGAGTT GGTTTTGATG AACAGATAAG GAAGAATACC
40901 AACACCCTAA AAGTTGAGGG CAATTCAAGT CCAGATGAGA AGAAACGTGC
40951 AGGATTGCAG ACTTGGAATC CCAAAGAGGC ACTTAGTAAT GGTTATAAAC
41001 TCTGAGGGTT ATTCGTAACT GATGCCTGGC CTTGGGGTAA ATGGATATCC
41051 TGAGGCTTTG GGCAGAACAG TTGCAAACTC CCCAACCTTC TGCTTTTCTT
41101 GGAGGTGATG TTTGTATGAA AAGAGCAGTT TTCTGGAATT CACACAATAA
41151 AATGAGCCCT CTCATTTCAG GCCCTCTGCT GGGTAATCTT GGGCAATATG
41201 CTTCCCCTCT CTGAGCCTTA TTACCCTGTT CCCTCATTTT CGAAGCAGAT
41251 TCTAACCTCC GATCTGCTTC TGTGGTGGCC TCACTGGGAT ATTCTGAAGC
41301 TCAAGTGCTG CTGCTGCTAA TAATAATAAT ACCAATTACT ATAGCAACAG
41351 CAACAACTCT AACTGTGAGC ACTTGTGCTG TGCCCAGCTC TGCGGATGGT
41401 CTCATGTGTT CCATCAGCCC GTTCTTACAG AAGTTCTGGT AGGTAGTTAC
41451 TATCATTATA CCCATCCCAT AGGCAAAAAA ACTCAGCCAC AGAAAGGTTA
41501 AATAGCTTGT CTCAGGTCAC ATAGCTAATA GTGGTAGAGT CTGTACTGGA
41551 ACCCAGCACT GTCCTGCATT TAACTGCTAT GGTACACTGC TCTGTAGATG
41601 TTAAAATTAC TTTTGGTGAA CTTTAAGTAA CTATCAATGG AAGATGATTT
41651 CTTTGCCATG CGACAGTTTG CTCTCCAAGC TTTAAGCGGA TCACCAAGGA
41701 GTCTAACTCC TCTGGCCCTG ACTGCCTCCA TCTTGGTTTC TTGCCCTGCA
41751 TGGGTTCATC TTTTCTTTGT TTCCCCTCTC TGGCATTATG AAAATGAGAA
41801 GCAGCTGTGA GCCCTGCAGA TTGCAAATGG GATTGTGAGT GTTGCTATCT
41851 CTCTAACAAC TAATTCATTA CCCAGTGGCA GATAGTTTCC GCTGTGCTGT
41901 TACAATCTAT TTGACTTCCA GGTGCCACAT GGAATAAAAA ACAATTTGTT
41951 CAACAGTTGG GCCTGGGTGT TTGCATTCAG ACAGGCATGC TTTACCTCCC
42001 TATGTCCTTG AGGGCTGCCC TCTCTGGTAA GGAGCCTTCT TTCTGGGCAG
42051 GAAAAGCTCA CTGCACAGGT GATAGACACT GAAGGATATG TCTGGACTTG
42101 GAAGTAACTT GATCTAACCA GCCATACCTT TCAGAAAATA TTCCAAAAAT
42151 AGTTACTGAA CACCTATGAT GTGCCAGTTA CTGTGCCAGG AGCTGGCTAT
42201 GCAGTGACAG TAAGATAGAC GCAAGCTCTG CTCTTAAAAT AAGCACATCT
42251 GCAGATAACT AATAGCAGTA ACTTCAGATA ATAATAAAGG TCAGGGGGAA
42301 AATAAGACTG GGTGATGTGA CAGAGAGCTG TTGGTCTGGA CAGGGACAGA
42351 GAGGGATGGT TGAAGAAGAG ATACATGAGC TAAGATGAGA ATGGTAAGTG
42401 AGAGTTGGCT GTGGGATAAT AGTGGGGAAA AATATTCTAG GCAGAGGGAA
42451 CTTCAAGTAC AAAAGTTTTT AGGTGGGTAC AAGTTGAGAT GGTTCAAGTA
42501 ATAGAAAGGA AGCCCACATG GGGGTTGGGA GGTGGTGAGC CCTAGAGGTA
42551 GAGTGCTAGG AGAGGTGGTT GTAGGGTCAG TCAGGGACAA ATGATGCAGG

FIGURE 3, page 12 of 122

```
42601 GCCTTCTAGA CCATGGGCCT TCCTGGGGAT CTTCTCTTTC AGCCCTCTAC
42651 GGGCCCAGCC AACCAAGGCA GGAACTGCCT TCTGTGTATT CATCATATCT
42701 CTGAAGTCCA ACCCCAAACC TCTCCAAGGC CAAGTCTGTG TCTTTTTCTT
42751 TCTAAATATC CTCACCCAAA TCTTACACAG TTCTTGACAC ATAGCAGATT
42801 CTCAGGATAG CCTGATGACT TCAAGGTATA AGTTAAGGAA GATATTGCAG
42851 ACCACAGATA TATTTTATTT ATAACCAAGG AAGAGCTTAT ATTTAGCAAA
42901 AGTCTGCACT TCCTCAGTAG GTACTAAGCT CCCTGTTACT AGAGGTACAT
42951 AAGCAGAAGA TGGAAGATCA GTTGGTGGGA ATGTATTGAA TAGAGGTAGT
43001 AGTCATGGTG TTTTGCAATA GAGATAGCAG TAGTGGTCAC AATGATAAAA
43051 ATAGTAATAT TCCTATGTAT TAAACAGTCA ATATATGCCA GACCCTAGAT
43101 GTATATTATC TCATTTAAGC TTCCTAAAAC AACCTCATAA GGAAATACCA
43151 TTATTATTTC CACTTCCAGT CACAGAGACT GAAACCTCTC ACATTTAAGG
43201 ACTGTGCACC TGGGGTCAGG TAGTGAGTAA GTGGTAGGGT CCACTTGAAA
43251 ACCCATACTT CCAGTCCATA CTTGAAAACC CTCTCTAGGG AAACTTAATG
43301 ATTGGAGTCC ATATTTTGAC TTCATGTATC TTGGCTTTTT ATTTCTATCC
43351 AGAGCTTTAT TGCAGGGTGT AGGGGGTGTC ACTCTTTTAC AGCCTTTACA
43401 GCCCTTTTAC ATATATTAGG TAATAATATA GAATTGAATT CTAAAATAGC
43451 TGAAAGTATG TTTTTTCCTC CAGCAAAATC ATTCCCCAAA GATCATCCCC
43501 AAACTGATGA GTATCTTGTT CCTGTGAGCA TTACTGTACT GATCTTTCTC
43551 CCGTCATGTA GTACTTTGTT ATTTGAGTCA TTTCAGCTCT TCAGGGTACT
43601 CAAGAGTAGG TGCTGTTGCC TTACACTGTT TAAGCATTCT CATAGACCTC
43651 TGAATTTCTT CAGACCTCAC ACTCACTCCT TGTTGTGATT TAATATCTGT
43701 CTTCCCAACA GGGACTCAAG CTATATCCCC AGTACCTAGC AAATGGCAAG
43751 TGGCAGACAC CCAATAGACA GGCTGAATGA ATGAATGCTA AGTTCTGTCT
43801 ATCATCTTCA TACCATGGCT GCTCCCATTT AGTTGGAACG TGTGCTCTTC
43851 AGTTTCCACA AACCCCACAG CAGTGTCTTG GACTCCTCAA CATTGAGGAT
43901 GTCATGTATG TGTCATTTAT TATTATCCTT GCTTTTGTGA CACCCACCAG
43951 GCTCACTGGA TCACATTGTC ACCCTAGCCC CTGTGGGCAT CTGGATTTGG
44001 GAACCTTAAC CTGAGGATCT TGGTAAAACC TCCTGGTGTT TCCGGTTTGG
44051 GAAGTAGGCT GTAGAGTCAA TACCTGCGGT CAAACATCAG CCCTACATCC
44101 TCACTAATTG TGTGACCTTG AGCAAGCCCC TTTACTTCAT CTAGCTAATA
44151 AAAAATAAAT AAATAAATAA AACAGTCACC TCTGCATAGG TGTATGGCAA
44201 GGACTGAGTC AAGAAATTTT TAAGAACACT TAGCCCAGGA CCTAGAAGAT
44251 TCTAGTAAGG GTTTAGTAAA TGTTAATTAT GGTTGTTAGT AACATCATCA
44301 AATTTTTAAA ATATTATCAC ACTGACTTTT TGTGAATCTA GACTTGCTAG
44351 CTCTGGTGTG CATCCAATGA TACAAACCCC CATATTCAAC ATTCCTCTTT
44401 GAAAGGTTTC ACAGAATGTT GTCTGAGCTG ACCTTAAAGA TACCTTGCAG
44451 CTCCAAAGTT CTGTGACTTT CACCAGGAGT CTCAAGGCAA ATGCACAGAA
44501 GGGTCAGGCA AGTATCGTGA ATGGAGGCTG GACCAGGGAG CCCATGCATT
44551 CTTCCAAAGG CATTTCAATT CAGTCTTGTT AAAGCACTGA GTTGCACAAA
44601 AGAAACGTCA CTGTTGGCCA GCCTCGGTTC TTCGGCTAGC TCCTTCAACC
44651 CAAGTGTATC ATCTAGGATG GAGGAGGCTT CTGAGGGACT GAGGGAGGAC
44701 AAATCTTGGA AAGAGAGGTA CAAGGAAGAG ATGGGATTTG GATAAGGCAA
44751 GGAAGAGCCA GGAGGCTTTG GATGAACTGA CCTCTAGATA CATTCATTTT
44801 TATGCCAAAA GTCCATTTCC CACTCTTTAA ACCCCTTCAC CTCTTCTCAA
44851 GAAACTTGTG TCTCAGCTTC AGAGAGCCAT GGCCTCATTT AAAATGTTGT
44901 GAAAGAAGGT GATGGAAGCA TCAGGTTCCT AGGCTGGTGA ATTTTTATTT
44951 TTATTTCTCC ATTGACACAG TTTAACCTTT GCTTTTGGCA GCTAGCATAT
45001 TGCTCAAATA AAGTGAAGAG AAGGGTGTGG GGGAGAAGGC AAGAGATATT
45051 TCGCTAGAAG GTTATGAGAA TCACAATAGC TGTCATATGA GTGCCGAGCA
45101 TTCTTCTAAG CACATCCCAT GCATAATCTC ATTTAATGCT CACAATAGTC
45151 CTCTGAAGTC TAATGTCTAT TTAGAAAAGG GAAGCTTATC TGAGGTTTAG
45201 CATAGAATAA CTCACCCATG GTCACCTATG TGAAAAAAGT GCAGAGCTAA
45251 GAATGGAATT GAAATCTGTC AAACTCCAGA GTGTAGAGAC TGACCAAGTA
45301 GACCCCCCAC TTCCAGGCCA ATGCATTTCG GCACTTGATT TGTGGCAAGG
45351 AGTCCTCTCA GGGTTTTGGG GCTATGCTGG TGCTTGCTAT GCTGCCTCGG
45401 AAATGTCACC TAACCTAGAA ATAGTGTTTA TTCTGTTACA AAGCAAGTTG
45451 GAAGAAAAGA AAACACTCCT TTTTTCTTTT TTCTGTGCCT CCTCTCCTTA
45501 CTTTCCCCTG AAACTTAAGT TCCAAGGAGT GCAATTAGCA GGTCAGCTTG
45551 TCTTGCTGAA CAGTCAGGTT ACTTTCCCTC AGTATTTGAT GCCAAGTGAA
45601 TGTTGAGCTG AAAGGCTGGC TGATAAATGC CCCTCTGGGG AGAAGGAACT
45651 GTGAAATAGC CTGGATCTAT TGGCAGATAC TAGGGCCAAA AAGTCCTTAG
45701 AAACTCAACC TGAAAAAAAT GTCTAGGGAA AGCAAAACGG CCAACTAAGG
45751 TAGTAAACAC TTCAGAAAAC CTTGATAATA GCAATTTGGA AAATCTTGCA
45801 TGTACAGTTT CATTTCATAA ACCCCTCCAG TCATGGGATG GATACAGATG
45851 TCTTGCCTGA AAATGTAACT GGTAAATTTA CAGATAATAA TGTATTGGTA
45901 GTTGCTCACA GAAAGACAGT ATCACGTTGT GGAGTAAGTG CTTGACTGAG
45951 ACTAAAAGGT CTTGGTATGA GCCTCAGGGT CATCATTACC AGCTGTGTGA
46001 CCCTGAAGAA GTCAGGCATT TTCTTGGCCA TCTATGAAGT TGGATTTTAA
46051 CTCCCCAACC CTAATCCACC AGCCATTCTT AATCAAGGAG TCAGATAAAT
46101 GTCTGGCCCC TGTGGGATTC ATTTCACTGT CTTCAGAGAA AAGGGCATAT
```

46151 TTGAAAAAGT GTATTCTACA CGGTAACCTT CTAGAGAGGC ACAGGCCTTT
46201 TTTTGTTTTG TTTTGTTTTG TTTTGTTTTG TTTTATTTTT GAGGTGGAGT
46251 CTCTGTTGCC CCAGGCTGGA GTGCAGTGGC ACAATCTTGG TTCATTATAA
46301 CTTTTACCTC CTGGGTTCAA GCAATTCTCC TGCCACAGCC TCCTGAGTAG
46351 CTCGGATTAC AGGCATGCAT CACCATGCCT GGCAAAGTTC TGTATCTTTA
46401 GTAGAGACAG GGCTTCCCCA TGTTGGCCAG GCTGGTCTTG AACTCCTGAC
46451 CTCAAGCGAT CTGCCCGTCT CGGCCTCCCA AAATGCTGGG ATTGCAGGCA
46501 TGAGCCACCG CACCCAGCCC AACACAGGCC ATTTTTAATG GGTTGTTAGG
46551 ATAAGGTGGG TAAATAGATG TGAACGTGCC ATGTAAATTT AGAATGTCAA
46601 ACACGTACAG ACTAATGCTA TTTACCCACC ATCCACCACC ATTGTTTATC
46651 CAGTTGTTTA TTCAATTGCA AATGGCTTCT TAGCCTGTTG GAGAAATGAT
46701 CTGAGGTGGT CAGAGGTATG GCCCATATCT GTCAAATAAA GCAACCTCCT
46751 GGCACATATG ATAGGCCAAA ACCCTATCAC TTGGGATTTG TGAACAACAT
46801 TCTCCAGTCA GCTGAACAAG CAGGTGCTAG AAAAGAGTGT AAATAATTCA
46851 ACTTGTTTCA GGACATGTGT TTAGGTGAGT AACGTGAATG TGAACAGTTT
46901 TTATCTTTTA TTTCTTGGTC TCAAGTTGGC ACTATTAGGC ATCCATTCCT
46951 AACATAAAAT AGTGTCTATG AATGGCAGCT GGTCATTAGA TGTACATATC
47001 CAAATCCAAG ATCAGTACAA TTTTCACCTC CACCTTGTCT TACCTCTTGC
47051 ACTCCCTAAC TCAGTGGCAG TGCCACAATC CACCTAATCA CCCAGAAAGA
47101 GACCAAGAGA CTTTTGATTC TTTTTCCCTT ATCCATGTCT TTGATCTGCC
47151 ACCAAGTTCT GGAGCTGTTA CCTCTACTGT CTCCCTCTAA TCTGTCACGC
47201 TGTCAATGGT GGCAGGAAAT ACCGACAGCA GCTCCTAACT GGCTTCTGCC
47251 ACCACTGCTT ACCCACTGCC AAATCCATCC CAATTCTTGC TGTCAGAATC
47301 GTCCTTTTAA AACAAATCAT CTACTGTGGC ACTCCTTGTT CCACACCTGG
47351 GGAAATCCAG CCTCCGTAGT GTGATATTGA AGGCTCAGCA GACTCTGACC
47401 CTGTCCCATC TCAATTGTCC TTCCACACCC CTCCCCTAAA TTATGCCACA
47451 AATTCTTGTC TGTGTTCTAA ACAATAGCCA GATTTCCCTC ATTTCCCTCC
47501 TGTTTCTGCC CTCTGACCAA ACTCAATTTG CCAGCAATGC TCTCTGGTTT
47551 TTTTCTTTCT TCATCCCTGT CTCCTCTCAA GACTTTTAAT CGTCCCTCAG
47601 GGCCAAGTTT AGATCTAACC CCTACCAATA AGCTTTCCTC AATCTCCCAC
47651 CCCTACCTCC ACAAGAATTA GCCTTCCCCC ATTATATCCC TTATCATTCT
47701 GCCGTACATT AGCAAGATTT GTATGCATGA CTGTTAGACT GACAGCTCCC
47751 TTTGGGGGAA AGGGCCTTCT TGTGCTCATC TGTCCATCTC CTTTCTCTCT
47801 TCTTCCTCTT GCCTCCTCCC TCCTAACCTC CTCCAGCCCA GCATCTAAGT
47851 GCAGTACATT TCACATAAGA GACACCCCAG CAAAGTGTGT TGAATAGAAT
47901 CCATTAATTT GCATTCCATT TCTTTGGAAA TAGCTTTTGG GATCCATTGG
47951 GCAGATAGTG AAAATTTCAA CTAACATGAT GGTGGAGAAA AACCTTAACT
48001 TTTGTGCTCA TGTTAAATTT AGAAACATTT TGTTTCATTC TATCACCTCT
48051 GCTAACCTCT TAACTAACTT GAGGTTATGG AGAAAGGGCA GAAGACTTAT
48101 TTTTCTACTT CTTTAATATT TCCGGTCAAT TCTCTCTTCT CCATCAGTAT
48151 TGCCAGTGCC TTCGTTGAGA CAGGTCATCT TTGTGGTTAA AGTTTGAAGT
48201 CCCTGAGATA AGACTATCTG GGTTTTAATA CTAGTTATGC TAACAGACAG
48251 ACCTTGGGTG AGTTAGTTAC TCTTTCTGGG CCTCAGTTTC CTCAACCATA
48301 AAATGAAAAT ATTAATGCTA CCCATTTTGT AGAGAGAGAT TCCACAGGCC
48351 TAGTTGGTGG CCAGGGAACC CTGGGATAAT AAAAGCAATC GGACATCTTG
48401 GGAACCAGGT AATCTCCTAA CATTCCAAAG ATACCTGCTG TCCCCTCTCA
48451 ACGCCATACA GTGTGTGCCA GTAGATTATA AACTGCATAA GGAAAGAGAT
48501 GATGTCTGCT CTCCTCCATA TCCCTGGCTC CTGACACATA AGAGGATCAT
48551 AAACGCACTT TGCAAAGCAA ATGCCAGCTC TGGAATTCTG CAGCAGCCTG
48601 GAGACCAGAC CCTGCACATC AAGGCCCAGT GGAAAACTAA TGATTTCTCC
48651 CCCGCAGACC TGCCTAGCGA AGGGCCCCGT GGAGCTTGGC TGGTGAGAGC
48701 ATTCTTCATT CTCCGCATGT CCCTGGCTCT CCCTCTCTCT CCCCACCTCC
48751 GCAGCCTCCC AGTCAAGCTA TTGTGCATCT CCTGCTCTCT GTGTCTCGCT
48801 GCCTGGGTCC CTTTCTGCGC TGCTGCCTAA GCATTGTCTG TGATGTCTTT
48851 AGTGTGAAAG GTGATTCACA GAAATAAATT GCATTGTGTT TTAGGTCCAT
48901 AGCAATCTAC CTCTGTAATC ATGTCTGTAA GGGACTTCAT AATAGTGTGA
48951 GGGCCTTGGT GTCAGAACCA GGGTCTCCAG TGGCTTCAAG ATAGATAAGT
49001 GCTGCAACCA AATGCACATT CAGCCAGTGA AGTTGCAAGT TAGAGGTGAA
49051 GATGGAGGTG CTGCTGCTAT GAAGCAACCA TACTCTCAGC CCTTTTATCT
49101 GCAGGTTGAT AAAAATCAAT CAAAACATGA GATGTGGTTT TTTGTTTGTT
49151 TTTAATAACC ACTGGAAAAC TAAGACTTGT TTAATAGAGT CTCAGCCAAC
49201 AGCTTGTGCT CTTACCAGCC CTGTGATTAG ACGAAAGGGA AAGTTCAAAG
49251 TGTCACCTAG AAGGGGGAGG CACCAAAGAA GAAGAGGCAG GGAGGTGATA
49301 CAGTGAAAGG CAAGGAGGAG CTGGGCTGGA ATCTGAGAAA CCTGAGACTG
49351 ATTTGTTCTA ATCATCATCC TATGTGATGG TGGAAGATAA GAACCACAGA
49401 TTCTGGAAGG AAATTGATGG CATAGACTCA ACAACAGTGG GATGAATATT
49451 TATACACAAT AAAAGGGGGG CAAGCTGGTT CTCCCAAAAT ATTTAGAAAT
49501 GATGGGAAGT AGGGGGAATT GTGCTCCCTT GATCACATTA TTCAGAAGTG
49551 ACTGCATTCT TATGGCATTT TTAACAGTTT ATTGAGATAT AATTTATATG
49601 CCATAGAGTT TACTTATTTA AAGTGTATAT CTCATGACAT TTTAAGGTGA
49651 TATATTGTTA AGTCTATGAC AAAAAGATTT AAAGGAAGCA ATGTGAAACA

FIGURE 3, page 14 of 122

49701 AAGACCACAA GATGAGTAGA GAGGCTGTCA AAGGTGGAGG GGTGTTTTTT
49751 TAATGTGTCT GCTTCCCCAG CAACTGGTAG ATCTGCCCTC ATCCCACCTC
49801 CCACCACCCA AGGTCTGGCT ATGCCTGCAG GTTCACTACA TGAAGTAAGA
49851 ATAGGTGGCT CTTAGTCAGC TCACAGGACA CTCACACAGC TAAATGCTAG
49901 GAATCCCTCT GGGAGGTCTA CTGCAATCTT GGAGGTTTAG AATTTGTTCC
49951 GCTTGAACTT TCAGATTATG AGTCCCACTG CACAGCCACC CACCCACCCT
50001 TTTTGTGTGA CACTTGCGTT AGCACAACAT GTCCCTATTT CTCCCTCTAA
50051 TTAGGTCTTT ACCAATTGAT TTAGAGGCCA TGTTCAGTTT CCATAAGCAA
50101 TCAGGTACAT CCTACAGGTG CGTTCATATG GTATCATTTG TCCTCATTCC
50151 TCTGGATGGT TATGATCCTC AAAACTACCT TACCTGTAAC CTATACTAAA
50201 ATATCTTAAT CCTAGCATGT GTAATTCCAA TGAAGTCCTT CCTCTTGAAA
50251 ACTACTCTTG GTTCTGTTCT TGAATTATTT TCTGTCAATA TCTTCCTTGG
50301 AATGACACTG GCTGGGTTTG TGAACTAATC AAACCTCATG AAGGGGTAAC
50351 TAGCTGGCCA GGGCTGAGAG AATGATTAAA TTAGGTCACT GTTTCCTAAA
50401 CACAACCCTT CTCCTATCTT CATGTATTTA TCATATCTGT GCATTTACTT
50451 ATATTTTCCT TTAACAAACA TATTTTAATT AAAGTTATTT AAAAAGGAAA
50501 CATATCAACT ATTGCAAATA GAAAAACCAG TATCACTATT AATAGGTAGA
50551 AGCTATAAAA TTAAAACAAA GCATTGTTAT TATATTCTAG CCATATGCCA
50601 TTGCATTCAT AGCGTTCTGA GCCTGATTCT TGCCTCTTTT TGTTTAAAAT
50651 AAAAGGGAAA TGGCAAGGTA TGGAGATAAA TAATTTACCA AACAGATTTT
50701 CTTTTTCACT TAATAGCAGG AATAAAAGGA AATTTAAAAT GAATGTGCAT
50751 ACGCATTGTG AGTCTGTTGT TTAATGCCAT TCTCACATTG GGAAATTCCA
50801 CTCACCATAC CTGGGTTCTA GTCTTTACTG AGCAATTAAA TTGCTATATG
50851 GCTAGCTCAC CTTCTTGTAC CTCAATTTGT ACATATGTAG AATGAGGTTG
50901 GTGAGTTGAA ATACAGAATT CCTTTAAACC CAAGTTTCTC AATGTTGCTC
50951 ACGGGCAAGC TGCACCTGAA TTTTCTGTGT AGGTATACTT GTTGAAAAAT
51001 GTTAATTTCT AAGCTCCATC CAAGATATTC TGAAAAAGAA TTTCTGGAAA
51051 TTTTTCCTGT TTTTATCATT TGTCCAGTTG ACCATGGGAT ATTATAAGAT
51101 TCAAACCATC ACCTTAAAGC CTGTATGATA AACTGAAGAG TAGAACTGAA
51151 CTGTGAATAG GAATCAAGAG GTCTCCGTTT CAGCAGCAAC TTACAGTGTA
51201 AGCTTGCGCT CAGCTAACCA CTCTCATTTC TCCATTTGAG CAGTCAGGTC
51251 ACATTCGGAA GGCTCCAAGT CCCTTCCAAT TCTACAAATA CAGTGTTGGG
51301 TTGCTTTGTT CAAAGTTTTC TCTGAAAATC TGTGCTGAGG CCAGGTGCTT
51351 GGTAAGGTTG AAGGTAGAGA TGGCCAAATG ACAGCTGTGG TCTGTGGGGT
51401 GCATTGTCCC CTCTGGAAAG CCAGCCAGTG CACGTGGAGA CGAGCCAGAG
51451 CTGCCTCTGC CTGCCTTGCC TTAACAGCAT ATATCCTCCA GCAGGGCCAG
51501 CCAGATCGGG CAAGCATCTG CAGAAAGGCT TAGCGAGATC TCTTGCAAAG
51551 TCAGCTTAGG CCCTGCTGGA GAGACAAGAA GGAAGACTTC TATGAATGCT
51601 AAGTGGGTAG AAAGGAAACT ACAGCAGGGT CTGGCTTGGA TTAACTCTTC
51651 ATATCCTGGA TGCCCTGGAT TGAGATCTGA GTCTATGACA TGTGTGTCTT
51701 TTTCAAACTG CCTCCTAATG AAACACATAT ATCCATCATC CAGAGACTAA
51751 AAACTAAGTC TCAACCTGAA CTTCATGGCC CCCCAGAGCA CTCCTAGCCT
51801 GTCCTCTCTG CCTCAACTCC CATGGTTGGC CAACTGGTTC ATTGATCAAC
51851 TGATTAATTC ATCCACCAAT TATTTTTGAG ACAACCACTC TGGGCCAGAC
51901 CCTATGTTAG TTACTGAGAA TATACTTGTG ACCAAGATGA ACAAGGTCTC
51951 TTTTCTCATG AAATTTAAGG GAAAAAATAA ACAAATAAAC GGGACAATCG
52001 CAGATGGGGG AAAGTGCTTT AGAGGGAAAG AATAAGGTAA AGCGATAAAG
52051 ACTAGCAAAG GGGAGGCCTG TCAAAAGAGG GGACATATGA GACCCAAAAA
52101 AGGAGAAAAA CCCAGTCCTA CAAATATTGT GGTAATGTTC CAGGCAAAGG
52151 GAAGAATCTA TACAAGCCTC TGAGGCAACA AAAGGCTTGA GTAGCTTTGG
52201 GAATTGAATG AACGTTGGTG TGGCTGGAGC TAAGTAAGAT AAAGTAAGAA
52251 TGATATGAGA TGATGTAGGA GAGGCAGGCA GTACCCAAAA CCTGCAGGAC
52301 CCGGGAGGTC ACAATTCCCA TTTCCAGGCT CTTCTCTTCA GCCTAACTGC
52351 AATACATTTT TTCTTGAGCA TACCTCTACT TTCCCACTGC CTTCATTTTG
52401 CATGTGCCTA ATGCTTTTGT CTGGCATAAC TTGGCCCCTA ATCACAGTAT
52451 AAGCAAATTC TTCCTCCATT CTTTCGTACC CAGCTCAAAC ATTACCTCCT
52501 TCACAGAGCT TGTCCTAAAT ACCACATTTA TGCTGAGTAG ACATGAGCTT
52551 TTCCTTCTTC TGACCACTCA ACTTCCCCTG AGCTTCATTT ACTCTTTCTC
52601 TTTTGTTCTC ATTCCCAAGA TTAACTTTCA GTCTAAAAGT TCCTTGTGGG
52651 AAGAGGAAAG GACCTAATAT TTGAAGGACA CTATTTGTGC CAGGTGACAT
52701 GCTAGGAGCT TCATATATCC CATTTCATTC ATGACTATAG TCTTGTAAAT
52751 TAGGTGTTAT TAGCCTCATT TTAGAGGTAA GAAACCAGTG TTAAATTACT
52801 TGAACTACAG CACAAAACTA CATGATGCAG GTATTAACTC TAAATTCCCT
52851 CAGTATACCT AGCATTGCCC CTTGCTCATC ATTAGTACTA ATTTCTCGAA
52901 GTGACTATAC ACTCTGGCAA CTTCTAATCC TCATTTAAGA CCAAGAAAAG
52951 GCCGGACACT GTGGCTCACG CCTGTAATCC CAGCACTTTG GGAGGTCAAA
53001 GCAGCCCCAT CAAGAGGTCA AGAGATTGAG ACCATCCTGG CCAACATAGT
53051 GAAACCCCAT CTCTACTAAA AATACAAAAA TTAGCTGGAC ATGGTGGCCC
53101 ACACCTGTAG TCTCAGCTGC TTGAGAGGCT GAGGCAGGAG AATCGCTTGA
53151 ACATGGGAGG TGGAGGTTGC AGTGAGCTGA GATCACGCCA CTGCACACCA
53201 GCCGGGTGAC AGAACGAGAT CCTGTTTCAA AAAAAAAAAA AAAAAAAAAA

FIGURE 3, page 15 of 122

53251 CAAGAAAAGT GTTGCCAGGT ATGGGGCACA TACCTAGAAC TGTGGCCATT
53301 CATCCTGCAA CTTGAACTTT GGGCATCACC TTGATCCCTG ATACCTACTT
53351 CTCTTCATCC CAATCTGCTC TGTCCTTCTG GGCCAGCCTG TTCTTCCTGA
53401 TGATAAATAA GTATTGAACC TGAGCCTATT ATACCCCAGG CCTCAGCTGA
53451 AGTGTCTATC CCAAAGTGCT TGATGTTCAG AGAGTAGCTC TAACCAAACT
53501 TTCCCCATCC AGAAGGATAT CCAAAGACAA ACTCATTGTC TATAACACCA
53551 AGAGATAGAA CCCCTATAAG TCAAACTTCT ATGCCTCCCC TACATTCTCC
53601 ACTTTGTAGA GAGATATTCA AATCCTCTCT TTTCCTGTTA ATTACTGAGC
53651 AGCTGTGGAA TCAGCATGGA TCACAATTCT GCCTTCCTTT TGAAGGAATA
53701 ACATGCAAGC AGGAGTTGCC ACATTGTGAT CATGGACTTA CTTCAGATGT
53751 ATAATAAATG ACATCCCATG AGAATGGCTT GACAGCAGCT GATGGCACTT
53801 GGCAAAGCAT TCTTTATTTG CCATAGGATG AAATTATCAC TTTACTAAGA
53851 GTAAGTGTTT ACAAGCAACT GGAGATCAGG AACTAGAGAA AATAATTCCA
53901 TGTCCCAGAT TGAAGGTTTA CAGCAGATAT ACAGTGGAGT GAACTAGCAA
53951 TCACAGAGTC TAGTCTTTGC TCTGCCATTT GCTAGCTATG AAGCCTTGGC
54001 TAACTTCATT TCATTTTCTA TGATTCATCT CATGGTACCT CCTCCTAGAA
54051 GATTTCCTTA ACCACTTCCT CTTCTCCCAG TCTGGCCAGG TGGCCCTCCT
54101 ATGTCCTTCC ATAGTGCCTT TTTTTTTCAT TTATCACATT ATATTATAAT
54151 AGTTATATAA ACACTTTCGT CTCTCACTAA ATTATGTGAG TAAAGTATAG
54201 TGATTAAGAA CAAGAATGTT ATAATCAGAC AGATATGGGT TGGAACCAGG
54251 GTTTGGCTGT CATCTAGCTA TCTGATAAAA ATACACTTCT TAGAGCATTG
54301 TTATAAGGAT TAAGCATACA TAAAGCAATT AGCATAGAGT ATGGGTCATA
54351 ACTAGTAAAT GTTTTGCCTT TTATTTTTGC CTTTATAGCC ACAGTGGCTA
54401 ACGCAATACC TAGCACACAT GGTAGGAGGG TTGGTGATGG TGATGGAGAT
54451 GTGATGGAGG TGGTGGTGAT CCTGGTGATA CCTGAGTGGA GGTAATGGTG
54501 GCAATGTTGG AATGGTGACA ATGTTGTAAT CCCAGTGGTA ATATTATAAT
54551 GGTGGCAGTT GTGGTGGTGG TGGTGATGAT GATGATAGTA ACAAATGAGG
54601 ATGATAAGAA TCAACAGCTA ACATTTGTAG AGAGTTTACT ATTGTATATA
54651 CAAGGCATGG TACTAAGTAC TTGCATATAT CTAATTTCAT CCTTTTGACT
54701 TCTTTTAGAT ATGGCCAGTA CTCCACATCT TTCAAGTGGC TGAACTGAGG
54751 TTTCAGAAGT TGAGTAATTT CCTGAGAGCC TACATTTAGT AAACTAAGAC
54801 AAAGTCAGAA TTTGATACAG GCCATATGAT GTCATCATAT ATATGTAAAG
54851 TGCTCAACTG TTGGTTACTT GAATGAGGAA GGAAAGAAGG AAGAAAGAGA
54901 AGGAGTGAGG GAGGGAGGAA TTTACTTGTT TTCTAATCTT AAGATTCCTT
54951 TTCTGAAAAT AGAGATAATT CTAGCATTTA TGGAAATCAA ATCAGATTAA
55001 AAAAAGTCAA AGCTCTTTGA AAACTGTCAA GTCTTCTCTA TGTACGAGGG
55051 CTAAACCATC AGAGGCAGCT TCATAATTAC TCATTCATTC ATTCAATAGA
55101 TATTTGGTTT TCTGTTTTAG GCACTAGAAT ATAGTGGGCA AAACAAACTA
55151 AAGTGCCTGC CCTCAGTGAG CTTTCAGTCG AGTCTAGTGA CAGACAAGCA
55201 AATGCCAGGT GAAATATATA GTCCTGTGGG AAAAAATAAA GCATGGAGGG
55251 GGTGAGGGAA TATGTGTGTA TGTTGGGGGT GGGGTCACTC TTTAAATAGG
55301 GTGGTGAGGG AAGGCCTCTG ATAAGGTGAT ATCTGAGCAG GGCCTGAAAA
55351 AGGTAAGCCA GGGAGTCACA CAGAATCTGG GAAAAAAGTG TTTTATATCC
55401 CACAGGGGAG TTTAAAAGTC AAATGAGGAA TGATATCACT GTGATAAGAA
55451 TGCTAGGAAT GGGATTATGC AGGAACCCCA AGGCCTGCTG CCAGTGACTA
55501 TGCAGTCAAG TCAGTCTTTT CCTTGGTAAC CTCCTCTGGT GGGGTCTCTG
55551 AAGGCTCAGT CAAGGTGTGA TGTCCCAGGG GAGATACTAT TATCTGAAAG
55601 CATGGTTCCT CTGGCAACAG GCAATGGGTC TGAGGGAGAT ATCTTCTATT
55651 CTCCATTCAA CCATCCATGA GCATGATGAC ACTAGGCAGG TCATCTGTGC
55701 TCATGGCATC ACCCCTTCCA GCTGGGAAAG ACAAAGGAAA GTCAGGGAGG
55751 TTCTCCCCAC ATCAAATGGA AAAGTCCTGC TCCACCAGGG TCTATAATGA
55801 AATGGTTTAT TTAAGTCTAT AATGACCTAA GATAAAGTTA ATTTACTTTA
55851 TTCAGATTTA CAGACATTAC CAAATTACAT AGGATTGCAA ACACAGGAGA
55901 AGATAAAATA AATTACCAAC CAGATTGAAG AGCTTAGAGA AATAGGTAAA
55951 TAGTCATGGG AAGAGATTTA ATTTAGATAA ACCAAAGGCA GGATATCTGG
56001 AAAATGCCAA GGTCAGGGAA AAGCCGAGAG GAAAAGATAG CTAGTAAGAT
56051 GGAAGAGACA TGGAAAGGAT TCAGAAAATG ACGTTGGTGA TAGTGAGTGT
56101 GGCCAGTATT ATGATAAAGA TAGAGGAAAT GGGAAAGATA TTACTGAAAA
56151 ATATGGCTTC TCCTTAGAAT CCCAAAATAA ATGAGGTAAT TTGTGGAAAG
56201 CAGTGCCAGA CTGGATTCTG TGGTCTTAGT TCCAAGTCTG CTAGGAACTG
56251 CCTCTGCAAC TTGGGAAAGC TTTTTGATTT TTTTCTAACC TTTAGCTTCC
56301 TCTTCTGTTA TGACATACAA TACGGTTCTA AGTCTAAATG TTTCTAGTTC
56351 TCTTGTGTTT AAGGAAGGCG CCATGTGCTC TGAGGAGACC CTGAATCCAT
56401 CCCTGGTCCT CCTGGCTGAC CTTAATAGAA ACATTGAAAG ATGGAGATTC
56451 ATGACAAGTA GTCAAACGGA AAGGCATTCA TTTTGGAGAT GGATCAAGGG
56501 TCCAGGCTCA TCGGAGACAC TGAAAAAGTT GAAAGGTTGC AAAATTGAGG
56551 GAGAACGACA GTTATGATAG TTCAGTATAA CTGGGTTTTG CCAGAGGTTG
56601 TAGAAAAAAG TTAAAGATTG ATTTGAAATG GTTGAGGGGT ATGTACAATG
56651 CAGAAGGAGG GGTGAGTTAA ATAAGACAAT TTATAGGCTG GATGTCTTCA
56701 GGGACTGGGG GGAAGTTTGG GTATCTTTAA GATGGCATGG CAGTCTGACA
56751 TACAGGAATA GTTGTATCCA CTGCAAATCA TAACCTTCTA TGCATTTCAG

FIGURE 3, page 16 of 122

56801 GGTCGGCTTA AGGATATTTG CAAAGAACAT ACTGGAGGGA GAACATCAGA
56851 CTTGTCCTAG TTGCTTGGGT CCCGGGTTAG TTCACCACTA CAGCAATGTG
56901 GGAGCTAACT GCATGCTAAG CTTGGCATGC AGGGATTGGC AAACCTTTTC
56951 TGTAAAAACC CAGATAGTAA ATGTTTTAGA TTTTGTGAGC CATACGGTCT
57001 CTGTCACAAT TACTCAACTT TGCTGCTGGA GAGTGAAGGC AGCAACTGAT
57051 TGGTCCCTCT TATAATTGAA GCTCCTGAGA TGGCATTCTC CTGAATGATA
57101 ATATTTAAAT GAAGGCCATA GCTGTATTCC AATAAAACTT TATTTACAAA
57151 CAGATAGCTG AATTTGGCCC ACACACCATA GTCGGCCAAC CCCTGTTTAA
57201 GGCATGATGG CCCTGCCTAT TAGCAAATAT GTCCTCATCA GTGTCCTGAA
57251 ACATGTTCAA TTTTATGTGT AACTCCTCCC TATTGGGAAC AAAGTGAGGG
57301 CCAACAATTC TTTTCCAGTA GGTGGTCCAA AGAATATAAT TACTGAGGCG
57351 TGTGTCACTG GAAATGCATT CCAATATAAC AAACATCTTA GGTACTTAAC
57401 TTGTTCATTG ATGTTTGAGG ATGAATTTGT AGGGGAACAT TAGATGTTCG
57451 TATGATTGAC CTATGTTGAA AGGAGACTTA CTAAGGTAGA GGCAGGTTTT
57501 CACTTTCTCC AAGAAGGAAG AGTTGAAGAA GTCCCTTCAA TCTAGAGGAA
57551 TCATCATTGT GCAAACATCA GGGAAGAGAT GGAGCAAAGT TAAATGGCTG
57601 GAAGTCACAG GGAGCTCTGT TATGGCTAGT TGTAACACAG ATTATGCACC
57651 TGGAGCTTTA CATTTTATAA AATTTTTTGG AAGTGCTTTG TTACCTTACT
57701 TATCAGAAGA TGCTAAAGTC ATTCCCATAG GTTCTCCATG AATGAAGGAA
57751 TTCAATAATT ATTACCGATG ATGATAATTT ATGCTTATTA TAATGTAATG
57801 GTCATTAGCA CAGCAGCAGC CATTCACTGA GGCACTGTGC CCAGGGCTCC
57851 ACAAGCATCA TCTCAAGTTG TTCCAACAGT CATGGGAAGC AGGTATGGGG
57901 AACGTCTTAC AGATGAAGAA ATTGAGAGTC AGGTTTGATA ATTGGCCCAA
57951 GGAAACACAG TTTATTATAA GTGCCAAAGT CAGGCCTCAA ACTCAGCTCT
58001 GCTCCCACAG CTGACACTCC TAACCAACAC ATTGTCCTAT TGCACAACTG
58051 CAGCATTCTT TCATTAGTGG GTATGTTAAT GTGAAGAACC AGCACTTGGA
58101 CCAGTGCCTT ATAAGGATCC TTTGAAACCA AGATTTTATT GTGGTTGAAG
58151 GGCAGAGAGC TAAATCACCA AAATGTGTAA GTAGAGACAG ACCAGAATGT
58201 AATCTCCATG AAAGCAATGT CCTTCTCTGT TTTTTAATTT TTTCACCATG
58251 TTATCCCTAG CACTTAGTTG TGTCTGATAA ATATTTGAAT AAATGCATCA
58301 GTATGTGAAC ATTATTTGGA ATTATTTTTT CTTTTTAATA TCAAAAATCT
58351 CATAACCACC TAGGCCAAGC TTAACCCGTG GGCCTCAGGC CGCATGCAGC
58401 CCAACACGGC TTTGAATGAG GCCCAATACA AATTTGTAAA GTTTCTTAAA
58451 ACATTTTGAG ACTTTTTGTG TGATTTTTTT TTTAGCTCAT CAGCTATTGT
58501 TAGTGTTAGT GTATGTGATG TGTGGTCCAA GACAATGCTT CTTCTTTCAA
58551 TGCAGCCCAG AGAAGCCAAA AGATTGGACA CCCCTGATCT AGCCTGTCTC
58601 AATGTCTAGG CTTTGAGACA CCCCTGATCT AGGCTATAGA AATGTCTCCT
58651 ATTTCTCTCT CTTTTAACCA CATAGTTCAA TACCCTGGAC ACAGTAGGCA
58701 CTTAAGGAAT ATTTGCTAAG GATGGGGCAT GATAGCTGAC CCTTAATAAA
58751 TAAAGTGCTA CATTGCTACA GTAATCAACA ACCTTCTACC CTTCCTAGCT
58801 CCTGTGACAG ATGCAACTAC TTCTTATTCC CCATGTGGGA GTTGTAACTC
58851 AACACTTCTC TCCCCTATTT ATGGATGCAG ATTGGAAAAT ACATTAGAAA
58901 GGGAGAAGCC AAAATATCCT CTGATTTATA ATCAGTACTT TGGTTGAAAC
58951 TTTCATGACT ATATTAGTAA TAGCTAGTTA CCTGTAACAC AGTTTAGAGC
59001 CATTAATAAA ATACCTCGTG GAACTTTTAT GTGGCTCCAT GTAGCAGAGC
59051 TCAGACCTGT GGAAGAACCT GGAGTAATTA GCTGGAAGGA TGTTATCACA
59101 GTTAGCACCA TCCAAAGAGT GAATCCACTG CAGAGTGAAC TAATGAGCCC
59151 TGGTCTGAGA GACACTGAAT CAGAGGTGAC CAGGAGTCAG GTATAGAGGG
59201 GCTATACTAG GTATAGGTCA GATATAATTA TCACTAAAGC CCCTTTAAAA
59251 TATAAACGTC CTAGATTTTT GACATACCCC ATGTCTCCAT TTATTGTGAC
59301 ATTGTCTTTT GGTAAATGAA CCCCTTCTCA TAAAAAAAAT TTTTGTTGAA
59351 ATATAATATA CATCACTTGC ATGAATTTTT ACTCCTGCTT GAGCAGGCTG
59401 AGCCTGGTTG GTAATGTTAG CAGGATCTCA GTCTATGGCA GACATACTGA
59451 CTCTTCCTTT GCTTTTAAGG TGGTGTGATT TCAACTAACA GAATTCATGT
59501 TGTATTAGAC CACATAAGCT CATGTCCTGG AAAGAGAGCC ACCTTGCCAA
59551 CCAGTTCATA AAAATTAGCT CAGCACTTTC TCGTGAGCTC CGCATGGTCC
59601 TGGGATGGCC TGAGGTGGGT CCCAGCAATA TGTATTTTTT AAAAATCTTC
59651 TCAATTGTGA AACACAGTTC TGAAATAGAA CTTCATCATT TGGGGTCTGC
59701 AAGGCGAATG GTGTTGTACC ATTGTATTCA CAAGTAAACT GAGACCCAGA
59751 GACTAAATGT CCCTGTTGTC AGAGGTACAG CAGTAGTTAG GGGCATATTT
59801 GGGACTAAAA TTCATATTAG TTTTCTCTAG ATACAGAAAT ATTTCAGTCA
59851 GGCCAATTTT TATACAAAAC TAACTTCAGG ACTGATGGTT TAGCCAGTTG
59901 TTGGTCAGTT ATATGTGTAG GTTTGTGTGT TATTGTTATA AAAAGCAGTA
59951 TCCTTTCAAA TTATATGAGG GATACATGTT TATCATGGGA AACTATAAAA
60001 TGTGAGAAAA AGGGGAATAG AATCAAAGTA TCTATCATTG CACAACTCTG
60051 AGATAACCCT CTTATTATGT TGCTATATGT CCCTTTAGAC CTGCTATTCA
60101 TATGTTGGGT TTTTTATTAT TTTCTAAGAC TGGGATTATG GTGTATGCAC
60151 AGTTTTTCAT TCTTCACTGT TATTATATTA TGAGCATCTT TCATGTTAAT
60201 AAATAGGCAT TCACACTAGC TCTTAAATAG CTATGTCGAA TTCCTTGATG
60251 TAATATATCA TAATGTGTTC AACAGAGTCT TTATTGGATG TTTAGGATGT
60301 CTGTGTATTT TAAAAACAAC AAACTTGAAT AAATACTATA CAACTTCTAA

FIGURE 3, page 17 of 122

60351 AGCTCAGAAG TGAGATATTT AGGTAGCAAA CAGCTCTGAT GAACTTAAAG
60401 AGTTAACAAT CAGCTAACCA GAAAATGAGC TCCCCCTCCT TTCAACCAGG
60451 TTAAAACCTG GTTCTTTCAA CCAGGCTGGA TAATTGAGAT GGTACACATT
60501 AATGATCCCT GTTCTCATCA TTGTTCAGTG CCAGGCATGG CCAACACTTT
60551 GAAATATTAG TAATCAGGCT CACTGAGTTT CTTTTCAGGT TTGAAACAGA
60601 GCTCTGCACA ATACATTATT ACTTGTGGAT CCTTGAGACT TCTCTGCCAC
60651 CTCCAAGAGC AGAAGCAGGG TCTTCCGAGG TTAACAGTCA CCACTGGGTT
60701 TTAATCAGGA AAAAGAAAGA AAGCCATAAA TTTAAACTCT GAAAAACTCA
60751 GTACCCACCC AGAAACAGCA ACAAAATCAG ATTGGAGTCT GGAAGAAAGG
60801 TCCTCTAGAC TTGAGAAAGT TCAGGGTGAA ATTGGGTTTA TTGTGGGTCT
60851 GAGATCAGAA AGTAAAATTC TAAAGAGCTC AAGGCAACAA CATCCAAAAA
60901 GTGGGCAAAA ATCCCCAAAG AATGGACTGT GGTATTTTCT GGGAAAGAAA
60951 ACGATTTCCC CTCCCTTTTC AAAAATTTTC CAGGAAACTA ATTGTCAGGC
61001 AACCCACTTG TAGAATGGAA GCATCTCTCA AAGTGATCTA GAAATTCCAA
61051 GAAGATTTTT TTTCTACTGT TATGATGCCC AGGGGAGATA GAAGGGTGGC
61101 TTGCAAAGTG GACTCAGGTC TGCATTCCAA AACTGCCTTC ATTCCCTTTA
61151 TGTGGGACTA AGAAAATTAT ATTATCCATC TAGGCATTTG TCCTCCATCC
61201 ATTAAATAAG AAGTAGAGAG GCGTTACAGT ACTCATCAAG AATTCCAGTT
61251 CTATCGCTTA CTATCGGTAT GAAATTGGAT CATCTCTTTA ATCTCTTTGA
61301 GTCTCAATTT CCAGTCTTTA AAATAGAGAC AAAAATATGT TCCTTAGAAG
61351 ATTGCATTGA ATATTAAAAT ACAATGAGCT ATAGAGAAAG CTTAGGCTAG
61401 GATCTGTGAC ATGGTTGGTG TTTAATAATT ACAGGATTCA GCAGGTGTTT
61451 TATTTTTTTT TCCTTTCCAG CTCCAAATTA TTCTATGTCA GGTGTTAGGG
61501 GTATATAGAT ATGCTAAGAT ATGTTCATTT CCCACCAGGG AGTCGAGTCC
61551 ACTGTGGGGT AAAGACGTGT ACACACAGCT GTCCTAGAAG ATCAAGAAGT
61601 AGAGAGCTGT GTCATGAAGG CTCTCCAGGG GTGAATGGGA GAGGCTAACA
61651 GTAGAGGCAG GCATTGGGGT GGGCTTTAAA AGATGAAAAA AAAAATTAAG
61701 GCAGGGTAGG AGCAGAAGCA CTCAGATAAG GAAAAAATGG CACAACTGGT
61751 TGGATGAATT GTTACTATTA TTGCTTGAAT GGCACAACTG GTTGGATGAA
61801 TTGTTACTAT TATTGTACCT ATTCTAATAG GTACAATTGT TAAGGTAAAG
61851 GAAAAAACCA TATTTGCAAC TAGAACCAAA TCAACTACTG CTAGAAAATT
61901 TAAAATCTTC CTTCAATATC AAGGTAGAAA AAGCTTAGCA TCTTCATTTT
61951 GCTACTAACA TTCTGACCTT GGACAAATAA CTTTACCTGT TCCTCAGCTA
62001 AAATGAGGAT GTAAATCCTA ACCTGTCTAT CTTAATAGGA TGTTGTAAGA
62051 ATTAACTGAA ATAATGTACA GTCTGCCTCA CAATCATCTG GACGGCTTGA
62101 GAAAGCACAG ATTGCCAGAT CCCACCCCCA GAGGTTCTAA TTCAGTAGGT
62151 CTGGGGTTGG ACCCAAGAAT TTATATTCTT TTTTATTATG ATGATGATTA
62201 TTATACTTTA AGTTTTAGGG TACATGTGCA CAATGTGCAG GTTAGTTACA
62251 TATGTATACA ATGAATTTAT ATTCTTAACA AGCTCTCAAG TGATGCTGAT
62301 ATAGCTGGTC TGGGGATTAC AGTAAGAAAA CCACTGCTTT AGGTCAATGC
62351 AGTTTTTTTT AAAAGCTATT ATTCATAACT GGCTCAAGAG TCATGTAAGT
62401 GTTGATTATG TTTTATTATG TGTCTAGACC CTTAATAGAC TACTCAGGAT
62451 ATGCACAAAT AGAAGATGTA ATATTTTCTG TAGCATTCCC TACACCAAAT
62501 CGGCCTTGCT CGGTCATGCA TAGTTAATGT ATGTGTTGAT TTTATTTGTC
62551 TTCGTGTGGC TTCTAGTCTC ACTAGAAAGA CATACATTTA TTTGAATGTT
62601 GTAGAATGAT ATTATTCATT GGAATAAAAT CGGATCTTTT TACAGTTTTT
62651 TTTGTTTGTT TGTTTCTTAA TGAGCAGGCC TATGATTCCT AAAGGACTTT
62701 TTATTTTATT TCATTTGAAC CTTTGATAGA AACTGCATCT TTCATGTGAC
62751 CACTCTCCAT TTTTCTGCTC ATATGACCAC ATTTCCCAGT AGTCTTTAAA
62801 GGCTCCAGTT TGGATGGGAT TTCGATTAAT GGAAGAGAAC AGATAGCTCT
62851 GTAAATAGAG CCAGATGTCT CTTGCAATAT CTGAAATGAA CTGTCTCAAC
62901 CATCAGAACT GTAAATCACC TTCAGAAGGC TCCTTCTCCC AGGAGTAGTC
62951 TTTGCATTAT TCATAGCCCT TTTGCTGTAG TACATTCTTG TCTCATGAAG
63001 ATTACAGCCA ATCACTATGC TTTCATAGCC CATCCTCCTC CCTGAACCCC
63051 TGCTTTCATG CTGTGTCATA GCCTTGGCAC TCTGTTCTTT GAACTTCTTT
63101 GAGGAGTAGT GTTTTCCAGG ACCTAGCTTC AGTTATGCCA AGAGTGTTTC
63151 CTTTCTGTGA TCATGATACA TTGTAAAGTA TGTGGTTCCT TTTTCAAAGG
63201 GAAAATACTA TAGTCACCCT AATTCCTTCA AGAAAGAAGG CAGAGAAAGC
63251 CCCCCCTCAT CCTCTCCGAA GCAGTCACAT GCTCTATTCA GAATGAATCA
63301 TCACTTTGGA ATTGTCTGCC AGTGTTTTGT GGGGTGAGGC TCAGACTCTT
63351 TCTATGGGTA GATCTGTAGG CCTGTTTTCT CTGCACCAGA GGTCCCAAAC
63401 TGGTGTTCTA TGGATTGCAT CCAGTGATTT TATGTGTAGC ATAACTTTTT
63451 AAGAGGAAGA GAGAAGAAAA TTGACTTTGC GATCAACATT ACAAAAAAAC
63501 ATCATGAGAC TTTGAATAGA AATTTGGATT TTCAGCAAAA AAAAAGAAAA
63551 AAAAAAAGAA GAAGGTTTGG CAGTACTGGA CTCCCATCTT TAAGGGTAAC
63601 AGCCGAATGC TGGCCACGTC CTGTAAGAAC CCACACTCTC CAGTTTGCTG
63651 CTGTCCATAC CAGCTTGTGT GACTCCTTTA CATTACCTGC TTGACTCCTA
63701 AAGGTATTTC AATTAGTGGC CTGTTTTTGC TCTTTTTGGC AAGTTCACAG
63751 ACTTACAGAG TTTGAAAGCT AAAGGAGTCC CTGAGAACAA GGATTTTCTA
63801 ATGTTACTTC ACATCAAAAT CACCTATACC CTATAACCAG GCTGCATCCA
63851 GTACCAATTA AATAAGAATC TCTGGGGAGG ACCAAGCTGT CAGGATTTTT

FIGURE 3, page 18 of 122

63901 TTTTTTAATT CCCCAGATGA TTCCAGTATA CAGATCAGTT CATCTAAGAA
63951 CCAGTACCTT GGAAGAATAC TACTCAGAAT TTATTGTGCA TACAAATCAC
64001 CTGGAGATTT GTTAAAATGC AGATTCTGTG GGGGCAGGGT CTAAGGTTTA
64051 GCATTTCTTA CAAGCCAATG CTTCTGGTCC CCCAATCATA TTTTGCATAG
64101 CAAAGCCTAA GAGATCTTCT GGTCTGTCCT TTTTCATAAG TTCAAAGAGA
64151 TGTCAAAATG AAGCTTTCCT TGTTAACTAT CTAAGCTTAG GATGAATTAT
64201 TTATTTATTT CTCCAGCTTT TCTTTTCCAA ACAACCTTTT TCTGTAGAAA
64251 CAGGGTCTTG CTATGTTGCC CTGGCTGGTT TCAAACTCTT GGCCTCAAGC
64301 AATACTCCCA CCTTAGCCTC CCAAAGTGCC AGGATTACAG GCATGAGTCA
64351 CTGCATCTAG CCAGAGTTTG CTTTTAAAAG CATAAATGAC AGTGGTGTCA
64401 AGGATATTCC TGTGGAAAGT AGTTTTTCCT CTTATTTACT TACATTCCAA
64451 CATTCCTTCT TAACTAAAAG AGAAAGAAGT GGGTCTTCAG CCAAAAGAAC
64501 ATTATTTCAC CCTGGTGATG CTCATGGGAT TCCCATTTTA TGATGGTAGA
64551 TGTGTTACTG GTGGTGAATC CATACAGGTC TGCAGCAACC TCAATTCTTG
64601 CCTCCTCAAA AGAAAGAATT CGAATGAGAG GCATAAGACA GAGTGAAAGA
64651 CTGAGGCAGG TTTCAGAGCA GGAGTGAATG TTTATTAAAA AGCTTTAGAA
64701 CAGGAATGAA AGAAAGTAAA GTACACTTGG AAGAGGGTTA ACGGGGAGAC
64751 TTGAGAGACC AAGTGCATGG TTTGACCTCT GACTTGGGGT TTTATGTGCT
64801 GGTGTGCTTC GGGGGTCTTA CATTACTTCT CCACTGATTC TTCCATTGGG
64851 ATGGACTGTC CATATGCACA GTGGCCTGTT AGTGCTTGTG AGGAGCCGCA
64901 TGCACAGTGT GTTTACTGAA GTTGTATCCA TGCTCACGTG AGGCATTCTT
64951 CCCTTACCAG TATTCGTAGA ACCATATGCC AGTTAAACTC CACCATTTTG
65001 CCTCTTAGTG TGCATGCTTG AGCTCATTCA CCCAGTTTCT GAGATATTGG
65051 GAAAATGCGA TCACCAGTTT CAGGTTTTTC TATCCATTGG GAAACTGCCT
65101 TTCCCTGGCA CTGGCTGCAA CCAATTATTA TTTTAGAGAG ACAGTTTAAT
65151 AATCGCCTAT CATCTGATGG TTGCCTGACA TTTCTTGTGG TGGCAGCAGG
65201 GGGGACCCTC TCCTGTCCTG CTCGTGTCTG ACTAGCTACC TACTGTAATA
65251 AATGGGGTGC AGATTAGAAA ACAGGTCCTT ACCCTCCCCC TTCCCCACCC
65301 AGTTATTGCT CAAGATCACA TAATTATGAA ATAGAAGAGC TGATACATAG
65351 AGAAAAATAG TTCCAGTTGT CTTTATAAGT GGTTCAAAAC TCTGTGAGCT
65401 TCTTTGATGG GTTGAGTTGT AAGTTATGTG GCAGCCTCTC CTTTCAGGTG
65451 AGAATGAAGC AGTCAGCCAG GTCTAATTCC CTAGTTATAT GAGTGTACTG
65501 AGTAGGTAAC TCTCTCAATA GTTTAATTTG AGGTCTGCAA TTGGAGAGTT
65551 GATGCTGAAA CATTTCTCAG GACCAGAAAT TTCCTTTCAG GCTAGCCACT
65601 TCTCTGAGCT GAAAATGCTG TCATGGTGAA TTCATTCTTC TAGATCCATG
65651 TTTTTTAAGT ATATTATCAA AGGACTATGT GTATCGGAAT CCCTTGAGAC
65701 TCTAGTTAAT GACTGTCCAC GTCCCACTCC CAGAGATTCC GAGTCAGTAA
65751 ATCTGGGGTG GGGCTCAGGA AGTGGTTTTT TGTTGTTGTT GCTGCTTTGT
65801 TTTGTTTTTG AGATGGAGTT TTACTCTGTT GCCCAGGCTG GAATGCAGTG
65851 GCGTGATCTT GGCTCACTGC AACCTCTGCC TCCCAGGTTC AAGCGATTCT
65901 CCTGCCTCAG CCTCCCAAGT AGCTGGGATT ACAGGTGCCC ACCAGCATGC
65951 CAGGCTAATT TTTATATTTT TAGTAGAGAC GGGGTTCCCC CATGTTGGCC
66001 AGGCTGGTCA CAAACTGCTG ACCTCACATG ATCTGCCCAC CTCAGCCTCC
66051 CAAAGTGCTG GAATTACAGG CATGAGCCAC TGCACCTGGC CAGGAAGTGG
66101 CATTTTTCAG AAAACTCATC CAAGTGATTT TGATGCAGGT AGTAGGCCAG
66151 ATGCAGAGAA ATATGATATA AAGGTAAATG TCCTTTCTTC CCTGTCTACT
66201 AGTATAGTGA CCATTTTCTC CTGAATCAAA TACTGCAGCC TTGAAACTAG
66251 TTAAAACCAG GGTTGTGCCA TACTTCTACT CAGCTCAGAA GGAGGCTCTC
66301 CATTTGAGAA CACATGGGTT CCTTTTGCTA CCAGGACATG CAGCTTGGAA
66351 CCTCTGATTC TCAGTGATGT AGGCATTTTC TTAGCATACA GCAGCCTGGA
66401 ATTTATCATA ATGTACATGT CACAGGAGGA TATGAAATAG AGTAAACACC
66451 TTTTTTATAG ACTTTAGATT TTGAGGTCTC ACTACAGCAG CGTTTTGCAA
66501 CTTTTTAAAA AAGAACCAAT AATGATCTCT TTGGATGTTC ATAAAAGCCT
66551 CACACTCTGC TGTCCCATAC TAGATTCTGA TATACCTAAC TTTGAAGGAT
66601 GTCCACCATT GAGTGTCACT ACATACAGGG AGCAAATTCC ATTTCATTTT
66651 TCGCGCATTC CTACCAACGA AGAGAAATTT GAGGCACATT ATTTTAGGAA
66701 ATTTGTACCA TAAAAACAAT AGGTATACAT CAATGTTTTA TCATTTATAA
66751 TGTTTCAACC TTAATATGTT TTTGACACTG CTCCTGCTGC ACTGGAGGAA
66801 TGTTGTAATA GATTGTTACA TAACCACTTC TCCTGGCAGG TATTTTCCCC
66851 CTTCCTTATT CCACTAAGAC TCACTTGCAA CGCAAAGACC AGGGCCTCAT
66901 GGAAGAAGGC AGCTGGGCAC AAGCCTGTTG CCATGGAAAG CTTAGGGCGG
66951 GAAGCGATTG ATTGGTCTCT GCATACAGAG ACTGATCTAG AAGGCTTCAG
67001 TGTGTCTGAA TGGACCTGTC TGGGCTGGAA TTTCAGTCAG TCTGACAGAC
67051 TGCTAAAGGA GACTCAGGTG TACACTTCAG CAACTTGATA ACTCTTCCCC
67101 AGCTGAAAGT CGAATCATTT GATCCAACGG GAAAGAAGCT AAAATTGTCC
67151 TGACAGCTAA AGAGCGATCT GACCTTTGTG ATCAGGAGGA GAATTTCTTG
67201 TGATACAGAA AGTGAAAGTA GAAACTGGAA TGATGGTATT GATGATGAAG
67251 GCATTTAGAG CAGCAGGCAC TGCCATTCAT TAAAAGATTG CACTGTGTCA
67301 GGCACATGCT TTATCCTATT GAACCATCAT GCCAAACTTG GGACACTTAG
67351 GTATCATTGT TTTTCATTTT CCATTAAGAA CTTGAGGATT AAAGCTGTTA
67401 ATCTATCTGT TCATGGTGAA ATGAGTAGTA TGTGGCCTGG GTTTGAACCT

FIGURE 3, page 19 of 122

67451 TTGTTATAGC TGCAATTTTT TCAGAGCTTT TAATTGTTGA ACTACACGGT
67501 GTTTCTGGGG CTATTCTTGA TCTTTGCACA GTGTGGGGGC GAAAGTTGGT
67551 CCTTTTAGGA ATTCAACTAT TCTCTCATTT AGTTATGGCC AAGAAAGGAG
67601 AGGCTCAGAG ATCAGTTGGT GCCTCAAAAG GTCGCTCTTC CCTGCAGCCG
67651 ACTTAATATG TCTCCTAGCT CCCAGTCCAG TGCTCCAGCA AGATCCGGAA
67701 GCTAAATATT CCCTGAAGCC TTTATAATCT ATTCAGAATA CACAACAGAG
67751 TTGCTGGCAG TTTTTCCAAG GCAGTAAGTC TCATTTTTCT TATTAGTTTG
67801 GATCCCCTGA ACCCTTAAGG TAGTATCTCA AATGCAGTTA AGTGTTCAAC
67851 CAATATTTGT TGCAAGAATA AACATTACTA GTAAGAAATG TGATCTTGGA
67901 GACAATATTT TATGTTCCTA GTCTCTAGTT TTCCTATTTT TGAAATAAGC
67951 AGGTGTGTTC TAGATATTTC GAAAGGCCCT TCCACTTTAA AACTTATTTA
68001 ACTCTAGAGC AAGGATCTCT CACCTGAAGT CTGAAGATTG GTCTATGTAC
68051 TCTCTGTAAC CCTACATGAA ATGCTTTAAA ACTTCATTTA CAGTTATGTG
68101 TCCATTAACA ATTGGAATAC ATTCAGAGAA ATGTGTCAGT GGACAATTTC
68151 ACCATTGCTT GAATATCACA GAGTGTTACT TACACAAATC TAAATGGTGT
68201 AGCCTACTAC ACACCTAGGC TATATTGTAT GATACAGATT ATAGCTCCTA
68251 GACTACAAAC CTGTGCAGCA TGTTACTGTA CTGAATACTG AGGCAAGTGT
68301 AACACAATGG TAAGTATTTG TGTATCTAAA TATATCTAAA CATAGTAAAG
68351 GTACAGTTAA AATATAATAT AAAAGATGAA AACTAGTACA CCTGTATAAG
68401 GCACTTACCA TGAATGGAGC TTGCAGAACT GGACGTTGCT CTGGTGAGTC
68451 AGTGAGTGAA TGATGAATGA ATGTGAAGGC CTAGGACATT ACTATGCACT
68501 ACTATAGAGT TTATAAACAC TCCACGGTTA GGCTACACTA AATTTATTTA
68551 GAAGTCTATT TTTATTTCAT TTTGTTTTTG AAATGGAGTC TCACTCTTGT
68601 CACCCAGGCT AGAGTGCAAT GGCAAGATCT TGGCTCACTG CAACCTCCAC
68651 CTCCCAGGTT CAAGCGATTC TCCTGCCTCA GCTTCCCAAG TAGCTGGGAT
68701 TACAGGCACC TGCCCCCATG TCTGGCTAAT TTCTTTAACA ATAAAGTGAA
68751 CTTGGCTTAC TGTAATTTTT TACTGTACAA ACTTTTAAAT GTTTTAACTT
68801 TTTGACTCTT TTGTAGTAAC AGCTTAAAAC ACAAACACAT TGTACAACTA
68851 TACAACTTTT TTTTCCTTAT ATCCCTATGC TATAAGCTTT TCTTTTTCTA
68901 TTTCTAACTT TTTGTTACTT TTTAAACTTT TTGGTTAGAA AATGTTTAAA
68951 GGGTAAAGAC ACAAACTAGA GAATTTATAT CTTTAAACTT TAAATGTTTA
69001 AGAAGTAAAG ATATTAAGAC ACAAACACAT GCATTAGCCT AGGCCTACAC
69051 TGGGTCAGGA TCATCAACAT CACTGTCTTT CTTCCACCTC CACAGCTTGT
69101 CCGGCTGAAA GGTCTTCAGT GGCAATAGCA CGCATGGAGC TGTCATCACC
69151 TATAATACTG CCTTCTTCTG GAATACCTCC TGAAGGACTT GCCTGAGGCT
69201 ATTTTACAGC TACCTTTTTT TATAAGTAGA AAGAGTGCAC TGTAAAATAA
69251 CAACATATAT AGTAAATGTA TAAACCAGTT ACATAACTGC TTATTATCAA
69301 GTATTATGTA CTGTACATGA CTGTATGTGT TATACTTTTA TATACAACCA
69351 CAGCACAGTA GGTTTGTTTA AGCCAGCATC ACCACAAACA CATTAGTAAT
69401 GCATTGTGCT ACATTACTAT GGCCAAGATA TCACTAAACA ATAGGAATTT
69451 TTCAGCCCCA TTATAATCTT ATGGGACCAC CGTCATATAA GCAGGTCATT
69501 GTTAACCAAA ACATCATTAT GTGGTGCGTT ACTATATTTT GGTATAATTT
69551 ACATATAGTA AAATTCACTC CTTTTATACA GTTCTATGAA TTTTGACAAA
69601 CCTATATAGT CATTTAACCA CCATTATAAT CAATATATAA AATATTTTAA
69651 TTATCCCAAA AAGGTTTTTT AAGCACATTT ATAGGCAATT TTCTCCCCTG
69701 CAACCCCAGC CTCTGGAACC ACTGATTTGT TTTCTGTTTC TATAATTTTT
69751 TTCTTTTCCA GAATGTCATC TACATGGAAT TCTGCAGGAT GTAGCCTTTG
69801 CATTCTGGCT TCTTTCACTT AGATTCATTT TGAGATCCGT TCACATTGTT
69851 GTGTGTATTA GTAGCTTGTT CCTTTTTATT GCTGAGCAAA TTTTTCATTG
69901 TATGTCTGTA CCATAATTTG TTTATTCATT CCCCAGCTGA TGAACATTTA
69951 GTCTGTATTC AATTTGGGGC ATTTATAATG AAGCTGTTAT AAATATTCAT
70001 ACATAGTTTT TTATGTGAAC ATATTGCTTA ATTTCTCTTG TGTAAATATT
70051 ATGGGGAGTG GGCTTATGGA GAATTGAGAA ATATACATTA ATGTATCTAT
70101 AATTTTTTTT CTGGGAAGAT AGTACACAGC TTTTGTCGGA TTCCCAAAAC
70151 GGGCCAGGGC TCACAAAAGG TTAGGCCCCA CTGACCTTGC TGCTTCCTCT
70201 GGTTTGTGTT GGGTTCTTTA AGCTCTGTGG TCTGGCTTTC AAGTGGAGCA
70251 TCAAACTGAG AGGCAGCCTG GCTTAGGAAA ACAGGCATTG GGTTAGGATT
70301 GAAGTGCTTC CCACCTTAGT CTAGTCTTTC ACTGTGTGAC ATTGCCAGCC
70351 TTCTTTCCCT TTCCGGGACC TTGGAAACCC TGTCCATTGG TAACCAGTTT
70401 GATGGCTAAG CTCCATTTTT CCATCATGTT TCCTAGACAA CGCCATGCAA
70451 GCTTCTGCTC CAGCCCCTTT GGAGCTCTGA TTCAGACACT AATCTCAGGC
70501 CCTCCAAGGA AGCATCATTC AGACCTTCCC TGCTTCCTGC AGAGGCACAT
70551 GTAGTACAGT ACGTGAGGCT TTCTATGGAG CTGCTCTCAT TTTTGTTCAT
70601 TAACTTCTCT CCCTGGGAGG AGGCATGCCA GGGAGGGCGT TTATCAAGAT
70651 GAGGCACATG ACAATAGGAG CACCAGATTT CCAGTCCCTG TTTTGTTATC
70701 AGAAGTTCGC TTTCCAGACT TGGGCAAATC ACTTTAATGT CTCTTGCTTA
70751 AAACCTTGAC TAGCTTTTCA ATGTTTTTGG GGACAAGGAC TCAAGGCCTT
70801 AGAGATCTTG TGATCTCTCT ACATGTGTAA TAAATATATA AACCATAATA
70851 TAGCTGCTTA TTATCAAGTA TCATGCACTG TACATGACTG TATGTGCTAT
70901 ACTTTTATAT GCAACTGGCA GCACAGTAGG TTTCTTTAAA CCAGCATCAA
70951 CACAAACACA TTAGTAATGC ATTGTGTTAC AACATTACCA TGGCAGAGAT

FIGURE 3, page 20 of 122

71001 ATTACTAGAC AATAGGAATT TTTCAGCTCT ATTATAATCT TATGGGACCA
71051 CCATCATATA AGCAGGTCAT TGTTAACCAA AACATCATTA CATGGTACAT
71101 GACTATATTT TGGTATAATT TTATACAAAA AAAAATTGCC TGACTTTTGC
71151 CTACCTACCC AGCTCCTACT TCCTTGAGTT CACTCCTTTG TGCACTCCAA
71201 CCCCACTCAC CTATCTGTTA TCCTTCTGAC ACACCCTATT GCCTCCTTCC
71251 ATTTGGCTTT ATCCTACAAA GTTTGCTGTT TACAAAGTTT ACTCTGAAAT
71301 AGAGGTCATC ATTTTGAAGA CTAGAAAACC AAGGCACAGA GACTTACATG
71351 CCTTGCCCAA GTTTGCATAG TTTGTAAATG GAAAAGCTGG GGAAAATCCA
71401 CGGAAACTTG GCTCTGGATT CCATGCTATT GACCAACTCC TGACTTCCTG
71451 CCCTGCTAGA CCTTAGTGGG TGGTCATGAA ATAAAGGATG TAGGAACAGT
71501 GTGCCAAGAG TTCTGTTGGA TTATTTTAGC TGAAATCTCA TAATGGCTTT
71551 TTATAGAATA TTAATGACTT ACAGAGCTCT TTGCTCTGGG TTATGGACTT
71601 AGGTTTCTAA ATTGTCATCT CCTTCTAGAT AACTTTTCAG GAACTTATCA
71651 GCACCCACAC AGGACTGGAT GTGCTTTTGG AAGGTACCAT GGAGGCTGAT
71701 ATGGTGTGGC TATATCAAAT CTCATCTTGA ATTGTAGCTC CCATAACCCC
71751 CACGTGTCAA GGGAGGGACC AGGTGGGAGG TAATTAAATC ATGGGTGTGT
71801 GTTTTTCCGT GCTGTCCTCG TGACAGTGAA TAAGTCTCAT GAGATCTGAT
71851 GGTTTTATAA AGGGCAGTTC CCCTGCACAT GCTTTCTTGC CTGCCACCAT
71901 GTAAGAAGTG CCTTTGCTCT TCTACCATGA TTGTGAGGCC TCCCTAGCTG
71951 TGTGCAACTG TGAGTCTACT TAACCTCTTT TTCTTTATAA ACTACTCAGT
72001 CTTGGGTGTG CTTTTATTAG CAGCATGACA ACAGACTAGT CTAATACAGA
72051 GGCTTTGGGC ATAAGCTATG GGCCTTTGGT TTTGAGGTTC TCCAATATTC
72101 AGCTGGGAAA TTATGTACCA CTAAGATGAG TTTTGGAGAA GCCTCCTTGA
72151 GAGTAATTAA ACCAGAGCAG CAAAACAATA GACTCCTACC TGTATGGAAA
72201 GGACAGAGTC ACAAGTCAAA GCTTCAGGCT GAACCTTTCT TAGCAAAGTG
72251 AGAAGGGTAG ATCTGAGACA AAGGAGCAGG GATTTTTTTT AGGTTGATTC
72301 CTGTATTTAT GTAACTTCTT TCTCCTCAAC AGTACAGGTT TCTTCATGAT
72351 ACATGTCTTC AAGACAGCAT TGGAGTAAAG GATTCTCAGT GGCCTTGTTT
72401 TATTCAATGG CATTTAGTAA ACGTGGGGAA GGGATCAAGA GTCCACATCA
72451 GATCCTGGCC CTGGAGCAGC TTTTCTAGTC GGGGGTCATG ATAGCTACAG
72501 TCTCTCTAGT ATCTTCTCTG TGCCATTTAA ATAAATAAAT CAGAGAATTG
72551 GACTCAGAAT CTGATTCTCT GATTCCGCTG AGTCAGTTCT TGGCCAGGGT
72601 CATGAAACTG GTAACTTGTA CAGCCTGGAC CCGTACTCAA GGATGTCAGA
72651 CTTGGAGTGG GGGTTGAGAG GAGGACAGTT CATGACAAGC CTGACCCAAC
72701 ATAGTGCTGT GCCCAATTAG CTAGCTACAC AGATAAGCAA ACTGAGGCTA
72751 CCACTGGGTC AGTTCTTGGC AAGGGTCAGG AAGCTGTAAC TTGTAGAGCC
72801 TGGACAAGTG TCTGTGATGT CAAACCCCGT CCATGTAACT GCTAGTTACT
72851 ATATGGGAAC TCAAGTTTAT TACTTAACTG TATTAAGCTT CCATTTTCTC
72901 TAAGAAATGG GGGAAAAAAA GCTTTTACCT TGGCTTAAAG CAGTTGCAAG
72951 AATTAAAAAG TTAATTCATG TTGTTTATTT ATCAGAATGC CTAGCACATT
73001 ATAAGTCTCA GTATAGGAGA ATTGTATTAT TCTTACCATC ATCACCATCA
73051 CCACCATTAT TTGCCAAGAG AGAGGTATAT GCAAAGTGCT ATAGTGGTTC
73101 AAAGGAGGGG GCAATCGCTT CCACCAGGAA GACAGTGGAG GGTAGTGTGA
73151 GGATAAATGT AAAACCTGAA AATTTAAACT TGAACTTGAA AGGAGACTGT
73201 GTATGTGGGA ATTTTGGATC AAAAGGGGAT TCCAATAGAA GAAACAGCTG
73251 AGTTAAAGCA AAGCGATAGA ACACTGATAA CGACTATGAA TGGTGAATAG
73301 AGCATTTTGG CTGATTGCTG TGTACCTAAA TGGAGATGAG GGTGGAAAGA
73351 TGCATTGGGG GGTAAGACTT TGAGAACCAA GTTCATTTGA GAACCAAGTT
73401 CATTTGAGAA CAACTACGAA TGGTGAATAG AGCATTTTGG CTGATTGCTG
73451 TGTACCTAAA TGGAGGTGAG GGTGGAAAGA TGCATTGGGG GATAACTATG
73501 AGAACCAAGT TAAGGGAAGT GTCATGAGCA GAGCTATGCT CCAAAAAGAT
73551 TTAGCAGGCC ATCTATACCC ATTATGTCTG GGGTGCATAT GAGGGAGTTA
73601 CAGGATGTGA GACTTGGAGT GGGGGTGGAG GGAGGGCAGT TCATGACAAG
73651 CCTGACCCAA CACACTGTTG TGTCCAATTA GCACGACCTA TTTTGGCTTT
73701 GAATGGGGAA GGAGAATCTG TGACCTCTGA GTCAGCCTTT ATGGAATGCT
73751 CAAGACTTAA CAGGTCTTGC AAGATGCATT CTCTATCAGT CATAGTACTT
73801 TAATAATGGT TCCTTACTCA GCTTCATTCA TTCATTGGAA ATTCATGCAT
73851 GTCTTTGTAG TCCATAGGAT TCTCAGAATA ACCTTGTGAC TAGACGAGAG
73901 AAATATTGAC TGTGCGATTA CTGAAGGCAA AGACTGTTTG TGATGCTTGA
73951 TTACTTGATT TTTGCATATC CAACAAGTGA ATGAGTGAGT AAGTGAGTGA
74001 GTGAGTGAAT GATTGAATCT CCACTTGACT CCTGAGGCAA CTGAGATGAG
74051 GAGATATTAA AATATCTCAA GGTGTCATTA TTGGACACAC ATATGACTAG
74101 GACTTTTGTT ACTTTCATAC TTCTCCATTT ACAATTTCTT AAAAGAGTAC
74151 TTTCCAAAGT ATATACAATT TAATGATTTG AAATCCTGCT TGCGGCCAGG
74201 CACGGTGGCT CATGCCTGTA ATCCCAGCAC TTTGGGAGGC TGAGGCGTGT
74251 GGATCACGAG ATCAAGAGAT TGAGACCATC CCGGCCAACA TGGTGAAACC
74301 CCGTCTCTAC TAAAAATAGA AAAATTAGCT GGGCATGGTG GCAGGTGCCT
74351 GTAATCCCAG CTACTTGGGA GGCTGAGGCA GAAGAATCAC TTGAACCTGG
74401 GAGGCAGAGG TTGTAGTGAG CCAAAGACTG TGCCACTGCA CCCCAGATTG
74451 GCGACAGAGC GAGACTCTGT CTCAAAAAAA AAAAAAAAAA CCTTCTTGCT
74501 TTTGTTGCTG TTTTCTTCCT AAAAGTGGAG CTTTGCCTTT TCCCTTTTAA

FIGURE 3, page 21 of 122

74551 GTCAGTCACT GAGACAGTAT TTGGTTTTGT GCCCTCTGAG AGTTATTTTC
74601 CAGCCCACGA GCCCCACGTT CTGATTCTGA TGTGAGATAA TGGAGCTTAG
74651 CCCTCAGAGA TATGGAAGAC ACCAATTGTT TCGTTCTCTA AGTGTTCAGA
74701 AACAACTGTT CTTTTCTTTT CTTCCTTTTT TACTTCCCCT TACAAGACTT
74751 TCTTTTCTTT GCCTCAAAGA GGGTAAAGGA TGGAAGATAG AAGGAGGAAC
74801 TCAGGTTAGT CTATGGCTCA GAGGCCTTGA ATAGTTTGGG AAAAAAATTA
74851 AACAACATGA AACTATAACT TCTCATTGTT CTCTGCTGCT TCCACCTCCC
74901 ACTGACAGTG TATGCTTTCC ATCAAATATG TGTAATATTG GTTGTGGAGC
74951 AGATCAAAAA CATCTATTTT CTCTGGAATG TACAGTCAGT CAATCTTGAA
75001 GAAGGAGCAT CGTATCAAAG AGGTCTGTTG TCAAATACCT ACTTCCCCCT
75051 TTCTGTCCTT TCTCTTCCCC TTCAAGGGAA ACAAATGTCT GGGTTGCAGA
75101 AAGGCCCTTT CATCTCAAAT TGTTCTCTTT TCATTAGTGT CTTGGTTTGG
75151 GCAGGGGGTA TGGAGGCAGT CTACTATGAG TAGTATTGTT GAGGACATGA
75201 AATGTTAAAT AATAAGATTT TACATTTGTA AAGTGCCATG TTCCTTGCTT
75251 TTACAGACAG AAACTTAGGC TGCTGGGTTT TGAACAATTA AGTTGAGGAG
75301 CTATTTGGGA TATGTTGTAT AAATCATAAC CGCTTGTTGA AGGGTGTGCT
75351 GAAATCAAGG TGTGACCTCT GCACAATTCA GGGACCTCCT CTTGGGCAAG
75401 TCTAGAGTCC CAGCCTTGCC AATGCTTCAG AAATGATTAG ATTCAAGGTG
75451 CCAACATCAG GCCAACTGAA CCCTTGAGAG ATTGCCCTAT AAACTGTTAT
75501 TGGAGCAGCA TCTGTTTGCC AGGGTAAATA TTCAGTCATA TGGACTGGGC
75551 CCTGGAGTCT TCAGATGGTG CAGCCCTTCC CAGAGGGAAG ACTTCATGGG
75601 GGTCCAAATG CTGGTAAGAA GTTTTTGTTT GTCTGTGTCT GCCATCACAG
75651 CATAGAGATT AAGAACCTGG TATTTGGAAT CAGACAGATT TTTGTGTATT
75701 ATTTACCTGT TGCTGCATAA CAAATTGCCC CCAAACTCGG TGACTTTCTA
75751 CAACAATCTT TGTTTATTAT CTCTTATGGA TCCCTGGGCC AAGAATTCAC
75801 ATGGAGCACA ATGGAGAAGG ATGGAAGACC TGAAAACTAA ACTGAAATCA
75851 TCTAAAGACT TATTTACTCA TGTGAGCTGT GTTGGAGCTG TCAGCTGCAA
75901 CACTTACACA AGGCCTCTGC ATTGGGCCTG AACTTCCTCA CAACATGGTG
75951 ACTGGGTCTT AAGGATTGGC CTAGATAAAG TCATGGCAGA GACCACTCAT
76001 GGAAAGCTAT GTCAACAATG GAAGATGAAT GGCCAGGATG AAGACAGAGA
76051 GAGAGAGAGT AAAGAATTCC AAAGGTTGCC ATGTTTGTCT AACCCTGCTT
76101 CACAGAACCA ACAGACAAAA TCTGTAGCCT CCTCTCCTTG TCAGATCTGT
76151 GTATTTTGTA TGGGAATGAA TATGTCAGAA AGTAGTAGCT TAGTGATAAA
76201 TTATGCAACA GCCTCTTCTT CATTCTAGGT TCACCAGTAC TGCCAAATTA
76251 ACATTACCTG AGCACCTCCT TTGCCCAAGA ATTTTTACAA GTGTAATTTC
76301 ATTTAATTCT CACAACAACC CAAAGTTATA ATTTTAATTT TCCCCCCTTT
76351 GGATTAGAAC TTAGAGGATA TGGAAACCTC TCAGTCACCC ATATATGTAA
76401 ACTACTGCTA AAAAGGTTTA TTTTAAAGAA GTGGAGCTGT TATTTACTCT
76451 CATACATTCA CCTATTTTAG TTTCAGGGAG TACTTCTATG GCGGACTTAT
76501 GTAATACCTG TGATCGTATA AGAAAGTCTT TTGGTTCAGG TATTCTTATC
76551 ACATTATCTA ACATATCTGT GAGACTTACC TTTGATCTCC CATGTCGTTA
76601 TACTTCCAAA GCCACCTTCA ACTAAAATCT ACACTAAACA AAGAAAAGTG
76651 CTTCAATAAA TCTGTGTTTC TAAGCAATTG TCACCTTTCC CAAAAAAGTA
76701 AAATAGCAAT TTCTATAGCT GTTTTTTCTT TTAATGGCTT TATTGAGATG
76751 TGTCACATAC CATATCATTC ACCCATTTAA AGTGTTCAGT TCAGTATTTT
76801 TTAGTATATT CACAGATATA TACATTCATC GCCATAATCT AATTTTAAAA
76851 CATTTCTCTC TTGCAAAAGT AGCCCAGTAC CCATTAGCTG TCATTCCCCA
76901 GCACCCTCCC ACCATCAGGT TCTAAGCAAC CATGAATCTA CCTTCTATTT
76951 CTGTAGATTT GCCTATTCTG ACCATTTTCT ATATATGAAA TCATACTATT
77001 TGTGGTCCTT TGTGACTGGC CTCTTTCACT TAGCATAATG TTTTCAAGGT
77051 TCATTCATGT CTTAGCATGT ATCAGTGCTT CATCCCTTTA TGGTATATCC
77101 ATAAAATGAA ATATTATAGG ACTATAGTAT TTCATTTTAT GGATATACCA
77151 TATTTTGTTT ATCCATTTAT TAGTTGATAG ACATTTGAGT TGTTTTTACT
77201 TTTTGACTAC TATGACTAAT GCTGCTATGG AAATTCTTTT ACAAGTTGTC
77251 ATGTGGCCAT ATGTTTTCAT TTTTCTTGAG TGTGTACCTA GTGGTGAAAT
77301 TGCTGTGTTA TGTAGTAACT CTATGTTTAG CCTTTTGAGG AACTGCCAAA
77351 CTGTTTTCCA AAGTGATTGC ACCAGTTTAC ATTCTCACCA GCAATATATG
77401 AGGGTTTCAA TTTCTCCACA TCCTTACCAA CACTTGTTAT TGTCTGTCTT
77451 TTTCATTATA GTCATTCTGT GGGTATGAAG TGGTATCTCA TTGTGGTTTT
77501 GATTTACATT TTGTAACGAC TGATGGGTGT TGAACATCTT TTTTATTTCC
77551 TATTGGTTAT TTTGTATATC TTCTTTGGAG AAATAGCTCT CCAATTCCCT
77601 GCCTTTTTTT TTTTTTTTTT TTTTTTCCAG AGACAGAGTC TCACTCTTGT
77651 CACCCAGGCT GCAGTGGAGT GGTGCGATCT TGGCTCACTG CAACCTCCGC
77701 CTCCTGGGTT CAAGCGATTC CCTTGCCTTA GACTCCCAAG TAGCTGGGAT
77751 TACAGGCATC CACCATGCCA AGCTAATTTT TTTGCATTTT TAGTAGAGAT
77801 GGGGTTTCAC CATGTTGGCC AGGTTGGTCT CGAACTCCTG ACCTCAGGTG
77851 ATCTGCCTGC CTCGACCTCC CAAAGTGCTG GGATTACAGA TGTGAACCAC
77901 CATGCCCAGC CTCTTGTCCA TTTTTTAATT TGGTTGTTTG TCTTATATTA
77951 TTGAATTGTA AGAATGTTTT AACGTATTCT AGTTATAAGC TGCTTATCAG
78001 ATATACATTT GCAAATATTG TCTTTTTTTT TTTTTTTTTT TTTGAGACGG
78051 AGTTTTGCTC TTGTCGCCCA GGTTGGAGTG CAATGGCACA ATCTCGGCTC

78101 ACTGCAACCT CCGCCTCCTG GGTTCAAGCG ATTCTCCTGC CTCAGCCTCC
78151 TGAGTAGCTG GGATTACAGG TGTGCACCAC CACGCCCAGC TAATTTTTGT
78201 ATTTTTGATA GAGACGGGGC TTCACCATAT TGGCCAGGCT GGTCTCAAAC
78251 TCCTGACCTC GGGTGATCCA CCCGCCTCGG CCTCCCAAAG TGCTGGGATT
78301 ACAGGCATGA GCCACCGTGC CTGGCCACAA ATATTGTCTT TTATTCTATG
78351 GGTTACCTAT TAGCCTTCTT TATGGTATCA TTTGCAGCAC AGTTTTAGAT
78401 CTTTTTTGTT GTTGTTGTTT AGCTTGTTTA TTTGTTTCAT TTTATGTGCA
78451 GTACTCACTT CTGCTTTCAT TCATTTATGC CTTGAGTGTC CATTATGTGT
78501 CAGGAACTTT TCTAGACACT GGTGATATGT CAGTGAATAG GATAGAACAA
78551 TGTCCTTGCT CTCCTGAAAC TAATATTCCA CTCAAGAAAG GCAGATGATA
78601 AACAAATAAA TCAAAGATTT CAGACAATGA TAAATATGTT TAAGAAAATG
78651 AAGTGAGATA ATGAAGTGGA AAATTTTTAT GAGGCGTGTG TCCAGGGTGG
78701 GGAGGCAGCT TTAGGTAGAT TCACACTGTT GGCATTTGGG GCCAGATAAT
78751 TCTTTGTTGT GTTGTAGCTG TCCTGTGCAA ATATCCTACA ATGCAAGGAC
78801 AGCTGCCTGT GTAAGGATAT CTGTAGCAGG ATCTCTGACC TCTACCCACT
78851 AGGTACCATT AGTACCTCCC TCACTTGCTA TAATCGTACA AAATATCTAC
78901 AGACACTGCC AAATGTTCCT CAGAGAGAAA AATCACTCTC AATTGAGAAC
78951 CACTCAGATT AATAGTTGAG AAAGGCATCT CCGAGTGATG ACCTGAAGAC
79001 AGAGTCCACC TTATGGGAAG CAGTGGAGCA AAAGCATTCA AGATAGATGG
79051 TAAATAAGTG CAGAAGCAAG GTGGGGATGC ACTTGATGTG TTTGAGAATA
79101 GAAACAAGGC TTTAGAGTGA CAGTGTGGTG AATAAGGGAA AGAATAGTAG
79151 GAGATAAAAA TAGAGAGGTA GGCTGGGGTC AGATTATGAA GGATCTAGTA
79201 GACAGTAATA AGAAATTTGG AATTATTCCG AGTACAGTAT AATTGGAAGC
79251 CAGTAAGTCA GGGATAAATG GGTGCTCTCA AATATAGGAA ATAAGCTGTA
79301 GATTTGGGGT TTTGTCCCAC TTTATTTTAT TTTGAGTTTT TGTGGGTTTT
79351 TGTTGTTGTT TTTGCTCAAG GATCCACAAT CAGAGAGTGA TAGAGCTAGG
79401 ACTAAAACCC AAGTCTCCAG GCTAGTAAGC TATAGGTCTT TCTATTAAAC
79451 ACGGCTGACG AAGCAGTCTA CATTTATTAA CTGTAGGATT GCAATTGGCC
79501 GTTACTCTAA CTGACCTTTC CCTGAATCCA CCTTGTTTAA GAATTCCTAA
79551 TATAGTACTT AGCATTTGGC ATGAAAATCA AAGAAGATGA ACTTTAGCAA
79601 GAAGCTAATC CAAATCTGCT TCACAGACCA GCAGCATCAG CATCACCTGG
79651 AAACTTGTTA GAAATGCAGA ATCTCAGGCC CACCTCAAAC CTACTGAATT
79701 AAAATCTGTG CCTTGATAGT CCCTAGTTAA TTAGTATGCA TGTTAAAGCT
79751 TGAGAAGCAC TGATCTAGTT TATCAAAATA TCATCAGAAA CAGTCGAGTG
79801 ATTCAAATGG TTTTTTTTAA TGGGCTTTTA CTGAGTCAGA AGACTAATGA
79851 TGGTGTCATC ATTAAGCTCT CATTATAACA TCTTTTTTAT TCCTTTCTTT
79901 CTTTGGCTCA CAGCAATTCT TCACTCACAA AGTCCTATGT AGTCTTCCTT
79951 AATAACAGCA TACATTCTTT CCTTTCATTT CTGCAGCCAC CACCTTTGTC
80001 TTTACCCTCA CTAATTTGTA CCTAGCTTAT TATAGCCATA TCAAAATTTA
80051 TGCCTTCCTC CCTTCATGCC CTTCATTGCC TAGAGCTCTC CGAATCTCAA
80101 ACTTCATATG GCTTTTTCTT GTCTTCAGAG TAAAATTCAC ATTTCCAACT
80151 CTGACTTTGA AGGCCTTCTA TATCAAAACT CCAAACACGT TTCCCAGAGA
80201 ATCTGTTGTG TGTATGTCTT TAAGTCCATG TCTTTGTTCA CACCCTGGAA
80251 TGCCCTTTCC CATCCTTTCT ACTGCCTTCA AGGCTCTGCT GAAATCCCAC
80301 TTCCATCAGT GATGTCAAAT CTACCCAGTT GCCTACCCAG GTTCTACGGC
80351 ACTTGTTGCC TGTACCAATT ATTTTTTGGT GGGGGGGTCT GATAGCATTA
80401 TAATTTCAGG CACAAGCACA GGTCTTCATA ACTAAATTGT AGTTCATGGA
80451 GAACAGAGGC CACATCTTTG TCTGCTCCCA CTCTAATGCT TAGTAAGGCA
80501 CTAAGCATGT AGTAGGTAAT CAGTAAATAT TTTGCCTTTG AATCTGAAGT
80551 TGTGGAGTAA TGCCCAGATT TACAAGCACT TCGTTTCTAC TAATTTATTT
80601 TCTCTAAGGG TCTATGCTAC AGTTCAGCAA TTGTGTAAAC AGCATTGTTT
80651 ATAAAGCCAG CCATGGGTAA GCAGTCTCAG ATCAGCTGGG TGGTAGGCAA
80701 TGGATGCAGT CCAGAATTTC AGGCCAAATA AAATTGTGAA TCTTTATTTC
80751 AAGAACCACT GTATTCTGTG GGACCAAGCT CTGTTCCGGG TGTCAGAACA
80801 ATAGGTATCC CTCCCTGCTG CTGAGCAGCT GTATGGGGCA AAAAGCCCCG
80851 ATTGAGCCTG GCCCGCCTGA ACCTGGGATA GCCCAGATAT AAAATGATAA
80901 TAACATTGAC CTGAATTCTG TATTTTGTTA CATTTTTGTG TTTGCTTAGT
80951 ACTTCTTTCT TAAGGTTGTT GGCAAGAGCA TCTGCTGGTA ACTTGGCTCA
81001 GTGTGTTGTA GGTTTTTGTA TATGGTTTGG GTTTCCTATT CCTGGGCATT
81051 GAACTATTAA GATTCCTGCA GATAGGCATA ACTACTTACA GCCTTTTCTG
81101 TGTATATATT AGCTCTTACG GACCTCATAA ACCTAAAGAG GTGCAGAGGA
81151 AAAGTGCCAT CATTCTCATT TTACAACTGG GGAAGCAGAG GCCCAGAAAA
81201 GTGATCTAAC TTTCCCAAGT TCACAAATGT GTTATTAGAG CTGCAACCAG
81251 AGCTAAGGTT GAGGCTTTAT GAACCTTAGG TTACTATTCG GTTAATAGGC
81301 TCAGTGCAGC CTTACCTTAC TAATTATTAA AAATAGACAA CATTAGGATT
81351 TAAACCAGAT GGTCTTTTCC TGTTGTTCAC ACTCTTACCC ACTGTCAGCA
81401 ATGGCCCATC AGATAATCCA CACTGATTCA TGAAAAGGCA AATATTTTCT
81451 GTTTCTGTTC TAAGCTAGGC TTGCCAAAAC CGAGAGCAAT ATTCTCTATC
81501 CCCGAGATGC ATTGCTTCAA GCACCTATCT ACTTTCTCTG CAAAGTTATC
81551 CCTTTGGCAA TGGTTCTTCA ATTCTGATTA TATCTGGGAG AGAAATAATA
81601 AACCTATTTA GATGCTAATT GGCTTTAACA TCTCAGTGAG TCAACAGGCT

81651 CATGTATGTC CTACAAGAAG TCTCTCAAAC CTGGATCATA CAGCTATCAA
81701 ACAGTGTTGC TCAGCCACCA ACTTCAAAAT GGCTCAATCC ATTTGAGTTT
81751 ACAAAGCATT CCATTTTATA GCAAAGGACA TCTGTGCTAA GGATAGTGTC
81801 TTAAAGGCTA GGCTTTTGAG GTGGCAATTA TTTTCTTGCT GAGGTTTCAG
81851 AATAGACAAT TTTTTTTCCT ACATTAAAAC AGAGAAATGA AGAGTCTGAG
81901 TATTCTAGGA AGTTCATGGC ATAATGGTAA GCAGATAAAT TTCTGATATC
81951 CTTCTGAAAA TTAACTTAGT AGCTTTGTGA CCTCTGGCGC CTTATCTTCT
82001 CCAAGCCTCG GTTTTCTCAT CTGTAAAATG GAAGTCATAA TGGTACTTAC
82051 AAGGCCAAAA TGATGACTAA ATGAGAGGAT AAATTTAAAA TATTTAGCTC
82101 AATGCCTGGC ACATAGTAAG TGCTTCATAA CAATTGAGTA CTAGTATTAC
82151 TATTATTTAT TAATAATTCC TATAGTCAAA TAGAATAAGG AGTCCCCCTT
82201 GTTCACTATA GATATTCAGA ATGTCCTTCT CTCAGGCCTG AATGAGTAAT
82251 TCCTTCTGGA TTACTAATAT CAAAAGTCCA TTTGTATCTG ATTGAGATGA
82301 GGAAAGAAAT GCAGGATGGA GCAGGGAACC AGTCCTCACA CTACATGGTT
82351 TACTCCAGCG ATTCTCAACG TTAGCACTAC CTATGTTTTG CACAGGGTTA
82401 GTCTTTGTTT TGGGGGGCTG TCCTGCACAA TGGAGGATGT TCATCAGTAT
82451 CCTTGGCCTC TATCCATTAT AAGATGCCAG CAGCAAACCA ACCTCCTCCA
82501 AGTTCTGATG ACCAAAACTA TATCCAGATA TTTGCCGACT GGGGGCACTT
82551 GCCCCCAGTT GAGAGTCACT AATTACACAG TACATTTGTC CATGATGGGG
82601 ACATGTAGGC TCACGGGGTA GCCAGTGACA GGCAGGCAGA CAGGAGTGGG
82651 GAATTTTTTT TCTGTAAAGG CCCCAAGTAG CAAATATTTT AGGCACTGTC
82701 TGTCCCAACT ACTAAACTCT GCCATGTAGC TTGAAAGCAG CCAAAGACAA
82751 CACATAAATG AACATGTTCC AGCAAAACTA TTTATGGGCC CTGAAATTTG
82801 AATTTCATAT AATTTTCATG TGTCACTAAG TAATCTTTTT AAAATTTTTA
82851 TTCAACCACC TAAAAATGTT AAAACTATAC ATGAGTCGTA CAAAATCAGG
82901 TGGTGGGCTA GACTTGGCCC ATGAGCCATA GTTTTCTGAC CTTTGGACTA
82951 AGAAATACAT GAAGCCGTAA CTTCATATTT ATCCCTAAGA TAAACATGGG
83001 ATAAATATGA TACTTCTCCT AACACCATCA AATTTACATA TAAATTTTAG
83051 AGAAAGCATA TTATTTTATT AAAATGAGCA TTGCTATATT TTGGAATAGG
83101 ACCCAAGCCA AAATGAATTT TAGAGATAAA ACATTATATT CCAAAGTTAT
83151 ATCTTGCTTC CCATGGGCTG TTGACCCATG CCTCAGGTCC CCAGAGGCCT
83201 TCATTTCCTG CCTTCATTTT CCCTTGCTTT TAGGCTACCT TGGTAGGAAA
83251 ACTTAAGAAG TTGCCATGCC ATTTTAAGTG AGAAACTAAG TCATATAAGA
83301 GCCTTTTAGA CTTCCCATAA CTGGTTACCC TTAGATAGTG TCCAATAAGG
83351 CACCTCAAAA TATTCTAAGT GCTCTAGTGG TTGTCTAATA TATTTCATCA
83401 GAGAATGGTT GTGTAATATA CGATTGTTTA ATCCAAGGTG GCTCCTATAA
83451 ATCCTTTTTG AAATGTTCAA GTATCTCTGT CACACACTTG GGGTATGAGG
83501 TTTATTCACT TCCATTGTCA ACTAAGCAGC ATGTGTACCC CACAGCTTGA
83551 TGAGTACCCA GAAAATCAGC AAATGGTGTG GGCCCTACTC TCAGGAAGCT
83601 GGAATCTGAT GGTGATATTA GGACCTGCTC ATATGAGATG ACCCGCAAAG
83651 AGTACACCAT CAAGAAAGGT GTTGTGGCAG AAGGAGAAGT GGAGTGGCAA
83701 GCGGGAGGCA CATTTTCTAG CACCTCCTGT GCATTCATCC TGAAGGAGAG
83751 AGTTACTTTA CCTTTAGATA AGTTTTTCTC TTCTGCCCAG AGTGCTTTTT
83801 TGAGACAGAT TCTGAGACAT CATCCAAGTT CAGCTGGGAA GAATGCCACA
83851 ATTGATTAGA GCTGTCAGCC GTGGATGGGA GATCAGGGAT TGGCTGGCAA
83901 AAGTGCCAGG GTGTTGACAG GCATAGTCTC AGTCATCTCC ACAGTTCTTC
83951 CTGGCTGGAA ATGCCTCTGG CTATATTACC CTTATTGCAT GATTTCATGG
84001 TACTGATCAG ATCCAAAGAA GGAGGATGAT TGTGAGATGC AAAGCTCAGG
84051 GGACGACTAC GCGGTGAAGG TGAGAGAATG CCCAGAGCTT TGAAGAGGCT
84101 GCTTCTTCTT CAAAGCTGTG TTCCAGCAGA GCACATTTTG TGCATACTTG
84151 AATTTTGGTT GGCTCTAGGC TGAGCGCATT CTATTGTGGC GTTGGCATGG
84201 GAAGAGGGAG GCATGCGAGA AATATTGCAT CTCTGCTATT CTCCTGGGCC
84251 CTTGTGAATG GGAATGTCTT CTTAATGAGC CTATCCCAGA GAGTCTGGCC
84301 TTTCAGATAA ACAAATAAGC ATCAGCAGGA GATGCTCACA AAAGGACTGG
84351 GCAAAATAGG GCCACGTTGA GTGACAACCC AAATAAAGGA GTCCTAAGAG
84401 GTCTGAAGCT GGTGGCTAAT GAGCACATCT CCTCATTTGT GATTTCTTGG
84451 CCAGGACATG TATTGTTGAG GGTGCCAGGA AAGTCTGTCT TATTTTATAC
84501 AGGAAGAAGC CTTTCTGGCC TTTGTCCTGG TACTGGCTTT TATATTTTAT
84551 GTTGGGCTAG GGGCCTGCCT GGAGGACATT TACAAGGTGA GGAGAAATCT
84601 CAAGCTGATT TTAACCTAAC ACAATTTTCT TATCTTTCTA GTGATATATA
84651 TCAGTTTTCT CACTTGGGAA ATGGGAATAA AAATACAACT CACCTACTAG
84701 AATTGTTGGG ATGATTAAGT CGGATGATTC TCAGAAAGCA CTTCCCACAG
84751 TTTCCAATAT GTAGTCAGCA TCTGATACAT GTTGGCTGCA ATCATTATTA
84801 GTAACAGTAT TATCATCATC ATTTTCATAT GTGGAAAGAT ACCAAAAGGA
84851 GTGTCCAGGG GTGAGGGATC TAGTTCCAAT TCTGCTACCA GCTGGCTGTG
84901 AGATTTTAGG CAAGTCATCT CTCATGTCAA CTGAGAGTGC TGGACGGGAG
84951 TTTTTATTCA TTTTGTAAAC ATATTTGGAG GACCTACTAA GTGCCAGGCT
85001 CTATTTCCAG GGAGCAAATA TATAAAGGTG AATAAGACAC ATTTTCTGTA
85051 CTCAAGAGAT CCCAAAGGTA ATGGAGGAGA CAGGTAACAC ATGTGACCAC
85101 ATAGCATGAG AATTGCTCTT ACTGTGTGGC TGCATGCCAA ATGCTCGTGA
85151 GGCCTGGCAC GGAATTAGCA AGACTAAAGG CTCTGTCCCA GTCCAACCTT

FIGURE 3, page 24 of 122

85201 CTGTGAGTCT ATAACTGAAG CATCCAAAGT ATAAGCTGGG TGATTAGGGG
85251 AAGAAGAAGT CACCTAGCTG GCAAGGGGCC TAAAACTCAA GTCCCCTCCT
85301 TCTAGGACCA GAGTACTCAC CAACTACCAA GCTGCCTTAA AATAAAAACA
85351 TTCAAGAACA AGTGATGTGC AGAGAGGCAA CACAGTGATA AGTAACTGGG
85401 GTCTGGAAAT GGGAGACTTC AACTTCAATT TCAGCACTGT TATTTTGGTA
85451 GTTTAATGAT TTAGAGTCAG TTGTTTAATC TCTTAGAGAC TCAGTTACTT
85501 CATCAGCAAG GGTGTTACTA TAGTAATACC TGCTAGACAT TATTATTATA
85551 TGGAGAGAGA GAGCTTGGTA AGCTGTGACA TATACATTCT AGTTGGTGGT
85601 TGTTTCTGTT GTTATTATTA ATAGTAACAA CAATAAATAT CCTGTTGTTT
85651 ATTTTTTTGA AGTGTTCAGT GGCTGGTAAC TGAATTAGAG TGCCTGGAGA
85701 TATAGGTAAG GGTTTTTTGT TTTAATAATC ATTATCTTTG TTCAAGAGAA
85751 TAGGAAAAAT ATAAGCCTCT TTTTAACTTT AATGCAAAAA AGTCTTTATA
85801 GCTTGTGTGT GAAAAACAAG AGGAAGGGAG GAAGGGGAGG AAAGAGATTG
85851 TCTATTTCTA CTTAAAGCTA ATTAGAGAAG TAATTTTAGG TAAGAGTATT
85901 ATGACCTGAT TTCTGATTAA TTTAAGTATT ATTATACTGT TGTAATAGAA
85951 ATCCCTGAAG TGCTTTATTG ATTATCTGTT GGTAGAATGA AAGGGTAAGC
86001 AGCTGTAGTA AATAAAATTT TTGTCTGAGG CAAAGCAAAG GAGAAGTAAT
86051 ATAGGAGAAA TTATTATAAT AAAGATGGGA GTGAGAGAAG AAACCTGGGT
86101 TCTAGTTCTT TCAGATAGGT GACCTTGAAC AAATCTCTTC CCTATACTTG
86151 GCCTCGGTTT CCCCATCGGA ACAACCTAGG GCATACTCTA GATAATCCCT
86201 AAGGTCCCTT TCAGCCTTGA CAAACTATGA GATTTCTACC TGTACAATAC
86251 TGAAACAGTG ATTAAGAGGG AGAGACACCC ACAAAGAAAG AAATAGTTTG
86301 TGCTGTGCTC AAATGCCTGA CTGATAAAAA AGAGAACAGA CTCATAAAAC
86351 CCACTAATTC AAATTAAATG GATAATTCTT GTTGATTTTG AGCTGGCAAT
86401 CTCAGGCTTC TAAATCACAA GGAAACTCCA TTTGATCCTG CAATGGTCTC
86451 TTGGTCTCTT TCTTAGCTCA GTAGTGCTAA GCACAGAGGT TTCATGGAAA
86501 TCAAGAGAGA AAGAGAGAGA GAGAGAGAGA GAGAGAGAGA GCTGTTTAAA
86551 AAAAGAAGAA CAATATACTT GGATGAACTA AAGAGTGGTC CTCATGAAAG
86601 CCTCATAATG TCCATTGCCT ACCTGTTTAA CCCTTTGTGG CCTGATTTTT
86651 GGTCCTCAAC TGAAATCAAA TTAGGTAGTC TTATGTAGGG AAATGAATAA
86701 CTTGTACACT GTTGTTGTTT GCCATCTTTA GGACCACCAA AGGGTAACGA
86751 ATTCAGCAGA CCCACAATCC GGCACTTCAG GTTTTTGAAA TTTACTCATG
86801 AAAATTTAGG AAGTCCTAAA GGCTGTGAAA AATCATTGAA CTTCATTGGC
86851 AGGCAGGACC TTGCTTTCAA AACTCTATGA GGCTACAAAT CAGAGATTGA
86901 AACCTAAAGA GGGAACAGGG CTTTCCCAGA GTCACCTGCC TTCCCAGGCA
86951 GAACTGGGAC TCGAAGTCAC AGCTAGACTA GAACTCCACT GATTCCAAAT
87001 CCAGTATAAC CAAGTCTCCT GTGGCCTTTC CCATGATCTG GACCCAAAGA
87051 CTTTCTGATG TTCCCCAAAA GAGTTGTAGG TGCACTCTGT TCTCTGGTTC
87101 TTTGCAGTGT AATGGCAGAA CTGAGGTTAG AATTCTCCTT GGATGTAAGG
87151 ATCACCAGCC CACCAGGCTG GCAGTTAGAC AAGGGAGTGA TGGATTTGGG
87201 ATGCTTTGTG TGACCTTGTA TACAACAGGT TCTTAGACAC AACCCTAGGA
87251 CATGGAAAAG AATTACATTC ATCCTGAGCC CCAGCTACTG TTACCAATTC
87301 AAATTAGGAC AACATATTGA TTAAGATACA GGTAGTTATG CTACCCTAAG
87351 AACTGGAATC TGAATACCTA CTTTTTATTT CTACTTCTAC CGCTTGTTAG
87401 TAACCTATTC TTGATCCACC ATTTAACTTC TGTGAGCCTC AGTTTCTCCA
87451 TCTTTAAGAC AGTGATGATA ATGACAGTAT CTGTAGAACA GCTTAACTTG
87501 AACTAAATGA GAAAAACTAA ACAAAACACA TAGAATTAAG TATGAATTTC
87551 TGAGGTTAGT TTATACATGT TTTAAGAGCT TAGAGAAAAG GAAAAAAACAT
87601 AAGTATCCTA AGGAGATTAG GAAATGTTTC CTTGGGGAGG TTGGAAAGCA
87651 GCTAAGCCTT GAAGAATAGG ATGTATTTTG AACACTGGGA GAAGAGATGA
87701 GAAGGTAGTG AAGTGGAGGC AATAGCCTGC ACTATCCAGA GACAGTTTCT
87751 GATTGTCCTA ATGCTATGGG CTCTCTACTT CAGTTTAAGA AATATTCCAA
87801 TCTTTGATAC CTTCATTCAA CAGTCCTTTC TATTTTTCTA ATTTCATTTC
87851 CTGAATTGTT TCCCTGCGGA GGAGTGGGCC TACTTGTTGA AATAAATCAC
87901 ATCACAGATA CCTCTTTTCT TCTCTTTTGT TAAAAGTTCT GTTAAAATAT
87951 ATATATTGTT AAAAAAATTAA AGGTTATCTC CAGATAATTC CCCAAATGAG
88001 TAGGCTTAGG CTTTAATCAT ATTATGTTCC CTTCCTTCTT GCTCTTCACT
88051 TGCCAAGTTA TACTAATGAT CATAATCTCT TCTATGTGTT TTGGACTTTA
88101 CAGTGTGTGA AGGTTTTATT GCCACTGTTG GCCCTCTCAG TGAGCTGATG
88151 CAATAATTTA GGTTATAATT GTTGGACTCT TTATACGAAT GAGTTGCTAG
88201 AGCTTTAGAG ATGTTGCCTG ACACGTAGCA GGCTCTCAAT AAATATTGGA
88251 TGGATGGATG GATGGATGGA TGGATGGATG GATGGATGGA TGGATGGATG
88301 GTCCTCTCCC CCCTCGCTTT CTTGTGTGTT GGTGCCCGCC TCGCCGTTTG
88351 TGCGGTGTCC GTTGGTTCCG GCTCCTCTCT TTCGTTCTTC GTTNGTTTCG
88401 TCCTCTCTTC TTCGTGCGTG CCTTCTCTTC CCTCGCCTCT CGTCCGTTGT
88451 CTCTTTCTCG CGTCTCGCTC TTCTCTTCGT CGCATCTGGG TTCGCTGTCC
88501 CCTTGTGCGG TACCGTCTCT GTTCCTTGCC TCTTTCGTTT GTCTCGAGCG
88551 TCNCTCATTG CGCCGTCCTT CCTAGCCATC GATATCGTTC GTCTGGTTCT
88601 CGCGTCCTCT CGTGTCCTCT CTCGTGTCGT CGCGCATCAG ATCTCGTGCG
88651 CGCCCCCTCG CCGCTTTTCT CTCTTGTCTG CTCACGCGAT TGCGTTGCGC
88701 TCGCTTTCCC GCCCGTTGCC GTTCGCGCTC CGTCCTCTTG CCCCATGCCT

FIGURE 3, page 25 of 122

88751 CCCCCCAGAT AAATCANNNN NNNNNNNNNN NNNNNNNNNN NNNNNNNNNN
88801 NNNNNNNNNN NNNNNNTAAC TCCAGCTTCA GCAGAGATCC CAAGGCACAG
88851 AAAGCAGGCA TACCCTGCAA TCATTTATCT CTGGGATGCC CTGGAGCCTG
88901 TCAAATGGAG ATAGGGACCA AGATGGTATG TTGTAATTTT GTGATATAGA
88951 AAATCTGGTC AATTTCCATG AAGCAAGGCC CTCACCCCTA TGGCTGCTTG
89001 TATAAGATAC TGTCCCCTTT TGTACCCTGT GTAGATAATG TGTTTGGAGT
89051 TCCTCCTTTA GTTGAGAAAA ATAGAATCCT TGCTCACTTC CATCCCAAAG
89101 TCTGGATTTG AGAGGGATCA ATGCTTGGTT TGCAGGGAGA ATATGCAGAA
89151 CAAAGGAAGG ACCAGAAAAC TAGAAGTCAG AAGACCTAAG TTCAAGACCC
89201 AAGTTCAAAA CTTATAAACT TAACTTATTT ATTCATTGAT TATGTATTGA
89251 TTCCTTACTC TGAGGCAGGC TTTGCCAGAC AGTGAGAACA CAGTAGTGAG
89301 TAAGGGGGAC AAGACACCTG ACTTCATGGA CCTTAGTTCA AGTGGGGTAA
89351 GAGAGAAAAA TTAAATAAAT CAACTGAATA AGCAAGATAA TTGTAAGATA
89401 AAGATTCCCC AGGCACAGTG GCTCGCGCCT GTAATCCCAG CACTTCGGAA
89451 GGCCAAGGCA GGCAGATCAC CTAAGGTCAG GAGTTCGAGA CTAGCCTGGC
89501 CAACATGACA AAACCCAGTC TCTACTAAAA ATACAACAAA TTAGCTGAGC
89551 ATCATGGTGC GTGCCTGTAA TTCTAGCTAC TCGGGAGGCT GAGGACATGA
89601 AAATCGCTTG AACCTAGGAG GCAGAGGTTG CAGTGAGCCA AGATCACACC
89651 ATTGCGCCCC AGCCTGAGCA GCAGAGAGAG ACTCTGTCAA AAAAAAAAAA
89701 AAAAAAAAAA AATGAAAGTA AAGAAGAAAG AAAGAAAAGA AAAGGAGAAA
89751 GAAAACACGA TTCTCTGAAG AAAAAAGCAA TACACTGAGA GAAGGAAACA
89801 TGAAGGTATT CGTTTAAATA GTGGGTCAGT GAATGCCCTT ACTGAGTAAA
89851 AGTGACATTT AAGCCTAGAT TTCAATGCTG GATGGTATTC ATGCTACAAA
89901 ACAATTTGGA GAATATTCTA GCCAAAAGGG AATAATTTGT GCAATGATTT
89951 GAAAAATGGA AGGACAACCA GGGTAGCTGG AATGTTTATG GCAAGGGAGA
90001 GAGTGATAGA AGATTAAATC AGGAAAACAG AGAAAGTAAC AGATGAGGCA
90051 GTGCTTGACA GGCCATGAAA AGAAGAGTGA CTTTTATTTT AAGTGCATGA
90101 GAAGCCACTG GAAGGTCACA AGTAGAAAGG GATGTGGTCT CATCTGTTTT
90151 AAGAATTTGG TCCAGTCGGC TGGCCGCGGT GGCTCATGCC TGTAATCCCA
90201 GCACTTTGGG AGCCCAAGGC GGGTGGATCA CGAGGTCAGG AATTCGAGAC
90251 CAGCCTGGCC AGCATGGTGA AACCCCGTCT TTACTAAAAA TACAAAAAAT
90301 TAGCTGGGCA TGGTGGCGTG CACCTGTAGT CCTAGCTACT TGGGAGGCTG
90351 AGGCAGGAGA ATTGCTTGAA CCCGCCAGGT GGAGATTGCA GTGAGCCGAG
90401 ATAGCACCAT TGCACTCCAG CCTGGGTGAC AGAGGGAGAC TCCATCTCAA
90451 AAATAAATAA ATAAATAAAT AAAAGAATTT CGCCCAGTCA CTGAACTTCT
90501 TTGTGACTCC CTTTTCTCTC CTGAAAACAA GGATTAAACT ACTGATTGTC
90551 CTTCCAAGAG GTTGTCTGAG TGTCAGATCA TCTTCATTAT AATACTTTGC
90601 TCCAAGTTGT GCTTGATAAA TTTTGAACTG AATTGTTTCA TAACAATATG
90651 AAAATGCTTT ATAAACTGTA AAGGGCCATG CAAGTATAAA GTATTACCAA
90701 TAACCATCAT TTCCCCAAAG CTCTGACTCC TTTCCAGGAG TTTGTGTGGA
90751 ACAGGTAAGA TAACTGGCCA TAAAATGCTT TGAAAACCCT ATGCTAATAA
90801 AAGATACTTT ATATTTATGT TCATTTGTTT ATTGAAGTTT GCATTTGGTT
90851 CCTTTATTCC ATAGCACCAA TGTATTCTCT ATTTTTGGGC TAGGAAACAA
90901 CAAGCAGACT CAAGTGTGTT ATTTAACCTC AAGAAATAAA AATATCCAGA
90951 GATAATATGA TGAGTGAGGC TGAGAGTCAA GTCAGCAAGT CTTTGGTTAG
91001 AACTGGGCAC TTCTTCACTC TCTTACCTGA GTAGATGGGA GCTTGTCCTC
91051 ATTAGTCATA GGCCCCCCGT TACTTATAAA GAAGTTGTGA AAAATAATAC
91101 TGACAATGAT GATAATTTGA ATGACACATG TTTAGTAATG CATATAGATA
91151 TATACTCATG GGTATGTATA TACAGTCCCT TGCTACTTTT CTCAAAGCAT
91201 GTTTTTCTCA TCTATTGTTT TAATTTAGCT CACACTCACA TGCAGAGGTA
91251 GAGTAGGAGT ATTCCAATTG GAGAAATGGC CATGAAGTGC TTAAGTGGTT
91301 TGCTTCAAGG TCACACTGTG AGTGATAGAG GAGTTGAAAC CAAGTCACAG
91351 AGCTCCCTAG TCCTGTGCCA GCACTCTGTA TCAAGACCCC TCAGCTCCTG
91401 CGGGGCCTTG TGAAAAAACA AAAACAAACA AACAAACAAA CAAAAAAAAA
91451 CAGGATCCTG AGCCTCACAT TAAACAATTA GGAACTGGAG CATTTTCACA
91501 CTTTAGAAAA TATTTGATCC ATGTAGCCTA GCCCTCTTCC CTCATGTCAC
91551 ATACAGGGAA ACAGAGGACC ACAAGTAGGA GCCCACTTGG GCAGGTGAGT
91601 TTTCTGCCAA CTGCTCAAGC ACCTACTGAT GCTTCAGCTC TCTGTCTTTT
91651 AACCTCATAT GTAGCTGGTG ACTAAGGTGG ATGGAGATAA TGCAGTAGAA
91701 GTCAAGGTGG TCCCCTCTGA GGACCATCTT ACCAGAGAGG GAATCACAGT
91751 AGGAAGAGAA CTCTTCAGTT AATTGATAAT TTTTTCTTTG CAATGGAAGG
91801 GAGGTCTCTG TGACCTTGGG TCTGACCTCG AGCCTGACAT GCCTTTTTCC
91851 CTAGCCCTCT CTTGCTCTCC CTTCAGGGAT TTGGGCAAGG TAAATCTTCA
91901 AGTTCATTTA CCTTCTTTAA AATTGGGCAG CTTTACACAT TATCTTGGCC
91951 AATTTGAGCC TAAAAAGTGA TGTAGCTCAG AAGCAGTCAA GTTTAGTTGG
92001 ATGAACATGA GTATTAGGCT GGGAAGCTCA TGCCCAAGTG TGAACCTTGT
92051 AGCCTTAATC AAGTGTCTGC CTTAGAGCTA AGCTTCTCTC TTGGTGAAAT
92101 GGTTTAAAAT ACCCATCCAG TACATGTCCT AAAATGGACA TGAGGTTCCT
92151 CTGGGATAAA GGATGAGAAG ATACTTTGTA TTTTGTAACA TTCTACTCAG
92201 ATGCAGGATG TTCATCTCAT TAATATTACA CTCTGGTGCC AGTTTCTGGG
92251 GGGTCAGCTG CAGAGAACCT AGTTCAGGCT GCAACATCTC ATTAGAAGCT

FIGURE 3, page 26 of 122

92301 GAAATTTGGA TTCAGGAAGA GGAGCATGGA GTGGGTGAGA GCCACTGTCT
92351 GCTGCTCAAG TTCCTGCTGC TATCTGTATT CAGAGAGGCA TCCTGGTACC
92401 TTAGCAGTGC TGCTCAGTGG GACGTCTCTG ACTTTGATGT TGCACGTGTC
92451 AACATTCTAA TAGGGCAGCA GCCGAGATGG GGTATGAGTT TGGAAAGACA
92501 TCTTATGACA GCTTTTTCCT AAAGATGTTT CAAGAGATAA CCCTTTAGAA
92551 ATAACGAAGG TAGTTTATGC ATTTCATAGG AAACCCAGCG GCTTACGTAG
92601 CAGCTCACTT CGAAGTCTGG CATGCGGACG GCTTCCTACT GTCCCGTTTT
92651 TGCCCTCCCT GCACATCTGT GAGAAATCAT CACTTGTCAC AGTAACACAG
92701 TATTGTATTT AGTTACATTG ACAGCAATGG TGAAAGGACT ATAAGCCTAT
92751 TTCCTTCTAA ACTGTTCACA TCAAATGAAC CTTAAACATT TACTCCTCTC
92801 TTAAAATGTA AATCAGATCA CCTCAGCCTA CTGTTTAAAC ATTCTATCAT
92851 GGCTTTCCAT CATGAATAGA ATCCAAATGC CTAACACAAG CTGGATGGTA
92901 GCCTGATCTG ACCTTTGCTG ACCTCTCTGA CCTCCCCTCA CACACAGCTC
92951 CCCTTGCTCA CTGTGCTTGA GCCACACTGG TCTTCATTTG TGCTCAAATA
93001 TGCCAAGTTT TCTCCTACCT TAGGAGCTAC TATTAAAATA CCTAACTAAA
93051 GCTCTAAAGC TCTTCATGCC TGCACCACTC TTTTCTAAGA TATTTCCTGC
93101 CTGCCTCCTT CACATCGAGT CTCAGCCCAG CTCAGCCATC TCTTCAGTCA
93151 GTACTTCGCT GACCTTCCCC TTTGGCCCCA CTCCTACCCC TCTGTACATC
93201 TCCATTACAT TGCCTTTGGT AATGTCTTCT TAGCACATAT CGATTTGTTT
93251 ACCTATTAAT TCCATGCCAT GAGAGGAGAG ATTCTTTCTT TTCTCTTTTT
93301 TTTTTTTTTT AGAAGGGTGT TGTTCTGTCA CCCAGGATGG TGTGCAGTGG
93351 CATGATCTCC GCTCACTGCA ATCTCTGCTC CCTGCCTCCA AGGTTCAACC
93401 TATTCTCCTG CCTCAGCCTC CCAAGTAGCT GAGACTACAG GCACATGTCA
93451 CCACGCCCGG CTAATTTTTG TATTTTAAGT AGAGATGGGG TTTCACCATG
93501 TTGGCCAGGC TGGTCTCAAA CTCCTGGTCT CATGTGATCT ACGTGCCTCA
93551 ACCTCCCAAA GTGCTGGGAT CACAGGCGTA AGCCACCACA CTCAGCCTGA
93601 GATCCTTTCT TTCTTATGGT CTCCTGAATC TCTAGCATGG AAGAATAAAG
93651 GTGCCGTAGC ACAGAATAGA TCTATTATCC AATGAATATT TGTTGGAGGA
93701 ATGAATCAAT CCTCTCTTTT TACAGAGGGA GAAGTTAGGA CCAGAGAAGA
93751 GTAGACATCA TTGTGTTTCT GAAGGTTTTA TGTTAGCACC TTTGGGCCAT
93801 GCTGGGACCT TGGCAAATTA TAGCATTCAA GGGTTTTAGG GTAATGTTCA
93851 TGGATCCCTA GAAAGTCAGC AAATGGGGAT CAGGGTGTCT TGAGCCCTGT
93901 GAAAGTGTTG GCATATTTCT GGGGAGAAGA TTCATAGCTT TTATTAGTAC
93951 TTCAAATAGA TATTTGATCC ATTGGTAGCA CCCATCAATT TTTCCTTTTA
94001 ATTAGCTTAG TTTGGGGAAT GTGGAGCGAG CCTAAAAGAG GATAGATGTC
94051 TCAGCACCAC CTTGAAGACC TTTCTTCTTT TTCACTGACA GCATGGTTCC
94101 ATCGTTCTGC CCCTGAATAC GGGGACAGCT CCTCTTTTTC TATTACCAGA
94151 GCATATCTTT CTTAAATTCA CTATTTCCAT GATGAATCTA CAGTGCCAGA
94201 AGCTAGAGTC TGGAATCAAA GAATTCCAGA GTTGGGAGAG CACTTAATTC
94251 AGTGTTCATA AACCAAAGTG TACAGCAGAA TTTTCTGGGG AGCTTTTTAC
94301 AACTATGCGT TTCCCACTCC TTCCCCTGAC TTTTATTTGT TTGTTTATTT
94351 TTGTTAGAGA TAAGATCTTA CTCTGTCACC CAGGCTGGAG TTCAGTGGCA
94401 CGATCACAGC TCACTATAGC CTTGAACTCC TGGGCACAGC AATCATCCAC
94451 CTGAGCCTCC CAAGTAACCA GGACTACAGG GGGTGTGCCA CCATGCCCAG
94501 CTAATTTTTG TATTTTTGGT AGAGACGGGG TTTCATCATG TTGCCCAGCC
94551 TCATCTCAAA CTCCTGACCT CAAGCAATTC TCCCACCTCA GCCTCCCAAA
94601 GTGCTGGGAT TACAGGCATG AGCCACCACA CTTAGCTAAT TGTAGTATTT
94651 TTGGTACAGA TGGGGCTTCG CCATGTTGCC CAGACTCATT TTGAACTCCT
94701 GGGCTCAAGT GATCCGTCTG CCTCAGCCTC CCAAAGTGCT GGGACTGCAA
94751 GTGTGAGCCT CTGCACCCGG GTCCCCTGAC TTTTAGAAGT GGAGTATATT
94801 AGGTTCCTAG TGTTTCTGTA ACAAAATTCC ACAAGCAGGA TGGCTTAAAA
94851 CAACAGAAAC TCATGGTCTC ATAGTTCTGA AGGATAGAAG TCTGAAATGA
94901 AAGTGTTGCT AGGGCTGTGC TCTCTCTAAA ACCTGTAAGT GAGAATCCTT
94951 CCTTGACTCT TCCTAGCTTC TGGTGGTTGC CATCAATCCT GGGTGATCCT
95001 TGACTTGAAA CTGTCAAAGA ACTCCTGCAC TTTAATTTCC TCCTCTGTCA
95051 CCACATGGCT CTTTCCCCTC GTGTGTCTGT GTGTCTTTTC TTCTTATAAG
95101 GACACCAATC AAATTGTATT AAGGTCCACC CTACTCCAGT ATGACCACAT
95151 CCTAACTTTT TATGTCTACA ATGACCCTAT TTCCAAATAA GGTCACATTC
95201 TGAGGTACTG TAAGTTGAAA CTTTGTTTTC AGGAGATACC CAAAACATGA
95251 CATGACATGG GGTATGGGAA TCTGTATTTT TTAAAAAAAC TCCACCAGTG
95301 ATTGTGTTGA GACACATTGC TCTTATACAC ATGCCCTTCA CTGAAAAGGT
95351 GAGAGAAACT GAGGGCTGGG AAAGGGACAA GCTCAGAGTC ACTCAGAGTC
95401 TCAATCACCC AGACTGGGGC ACCAAGTATC ATGATTCCCC CAACATTCTT
95451 TCTAATGTGC CAAGCTGCCT TTTGGAGTCT GGACCTGGTG ATGCTCTCAC
95501 TGGTCTCCAA GGACCAGCAT TTAAGTGAAT ATTTCCAGTG GTCCATGTCT
95551 GCCCCAAGGG GCTACTTACT ACTCCAGTGT AACTAGAGGG GCATTAGTGG
95601 ATCTTTTGGT CAAATCAACT GCCTCCATCC CAAAGGATAT GGTTTTGGGG
95651 CAAGTTGGAC TACTCCAGCA GTCATGGACA GGCACCCCAG CTTCCTCCAA
95701 GTTGTACTCA TGTTGCCCCA AATTACTGTG GCGGATGGCT GGTACTATGA
95751 TGAAATTCTG TGTTATATGT GTGAGAAGAC TTCCTTCCTC ATCCATCACT
95801 TACCCAGAAC ACTAACATGT GGTATATATT AACACGATCC TCTCTTGGGT

95851 TAGCATGTGG GTGGGTTCTT AGGAAAATAA ATTAACATCT GGAAAGACAA
95901 CCCAAGCCTT GCCCACAGTG TTTGAGATGT TACTCAGTGG AAATATTGGT
95951 TGTCGTGCCC AATTTGTGTC CCCTCCCATT GTGTTTTTAT GCTGGAAGTC
96001 TGCACAATCT GTTGATCCCC GTCTCAACTG GCTCCCTCAC AGCAGATGCA
96051 TTTAAAGTCA CAGATCTCAA AGTAAGCAAA TCTAAAGTGT TTAATCTATT
96101 ATTAATCAGC TAGTTGCCCA AATGATAGAG CTCTAGGGGA CCCTGAGGAA
96151 GACATCAATA TTTATGGCCT CCTTAGGGAG TGCATATTTT TCTCTCTCTC
96201 CTTTATTCCC ACCTTTCTTG CCTTCAGATG AGAATGGAAA TATGAAGCCT
96251 GTTATGTTTT ATGCCATTGT ACAAGGCAGG AATGTCATGT TTTGAAATGA
96301 GATGACTACA ATGTGGTATT TTATGTTTGT TTGAGAATAT TAGCTGTTAG
96351 GGCTGTGGTA ACCTCTACCA GATTGGGTTA AACAAAAGCA GTCTGCAGTC
96401 CATGATAATA CAATGGAAAA GCATAGGGAA CACAAGAAAC CTGGGTGAAC
96451 TTTTTCACAA ACAATTCATT TTTCTAATGA GGCAACTAAA GCTCAGAAAA
96501 GGAAAGGGTC TTCCTTGTGA TCATACATTC ATTTTATCAT TCAACAAACC
96551 TTAACTGAAT ACCTCCTATT CAACAGTGCA CGAGCTGCCA GGAACAATGA
96601 AGTAAGTATT AACAGAAATG CCTAACATTT ACTGAGCACT TCTTAGGTGC
96651 TGGGTACACA CTAAGTCCTT CAAGTAGTCT CTCCTGCTGA AAGTGCTATT
96701 CCAAGTGCAA GTTGGAACAG CAGGTGCCTT GGCACCAAAG CTCTATGTGA
96751 CCGACCTTTC TGACCTGGCC TCACTTCCTT CCCCCTCCCC TCATTTCTCT
96801 CTCTTCTCTC CCTTTATTTT TCTTTTCTTT CTCTCTCTCT TTTTTTTTTT
96851 TTTTTTTTTT TTTTTGAGAC AGACTCTTGC TCTGTCGCCC AGGCTGGAGT
96901 ACACTGTCGC GATCTCAGCT CACTGCAACC TCCACCTCCC GGGTCCAAGC
96951 AATTTTCCTG TCTCACCCTC CCAAGTAGCT GGGACTACAG GCACCCACAA
97001 CCATGCCCAG CTAATTTTTG TGTTTTTAGT AGAGACAGGG TTTCACCATA
97051 TTGGTCAGGC TGGTCGTGAA ATCCTGACCT CAGGTGATCC GCCCTCCTCG
97101 GCCTCCCAAA GTGCTGGGAT TACAGGTGTG AGCCACTGTG CCCGGCCCCT
97151 GTCCTCATTT CTTATGCTCC AGCCTCAGTG GCTTTCATTG TTACTGTTTT
97201 TGGAATATAA ATCAGGCTTA TTGCCCCTTT GGACCTTTGA ATCACCTGTC
97251 CATGCTGACT AGATTCCTCT TCCCATCCTC ATTTCTGGCT ACTCATATTT
97301 CAGGTCTTAG CACAAAATCT TTTTCAGCAA TTTCTTGAAA GTGAGTCACC
97351 CCATTCTCAC CCATTAAGAG ATAGTGACTA TCGCTATCAT AAGATAGTCA
97401 CTATCTCTTA ACAAACCTGT TTTAGTGTCA TCCTACACAG TGATGTGCTG
97451 TCAAATCCTT AACACCTGAG TCTGATGGGG TGGTGGTGAG GAGGGGGAGT
97501 GTGGTGAGGA GGGGGAGTGT GCTGATTTCA AGCATTTGCC AATTTTCATG
97551 ATGTAAAGAC CTTTACTATG GCTGATTCAA TAGTTCAAGC TATCAGCATG
97601 ATGTCACTGA ATGAGAAGTT GGGAAGAGAT ATACACAGTC CACTCTTGTG
97651 AGCCACTATG CACCAGCTCT GACATACTTC TTGTTGTCTG AAATTATCAT
97701 ATTTATTTGT TTAGTTGTAA TTCTTTTACC CTCCTATGCA ATGTAAGCTC
97751 CAAAGGAAGA GGAACCTTAT TTGTTCTGGT TATGGTTGTA TTTCTAGCAT
97801 CTGGAACAGG GCCAAGAATA TGATAGTAAC TTAATAAATA ACTGTGGAAT
97851 GAATTATGAA TGAATGAATG AGAATTCTCA CAATAACTCG GTTAGGTAGG
97901 TGCTACTATT ATCCTCATTC ACCGAGTAAG GAGACTAAAA TGTGGCTAGA
97951 GATTAAATAA CTTGTCCAAG CTCACACAGT CAGTGCATGG GATTGCCAGG
98001 ATTTGAATCA AGGCAATTTT TCTCCAGAGT CTCTTCTCTA AATCCCAAGT
98051 TATATGAATT TAACAAAGTC ACTCCTCTTG AAGAGCTCAA AGTCTAGAGA
98101 AGAAATAGAC ACTTGAACAA AAGGGGAATA ATGCACCCAT GACAATGACA
98151 AATATGTACG TAATATACAC TCAGAGACCT CGGTGAGTGA GAACCAGGAG
98201 AGTGGCATGG TGATTAAGTA AGGTAATATT TGATGGAGTC TTGGAGGATA
98251 TCATTGGAGT GCTTTTTCCA CCATGCCAAA GTTGCTTCCC ACCTGGAAAA
98301 ACTGACATTA TGAAATCTTT CTTGGATAAG GAAGAGAAAT CAGGCTTTAC
98351 TCAAATGTAA AGAAAAGCAC AGAAGCATTA TTGAGATGGT TTGAGGGTCA
98401 GCCGGATATT TCAGTACACA AGAAAACTGA TAGTCCACTT GAGGCACGTT
98451 TCCAGACAGG GTCTTAACTT CTCCTCACTG CTGATCTTGT GACATGTTCT
98501 CTGATGAAGG GCTTTTTTAA GCTCTAGGTT GAATTGCTCA CCCATTTCTG
98551 CTTCTGATTC TTTGCCTCCT GCATCAAAAT TTCAGGTGGC TACTCACCTG
98601 GGATGGTAGT GTGATATAGT TTGGATGTTT GCTCCCACCC AAATCTCATG
98651 TTGAATTGTA ATCCCCAATG CTGAAGGTGG GGCCTAGTGG GAGGTGTGTG
98701 GGTCATGGGG GCAGATCCCT CAGGGCTTGG TGCTGTTCTT CCAATAGGGA
98751 CTGACTTCTC ATAAGATCTA GTTGTTATAA AATGTGGCAC CTCCCCCACC
98801 ACCCTCTCTC ACTCTTGTTT TTGCCATGTG ACATGCTTGC TCCCACTTCA
98851 CTACCCACCA TGATTATAAG CTTCCAGAGG CCTCCCCAGA AGCAGATGCT
98901 GGTGCTATGC TTCCTGTACT GCCTGCAGAA CTGTGAGCCA ATTAAACCTC
98951 TTAAATAAAT TATCCAGTCT CAGGTATTTC TTTACAGCAG TGCAAGAACA
99001 GCCTAACACA TAGTGAGTGG ACAGAGTACT ATTGCAGTCT CTGATTGTTC
99051 TAGTAGCCAG GCTTGAGAAA CCACAGAGTC ATCACTGACA ACTGCCTTGG
99101 CACTCCCTGC CTCTTCTTCT CCCCTCCCCA ATCCCAAATA GCTACTAGGT
99151 TCCTTTGTCA GGTCTTGCAT CATACCTTTC CCTTCATCTC CACAGCTATC
99201 ATTCTGGTCC AAGATATGGG TCTATTCATC CACTCATTCA TTCAACATAC
99251 GCTGAGTTGT TGTCTGCTCT GTCCCAGGCA ATGTGGTAGG CTCAGGGAAT
99301 ACAATGATAA CCAAAAGCAG ACATGACTCC TACACTCACA GATCCTATTT
99351 CCAGGGGGGC ATATTCTAGT GGGGCAAGCA GTTGTAAATC AAATAACCAC

FIGURE 3, page 28 of 122

99401 CTGCATAAAT GGATAATGCC ACTGTGATGA AAATTACCAA GGGGAGAAGG
99451 ACATGGTGCT GGGGGAGTCT CTAACAGGGC ATTTGACATA ATCAGGAACA
99501 CCAGGGAAGT AGTCACATTT ATACCAAAAT CTTAGGTTCT AAAAAATGAG
99551 AAAGCATTAA GGTATCGAAT GGAGGAAAGG TCATTCCTGC CAATTGAAAA
99601 GACATGTACA AATATTCTTC AATGGAAGGA CCTTAGCTCC TGCCAGGATA
99651 GTGAAAAGCA GGTTGGTTTG GATGGGGACA GAGAACACAG GCAGAGAATG
99701 ATGTGGGATC AGGCTGAATA AATACGGCAG TGTTAGCCTC TGTGTCTAGA
99751 TATTTGAGGG AATCAATTTT TGCACTCCCT CTATAATACC TAGTCTCCCC
99801 TTCTGGCTCA TTTTGTGCAC CCTTTGCCAA ATTCCTCTTT CTAAAGCACT
99851 GGGTTTGTGT GTATGTGTAT GCACGCACTT CCCCCAACCC CCATGCCTCC
99901 ATTACTCCTC TACTCCAAAA AATGTCAGTT GTTTTTCTAG TGCCTGCAAT
99951 GTAAGGCCTA AGCCCACTGG CATCAAAGAC TTCTGTAATT TAGCATCAAC
100001 TAAACTTTCA GCTGTCACTT CCCACTGTTG GGAAACCATA TAACATGATG
100051 TTAGAACATA GTGACAGAAG GAGCTTTGGA GTCAAATAGC TGATGTAAAT
100101 CTTGTTTCTT CCATTTTCTG CCTTTGTGAC CTAGGATAGA TTGCTTAATC
100151 CTGCTGAGCC TATGGTTTTA TACTTTTAAA TTGAAATTAT AGTGTAAAGT
100201 TTAAATCAGA TAATTAAATA AAGCCTTGAG CATAATCCAT GATGTACTGA
100251 AAGTAATGAT TAAATAATAG TCTATTAGAC TATACAGCCT ACTCACTATC
100301 TCTCATTCTT ATCTAGTATT TACTAGCTAG TTAGGCACTA TTTCTATTGC
100351 TTAGAACAAC TTCTTTCGCA TCTATCCAAA ATGTATAACC CTTTGGTCAC
100401 CAGATCAATA TCTTCAGCTC CTTCCTTTCA GGTACTATAT ATTGCATTTG
100451 CTTCATAACA CCTAATACAA TGCATGAAGC ATGCTTTTAA TAAACATTCC
100501 TTGGATGGAT GAATAAATAA ATGAATAAAG AAATGAAGTA AAAGAAAGTC
100551 AATTTTTATA TTATTCTAAG TGAGGGAAAA AAGAGAAACG AATCAAAATA
100601 TCTTGGAAAT AAAATTCTGT TCCTCTCTGA GCTTTTGATT TGTTTATAAG
100651 CTGGGGAGCA TGTTGCTTAC CATTTATTTA GTCTCACAAG TATGTTAACA
100701 TCATCAACAT AAGGTTTATG AAGTACTTTA TACTGCCTGG AGGAAGGATG
100751 GTATAGAAAT TTAAAATATT ATATATGATC CTTCCAGGAA GAAAAAAAGA
100801 AGCAATATCT ATTCTGTGAG GTGCATCAAT TTTGGATCAC TCTAATGGAA
100851 GTGCCCCGAG CAGTTGGTTT ATTTCTTCAA ATGTGAATTA ATTTATACAT
100901 TTCAAAGCTC CTGATGGATA CTTTTCATTT TAATTAAGTA CATTTTTGCC
100951 AAATTTCAAC TTTAAAAACT CAACAAATTT GTTCCCACAC TTGCTTTGTA
101001 GAATTTGCAA TATTAGATAT AAATTTATTA TAAAAGGGTA TGTTAGAAAC
101051 TTCTCATACT GAAATCGGCC ACCCAGCAAC TTTTTCTTAG GATTCAAGTG
101101 CTCTAACATG TGCTTGCTTG TTTGTCTGTG TGATTCGGTG GTTTTATTTT
101151 GATTTTCATA GAAAATAATA AATATGTCTT GAAATGATCA TTTCATTACT
101201 GAGTATTGCC AGAGGTTCAG AGTCCTTGTG TGCATCTGCA TTTACTCTCA
101251 GGTTGGCACT ATAAACTGCT ACTGCAATTG TGATAAACTA TCGAGAACAG
101301 AAAAAAGAAA ATTTGATACA GAAATAATGC ATAGTAAAAT AATGCTGGGT
101351 GAGGGCTCAC TGACATAATA ATGTACTGTA TGGAAAAAGA GGGAAGATGC
101401 TGTTGAAGAA ACTGAATATT CACGCAGCGC ACAGTAGTTC AGGTGTGCTG
101451 AGCTCACAGA ATCAATGTGA TTGCACAGTA CTATATTGCT GTCACAAATG
101501 GTGTTTTGGA GTAAACAAAT ACCATTGTTT CTAACATTAA ATTAATATTG
101551 GTGATTCAAA ATGTACTGAA ATTATAATTT GTGTTTGTCT CATTTGTAAA
101601 TTTCCTTTGG TTTTATAGTT TTAAGATAGC TATAAATAAA GGATTGATCT
101651 CTGACTTCAT GTTTGTACAT TTTCAAGTAT CATTATAGTA AATATAATTT
101701 GTCAACATTG TGGATTCAGA AGAACAGTTT CCTTCAAAAA GCGTTCATAA
101751 ATTACATCAG TTCGAAAAAA TTGCATTAGT AGATGATAGT AAAAGCCTCC
101801 AAGAAAGTGT TGCATTATGG CCAAGCTTTA TTATACCAAG TTCACAAAAC
101851 ATAAAGGGAG GAATCAGAAA TGCAGAGAAT GGCAGATATG GAAACAGCAG
101901 CTTTGCAGGT AAGAGTAAAA TACTGAAGTT CTAAGAGGTT TTTAGGGTTG
101951 GATAAAATGG AAAAATCAAG ACTGAGAGAC CGCCAGAGTC CTGTGAGTAT
102001 TGTTGATGAA CTCTTAAAAT GTGCAAACTC AACAAGCTAT TGAAATGTGT
102051 GTGTGTGTGT GTGTGTTACA ATATATGTAT CTCTTCTTCA ATGCTTTGGA
102101 GATCTTTTTC CTACAGGACT ACTTCTCTAA TTTACCAATA ACAGGCTTTG
102151 TGGAAATGAT ACCAATTTTA AAGAAATTTA CTTTACACCT ATATTTTCCT
102201 AAAAAAAAAT TTGTGAAACA AGGGCATCCT TATTTTACCT CTTCAAAACT
102251 GTTATCTATA CCAAGTTATC ATAAAAGCAG TAAACCTGCA TTTGTTAGTT
102301 TTTAAACTTT ATTTTCAACT TCCTATGTCT ATAAATGTTT GTTCTTGTTT
102351 AGGATGTGTA CTGTGCTTGT TAGAAGAATA CCACCTTTTT TTCTTACCCT
102401 TTTAAAGTTG AGAAGATTAT TTGTAAGAGT GTGAAATGGT CTAAGCATTG
102451 CCCCTTTAAA TGGGGGTATT GTGTTAATTG TAAGCACTGC AAAGTGGGTT
102501 GCTATATTGT GGCTGTTGTA CTCAGTGTCA AAAGATTTAG TTCCTTCTTG
102551 ACCCAGTCCT AGTTATTCAA GAGTCATCAA ACAGAGATAC ACAATTTTAA
102601 ATTGTTTTTC AGAATGAATC TGAAGAGAGC GAAGAGTTGA GTGGAGAAGT
102651 CAGCTAGATC ATCCTTGTCT ATCTATGCAG ACTCCTTCCC ATAATTTTTC
102701 CCCAATCTAG TTTATGCCTA ATTTTATACC AGGAATTTCT TCCTGACCTT
102751 TTAATTGCCT GTCCTTAGGG CATGAAAATT ATGAGTGTAA TTTTACAGAC
102801 CATTCTTAAC TTTTCAAAAC CATTCCAACG ATATTCATCT AAGAAATGGC
102851 CAGTGTTTGT GGAGCACTAA TTTGTCACGC AGCATTGTGC TAGACATTCA
102901 AGATATCCCA TTGAGTATCG CACGAAAACC CTGACCAACA CATCCCTATA

FIGURE 3, page 29 of 122

102951 CCAACTAGGT CAGATCCTCA TTCACAGGTA TTCATAATAC ATAAAATTCC
103001 CCTGCATAGC ACTAGGTCAC ATGTAGGCAA TAATTATTTA TCTTGTATAT
103051 GCCTTTTCAC TCAACTGTGA GCTCCTAGAG GACATAGGTA AAATCTGTTT
103101 TGTTCACTGC TGAATTCCTA GAACCCAACA TAGTATCTAG CACCAAGAAG
103151 CACTCAATAG AAGTTGGATG AACTAAAGAA GAAATGGTTG GTCTAGGAAG
103201 GGGTTGGGAC CATAAGAAGC ATACTGTTAT TTAAGAAGCA AGGAAGGCAT
103251 TTAAAAAGCA CAGAATTGAA TAAAGGCAGA TTCCTGCAGC AAGAATGCCA
103301 CACAAGTCAG AAAGTAGGCC AGATTATTAA CTACAAACTA AGGAAGTAGA
103351 ATAACCTTTT GTGATTGCAA CATGAAAGCA AAAGTCCAAA CCAAGAATCA
103401 TCTCAAAAGA TAGAAAGTAT ATTAGGAAAA CATGCTTTAA CTGTACCCGG
103451 AAGAAAAAGA AGTGGGCTAC CCCTTTTAGT GTGTGAGGAG GGAAAGCAAA
103501 TGACTGATTT CAAAAGGCAA AAACATCTCG GGCTTTATTC TTTTGCCCCA
103551 CCTTAGTTTT TCTTTCCCAG AGTAAAGGCA GTGATATTAT AAAAGCACAC
103601 AGCATCCAGA GGGGTTGGGG AGGAGTATGG CCATGAAACT AAGGGCTGAT
103651 GAAAGATGAT TTTAGAAGTT GGTTCTTTTC ATAGCAAGAG GCTGTATTCC
103701 TTGAACTGTC CAAGCCATGG CCTGTTGTTT TTCAGAACTC ACAGAAGGTG
103751 GTAAAGGTCA GAGAGTGTCC CTGAAACTAG TAGATGGCTC TAGATTCCAT
103801 TGAATTCCTG CCAAGGGGCC TGACAGCATA GATGAATTCT ACTACTTCCA
103851 GCTTCCTCTA GAGTTAGCAG AGTCCAGGTT TGGGAGTCAG GAGACCCAGA
103901 TTCTAGTCCT GTCTGTGCCG TGGTCTCTTT GTGGTTTTGA GCATATCACT
103951 TTATCTCTTG TATCCTCAGT TTCCTCTTGT GTAAAAAGGA GATTTTTCTC
104001 ATCACTAGTT GGTAGGACAA GGACATTTTT AATTTATTTT TTCTCCCTAA
104051 ATAATGCATG CATAACTTAC AAAATCAAAT GTTACTTCAA GTCATAAGAC
104101 AAAATTCAAC ATTCTCTTCC CTCCTCCCTT TCTATCTTGG ATTCCAGCTC
104151 TCATAGGGGA TCACTTTAGG CTCTCTTAGC TGTTTCTTCT GATATTTTAC
104201 CTTTGTATCT CTTGTATTGC CTGTTCTGGT TTGGGCTGCT ATAACAAATA
104251 CTATAGACTG GGTGGCTTAA ACAAAAGATG TTTATTTCTC AGTTCTGGAG
104301 GCTGGGAAGT ACAAGATCAA TGTGAGGCCA ATTTGGGTCT TGGCAAAGAC
104351 CTGCTTCCTA GTTTACAGAT GGCCACCTTC TTGCTGCATC TTTGCATGAA
104401 AGAGAGAGGA GAGACAGAGA GAAATTGAGT CTCTTTCTCT TCTTAGAGTC
104451 TCATCATGGG GCTCCACCCT CGTGACCTCT TCTAAATCTG ATTAACTGCC
104501 AGGCGCAGTG GCTCACACCT GTGATCCCAG CACTTTGGGA GGCCGAGGTG
104551 GGTGGATTGC TCAAGGTCAG GAGTTGGAGA CCAACCTGGC CAAGATGGCA
104601 AAACCCTGTC TTTACTAAAA ATACAAAAAA TTAGCCTGGC TTGGTAACAC
104651 ATGCCCGTAG TCGCAGCCAC TCGGGAGGCT GAGGCATGAG AATCACTTGA
104701 GCCTGGAAGG TGGAGGATGC AGTAAGCTGA CATCACGCCA CTGCCCTCCC
104751 ACCTGGGTGA CAGAGTAAAA TTCCATCTCA AAAAAATAAA AAATAATAAT
104801 AAATCTGATT ACCCCCCAAA GACTCCATCT TCTAATCCTA TCCCACTAGA
104851 GATTAGGGTT TCAACTTATG AATTTGTGTA GGGGGCACAA ACATGGAGTC
104901 CATAGCAATG CCGTTTCCTG ATTTTTCAAT TTTAGATATT AGTTTTTGAC
104951 TGTACTATGG CAGATGCAGA ATATTAAATT AATATTCAGT ATTTACGTTA
105001 TGATGACTAA ATAAATACCT TCACAACCAA GCCAAATAGC ACACTCTTAA
105051 ACTTTTTGTG TTTCTGCTTT ATTGTTTTTT GTTTGTTTGC TTGCTTGCTT
105101 GCTTTGTTTA TTTTATTCTG CATATTTTAT CATTGACTCA GATCCAAAAT
105151 TTCTGAGCAA ACCACAGAAT TCCTCCCAGT TACAATCAGG AGTGTGAGAT
105201 GATCTCTCAG TTGCATGGTT TTCCCAGAGA CCTTCCTCTG GGAGCCCCAT
105251 TCAGCTGAAG CCTGACCTGG TTGCTGCTGT GACCTGCAGG AGAGCTATCT
105301 TCCTGGGACC AACACTTTTC GCTAGTTCAG GCTCTCCTAT TCTCTATATC
105351 TCATTCTTCC TCATTACCAG TTATGCTCTC ATTTTGGCAG AATGCATTTT
105401 CCCGTAGTTT CTTAAGAAAC ACAACATGAG GGTAAATTTT TAGATCTTGC
105451 ATATTTGAAA TAGTTTTTAT TCCACTCTTA AACTTCATTG ATTGGAGATG
105501 AAATGCAAGC TTGGAAATAA TTTTTATTCA GAATTTTGCA CACATTATTT
105551 CATTATCTTC TTTTTTCCAT TGTGGCTGAT TAAAAAGTCC AATGTTATTC
105601 TGCATGCTCC TTCTTTGTTT GGGATTTATT GTCCCTTCTC CTCCTCCAGA
105651 AGCTGTTACG ATTATCTTTT TGTCTCTAAA GTTCTAACTT CAAGACGATC
105701 GCCTTTTTTA ATTCACAGGT CATTCATGGG GCTAGAAAGA CATTCTGTAA
105751 GCTTTTTCCA CCTGAAGACT CAGACCCTTC AGTTTTAAGA GATTTTCTTT
105801 TGTAATTTAT TTGATATCAT CCTTGCCTTC ATTTCTGCTC TTTCATTTGC
105851 AGTTCCATAT GTTAGGCTTC CAAGATTCTA TTTCTTTGAC TTTTATTTTA
105901 TTTTTTGGGT GATACCTTCA ACTTCGTCTT TCAGTATTTT TGTCAACTAA
105951 TATATTTATC TACTGCATTA ACTTCCTAGA GTTCTTTTTT GCTTTTTGAT
106001 TTTTCCTTCA TTATAGCATT CTATTCATAC TCTAGAATGA GTGTATGTTT
106051 TTTTAATGTG TTCTTTTGGT CCCTAAATTG TGCTTGTTTC CCATGATTTA
106101 TTTTCATTCA TTTGCTTGTT AATTTTAATT TCTCCCTCTC CCTCCTCCAT
106151 ATTTAGAGGC CCTTGACTAT CTGCTCTTAT AAGTACCACA AAGCCAATGG
106201 GCTCTTCTGC ATGCAAGTAG GAAGATGGCC AGTAAGTGTC CTCTCCCTTA
106251 TTCTCAGCTA TACCTGGTGA TCCTAACCTA GAGTCTAAAT ACTTTGTCTT
106301 CTTCAGAGTC CACCCCCAGT CTTCTGCTTG GCTGAAAAAG AGGGATTACC
106351 TGGCTGCATA GGCTAGGGCA GGGGCTCTGG GGCTTTCCAC CAGGTTTTAC
106401 CCCATCCCAT ACCTCAGACT TCAAAGTATC CAGTGCTTCA TATTTTTACA
106451 CCTTTCTTGT GATCTGTGGT TTTATGGCTT TCTTCTTATT GACTCTACTC

FIGURE 3, page 30 of 122

106501 ACTTCCTCTT CACAGATGGT TATTTCAGCT TTCTTCACCT TGCTAAGTCA
106551 GTTACCTTCA TCCACTCTCC ATCCTTCAGA TGTTGTACTT CCTTTGTCTT
106601 CTCTTCCCTC TTTTAAGTTT CTCTTTGATC TGTATATTCA CACCTATTTT
106651 ATTATTTTGC TGTGATTTAT GTGAGTTTGG GGGAGATAGC AAAGATAAGC
106701 ATGTATGTTC CACATCACAT GCATCAGACA CAGTGTTGTG AAACTGTAAT
106751 TTTTAAAATA AACTTTTATT GTAGTTTTAG ATTTACAGAA AGTTCACAAG
106801 GTTAGTTCAG AGAGTTCCCA AATACTCTGT GCTCCATTTT TCTCCCCTAT
106851 GATTAAAATC TTACATTAGT GTGGTGCATT TGTCACAGTT AATGAACCAA
106901 TACTAATACT AATACATTAT TATTAACTAA CACTAAATAC TTGTTTAGCT
106951 AGCTCTTTGG AAAGAAGTCA CTATGTCCAG TCTACATTTA AGAAGTGATG
107001 AGTTACACTC TACCTCTTTG AGGGCAGAGT GTCTATGTAA ATTATTTCAA
107051 ATTATTCTGA CTGGGAAATT TGTTTCTTCT CACTATTTAT TTACATATCC
107101 AGTCATTTAT TTATATCAAT ATGGATTCAA GGATATCTAT TTTATACTTT
107151 GGGTTATAAT TCAATACCAT TTCATTTATT TTATTGCTCA CATTGTGAAA
107201 TGCTTTTTAA TTGTAAACCT TTATCTAAAA AGCAAGATAT GAGTTAAATA
107251 ATATAATATA ATATATATAT AATTAATATA TATAATATAA TGTAAATACG
107301 GTCTACATCT TAGAAATAGT TCTTTAGTCC TTTACTAACT AACAAAGTGC
107351 TAGACACAGA ATGCTGGGCA GGCACATAGG ATTGGAACAC TAAATACTTC
107401 TTTGGCTAAC TTAGTGCTTT TAAATATATA TTCAGTCATT TCTAAATTCC
107451 CAGTGTCATG TTCCATGAGA GGTCACATAG ATGCATAAAA GCTCCCTCAA
107501 GGACTGTAAC CTTATTAGGG AAATACACAT ATATAGACAA TAAAAAAAAA
107551 AACAGGTCAA CACTGTCACT AAGTAGCAAA TTATGTCATT TTCATAGTTT
107601 AAGAGTGACA GATTTCATGG CCTGAGTGAT CAATTTGGAT GCATCCATCA
107651 TGGCTGGCAT CCCAGAAAAG GCTGGGAATG ATTTAGACAG AGTGAAATGA
107701 GAGAGTCTTT TAACCACACA GGGTATAACA AGTATGCATC TATTCTTTTT
107751 GGAATGTTTA AAAATTATCA AATCAGAAGC ATCTTAAAAT TCACTTTTCT
107801 TTGAAAAATG TATGCAAGAT CCAGCCACTT TATTTTTGTT CATATTTGGT
107851 TTTCGGCTCT GTCCACATGT ACATTTCAAA ATCCAACAAA CAATTCCATT
107901 GTTTATACAT TGTGGCTTCC AGCTGACAAA ACCCCTTTAT ACACTGGCTC
107951 ACTGATCCCC ACAGCAGGCC TGTGAAAGAG GCAGTTACAA CAGGTATTAC
108001 ATAGAGCTCC ATTTTGCAGA TGGGGAAATG GAGGCCCCTG ATTTTCAGGA
108051 GGTTGCACAG GTACAAATGG GAGAGGTGGA TCTAGAACTC AGCACTCCTG
108101 ACTCCAAATC CAAGGCTCTG TTCATCAACT TGGAGCCCCT GTTCTGACGC
108151 TGGAAAAGCT GGGTGGAGGA GAGGCAGGAG AGATGGAGAC TCTAAAAACT
108201 CAGTGTTGTG GTTTGTTAGG TCTCTGGTGT CCTTACTCTC CCTTCTCAAA
108251 TGAAATGTAA TATCTCAGCC TTAGAGATTA AAATGGGTTG CCAGTTATTC
108301 TCCTTCCTTT TCCAGGAAGA GGGGATTCTG CACCACTAAT CTTTGCTAGT
108351 TGAACAAGTT GTTTAATGAA AAATCATATT TGTTTGCTAA AGCTGGTCCC
108401 ACCGGCAAGC CGGTGCTAGT GCCACTCAGC TGTCATACAG GCTGATGGGT
108451 CAGGCAAGAG GTGGACCTAG GGTCTCTGGG AATGGTCTGA GCTCACCCGG
108501 TCCCGTGGCC TCCCCAGGCA TTCTGCACAC TTGGCTGTCT GCAGCCTCCT
108551 CTGCTAGGAA TGAAGCAGAG AGAGCAAGCA AACACCACCA GGAAAGCTTC
108601 TTTAAGGTCC TTTGAAGGGT TCACTCTGCG GGAGACTGAC GGTTTTGAAC
108651 ATTTCAGCTC TGCAGAGCCT TAAGCCCTGT TTTGAAGGGG CGCTTTGGTC
108701 AATAGAAATT TGGTCCTTAG AACTCACTTT CCCTCTTTTC CTTTGTATAC
108751 TTCAACTCTT AGTACGTTCA GGGACTACCT GAATATGAAT TGGTTATTGA
108801 GACTTTCAGA GGCAGGATCT CTGAAGGTCT GTGCCATGGA TCCTGCACCC
108851 CATTTTGCAA TTTTGCATGT TATTCTTCTT TCTAGGTTTG TGGCCCAATT
108901 AGGGGATCAC CAAATCTTTT TCAAGAACTC AGGTTCTATA GGCAGACTGC
108951 CAGGGTTTGT ATTCTGGTTG CTTCATTTCA CATCTATGTG GCCTCAGACC
109001 AGTTATTTAA AGCCTAGGAG CCTCACTTTT CTCATCTAAA AAGAAGCAAT
109051 GAGTTCTTGC TTCAGAGGAT GATTGAGTAT TCAGTGAGAT AATGCAATGG
109101 TCCCTAGTAC ATAGAAGCAC TCTTAAAATA TTAACATTAG TTTTACCTAT
109151 TATTGAATAA ACTTTGCTAT TTCTGAGTGC CAAAGGAAAT ACCAAGATGG
109201 CTAAAAAACC ATACTTGCCC TCAAGAAAAT CACAGTCTAG CTGGGTCCAG
109251 TGGCTTATGC CTGTAATTCC AGCACTTTGG GAGATAAATG CAGGAGAATT
109301 ACTTACACCT AGGAGTTCAA GACAAGGCTG GGCAACATGG CAAGACCCCG
109351 TCTCTAAAAA AAAAAAAAAA ATTAATTAGC CTGGTGCTGT GGCATGTACC
109401 TGTAGTCCCA TCTACTCAGG AGGCTGAGTT GGGAGGATTG CTTGAGCCTA
109451 GGAGGTCAAG GCTGCAGTAA GCCATGTTCA TGCCACTACA TTCCAGCCTG
109501 GGTGACAAGG TGAAACTCAG TCTCAAAAAG AAGAAGATCA CAGTTTAGAA
109551 GCAGATCTAG AGAATGACAT GTAAATAACA GATTACATAT ATAATGACCA
109601 TTGTATAAAT GTGATTTTAT ATGTATAATG ATTATATATA GTGGATATTT
109651 TATATAATAA TATACTATCA CATGTTATTA TATATTATGG CAATTATATA
109701 TATAATCAAA TATACTAAGT CTTGTCAAAG TAGTATACTC AAACTACTTG
109751 GGGGAGGGAG AATGCAAGAA TAGGAAGAGC ACATCCTGTC AGTGCTGTTA
109801 CCTTTGATTT GATTCTGATG GTTTCAGAAA GGAAGCACCT GACTGGGTTC
109851 AGTTAAATTA TGGGTTGAGT TTAGTACCTA TTAGAGGAAA GGGAAAAATA
109901 AAAGCAAAGA GACTAGCACC AAATTAAAAG TATATTTTAG GAACACCAGA
109951 CAATCCATTT GCAGTTACAC AGGGGAAAAA GTAAGAAAAA TATAATAGAT
110001 AAGGTGGAAA AGCAGTTTAT GCTTAGAATC TGGAAAGCCT TGAATGCCAA

FIGURE 3, page 31 of 122

110051 GCAGCAGAGG TGAGGGAAGG ACTCAGATCC TAAGGTGGTC TCGTGGAGAA
110101 CTGAGTTTGA CAATCTTACT TATTAGCCTC CCTTAACTGC CTTCCTTAAC
110151 TGCCTTTGGA TCTGTATTTC CTTCTTAGGA ATTTCTTGTT TCTTCCTTTC
110201 CTTATAGCCA ATATTTATTG GGCTCTTGAG TTTATGATAT GGTCCACTGA
110251 AAATCTACAA TCTATCTGTC CAATGATACT TTAACAGAAT AAAATGAAGG
110301 TTAAACCACG GCAGCTTTTC TCACTAACAT TCAATAATTT AGGTTTAATA
110351 AAGCTTCCGT GGAGTGGGGC TATTTTGTTT AGGTTTTTTA TTGTATTTTA
110401 TTTTATTTGA GACAGAATCT CTCTGTGTCA CCCAGGCTGG AGTACAGTGG
110451 CACAATCTCG GCTCACCGCA AGCTCCACCT CCCAGGTTCA TGCCATTCTC
110501 CTGCCTCAGC CTCCCGAGCA GCTGGAACTG CAGGCGCCCG CCACCACGCC
110551 TGGCTAGTTT TTTTGTATTT TTAGTAGAGA TGGGGTTTCA CCCTGTTAGC
110601 CAGGATGGTC TCGATCTCCT GACCTCATGA TCCACCCACC TCAGCCTGCC
110651 AAAGTGCTGG GATTACAGGC ATGAGCCACT GTACCCGGCC AGGGCTGTTG
110701 ATTTTATATA ATTTCCTTCC TTTTTGGCTG ATTGAAGTCC ATTGCTAATT
110751 CTAGTTTGAC ACTTTTTATT ACCTCAACTA GATTATTTTG TCCAGAAAGT
110801 TTACTGAGCA TCTTCTAGGC TAAGCACTTT AGAAACTATG AAAGAAGTTT
110851 AATTCACAAT ACTTATCCTA AAAGATCACA ATCTTGCTGA TGGCACTTAG
110901 ACAGTACAGC AATCCCTTGA TATCCACAGG GGTTTGGTAC CAGGACTCCT
110951 ACAGATACCA ACATCTAGGT ATGTTTAAGT CCTTTATATA ACATGGCGTG
111001 GTGTTTGCAC ATAACCTAGG CACATCCTCT CACATACTTT AAATCATCTC
111051 TATATTACTT ATAATACCTA ATACAATGTA AATACTATGT AAATAGCTGC
111101 CACACTTTAT TATTTTGATT GTTATGTTGT TAATTTTATT TTTAATATTT
111151 TCAATCTGCA GTTGTGAATC TGCAAACGTA GAACCCACAG ATACAGAGGG
111201 GCAACTGTAC TCAAATTATT TGAGAGTGGT GCAAGCCCGC CAGTGAGTTT
111251 GTCACCAGTT GAGAAGACTT AAACGACTAA CTCTATAATA TAGAGATTTA
111301 TTCTGGGTGG TCAGGAAGGG CCAAGATCAT AGATAGTTAA AGATCCAGAG
111351 AAAATGGGAC TTTGAAGTAA ATGAAGGGAG GGGAAAAGAA AAATGTGCCT
111401 GAGAAATAGC ATAAGTAAAA GTCCTGAGGT ACATGGTGGA GTCACAGGGG
111451 AAAGGAAGAA GGCTGTCGGC TTGACTAAAG TGTGTGCAGG GAGATGAAGC
111501 CAGCTAGATA AGGTGGACAC GGAGGCACTG CGCACCTTGT TGCCAAATAG
111551 CGCCGGTCGT CAGAGAGTCT ACAGTGAGAG CCATCTCTTC CTGTTTGTAA
111601 TAGAAGTATG GAGTCTGGAC CCGGCGCGGT GGCTCACGCT TGTAATCCCA
111651 GCACTTTCGG AGGCCGAGGC GGGTGGATCG CGAGGTCAGA AGATTGAGAC
111701 CATCCTGGCT AACATGGTGA AACACTGTCT CTACTAAAAA TACAAAAAAA
111751 CTAGCTGGGC GTGGTGGCGG GCGCCTGTAG TCCCAGATAC TCGGGAGGCT
111801 GAGGCAGCAG AATGGCGTGA ACCCAGGAGG CGGAGTTTGC AGTGAGCCGA
111851 GATCGCGCCG CTGCACTCCA GCCTGGGCGA CAGAGCGAGA CTCCATCTCA
111901 AAAAAAAAAA AAAAAAAAAA AAAAGTATGG AGTTTGTAAG GATAGGTTTT
111951 CAATCAGTAG AAAAAGAGAA ATGCCCTCAA ATCCAGAATT TATTTAGGAA
112001 AGAAATAGCG CTTTTCCACC CAGGTTTTTG ACTGTGGAAA GTCAAAGGAG
112051 GCACCTGAAA TTTCAGACCA CTATACCCAA AGCACCTACA TACATAGAAA
112101 ATGGTGATCT CAAGCCTCAG AGTGAAAAAT GAACATCCCA GGGAGACCAA
112151 AGAGGAGAAG TGCCTGTCTG TTTCTTGCCA GGCTGGGGGG CCAAAGGGAA
112201 ACTGGGAGAA GAAGCAGAGA CACGTCTACC ACCATGGAAC CTTGCTGCTA
112251 AAAATTGATT TCAGAGTTTC CTTATGTCTC ACAGCCTGGG AACTTGAATT
112301 AAATGAGCTT TGCACAGAGA TTGCCAACCC AAAAGACCTG GGAGGTGAAG
112351 CCTTCTGTTT ATTTCAAGTT TAACTGTAGC TTCAGCTGTC AGAGCAGCAT
112401 CACATCTTGG GATCCCACCT GGAGCATCCT AGCCTCGGGG CACTTCTTTA
112451 TCTCATGAGG AAGGTGGAAG TCTGAGCTGA TCAGATGCTT GATGATGAAG
112501 TGGATTCCTC CTGAGGTAGA AACTTCCTCT CACTGGAAGT TTTCAAGTAG
112551 AGGACCACTT TGCAGGGACA TTGTCAAGAA AATTCATTCA TTCGCTGGAT
112601 GAACAGAATG ATGATAAACA GCTAACACCG ACTGAGCACA TGCTGGTGCC
112651 AGACCCTGTG TTTAGCACTT TAAGTATTTT GCTTCCTATG TCTCCATGAG
112701 ATAAGAGATG CTGTTATCCC CATTTTACAA GCAAGAAGCC AAAACCTCAA
112751 AGAGTTTGGA ATCTTACCTA AGATCTCATA ACTCATAAGT GGTAAATATT
112801 TAAACCAAGT CTGTCTGATT CTGTGATCCA TATTCTTACT TTTTAACTTC
112851 TTATTTCCAG AAAAGTGCAC TAAAGCCCAC ATACTTCACA AAGAGACTTT
112901 TTTTAATATC TTACAGCCCT GCTGTTTTAT AATCTCACTG CTAAAGATGA
112951 AGGCATTTTT GGTTTCTGAC CTTTTGCTGG GACATGAAGG TCTTGGGATT
113001 AAGGTTCATA TACTCTCACA TGTGTGAGTT TCATGTCCTC AGTGCCCATG
113051 TCTAAAAGCA AAAGTGAAAA TTAAATCAGA GCGGAAAACA CCTCTCTATT
113101 CAACACCAGA TTGTTAGGGC TGAGCTGAAA AGCTCCTAAG TAAACTAGTT
113151 CATGGCCAAG TGGCCAGAGA ACAAATTCTA GGAGCCTGAA ATGTGAGATG
113201 GGAGAGCCAG TTTGCAACCC CACCTTGTTC ACAGGATGAT TTCAGGCAGG
113251 TTCCTTAGAT GACTGAAGTT TTTGAATTGT AAGGGACCTT AGAGAGTCCT
113301 AATGCAGATT GTTATCAATT ATGCTGTACA GAATTATAGA GTTCACAACT
113351 TATTCTGCAA ATATTCATTG TGAACTTGCT ATGTGCCTAG TATTGGCCAG
113401 GAGATGCCTC CAGGGCTGCT AGAAAGGAGA AGGAGGAACA ATAGGACAAA
113451 GTTGTTCTCT CATCCTCACT TCTTTAGCTG TGCCCTCCAT TGTCTGTGTC
113501 ATGTCAGCAT TGCAGTTAAG ACTTATTTTG AAAAGGACAC TATATACCAA
113551 AGGACTATAA ATCATGCTGC TATAAAGACA CATGCACACT TATGTTTATT

FIGURE 3, page 32 of 122

113601 GCAGCACTAT TCACAATAGC AAAGACTTGG AACCAACCCA AATGTCCAAC
113651 AATGATAGAC TGGATTAAGA AAATGTGGCA CATATACACC ATGGAATACT
113701 ATGCAGCCTT AAAAAATGAT GAGTTCATGT CCTTTGTAGA GACATGGATG
113751 AAATTGGAAA TCATCATTCT CAGTAAACTA TCGCAAGGAC AAAAAACCAA
113801 ACACTGCATG TTCTCACTCA TAGGTGGGAA TTGAACAATG AGAACACATG
113851 GACACAGGAA GGGGAACATC ACACACTGGG GCCTGTTGTG GGGTGGGGGG
113901 AGTGGGGAGG GATAAGCATT AGGAGATATA CCTAATGCTA AATGACGAGT
113951 TAATGGGTGC AGCACACCAG CATGGCACAT GTATACATAT GTAACTAACC
114001 TGCACATTGT GCACATGTAC CCTATAACTT AAAGTATAAT AATAATAAAA
114051 TAAAAGAAAA TAAAATAAGA AAAAGACACT ATATAGCTTG AATTGCTCTT
114101 AGACAGCAAT GTTCTATTCT AACACTCCCA TTTGATAGAT GATGAAGCCA
114151 AAAAAGATAA AGTAATTTGC CCAAAGTCCA GCCATCGTTG CTAGCTAGTT
114201 GCCACTTTAC CCCAGTACCT CCTACAGCCC TGGGCTACAG TTCCCACATC
114251 TCTACGATGG AGGAAGGGGA ACAGACTCTC TCTAGCAGTC TTTTCCAAGG
114301 CCAAAGTGTT TTCATTTTCT GAATTTCTTG AACATCCACT GTTTGGCCAG
114351 TATTGTCCTT AGCTATCTAA TAGTCACAAC CCTTAAGTTC TTTTCTTTCT
114401 GTCCCTCGTG CCCTTTGTCT TCAGGCTGGT AAACTGTCAT AGATATTGAT
114451 CTGAGCTTTG TTTAATCATG CTAAGCTTAT ACCATGGGTC CCAGGGAAAC
114501 TAGGAAGATG AACAGTATAT AACAATTACA ATTAACTTGT CATTTAGCAT
114551 TAGGTATATC TCCTAATGCT ATCCCTCCCC TGTCCCCCCA CCCCACAACA
114601 GTCCCCAGAG TGTGATGTTC CCCTTCCTGT GTCCATGTGT TCTCATTGTT
114651 CAATTCCCAC CTATGAGTGA GAACATGCAG TGTTTGGTTT TTTGTCTTTG
114701 TGATAGTTTA CTGAGAATGA TGATTTCCAA TTTCATCCAT GTCCCTACAA
114751 AGGACATGAA CTCATCATTT TTTAAGGCTG CATAGTATTC CATGGTGTAT
114801 ATGTGCCACA TTTTCTTAAT CCAGTCTATC ATTGTTGGAC ATTTGGGTTG
114851 GTTCCAAGTC TTTGCTATTG TGAATAGTGC CACAATAAAC ATAACGTGTG
114901 CATGTGTCTT TATAGCAGCA TGATTTATAG CCCTTTGGCT ATATACCCAG
114951 TAATGGGATG GCTGGGTCAA ATGGTATTTC TAGTTCTAGA TCCCTGAGGA
115001 ATCGCCACAT GTGCCCTAAA ACTTAAAGTA TAATAATAAT TAAAAAAAAA
115051 CAGTTACCAG TATTTATTGA GTGCCTAAGG TAGTAAAGGC TTGAGAAGCT
115101 GGAGCCTATT TTCATACCGA ATATGTAAAT ATCGACATCT CTGCTCTAGA
115151 AGATCTAGGA CACTCTGGAA AAGTGTCTGT ATATCTTATA TTAGGAGTAG
115201 TGGCCTCACC AATGTGGTGT CATGGTTAGT AAAGGACAGG CTGAGTGAAC
115251 AAGAAGGGAC TGATCATGTC TTTGCCAGTT GCCACCGCCT AGCTACGTTC
115301 TTGGGCATGG GACCTAATTT GTCCAGCCTC AACTTTCATC TGTGTGACAG
115351 GTCCAATAAT TCCCCATACC ACAGGGATGT TGTGATGATT AAATGATAAG
115401 CAGAGATTTT AGTACAGGAT TGGATATATA GTAAGCTCTC CATAAATGGT
115451 AATACTATTA CTATACATAT ACATGTATTT TACATACCTA TATATATTTA
115501 CATACATTTA TGATCTAGTT TATAATCTCC AATATGCCTT GGAAGCTTCA
115551 GAATGAGTCT TATTTCATTT TTGTAATGTT ACTATCATAC ACAGCAATAA
115601 CAGAAACAAG TTCTAAAATT TCTCCCTGGA GCTTTACTTC AGGAGTTTGC
115651 TACCAATTAG AGGGGTGGGG GGAAGAGGAA GAGATGGGAG AAAGAGAATT
115701 TCACCTGTTT TAGTCTCTAT ATACAAATAA AGTGGGTGAC CCCTAACTTT
115751 GCCAAGCTCT TGCCTCAGAA TGAAACCACA CCCAGTGCCT GTAACTTCCT
115801 AATCAAACAC GTGAGTTACC TTCAAGGGTT ACAAAATCAT AGTTCATGGA
115851 TGAAATATGT GTGGCCCAAA CAGAATTCTA ATTTGTTAAA AAAAACAGTT
115901 GCTAACCTTT CAAAATACAA GAATTTCATT TGAAAATCTA GGTTTCTGTC
115951 TTCTCACTTA CTTTTAACTT TCTTAATCTG ACCTACATAC TCAAGGCAAA
116001 ACTATATAGC ACACTGTTTT ATCACAAAGG TAACACTCAG CCAAGTCAAG
116051 AATTGTAGCG TTGTCAGCCC CCAGGAATGC TCTTGTGCCC ATCCCTAGCT
116101 CTATACACTG TCTCTCCAAA CAGAACCTCT ATCGGGATTC ATCATAACAT
116151 CCTTGTTTTT CTTTAGAACT TTACCACCTA AGCATGCATT TCTAAATGTT
116201 AGAGTTTAAT TTTGTCTACA TTTTGGAATT CAGAATATAC TCCTGACCTC
116251 ACGGTAGGAA AAATCTTCTT AAACAAAATA TAAAACCATC CATAAGGAAG
116301 AAACTGATAA ATTGAACTGT ATTAAAGTTA ACAGTTTCTG TCCTATAAAG
116351 CAGGAGATAC CATTAAGAGA GTGAAAATGC AAGCTACAGA AAGGAACACT
116401 CACATTTAGA ATACCTAAAA TCAGTTTAAA AAGAGGAGAG ACAACCAAGT
116451 AGAAAAACAG GCAAAAGGTG GCCAGGCGCA GTGGTCAGGA ATTTGAGACC
116501 AGCCTGACCA ACACGGCAAA ACCCCGTCTC TACTAAATAT ACAAAAATTA
116551 GCCAGGCCTG GTGGTGCACA CCTGTAATCC CAGCTACTAG GGAGGCTGAG
116601 ACAGGAGAAT CGCTTGAGCC CAGGATGTGG AGGTTGCAGT GAGCCAAGAT
116651 TGCACCACTG CACTCCAGCC TGGGTGACAG AGTGAGACTC TGTCTCAAAA
116701 AAAAAAAAAA GAGATGAGCT ATTAACACTT AAAAAGGCAC ATCAACATTT
116751 CAATAAGCAT CCAGTATGTA TTTATGTGTG TATCTGTTTA CGTTTGCTTA
116801 ATATAACACT CATAGGATTC ATCCTCATGA TTGTAGATAG GTGTAGTTTA
116851 CTCATTTTCA TTCCTGTATA GGATTCTATT GTATGAGTAT GCCAAAATTT
116901 ATTCATCCAT AATTCTACTC TTGATGGACA TTTGCGCCCT TTACACTTTT
116951 GAATAATGAG TCTATAAATA TTCTTGTATA TGTGTCTGGG TGCACATGTG
117001 CACATATTTT TTGTTGGATA TAAACCTGGG AGTGTTATGT GAATGTTCAG
117051 CTTTAATAGA TACTGCCAAA TAGTTTTTCA AAGTAGCTGT ACCAATTTAC
117101 ACTCCCACCA TCAATATGTG ACAATTCCCA TTGCTCCAAA TTCTCTCAAA

FIGURE 3, page 33 of 122

117151 CACTTGGGAT TGTAAGTCAT TTTAATTTTA GCCCTCCTGG TGGGGGTGTA
117201 GTGATAACTC ATTGTGATTT TAATTTGTAT TTCTCTTGAT TATTTGTGAG
117251 TTTTAACTTC ATTTCATGTG CTTATTGAAA TGCTGATATG CTTTTTTAAG
117301 TGATAACAGT TAATACCTTT TTTAAAAATT GATTTTAGGT ATTCTAAATG
117351 TGAGCCTTCA GTCAAATGTG TATGTTGCAA ATATCTTCTT CCTTTCCATA
117401 GCTTGCATTT TCACTCTCTT AATGGTATCT CTTGCTGTGC AGGACAGAAA
117451 CTGTTAACTT GAATGCAGTC CAATTTATCA GTTTCTTCCT TATGGATGGT
117501 TTTATATTTT GTTTAGGAAA ACTTTTCCTA CCCTGAGATC AGGAATATAT
117551 TCTTCTATAT TAACTTTTGG TGGCCTTATG TTTTTCCACT TAAATTAATG
117601 ATCCATCTGG TACTGATTTT TATTTAGGGT ATAGTATAGG GGTCTAGAAT
117651 CAATTTTTCT ACATAGATAT CCAGTTGTCA GCATCATTTA TTGAAAAGAT
117701 CACCTTTTCT CCACTAAACT TCAGTGGCAT CTTGGTCATA AATCAAGTGA
117751 CCAAGTATGT CTGGTTCTGC TTCTGGTCTT TCTTTTCTGT TCCACTGGTT
117801 TGTTTATTTC TCAGGTACTT AGATTTAAAC TGAGCCTTTG TATCTGGAAC
117851 AGGAAGCTTT TCCCCTTTTT CAAAATTGTT TTGGCTATTA TTAGACCTTT
117901 ACATTTACAT ACAAATTTTA GAACCAGCAT GTCACATTCC AAATAAAACC
117951 TACAGAAATT CTAATTGGGA TATAATTTAA TTACAATCAG TTTGGGAGAG
118001 TTGATATCTT TACAATATTG AGTCTTCAAA TCCCAGAGCA TAGTATATTG
118051 CTTCAATTAT TAAGATCTTC TTTTATTTTT TTCAGTAATA TTTTGTAGTT
118101 TTCAGTACAG ATCTTTTGTT AGATTTATTT TGTAGGTATT CAATGTTTTT
118151 TGATATTATA AAAAGTGTTC TTAAAATATT ATGTCATAAT TGTTTGGCGC
118201 TGGTAAATGG AAATACAAAT GATTAATTTT ATATTGATTT TATGTCTCGT
118251 GACCTTGCTA AATTCACTTT TTTCTACAGT TTTTCTTTCT GTGAATACAG
118301 TCATGTCATT TATGGGTAAT GAGAGTATTA TTTTTTCCTT GCCAACTTGA
118351 CCATAATATC TCCTTATTCA GTTTGTTAGT ACTTTAAGAT GTTTTTCATC
118401 CTGATTATGA AATAATAAAG TATGTGTAAT TTTCTTTTCT TACAATACCC
118451 TTGTTCAATT TGGTATTCAG GTTATGCTGA CCTCAGGAGG AAAATAAGGC
118501 AGTGCTCCCT CTTCCCATTC TTTAAAAGAA TGATATAAAC ATATCACAAA
118551 AGATATATAT ATATATATAT ATATATATAT AATCACAGTT TCTTTATCCA
118601 CTCGTTGATT GATGGGCATT TGCATTGGTT TCACATTTTT GCAATTGTAA
118651 ATTGTGCCGC TATAACATGC ATGTGCAAGT ATCTTTTTCA TATAATGACT
118701 TGTTTTCCTC TGGGTAGATT TATAATCTCA CCTTCTATAC TATTGACATT
118751 GGTGGATTTT TTGCTTGGTT GCTCTCATAT TTTCTCTCAA ATTATTGAGG
118801 GGTTGGTTTT GACTTTGTTT ATCTTGTCTA TTGTACATTT ATTTCATTAA
118851 CTTCTACACT TTATTTACTT CTTCTTTTCT ATGTTTAATT TGCAGGGCTT
118901 TTTCCTGACT TCTTAAAATG GATGCTTGGT TCATTGATTT TTTTCATATC
118951 TTTTCTTCTT TTCTAATATA TGCATTTGTA AAGCCTTGCA TTTCTCTCTA
119001 AAGATAGACT TAACCACATC ACTATTTTCT TGGCTTGTTT CAGATTTACT
119051 AAATTTTAAA TTTTTTTGAC TTTTTACTCC TGTATTAATT TGAATATTAG
119101 GCACCCCTTA ACTGTTCTTC TAGTGCTTAC ACTGATGATT GCAACATTCA
119151 TTCTTGGCAT ATCAAATGTT ATTGTAATTG CCACTTACAC CCTTTTCCCA
119201 GATGGTACAA AGACCTTGAA TACTTAGTTT TATTTATTTA ACTGCTAATG
119251 TACATGTTAT TATTGTTGCA TAATTTTTAT ATTTTTACAG TCGACAATAT
119301 GGTATTATTG TTGTTGCTGC TCTTTTATTC AGTCAGCATT ATTTATATTT
119351 ACCCATATAT TTATAATTTT TATTACCTTT TATTCTATTT GTTATCTCAA
119401 AGTTTCCATC TGGAATAATT TTCCTTCTTT GTGAATAATA TCATTCTGTA
119451 TTTCCATTAG TGTGGGTCTG TTGTTGACAA TTTTTTTTCT TTTTCTTTGC
119501 ATCAAAATGT CTTTATTTTA CATTCTCTAT GGAAAAAAGT TTTTGTTGGA
119551 TATGTAGTCT ACATCACAGT TATTCTCTGT CAGCACTTTA AAGATGTAAT
119601 TTAGTTGTTT CTTGTGAAGG GTCAGCTGTC TGCTTTATTG TTGATCTTTT
119651 GACAGTAATC TGTCTGCCTT TGCCCCACTT CCAGGTACAG AGTTACTGTC
119701 TTTGGTTTTC AGCAATTTTG CAATATTCTG GTTAGTTGCG ATTCTTTTTT
119751 TTAATTTAAC ATCATTTGGG TACATTGGAC TTCTCAAATT TGTGTCTTGA
119801 TGTCTTTTGT CAGGTTTGGA GAGCTTTTGG CAATTAATTC TTCAGACATC
119851 ATTTATGTGT CCTTCTTTTT TCACTTTATG AAATTTCATT TACAATGATG
119901 TTAAGGTGTT TCACTGTAAC CCACATTCTT TTCCATATTT TCTATCATTT
119951 TCTCTTTATA TGTTTCAATC CTGTTATATT CTTCTGATCT ATCTTGATGT
120001 TTGCTAATTC TCTTTTTGGC TGCACCTAAT CTGCCATTGT TCCTGTCTAT
120051 TGAATTTTAG ATGCCAGTCA TTATACTGTT CAATTTTGGA AAATTTTTCG
120101 TGGTTCTTTC ACATGGTTTT CAGTCCTCTG ATAAAATTAT CAATCCTTCA
120151 TTTAATCTCC TGGGAGATAG TAAGCATAGT TGATTATGAA ATTTATGTCT
120201 GTAATGTCTG ATTACTCTAT TATCTTGAGC CCCTGTGGGT CTATTCCTAT
120251 TTTCTCTGCT TTTCTGTTCA TTTTAATTTA TGTTGTCTTA TCTTCCTGTA
120301 TAACAGTTTT TTTTTACTGC GTTCTGGACA TTGAATTTGC AAAATTTCTT
120351 TGCAGAAATA ATTTGAGGCC TAAGCTGATG TTATCTTTTT CCCTAGTAGA
120401 TATATGTTTG CTTGCTGCAC TAGTACTCCA TTATCAGGTC AATCCAATTT
120451 CAGGGATTGA GATGATTTGA AGCTACACTG CAACCCTTAC TAGTACCTGT
120501 CTATTTCCAG TTCAGCCTTA CTCCTATTGG GCAGCCCTTC TGAGTCCCAG
120551 CCTAAAGTTG GGTTTAACAA GCTTCCCCCA CTGCAATCAC CATATTTTGG
120601 TCCTGGACTC CAAATTTCAT CTTTCTATTT CTGGCAAGCT CTTAAATGAG
120651 CTTCCTCTTA GTTGTTTAGT TGCTTACTCT AGAATTAGTA AATATCCCCA

FIGURE 3, page 34 of 122

120701 AGGTGCAAGC AGCTCCAAAC ACAAAGGTTA CCTCCCGGGC TTCCTCCATC
120751 CTTAGATCCC AGCCCTGCTA TTCTTTGCTC TTTTGTTAGC TCTCCTACAT
120801 CTTCAAGTAG ATTTGTAAAT ATTTTGCCCA GCTTTTCTTG TTGTTCTCAT
120851 TGGGAGTATT CGTCCAAATT ACATAGTCTT TCATTAACAC AAGAGGAAGT
120901 CCTGTTCCTG ATCTTGAAAA AAATGATAGA TATGTCCACA ATAGGCTGAA
120951 ACAAGGCAGT GATTTCTCCC TTCATATGAG GAATACATTC TCCCACAATG
121001 TCCAGCTAGC CTCCTTCTCA TTCACCTTAG CCCAGTGACT TTGGCATTTG
121051 GGATTCAGAC TCTTTTCCTT TTTTTTTTTT TTTTTTTTTT TGAGATGGAG
121101 TCTTGCTCTG TCACCCAGGC TGGAGTGCAG TGGAGCAATC TTGGCTCACT
121151 GCAGGCTCCA CCTTCCGGGT TCAGGTCATT CTCCTGCCTC AGCCTTCCGA
121201 GTAGCTGGGA TTACATGGCC CACCACCACA CCCAGCTAAT TTTTGTATTT
121251 TTAGTAGAGA CGAGGTTTCA CCATGTTAGC CAGGATGGTC TCGATCTCCT
121301 GACCTTGTGA TCTGCCGGCC TCGGCCTCCC AAAGTGCTGG GATTACAGGC
121351 ATGAGCCACC GAGCCCAGCC CAGACTCTTT TCTTAAATAT TCCAATAAGG
121401 TACAATTTGA TCATCCTAGG TTTCTTTCCT CTAAGTCTGG CATGATATGG
121451 TTGGTAAATG GAGGTTAACT ATTTTATTAT TTTGCTAGAG AAGAACTCCT
121501 AAAGCCCCTA TGGGGTTGGC ATCATTCTAC TGTCTGCATG CCTGGAAGAT
121551 CTAAAATATT TAGTGGGCCC AGAACTCCTC TATGAGGACA GATTGCCAGA
121601 CTGCTTTGCA CTGCAGAGCC TTTCAATGGA AAACTGGATT TCTAGCCTCA
121651 GTTGTGATGT GAGACCAGGA CAGTGTTGAA TGGAGACTAA AAATAGGGTG
121701 ACTTACAAAC AGATAGTGTG TATCTCCCAG GGAGTGTGAA GTCCACTTTC
121751 CAAAGCAACT GCCAGCATAA GGAGTGTTAA TGCCCTCTGG GATCCAAGTA
121801 GGATGAAAAC AAACCACAGA AAATGAGGTA GGATGTTCAA CTCTCCCTTT
121851 CAGTGATCAG GAAATCTACA TGCTCATAGA CTGGATTATT CAGAATAGAC
121901 CTTGTTGAAA GTTACTGGAA TGGAGGAAAA CCCTACAAAG ATTTCCAGAT
121951 TCCCTGGGGA AGACAAAAGT ATTTGGTCTT TGTTGTTATC GTTGTTGTTG
122001 TTTAAAGTGA ACTCCTGTCC TTTGCTCTAA TTCAAGGAAG AATTTCTGAG
122051 TATAGCTACT CTATGCAAAA TAATCTCTGC CTTTAGGGCT TCCCCTAATT
122101 GTGGTCGAGA GTGTAGTCTC CAGAGTCAAG ATGCCTAGAT TTCAATCCTT
122151 ATTCTACTAT TTATTAGCAT TGTAACCTTG GGCAAGTTAT CTAATTTCTC
122201 TATGTTGCAA TTTCCCCATT TATAAAATGG AAGTAAAAGT GCTACTTTAT
122251 CTCCAAGGGT TTTTGTGAGG ATTTTAAAAA GTCATGCATA TAAAGTATCT
122301 AGAACAGTGT CTGGCACATG GAAAAACTCA AATAAAAATA GCTATTTATA
122351 ATTAATTTTG TTTTAGTATT ATAATTGTAT AGTAATGCTC AACACGTTTA
122401 TCGTGTGTCT CTCAAAGCCC TGGATTTCTT ATCTCAGTTC TGCACTCTTT
122451 CATTTAAAGT TCTGAACAGG CTGTCTTCAA CCTGGTGGAT GGTTCAAACA
122501 GGCTGTCCAA CTTTCTTAGT TGGATATCGC GATTTCCAAA TCTTGCTGCT
122551 CATTTCAGAA AGCTTTTTGA AAATATAGAC TCCTAGGATT TGCCCACAGA
122601 GATTCTGATT TAGTAGATTT GGAGTGAGGC CTAGGAAGCT ATATTTTAAA
122651 AAGCTTGCCA CTACGTATAA TATGCAACCA ATTTGGAATG ACTGAACTAT
122701 GATGACCTGG TACCAATTAT TAAATATATG GAGCCAATTA TTAAATATTC
122751 ATAAATTTTG CAAACTGATT GTTAAACCAT TAGTAGTTAT TAGCTATGGT
122801 AGGAATATTT ACACCATGGA AACTGGCAAA TCCTACATTC TTTTTTTCCT
122851 GGAAAGCTGG TTTACTGTCC CACCACTGGC ACAATCTTCT TAGCCCCTGG
122901 GATCTGGAGT ATCTCTGTCT GAATCTCCTT TGGTTAGAAC TTTACATCTC
122951 CATGATTTTC TGTTCTCTAA TTGAGGTTTT GATCTGCCAG GCAGTAGATA
123001 TTCCTGTGAC TGAAAGGGCT TCCAGCTAGA TATCTCTGCA GCCATAATCA
123051 AGCTCTCCAT CATTGCTTTG TTTTGAGGCA GAGGTGGAAA ACTGGTGGTC
123101 AGTGGTGATT CTGGTTCACA GATGCATAAT TGTTGGCTCT CACGAAGACT
123151 TAAAATTAAA GTCGGAGGCA GCTTTTTAAA AAATTATAAG ATGGCATATA
123201 AAAATCCAGA TTCTCACCTT CTCTTTCAAA AAACAAACAA ACAAACAAAA
123251 ACTAAGTTGA AAGAAGATCT GGACCTGCTT TTCAGTGGAC AAAGTTCAGC
123301 CAAAGCTACG TGAGCACTGG CAGGGGAAAG GTGTTCTCTC ACCGGCTCAT
123351 TTGTTCATTT ATGTTTTCCG CCTGGCCTTG AGCTTGCAGC TCCTCTGGGA
123401 AGCAGTGTGT TCTGTTGGAA AAGGTGCCAG ACTGGGTCTT TGGAGATGTA
123451 GGTTTGTAAT CATGACTCTG TTTTTTAATT TATCGTGTGA CCTTGGTCAA
123501 GTCATTCTCC CTAACAGAGC CTCAGTTTCT CACCTGCAAA CTAGGGAGAA
123551 TGCTTGCTTT GTCTGCCTCT CCAAATGTGA GATGGGGAAA TGTGAGTCCT
123601 TGACCACCAG CTGTAGAAAA GTAAGGAATT ATTGCTAAAT ATTGATTCCT
123651 ATTTCCTGCC ATTGGCACCT AGGTGGGAAT GAATAATCCC AGAACAGGTT
123701 CTGATAGGAG AAAATATTTG AATAGATAGG AGTGCTGAGA AGGGATAAGG
123751 AGAGAGTGCC TATAATGAGA AAAGTGCACA AAACAGAAAT ACTAGTGAAT
123801 ATGCTGAATC TACAGTCTTC TTAAGGGAAA TTTGGGAACA TGAGAATTTG
123851 AAGTTGATAC TATTAACCAA CCTCATGTCA CATATAAGAA AATATGGGCT
123901 TGGAAATCAA ATCTGCACAT AAATTCCAGA AGGCTATGCC TTTGTGCAAG
123951 TTAACTTATC TGAGCCTCTG TTTCCTCATG TATACAAGGT GGATATTAGA
124001 ATCTATCTTG CAATGCATTG TGAAGATTCA GTGGGATAAT GCATATTAAG
124051 TGCCTGAGAT ATTTTGTGAA TGTCCAATAA ATGGCAACTG CTGTTATCAG
124101 CTCAAATCAG GCATATGCAA ATTGAACTAC TGGCAAATAG GGAAGTAGTT
124151 AGGAGAATAT GATGTATTGT TAGTGGATAT TTCCTTATCA GAAAAGAACT
124201 TTGCATAATC CGTAAGGGAC TTCTTCTACT TCCCATTCCA CTGAAGAACT

FIGURE 3, page 35 of 122

124251 TCAATTTAGT ATTTTACCCA GCATTTGCTG CAAGCTTCGT AGGATACCCA
124301 GCCACACATA CCCATATCAG CAGCAAGTTC TGAGAGCCAG CGGCAGTATT
124351 AGCATTATAA AGTGTTTCCA GAGTTGGACC AGTGTGTGCT TCCCCTTCAT
124401 AAATCCTTAA ATCTTAGGCT CACTCAGCTG GAAAAAAAAA AAAGAAATCT
124451 GGGTTTGAAG AACACTTATT TATTTTTGAT TTTCTCTGCC TTGTGTGCTT
124501 CTTTTGACTG CGCATCTGAA TATCAAGGCA AGAAGTGCTC AAGTTCCTCT
124551 GGGCTCTGGA AGGCTGGAAC CAATTGGTAT TCTTGGAGTC GGTCCTTTTT
124601 GGACTAAAGC TCCTTTTTCT TTTCCTCCCC CCAATAAAAA TTTCTGTTCC
124651 AGGGAGTACT TTCTCAGTCA CTCCTTTCCT AATGTAATTC TGTTTGATTT
124701 CCACTGAACG GCTCCTGAAA GGAGACACTG AACCATGCCT CCACAAGCAT
124751 TTCAATTCCT CAACACCAGC TTTCAGGCAG GAGCAGTTCC AGATGCATTT
124801 TTATATCCAG TAATCATGCA TTTAACCAAA ATGATTGATG CAGCATTTTT
124851 TCCCCTCTCT ATCATTTCCA GTCCATTAGT CTTATTTGTT TTCCATGGTT
124901 TGGGTTCCTG CCAAATCAGT GAATATACAA ATACTTGCAT AAGTCATGCA
124951 CATCTACACA CACATACATG TAATAGGTAC TGGGTCTGTA TCTGACTTGA
125001 ATATTCAACA TTTTATTTCC AGGCTTCATG TCTCCACTGA AGTTTTAGCC
125051 GCTTCTTTCC TTCTTTCTTA CTTCCCTCTC TCCCTTCTTT TTTTCCCTCT
125101 CTTCCTCTCC TTTATAGTCT ATTAAGTTGG TGCAAAAGTA ATTGTGATTT
125151 TGCCATTACT TTTAATGACA AACCACAATG GCTTTTGCAC CAACCTAACA
125201 CTTTTCCCAG AAACAGCCAC TTTTTTTTTT TTGTCAGCCA TCATAGAATC
125251 TGATATTCTT CAGCGTTAAA GGGGCTTGAG AGAGGCATTT ACATAATCCG
125301 TTCACTTTAG TTTCAGAAAA TCAACAGGCC AGAAAGGAAA CCATGTGCCA
125351 TCCCAGGCTT TCCTTGGCCC TTAGGCAAAC ATTCCAGTGC CACGTCCCCC
125401 ATCAGCCCTT GCACGCCCTG GACCCTGCCC GCTGCATCAG CCACCTCTCC
125451 ACCTCAGTCT TCACACTGAC CTCTCCACTT CAATCTTCAC GCTGTAGCCA
125501 CACAGGCCTT TAGTCCTTGC CTTGGGGCCT TCACACCTGC TTCTCTCGCT
125551 GCTCGGACAG TTTTTCATAC ATAGGTGCAC ACACCTTCTT CACTGCTCCA
125601 CCTCCTATTT ATTCTTTAGG TCTCAGCTCA AATGACACTT CTTAGATCAC
125651 ACACCATACC ACCCTCTCCT GACTTTCCAC CCTTTCTCTT CTGACACTTA
125701 TTACGATTTG TAATTTTGTA TTTACTTGGG TATTTAGTTG TTTAATGTAT
125751 CTTCACTTAT TAGAAGACAA GCCCTATAAC CACAAAGACC ATGTTTTCCC
125801 CGCCCCTCAA TTGTTTCCTC AGTGCCATAG ACAGTGCCTT GTGTTTGATA
125851 GTGACAATAG TTAGCAATCA TAAAGTGACA GTATCTAACA TCTGTTAAAA
125901 ACTTGCTAGT TCCAGGCACA GTGTCCTATG ATTTTTATAT GTATTTACTC
125951 ATTTAATACT TACAACAATT ATCCCGTAAA GTAGGTGTGA TTATTATCCC
126001 CGTTTTGCAA ATAAGGAAAC TGGTCAAGTC ACTCACCCAA GATTATATGG
126051 CTGGAAAGTG GCAGAGTTTG TTTGTAACCC AGGCATTGAC TCCAAAACCT
126101 GAACCCACAA CCAGGCCATG CTACTCCTGT TAAGCACTTC ATTAATATTC
126151 ATTGAGAGAA TAAGTGAAAA ATATACCTTA ATCAATTAGT AGCAAAACTG
126201 AAAACCTAAA TTGTTTGATT GATAAGCCAT TTCTCTTTCT ATGCAAACAG
126251 AGAGCCTCTC AGGTACCACC AGAATGCAGC AGAAAGAAAG AGAAGATTAA
126301 CAAATTCATT TATTGCTGAT AAGAACTATG AGAGGGACGC TGTGATATAG
126351 ATCATGAAGT GAAGTGGAAA TTATTATTTT AGATTCAGGC AGGACCCAGT
126401 GGCAGGTGGA AAAAATACAG AGTCAATTGA AGAGGCCTTA AGATAAGGAA
126451 TCAGATTCTC CAGAAACATC AAGTGGGTTT ACAGTTATTA TCATTAACAA
126501 TTTAGGCAAT TCTTATGCTA TGGATAACAT TTTCCAAATG TGATTTTAAA
126551 GTATGAGTAA TCATCAGTTT TATGAAACTG CTGCTCAGAA TTCTAGGATA
126601 AAAACTCCAA TAATGAGCCT TGTTCAGTTG TTCCATGGCA TGTGGAACAG
126651 TTCCTAGCAC ATATAAGCAC TCAACAGACA TTTATTTAGT AATTAATGGG
126701 AAATGAACAT CAACAAATCC ATCAGCAAAT ACTTACTAAG TACTCGTTAT
126751 TAAGTCTATA CAGATCAAGG CACAACAAGG CACAAAAGTA AAATGTCAGA
126801 TTTCTTTTCA TGGAGAGCTC ATAATCCAGG TAGACCCAGA AATAACCACC
126851 ACAATGAATA AAAGCTGCTA GCTGGGCATG GTGGCACATG CCTGTAACCC
126901 CAACACATTG GGAGTCTGAG ATGAAAGGAC CGCTTGAGAC CAGGAGTATG
126951 AGACCATACT AGTCAACATA GTAAGGCCCT GCCTCTACAA AAAATTTTTA
127001 AAAATCAGCT GAGCATGGTG GCCTGTGCCT GTAATTCCAG CTTCTCAGGA
127051 GACTGAGGCA GGAGGATCAC TTGAGCCCAG GCGGTCGAGG CTGCAGTGAG
127101 CTATGATTGC ACCTCTACAT ACCAGCTTGG GCAACAAAGC AAGATCCTGC
127151 CTATTAAAAA TTGTTGATAA AATAAAAAAT AAAAGTAAAC GCCACCATCA
127201 CTGGGGAGTT GCTTTGTCCA GGGGCTCTGC CATGTCCCTC TGCATATATT
127251 AGGTCATCTT TATACTCCTA ACAACTTTAA GATGATGGTA CCCTTCCTCA
127301 TCCCCATCTC TAGATGTTGA AACTGAGGTT TAAAGATGCT AATTTCTGTC
127351 CTAAAGACAC AGAAACAAGA ACTTAGTGCA GCCAGGATTT GAACTCAGGT
127401 CGGTTTGAGT CTGGAACCAA TGATGCCAAA TGTCTTCATC CCTTTATTTT
127451 GAAAGCACTA TCTGTGGGTG AGGCATACTA GAACTACAAG ACTTTGCAGT
127501 ATCAGAGGAT GGGAGTGGCT ACAGAGGGAT CAATGAAAGC AACATTACCC
127551 AGTCTCTCCA GGTCTGCATA TCCTGCTTAC CTGGGTATGA AACACTCCAT
127601 CTCTCACCTG CCACAGTCCT GTCATTCAGG TCCCAGATTC AGTATCACTT
127651 CTGCATATGC TGCTTACTTG GGTATGAAAT ACTCCATCCC TCACCTGCCA
127701 CAATCCTATC GTTCAAGTCC CAGATTCAGT GTCACTTCTT CCTGGAAGGC
127751 TTTTCAAACA TGGTACAATT TGATTGTTTC TTCCTTTATG CTCCTTTTAG

FIGURE 3, page 36 of 122

127801 AATCCGGTGT GTTTCCTGAT TATAATTCTT ATCTCGCATT CTGATTACTT
127851 GTTTCCCATT AACTAGTCTT TGAGTTCCTC TAGGACAGGG GTGACCAATC
127901 TTTTGGCTTC CCTGAGCCAC TTTGGAAGAA GAATTGTCTT GGGCCACACA
127951 TAAAATACAC CAACATCAAT GATGAGCTAA AAAAAAAAAT TCGCAAAAAA
128001 AAAATCTCAT AATGTTTTAA GAAACTTTAC ACATTTGTGT TGGGACATAT
128051 TCAAAGCCAT CCTGGGCTGC ATGTGGCTCA CAGGCCACAG GTTGGACAAG
128101 CTTGCTCTAG GATACAATTT TATTCTCCCA GGGCCTAGCA CAGCCCCTAG
128151 CATATAGTAA GTCATTTAAT AAATAAGTGT GGAACGAATG AATTTTAGGT
128201 AGAAATTGTC ATCAGATGGT TCAACTAATA TACAGCACAA TTCCAAGAGA
128251 GGAGTGTATT CTTGGGCATC AGGGAAAAGG GACTTTGGAA AAGTTGAGTT
128301 GGAGGCCATG TGGCTATTAA GATATCTGTC TCCACATGCC TCGACTGACT
128351 GTGTGAGCCT TGGAAAGTTA TTCTCTCTTC ACTTCAGTGT TTTCATCCTT
128401 ATAATTAAGA TGATAAAAAC TGGGTTGTTG GGAAGTTGAA ATAACTTAAC
128451 ATGCAGGAAC TCAGCAGAGT GTCTGTTCAT TGTAAGTACT CAAATGTTGG
128501 CCATGGCTAT AGCTGCTGCT GCTTGTCTTC TCTGAATTAT TATTATGGAA
128551 ATTTGGGTGA GTACAGCATT TCAGGCAGCA GGTCACTTCT GAGTAAAAGT
128601 ACAGAACTAT GAAGAGATCT CCTACCCTTG GATATAAAAA CAATTCACAG
128651 CATTGCCAAG AAAGACTGTA GATATTCAGG GATGAGAGTG AGATTCCTAT
128701 GAGCCAGAGA ATCAAAAGCT CTGTAAATTA GTGAGTTCGT GATATCATGC
128751 TACGCTCCTG TTTTTAAGAG CTAGATATCA AAATAAATGG TCCAGTGTAT
128801 GTGCCTGATG GCTATGTCTT TTCCACTGTA CACACAAGTA AGATTCTGCA
128851 TGGTGACTAT CATTTTGTTT TCAGGAAGTA GATGAATCAG CCGTTTGGTT
128901 CCCTGGGAAT GTGGGCTGCT GGCTTTTAAT TCTTTTTGGG GAAGATTTCT
128951 ATGTCATCAG CCATCTTGTT TATCTGGAAA CATGGGACAA ACGTTGGCTC
129001 TCTTTCTACC TATGTAGTCC TTTGCTAGGG TTGTACAGCT TGAGTAGAAT
129051 TGGGAAAAGT GATTTGGATC CTTGTGACTG GGATTAGGGA GAATTGGTAC
129101 ATGAGTATAC AGAATCTTTT CATTGATCTC CTTGCCTCTG ACCTTGATTT
129151 AGCCACCTAC TTTCAGTGGA TAAGGCCCTA CAGAACAAAC CAACTGAAGC
129201 ATACTTTAGG ATAGGCCACA CCTCTAATCT CATATTTATT ATGACCAACT
129251 AAAAACTGCT TATCCTTCTC TTTATGTCTA TTATTTAACT TTCCCCTCCT
129301 CTCTACCTTC TTTCCCTTAA GTCCTTCTGA TACACTACAT GCTCCTGCCA
129351 TTGTGACTAT GAGTCTAAAA AGCTGGTGGC ATTACCCACC TTCCCCTCCA
129401 CCTTCAAAAC TCACATGTAC ACCATGCTTT GGGCTTCTCT GATTTGGCTC
129451 ACTATTTCTT CAACTTAGAA CGCCCACTTT CTATTATGAT CATTAAAAGA
129501 TCCTGGATTT ATGTGTGGGG TGGATGTAGT AACAACTGGG AAATAGCATA
129551 AAATTATTTG GTTTCTTGTA TGCTGGTTTT CTTCCCAGAG GTAACCTGTT
129601 TGGTTTGACG TTTGGCTTAA TGTTGTTAAT TTGACGAAGG TGGAAATGGA
129651 TGGGCTAGAA ATCTTTGTGG GACTAGGATA AGGCTTGAAT GGTCTAATCT
129701 AGGGATTCAA ACTTTCTAGT TAAGAATGTA CAACCTGTGA GGATAATTTG
129751 CATTTTATTC TACATATATC CCAATTTAAC CAGCTTTCAG ACTTTAAATC
129801 ACCATAAGAT TTTGGAAAAC TTCTACTGTC TAAATACAGA ATAAAGTTTT
129851 CTAAGCCAGA TGAAAAAAAT TGCATCATTC TTGCACCCTG CAGGCAAATG
129901 CATGTTGACT GCAAAGCTAT ATAAATGTGT GTTGAGTGAT TTAACAGGTC
129951 TGGCTATTGA ACTTGTTAAA AATGGATGTC AGGAAAGAAA AACAGCAGGT
130001 GGGTGTAGAC TGGAGGAGTG GGCAATGCCT GCTGACAGAA AGAGGAGTGA
130051 CAGCTGACAA GGAGGGAAGG CCCAATGGAG ACTTCAGGCT CACCACGTAT
130101 GGAGCAGTCT GGGGACCGAA ACAAAGAAAT GAAAACAAAC AGAGCACCCT
130151 ACCACCTCAA GAATCCCTAA GGGAGTTATA ATATGCACAA ATGCTCATGA
130201 TTATTAACTA GGAACCAGTT ATTCTATGCC TGCTATGAGC CAGGATTCAT
130251 TCCAGGAAAT TAAAGAGAAT AGAAAGAAGT ATAAAATACA GTGCCTAGGT
130301 CTGCAAGTAT TTATTACCTG TGACACTACT ATGTTGGCCA AGGAGAAGTT
130351 CTGTATATTA TGCTCTTTTT ATAAAAGCAG AAGCATGTAT AGAAACTATT
130401 AGGATATTTT TCTTCAAAAT GTTTAAAATT CTTTAGCTGC TTACAAGAGA
130451 AATTTATTTA GTACTACTTT CTCAAAGATC CCATTTCCTG ACAATGCTAA
130501 TAATGGAGGC ATTTCAAGAT AATGACCTCA TAAAATTCAC ACAACTGTCT
130551 GTCTGTGCAG ACTTAGATAG CACAGTCATG ACCTCACTTA GGTCAGGGAC
130601 AGATCTTAGC TTGATAGGGC AATGGTCAGA AATGCAGTTT GGTTTAAACA
130651 GTTTTTTCCT CTTCTCTGTT GACTCATTTA ATGAAAGAAA GTGTCTCATT
130701 CAACCTGCAT ATTTTTTTCA AAGATTCCAC AATGATGGGG CCATGTCTCC
130751 TATGAGTTAT TATACAAAAT GGACACTGAG TCCTGAGGTA CATTAGGAAG
130801 CCCCAAACTT ATCCTTGTAT TTAATTCATT TGAACATTTT GGATATTTTA
130851 TTTTATCAAG CCAGTCATTT CGAGTTGAGA AGTCCGAAGA TCTTACTCAT
130901 TTTAGAAAGA CTAGGTTAGG GCATTTTCTC TGGGGAAAGA CCTCTTCTGT
130951 AAGGGAACTT CAAGAAAGGG AGCAGATGGG CTCTGTGTCT ACTGAGAGAC
131001 AGGAGGATAA TCAGGCAGTG ACATAGCCCA TGGTACTGGA GAGAAAGACA
131051 AATCGCTATC CACATAATGG AAGGCATGGG GTAGGGTGAG CCAAATGGAA
131101 GGCTTATAAA GGCAGCAAGC AATGAGGACT AGCCATTTAT TTAAAATGGA
131151 AAAGGGACAA GGTATCTTTA TCCCACTTTA TCCCACTGTC CAACAAAATT
131201 ATTTTAAAAA AAAGAGAGAG AGAGAGAGAA GATGAAGAAA TTAAGAGTGG
131251 GAAAATACTA CTACAACCGT TTGGCCTTTC TGGCCTCTTA AAATCTGAGG
131301 CAGGTCAGGG AAAACATGGC AAGAACACTA AACTTAAAGA GTCAGGAAAT

131351 GGATGCTCAA GTGTTGTTGC TGCCTCTGAC TCAGCCTTAC TGTGTGACCT
131401 TGAGGACAAT ATTTCCCCAA ACTCCACCCC AGAGCACTTA CCGCTTCCCT
131451 GTAGATAAAT ATAAGGAAGT TAGAACAAGT CTCTACAGTT CTTTCCATTC
131501 CTGACATTCT AGGCTTTTAT AATGAGCTAA AACAAGAAGC TTGTTTTTTA
131551 ATGTGTGACA CACCATGAAA TGTATACAGA GAAGTGACCT ATAAATTCTG
131601 ATTAAGTGTG AATTAGATGC AAATACAAAA TGCAAGATTA GAGTGAAAAG
131651 CATTACCCCT CTGTAGGTCA GGAAGTATAA TGTGGTTTCT TTGCACTATG
131701 AATAATGAAT ATTGTACATG CCGAAATGAG CACTGGAAAA CATAGAAGGA
131751 ACTAGATGCT CTTCTAGAAT GGGCTTTCTT CCCTTTGGGA TAGACTTTTT
131801 TTTTTTTTCC TATTTTTGCA CCCATGCTTA GAGAGGACAC AAACATCTCT
131851 GAGATTCTAC TTGAGACAAT GCGACAAGCA CTTAAAGGAA CACCAAATCA
131901 TTTGAGTGCA CAGGCAATGA CACCATCTGT AGACTTATCT GATCCAGAGA
131951 ACCTGAGGTG GAGCCTATAG CCTCTGGTCA GTTGGAAGCG GTGGGGAAAT
132001 CTCAAGAACA CTTGTCCTGA GAGAAAGAAA ACTTTATCTG CTTGTTACAC
132051 ATGAGCCTGA GCTGAGGAAA TAGACCTGGA TCCAGGGAAT TCGTGTTTAC
132101 TGGGTGCCAC AACTTGTGTT AGCACTTGAC ATGATTTCTT CTATTTAAAT
132151 ATTAGACTAA AAACACTCTA TCAGACTAGG GTTTTAAAAT ACTATTTCAT
132201 TTTTTTGGTA CCTATTTATA AAATGGGGAA ACTGAGTCTT GGGGGATATT
132251 AAGGTCTTAT AGACTGTAAA TGGTATAATC CAAGGTTGAA AGGTTTCCTG
132301 ACTCTAATGC TGGTTCTCTT TCACAATACC TCATTGCCTT CTGGAAGTTG
132351 TAGTTCCTAC CCTAGTTCTG CCTTTATTTG GCTGTGGTAA TCAAAACAAA
132401 TCACTTAAGT TCTTGAATCT CATTTTGTTC TTCTGTTAAA TATCACAAAA
132451 CCAACCAACC AACCAAAACA GTGAGAATAT AGCTTTGTTA TGCTTCCATG
132501 ATTTGTGGAT GGTCTTCACA GGCAACAATT AATTCATGAG GAATGATGCC
132551 CACTGCTGTC ATGCAACATA GTGGCCCTGG ATTTTAAGGA ATCCATGTAT
132601 TAATACATGC AACCTGAAAT CACATATGTA AATTGTATTA TATACTTGCA
132651 TATCTATATT GTTTTAGAGA AGAGGCTAAA GCTTTCTTGA GAGGCTTTCT
132701 GTGGCATCTA TATCCCCAAA TTCCTAAAAA TCATTAGGTT CTTGGCAGCT
132751 CATTAAGTGA TTAGTAGGTC TCCTTATGAT GTGTTATAAC TCAAAACATC
132801 AGTAACCATC TGAAAGAAAT TAAGGTTTAG GACAGGCATG GTGGTACACA
132851 CCTGTAATCC CAGCATTTGG GGAGGTAAAG ATGGCAGTAT CGCTTGAGGC
132901 CAAGAGTTTA AGAACAGCCT GAGCAACACA GTGAGACCCT ATCTTTACAA
132951 AAAATTTAAA ATTGTTATTA AAAGAAATTA AAGTTTAGTA CATGAAAGCA
133001 GCTGAAACTC AGAACTGACC CTTACATCAG AAACCATGTG GTATCATGGA
133051 AAGAAATCTG GCAAAGAATC AAAGATTCTG GGTCCTACTT TACTCTGCTG
133101 TGAACCCACT CCATGAATCT GGGCACATAC TTGGGCCCCC ATTAGTTTGT
133151 CATTCAAAAA GAGATGCTAA GTTCCAGCCT GCCTCTCCCA AAGCACTTTT
133201 TAAAAGAATC AAATGTGATA ATATGGATGA AGGCACTTTG GCAAAATATG
133251 AAGTACCCTG CAAAAGTCTG ATATTAACCA TGAGATATTA AAGTATCAAG
133301 TCATTTCACT AGTTGTCAAC TGAGAAAAAG GGAAAATTGC AAGTTCCATC
133351 AGCAAAATTT AGAAGCCTTG CTTTTTCATT CCTTCAGCAA GGTCCTACAG
133401 CTGATATTTA TGCATAAATT TTCTTGACTT TAATGAGAAT TGGTTGCAAA
133451 TACACCTTAC AGGATTCAAA TGGAGATCAT CACCATTCTA GGAGCTGCTA
133501 AACAGAACAT GTGGCTTCTT CTCTAGCCAA GAGTTCTCCT CTTTTATCAC
133551 CTTTATTTTA TGATCAGTGG TTCTCAAGGA ATGGTCAAGC ACCAGCAGCG
133601 TGAGCATCTT CTGGGAATAT GTTAGAAATG AAAATTCTCG AGCCCCATCC
133651 CAGACCTACT AAATCAGAAA TCCTGGAGGT GGAGCCCAGC AGGCTGTGTT
133701 TTAACAAACC CTTAAGAGGA TTCTGATGCC CTGCACACTT AAGTGTGAGA
133751 ACCACTGCCA TAAGTGAGTA TCCTTGGAGA GACCTACTTT GGTCCTGGGT
133801 ACTTTAAGGA AAATCGTGGG GCCCCAGTAA TCCAAAAGAG TACCTCATCT
133851 AAGTCTCTGA AGGGCTGATG TTAGAGCAAA GGTTGGGCTA GTGAATGTCA
133901 ATGTTAGCAA ACATGGTGGG TGTGACCCAA AACATAATCA AATAGGCCTC
133951 TTAGGTTAAA GTCCTGATGT TAGGTTTGCT GGTTGAGAAG GAATACAAAT
134001 GTATCTCAAG GAATGCAGTT CTCTCAAGAT TCAGAAAGTA TGGATACCTT
134051 TGCCATGCCT GGCAGCTTGA AAGAAATAGC AATGTAAAGT TAAACCACGC
134101 CTATGTGAAA GTTAGCTCCA TAGCAGGCTT TCTTCTCTGA GATTTGAATT
134151 TATGGAACAT GATAACAAAT ATGAAAATAG ATAATTTTTA TTGAATATCA
134201 TATCACTACC ACTATTTTAA GTGATTTGTA TGTATTAATG GCTAACCTTT
134251 TTTCAGGTAG TTACTCCACC AAGCTCTTTG CTGGGCCCTG AAAATGTAAC
134301 AGTGAACAAG AAAAAAATCT CTTTCCTCAA GGAACTCACA CTTCAATGAA
134351 GGGAAATTAG AAGAAATTAG CCTATTACTG TTCAAGTTCA GGGTGTTTGC
134401 AGAGGCCTAG ATGCGGCACC TACACTCAGT CTTATGTAAA TAGAGGTTTC
134451 TCAAAGGAAG AAATGTATAA ATTTAGACCT CTGTAGAGTG AGAGGAGTTG
134501 ATCACTTTAG AGTGGAGAAA CAGATTTAGG ATAACTATAC TCTAGATCAC
134551 ACAGCAAGTA AGTGATAGTG TTGGGATTTG AACTCAGGTT GGTTTCATCC
134601 AAAGCCATTG CTTTCAACCA TTAAGGCAAG GGCAGAAAAT GGGTTTTATC
134651 AAGCCTGTCA ATTCTGACAA ATTAATAATG GCTTCCAAGA ATGTGGATGG
134701 TGAATACTCG GTGAGCACTG GGCTCAATTG GAAAAAAAAA TGCCATGATT
134751 AATTAATAAT GTCTTCCCTG GGTTCAGAGA GGAGGGTGTA TGTGTCATGC
134801 ATTTGCCTAC CCTGCAGTAC AGAGTACTGC CTCCAGGACT TAGCACGAGA
134851 GCATCAAATC TGCGGTTGTT TCTTATTCAT GTAAGAGTGT CTATGACTTC

134901 AAGGAACCTT AGAGCTCAAT GGCATCAGCA GGGGCTTATT ATATGTTAGC
134951 AAAGGTAGCA AGTGACAGCC CAGGATGGAG CATTCAGTAA AAAAGAGAAT
135001 AAAGTTTCCT GTCAAAAGAG AAGACACTAA TTAAGTTTAA CAGTGAAAAA
135051 CAAACAACAA AGCAATTGGT CTTACTAAGA GACTAAACTT CAAAATTTGT
135101 AAGCCAATTT CATTTTCATC TTTTACCTCT GTTAGTTCTA TCAACATGGA
135151 CGGCGTTAAT ATGACAGAAT ATTTGTTTGG AAATAATGGG ATCCATATGT
135201 ATTGAGTCAG CTTCATCACG CCCAGGGGAA ACTTAAATTT TAAAATGCCA
135251 CCCAAAATAT ATGCATTCAA CATGCATAAT GGCTCATCTG TTGAATAGTT
135301 GGGAAGTGAT ATCAATCAGA AGGATTAAGA AGATGGCTGT TTAAGGCAAT
135351 GATGATAATA AATTAGTGCC AGTTTGCTTC AATATGTTTT ATGGCGTCAG
135401 TAAGATGGTA GGTGAGCTCT TTGAAGTCTC GTTGAATATG GTTGTTTCTG
135451 CAGCACATTT GTTAAACCCA TATATGGATT GAAATCATAC TAATGACAAT
135501 AACTGCTCCT ATGACTCAAA AGGGAAACAA ATGGATACTG TCAAGTTAGT
135551 CAGTGCTTGG AAATGGCTTC TGGATGAATT TCCTTTGCAA AAAGTCTCTT
135601 TCACTTTCCC CAGCTCACCT TCACATTTAA CCGTAATAAG CACTCTTTAC
135651 TCTAGACATT TAACAGATGT TTTTAAATAA CTCAGTTATT GGGTATATAA
135701 AAAGAAGAAG ATGACCTCCC CAAAAGTCCC AAGGTCAGAG CTATTTGCCA
135751 TCTGAGCAAT TGTCCCCAGG AAGAATGTTG TGAATGATCA CTTCTCTCTA
135801 ACCGTGACTC AGCACAGCAC ACCAACCTGC ACCCATTTTC AGAGGCTCAC
135851 CTTGGGTTGA GGGTGACTTT GAGTATATGG GCCTCAGCAG TCACCGCCCA
135901 AGGGCTGTGC CTGCTTGTCA TGCTTCTCTA TCACCCCACC CACCTGCAGC
135951 CATCAGAGAG GACCAGTTTC TCACTGATCC TCCTCCCCTG ATGCATTTAC
136001 ATGAGAGATG GGGGAGGAGC TTTCCCCCTT GAGACTTGTT CACCTTGTTT
136051 TACTTTGGAA GACAAGATTT TACAGTACCA GGAATCAAAA CATTTCTCTG
136101 ATCACGTCAT GCTGACCAGT GCTAAATTAT CTCTGATTCA TTGTACATTT
136151 TACAGGTTAT TTGAAACCTC AACAGGGGGG AAAAAAATTG ATAGTATTCT
136201 GTGTAGAAGA GGCTCTGGCC ACAGACCGAA AAGGACTTTA TCTTTACTCA
136251 TCCCTACCAG ATTAGATAAT CACGTGGAAA ACTGTAAGAA ACATCTTCAA
136301 CATACAAGAA ACATGCATCT TTAGTATCTT CTGTATGCAG ATTCCAACAT
136351 GGAGAAAGTG TTCTAGAGCC TAAGGTTTGA GGACTCCAGG TTTGAGTCCA
136401 TGTTAAATGG AAGCAGGAAG AGAACCATTT AAAGGTTTGC ATTTAATGCT
136451 TTTAATACAT TCAGGACTCA GTAACGTCTC CTGTGCAGAG CTCCTGATCC
136501 ATTCACGGCA GCAGAGACAT ACCAAGTCAG CACAGAGAAG ATGCCTTGGC
136551 TATACAATTC ATTCATGTGC CGCAGCCCTG GTTGGCTGCT GAATATAAGT
136601 CCCTAGTACA TCTCTATTTT TTTTTTAGCA ATATTGCTGC TGAAGCTTAG
136651 CTGTGTGCTC TCGTGTGTCC CATCCTGCTC TTTCTGCCTC AGGTGTGTGG
136701 TCTAGTTAAT CCTCCATTCC ATGGGAGAAA CATAGCCCAG GAATGCTGGT
136751 TGTGAGGAGA TTTGATTTCT ACTCCTACTT CTGCCATTAA CTGTATGACT
136801 TTGGGCAAGG CTCTTTCCTG GTCCCAGCCC AGCCCCAGCT ATTCAGCATC
136851 CATTTAGGAT AGGTTGGTCT CTAAGGAGCC TTTCTAGCCC CAGCATTCAA
136901 GGACTTAGTG GAAACTAGAA TTCTGGGTTC AGTTGAGTTC AGTGCCACCG
136951 GCATTTGCCG ACTGACTTCC TCTTTGTCAT CAAGCACCAT ACGGGGCACT
137001 GCAGGGGATA TGTTTATATC AGAGCTCTCT CTGATACCAC GGCACTCACG
137051 GGCAAAGGGA GAGTGGGATG AGAAAAACAA GTGTATTGAT ATACCAGTGC
137101 AGAGCAGACT ATGTTGTATG CTGGAAGCAA AGTACAAATG ATTATAGGGT
137151 CCAAAGGAAG CAGAAATTTC ATTTATTTAT GAAAAGTCAG AATAAAACTT
137201 CATGGCATTT CAGATCAGCC TTGAAAGAGA AAATTCAAAC AGGATCCAGT
137251 GAAGTTTCTA TAGCAACATT TACTGAGCAA ATATTATGTG CCAGCCAATG
137301 TTCTGAGCAC TTTGCACACA GTAACTTATT TATTCCTCTC AGTCTTTTGA
137351 GATTAAGACT CTGGTTATCT GATTCTGTAT ATGAGGAAAC TGAGGCATAG
137401 ACTGGCTAAG GAATAGGCTT AGGCTCATGC CACAAACAAG CACAAGCACA
137451 AGGATTCAAA GCTTAGCGAT CTGGTGCCTA CGCCCGTCAC TTAGTGTGGA
137501 GAGTCAACTG ACTGTCACAT AAACAAGGCC ACCGAACCTG GAGGGAGGGA
137551 GACCTGACTC TGCAGATGAG CTTTGTGTCC CTGGGAAAGT CTTTTCAGCC
137601 TCTGACCTTC ACGTTTCTTA ACTCTGAAAT GCGAATGAAA AATAGTTTCC
137651 TCGTTGGGTT ATGATGATTC AGCAAAATGG CAGGAATAAG AATAGATTTT
137701 AAATGATTAA AAGTTCTAGA TGATTTTAAA TAGGAGAGAA AAGCAGAGGA
137751 GCTGATTGAG CAAATGCTGA GAGGAGGTAA AGTGTGGGAC ATATTTAGGG
137801 CAGAGTGATT ATTCAGTATT AGGGTCTCTT CTCCACAGTT TGAGAGGTTC
137851 CCACCTGAAG TCTTGTTCCA TCTCATCTCT TCCAGCTATG CCAGGCCTTG
137901 ACTCTGCTCT CTCTATGTGG AGAATGACAA ATCTAGTCTC TGTGTGTGTG
137951 TGTCTGTGTG TGTGTGTGTG TGTGTGTGTG TGTGTGTGTG TGTGTGTATG
138001 TGTTGTGCTG TTGAAGCTGA ATGCCAGCAC AATTCTCATC AGCATTTGAG
138051 TTCATTGGCA GCATTTGAAA GAAAGTATAG ACCCTTAGCT CTCAGTGCTA
138101 ATATAGACAT TGGCACATTA GTTTCAGCTG AATTAACTCA TGTAGGACTG
138151 ACGCTAAGGG ACAGTTAGAG TGGAGTGGAA ACTTCTCTGC ATACAGAAAT
138201 AACATCTCAG CACTGTCTGT GTAGCAAGAT GTATTATCAT CATCTTATTG
138251 GTACTGGACA AAGCAGGATC TTCAGATGGT GCCCAGCGAC TATAGGGACT
138301 AATGGGAAAG CAGAAGGGAT GCAGCGTGGT TAAATCCAAA AAAAGAGCAG
138351 CAGCTCAAGA GACAGTAGGA AATACGATGG ACAAGGGTCA GGAGACCAGG
138401 ATTTGAGCCC CAGCTTAGGT GATTGGTCCT GGAAATGTCA TTTCTATAAA

FIGURE 3, page 39 of 122

138451 TTAGCACAAC TGATAAAGAT GCTCTCTAAA GCACCTTCGG TTCTGATAGC
138501 CTAAAAATGC ATGAGTTATT TTTAAGCAGA AACTTAACTA CAGCTATTCT
138551 TAGTCTCTCA ACTAGAAGCT ACATGTGATT CTGCATTTCT TATTAACTGA
138601 GAGGTACAAT TTTCCACTGC ATGTTGCTCT TATCTTTCTT AGTGGCCAGA
138651 TAATGTTATT TATAAAACAA TAACAATATA GCCTCAGATA ACTGCAGCAA
138701 CAGAAACAAT AGTAGTCATT TACAGGGCCA GGAACTGTGC AAAAACACGT
138751 TTTACATGCA TTTGATTCTC AGAGCAGCAC CATTGGGTGG GTACTATTAT
138801 TTCCATAATA CAGATGAGCA AGCAAAGGTT TCAGAGTTAC TAATTAACTT
138851 GCCCAAGGGA CGAAGCACCG TTTTGAATCT GGCTTGTCCA CCATCAAACC
138901 CTTTATCCTT AACCACTCAG GTGTCTAGCC CAGAGTAGAC ACAGGCACGT
138951 GAGCCCAAGT GTTCCAGGTG GCCTTTCAGC CCCAGAAATC TCCCCTCACT
139001 TGAAAAATAA TCTAGAACAA TTTTTTTCAG AGGAATCAGT CTTTCTTCCC
139051 CAGTCAGAAT GAAGTCACTA ACTCCAGAGT AAAAGAATGG GGCAAGCGAT
139101 GCTCTCTGTA AAGTGAATTC TAATGAGGTA AAAGTGGGCA GGTCTCTACT
139151 GGAGGAGAGA GGACAGCAGC GAGGAGAGTG GCATGGGAAG TGGAGAGAGC
139201 TGCATATGCC CCCACCTCCC CAGTTCTCTG AGAGATATTC CACACAGGAA
139251 TTCCTGACCC TTGCCCAGCA ATTGTTCAAT GACTCTGACC ATGGAAAGCA
139301 TACGAGAAAA AGTACGCCAG AAAAGTTGTA TCATGGTCGG TAGACCAGAG
139351 ACAACAGAGA AACTGGCTGC AAGTCTCAGC ATCACTCAGA AAGCCTTTGT
139401 TCCCAAGGCA CTATTAAGTA TCAGGCAGAC AGAGAGATTC CTGAGACACA
139451 GCTCCTGTCC TCACAGGAAG GACTCACTGG ATAAGATGGG AGGCAAACCC
139501 AGGCAGGCTA GCATTGATGC AAGATGCTGA GTGCCATAAC AAACGTCTAA
139551 GCAGCTTGCT TTAGGTGTAG TGTGAAGGGA GGATCAGACA TAGTTAATTC
139601 TAACACGAGG TAGGAAGTGT TAAGTGTGCT AATAGCAATA CAAGCCAAGA
139651 ACTATGAGAG CCCAGCGAAG GATGGATTAA TTCTGACTGG GACTCTCACA
139701 GAAGAGGTGG TGTCTAAGTG GGACCTTGAA GGATTGGAAT GAGAGATAGA
139751 GCAGTGATGA GATTCTGCTC ATCACAGGGG AGTTGGTGTA AAGAGGAAAG
139801 TCTATTTGCC TGTGCTTGCT TTTCCGAAGG CAGGACGGCT ACAAGCATGG
139851 AGCTGAAGTT CAGACTGACC TGGCTTTGAT TTCTGTGTCT GTCATTTCTG
139901 TGTGCCCTTG AACTTTCATA TTTTCCTCTG TAAATGGAGA TTCTAGTACC
139951 TTCTTCATGG CATTGTGATT GGGAACAATT ACATTACAAC ATGTTTAGTA
140001 ATGCAAGTGT TTAAGTACAT GTTCAATAAA TGATAGTTTT TATTGTCTGT
140051 GCTATGACTA TTTCAGTGAA CATTATCTCA GTCTTCTGGG TAGCATCTGA
140101 GGCTAATTGG CCACTGTTAG GCAATTTTAA AAGTTAACGA AATGCACCTA
140151 CAACTTCATC TGCATTTGTC CTCTCTTCAG ATCCTTGTAT ATGAGCATCT
140201 TTGCCTATTC TTGGATCATA GTCTTGCTTT TTTGTTTTTG ATTTGTTTGT
140251 GGGTTTTTTT TCTATACAAT AGAGCAAATT ATTGATTCCT TTTTATAATT
140301 TCCTCTTCCT GTTCTAAAGT CCTACCTTGG ATGGTCCACT CTTTGTTGTG
140351 TGTTCAGATC CAGTAGTGAG TGCAGAAGGA CAGTTACCAT AGTCAGCCTC
140401 TCAGTTAGAA TTCTGTCGTG TCTACAGACC AGCTTTGTTC CTCTCCTAGT
140451 CACCACTATG CTGCTGAGAA TCATCATAGA ATATGGGAAC TGCAGGCAAC
140501 TGCAGCCAAA TCTTTTGTTT TACCAATGAG AACCTCCAGC CCAGGGACAG
140551 GAAGAAAATT GTCAAGTTTG TACAGAGAGA CAGGCAGGGG TGGGCCTGTG
140601 TACTAGTCCT CAAGTGTGCT GACTCACAGG CCAGTGCCCT GGATGGTTTG
140651 CATGCCCTTT CTGCTTTTCT TCCGCAGACT TAGGCTGTGA GGAGGGCAAA
140701 AATGCCTTTC CTCCTCCTCA TTTCCTCTTC CCTCCCCCTT CCTCCCTGCT
140751 TTGGGTAAAG CTGAAACATG CAGCTCGTGC TTCCACAAGG CATCCTCAGC
140801 ATGCTTTTCA CAGCACCCTC TGCTGACTCC GGGGCCTTCA CAGCTTGCAG
140851 CCCAGTTGAC AGCCAGTGAA GTGAGAAGAT TGGAAACACT TTAAACTGTC
140901 TCAGCATTGA AGAAAGTGAG AAGAAGGCAG GTGGGAAACG TCTGTGATGA
140951 GCGACATTGT AGAGAGTTAA CAAAAACTGG GAGACTTTCA GGGTTTCCTT
141001 CTCCTGCTCC CCTGAAACCA AGGATTATAA ATACTTTCAA TCTTACAGGA
141051 CAACTCTAGC TGTGCAGTGG TGACTAGGTT GAAGAGGATT TGGAAGCGGT
141101 ACTTGGGCTC CGTGTACACA CACTTGGGAA CACATGCACA CACGCATTTA
141151 TGCATTTGCA CTATGTAGTA GGCATTTCTG CCTTGGACTT TTAAAAACAT
141201 GCTTGCCCTT TAGGATCCTC ATCTTGGAAA TCTGCCCTCT TCTCCCTCTT
141251 TAAGGGATTG CCCTTCCCTC TGAATGTGCA GAACATGCTG TTCTTCTACT
141301 GCAGAATTTA TTTCATTTTC TCATGCAATT TTTATTAGTG GCTCATAAGT
141351 GTGTCTTTCA TCGCATTGGA ATGACCCTCT TAGAGGCAAG GGTCTTGACT
141401 GTTGTTTTCC CCATACTATA CCACATACAC TATGTTGAAT TGATAAATTT
141451 ACTTATTCAG TGAATGTTTT GGTATTATAA TAGACATGTT GCAAGGTAGT
141501 TTAGCAAAGT GATAAGGACT CATGTGGAAT CAGACATACA GGGGTTTGAA
141551 TTGTAGCTCC ACTATTATCA GTTCTGTGAC CCCTGCCTAC CTATGTTTTA
141601 GTCCCTCTTT TGTTAAATGG CAATAATAAT AAAGTACACC CTCTTAAGCT
141651 GTTACAGAGA TTAAAAGAAT TGATGAAAGT AAAATGTGTA GTCTATTTTC
141701 TAGCATTAAA GTGCTCAGTA TATGCAAGCA CCTATTAGTA ATTAATGTTA
141751 GAAATAATAA TGATAATTAT CATCATCATC ATCATCATCA TCATCATTTG
141801 TTGCCACTGT GGCTGTGCCA GGTTCTCCAG ATCCTCAATG ATCCCCTTTC
141851 TTTTCTTAGA TATGTGAGGG AGATAAGCAA AGGAATATAT TGAAGAGAAA
141901 AAGCCCAATG TTTATTACTG CGTGGCTGTT GCTATGCTGT GGGCTTCTAT
141951 GAGCTGGAGG ACCCAAGAAA GCTACTTTCC CTGTGGCCCT CACCTATTCT

FIGURE 3, page 40 of 122

142001 TGGCTGTCTG GATCTCAGCA CTATGGGGAT CAGAAGAGGC CACCCCAAAA
142051 CAATAGGAAA TAAAAAGGAA TTTTTGCCCA ATGCTTTGAA CAAGGCAGGT
142101 CCAAGCTTCC CACCTCAGAT CTTCAGAGTG AAGTCCCCTC CCTCCCATGC
142151 TCAAAGCAGC TCTAGACCTG CACAGCACCC TCAAAGAAGC AAATCCAGCA
142201 GAGATTTTAT GGCTTTAGCA CCATCTGGCC TTATCTCCTT AGCTGTCTTG
142251 AAGGAGACAA TAGAGGGTGG AGGAGAAGTA ATCATCCTAA AACCAACAGG
142301 TGGCCCCAGT TGTAGGCTAT GTAGCAGCAT GGCTGTGGTG GTGGTGGTTG
142351 CTTGGTGTAT GTGTGGAAGT GCAAGGGAAG TCTATAATGC AGTGTTCTGA
142401 GTGTGTGCAG AACCTATGGA GGAAATCAGA ACTTGAGATA GAGAAACAAG
142451 TCCTGTTAAT GGTAACGCCA TTTGGATCTG GAAATAACTG TGTTTGCATA
142501 GTCCATGTCT GTTCTCTTAC AGATGAGGAA ACAAAAGCTC TTCATTTAAG
142551 GAGAGAAATA GTCCACTCTC TTGTTTACTC TTTTACTTGA CATTGATTGA
142601 ACCTCTCAAT GGCAAAGACT GTGTTGTGCA TTAGATAGAT ATGCTGAGAA
142651 ATGAGAAAGA GGCTGTGCCC TCAAAAATTT GTCCTAAAAG GGGAACATCT
142701 AGATAATCAA TGAGCTAATA AATGATTAGA TACAGTGTTG TCCCTTCAAC
142751 CATCTCTTTG GATTCACCAC ATTCTCCACA CTCTCTCTAA AGACTCCCAC
142801 TCATGCCCCT GGTGAGTCAA AAGCTCCTGG CCAGTAGCCT CTTCTCTGAT
142851 CAACTCATAT ATTTCTGCTC ATATCACCTT TGCTGGTGGC ATACCAGAAT
142901 CAAGAATCAA TTCTGTTTGT TTTCAAACCT GTTTATATTT CTGTGTTTTT
142951 ATTATACTTG GACAATTTAA TTAAAATGAT GTGAACTAGT GAAATATGAG
143001 TGCAAAAGAA AGTCTTTTTT CTGAAACTAA ATACTTTTGA AAGGCTATCG
143051 GATGAATCAC TAAAATCATT GTAATATTAG GTATCAGAGA GACGACTCTA
143101 AGGTTGGGGA AAAGCATGGA AGAAAATCTA AACTTATATT TATTTTATAA
143151 GTGCCTTCAA GTTCCTGATA TCAAAATATT GATCAATACA TGTGCTTCAC
143201 AGTGTTTTAA GTTTTTTTGG TATATTTTTT AAATAATCTA ATTGCCATCC
143251 ACGTTGCATC AGTTAAGAGG GCTTCAACTG TAATTAAGAC TTTGAGTAAA
143301 GTTCTGTGAA GGATACAAAC TAAATGTTGT GACCGAGAAC AGCAGGATGA
143351 CCTGCTTAAG GTGGTCCTTG CAAGATAACA AGAAGCCAGC CAAGCAAAAG
143401 TAGGGGAGAA GAGTTTTGGG CAGTGAGAAC CGCATCGGGG GAGGTGTGGT
143451 ATGTTGCAGA AGCAGCAGAT GAGGGAAAGG GAAATGATAA GGTTTTTCAG
143501 GTCAACAGCG CTTAGACAGT GCAGATTCTC AAAGGTCATG CAAAGGAGTT
143551 GGGACTTTAT TCAAAGCATG ATGAGAAAGC ATGAGGGGCT TGAGGGGATC
143601 TGTTTGACAG GATGTGATTT CCATTTTCAA AAGAGCTTCC TGGCTGCTAG
143651 ATGAAGGATG GATGAGAACG GAAAAAGGGA AAGTGGGCAA GGTGGAGGCA
143701 GGGATGAATT AAAGTGACAA AGGCAAGTGA TAAAGTGCAA TAAGTCTACA
143751 GTGACAGGTG AGCAGTGGCA GAGCCCTAGG CCAGGGTGAG AATGGAGATG
143801 TAAAGTGGGC ATTGTAAATA CATTTGTGAC ATCTTTAGAG GGACGTGCAT
143851 CCATATTTTC TTTAGTCAAT CTGCATGACC AAACTTACAG CTAATTTTTG
143901 AAGGCATAGG TGATCTGATG GGGGAGAAAA TCCTACCAAA AGTCAGGCAG
143951 CTGGGTTTCT TTTTCTAGTT TGATATTTAT TGGCTGTGCT ACTCAGAGCA
144001 AGCAACTTAA CTCTTGGAAG CTCATCTAGA AAAGGACAAT AATAATATCC
144051 TGTGCAGCCC ACCTCATATT TGGGTTATGC AGTTTAAATA AATAGATGGC
144101 TTACATGTAT CTAGGACTTT GGTAAGCTTA TTCCTTCACT TGATCCTCAC
144151 GGCGCATAAG GCAGATACTA TGGTCCTCAC GTCACAGGTG AGCAGACCAG
144201 TACCTGTTCA ATAAACCGTT ATTGAACATC TACTATGTCA GGGTCAGGGA
144251 CAGGCCCTGA GACTTTTGAA ATAGATTAGA CCCAGCCCTG TCCTACAGAA
144301 GTTCACAGTC TGATGAAGAA GACAGATATG AAAATGTGAA ATTATAGAAT
144351 ATCAAGATAC ATGCTAAGAC AGAAAGTACA TTAGAACCTT AGAGGAGGAA
144401 GAAATGAATT TTTTCTGGAA GGAGTGAAAA GCTTTCCACT GGAGTCAACA
144451 TCTGGCTGGG GTCTTGAAGG ATGTGTAGAA GTTTTCCAGG TATGGAGGGT
144501 CATTTTTGAG AAGGATATGC AAAAGTATGC AGGCCTGGAA GGAAATGGTT
144551 CATATGCATC TATGTGGGTG GGGCCTCAGG TGATTGGCAA ACTGTTAGGA
144601 ATGAGGCTGG AGAGTGAATC AGGGGCAGGG AGGCTCCTGC TCATGGATCT
144651 GTGAGTGAGT GAGTTATGCA AAAGCAGGAA AACTAGTACA TTTGCTTCAT
144701 TTTCATTCTT TCCTCAAATG CTTCCCCCAG TTTCATAGTA TACATGTTCC
144751 TGTGCCTTAT ACTCCCTTCT TCCTTGCTTA CTGTTTCCTC CAGAATTAAT
144801 TTGAATCTCA GCCTTTTTCC TGGAACTCTT AATTTTAGCA GGGATATACA
144851 AAGGGAACAC TCCAGGATAG TGAGAAATGC CTTTTTTTCT CCAAATGTCT
144901 TCCGGAATTC TGTTACTTAG CAGGAGTTGT TTCCTGCCAT GTTTTGAGAA
144951 ACTTTGAAAA GCGATTCAAA CGTTGGTGCA AAGGGAACTA AATACTTGGT
145001 AGTGAGGAGC ATCTTGGCAG AGAAGGCAGC TGAGCTTTTG CTAAAGTCTC
145051 AGTGGTTGAA ATTGTCCAGG AGGCCTGAGT TTTGGTCCCT GGGCTGGGCA
145101 GCATGTGCTC TTGGTTGTCA TGCCTCCATT CCTCCTTCTG GAAAATAGTA
145151 AAGAAGAAAA TGTATAAGTT AGAGAGGTGA AAGAGTGTTA GAGCTAATTA
145201 AATCTCACTT ATTTTACTTA TGAGGAAATA ACTCCCAAAG AGGAGAAATG
145251 ACTAAGTTCA TATAAAGAAC CTGCAGCTAA CTTGGTCATT TAGTCATATA
145301 AAGAACCTGC AGCTTACTTG GTCATTTATG CATTTATTCC ATTCAGCAGA
145351 CATGTTTCAG TGCCTCCCAT GTGCCAGGCA CTGTGGTAGA TGCTAGGACA
145401 ATAGTGATAA GTAAATAAAC ATGATTCTTG CCCTAATCAG GGAGATGAAA
145451 TTAAACAAAT AAACCAAAAG TTAAACAAAA TAATTAAAGA TAGAGATAAG
145501 GTATGATGGA AAGAAACAAG GTACCGCAAT AGAGAATAAA GAGTAGGGAC

FIGURE 3, page 41 of 122

145551 CGGGCACGGT GGCTCACTCC TGTAATCCCA GCATTTTGGG AGGCCGAGGC
145601 GGGTGGATCA CAAGGTCAGG ACATCGAGAC CATCCTGGCT AACACGGTGA
145651 AACCCCATCT CTACTAAAAA TACAAAAAAA ATTAGCCAGT CGTGATGGCA
145701 GGCACCTGTA GTCCCAGCTA CTCGGGAGGC TGAGGCAGGA GAATGGCGTG
145751 AACCCGGGAG GTGGAGCTTG CAGTGAGCCG AGATCGCGCC ACTGCAATCC
145801 AGTCTGGGCA ACAGAGTGAG ACTCCATCTC AAAAAAAAAA AAGAAAAAAA
145851 AAAAGAGTAG GATGAGTATT TTAGAGAAGG CCTCTATGAA GAGAGAACAT
145901 TTTAAGCTGA GATCTGAAGA ATGCGAAGGG GTCAGCCACT TAAAGAGGGT
145951 TGGAAGAGCT TTCTAGGAGA TAACAGCTTG TGTAAAACCT CAAGGCAAGA
146001 AAGTCGGGAC TGTCCTGAAA GGTAAGAGAA AGACCAGCAT GAAGCCCAGG
146051 CAGAGGTGTC ATGGCCTGGA AGCAGATGTG GTGGGAGAGA TAGGCAGGGC
146101 CAGAACTCAG AGCCTCAGAG TTCAAAGTGC CCTTATTGGC AGACTCTTGA
146151 TTGATCTCAC ACCCCTGCGG AAAAGGAAAG GCAAGTATAC GTGCATTGCA
146201 AGACTCTATT GGCCGAGCAT TTGTTTCAAA TGTCGTTTTC GCAGCATGCT
146251 TTGCTGAGAC CATAGATTAC AAAAACAGAA ATAAAAATGA TTCAGCTTTT
146301 CTTCTGTGTC TACCCCTCAA CTTAATTAGT GCTCACAGCT CCAGAAATCA
146351 GTTGAGGGCA GGGGTCAGGA GTGAATTCAG ATATAGATGA AGTGGGACTT
146401 AGTTTCTGGT GTTGCCACTT GGTTTTAAAG ATGCAGAACT TCTTATCTTC
146451 CATAGCTTTA TTTTATCCTT CATTTTTGTC CTTTCACTTC CTCAGTGGAT
146501 AAATCCTAGC TAGAAGATGA ATTTTGCTGA TTTAGGGCAC CCTCGGGCTG
146551 TCCTCTGTAG CTTTCAGTAA AGCTTTGTCT TGATTGACAG ATGCTGATCA
146601 AGTTCATGGG TATGCATTAC AGTGTACGTT TGCTGGTTGG CCTAGGAAAA
146651 CCCATTTGCA CGTATGACTT TCATAGGAAA AGAATGGCAA ATAAGAAACA
146701 AAAGATTTTT TTTCTGCCAC TCACCCAAGG AACAGAAATT AAGACAGCCA
146751 AAGGAAGAGT CTGCCTTCAT TTAACGGATG ATTTACCTGG TGTTCCTTGC
146801 GGTAGTGGTT CATTCGTGAA CCAGCAGAAG GTATTTTGTG ACTATGGGGA
146851 TTGCGGAGAT GACTGGGCCA GGAGGGGAAG CTGTAAAGCT AATCTCTCCC
146901 ACAACCCACT TCTCTTTGGC TAATGGCTTT GCTTTTGTTT GTTCTGCTTT
146951 GGCTGGTTCA TGTGCTAGTT CCCAAAGGCT GCACAAAGGC AGAGCTAGGT
147001 AGATGTACTC CCTACCAGGG CTCTTTAGTG AATCCCACCT CCTAGCCCCA
147051 GATGAGGCTG AGTGAACACT CACTCCAGCC TTGGACTGTA GCCTTTACTG
147101 TGGCCCCTGA ACCTAACCCA AGAATGAGAC TTGTTGACCC AAGGCTCAGA
147151 CCCCAAGTCT CAGATCCCTT ATTTCAAAGA GAGCTCCTCA CCCCAGCTCC
147201 AGACTGAGCC CCTGGCCCAG CATTCCTGGC TGAGTCCCCA CACGTGGTAG
147251 AGCCTTGGCC TCAAAGGGTC CATCCACAAT GTTGTGAGTC CCTTGGTACA
147301 TATTCACTTT TTGAATGAAC CTCTGAGGAC CCCTGCCCTC TCAAGACTGG
147351 CGTCTCCTCT GCCATCTCAT CAGAGTGGCT TTTAGCCATG GAGCAGTGTC
147401 ATAGCCTCCT CTAGTCCAAA GCTGGCCGGT GCTAAGAAGA GGAAGCCTGG
147451 AACTCAGAAC CTCTGTCCTT GTGCCAACAT GTTAGTTGCA GTCTATCTGT
147501 GAGCTTCACA GTCCCATTGA CTCTTGTACA GAAATCAGCA AGCAGTGGTC
147551 TTCAGTCAAA CTGGGACCTC AACAATCGAC TTTGGTCCTG TCAGGGTTCC
147601 TTTCCCTTAC TCTTCTTAAG AGCACCCAGA GTCACCATGA AAGAACCACA
147651 AGTGGAAAAG GAATACGTGG GCTCAGACGT GTGTCCATCC TTGCATGACC
147701 CTTGGCTCCT CATCTGTTCA TGGGTTTAAA GGTCATCCTT CCTGCCCTGC
147751 CTACCTTATT GAGTATTCAC AACAGAAAAT GAATGTAGGA GATTGAAAAT
147801 TGTATAATGC ACTCTAAGTT ATTATTACCT CTCCCAAATT GTCAGCATTT
147851 CATCCTTGCT ATCTAGCAGC AGAATAGTGT AGGGTAGCAG TTTACAAACT
147901 ACAGCCCACA GGCCAAAGCC AGCCCAAGGC CAGATTTTCT AAATAAAGTT
147951 TTATTGAAAC ACAGCAATGT AAATATGTAA ACTCATTTGT TTACATATTG
148001 TCTTTGGCTG CCTTCATGCT ATAAAAGTAG CACTGAGTAG TGCAGCAGAG
148051 ACCACATGGC CCGCAAAACC TAAGATATTT ACTATTTGGC TTTTTGCAGA
148101 AAAAGTTTGC CTATACCTGG CATAGAGGAG CAAAGTGAGG ACTCTGAAGT
148151 TGGAATGCCT GTGTTTGGAT TCTGAATCTT CTACTTAATG GCTATATGAC
148201 CTTGTGCAAG TTAATTAGCT TCACTTTTCT CTCTATGAAA TAAAAATAAA
148251 CATTGTATCC CCACCCTGTG CTATCAAATT AGCATTAAAT GAGTAATTCA
148301 TGTAAGGCAC TTAGCTTAGT ATTTGGCACA TAGTGAGTGC TCAGTGTTGG
148351 CTGTTATTAT TATCCAAAGA ATGAAAGCTC TGGTTTGTGT TGATGGACTC
148401 TCAGGGGATG GAGTAGCATG GTTTATGGCA CAGGCCATGG AGTAGGACAG
148451 AACATTATTT ATATCCCAGC TCTGCCACTC ACCACATGAA TGACTCGGAG
148501 AAGATTAATT AATCTCCCTG AACTTCAGCT TCCTCATGCA TGAAATAGGA
148551 AAAAGAAATT AAAGAGTTAT TGTGAAGAGT AAGTGATAAA ATGCATGTGA
148601 AGTGCCAAGA ATAGAATTTG GAACATAGTA AACACTCAAT AGGTGATATA
148651 AATACAATAA TAAATAAGAA GAAGAATGGT ACTTTTCTAA GTAGTACTAG
148701 CTTCTCAGAA CAAATAGACA GTTGGTAGTG ACTACTATGC AAACATCATG
148751 TGAGGTAGGA GGTTCTACTT ATCATTAATA ATGCTCTGGA CACCAGGTTT
148801 TGCATATTCC AGGCACATGT AAATTAAATA CACTTTAAAA TGGAGTTGTT
148851 TAGACAGCTG TCTAGGCTTT TATCTAGGCC AATAGTCCTT CAAGACCAGG
148901 TACCTTTCTG TACTAACAAT CCATGACTCT ATGACTGTTC TTAGGTGAAG
148951 TGATAGGTCA AGGAGAACAG CATACACGTT GAGTCACTCT ATGGACCATC
149001 CCGGAAAGAT CCTCTTCTCA TAATAACACG TGGGTACACA GTGATGCTAA
149051 GGAGTTTGCC ATATGGGGTG AAAATGCTCT CATTTTGAAC CCATTCAACA

149101 TCTTCAGGGT TGAGTTCTGT AATGGGATGT AAATCTTCTT TCCTGGGGAG
149151 AAACGGCTGA GGAGACTGGG TGTTGTAGGT GGAATACATT AAGGCTGGTG
149201 GGGTTTGAGT GCCAGCCCAA GAGCACAGCT CTCATTCTCA GTTGGCCTAA
149251 GCTAACAGGG AGTGATCAAG TTCAGTGGAC TGAAGCACAG GGGAGTATTA
149301 CGTATCTTCC AGACCTGTGG ATGCTAGATG GGCAACCTAA TTTAGAGGAA
149351 TATGAAACAA GTAACAGCAC CGTGCAATTT TCGTTATTCC CTACCTAGCT
149401 CTTTATGAGT TATTGTTCAT TATATTAGCA GAAAAATGAG GATTTGGAGA
149451 GCCTCTTCCT TCAAGGGGGC TTACATCTCA ATTGCAGGTG AAAAGGCATA
149501 AATACACAAA AAGTTACTTG ATAATATAAA ATAAAATAAT CAATTCATTC
149551 AGTGCAAGAC ATGTCATGAA AGAAAGATGG GTCAACTTAG TATCCAGAGA
149601 TTAAAATAGG TAAATGACTT GCATTCATTC ATTTATTCTC ATATTCATTC
149651 ATGTCCAAAA ATATTGTGTA GTCATTATGG GAACCCTTCA AAGGGATATG
149701 AATAATAATA TAAGCTTTAT GAGGGCAAAG GCATCATCTG TCTTATTTAC
149751 CACTCTATTC CACAGTGTCT AGCCCATAGA GGAAAGACAA GGACTGAGTT
149801 AGACATAGAT CCTTATTTAA TACTCAGTGT TTAGATGTAT GTAGTTCCTA
149851 ACACATTTGT GGACATTTAT GGAGCTCCTA ACATGATTTT GGGCTCTAAT
149901 TTATGAAATA CTGCAATCAG ACATTTAGTA GACATCTGTT GGTTTGATAT
149951 GCCCAGCATG CATCTCCTCT CTGTTCACAG CACCTTAATT TTCCTCTGGC
150001 TGGTAGCTTA GTAACGTGGA TAGTTGTTCT GCTTCCCTTG ACCCAGGGGC
150051 GGCCCATGCC CAAGCAAGGC TAATCTTGAA CTGTGTAAAC AGTTATCACA
150101 AATGGCTGGA GCAATGGTGA GACCCTAAAG AGACTGTCCA TGAAATGCTG
150151 ACATCTAGAT TTCTAGAGCT GCTGCAATTT CTGTCTTATA TGAGGCACTT
150201 TTTCAGCTGG GGCTTCCTCA TATCCTTCCA AAATTCTGTT CTTACAAATT
150251 ACAGAACCTA AACTAATAAA GCATGGGTGT TAGATAAAAA ATTGATAAGA
150301 CGCACACATT TTTATGTACA TTTAAAAGAT GGGTGGAGAC TTTCAGTTTA
150351 TAGCTAGGAG TAGGGAGGTG TAAGGGTCTT TATGAAGGAG ATGGCATTTG
150401 AGCTTAACTT TTAAAGAATG GAAAGGATCT GCAAAGATCC TTAAAGAAAG
150451 AAAGCAGGAG GCAGGAGGCC TGTGCAGGCT GGAGCAGGGG CATGAGTGTA
150501 GGCCCAGAGC CTACGGCCGA GAAACAACTG AAAAACAGCC ACGTCTGTGC
150551 TGGAACTCAG TGAACTCACT GAGCATCCCA TGTCTGTCGT GCCATTACAC
150601 TTAAGTCAGA TGTTCCTGTT CCCATTTTCT AGCTTATCCT ACTGAGTCAC
150651 AACAACCTTC CCCTCCATTG TCTCTCATCC ATGGACTGGA CTTGAGCTAT
150701 GGGATGTTAG AGAGGAAAGG TCTTGTGAGA CCAGCTAGGA CTGACCCTCT
150751 TAGGCCAAAG TGATGCTAGA GCCCTCCAGG CACCCATGCC ACACATGAAG
150801 TGCCGGATAC CTTAGAAGAG CTCAGTTTTA CTCAGAGAGC TATGTGATCT
150851 CTTTCTCCTC ACCTGCATCT CTACTGCTTT CCTCCTTTCC CCCTATACTG
150901 TGTCCACATG GGCCTTCTGT TTCTCAAGCT CTTCAGTCTT GTTCCTGAGC
150951 CTCATTCAGA GCCTCTGTTC CATTCCTTCT GCCTGAGACT GCTTCTTTAG
151001 CCTTTAGCCT GGCTGGCTCC TTCTTAGGGT TCATTTCTCA GCTCCAATGC
151051 TAGTGACACA GAGAGGTCTC CCTGACCATC CTGTCTAAAA TAGTCCTGCC
151101 AGTCACTCTC ACATCATCCC GTTTTATTTT CTTTGTAATA TTCGCAGCAT
151151 CCAAAATGGC CTTGTTTATT CACATGTCAT CTCTCTCCCT CTCTAGAGCC
151201 TAAGCTCCAA GAGAGCAGAG ACTTATCTTT TTATCCAGTG ATGTATACCC
151251 CTAGCACCAG CTTGCTGCCT AGCATACACT ACACATTCAG GAAACTTGTT
151301 GGATGGGTGA ATGATTAGGC AGAAGAAAGA TGGAGAGAAG AAACAGAAAA
151351 TTTCAATCTG TAGGACCTCA CATCCCCAGT GAGTACAAAA GTTCTATTAC
151401 AGCTACTTCA CCAAAACAAA AAAAGTTTGA GAAACACTGA TTTAGTTTAA
151451 ACTCTGTTAT CCAGAGAGGA AAAATGCAGC CCAGAGAGGA GAAGGGGCTT
151501 GTTCACAGAC GTGCTTCTTT GCATTTACTT CTCCACAATC ATGTCAGGCA
151551 CCTGAAGATT TTTATAAGGG AAGCTCCAGT TGATCAGTCT GTTTGCCCTG
151601 GCCCCCTGCC CTTGGTTACA TATGTCAGCC CACAGGGTGA GTCTAAATTC
151651 CAGGACCAGT GAGCCCAGCC CTGTTCTAAT TCTTAGCCTC GTATGCAGTA
151701 CCACATCTCA TTGGCTTTCA ATGCCTAGTA ATTAAGACCC ATGCTTAATA
151751 ATAAATACAC AAATATGACC TGGGAGGATG GCTTTTCTTC CACATCTCCT
151801 TTTGCAGCCA TCTTCCAACT GGGCATCAGG GCCTGGATGA AGAAAGTTCT
151851 TGTGAGTCTC AAATGAATCC AAAACCAAAG TGAAATGCTA CATTGACACA
151901 TGACACAATG ACCTAACTTC TCCAGCCCGG GCAAGGCCCT TGGCAACCTA
151951 GTCCCCACCC ATCTCCAACT CTGTGCCATA CCCCGACCCC AGTCATACTG
152001 GTGTTTCTGG AGTTTTTCTG TTGTGCCCTT CTCTTTTATC TTGGTGCTTT
152051 GGATAAAGTG GTCCCTCTAT CTAGACACAG GAACAAGGTG CTTAACACTG
152101 TGCCCGGCCT CTGCTAAAGG ACCCAGTTAA CACTGACTAT AATAGCAGTT
152151 ATGATCATTT ATCCTGTGGC TGATCCCTTT ATTACTCTCT CAAATCACCC
152201 TTTATTTTCC TTAATGTAAA ACTCACTGAA CACTTGCTTA AGCTCTGTGA
152251 AGGTAGAAAA CATGTCTGTC TTGTGTAATT GTGGTACCCC AATTTTCTGG
152301 CAATATTAGT TTCTGGTGCC AATAAATATC TGTTGAATTT ACTAAATAAA
152351 TGATAACATT GTATCTAGTA AATGACAGAC ACCCTGGATG TGTCTCAGAA
152401 TCCTAAGTAA ATGTGATATT GTTTAAGGGC TTTGGGATGA TTTATATCTA
152451 TTATGGTAAT TCTTTGCATG TCAGCATTAT ATCTACGATA CAAGAGAATA
152501 TAAAAAGGGA TGGACAGGCA CTCTTATTGT CCTCTGAGTG ATGGAAATGA
152551 AGCACATCCC TTGATGTTAC AACGTTAGAG TAAGATGATG AAGAATGTGA
152601 TTCCCACCAA TAAGGATAGA ATTATTCCAG GAGGGGAATG AGTGCCTGAA

FIGURE 3, page 43 of 122

152651 AGTCCCCCCA TTCACACATA CTTTTGATCT CCCTCCCCTA AAATGAAGCT
152701 GTCCTGTCAC CTCATTATCT GCTATTTACA ATGAGGCTGC CACATTCCCA
152751 GGGACAGGAG CCAAGGAGAA ATGTCGGTGT GAGAGGCCTT AAATGAAGTG
152801 ACAATAAAAA AGGAGTTGTT AATGCCAGGA GTTCCCTCCC TGGGAGACAG
152851 CTGTCAGGGC CAGTACCCAG GGCTGGGAGA TTTATTGATA CTAAGTGGAT
152901 GGTGCCCTAA CCAGGAGTGA TTATCAAAGA GGTTTGAGTG AGGTGAGGAT
152951 AGAATTGGAC AGCCCACGCC ATGCAGTGTG TGGGTTTTCC TGCTCTCACT
153001 GGTTCCTGCC CTCCTGCTTC CCCAAGAGGG AATTCCTGGC CTCGTTTTTT
153051 ACTTACTCTG ATTGTTGGAC ACGCTCTGCT ACAGAGTTTC TTGGAGGCAG
153101 GGCCCTCAGA ATCTGACACT CTGGCAGGGC TCCCTGAATG CTCTCTCTAT
153151 CTCTGCCAGG CCTTTGCTGT TGCTCTTCCT TCTACCCATA TACAGTACTC
153201 TTTATGCACA TGTAACTGTA CCAAAACCTC TCTCCTGGCT GATTCCTCCT
153251 TATCTTTCAG TGTCAAAGCT GGCACTTCCT CTTGGAAGCT TTCTTTGAGG
153301 TCCCCAAAGG ATGGGGTTAG GTGTCCCTGC CTGCTGAACT CATCCTTAAC
153351 ATAGCATGTA GACTGAATTG CTATTGCCTA CATAGTTGTC AGTCTCTCCC
153401 ATTGTCAAAG TGACAATCCC AAAGTGGTTG GGGATGGGCT GGTTTACCAC
153451 TGTATCTCCA TTGCCTAACA TAGTGTCTTC ACAAGTGCCA GATACTGGGT
153501 GTCGAATGGT GGGTGGATGG ATAGATGGAC CAAAGAATAG GTGTGTATGT
153551 GTATAGACTT CCCAGGGATG AGACAGGAAT ACATCAAACA TACCACTCAA
153601 TTTTATTTGC TTATATTTCA ATAGATTCTA ATGTAGTAAT GCCTCTTTAT
153651 CTGGCATCAG GGGAAGACAG TGTGCTACAT GAGAGGATTT TCCAGAAACT
153701 GAAGCTGACC CATGTCCCAA GACTATTTCA AACATCCATG ACATATCACA
153751 GACATTAAGG ACTCAAGCTC TGTCGTCAGA CTGGTAGAGG TCATCTCTCA
153801 ACTTGCCTTG TGCTGTTTCT AGACCTCACT TCTCCAATTT GAAACCCACC
153851 TCAGGGAATG AAAGGAGTTA ATGTAGAGAA ATGTCTTTGG CACAGTGTCT
153901 GGCACTTGGC AGGTGTTGAA GTATCAGCTC TTAATTATTA CTATCAGAAA
153951 GCATTACAGG CCAGTCACAG TGGCTCACAC CTGTAATCCC AGCACTTTAA
154001 GAGGCTGAGG TGGGAGGATC GCTTGAGACC AGCAGTTCAA GACCAGCTTG
154051 CGCAACATAA TGAGATCCCA ACTCTACAGT TTGGAGCTGC AGTGAGCCAT
154101 GATGGCACCA CTGCACTCCA GCCCAGGTGA CGGAGCCAGA CCCTGTTTCA
154151 GAAAAAAAAA AAAACAAAGA AGAAGAAGAG GAAGAAAGAG AACACCATAT
154201 TCAAGTGCTT TCTAAATGGC AAATACTGCG TTTCATCCCA GCAACATGAT
154251 GGAAGTCTGT GCATTAACCC AGTACACACA GAGTTCTGAT TCTGAAAAAT
154301 GCCCCATCTC TTCTCTCCTA CTTGTCATAT CTGACAATGT AGTCTCCATC
154351 TCTGGCTCCC TTTCTAGTCT GCCTCCTTTC ATCTCTCTAC TGGGTAACTT
154401 ATTCACATAG CAGGTTAAAA GTTGTGTCTT AACACTTAAG ACTCCAAATG
154451 CATCTATTCA GAAGTCACAA AGGTAAATCT GTTCAGGAAA GTGAGATATG
154501 GGCTGAGGCA CAACTCCTGC AGAGTAGTGA TCTTTGCAAA GAGGTAAGAA
154551 AAGCAGGCTG CAGGCAGGAG GGGGACAGTG CAGGATCCCA GGATTTTGTT
154601 ACAAGGGAAT CCAAGAACTC AGAGACTTAC CTGCTTACTG GATTTGAAAA
154651 AGTGCACTGG GGGTTGCTAG AATTTGACTA AATAACTAAA ATATTGTCGA
154701 ATCAGTAAAC ATTTTCCAAT CAATTAGACT AGACTCTAGA ATGTCAGAGT
154751 CTGAAAGGGC ATTAAGCATT ATAGAGATCA AACAATCATT TCACAGATGG
154801 GAAAGCTGAG GCCTAGGAGA GCGTGGGATT TACTTAAAGT CATACAAGTA
154851 CTCTGTAATG ATAAAACCAA AAAGAGAATC GTCCAGGTCT TCTGACAGCT
154901 AGCCTAGTAC TTTGTCTACA GAACCATGTT ATCTCTTCTG ATTGAATATT
154951 GGTTGTGACA GATTCAAAGT AGATATAATA CCTCACAACT ACTAATTATA
155001 TTTATCAACA TTTAACCAAT GACTGCCTTC TCCCACAGGC CTTGGGCCTA
155051 TAGGGTCTGT CTGTCTGTTT CTGTCTCTCT CTCTTTCTTT TACTTCCTCT
155101 CTCTCTGCTG TTGCTTAGGT TTGGCTGAAG TGTAGAAATG GTCTGACAGT
155151 CAGGCACTGA GCAACTCTGG GAGCCAGGGT TCACTCAAGT AAATCCAGGC
155201 CAGGCTACCT CCAAGCCATG CTCTTTTAGG GAGTAGTGCG TAAATGCACC
155251 CTCTTAGCCT TAGAGGAGAA AGCACTCTGT TTAAGGTAAG AGATGTTTGC
155301 AGAAGGGGAA AATGAGGAGA TAATTTGAAG GGGAAAATGT CCTGGCCTCC
155351 TGTGTGTCTA AGGATTTGTT GTGTCTGCCT GCTCCCATTT CGTCCACCCC
155401 CATCTCACCC TTTCCTACTT CACTTCTAAA GTCCTAGCAA GAAACACCAT
155451 CCATGAGGGC CCCAGAGGCC CAACTAAATG TGTGAAACCA AGTAGGTGAC
155501 ATGAGGGAAT AGATCTGGAT CATAAGATTT ATATCCTGTA GGATAATATT
155551 TTATTGCAGC AAGGGGAGAG AAGAGATCCT AAAAATACTG TAGAGAGTAT
155601 ATTATAATAT TTTAATGAGG TTTATGTGCT CCCCATATAC ACTTCACCCT
155651 GGATGATGGA TTGTGCATTT TGACAAATCT ATATTTAACA TTGGGAGAAT
155701 AATATGTGAT GTATGCTTCC TGGTAGAGAA ATCATATTTA TGGAAATCTT
155751 TATTCTAGTT ATTATAATAG ACATTTAAAG ACAGTGCCTA TTGTGGGCTG
155801 TGGATAGATA GAGTGTCCTC ATTAGGGTGG AGGAGAAAAT AGTGTGAGTG
155851 GCAGAGGATA AATGGCTACC TTAGAAGACA GCAACCCAGG CAGGGGAGCA
155901 ACTAGTTCAG GGTGACCCAA CAGTCACATC TCTGTTTGGG TTCAGCTCCT
155951 CCTCAGCCCC TGCTGCAGGT CATATGCCCT CATCAAGCAC TCATCATTCA
156001 TTTATTTATC AAATATTTAT TAAGCATCTA CCATGTCCCA GACACTCTGC
156051 TGGCTTTTGG GCACAAAGAA GCATGTCCTA ATTTTCAGGG AATTCACATT
156101 GACTAAAACA GCCACACATA TATACAAATA AACAAAGAAA ATTATTTTAG
156151 ATTAATTAAA GAATGGGAAA TAAGACAGAG TGATGTGATA CAGACTGATG

156201 AGGGGTCACT ATTTAGAAGA GGTGATGAAG CAAGATCTAT ACAGAGAGGT
156251 GAGATTTGGG CTGAGGCACA ACTGCTACAA AGGAGTGATG TTTGCAAAGA
156301 GGTAAGGGAA GAGCATTGCA GGAAGGAGGG GAACAGCTGG TGCAGAGTCT
156351 CCCATGCAGA ATGAGCTTGG AGCCCAGAGG AAGAGAGTGA AAGCCAGTGT
156401 GGCTACAGCA GGCAGCAAGG AGAAGACGGT TGTAAGTTAG GTGAAGTCAG
156451 AGGAGCAGGC TATTCATGCT CTGTGTGATG GTCAGATGTT GAGACTTTTC
156501 CTGTGTGCAA TGGGAAAACT TTGAGTGGAT TTGCACAAGG AGAAAGAACA
156551 ATGTGTTTTG TTTGTTTTGT CTTTGTTGTT TAAATAAGAT CTCTCTGGCT
156601 TCTGGGTAGA GAAGTGATTT TGTCACTGAA AACCAAATGT CCTAAAGCTC
156651 AAGGCCATGA ACACCACCTT CAGATACCAG GAGGGCTATA GAGTGGGTCA
156701 AGAGCAAGAA TTGTGTGAAA CCAGAATCTC AGTAACTAGA AGTATGCAAG
156751 CAGATGTTAA TGATCACCTG CCAGGTTTCC TGCAGATGGT ATGCTGGTTT
156801 TCAGTGGGAG TAGGACAGAT GGGTTATATG GTTCAGCTGC AATCTTTAAG
156851 AGATTATGAC CTTTAAAGCC CATTTTCTCT AGGGACTAAC AGAAAACGGA
156901 GACTCACAGT AGACAATTAG GTACCACTGG TTAATTGCAT TCTTTATTGC
156951 AGCATGGGCC AAAAGATTTT CAATAACATT TCAAAAGTAT TCACCAAAAA
157001 AAGGTCTTGG ACGCAAATAG ATTTGACAAA ATCTGGGATA AAAATGGGTA
157051 GAATTCCTCA CAATCTTTTA TGCAGCTAAT GTGAAGTATG AAACTCTAAA
157101 ACAGGGACAA AGTATGCACC ATTTCCCAAA TGTATTTGAC CAAAGAAGAC
157151 TTATTTTTTA AGGAGCATCT TGTGGGGCTA TAGTTTCATG AAACCTTCTG
157201 GGCAATGGTC GCATACTGTA ATTTGAGATC CCATACACAG TGGCAATGTG
157251 GGGTTCTGGA AACAGGTGAT ATGGTAAAAA GAGTAAAGGA TCTAAGAGCA
157301 TTAACTTTTT TATCTTAAAA GAAAAAAATA ATAATACCTA AGTCACAAGG
157351 ATGTGATGAG GACTAAATAG CCTAATATAT GTAANAAGGA CCACAAAGCA
157401 CTCTAAAATA CTGTTTTCAT GACAAGGATG AATGACTTTC CTCACCATCC
157451 ACCTTGGAAG GGCAATTTTT AGGCATTGAA GATGGCCTTG GGGTTGGTCT
157501 CACTGGGGCA AAGATTATGA ACTCTCATCC TATATCATAT AGTAAAACAA
157551 AGTTTAGGAG CTGACTGACT TGGAGTTTAA TCCCATGACC TTGGTCTTAT
157601 TAGCATCGTA TTTTAATTAG AAGTATAATC AACCACAAAC CAGGATTGGC
157651 AACTGCATTG GGATTCTACA GAATCGGTCC TGTGGGTATG TTCTCACAGC
157701 TAAGCTATTA CTATGGCTGA TACACTGGGG GGTCTGAAAA TCAGCTAGCA
157751 AGATGTACAA GCACAAAGTG AACATTAGCA GACAAATGAA CACTGAGAGT
157801 TAAGGGCTAG ACTGGGAAAA TCGACACTTG TTTTCTTAAA CGTGTATTAG
157851 CAGCAATAGC TGGATTCTTC CTGTAGCACC TTTTTATGCT TTGCCTTTAA
157901 TTGATAGACA ATGTGAGGGG AAGATCGTTA GATTAAGAGT CAAGAATATC
157951 TGCCCAAGTC ATATGTCCTA GCTGTGCTAC CTTGAATATG TTCATTAAAT
158001 TTCTGAGCCT TGGTTTCTCC CCTTTAAAAA AATGACCCAG TCATCCCTTT
158051 CTAGCCTCAA TAGGGTCATT GTAGAGACCA AGTAAGGTAA TAGATGAAAG
158101 TGTCTTATAT ACATGGCTAC TGTAATTAAT AACCATGACA ACTTCTGGCT
158151 TCTAATAGAT ATCTAATAAA ATTGGATTTA CACAGATGAA TGAGGCATCG
158201 AACAGGTGAA TGTGTGAGTG GGGTAGTTAG ATGGGTAGGA TGGATGGACA
158251 GTTGGATAGA CTGGTGTGTC GAAAGCATGA ATGGATGGAT TGGTTTGTTG
158301 GATGGGTAGA TGGATAGATG ACAGTTGGGT GGATAATTGA TGGGTTGGAT
158351 GGATGAACTA GTGGATGGAT TCATTTTGGA GTCATCTGAC CACTTTTTGC
158401 AGTCTTCTAT TCATTAATCC TTCTCTTCTC TTGTAGTCTG TTCCCAGTTC
158451 TCCAAAGGAG TCTATGCCAT CTTTGGGTTT TATGAACGTA GGACTGTCAA
158501 CATGCTGACC TCCTTTTGTG GGGCCCTCCA CGTCTGCTTC ATTACGCCGA
158551 GCTTTCCCGT TGATACATCC AATCAGTTTG TCCTTCAGCT GCGCCCTGAA
158601 CTGCAGGATG CCCTCATCAG CATCATTGAC CATTACAAGT GGCAGAAATT
158651 TGTCTACATT TATGATGCCG ACCGGGGTAA GCCAAGGGTT AGGGGAGGGA
158701 GACTTTTGAG GGATGGAGAG AAAATTACCA GCAGAAAGGA GAATGATGCC
158751 TCACTGCTTC CCTGAAAAAT ATGGGAAAAT TATCCAAAAT GCTTTATTTC
158801 TGAGAAATCT GACTGATTTA TCAGTAGCTG ACCTCTAATT CAGTTTGGAA
158851 ACGCATTCTG AGAATAATTC TCTTAATGCA CCATGTCACT CTACAGCTCA
158901 CTAAGCTTTC ATGGCTCCTG AGTCCAAACT CAATGCAAAA GGACCTCAGA
158951 CTTTGGAGTC AGGCAGATCT GGATCTGAAA CCTAGGTTCT GTCCTCTCCA
159001 GCTGTTTGAC TTTGGACAAA CTCTCTCTGC CTCAATTTCA GCACTTATAT
159051 AATGGGGATA AAATTCTCTA TGCCTTCATT TTCTCATGTC TATAATGAGG
159101 ATAAAAACAA TGTCTATCTT ATAAAGGTTT TGTGAAACTG AATGAGATGA
159151 CTATGAAGTG TTCAGTGCCT GCAACATAGT AAAAACTCAA AATTCTTTCT
159201 CTGTTTTAGA TGTTATCATC ATCATCATCC TCCTCATCAT AATCTTCATC
159251 CTTCTCTGGG CTTTCTAATT CTTCCTCCTT TGAATTTAAC ATCACATTTT
159301 CCAAATGTTT TCTATACTTT TTCTTCTCTA TGTCTTTACT CATGTTATTC
159351 CAGTTTTCTG GAATGCACTT CCCTTCTCCA ATTTACATCT GTAAATCCTT
159401 CTCCTCTTTT GCAGGATGTC CCTATTCCCC AATTCTGTGG ATGGGAGCAC
159451 TCTCTCCAAC TCCCATGATG TTTGTCTTGT ACTGTCCTAC CTTCTCATTG
159501 TATACTAAAT AGTCTTGTAA TAATTTATTC ACTACTGGTG TAAACAAATA
159551 AATGGGTCAC GCAAGACCTG AAAGGTGAGA CAGAGGAGTA CAGTACTGAT
159601 GTGGTTGCCT GCAGGGAGTC TTAGAAAACT TTTGAGTTGG AGAGAGGTTT
159651 GTGAAAGTGA TTTTTCAGGC AGTTAGGCAG GCGTCGTTCA GATGGGAAGG
159701 AGCCAACAGA AGAAACCAGG AACACCCTAT TTTCTTTGAT TTTCTCTTCA

FIGURE 3, page 45 of 122

159751 CTGTCCCCAC TTTGATGACT TCCCTTCTCA GACTGCGACT ATTGCAGGGG
159801 TCACCTGGAA GTCTATTTCA GGACAGCTTT GCAGCATAAT GTAGCTGGAG
159851 GCCTGGAAGT AATAAAGCCA GAAAAATGTA CCTTTGCTTG TGGGAGATCA
159901 TCTCTGGGGT CAGCAGAAGC ACCCACACTC TCAAAAGAGC TCCACCTACC
159951 TCAGAACTCA GAGCTCAGAG CCCTGCCGTT TGTCAGCTGT GTGACCTTGG
160001 ACTAATGACT AAATCTCTCT AAGCCTCAAT TTCCACACTA TAAAATAGGG
160051 ATAATAATAG TATCTACCTT GAAAGATTAA GTGGATTAAA ACCAGTAGAA
160101 CAGTGCCAGA CACACAGTAC ATTTTCAGTA AATGTTGGTC TCAAACTCAC
160151 CAAACAACTT GCACTGAAAA GGAAACAAAG ATAGGAAGGC ATAGCAGAAC
160201 CAATCTGCAG ATGATTCTTG AGGCCAGATA CCATATTGGT CACTGTGGAA
160251 GAGGTTAACT GTGTTACTGA AAGTCAGAAA TGACATACAT ACAAAAAATT
160301 AATCCATGCA AGATCAAAAT AATATCTGTG AATAATTAAT AATGACACCC
160351 CCCCCCCAAG ATGTTCATGT TGCAATCTCT AGAACCTGCA AATATGTCTA
160401 TGTTACATGG CAAAGGAAAA TGAAGGCTGC AGTTGGGATT AAGGTTGCTA
160451 AACTATTGAC CTTTAATAGG GTAATTATCC TGGATTATGT TGGGGGGACA
160501 CAATGTAATC ACAAGGTCCT TAAATGTGGG AAGTTGGAGT CAGAAGAGTC
160551 AGTGTCAGAG TGGTGCAATG TGAGAAAGAC GACCACCATT ACTGGCCTTG
160601 AAGATGGAAG GGGCCATATG CCAAGAAATG CAGGTAGCCT CTAGAAGTTG
160651 GAAAGGCAAG AGAGTGGATT CTTCCCTAGA ACCTTTAGAC ACCAACACAG
160701 CCCTGCTGAC ACCTTGATTT TAGCCTGGGA CACCTATCTC ATGCATCTTA
160751 CCTCAAGAAC TGTAAGATAG TACATTTGTG TTGTTTTAAG CCAGTAAGTG
160801 TGTGATAACT TGTTACAGCA GCAGTAGGAA ACTAATACAC CATCTAATTC
160851 TCCAAGAAGA AACAAAGCAG CATTGAGTAA TGGCCTCTCT ACTCATTTAG
160901 CTATAGATCA GAAGAGAGTA GTTTAATTCA GGACACATTT TATTTATTTA
160951 TTTATTTATT TAGTTAGTTA GTTAGTTGAG ACAGAGTTTC ACTCTTGTCA
161001 CCCAGGCTGG AGTGCAATGG CACGATGTGG GCTCACTGCA ACCTCTGCCT
161051 CCCAGGTTCA AGCAATTCTC CTGCCTCAGC CTACCAGGTA GCTGGGATTA
161101 CAGGTACCTG CCACCATGCC TGGCTAATTT TTGTAATTTT TTTTAGTAGA
161151 GATGGGGTTT CATCATGTTT GCCAGGCTGG TCTCAAACTC CTGACCTCAG
161201 GTGATCCACC CACCTCGACC TCCCAAAGTG CTGGGATTAC AGGCGTGAGC
161251 CACTGGGCCT GGCCTGCCAG GACACATATT AAACACCTAC TGTGTGAGAG
161301 ACAAAGTATT AGGTATTAAA GATACTATAT TGAACATTCA CAAATTTGAT
161351 CAGCAGTTAT TAGGTGACCA TTTAGATGCT AGGTTGGCAC ATTTAATAAG
161401 CAGTTACTGA GTGCCGAATA AAACTAACAG CTAATATTTA TAAAACCCTT
161451 GCAGGTGTCA GGCTCTGCTA TGTATCAAAC ATTCTCACTT AATCCTCATA
161501 ATGACATTAT GAGGTGAGCA TTATTTACAC CACACTTTAC CTTTGAAGAA
161551 ACTAAAGTTT GAAGAGGCTA ATGAGCCTGC ACAAGGCCAT TTAGCCATAT
161601 GTTGGATTTG AGCCTCAGAT TGTTTTTTAA TCACTAGTTC TACCATCTAT
161651 GTTCAGAAAC ACAGTGTCTG ATCTCACAGA GTTCAGAGTT TTGCAGCCAG
161701 AGAAAACTAG AACTGAGTTT GGCAGAAGAG TGGGTTTGGG GGTAGCCAGG
161751 GGAGGTAGGT GCCTGATGGG AGTGGGTGGT GCCCACAAAT CCTGACTGTC
161801 ATTTCTCTTC TACTCATCTG AACTTTAGGC TTATCCGTCC TGCAGAAAGT
161851 CCTGGATACA GCTGCTGAGA AGAACTGGCA GGTGACAGCA GTCAACATCT
161901 TGACAACCAC AGAGGAGGGA TACCGGATGC TCTTTCAGGA CCTGGAGAAG
161951 AAAAAGGAGC GGCTGGTGGT GGTGGACTGT GAATCAGAAC GCCTCAATGC
162001 TATCTTGGGC CAGGTAGTGA AAGCAGCAAG GGCTCAGGGT GGGTGCGGGA
162051 GGTGATTCAG GAATAGCCAG ACACACTTTT GCCTTGGGTG TTATAAAGAG
162101 GGTTATAAAG AGGGTTCTTG ACTAGGTGAG ACTAAAAGAC CTCTATCTCA
162151 TTTTCTATAA TTCACAAAAT TTAATTCTGA AATAGCACAA ACAATGGGAG
162201 CCTTGACATA GGGCTTCAAA TGGTTCTCAG ACCTGTTAAC TCCAATGTAT
162251 CCCTCTATTG TTTAAAAAAA AAAAATGCTG GATGCAGTGG CTCAGGCCTG
162301 TAATCTCAGC ACTTTGGGAG ACTGAGGCAG GCGGATCACC TGAGGTCAGG
162351 AGTTCAAGAC CAGCCTAGCC AACATGGTGA AACCCTGTCT CCACTAAAAA
162401 AAAAAAAAAA AAAAAAAAAT TTAGCTTGGT GTCGTGGCAT GTACCCATAA
162451 TCCCAGCTAC TCAGGAGGGT GAGACAGTGA GGCAGGAGAA TCCCTTGAAC
162501 CTGGGAGGTG GAGGTTGCAG TGAGCCAAGA TTGTGCTACT GCACTCCAGC
162551 CTAGGCAACA GAGCAAGACT CCATCTCGAA AAATAATAAA AAATAATAAT
162601 GATAAATTAC ATTCCATTTT AGAGTTTATG AAATGTTATC ATATTAGGAA
162651 CACAGCTTAT AGGGCCAAAT TTCTGGGTTC GACTCTGGAC TCTGTCACTC
162701 ATGATCCAGG GTTTGGCATC TCATTCCTTT CACCTTCTTA ACTGTTTTGA
162751 AAGGCTAAGG AAGCAGCAGC CACCTTTATT TCCATTGTTT CCCTGAACAT
162801 GCCCTTCCCT TTGAGAAATC AATTGACAGT ACATTCTTCT ATAAACAGGC
162851 ATTGTAACTT CAACAGTCTT GAGCTAGATC TCTCTAAACT GTGCTTCCCC
162901 TGGTCTCAAA ACAAAAGCCC ATGCCCACCA CAGAATTAGG ATTTTTTGTA
162951 GATTCCTTAT CTTTTTAAAC TACATTTATG TATTCAGATT CAGAGCTAGC
163001 AAGGTAGCAG ACGTTGCAAT AACTTTTGAA CAATGTCATA CAATAAAATT
163051 GATAGTTTTA GGTACTTGAC AACATGACAA AGTTTGTTAA TGGCCTTCAA
163101 GACCCCTGGG GCCCTCACAG AGAATCTTGG TACTAGGACA GCTATTACTC
163151 AGAGGCCTCA GCAATAGAAC ACAGACAGAG TTTGAATGTT ATGGATTCTT
163201 TAAGGCACTA ACTGTTCTAC TTTATGAAGT ACAAATTTGG CCTTCCCTCT
163251 TGGAAAGAGA AACCCAGCAA AACTTGTTCC ATTGAGATGG AAGTTCTCTG

163301 GGCCGGAGTC AGGGATTTGA ATTGCAGTTT TCAATTCAGG CAGGATAAGA
163351 TAATAGTTAA GAGCAGAGAT AAAACCAGAC TGGCTAGGGT TCAAATCCCA
163401 GCTCTAGTAT TTACTGGCTT TGTGACCTTG ACCAGGTTTT TAATCTTTCT
163451 ACATCTCAAG TTCTTGATCT GTAAAATGGG CATCATCATC ATAATAATAG
163501 CCACTTTTAG AGGGCTCTTG TGAGAATTAA AAGAATCAAT ATATGTGAAG
163551 CACTTAGAAC AGAGTCTGCC CCACAGTAAG TGGTACAAGC AAGCATTTGC
163601 CTATTTTTGC TATTCCTAGT GCCTACTAGG ACCAGCTTCT TGAGTCACTT
163651 TCTTCCTTGG GCATAAGTGA ATCCGTCTGT AAAATGTGAA TGAAGGCCTC
163701 TGTTCTATAA AACTGATAAA AAGGCAAGAT AACATAGTCG ATGGAAAAAG
163751 TGCCAAATGA TAATGACATA TTAATAGACA GATGACCTAT TGTATATTGT
163801 TCTATGGTAC AGACAGTAGC TATTACTACT ATTTTTTTAG TGTGTATGGT
163851 ATACCAGATA CTATGCCAAG ACCTTCCCAT GCATAATCCT ACTTCATTCC
163901 CACATCAACT TTGTAAAACA GCTTTTTTCA ATTCCCCTAT TTTATAGATG
163951 AAGAAAAGAG AGATTATACT TGCCCAACAT CTCACAGCTA GCATATGATA
164001 AAAGCAGGAA GTCAAACCTA TCTTGGTCTG GCCAAAGAAC CTAGCTTCTT
164051 AAAAATGCAA CTTTTCTGCT TCTGCTATCT ATAATTAACT CCTCTCTCAA
164101 AGGGCAAACT TGCGTTTTGT AAAGAAGTGA CCCGTTTGTA TGGGTATTTT
164151 AGATTGTAGC ATATTGACAT TTTTTAAAAT TGTTTCATTC ATCTATTTTG
164201 AAAAGTAAGA CCAAAGAGTT GAAAGGATTT TACAGATCAC TTGATTCTTT
164251 GCTTATGCTT ACATTTTATA GATAGAATGA CTGACAGTCA AATTGATTAA
164301 GTTATTTGCC TTAGACAAAT AATGAATGAC AGTAATGAGC CTACAACTTA
164351 TATCTCTGAC TTACAATCTC ACACTTAGCA TCATCCTGGA CTATCTCACA
164401 TTCAGTAACT GGGAACGTAC CTGGGATACA GTTACATTCA GTAACTGCAT
164451 ACAGTCTAAC ACAAAATTTT CCACCTAATC TGAGGAAAAA AACAGTGACT
164501 CAAAATTCCA AATAGGGAAT TAACTGCCTG TGTCTGTCTC CAGCCCCCAC
164551 CCAACTAAAA TCTAAGCTCG ACGATGCCAG GGATTTTTGT TTTATTTTCT
164601 TCCCTGCTGA GTCCACAATG CCTTGGATAG TGCTTGACAC CAAATAAAGT
164651 ATTCAATACA TTCTTTTCAG TGAATTAAAA GAATAAGGAA TCAATGAAGC
164701 CTCTAAGAAA GTTCTTAAAT GTAAGATAAA TCTGGATTTC TATAGATAGC
164751 CATTGGCTGG ATAAGAGCCT TTAAGATGGA GGAAAAGGCA TGTCAGGAGG
164801 CCCAGAGGGC ATGTGAGGGC TGGGTTTCAT ACTGCAGTTT TGCAGGCTGA
164851 GTGATGGATG CTGAGCGTCC ACTGGAGAGG ATGGCAGGAA GATAAACACA
164901 CAATCAAGAA TATCCTTGGA AACCATTAGA AAGAGTTTAG GGTTTATTCT
164951 GTAAACAATG GGGAGTCAGT GAAGGTTTGT GAGCAAGGAA CAGGATTATT
165001 AGAATATAAT ACTTTATCAA TATATGATGC CAAAGCATAT AAAACAGTCA
165051 TTAAGCACAA AATTAGTTAG AAGTGAGAAT AGACCAGGAC CTGTTGAGGT
165101 TATCCATCAC ATCCCCCTAT GTTATTGTCT TCATGGTGCT TGTACCTGCT
165151 GAAATCTTGT TCATTTATCT ATTTATATAT TGACCATCTG GCACCCTACT
165201 AAAATGTTAA CTCAACTCAA TGAGGGCACA GAGACCTTGC CTCACTTGCT
165251 CAATGCTGTT TCCCCAGCAC ATAGCATAGT GCTTGGCATA TAATTTATGT
165301 TAAATAAATG TTTGTTGAAT GGATTAATTA GTTAATCATA GAGGGTTTTA
165351 CAGAGGAGTT GAGATTGGAG CTCAGCCATT AAGGATACGA ACAATCAGAG
165401 AGAATGGGAG AGGCCATTCA GACACAAATA TTGTGAATGA AGGCAATGCA
165451 TTGGGAATGA GCTTTGAAGT AATGGGGGTC AGTGAGGTGA TGGACCCCTT
165501 GTGAAATTGC TTCTTACATT TATAACACCT TTCTCAGTTT GTTACCCTGT
165551 ATATATTTAT CCGTTCACCT ATTTATTATG GATCTCCTCT CAATGAAGTG
165601 TAACCTCCAA GAGGGCAAGC ACCATGCTTC TTTCACCTTT CCACTGTGTT
165651 GCCAATAGTG CTTCACCCAT AGCAAGCTCT TAATACATAT TTGTGAAAGG
165701 AAGGTATTAG AGGAGGGAAG GTCAATGTAT AGGTTGGGGA ATAGATAGAT
165751 GGGAAGGTTG GTATCAGGTT GGATCATATG AAATTGCCAG TTTTTATAAG
165801 TCAAAAGTCA TCAGTTATCA GCTGTTTCCT TTGTTTCAAT TTGTACTTTC
165851 ATCTTGTGGG GACAATATTT CTCCATTGCC TGAATGTGGT TGGTTTTAAA
165901 ATATCATGTC TTTGCTGTTT TGTGTTTATT AGAAGCTGAA TAGGTTCTTG
165951 ATAAAGGTGT CTCATTGTTG AAAAGGCAGC AAACCATTTG ACAAGCAGAT
166001 GAAAAAGTAA TGAAGAATTA TTAATAAAAC TATCATCCCA ATAGTATTTG
166051 AGCTCCGTGG TCTGGAATTT CACAATCTAA CCACTATTTC AAAGAATTCA
166101 TTGTGTGTGC TTGCATTTAA TTATTCCCCA CATAAAAAAA CATGAGTCAC
166151 TATGCACATA CATCCAATTA AGTAGATGTC TGAATGTGGA TTTTAATAAC
166201 CTTGAAAATT TATTCAGTTA GAGAAGAAGC CCAAGTGCTT ATCATCTGTT
166251 ATATGTCTCC TTGCAACAGT GCAGGGAGAG AGACACCGAG CAGAGTACAC
166301 TAACCCCAAT TTGATGATTA AAAAAAATAG GGAATTAGAT CTAGTTAATC
166351 TGCAGGCTGA GCTAGATCTA AAACCAAGGT CTGTAGTCTT AACCATTCAT
166401 TATTAGGTGT GTCTCCTGCC CAAGCAAACT TCTGGGCAGT TCTTTCCACA
166451 AATATTTTTT CTACCTGTGA TGATTAGGGA TAGTCTGCAT TTTGGGATAA
166501 AAGGGTATTC ATTGACACTG GTTCTTAATG ATTAACCATA ATCAAACATC
166551 AAATGGAAAA GTTCACAGGA GTCAGGTCCC TGTCCTGATA CTGCCACCAG
166601 GCTACTATCA GATCTGGGCA AAACATTTTC CCTCTGTGGG TCTTGACTTC
166651 CTATCTGTAC AGTGAGAGTT TGGACCAGAT GATCCTAACT TTCCCTTCCA
166701 GCTTCTAAGT TGGGCAATCC ATTAATGTCT GAGTACCTAA CTGATTCGGG
166751 GAGGAAGGCA CAAAATTCAG AAAAAGAAAG AAGAGCATCT ATATATGGTT
166801 CATGCAAGGA ATTGAAGGTG AAGTCATCCA CATACCCATC TGACCATTCA

FIGURE 3, page 47 of 122

166851 TCCACCATCC ATCTATTAAC TCATCTGTTT TTCCAATCAG CGAATATTGT
166901 CATGACAGAT TTCATGCAAC ATAAAATTCC CACCTAAAGA AGAATCTCCA
166951 CATACAAGGA AGGTTTATGA AAGAAAGAAC GCAGTGAGCA TTTCAGATGG
167001 GTCCTTGGGG TTACAGTAAC ACCACTCTAC CCTTGGAATC AGACAAAACT
167051 GATTTCAAAT TCTGTATCTG CCACTTAGTA GCTGTAAGAT TACAACTTAC
167101 AGAGGTTATA TAATAGGCAG TCCATGCCTA TTCCTTATTT GTAAAATAAG
167151 GATGCTAACA ATGCCACCAT CATTGGATGG TTGGGATATT GTAGTTCTAG
167201 TACTTAGGGT AGGGCACATT GTAAGCACTC GATATCAGCT GCCGTTATTA
167251 CTGTTGTTGT CGTGGCTTTA ACTGTTAGTA TGATTAATGA GTCTCCACCT
167301 ATTATGTTTT GTAGATTATA AAGCTAGAGA AGAATGGCAT CGGCTACCAC
167351 TACATTCTTG CAAATCTGGT GAGTAGAGCA CTGCAGGCTC TCAGCTCAAG
167401 TCCTTTCCAG GTTTGGGGCC CTACCTTGCT TCTGTTGTCC CTGGCTGATG
167451 TGAACTGAGT GGGTGGAAGG GGCAATTCAG GGCTGTAATA ATGAGTCTTG
167501 GCAATACTAC ATTTTTATCT TCTCCACATC CCACTCATCA AACCACAACA
167551 CACTATTCAT GAACCTCTAA CCTTCCTTGG AAGAGAGCAT ACTGGTGGGC
167601 ACGGCTTTAT CATCTTCACA ATTCCAGCTT TAATTGGCTC TGCCCCTTGG
167651 CAATAGGGAC AAAATCACCA CATCTTTGAA TTAATGCAAG ATGTCTTGAT
167701 CTTACTGGTT TGGGTCCTCC ATTTTGACCC CAGTGATAGT TTTACTTCTT
167751 ATAAATACAT TTACATCATA ATTACACTAG TATTGACAAA ATTTTAACCA
167801 GAAACAACTT CCCAGCATGA ACAATATTAT GTCCATTTAG TTTATATTCA
167851 CTTTTCTATA TGGCATAGAT AAGTTTGTTT TAAAATATAT ATATATATAT
167901 ATTTGTTTTA ATGTACTACA GATCATTGTA TTGAGTGCTA CTGTTTTTTA
167951 TATTACAAAG AAAACAACTC ATCAAATCAT TTTTTGTATA TATTAAATTT
168001 TACCTAGTAG CACATACTAT TATGAGTTTT CTTTTGTAAC CATTATTTCT
168051 GTCAAGTCTA TTTTTTCTGG GTCATGTTTT GTACCTCCAC CTTTTTTGTC
168101 ATGAAGTTTA ATTCTTCTAG CTTTTCTATC CAAAGCCAAA TGTATTTTTA
168151 TTTGGTGTTT AGCCCCATTT TTAAAGGCTT TATTGAGACA TATTTTATAA
168201 AGCACACAAT TCATCCATTT AAAGTGTACA ATTAAATGGT TTTCAATATA
168251 TTCACAAAGT TATGAAACCA TCACCACAGT CTTATTTTAA AATTCTTCAT
168301 CACTGCTAGG AGAAATCCCT TACCTATTAG CAATGACTCC TTATCATCCC
168351 CTAAGCTCCT CCAGCCCTAG GCAACCATTA ATTTACTTTC TATCCGTATG
168401 TATTTGCCTG TTTGGAGCAT GTCATATATG TGAAATCATA CAATATGTGG
168451 TCATTTGTAA TTGACTTCTT TCACTTAGCA TAACATTTTC AAGTTTCACC
168501 CATGTTGCAG CATGTATCAG TACTTGATTC CTTTTTATTG CCAAACAATA
168551 TTTCATTATG AGCATATACC ACATTTTCTT TATCCATTTT TCAGTTCATG
168601 CACATTTGGG TTGTTTTCAC TTTTTGACTA TTATGAATAA TGCTGCTATA
168651 AAATATTAGT GTACAAGATT TTCACTTTAA TATATACCTA GGCATGGAAT
168701 TACTGGGTTA TATGATAACT CTATGTTTAA CATTTTGAGG AACTCCAAAA
168751 TTATTTTCCA AAGTGGCTGC ATCACCCATC AAATTTTAAT CAATAACAAA
168801 TTTTTCCATG TGACAGTTTG AATGATGGCA AGTGTCTCTT AATGATAACT
168851 ATTTCTACAG TTTATTATCC TGTTCTGTCT TTGCAATTTT CCATGTTTCC
168901 ATTAAGAAGT GGTTTCTAGC TTTTTATCTA TAACGAATTT TCAGGTTTTA
168951 ACTTACTTAA CTGAACATAT AACTGGCTTC AGTTTTAACC ATGTTATTTT
169001 GTGTTGATTA TCTCTATGAG CAATAGTAAT TGAACAAAGG ATTAATATTT
169051 GTTACTCATT TCTGGAGTAA AGTCTGTTAG TAGAAATAAG GCACAGGGTG
169101 CATGAATCTA AAAATGTGAC CAAAGCATCC TGCCTAATCC ATAAATTCTG
169151 TCCTTCTTTC TGACCTGGTA TCCAGCCTTA GATAGATCCC TGCCTTACTC
169201 TTCTTTCCCC TTCTTCAACT AACTTGTCTT GGCAATATTT CGGAGTGAGG
169251 ACTTGAAATA AGAAGGGCTT AGAGAAGTAG GTTAATTTAG GCCCAGCTGT
169301 TAATGGCTAA ATATATTACC TTTCTCAGAG GTATTTGCAT TTTAAATGAG
169351 GGTGGCTCTC CAGACACTTT TGGGGAACGA AGAGTCTCAC CCTCCAAAGA
169401 CCATTTGCAA AAATGGAATT TTTGACTTCG GAGTGAGGAA AGCCCTTAAC
169451 ATCCCTTGAC TCCCAGATCC TTAGTGCTAG AGCGGACTTA GGAAGTCAAC
169501 TCCACTTAAA CCTCACTTGT TTATAGGGAA ACAACCAGCA AAGGGGTGTG
169551 ACTTGGCCAA GGTCACACAG TGAGGCAGCA CTAGAGCTAG GCCTGTCACC
169601 AAGGGTAGCA GGCAGTATTC AGGCCTTTTC TATAACTCCA GGTCATCTCT
169651 CAGTGAAACT TTGTAGGCAC CCTGCTGCTT AAGAATACAC AGAACAATAC
169701 ATAGAACAAG AATACACAGA ACAAGGGTGG GGATAGGCAT AATTACCTCT
169751 CTGGGGTGAG ATAGAAATTG CATGCCAGTG GCCTTAGAGA CACTGAAAGA
169801 CCCCAGGTAA TTACATTGCC AGCCTCCATC TGTTGCCAAG TAACCCCTCA
169851 GTCACAGCAT CACCAAGTCA GCCTCTTGGG TTGTTGTATC CTTCTGATCT
169901 GCATTTTTCT TCTTCTGACT TAATGACCTC TCAAATGCTT ACAACTGCCA
169951 GCTAATAGGA TGAAAATTGC ATATACCATC CAAATAAAAA AGACTTGCAT
170001 GTTTCGATAG ATTAGTTGAT AATTAGGCTT CAAATTACTA ATTAATTCAG
170051 TTTGAAACAT AGTCGCAGTA TGTGGTGTGT TTTCTTCCCC CTTCAGAGGA
170101 ATAATGCAAT TCATAAGACG ATAATTTTTA GAATTTCTGC CACATAATTA
170151 GCCTACTGCT GCATAGAACT GACCCACTCC TTCGGAATGT TTGTGATTAG
170201 GGTGTAATTA TAGAGTTAGA GACCAAGGAA GGCTTTGAAA GATTTAACAA
170251 AAGGAGGGAG CTACACTTTT ATTTTACAGT TCTTTCTGTC CCTGTCGGAA
170301 TGCATGAGCT TCAAAGTAGC CAGCAGCATT CTTTTAGCAG ATCACTTCGG
170351 AGGAATGCTT CTGGGGTTCA AATAGCCACC TTTGAAGGGC TGCCGGAAGA

170401 GAGGAGGGGA GGAGATTGTA GGTTAGAGAA GACAACTTAT AGGCAAGGAG
170451 TCAAAACAAA ACAAAACAAA ACAAAAACAA ACAAACAAAA AAAAAAAAAC
170501 CTTGTTTTTT GTCCAGATGC CCCTTTTAGC TGGCTCTGTA TTCTTGGACA
170551 ACTCTCCAAT CCTCAGTTTC CTCATCTGTC AATTGAGAAC AATAATTCCT
170601 ACTCTACCTA CTCATAGTGT CACTGGGGAG ACCAAATATG TTGCCAAATG
170651 CACCATGCTT TAAAAAGTTA AAAGTGTTCT GCACAAATGG AAAATTCTTA
170701 CTTCACATAT TAAATCCGCC CATCTGTACA TATTCACATA TGGTGTGTAT
170751 GTACATATGC ATATATATGC TTGCATATAT ATCCATATTT TATAGGAGAG
170801 ATATGTATGT TTATTTCCAT AGCATTGGTG TGGGCATAAG ATGAACTTGA
170851 ACCATGCAGA AATTGGAAAG CTATGCCACT ATCTCTCACA GATGTGCCTG
170901 GGTCCTGGAA CACACAAGTG CTGAGCCTGG CTGCCAGTGG TCCTCCAAAC
170951 CCTAACACTG ACTGTGCATT CACTCCCTGC TCTGAGACTG TGGGGAGTGC
171001 AGACATCTGG CAGCCAGAGT CCTTCAGAGT TGTAGTTCTT ATCTTTGTGA
171051 CTCACCAGAA GCAAATCTTA GACCAAATGA GTGTTTCTCA AAACAGAGGA
171101 CCTGTGGACC TCTGTAGTGT TTCTGTAGAG CCAGTTTGGA AAATGTGGCA
171151 CCAACAAGCG AATGCTTCAG TGCCACTGCA ATTGCCAATA TGAGTACCTA
171201 AACCATGGAG TAAATGGTCA GATTGTTATA CTGGTATTTA GAATTTTACT
171251 GGAATGAAAG CACATATTTT AAAATTCTCA TAGAGAACTA GAAGATTGGG
171301 AGAATTTACA CAGGGTTCAG CAGACTCCTG TCTGAAAAAT ATTGAATTTG
171351 TTGGACAACA TTGACCAGTG TGAACAATAT GGTGCCTTCT AGAGGAGTAA
171401 TAACAATAGT AATATCAACA ATCTCTCTCA TTTTTATACC ATATTATAGT
171451 TTATGTGATA TTTCTGTATG AATCATACTA CCGGGTTTTG GATGTCATAA
171501 TACTCCTATG AAGTAAACAA GGTGGAATTC ATCATCCCCA TTTTACAGAT
171551 GTGGGAACTG AGGCTGAGAC ATTACATGAC TGAGCTGCAG AGGAGAAAGA
171601 CAGGAACCTA ATTAATGGAG TTTGGCTGTC AGGAATATGA CAAAAACCAA
171651 GAGATGTGGG CATAAGAATA AGATGATCAG GCTAACCTGA TGCTGAGACA
171701 CTTGAGTCAC TGAATTAGAA TTCCTTAAAC CCCTAATAAA TTACAACAAT
171751 AATAACAATG GCAATAACTT CCACAATTGA CTGATTGCTA CATTCTAGAC
171801 ACTATGATAA ACACTTAAAT GCATGTCAAT TAAACCTTCC CAATAGCCCT
171851 TGAGGTTGAT ATTATCCTCA GATGAAGAAA CAGAGCTTCA GAAAGGTTGA
171901 CTTTTCCACA GTCACAAAAC ATATAAACTG ATGGAGCTGC ACTTCTCCTC
171951 AAGGGCCATG GAATCCCAAA ATTTGTGTTC TTATTACCGT GCCATGTGAG
172001 TGCTGGGCAG GGAGAGTTGG GGAAAGAGTC AGGAAAGAGA GGGGGTTGTC
172051 CTGGACAAGA CAGCTTGAGT TTAAATCTTG TCTACAGTAG CAGCAATAGA
172101 TCTGACATTC CAACCCAGGC TCTCAAATTC CCATTGGACA TCTGTCTCAC
172151 CATTTACTCC ATGGTTTAGG TACTCATATT GGCAATCGCA GTGGCACTGA
172201 AGCATTCACT TGTTAGTGCC GCATTTTCCA AACTGGCTCT ACAGACACAC
172251 CACAGAGGTC CACAGGTCCT CTGTTTTGAG AAACACTCAT TTGGTCTAAG
172301 ATTTGCTTCT GGTGAGTCAC AAAGGTAAGA ACTACAACTA CATTGATGGA
172351 ATTTTATTAA AATTATTATT TCTAGTGTGA CAGAAGCTGA GGAAGAGATG
172401 ACGGAGTTAG CCCATTCCAG GTCTTATCGG GGTACTTGGG AACCAGGACA
172451 GTTGGCCATT TCTGCCATGT GCTTGCAGAT TAACTCCTGT AGAATGTTAG
172501 ATTGGAAGTT TTAGTCTATT TGGCAGCTAT TCCAAGCCCC CAGCCCCATG
172551 CTGCTGCTCC TCTGCGGGAT CAGCCCTGAG CAGAAACTGT TCTTTAGTCT
172601 CCTTGCTCCC CTGTGGTGAT AAATCTGTCA GCTCCTTCTG CAAAGCTGAG
172651 CTCATCCACT TTCTTCAGTG CCTCTCTTCC TGTTGGCTCC GTACCTCACA
172701 GTTATGTTTA GTTTCTGCAG CTTCTGGTTA GGCAGGTGGT ATAGTAGTTG
172751 GGAAGGGTGG CTTTGGAGCC AGTTCTGGGT TTGAATTCTG ACTTTTATAC
172801 TTATTAGCTA TGTAACATTA GTCAATTTAT CTACCTTTTC TGAGTTTTTG
172851 TTGCCTTATC TTTAAAAAAG AGAATGATAT TATGTACATT CTTATAGGGT
172901 TTTATGAGAA CTAAGTGAGA TCCCTCAACG CTCTCGGAAA TGAAATCACA
172951 TCTACCTGTT TTATGCTGCC ATAGCCCCAG ATATTTTTTC ACTTACTATA
173001 CTTGAGATTA GATAACTGAT TCTCTATTAT TTCATGTCTT CTTCCCTGTT
173051 TATCTACAAG CTCCTAGAGG AAGGATTGTG TGTGACTTAT TCTCTGTTGA
173101 ATTCCCAGGG CCTGGCGAAG TGAGTTGCAC ATAACAGGTG TGCTTTAAAA
173151 AGTCAATGAA TGAATGAATG AATGAATGAA TAAATGAATT CCTAGAAAAT
173201 AATGTCTGCA CCTACATATC AAATGTACTT AAAGGCAAAA TCTTTTAGCA
173251 CCTATGCTAG AAGAAGTAGA GGTAGTAGGA ATATGAATTT AGTTATGAAT
173301 ATGCAAATAA GTAGTTAAAG ACAGGCCTAA GAGGCCTTCT AACCCACTTC
173351 ATGTAGAGAG CCAGAATCTC CTCTACAACG TCCCCAACAG AAACTCAGCC
173401 ATCAGGTTCA TGCTTGAATA ATACCCAGTG ATGGAAAAGT CCTACCTCTG
173451 AGACAGCCCC TTTTCTTCTC AAAGGGCTCA GACAGTTTCT GCACTCTTCC
173501 TGGAACAGGG CACGACCTGT GTGCTGCTCA CCCTGTGTCA CTCTCTCATC
173551 ACTTCTGACT CTAATGCCCT CTGGCTCTTG CAAAACTTAC CTGTGCCTTC
173601 CCACAAAGCA GCCTTTGAGT ATTTGAAAAT GGCTACCTTG CTTACTCTTT
173651 GGTGTTTGCA CCTTCAGTCT GGACACACCC CTGTTCCCCC AGTGCCTTCT
173701 CTCAGGATGT GGTTCTTACA GCTGTCCAGA CAACCACCAA ACATGGACCA
173751 GGCCTGTCCG TATGCCTGAT ACTGCACTGG GCTCATGCAA GAAGGACTAA
173801 GAAGCATGAG GCTGAACTTT GTCCCAGAAG CAACCTGACC TTTTCTTCCA
173851 GCTACATTAC AACATGTAAA ATAACATTCT CAAAAGAATG CCAGAGAAAA
173901 ATCACAGCCT GTGAAAATAT CTAAGCCTCA TAGATGGCCA CCTACCCTGT

```
173951 CACAGTGTGG TGATCAGAGG CCAGGGAGGC CGCCTCAGCT GTGGGGTGTC
174001 TGGGAAGGCT CGTGAGGCTG CATCTACAAG GCCAGCAGTC ATGTAGAGTG
174051 TGCCCTCCCC CTTGTTTGAA GAATCCAGCG GAGTGAGAGC TGAAGGGTAC
174101 CTATGAAACT CATCTCACCC GGCGCCTCAT TTTATAAAAT AGACACTCAA
174151 GAATGAGAGA AAGGAGGTGA TCTGTCTGAA TTCACCCAGA AGTTAAACAG
174201 CAAAGCTGGG CTAGGATTTG GAGTATTCAC TTGCTCCTTC TTTGTGGCTT
174251 CTTTTCTCCA AACTGCCTTT TCACAATGTG CCCATATGCC TCTGTGTTGA
174301 GGGTGGGGCA GGAGCAGAGA CAGAGACAGA GACAGAGAGG GAGCTCAGAA
174351 GTGCTTCCTA CTCCCCACTG TGCCCCTCTC AAGGACTCTC TTTGCTGATG
174401 AAGCTTATTC CAGTTTCCTC TTCTTCCTCC CACACAGCCT TCCCTCTCCC
174451 GCTCTGCTCT CACCTCACTG TTCGGTAACA GACACTGTGT GATCTCCAGA
174501 GCTGACACTG CCCAGAGCCT TTGGAAGGAA AAGGAGAGTG GGTGGATAGA
174551 AAGACAAACC CCAGATGCCA AAGGATGCTG TCTTCCAAGG TGATCCAAGC
174601 ATCCCAGTCT AGGTTACTCT TTGTATTCAC CCCCATCCTC TGAGAGAATT
174651 CACCCCAGAG ACCTCTGAGA TTTTCTGCCT CCCTCCAAGA AAAGTAAGAT
174701 TCTGGTCCCA TTTTATAAGG AGAAAAATGA AGTTCAAGTT GTTGAAAAAC
174751 CTTTTGTAAA GTCATTTGAC TAAAACTGGA ATTCAAACTT AAAACCTTTC
174801 CCATTCTAAG GATTAGGCTT GTTCTCCATT GGGCCACACT GCCCAAACTG
174851 GGGAAACCTT TGCAATTCTT AGGACTGGTA TTATAATTGA GCAAAGCCAA
174901 GAAATAAACT CCTTTCTTCC TTAAACTGCC TGGGTTTGAA ATCTGGCTCA
174951 GCTACTTACT AGCTGTTTGT CCATTGCAAG TCACTTCTCC TCTTTGTACC
175001 TCAGCTGTCT CACCTATGAG TGGGAATATT AATGTGGATC TCATAAGATA
175051 AAGATAAAAT GAGTTAATGT ATGTAAAGTT TTAGAACACA GAGTGCAACA
175101 GAAGCCCAGG GTCTCATCCT AACTCTGTCA CTTACTCATG ACCATTTATG
175151 CAAATCATAT TTTTCTGTAA GATCTCAATT TGTTCTAGAA TTGGCATAAT
175201 GTTTTCAAAA GGAAAAAAAT CAGCAAAACA ATCTTCCTGC CTGTGTGATT
175251 TAGGGTTCTA GTTTTCCTGA TTGTCTTCAG TTCAGAGGTA TCAAAAAATA
175301 TCTCTCATAG CCACACTGGC TCCCTTAAGC TTAAGGAAGA GGCTGTTCTA
175351 TTAATCTCAA GCACTTGGTG TGTGTATCTT TCGATCTTGC AAACCATGCA
175401 CACCTAGGCT GATTTGGAAT GGCCTTTTTC ATGCTGGGTC AGCATCCTTT
175451 GGACCATTTC AGATATGTAA GACAGTGACT ATGATTGCTC TGACAGAGCA
175501 TGGAAACTCA CTGTCACCAG CAGCCTTCAA GCAAGAGGGG CCCCTTAGCA
175551 CTAATTTTGG CAGATGGTTG GTGAGCTATG TAACTAGAAG AGTCTGGTCC
175601 TTGTTTCCTT ACCTATCCCT CTTTTTAAGA CAGAAAAATA GAGAATACAA
175651 TGGGAGGGAA ATGGAGCTCC AGGAGACACA GGATTTTAGG TAAATACTTA
175701 CTATGTGCCA AGCACTGTTC TCTAAGAATC TGACAGGTAA CATAGTTAAT
175751 CCTCACAACA GCTATGAGAA ATACCATAAT AATCCTTATG TTGCAGCAAA
175801 GGTTACTGAG GCACTAAAAG GTTGAGTAGC CCTCCTGAGG TTGCACAGCT
175851 AGGAGGTGGT GGAGCTAAGA TTTGAATCTA GGCTGACATG CACAGGCAGT
175901 TTCTGTGACA GAGGGCAGTA ACCCTCTGTG GCTCTGACTC TGAACCTCAA
175951 TACATGCATA TTTTCTGCTT GGTGTTCCCA GCCCTCTTCA CCCAACCAAA
176001 GGCACTTTTT TTTTTTCAGG CTTCATGCTT TTGCTGCAAG ACCTTCCCTG
176051 AGCTCCAAGA TCAAGTTTGG GTCCACTCAT TTTGCTCTAT AATTACTTGT
176101 GTAATATTGG CCTTTCTCAC TAGACCTTAG GTAACTTGAA AGCAAGGACC
176151 ACACCTGTCT TCTTCTCTGC TACATTTCTA TGTATAGCAT GGGCCTGACA
176201 GTGTTAAGCA CTCATGAGTG AATGAGTAAA TGGACAAATA AATGATTTAC
176251 TACAATATTT CTTACCTGGT TCCCAGTAGC TTTCATATTT ATCATGTTTG
176301 GACTTTCATT CTTCTTTTTA TCAAACATTC AATGGGCACC TACTATATGG
176351 GAGGCCTGTG AAGGTGTAAA CCGGCTTTTC ATCAAAAGAT GGGCATGCTA
176401 TGAGTATTTG CTTGGCCTTT TCTAGATAGG AAGGTTTTGA TCATGTAAAG
176451 GGTAGATGCA ATTGGTTTTA AGTCCACTGG GAACTGTAGC CATAAGGGCC
176501 CACCTCATAC CAGGAAATTT GCTCTTGCTC TGAAATGGCC TTGGCCAGGT
176551 GTCATTCCTG ACCACAACAG TTGGGGCAGA GTAAAGATGA AGGGACTCTC
176601 TGGAAGACCA ACTATTCCCA GGCCAGGTAG TACACCCATG CAGCCTTGCA
176651 CTCAATAGCC CAACCTGGAG TCCCTGACCT TCTGCCAGAA AGTGCCAGCA
176701 TTTTATCCTA AATCCCAGGG CTGAGAGAAA TTAGTTTGTG AGACCCTGAC
176751 TGACATTTAC AATGCTTTGT CAATACTGGA TACTTGTATG AGGTATGTCT
176801 GTTGGTGTGT TTGCAGATAT CCAAGTGTGC CTCCCTGGTT CCAAATGTAA
176851 CTGGATAAGT CAACACGAAT GCTTTTTTCT TCTCAATATT TATGGTGTTT
176901 TCACTGATTT AAGCACAGCT ACAATACCTT GTTTAATTAG AGGAAACCAG
176951 ACTACCCTCT GTGTTACCAG AGATTATATA GGGAGAGGAC ACCTTAAAGG
177001 TTTGGTTGGT TAAAGTGCCT AAAATAGGAA AATGTGAAGA CTTTTATGCA
177051 GAGACATGGG TATTTGAGGA CACAATTAAG TCTTCAGCCC AGGAGTATTC
177101 CACAAATTCA CACATATCCA TATTCATGCG CACATACCTG TGTGATCATA
177151 GAATTGTAGA TCAAAGCTGG AAGAGCCCTT AAGAGAGAAA TCAAGTGGCT
177201 CAGAAGTTTC CAAACTTTTT AGTTTGAGGC TCTATTTTCA AATGGAATCT
177251 TGGGGGAGAA CTCTCATATA TAAAACAGAT AAAAAGCAGA GCTACTATGG
177301 TGGAAAAGAG AGGGTGGGAT TTAGGACCAC ATCTTTCTGC CTTTTCCCTA
177351 ACCTAATATG GTAACTTCTA AAATGCCTGC AACCAGGAAC ATAGCTTATA
177401 AGATCATTGA TGTAGCCAAA GTTCTTATTT TGCAGATCAA TCAACTAATG
177451 GCTATACAGG TTGAGATAAT TGCCCAAGGA CAAACAACTC ATGAGATTCA
```

FIGURE 3, page 50 of 122

177501 AAGACAGGAT TTATGTGGTT CTCCCTAAAA CTCTTTTCCT GACACTTCTT
177551 ATTTATGACC TGGTTCACAA TAGACTACAC AAAAAAGTCA ATAAGAAGAC
177601 CTCTTTGATC CACAAGACAA AAGCTGAGGC TGAGTGGTGA CAGGATTGAA
177651 GCTTATAAAA AAATCATGAG AGGGTGAGAA GAAACTTTCT GTTCCTTCAT
177701 TCCTCCACAT GTATTGAGCA TGCACCCTGA TCCAGGTACT GCTTGTGGAC
177751 GCTGTGGGGG CCAACGTCCC TGCCCTCCAG GAGCTCACAG TCTCACAGGG
177801 AAGATGAGAA GGGCCCCTGC ACGTTCAAAG AGAAAGCTAG GAGAGGCCTA
177851 GAGAGATAGG AATAAAGTGC TGTGTGGTTC ACATTTCAAG TACCAGCACA
177901 CATTAAAGGA GCTAAGGGAA ATGCCCTGAT CTCATGGAAG CCTGATACTT
177951 CCTTCTTGGT ATAAAAATGT GTGCTGCTCT GAGTGCTTCA TTGCAGGACA
178001 GGACATAAAT GAATAGATTG GCCTCACTAG TGGTTGGGAG GCTTGATGTA
178051 CAGTGGTTAG AAAACAAGTC CTAGAGTCTT TTTACTTGTT GGTCTCTGTC
178101 CCTCACTAGC TATACTGTAC TGAGCAGGAG CTACTCCATT AACTTAAGCC
178151 TCAATTTTTT AAATTTCTAA TTTGCTAATG GGAATGATAA TAGTACCCAC
178201 TTTACAGGAT TGCTATGAGG ATTAAATGAG ATAACACAAA TAAAGTACTT
178251 AGCACAGTTT CTACTACACA GTACAGGTTT GATACGTGTT AGGTACTTGT
178301 AATTATTGTT TTAGCCAAAG TCTGCCTTCT ATGACATTTG CCCTTTCATT
178351 GGCTCTGGCC TGCGTTCCAG AGCCTCAGAG AACAAATCAT CCATCTCTTC
178401 CCCATGACAA CCCTTCTGGG ACTCAAATAC ATCCTTCACT TACTTTCTTG
178451 GTCTTCTATA CTTTTTTAGG CTGATAATTC CCACTTTTAA AAAAATACTT
178501 CTAATATAAG ACTTTTCAAA CCACAGTTTC CTATAACTAC TCTCTCAATG
178551 GAGCTGTCAT CTAAGATTTT ATCTGACAAT TTGGGGAAAC TTGGCATGTT
178601 CAACCTGTGC CATTCAGAGT ATACAGTACA AGTTCTTTGA TTTTTCTCTC
178651 AACTTACCTC CTGTGGATCT CAAGGGGATG GGATGGAGGA AGTGCTCTTT
178701 CCAGTGTCCC AGGATTTGTT TAATAAACCT TACTTGCCCG TTTCCTTGAA
178751 CAATGTTAGA TGCTCCTTCT TCCTTCTGAC TGGTGTGGTG TCAGCACAGG
178801 CAGGATGATG AGGGCTGAAC AGCTCGTATG TGACCCCTTG AAAGAATCCC
178851 AGAGCAAAGG AAATCCAGCT TTGAAGATAA AGCCTTTCAT CCTTCGATAG
178901 CTATGTTCCT ATACACCTGC TTCATGTTCT CTCAGGCTTC TTGCCTGACC
178951 CAGTCCCTGT ATTTGAAGCA GTTCTAACAC CTAACCTCTT TTGACCCAAT
179001 GATAATGATA ATGGTGAATG TGATGATCAT AATAATAGCT AACATTCATT
179051 AAGCACTTAC TATGTGCCAG ACATGGTACT AAGTGCTTAG TTTTATTAAT
179101 TCTTTTAAAC CGTTCACCAA TCCTGTGATG TAGGTGCTAT ATCTGCATTT
179151 TGAAGACCAG AGAACTGAGC CTCAGAGAGG TTAAGTAACC AGTAGACACA
179201 TATAATCAGT TCTTTTCTTT CCAATTGCAC GTGATAATTA ATAGTCATAA
179251 TGATGGCCCA GAGCCTCTTC AAGATTCTTA AAGCATTCTC CAAATCTTCA
179301 CAGCAAGATG AAAGCATGTC CAATGTAGTT GTAGTGTTAA ACACCTCTTT
179351 AGGATATCAT AATTACTTGA AATGCCTTTT CATTCTAATC CTTTGAAAAT
179401 TATAATTGGC ATATGATAGA TGGAGTGACT ATATTAACTA GTTTACTTAA
179451 TTGAGCGCAT TTACTCCCCA TCATTGTACT CAAATGCCTT TTCAACATTG
179501 TGTTACCTCC TACAGTGGAT ATACAGAGGA GACAGATTCT GTTCTCAACT
179551 AATCCTCTCA CCAGCCATAT AACCTTAAGC CACTATTCCC CTCTTTGGGC
179601 CTCAGTTTCC CTATCTGAAC AATATGAGGG GTTTGTTTTA CCTCCTACAG
179651 TGGATATAGA GAGGAGACAG ATTCTATTCT CAACCAATCC TCTAACTGGC
179701 CATATAACCT TAAGCCACTA TTCCCATCTC TGGGCCTCAG TTTCCCTATC
179751 TGTACAATAT GAAGGGTTTG GTCTTCTCTC CAAAATCTTT GCTCCTGTAT
179801 AGGTCAAAAG TCAGCAAACT ATGGTCCCTG TGTCAAATCC AGCCATCACC
179851 TGATTTTATA TGGCTCATGA GCTAAGAATG ATTTTTTACA TTTTTTAATT
179901 GTTGGGAAAA AAATCAAAAG AATGATATTT TATAATATGT GGAACTATAT
179951 GACATTAAAT TACCATGCCC AAAAATATTG GGACAGCCAT GCTCTTCCAA
180001 TTACTATATG CTAAATAGTA ATAGTAAATT ACTATTTTCT ATATATGGCT
180051 ACTTTCATGC TGCAATGGCA GAGCTGACTA GTTGTGACAA GAACCATATG
180101 GTTTGCAAAG CCTAAAATAT TTATAATCTG GCCCTTTACA TAAAAAGTTT
180151 GCTGACCCCT TGCATAGATG TGGAATAGGG GGACACTAAT AGGCTTCAGA
180201 TAAACTAGAC ACTTTGGAAG CATCTAAAGA CCCTTAGGAG GTTAGTGTCA
180251 AGGAGAGGAA CCTAGCGCAG TCCCACAAAT ATTCGTTCAA GAAAGACAGC
180301 TACATTTGAA GGCCCCTGCT CTGGCAGGGT GACATATTCT GGCTATTAAC
180351 TGTGCCAGCC ACAGTCTGAG GTTCATTGTC CCTCTTTGTC TGGAGCAATC
180401 TTGACACACC ATCCTAAAGC TAAAGTCATA TGTTTCTCCA CTGGTGGAGC
180451 AGTAGAACAC ATTTGTGAAG AAGACAGATT TTATAGTTGG ACCACAGTTT
180501 GAATTCTTGC TTGCTGTGTG ATCTCAGGGA AATTTCCAAA GGTCTCTTAA
180551 CCATAGCTCC TTAACAGAAA ATTAGGATGG ATACTCACTC ACTCATTTAT
180601 GCAAATAAGT ATTGGGTGTC TACTGTGCAC ATTTACCTCT TGGAATTGTT
180651 TAAGTAATTA AAGGATTATG TATATAAAGC ATTTAACAGA ATGCCTGACT
180701 CAGGAATAGA GCTTGGAAAA TGTTTAAAAT ACATCTCAAA CAATTATTAT
180751 TCTTTTGTTT TTAAATTACA GTAACCTCAA AACTCTTAAA AAGCTGTTTG
180801 AATAAAGTTA TATAATGCAT ACAAAGGGGC ATTTTTAGCC ATTATTGTCA
180851 TTTTTGTTCT TATAAGCAAT GCTTCTGAAG CCGTTTTCAG TGGAGCACTT
180901 AACAGCACCA GTGTGCTTTA ATTTCAGGCC AGGAGATAAA AAATTAAGCA
180951 GGGCTCTCTT AAAAGACCAT AACAAAGCTT CAACAAATGC AACAACTTCT
181001 CTCCCCTGTC TTGCCACTGC TACTCTGTCC CCCACTTTCC AGTGACTAAT

FIGURE 3, page 51 of 122

181051 GGATGATATC TAAGATACAT TAGAGCTATC TGAGGATCGA TTTTTATTTT
181101 TTAATAGTAT TAAAAATACA ATATATTCAC ATGATAAAAC AGATATTACA
181151 GAAGGGTATA AAGTAAAAGA TAAATGCCCA TTCTTTCCAA TTCTATACTT
181201 CATAGAAGTA ACTATTTTAA ACCCTTTTCC TGCATTTGGT TATTTAATGG
181251 TTTCCTTTAC ACTTCTACAT CATATATTTA TGTTTCTTTT TCTTGCTTTA
181301 TCAACTTTAA CTCCATATCT GACTTCCCAT TAGAAAGATG ACAAATCAGC
181351 TCATATTACA CCCCCAACAT CCCCTTCTCA ATGTTTGTTA GCCTATATGC
181401 TATTATTTGG AATTCTTCTG ATGATTACCT TGTATTTTTT ACATAGTGAA
181451 CCTTGATTTT TGATTCACCA GCATTAGAGC TTTGTCAAAA TACAGATATC
181501 CAGTTTCCTC TTTAGGGCTA CTGAATGATA ATCCTTGGGG ATGGTTATTT
181551 TGCAAAAGTG CCTCAAGGTA TTCTGATACG TCCCTCAGAA CCACTTTCTG
181601 AGAGCTTACA GTTTATTGGT CAATTTCTTT GCATTTAATA ATGACAGTAG
181651 ACACAGCATT CTTTCTCACC GATTTATTAG TCACACATGG GGCAATGTGA
181701 AATGCTACAT AGGTGCAGAA GAAGCAGACA AGAACACAGT GACCTAATAG
181751 CCCTAGGAAC TCACTCATCA CCAAGCTTCA CTTTAGGTGA GAAACAGTCA
181801 CTCAAAGAGA AGCATCTGGT ACCAGTGCTG GGAGGTCAGT GGAAGGAGAG
181851 TGGGTTTAGA CCTGCATTCT TGTGCTGAAT AGCTGGAAAA ACACTTGACT
181901 AACCTGAAAA ACAAGTACTC TGTAGATTAA TTTCATTTTT TTTTTGTCAG
181951 TAGTAACAGT ATATAGAGCA ATGGTCCCAG CATTTGGGAA CATGTTGTAA
182001 ATAGGCAAAG TGGCTCAAAG AGAGTAGTAA TCAAACTTCG TAGTTAAAAT
182051 TTTTAATAGA ATATAATTAG CAATGTAGTA TTTTTATATA ATACTATATA
182101 ATTAATAGCA CAAATAAAGC ACATAAAGAA AAATGTTCTA ATTACCAAAT
182151 ATTACCCTCT AAGGTTTTTT TTAATAAAAT GGCAAAGAAA ATTAGAAAAT
182201 TATTTAATTA AACCTTATTT AATGAGAGTT CCCAGGGGAA CAGAATGAGT
182251 GAATTGAATT TTCCCATAAA CCAGTGGGCA AAGAGTTAAC ACCTTTATTT
182301 CCCCCTTCTT AGTCAAGAAC ACAGTTGTGC AGGTTCATTT TCTTGAATTA
182351 TGGAGAAATT TAGTCTAGTA ACTATAATAG AGTCATTTCT TAGTGATTAA
182401 AAGCATTGTA GAGATGCAAG ATTATTATTC CCAGCATGAA ATCTGAAATA
182451 GGAGGGAAGA TGTCAGCTAT TAGATGAGAA TATAGTTCAT GACCACAAGT
182501 TATTTCCTAA TTTTGTTTCT TTTACTTAAC ATCATAGCTA TGAGCTTGTT
182551 TTATCATTCT CTGTCCATTT TTTCTTAGGA GGGGATGGGG GTTCAGTTGG
182601 GGAGTCTTAT TAGTTTGATC ATAAGTAATT AAGGTTTGGC TGCACTAACC
182651 TTGTTGTCAG ACATTCTGGT GACAAGATTG AGTGGCATTT ATGTTGAGCA
182701 GTTGAGGAAA CTCGGCCATT TCCTTTGGCC TCCATTATGT CTGAGATGGA
182751 AGCAGTCAGT ATGAAATGCC CAGGACCTTG TTACAGATTT TCAAGAGACA
182801 GAATTTGACT GCAGGAGATA CTTTCCATTT CAATCTCCCA GTAGTTACTT
182851 TATCAACATG TTCTTTTTAA AGTCTCTAAG AACTATGAGA AATCTTTCAA
182901 CTGTGCTCTA GCTTTTAACC AGTGCTGGGG TAAGTGCTCT CTTAGATGGT
182951 ATAACGTCTT GGAATGCATA TTGGGTACAG GAACCTAGTT CTGATTTCAC
183001 CTTTACTAAT GGCTTGCTAG AACCATTGTG CAAATCAGCT ACATCTGTGA
183051 AACTGTAAAC TGTGGCTGTG GAACACGTTA AACTCAAAAG GTATTTTCAA
183101 CCTGAATTTC TCTTTTCAAC CAATTACAAT CACCCACTGG TATTTGCTGC
183151 CTGCTGGTCA TATTTCTCCT GGATAATTGG CTTTCTTTCT TGAGGAAAGT
183201 CTCTGGCTTT TATTTGTTCA CTCAACAAAT ATATACTGTG CACCTACTCT
183251 GTGCCAAGCA TTGCTCTAGG AGCAGGTTCT AGGACACATC AGTGACCAAG
183301 ACAAAAAAGG TTCCTGCTCT TAGGAAACTG ACATTTCAAT AGGAGGAAAG
183351 AGGCTATGGG AACACATGAG TAAACAAGAT AATCTCAAAT GGTGATAAAA
183401 ACTCTGGAGA AGCTCTAACA GGGCACTGAG ATAGAGCAGA CTGGATAGGG
183451 TGCTGGGGGT AACTCTACTA TGTTCTTCCA GAAGCAGTTC CCTGAAACAA
183501 GGATTCAAGT ACAAGGGGCT TCTTGGGTGC CAATCCTAAA AAACCAGGGA
183551 AGGGAGGCAG AGAAGGGAAG TCTGCCTACA AAGTTTCATA AACAAGATGC
183601 CTACACTGCA GGCTACTGAA GGAGAACAGT CCCTGAGGGG ATCCCAACAT
183651 GTCAGTGTAG AACTCACCTC AGGGTCATGC CATGCAGGGG AGAGGATTCT
183701 GGGGCACTTA TCTACTGACT CTTCATCTGT CATTGATTGA AAGCTGCTTC
183751 TGGGCATATT AACTCCTTAA CATGTCTAAC TTAGCCTGCA GGTAGGCGGA
183801 GTAGCCAGGT GTTTGCAGTT GGTACGTAAA GTAGAATACC CATGTAGAAA
183851 GGGGAGTGGA AGCGAACAGG ATGCTGAGAT TGTCTACAAC AGGGCAAGAA
183901 CTAGTTCTTT AGATAAGAAG TCAGGAAACA CCTCTCTGAG AGATGGCAGT
183951 CTAGCTGAGA TCCAAAAAAT GGAAAGGAGC CAGACAGGGA AATCACATTT
184001 CCAGGCAGAG AGAATATCAA GGACAAAAGC TCTGAGTGTG ACTAAGCTTG
184051 CTTTGTTTAT AAAAATAGAA ACAATAAAAA ATCGCAGAAC TTTAGAGGCA
184101 TAGGGGTGGG GGAGGGTTGT TTTTGAATCA TAAAGTCTAT TCTTTTAGAT
184151 AGAAAAATCA GAGAAAGCCA ATGAGAAATT CAGAAACATA GACGGTATCC
184201 TAGGATCCCA AGAGGGAGCT GGGACCGCTG CTCTAATTCC TTGGCTCCCA
184251 GTTCAGAACT TCTCCATCGA CCATGGATCC CCTGCTCATT TTCCCATTTC
184301 ATTCATTGGA ATTTGGTGGT TTCCCCCAAG CCATGGAGCT GAAAGGGAAT
184351 TGCCTGTATG ATCCCACTCA AATTCCTTGG GCAGTTTTCC AAGATACGAT
184401 CAATGGCATA TGAGTGGAAG ATCTGCATGT GACTTCTGAA AAAAGTTCTT
184451 CATGAAGAAG TTGTGCATTC CATTTTTTTT CTTCCTGCTG GGCAGGCCCC
184501 CAATTATACC TAAAAGAAAC CCAAGTTAAC ACAAGGCTCT ATGTGACCAG
184551 CTTTGGGCTG CCAATTTGAC CTCCTTTCCC ACCCTTTCTC TTCAAACTCA

184601 CTGTGCCACA ATCACACCAG CCTCCTTACT GTTTCTTGAA TATGCCAATC
184651 ATCCTCTCAC CTCTGGGCCT TTGCTCAGAA TGCTCTTCTC CAAATATCCC
184701 CATAGCTCAG ACACAGGCAT CACTTCACTC AGGTCCCTAA GCCAAGACCA
184751 CCTCCTTGCG GAGGCTCATC CTCATCACTC CTTCCAAAGC ATGACACTGC
184801 CCCTCCCCAT CCTCTTACCT CACTTTATCC TTCATGGGGC TCATTGCTAC
184851 CGCAGAGTAT ACTATCCCAG ATTATACTAT ACTATGCTGC ATATTTACTT
184901 GTTCATTTAT TGTCTGTCTT CCCCACTAGA ATATAAGCTC CATAAGGGAA
184951 GAAACTTGCT TTATTCACTA TTAGAATAGT GCACTATGAC TTTTCAAAAA
185001 TGTTTGTTGA AATGATTAAT CAGTGAATAA GTGAGTGAGT GACTGAGTGA
185051 ACCAATGCCT AACAGAGGCC CTTAGTTCTG GTGCTCTCTC TGTTACTAAC
185101 TCCCTAAATG ACGCCTCTGC AAGTTGATTC TTCTACTCTG CCTCAGTTTC
185151 TTTATCTGGC AAATACACAT ATAATGTTTA CCTTAAAAAA GGATAAACTG
185201 AAATGAGGCC ATAGATATGA AAGTACTGCA CATTATTGAA TATATTATAC
185251 AAATGTAAGA TTTCCTTTTA CAGTCGAAGC CTTCTTGAGT TTTAGTAAAC
185301 TTCACCAAAT GGGGTGGAAA GTGTCATTAT AATAAACAAT CCTTCATGGT
185351 TGCTGGAATT GATCAGGCCT CATGGAGTGG TGAAAATTTA CCCTGTTGTA
185401 TGGAAAAGAG CACAGGGTGA GGATGGAGAC TGGGATCAGA ACTCGGCCTC
185451 TTCCACAGAC TTGCTGGTGT CCTTGGGTAA CTCATAGGAG CTTGCCCAGT
185501 GAAATTCAGA TTCCTCTTCT CTCAAAATGG TTGGGTATTG GGATGGTAGA
185551 CGAGATTATT CCCTCCTTAG AGGTTTCTAC CTTGTACTAT ATATCTGCAT
185601 CATCATAATA ATCACAGCCA CTATTTATTG ATCACTTGGT CTGCCCCATG
185651 CACTTGACAT GTGTCATTGC ATTGTATGTT TACCCCAACA ACCAGACCTC
185701 CATTATTCAG ACAAGAAAAC TGTCAAGTAA CTTAGTTAAT AGTGGTATAA
185751 CTACTGGCTT ATGCATAGCA GCGCCAGCAC TCCAAACTAG GCATACTGGC
185801 TCCTGAGCTG TGCTAATTTT GTGCACAAAC TAAGTAATAA TCAAGTTCAA
185851 AGGAAAGGAG GCCTAACTGT CTCTCCATTG AGTAGGTTTC ATCTGGTGGA
185901 ACTGAATGGA AAATCCTGTG GTTTTGGAAC AGGTTAAGTT GATTTATCCA
185951 GGCAGCATGT TCTAACTTCT CCCTCCTCCC CCTCTCACAG GGCTTCATGG
186001 ACATTGACTT AAACAAATTC AAGGAGAGTG GCGCCAATGT GACAGGTTTC
186051 CAGCTGGTGA ACTACACAGA CACTATTCCG GCCAAGATCA TGCAGCAGTG
186101 GAAGAATAGT GATGCTCGAG ACCACACACG GGTGGACTGG AAGAGACCCA
186151 AGGTGAGTGG ATGGGCAGCC AGCAGCAAAG GGCCAGCCTG GTCCCTTTGC
186201 CTGCCCCAGA TTTCTGAGCT GCATTAGTCT TTACAAAGGA ATCAGTTTTC
186251 TAAAGCAAAC AAATTCAGGG AAATATATTT GTAAAGATTA TTAGGTACAA
186301 GGTGCAGGGG TCAGACAACC CAAAATGACA TGGTTTTAAG GAGGGAGACA
186351 TTTTATTTAT CTCTCCTGTG AACAAAACTT AGGAGTCAGC AGTCCCAGAC
186401 TTGTAAAATG GCTCCACAGT TATCAAATAC CCAGGCTTCT TGTACCTTCT
186451 TGCTCTGCTG TCATCCACAT ACGGCTGCTG CCTAATAGTA CAAGAGGGCT
186501 GCTTAAACTA CAGCCATTGC CTCAGCATTC TACCCAGTAG GAAGAAAAAA
186551 AAACATGCAA TGCACAACTT CTTCATGAAG AACTGTTTTC AGAAGTCACA
186601 AGCAGATCTT CCATTCATAT GCTATTGATC GTATCTTGGA AAACTACCCC
186651 CAGTTGGCTG CAAGGGAAGC TGGAAAATGG TGGTTCTATT CTGGGCAGAG
186701 CCACCATGTT GCCCAGCTCA GGAGGATGCT CATTTCATTG TAGATTGAGC
186751 TTCTTTGTGT AGTGAGGTGG CCCTTATTCT GCTCAGCCAT GTGCCCAGCT
186801 AAAAATCAGG GCAACCTAAC TAAGGAATAT CCAGCAGATC TCTACCTGGG
186851 AGAGTCCACT CTCAGTAATC AGGCAGACTC TCTGCTTCTC ACTTCCCAGC
186901 AACACAGCTC TAAATACTGC CACCAAAATC TATTTTGTTT GTTATTTGAG
186951 AATGCTTGGG AATAAGGATA GCGAATGATT CTTTTTCTGA AGTCAAACCA
187001 GATAGCTTGA CAGTGGCCAT ATGGAACCCT GTGTTGAGAA GGATACTAAG
187051 GCCAAGTTTG TTTATCTGGA CAAACAGTGA ATCTTTGACA GACTTTCTCT
187101 TGCCACTCAA TCCATTTCTT TTTATAAATG GCAAACCGTA TAACGGAGAT
187151 ACTTCTTATC CCACTATTCA AACTGATTTA ACTCTTCAAT AATGAAGACT
187201 TATTTCAATA TGATCTTAAG CAAACAAAAT CGCAAATATG CTTTCAAGCA
187251 ATGAGAAAAC TACATAGGAA TTAATTAAGT AATGTGCAAT GATTGCACTC
187301 CAATTTCCAA AAGACTGAGC AGATGACAAA AATAACCAAA TGTAATTTAA
187351 TTTTTTTTTT TTTTTTGAGA TGGAGTCTGG CTCTGTTGCC CAGGCTGGAG
187401 TGCAGTGGCA TGATCTCGGC TCACTGCAAG CTCCACCTCC CGAGTTCACG
187451 CCATTCTCCT GCCTCAGCCT CCCAAGTAGC TGGGACTACA GGCACCCGCC
187501 ACCACGTCTG GCTAATTTTT TGTATTTTTT AGTAGAGATG GGGTTTCACC
187551 GTGTTAGCCA GGATGGTCTT GATCTCCTGA CCTTGTGATC CACCCATCTC
187601 AGCCTCCCAA AGTGCTGGGA TTACAGGCGT GAGCCACTGC GCCCGGCATG
187651 TAATTTAACT TTTTAAAAAA GAAGTGAGAG AATTAAATTT AAAAAATTAG
187701 AAAAATACCC ATTCATTCGT TCTTCAATTC TCTATTGTGA ACTTGGAGTG
187751 TGCTAGGCAA CATAATAAGT ATTAGGAACA AATTAGTGAA GAAAACAGAC
187801 ATAGGTTCCA AAGCCAGGAT ATATTTTCCT GGACTGCTCT CCTGATTTTG
187851 TTTCATCCAC ATCCTAGTCC CCTTTTTGTC AGGAGAGGGT ATAATTGATA
187901 GTTGTTGTGA GAAAGAATGA GGGGAAAGTT TACAGGATAT AAACTTACCA
187951 CTTAGGTAAG CCATATGTGG AAAAAATTAG GAGCTCACCC TTCTTTCATT
188001 TTCTTTTTGC TTTTACTTTT ACAAGAGATG AAAGAGTTAA TCGTTCCTCT
188051 TGGTTTCCAG CTGATGACTG TAATGCCGGG ATAAACCAGC TGATTTTTCA
188101 TGAACTGTAT CCAGCCTGCA GATGTGTTAT ATGTAATCTA TGCATTTTTT

188151 CCCAAATGAA CCAACATTTT AAAAATTGCA AGATTGCACA CAGAAACCTA
188201 GAATCCTGGC TTCTCTTCAA AAATTATAAC TGGCAGTACT GAACTCACAG
188251 TTCAAGGAGG TCAGCATTGA CTAGCATGGT CAAGCAGCAG CACCCATCTG
188301 CTTGAATATT TATGCTTCTC AGGGACACCA TCCCTGATTC ACCACTGTCT
188351 GCCCCACGTA TACCATGCAT CTGGCCCACT GCACACCCTT CTCATCACCA
188401 GAAAACACAT TCCCAAATAC AGCACCCAAA CCTGCCTTCC TGTCAGCTCT
188451 CTTTGATACC TAACTGTCTC CATTCCTCCC ACTAGTACAC CTCTGCGCTC
188501 ACCTACGATG GGGTGAAGGT GATGGCTGAG GCTTTCCAGA GCCTGCGGAG
188551 GCAGAGAATT GATATATCTC GCCGGGGGAA TGCTGGGGAT TGTCTGGCTA
188601 ACCCAGCTGT TCCCTGGGGC CAAGGGATCG ACATCCAGAG AGCTCTGCAG
188651 CAGGTAAGAC CACCAATGTT TGCCCCATCT CATAGGAGCC TACTGGGGGA
188701 TTTCAGCATC AAATTCCAAT AAAACACAGC TATTCTAAAG AAAAGGAAGA
188751 AAATGCCTGA AGTTCAGAAC AACCACTGCA TTGTTGGTGT TGGTGGTTCT
188801 TAGCATACAT TGAAGCTCAT ATAAAAAAAA AATGATATGG AACAGTCATT
188851 TCTTGTAGTG TAAAAGCTGT ATTTTCTCCT TAGCAATTTT GCTGAAAAAG
188901 GAGAGCTGGT GATTTTCTGT GTATGGGAAA GGGACTTGAA ATACACAAGG
188951 ATGAAACTGA ACCATGTTAA TGGTCTCCTG GAAACACTCC CCTCTTGCCC
189001 TGATTTTCTG GATTTCTTCC TTTGCTCTCT GCACACATTG TATGAGAGCC
189051 TGGGGTATGT GGACCCTAAA AATGTTTCTC AGTACTTCTG ATACTACCTT
189101 CTTGCTTCTC AGCATTTCAT TCATCAATTA TGTTTGCACT TAAGAATAGT
189151 TAAAGGGCAG GGATAGAAAA TGGCCACGCC AACTCCAATC AATTGGCTAT
189201 ACAAAAGCTT CTGAGGCTGA ATCCAGATAC AACAGAGAGA AGCATAAATA
189251 TTCAATTAGT GATATGTCTG CTGTGGAAGC AGCATGAGAC AGTGGTACAT
189301 GTGGGTGTAT ATTTAACATG CCTGGTTTAG AAGATTTTGG GGACTTGCCC
189351 TCAGCTTTAT TGCTCTTGGG GCTCCTGTAG ATCTCTAAAG CACCTCAAGC
189401 CCAGGCTATG ATTCTCAAAC TGCCAAGGAA TAGCACTATA TTTTTGTTCT
189451 GATGCCTCCT GCTAGAGAAG CTGTATTTCC GAAGGGACAG GGAGAGGATG
189501 GCCGTGCTTG CTGCAAAGGA ATAACAAAGC ATTGGCCACA ATGACAAACC
189551 AGCACAGCAA GATTATTTGG CACAAATGTC CCTCAGGACC CACCCTCCCC
189601 AACAAATGGA GTTGCCTGCC TAAGACCAGC TTTACTTTTA AGACGACATT
189651 CAGCAGAAGA TGAATTTGGG CTCCTTGGGG AGAAGAGGAG CATTTCTGAA
189701 TGAGAGAGAA ATGTACAGCA AAATGTACAA CTATTCCCAC TTGTTTGCCA
189751 ACCACACGTG CACAGCTCTA GCAACTTTCA CAACCAGGAG AAAGAGATGC
189801 TGAAGGAACC TCACCAGCTG TTCCTCAGCC CTGATGAGTG CCTTTCTGTA
189851 GAGAAGAATA TGTAGGTCTG TCCTTTGAAA TGAAGCTAAG CAGGATTTCT
189901 ACTAGCTACA TGAGGAACAT GCTAAGGAGG ACCTCCAGCT GCCATTTCTG
189951 CCCTCCCCTG GTCCCTGTGC AGGGTGGCTC CCAAGTCACT AGGCAGCAAC
190001 AACAGACACC AGGCAGCTTG CAGGGGAAAA TTGCCAAATG GACAGTGCCT
190051 GCGCCTCCCT TTCTACCCCC ACCCCAGCTT ATTTAAAATG CTCTTCCAGA
190101 CTCCACAGTC GAGACAGATT CTGTTTGCAA TGTGAGGCTG GTTTCAAAAG
190151 GTCCCAGAGA TTTGTCCTCA GCTTCACAAC CCTTCCAACT CCCTTGCCTC
190201 TCCCATCTTA ATGACGTCCT GAAAGGATAG TCTGATGCCA CCATGACAGT
190251 GATGAAGCCT GGGAGGCAGT TCAGGGTGGC AGGAAGGACT CTGTACTGGG
190301 AGGCAGGAGA GCTGGACTCC ACGTCCAGCT GGGCCCCTGG CTCTCTGGAT
190351 GACCTTGAAA CATTCACTTA GCTCTCCTGC TGCCTTCCCT TTCCTTCCCC
190401 ATGAAAATGA AGGGGGTGGA GAGAGGACCT CAAGTCTCAA CTGGCTCTGA
190451 AAATTCAAAC AGTCTAATTT TTTTTCTTAT GGTCTAACCC ATGTCCTTCT
190501 GGTTGTAGTG TATACTTAGC ACACTGCTTC TGCCCTCAGT AGGGTTTGAA
190551 AGGAAGCAGT TTCCATAGTC AAAAGAACAA TGACCTCTTT TATTTTGTCT
190601 TGGAGCCAAG ATATGTGTGT GCCTGCCCTT CATCAGCTGT TCTTTGAGGA
190651 TCTATGGTGT GCCCTGGCTT GGAGCCAAGC ACTGAGGACA ATAAAAGAAA
190701 GCAAGGCCTG CGCTCAAGGA ACTCCTGGCA GTGTCTATGG AGAAAAAGAG
190751 AGGAACAACT ATCCCAAATA AATAAATAAA TAAACAAACA AACAAACAAA
190801 CCAGAACATT CTGACCTTAA GATCAGAGGT TCAAATCGAT TCATTTTCCA
190851 ATCTTTGTTA AGCACCTAGA ATGAAAAAGA TTTTGTTGAA AGACACCTTA
190901 GAGATTACTG ACTCTTCTTT TCCCTCACTT TATAATGAAA CAGCAAATCC
190951 AGAGTGGGCA GTGACTCACC CAGGGTCACA CAGCAGCTTA GTGGCGGAGG
191001 CTGGACCAGA TCCCAGTCCA GGGCTCCTCT TCCCCCAGTT AGGTCTGTGC
191051 TATGGGCCCA GGGGCCCTTG CTTATAAGCA TTGACCTCTG GAGCCTTCCA
191101 TCCATAGTCA GGACTACTCT TCAGCAATGG CTTTTTCTAG ACCCATCTCT
191151 TGAAATAGCC ATGCCACCAG GGAGCTGGGT AAATCCTGAT GGTATCCAGT
191201 CTTAGAAACC TGAGGCTTGG AGGCTCAGGT CTCTACTGCC TTCACCTCTC
191251 GCCTTCAGGT CACATAGTGG GAGAGAACCT GTGGTTTAGC TTGTGTTAGA
191301 CCTGGGTTGT CTATAAGTTA GGCCAAGAGG TCCAGCACAG CCTACCTGGA
191351 GGGCAAGCAT GCTAGGGAGT TAAATTCTGA AAATAATATG TATGGTGTGT
191401 TAAAGGCTTA GTATACACAA AGCTCTAAAC ATTTACACAT ATTATATCAT
191451 TGGATCTTTG ATATAACACC TTGAGGTAGG TAGTTTTATT AACCGTGGTT
191501 TGTAAATGGA GAAGCCGAGC TTCAGACAGG TTATAAAACT TCCCAAAGTT
191551 ATACAGCTAG CTAGTGGTAA AGTTGGGACT CCAAACCACA TTTAGATGAT
191601 GCCTCCCTCT GTATGCTTCA CTGCTCTGAA ACCTCAAGGG CACGGCCAAA
191651 CAGGGAAGAC ACAAGAGCTA TGGCCCAGCC CCCAGCAGCA CATGGCCTTG

191701 GGTAATATCT GTGCACCCCC TCCCCCTTCA CTCCGCTGTA ATTTCCCTAG
191751 CAGCAGAATG AAGATAATCA GCTGCCTGCC TGCCCCCTGC TTGCCATCTA
191801 GGGAGTCATT CAGAATATTA ATGAACCCAC ATCCTGGAGG CCCTCAGCAC
191851 TCCAGGAAGG ATGCTCATAT GTCGCCTTCT GGACGGTGGA GAAGACTCAA
191901 CTCCCCAAGT CGGGTTCTTA ACATAGGGGA GGTAATAGGC ATTTGAGAAT
191951 ATGATTTTTT AAAAGAAATC TGTAGATTCT TTTGCTTAGA AAAATGCATA
192001 TGTGTACATA CATAATTTCT GCATGACCAG GAGTAGAGAG AACATACATA
192051 CTCCTAGAAT CCATCCCAGG GCCTCAAATT TAGAATACCT CCCCTAAATA
192101 GTAATCATCC CTCTTGGTCT TTGTTTTTGC AACCTGCCAG CCAACAATCA
192151 AGCATATGGA AGTGAAGGTA TGCTCAGAAC TTTGCTAGAT GGGGTCTGGG
192201 GTTGGGTGGG CAATGGAGTT TAAGACGCAG TCCTGCCTTT AAGGGCTAAC
192251 ACAGGTGGGC TTATGGTGCT GTGGATGATC AGAGCAGAAT GCCATCACTG
192301 AGGAATGCAG ACATCAGCAA GGCTTTCTGT AGGAATGTGA CTGGCCTTTC
192351 AATAGGATGA CCACTTTATT ATCCAAAATC TATCATCCAA ACGGGAACAC
192401 TTAGGAGTGA AAGGAAAAAC TACTATCAAT TATTCCAGAA CAAGAGTACC
192451 AGAACTCTCC TGCGTTAGTC CATGTGCATT GTTATAAAGA AATACCTGAA
192501 ACTGGATAAT GTATAAAGAA AAAGGTTTCA TTTTAGCTAA TAGTTTTGTA
192551 GGCTGCACAC GAAGTACACT GCCAGCATCT ATTTTTGGTG AGGGCCTCAG
192601 GAAGCTTCCA ATCATGGCAG AGTGTAAAGG AAGAGACAGT ATGTCACGTA
192651 GTAAGAGAAG GAGCGTGATA GATAAGGGAG GAAGTGACAG GCTCTTTTAC
192701 ACAACCAGCT CTCATGAGAA CTGAGTAAGA ACTTATTCAT TACCATGGGG
192751 AGGGCGCCAA GCCATTCAGG AAAGTTCCGC CCCCATGATG CAAAAACCTC
192801 CCACCAGGCA CCACCTCCAA CGTCCAGGGT CATATTTTAA CATGAGACTT
192851 GGAAGGGACA AATATCCAAA CTATATCACG TCCCAGGCAA ACTGAGATGG
192901 GTGGTAATGG AACCGTTAAA TGTATGGTAA ATTTGAACAT GGAGTAAATT
192951 GGGTTTTGGA GGTTCTGGAT GGGGATGTCA ATGATACCCA GCAAGAGACG
193001 AGGTAGGGTG AGGGTACAAG AAAGGACTTG CACATGTCAC ATTGGCCTGT
193051 TAACGAATTA GGGATAGAAG AGCTGGGTTC CAACCGTGGC TCCACGCAGA
193101 ACTATCTGGG GGATCTTGGA CTAATTGCTT GCCTTTTCCA GATCTGGATT
193151 TTTCCTGTCT GCTAAACAGA CATAATCCTC CTAGTGCTGC CTCCCTGACT
193201 GGCTTGTCAC AGGGCTCAGA ATTTTAAGAA AGCATCGTGC TTGTGGGCCA
193251 AGCATCGTGG TTCATACCTG TAATCCCAGC ACTTTGGGAG GCTGAGGTGG
193301 GCAGATCACG AGGTAAGGAG TTTGAGACCA ACCTGGCCAA CATAGTGAAA
193351 CCCTGTCTCT ACTAAAAATA CAAAAAGTTA GCGGGATGTG TAGCAGGCAC
193401 CTGTAATTCC AGCTACCTGG GAGGCTGAGA CAGGAGAATC ACTTGAACGC
193451 AGGAGGCAGA GGTTACAGTG AGCCGAGGTT GTGCCACTGC ATACCACACC
193501 AGCCTGGGTG ACAGTGTGAG ACTATGTCAA AAAAAAAAAA AAAGCATCAT
193551 GCATGTGTTT CTTTGAACTT CAGGGAAGCT GCATGAGACA GTCAGAGCCA
193601 AGATTATTCT TCCCATGACT CAGGTAGGAA AGTGAAGCTT AGGAGGGTTC
193651 TGAGATTTGC TCTGGCCAGA GTACCTAGAA TGTGACCCAG CAAGGACCTA
193701 GTCTACAGGC CTCACAGCCA GTGAGCATCC AGGAGGAAGG ATCCACCTGA
193751 GGGCAACTGC AAGGGGGATA CAGGAGCCCT GCGTCCAGTT TGACTGCTCG
193801 GCTGTCTCCT TCAGGACTGC CTTTCAGGAT CCAATGAGGG CAGGGGAGAG
193851 CAGTCACTGT TGACACCTGA CAAAGATTCT TTGCTTGACC AAACTTTAGT
193901 CAGGCTTCTG AACCTTCTCC TAGGCCCATC TGTGCAATTC TTGTGAAATC
193951 CAGTTTTGGC AAAGAACTTG CTAAGTCGGT TTAGCAAGAA CCCTGTCCAC
194001 CACGTCCACC CTCTTTGCCA TGATCATCTT CTTCAGCCCC CACCATCCCC
194051 CAGATTATGT CGGATCATCC TCGTCCATCT TCAGCAAGAA TCCTCTTAGG
194101 CCATTTTAGC CAGAATTCCT CTTAACCCCG ATGCTTGCTG TTAGCAATTT
194151 CCTATCCACT GACCCCCACC CTGCTCCTTG GCTATATATT CCCACGGGCC
194201 CATGCTCTAT TCAGAGTTGA GCCCAATCTC TCTCCACCTC TGCAAGACCC
194251 ATTGCAGGGG TCTCTATACC TATTGCTACG ATTCTGAATA AAGTCTTCTT
194301 CACTGTGCTT TAACAAGTGT GCTGATTAAT TTTTTCTTTA ACACAGCTGA
194351 AGTAATAGAG ACATTAACCC GCATTCTCTC AGCACCAAGC AGGAAAGGAA
194401 ATATATGCTT CAGCCTCCCA TCAGCAGCAG ACTCTGAGCT GGCACCCAGT
194451 ACCCTTTACA GGAAGCCCAA GGTTAATTCT CCATCTTTCA TGGAGGGAGT
194501 TGAGGGCGCC AGGATGGCGA CAGAAGTTCC GGGAGCAGGA ACCAAGAAGA
194551 AGTGCCTGGG CTCCATCAAT CTGACCTCAG ACACCCTGGG ATGGGGGGAG
194601 AGAGGGATAA GTGCCCAGAT CCCAGAGCTC AGACCTGATG GATGGGGACA
194651 GTGGTTTCAA GATACACATT TCTGAGAAGC TTCTTCCTCT GTCTCTGAGT
194701 CCTGACTCTC CTTGATAAAT GGTTTGGGGC TGAGCCATTC TCTTGAACTC
194751 TCCTTGCTCT GCCATCATGG AATGGTGTTT CTGGGATGTC TCTTTCGCAT
194801 TCTCTGATAC TTTGTTTTAT CTCAGTGCAA GTAAGACTTG GCTTCCCCAA
194851 CTAGATACTA AGAGCCTTCA GTTACCCTTG ACCTCTCAAT GACTTACTGT
194901 GAATCCTGGA GTCAAGCGCC ATCAGCTCTG AGTCTCAATA ATCTCATCTG
194951 TGAAACAGGC AAAATAACGT CTGCTCTGGC TACTCACTGG GTTTCTGTGA
195001 ACATGAAATA AGCAGCTTCT TGTGAGATCA CCGTGACAGT GCAAGGGGTC
195051 CTTGGGTCAC TAGAACTGTG CAGGTAGGAC CCTTGACCTT ATTGGAAACT
195101 GAGGAAGGCA GTAAAAGTGT CAGTGACATG ATCCTTCTTT CTTCTGAAAG
195151 AGTCCCCTTG TCTTAGACAA CCTACCAGCC CCAAGGCCTC AATTTAGAT
195201 TTTATTTTTC ATAACTTTTA CCCACTCTAC ACAGCACAGT AGTAGTAGTC

FIGURE 3, page 55 of 122

195251 GTCATTATCA TCATTATTAT CATCTAAATA ATATAAACTA TGCATTGAAA
195301 ACTTATGTCC CAGACAATGT GCTAAGTACT TCTTGGAGGA GGAAACTAAG
195351 AAGCAGATAG TTTGAGCAAG GAACCTATGG TCATACAGTT AGAATGAGCA
195401 GAGCACAACC TGGGAAATGC CCAGCAGCAA TAGCAGAAAG CAGGTAGAAA
195451 ACACTACATT GCACATTTTT GTGTTGTCCT CCTGAAGCCT AGCACAATAG
195501 CACTGGCCTG TGTTTCGGCG AACACTTGGT ACCTTAAGTG AAGATACCAG
195551 AAGTTACCAG AAGCTCCAGA TTTTAGACCT GCCTCTGCCA CTGGTTAGTC
195601 ATAAGACTTG AGCAGATCAC TTTACTTCCC AGAATTTGGC ATCTCCCATG
195651 TAAATAAAGA TCATAATCTC TAAATGGCAT ACTTCAGGGG GTTCCTGTGA
195701 CTAGAGATGA AATAATATGT GTGCAAGTGT GTCATAAACA TGAAGTTTTT
195751 AGAAAGTAAT ATTAGTATTA AGTATCACCA TTAACAACAA TAATAATAAC
195801 AGCTGGCATT TTTTGAATAC TCATCATGCA CCAAGCATTG ATCAAAAAAT
195851 ATCTCTTTTA ATCCTTAGAA CAACCTTAAG ACATAGTTAA CTCTAATTGG
195901 TTCCATTAAA CAAATGAGAA ACTTAGTCAT AGAGAGATTA TGTACTCTGC
195951 CATACTAATA TGCCATGCTG ATTATTAGTA TGAAAATTGA GACTGGGGCT
196001 GAAAAGTAGA TGCCTGTTTG GATAATTAAT GACACTTTCA GTTTGGGCAA
196051 ATCAGTCTAC CAGTCTACCA TCTGCACATC TATCCAAGTC TGTTTCTTTG
196101 GAATGAGTCA CTTACATGGT ACCCACCAAA CTAACACTAT CTTGAACTGG
196151 AAATAAGGGA ACACTAAAGA TTGGCAAGAG ATTACTGAGG TGATAAGAAG
196201 GTGAAGCTGC TGATGGACTG GAATTGCTCC TTTCTTTTAT TCTTTGTAGT
196251 AGAATCTGTA CTTTGTTTTC TCTCTGAAAA GCAAAGATAG CCCAGACATT
196301 TATGGAGCTG GGGATTTCTC CTGATTTCAT CTAAGAAAGT AAAGAGCATG
196351 TTGTAAAATT TGCTCAGTGC TCTGGGCCTG TTGTGACCTC CTCACTGAGA
196401 CTTCAAACCA GAAGGTGACA AGAGGGTCAA CCTCGAAACA GGAACACACA
196451 CACATGCACA CACACACGCA TTCTCTCTCT CACTCTCAAA CACACACAAC
196501 CCCCAACTCT TCTTATACGT TCTAACAACA GAGGAGCTAG CCACTGTCAG
196551 AAAAAAATAT AAAACTCTGC AAAGCTTCCT TTTAAGCCAT TTGAAGGAGG
196601 GAAATAAACA GTGCTGGGTC ACAGGGTTGG ATTTGTATTT GTAACAAGTA
196651 GACACCTCAC CTCACTGGCC TTAGGCAAGA GGGATCTGAG GACACATGGT
196701 GGATCACTAT TAGGGAATGT GGTTGCTTGT ACCTGAGCTG ATGATACACA
196751 GCTAGACTCA GACTCAGTTT GAGAGTGGTC TTGGATGACA TTTATCAGTC
196801 ACCTACAGAG CAGCAAGCTC AACCTTAAAT ATCTTGGATC TCCATGGTCA
196851 CCATTTGACT TTTGATATGA ATTTGAAGAT AGAAGGCCAT GAAAGTTTGA
196901 TTTTGCCCAT TTGTGGAGAA GTCTCACGCG GCATATTTGA GGGTTCCAAT
196951 ACAATTTTAT TTTAGCCAAC TGAGATTTCT TTAACACCTT GCATTCTCTT
197001 ATCTGAACAC AATGGGTTCT CCCTAGGTGC TTTGAAGTTT TCACACCACT
197051 TTCACATTAG CAGTTATCAT TTAAGATAAA AAAAGGGCAG AGATTTTTGG
197101 AAACTGAAGG CTTAGAGAGC TAAATTGCCT GAGGGCACTT GGCTATTAAG
197151 GATTAAGCTG GGGTTAAATC CAAGTCTTTC AATTGCCAAG TATTTTATTC
197201 CCTGGACTCA GGAATAAAGA AGAAATTCTT AAAGGAATTA AGAAGCCATC
197251 TCCAAGCATA GCTTAAGGCT TCATTCATAA AGCTGGCTTC TTGTCCTGGG
197301 TCTTCTGACT CATTAGTGAT GGTGCACCAT TTTCTTTCCT TTGCAGGCCC
197351 CCCATACTTT CTTCATCTTC AGATGTGTAT CTGAGAAGGG CAGTGGTCAT
197401 AGTGGTTGTG TGATGGGAGG TGTTTGGTTA GGGATGGTGC AGACATTTCA
197451 CATTAGTATG CACTCTGACC CATTGTTAGT ATTTGCCTAA AGAAATAGGT
197501 AAAAACAATT GTCAGGATGA ATCCCAATTT AGGGAAAAGA GATCTGTAAT
197551 GCATCCCTTG CCTGTGGCAA GGGAGTGAAG AGTTTTAGCA TTCAGGATAC
197601 TCCAAGACAT CATTCCATGG AACACTCTTG GGTTCTGAAT TTCTACTTCA
197651 GTGGAAAAAG CAAACACACA TAAAGTACAT CTGAGTTCAC TGCCCACCAC
197701 TTGGTTTTGT TTTCCAGGTG CGATTTGAAG GTTTAACAGG AAACGTGCAG
197751 TTTAATGAGA AAGGACGCCG GACCAACTAC ACGCTCCACG TGATTGAAAT
197801 GAAACATGAC GGCATCCGAA AGGTAAGGTC CCCCTTTACT TCTGTTCTGC
197851 AGAGAGAAGA GGCTGAGCAG GGACTCTGGC CAGAGCTGAG GGCCTGTGAG
197901 TCCACCTTTT CTGGACTGGA TCTTTGAAGA AACTCAGACA ACACAGATTC
197951 TAGACTTGGC TCTGCCACTA ACCAGCTGGG ACATTGGGCA AGTCTCGTTC
198001 TTCCTCTGAG AATCCATTCA TTCATTTGCA AAATTAAGTT TAAAAAAATC
198051 TCTACATTTG TCCCAGGATG CTTGTGAAAA TCCAAGGTAG AGGAAAGCAC
198101 TTCTAAAACA TAAAGTAATT GATGTGTATA AAATGCCACT CCCATTCCTG
198151 AGGGTTTCTA AACTAAGAAC TTGAGAATGA TGATTATTGA TGAGGTTAAC
198201 TATCTCTTCC TAATCGATAG TTGGTCATAT CCACTCTATT ATTTATACAA
198251 AAGTAAGGGT GAAAATATAT ATGTTTACAT ATATGTATAA TGTATAATAT
198301 GTTTGCATAT GAAAATTCTT AGAATAGCAT TCAAATCCTT GGAATAACAT
198351 TTCGAATTCT ACCAGAACCT ATGTGCCCGG GCCTCTGCCG ATTTCTTCAC
198401 CCTTAACCCT TGATACTTCC TTCATCTCTC CACTCCAGTC ATTCTGTTTG
198451 TCTTTCACCT CCCTGAATAC ACCATGTTCT TTCTCATCAT TGAGCCTTCA
198501 TACATGTTTC CTCTGCCTGG GACTTCCTCC CCCCATCTCC CTCCTCTTGC
198551 CTGCCAATCC CTCCTCAGCC TTCCACACTC AAAGTAAATG TCATTCCCCA
198601 GCGAAGCCTT CTCTGGCCTT TCTTATTATG CTTCATGGAA GCCTCTACTT
198651 CTCTGCTCAT GGCCTTCATC ACATTGCTAA TTCCATTTGG TGGCGTAGCA
198701 TAATGACTGG GAGGCATTGT ACAGCATGGC GTAGAGCTGG TAGGGTGCCA
198751 TGGATCAGAA TGCTGGCTCT GGAATCCTCA ACACTGAATC CTGGCTTCAC

FIGURE 3, page 56 of 122

198801 CACTTACTAG TCTGGGGTTC CGGATAATTT ATTTGAGCTC TTTGTTCCTT
198851 AATTCTCTTA TCTAGTAAGT GGGGATCACC TTAACCATGC CAACCTCATA
198901 GGGTCATTGA GAGGATTAAA TGATCTAAGA GTGTGCAGAA GTTCTAAGTA
198951 CTGGAACTGG CCCATTGAAA GTTGGGTCTT AATCTCTCAG ACTTAATGCT
199001 CTCTATGCCT GTGCTGTCAG ATAACCTTGC CACTAGCCGT ATGTGGCTGT
199051 TTAGGTTGAA TTTTAAATAA ATTCCCATTT AAAAATCAGT TCTTCAGTTG
199101 CACTATCTAC ATGTCAAGTG CTCAGTAGCC ACATGTGGCT AGTGGCTACC
199151 ACATCAGGCA GCACAGATGT AGAACATTTA CATCACTGCA GAAAGTTCTA
199201 CTTTAAAGTT CTCTTTGTCC ACTCTCCGTC CTCACCTCCC TTAAACCTGT
199251 CTTCTCTGCT CTTATGTCTA GAACCGCATC TTCTACCTCA CAGCCAATCT
199301 TATCTCATTC ATTAAGGCTA TGTCAGTTGT CTATTGCTGC TGTACAAATT
199351 ACCACAAACA GTGACTTAAA ACAACACAGA TTTATCATCT CACAATTCTG
199401 TAGGTCAGAA GTCTGACTTG AGTTTCACTG GACTAAAATC AAAGTGTTGG
199451 CAAGGTCATG TTTCTTCCTG GAGGCTCCAG AGTTAAGTTT GTTTCTTTGC
199501 CTTTTCCAGT TTCTTAAAGG CCACCTATAT TCCTTGGCTC CCATGTTACC
199551 AAGCTTTCTC CATATTCAAA ACCAGCAATG TTACCTCTCT CTGACCCTTC
199601 TTCTATCATC ACATCTTCTC GCTAACCACA GCCTTCCAGA GCCCATCTCC
199651 CATCTCTGAC TGGGAGATCT CCTCCTTCAG GAATCAGCTA CAGTAACCTG
199701 CCTTGACTTA CAGCAGGTAC CAAATAAGGG CACCCTATTT GGCTATGAAT
199751 GTAGCCACTG GGAACGTATC CACTTCTTCA GCAAACTTTT GGCATGTTGA
199801 TTGTACACAG ACACTCTTTC TGGGCTCAAA AACCCTTGAG AATGACATTT
199851 ATCCAGAAAT AGTCCAAGTC TGAGTTCATT TTTGTTGTCC CATGGTCTTC
199901 TGATTTTTGC TGCTGGAGAA GACATTTGCT AGGTCACTTA GCTCTTATAA
199951 CTTTCAATTT CCACATCTGT AAAACGGGCA CAGATCATGT CTGCATTAGC
200001 GCCTGATCAC TGTTCAGTGA ATGTTACCTG TGTTAGTGGT TATTAATAGC
200051 TATAGTAAAT GTTGAAGAGT TAGCACACGG CTGAAATCTG GAAAACACTG
200101 AGGTGGCTTG TTTATTTCTT TCAAAGCATT TAGCAGCTAC TGTTAAGAGT
200151 ACTGCCTCTG GAAGGGACAC CAAATATGTG ACCATCTCCC CAAGGCCATC
200201 TTCCTTTCAG ATTCTTTTTT TGTTTTTTTG GAGACAGAGC CTTGCTCTGT
200251 CGCTCAGACT GGAGTGCAAT GGCATGGTCT CGGCTCACTG CAACCTCCAC
200301 CTCCCGGATT CAAGTGATTC TCCTGCCTCA GCCTCCCGAG TGGTTGGGAT
200351 TATAGGTGCC CATCACCACA CCTGGCTAAT TTTTGTATTT TGGGTAGACA
200401 CGGGGTTTCT CACGACGTTG GCCAGACTAG TCTCAAACTC CTGACCGTGT
200451 GATCCATTCA CCTCCGCCTC CCAAAGTGCT GAGATTACAG GTATGAGCCA
200501 CCACCCCCAG GCTTTTTTTT CTTTCTTTCT TTCTTTTTTG AGGCAGGGTC
200551 TCGCTCTCTT GCCCAGGCTG GAGTGCAGTG GTACTATCAT AGCTCACTAT
200601 AACCTCAAAC TCCTGGGCTC AAGTGATCCA CCCACCTCGG CCTCCCAAAG
200651 TGCTGGGATT ACAAGCATGA GCCACTGTCC CCAGCCCCTT TCTTTCAGAT
200701 TCTGAGAACT GCTGGTATCA CCTCCTGCCT TGACAATGAA AACATAGATG
200751 CAGCATTTTT GTGTAAGGCC CAAGCAGGCA AGCCTATTGC TCCTAGATAG
200801 AAAATTGTTG ACCATAGACC TGGGCTTTTC CTCAGAATCC TCAGAATGGC
200851 CTTTTGCTCT CAGGGAAAAA AGAATATTGC TATTTCCTGG ATAGAACAAA
200901 TTGGCATTTC TACATTGTAT ATGAGTAGTT ATGTGTTTGC CATAATTAAA
200951 ATATGGATGT CGAACTGTTT TCCCCAACTC TGGAGTAGTG GATTAGCTTA
201001 AAATATAGCC AGATTATTTT CTACACGTTA GTGGTCACTG GGTATATTGG
201051 GGATATACTG AAGGTGCAAC AAGTAAGAAT AGAAGCCAGA GACTTCTATG
201101 CCATTTCTGC CATCATCCAG CTGTGTGGCC TTCAGCATGT CTCATAGTCT
201151 CTCTGGGTCT CTAAAATAAG TGAGAGACAT TGGGCTGTGC AAACCTTAAT
201201 TCCTCTCAGC TCTGACACCT TGGATGTCAG TGCCATCTGC TGCATTTTTA
201251 CCATCCTCTC CCTACTCACA TTGTTCCTCT CCTGGCTGGA CTTCGGCTTC
201301 CTCTGTGAAA GTAGAATTTC CACTGGGGCC TTCATCAATT GACAAACTGT
201351 CCTTTGGTAT GAAATTCCCC AGTTGTTACT CCCAGAACCA GAGGCCCCAG
201401 CCCTTTGAGT TGACCCTAAC TATTGCCCAG AGACTGTTGG GAGGCTTTTT
201451 ATCTCTTCAA GACTTGCTCT TCATCAAGAA CTTCTCAGAA GTGGAGGCAC
201501 TGTAGCAAGA TTAATGGTTC TCAAGCCTCA GCAAATAGAA GAATTACTGG
201551 GAGGCCTTAT TTAAAACGCA GATTCCTGGG TCCCAGCCCC TGGGTACTCT
201601 GCTTCTGGAG AACAGAGATG AAGCCTAGGA ATCTGCACCT TCTTGAATCC
201651 TCCTCTCCAA CCCACAGATT TTCTGGTTGG TGCGTAAAGA GTTTGATAAG
201701 AATCACTGGC AACTACTAAG GAAAGAAGAT GGAAGTAAAA GGAATACAAA
201751 TAATATAATA TAATATAATA TAATTTATAA TATAATTTAC AAAAAAAGAA
201801 ACACTGACAG GGTGGCTAAG AGCTTGGGCT TTAGAGGCAG ACAGACCAGG
201851 ATTTTAAGTC TGCTTTAGTC TTTACTAGGC ACATGACCTT GAACACATTA
201901 TTTAGCCTCC CTGCAAGTCA TTACATCATC TCTAAAAGGG TGGTAATACT
201951 CTTTGCCTCC CAGGATCACT GTCAGGATTG AATAAGACAA TGCCTGTTAC
202001 ACCACTGCTT GTAGTAAGGG ATTCGGAAAA GTAGCTCCTG GCACGTAGCG
202051 GACATTCAGC CCACATTTGT TTACTTGTTT GTACTTTTAA ACTCCCTTCT
202101 ATAGGCCACA GGGATTTTAT ATCAGCATTG CATTTGGGGG AGTCAGGCTG
202151 TGTAAGCCTG TGGAATGGAT AAATCAGCAA AGAGAAATAA CAGAGTACCT
202201 TAAAATCCAT GAGCAAATGG TTGTGCTTTA GTTTTCAGAT CCCAGGGCTG
202251 TTTTTAAACT TACCTTCCAA TGGCCAAATC CTTTCTTAGA ATGTGGGCTT
202301 AAACGTCCTT TGTTTATGGG GGATTTGCCT TTCAGAAAAT CAATTCCTCA

FIGURE 3, page 57 of 122

202351 CATCTGTGGC TTCAGGCTTT TTACTCAATC AGCCTCCTAA CAAAGTAATT
202401 TTTCTGATTT TCAAGGGTGA CCTAGTTGTA CTGGTTTCAG TGAGCATTAC
202451 ATGGCCTTAC CTGATTGTGT ATAGTAAAAA GGAGCTGTTT CTTCCAGATT
202501 TGGAGCCTCA GAGAAACTCT CCTGATCTTC AGGCCTATTT CCTGTTCACC
202551 CATGTGCCAA TATACCCTCT AGGTACCTGG ATACAATTTG ACATCCCACT
202601 GAAATGTGGG TGTTCTAAGC ATCCATTCAT CATAAAGTTT AGGGGCTTCA
202651 GATACCAGGA TGGGTACTTG CTCTACTAAA ATGGGATCCT TAGGAAATCC
202701 CGTTCAAGGA TACCACTTCA CTATGGGGTA CTGATTTAGG GTCTCTCTCT
202751 GAATAAAATA TCTTGTCAAA ATCTGGTAGA ATCACAAATT CTGATAAATG
202801 GCTGCCCAAT GGAGAAGTTT AGGGAAAATT ATCTTACATT TTCATCGAA
202851 GAACTGGTAT TGTTGATTTA ACCGTCTTTT CCCATCACCA TTGTTCCTAT
202901 AGCAATTTTT AGACTGGGTG GAGGAATCTA CTTCTCATTT CAATTCGATT
202951 TGAGTGGCCC TGCCCTGCCC CAAGTTTATT ATCCCCACTT CTGACCCTGT
203001 GTATAACTAG AATGAAAAGA CTGGGCAGGA AACAAGACTA AAGGGACACA
203051 AAGTCCTGCT GATATCAAAA GTAATCTTCT AAAGTCCCAA AGAATTTATA
203101 GCTTGCCATT CCATATGCTT TTTGGAAGTT TTGCTTTAAA TCCTTGTTAC
203151 CCAATTTTGA CCATACTGAA TCATGTTATA GCATCAGATA TAGACATAGC
203201 ATCTCAGATA TAGCCTAAAC CTCACCACCT CTCTCCATTT CTACTGCTGA
203251 GCCCAGAGCC CAGGCCATCT TCCACACACC ACACAGTAGC CTCCTTACCA
203301 GTCACGAGTC CTGCTATGTT CTTGCCCCTC TACAAGGCTA CTTTTCCACC
203351 ACAAGACGAG GACAATAATT TTCAAATATA TATCAGGTTA TATGGCTCCT
203401 TTCCTTAAAA CTTTTACCAC TTTCCTGTTG CCAGTAAATA TACAACATGG
203451 CCCTCAGAGC CCTCAATGCT GCTTCCCTGT GGCATCAGCT CTCACTCCTC
203501 TTTCTCTAGC TCATTTCTCT GCAGTTACAC TGGCATCTTT GCATTCCTTG
203551 AGCACAGCCT CGCACTTTCC TCAAGTCACT TGCATATGCT ATTCCTTTAC
203601 CTGGCATTTT CTATCACTAG AGTTTCATGT GCTGTGTGCC TCCTTGTCAT
203651 TCAGGTCTCA GTCCAAGTGA AGCCACCTTG GAAACGACAT CCTTGACCAA
203701 GCACTTTTAA AGTCACTCCC ACTCACCCAG CTCACAGTCA CAATTTCCTT
203751 TTTATTTGTA CTTTTCATGG TGCTTATTCC TTCTGATATA TTTTTATTGG
203801 TTGATTGATC TAGATTGAGG TTGGCAAACT TCTGCCTACT GGCCAAATTC
203851 ATCCCACCAC CTATTTTTGT ACAGCCCATG AGCTAATGGT TACATGTACA
203901 TTTTTAAATG GTTGTAATAA ATCAAAAGAA GACCATTTTG TGACATGTGA
203951 AAATTATGAG AGATTAAAAT TTCAGTGCCC ATAAAGTTTT TCTGGAACAT
204001 AGCTATGCTC ATTTGTTTAT ATATTATCTA TATCTGCCTC TGCATGACAA
204051 CAACAGAGAT AAGTAGTGGC AACACAGACT ATATGATCCA CAAAGCCAAA
204101 GATATCTACC GTCTGGCCCT TTAGGATAAA GCTTGTCAAC CCCTGGTCTG
204151 GATATGTATT TTCTTCATAC TTCTCTACCT CCTAAATGTT CTAAAACACC
204201 AACTCTTTAA AAGCAAGGAC CATATTTGTA TTTTTATTAT ATTCACAGTG
204251 CCTAGAATAT ACTGAAACAG AGTAAGCACA TACATATAAA AGGTTGTTTA
204301 TTACATCACT GGGAAGTTTA TCAAATGTTT CTGTGCAATC AGAGAGCACA
204351 CTATGCTAGC CCATATTTCA AAAGATCTGC CAATAAGTAA GGGAAAAAAA
204401 TGCCTGCAAA TTTAATAAAA TAACACCTCA AGCAGAACTC AGATAAAGTT
204451 ACACATAAAC TTATTAACTT CAAATCTTTT AAGTGTGTTA ATTTAGATAA
204501 TCCTAGGTGC TGTAACAGAT AAACTCTGAA ATCTCAGCTG TTTAATGCAA
204551 AAGAAGCTTT TTTTTGTTCA CTCAGTGACC ACTTTTTTGG CTGAGGGTTC
204601 TGGCTAAGAC TCAGGCTCAT GGACCCTCCA CTGTCTACTT GGGTCTTTCT
204651 GGATTTCAAC ATCCAGCTAA CAGATAGGAA TGAAAGAAAA TGGCAACTCT
204701 GCTGGAGATT TTTGGGGCAT CAGCCTACAA CAGATGCACA TCACTTCTGT
204751 TGTATTCCGT TGGCCAGAAC CCAGTTACTT GGCTCAATCA GAGGTAAAAC
204801 AAGCTGGGAA ATGTCATTGC TGGCCAGGTA GCCACTCTCC ACCAACATCT
204851 CTACACCATG GAAGGAAAAT AAGAATGCTT GGGAGTCAGC TAATTATCTT
204901 GGCCACAATA GACAACTTAG TCTTTAAAAA TTGATACTAA AGGATCTTAT
204951 TTTTTGAGGT AAGGGGCTGT GGTCTCAGAG GCAGCCTGGA GATACCAATT
205001 TCTGAATTTG ATTTGATGAC TGTGCAATAT AGATCAATTG AATTTTCAGT
205051 TCTATGATCA TCTCCTTTTA AGACTTTCTC CACTTAAAAA ATCTGATCTG
205101 TCATCTAGAT TCATTTTCTA CATTCAAAGA ATCTTTAGAG GTAGATGGAA
205151 AACACGGAGA TCAAAAATTA TAACTGGCCC CAGGAGAAGA CCTCTCACTG
205201 TCAGAATTGT TTAAATCCTC TCCTGACTGG TAGGCCCCAA TCTTTACCAA
205251 CTACTAACTC TGATTTACTT TTAGAAAGAA TCAAAATTCC TGCATATCCT
205301 CAGTAGAGAA TCAAAGTGCT GTATTATAAT CCAACCATTT CCCAAAGAAA
205351 GGAAAATTTG CTCTAATCTC CAAAGTGCAA TGTCTGTTCA AAAATCTTTG
205401 CCAGCTTTCT TTTCATCAAA CTGTGGAACC AGATTTCTCA GTCTACTAGT
205451 TTACATGAGG CATAGGCATG AGGCTGAGTA TCACTCAGCC CACTGACCCT
205501 GGCAATATTT TGTTTTATCT CCCTACAAAA GAGTTAGAAA TAAAATAGGT
205551 TTGTTTACAA TTTCTAACTA TTCTACTAGC TTTTGATATG AAAGTACCTA
205601 GCATATAAGC CAAGCTATAC CACATTTTTT TAGAGATCCC AATTTAACAA
205651 TAGTGCTAAA ATTAATAAGT AGTGCTAGCT TTGAAGGACA ACTATCCTTA
205701 AAAATTAAGG TGTCTTTCTA AGCCATATAC ATCTGGCTTA CACAGATTCA
205751 TCTTGCTTTT TTTTCCTATC TTGTATGAAA ACCTTGGGAT TTTACGGCAG
205801 TTTTATAATT TTTAAACCAC ATACCCTGAA CATTCTATAC ATAAAGAAGG
205851 GTTATATTGT CAAGTGAATT TCAAAATGCT CTATAATGCA TGCTTCTTTT

FIGURE 3, page 58 of 122

205901 GCAGATAATG TTCAACAGCA AATTGAAAAC AGAAATGTCT TGTAGTATAG
205951 AAACCTGTTA ACCTTCAACT AGGCACTACC CTAATGAATA TCATTTTTTA
206001 GCTTACTGAC AATATGAACC ATACACTGTG CTAATTGTTT TACATGCATT
206051 AACTAATGTA GTTCTCATAG CAGCCCATGA GGCAGGTACC ATTGTTACAT
206101 CCACTCTACA GATCAGGGAC TGAGGACCAC AGAGGTCAGG TAACTTGCTC
206151 AAGCTGATAG TTGGTAATTA GGAAAGCCTA GCTTTTAAAC CAGGTCTGGC
206201 CTGAGGCCAG AGACCAAGAT CTTGACCACT GGGCTCCCTC TTTTTTAAAA
206251 TAATACATCT TAATACTCAG TGGCTTTTAG AGGAATTGGT TGCATGTCAA
206301 AGGAAGCAAC TTCCTTTCTA CTGATGGTTG TGCAGTTTGA GTAGGAATAT
206351 TTAAACCTGT GGACTAATTG TGAAGAAGGA AGAAGAAAGA CAGGAAGGAA
206401 AGGAGGAAGA ATAGGAGGAA GGAAGGGAGA AAGGATGGAT GACAGGGAAG
206451 AAAATGAACA AGAAGGAGGA GAAAGGGAAA AGAAAAAAAA ACCTTAGGAC
206501 CATCTATGAG GGGATAAATC ATATTTGACA GATATTTTCC CAGGTTTGTA
206551 TTGATTTTAT TAAATAATCT TACCTTTGAG GTCCACAAGA CCTGGGTTCT
206601 ATGTTCTGCC ACTAATCTAC TATATAACCT ATTGTTTTGT TAGATCATTT
206651 AATCTCCCTA AGCCTAAGTT TTCCTATCTG TAAAGCAGAG AAAATAATCC
206701 TAAGCCTGCC TGCACTATCT GCATAGTGTA AAGATGTTAT AAAAGTACTG
206751 TGGAGATTTA AAAAACAAAA CAATACCAAA GGAGAAAACT TTACATCATA
206801 ATATACTACC AGAGTGCTTT TAAACATCTA TTTTTCAGCT AGAAGGCTCC
206851 TTGAGAAAGG CAACTCTTGC GGGGAATCCC AATAGGTGAA ATAGATAAAA
206901 AGCAGAGCTG ACCATTAGAG CAAGGATGAG GAAGCCAGAG CTCTCTCCTC
206951 TTCACTGCCC CTCACCACCT TCCATGAGCG GTGAAAGGCC CCACAAGTCT
207001 CTTAGGGTTC CCTAGAACAC AGTCCTTGCA AAAGCGAGGG AACTGAGACC
207051 ACACTGTCTT GAGCAAATTC TGTGGTCTCT GCGCCTCTGC TTCTCCCTGT
207101 GAAAAAGGAA AAAGTTGGAC AAAATGATTC TTCAGTCCCC TTCCAGTTCT
207151 GACATTCTAG AAACGTGAGT TTCTGGTTCT TCTGTCATTA GAAAGCAATG
207201 TCTCCTTCCA CCTTGACTAA CAGCATCCCT CACAGGGAAC ATGGTACACA
207251 TGCCTGCACT GAGGGTAAGC CTCCATGCAG TATCCTGAGA GACATGCTCC
207301 CCGTCAGACC TCCGAGCTGT CTCAGCATCG ATAGGGTGCA CCATGTCCAT
207351 GCTGGGTCAC TGCTGCCTGG ATGCATTCAT TCTGTCCACA AACATTTCCT
207401 GAGCTGCTTC TCTGGGAAAA GATGTTCTAG ACTAAGACAG GAACTCTGGA
207451 ACAAGTATGT TTATTTCAGT CTTGTCCATG AGAAACTCAT AGCACCATGG
207501 AGAGATGGGG ACAGACACAC AAACAGCTAG ACCCAGTGTT CTAATGGGAA
207551 CGTACACAAG GTACTCAGGG TTGTGTCTGG CATGCAGGGG GCACGGCCCT
207601 GGAGTTGGTC TCCCTGGCTC ATATCCTGGC TCCACGGCTA CCCTGTGGCC
207651 TTGGGAAAGT TACTTCACTT TCCACGTCTC GCTTTCTGCA TACTTAAAAT
207701 TGAAAGGATA ATTAACTACC CACTTCGCAG GTTTTGTGAG GATGAAAGGA
207751 GTTAAAACAT AAAAAGCACT TTAAAAAGTC CCTGAAATGC AAGCATTCAG
207801 TAAATGATAA CTAATATGAT TTCAAGTCCA GAGCCCAATC CCTTCTTAGG
207851 AAGAACAGCA TAGTGGCTAA ATGCAGCCTC TGGAGAGAGA TTGTCAGGGT
207901 TCCAGGACAA GCTCAACCAC TTTGCAGCTA CTTCACCTCG GGCAAGTTAA
207951 CACACTCCCA CAGGCCAGAC GAAATGGCAT GAAAACTGTT GAACACTTAG
208001 CCTCTGACAT AGCAAGAGCA TCATTAGTGC TGGCAATTAT TGTTGTTAAT
208051 GGCTGCGAGA TTACAGGAAA AACTATTTCC AACTGAAGGA ACTGGGAAAG
208101 ACATGAAGGT GAAGGTGACA TTTCAGCTGA CCATTTGGCA AATGCCTCAG
208151 TTTTTGTGAG CCTATGCTGA GTTCTGGCTG TTGATAGACC TGTTCATCCC
208201 AATGCATATG CACTTCTAGN NNNNNNNNNN NNNNNNNNNN NNNNNNNNNN
208251 NNNNNNNNNN NNNNNNNNNN NNNNNNNNNN NNNNNNNNNN NNNNNNNNNN
208301 NNNNNNNNNN NNNNNNNNNN NNNNNNNNNN NNNNNNNNNN NNNNNNNNNN
208351 NNNNNNNNNN NNNNNNNNNN NNNNNNNNNN NNNNNNNNNN NNNNNNNNNN
208401 NNNNNNNNNN NNNNNNNNNN NNNNNNNNNN NNNNNNNNNN NNNNNNNNNN
208451 NNNNNNNNNN NNNNNNNNNN NNNNNNNNNN NNNNNNNNNN NNNNNNNNNN
208501 NNNNNNNNNN NNNNNNNNNN NNNNNNNNNN NNNNNNNNNN NNNNNNNNNN
208551 NNNNNNNNNN NNNNNNNNNN NNNNNNNNNN NNNNNNNNNN NNNNNNNNNN
208601 NNNNNNNNNN NNNNNNNNNN NNNNCTACTG CCCTTTTGGG CTAACTCTAT
208651 CTTCCACCCA GGACCCACAG AACTTAAACA TCTGGGCAGA TTCCTGTCTT
208701 CATATCTTGG CTCATATTCT CCCTAACCTG AAAGGTTTTG GTCCAGACCA
208751 TTCATCTCTC ATGATCATAA GCCCTGATTC CTCCTGTTGC ATTTTTCCCT
208801 GTGTAAGATC CCACACTTGG CTTTTGCTTC TCTGAACTCC TTAGGCCCAC
208851 TCACTTGTCA CTTCTGCGGC CATGTCATGT CTTCCCATGG TAGACCAGAG
208901 GCGTTCTCAG AGCAAGCCCT ATCTCTCAGA CTTCTTTGCA TCTCGTCAAC
208951 CCTGCCTGAC AACAAGCAAC ACTAATGTTT TAGCTCAGAG CCTTGTGCAC
209001 AATAGCAGTT CAATTAATAT TTCTTGAAAG ACCTTGGAAA ATGAATTAGT
209051 ATAAATAACC TACTCAAATT TGAAAAATTA ATATTGTCAA CCATAATTTT
209101 TAGGCACTCC TATATATTCA ATATTGTAAT AGTTTATACT TGGAGACAGA
209151 AGAAATTTTT AAAAATAAAG GATAAACAAC CATCATAGGA AGTTAAATCT
209201 AGATGGAAAA ATACAGTTAA CCTAAAAATA AAGTAAAAGA ATGTAATGTT
209251 TAAATCATAT GATTCCAACT ATAGTTCAGA ATGAGTTCAC TGAAGTGCAG
209301 GGTTAGTAGA CATGGGGGAA AGAGGGGTTT GACCCTGTGA ACAACTGCAG
209351 GGAATTAAAT CCCATGGTCC TGGCTTGCAT TGTACAAAAC AGACTGGCTG
209401 TGTAAACAGT TAAGCCCTTA TCCCTCAGAG GTGGCAATTT CCAAACTGAA

209451 CCAATTATTG TGGGGATTTT CCCTGGGAGC AAAATTGGGG GCACCTGAAA
209501 AGCACTGTGC TTCTTATTAT TTCTGTTTAC CAATATTTTA GAGCTCGGTA
209551 TGTCCAATTC TTCATGAGCT CCTTACTTGC CTGTCTCTGG TATTGACTGG
209601 GTGACCCAGA GCAGGCCAGT TCAGAGGAGG CTGGCCCACC TGACACCTCC
209651 ACTCTCTTCT CATTAACAGA TTGGTTACTG GAATGAAGAT GATAAGTTTG
209701 TCCCTGCAGC CACCGATGCC CAAGCTGGGG GCGATAATTC AAGTGTTCAG
209751 AACAGAACAT ACATCGTCAC AACAATCCTA GTGAGTACTC AGTCCTTCAT
209801 CAAGGTTACT TGGGATTCAA GCTAGGCCAG CACAAGGGTT TTCCACCAGG
209851 ACTGAAAGCT GGCCTTTCTT CTTGCCAAAA CTGTGTAATA GATAAAAGCA
209901 GCAAGTCGAA AAGGGAATGC CCTGAAAATG AGAGGCTCTG AGTTTTCACT
209951 CTGTATCTCT TAGTTTCACT GTCTCATCCT TTGTACCCTT GGGTAACTTA
210001 CTTACTTTCT CTTGAGCCAG CTTTCCCATA TTTAAAACAT AAGAATGACA
210051 CTAAATTGTG CTGGTTTTCA TCTGTCCTCC CTCAGTAGAA GCTATTTTCA
210101 AAGAAAGTCC AATACATAAA GTAGCTGTAA GTGAAGATGC TGTAATTTTC
210151 AGTGACTGAT CATGAGAAAC CTGGAGCCTG TTTAGGGTCT ATTTCTCCTT
210201 CAAGATGACC CCAGAGGTAT TTCCAAAAAA ATACAAAATA TCCTGGAACA
210251 TAATTTGAAA AGCTGTATGC CATATCTCAG TGATAAAACA TTCTTATTTT
210301 AACAAAGTTT GCTTCCTTAA CACAAGAAGC TTGTAATGGG GTAGGGAGTG
210351 AAGACATTTA GGAAGTGAAT TGAGGGGCTA GAGAGCCTTC CCCAGTGTTA
210401 ACCAAACATG ATATTATGCT ATGCCAAAGT CCTCCCTACC CATGGGTGAA
210451 CCCATAACCC ACATTCTGCT ATCTCCCCAT TTCTCTTCCA GGAAGATCCT
210501 TATGTGATGC TCAAGAAGAA CGCCAATCAG TTTGAGGGCA ATGACCGTTA
210551 CGAGGGCTAC TGTGTAGAGC TGGCGGCAGA GATTGCCAAG CACGTGGGCT
210601 ACTCCTACCG TCTGGAGATT GTCAGTGATG GAAAATACGG AGCCCGAGAC
210651 CCTGACACGA AGGCCTGGAA TGGCATGGTG GGAGAGCTGG TCTATGGAGT
210701 AAGTTCACTG CAGGGTGGGA AATTAGAGGG CGGAGGCAGA GGGTTTGACA
210751 GGAAATCATT TGGTGGTTGG GTGGCCCTGC CCACAGATGT CTATGAAACC
210801 CTGTAATTGA GTGTTGTTGC TGCTGAACAG ATGAGTCATC CAAAATCCAA
210851 TTTCTTCAGA CACTCTTTGT TCAGGTTACT GGTCCCAGGT CCCTCAATCC
210901 CACTCAGAGT CTTGTGACGT CAGTTGATTG TCGTCCAACA CAGGTGACAG
210951 CATAGCTCCA AGATCAATTT TCTTGAGGCA GACTGCTGAG TTGTCTATAC
211001 AAAGTCACTT GTGGCTCTCT CAGTATCAGT TTCTTCTCTG ATATTAAATG
211051 CATCTGGAGC CAACCTAACT TTCTAGTTAC TTGCCTCTCT AGTTTCATGC
211101 TCTCTCATGA AATTTCCAAT TCAGTCAAAT GCCCCTTAAT TACTCTGTTC
211151 CCTAGAGTGC TCCCTTCCAC TCTCCACCCC TAAGATACTA CTCCTTCAAA
211201 ACCTATATCA AATAATACTT TTTTCAGGGT GTGTTTCTTT CTTTCTTCTC
211251 ATAATAGGTA TGAATGTGCC TTTTAATTGT TCTCGCCTTC CCCTATAGAA
211301 TTTAGTTGCT GGTTTTTTTT AATGGTTTAC CCTGCCTTAT ATAACGGTTA
211351 CCTGTGTAAC AGGGGTAGGA CTATTCTATC TTTATAGTGC TCACCACACT
211401 TGAAATAACT CCATGCACAA TTGCTATAAA ATCTTCAATA AATTACAGCA
211451 GTTTTGAAAA GCTGCTGAAT GTCCCACATT GTTTTAAGCA TTTGGGGAAT
211501 TATTGAGAAG CAAAAGATTT GATCTTTTGC TTAATACTTT ATGAGGTAGA
211551 AAAGACCCCA TCTTTTAACA TTTTATGGGG TAGAAAAGAC AATGTGAGAA
211601 AATAGTAAAA GGTAGTATAG AATAAGGAGT CTATATTGTA TGGCTCAGCT
211651 AAGGGCTAAC TAGAGTTTGT CTAGCCCTCA GTGGGGATGT GAAACTTGAA
211701 AAATGACCAT ATTTAAACAG ACCGAGAGGC CGGGCACAGT GGCTCACGCC
211751 TATAATCCCA GCACCTTGGG AGGCCGAGGC AGGTGGATCA CCTGAGGTCA
211801 GGAATTTGAG ACTAGCCTGG CCAACATGGT GAAACCCCAT CTCTACCAAA
211851 AATACAAAAA TTAGCTGCAC ATGGTGGCGG GCACCTGTAA TCCCAGCTCC
211901 TTGGGAGGCT GAGGCAGGAG AATCACTTGA ACCAAGGAGA TAGAGGTTGC
211951 AGTGAGCCAA GACCATGCCA TCGCACTCCA GCCTGGGAGA CAAGAGCGAA
212001 ACTCTGTCTC AAAAATGATA ATAAAAAACA TATGAGAGAA AAGCAGCCCA
212051 GGAATTTTTA AAGTATAAAC AATAGGATGG TGGTGGAAAT AAGTAAGGTG
212101 TGAGAGGAGA ATGAGAAAAC GCATGGTTTT TGTTGAGGAC TTGGGTTGAA
212151 GAGTAGTCAG GGATACATAT GAGTAAAAAA TAGCAAGAGG AAGAGTGTGG
212201 ATGATTCAGT GGGCATTGGG AGATCACGAA GGTATTTGAG TAGAGAGACA
212251 ACAAAAGGCA ATGGAAGAAG CCTCCAGCTG CCTTGTGCAG GGAAGGGACC
212301 ACCACGGCTT CACTCATAGA AACTAAAACA CATGCCAAGC CCCAGGTCAA
212351 TGTTAAGTGC TCATAAGGAC AAGCAGCCAC TGAGGAAGAT GATAAATCTT
212401 GTTTCATATC AGGGCAAGAG GAGCCATGAT GGCCCTGAGA GACATACAAA
212451 GGGAATTCAA AGAAGAAAAA GATGGAATAA AGGAAATCTT CCTCAGGGAG
212501 GTAGCTTTTG AGATGACATG TGAAGGTGGT TATTGAGTTG GGGAATGGGA
212551 TGTGCTTCTC TCCTTTCTTA TTCCCTTTAC CACCTCTCAC TTTGGGAAGC
212601 TCCATGGACA AAAGGTAGAG ACCTGGATAG TACATGCTGC ATCTGGAGGC
212651 TGGTTTCCAT GGGAACTCCC ATCAAGCTCT TAAGGTCATC CCCATGGCAA
212701 CTGCTGTGCA CTTTTCACCT TCTCTAGCAT TTATCTTCAC CTTCACCTCA
212751 TGTAATGTGG TTTGCTTGGT TAAAAGTCTG CAGTGTGGGC AGAACAATGC
212801 CAGGATCATC CCCAGTAGCC AACACAGCTG GTGGTGAGTC ACTGGCACAG
212851 CAGGGCTCAG GCCAGCTGGA GTTACCTATG GGTGCCTCAG CAGCCAGGCC
212901 TGCCTCAGTA GCCTCCTCCT TATCAGGCCT ATTCCTCTGC CCAGTAAAAA
212951 CTGTTCTGAC CAGGTGCGGT GGCTCATGCC TGTAATCCCA GCACTTTGGG

213001 AGGCTGAGGC GGGTGGATCA CGAGGTCAGG AGATCTAGAC CATCCTGGCT
213051 AACACAGTGA AACCCCATCT CTACTAAGAA TACAAAAAAT TAGCCGGGCA
213101 TGGTAGTGGG CGCCTGTAGT CCTAGGAATT CGGGAGCTGA GTAGTTAAGG
213151 CAGGAGAATG GCGTGAACTG GGAGGCGGAG CTTGCAATGA GCCAAGATGG
213201 TGNNNNNNNN NNNNNNNNNN NNNNNNNNNN NNNNNNNNNN NNNNNNNNNN
213251 NNNNNNNNNN NNNNNNNNNN NNNNNNNNNN NNNNNNNNNN NNNNNNNNNN
213301 NNNNNNNNNN NNNNNNNNNN NNNNNNNNNN NNNNNNNNNN NNNNNNNNNN
213351 NNNNNNNNNN NNNNNNNNNN NNNNNNNNNN NNNNNNNNNN NNNNNNNNNN
213401 NNNNNNNNNN NNNNNNNNNN NNNNNNNNNN NNNNNNNNNN NNNNNNNNNN
213451 NNNNNN
(SEQ ID NO: 3)

FEATURES:
Start: 2189
Exon: 2189-2270
Intron: 2271-5227
Exon: 5228-5365
Intron: 5366-158436
Exon: 158437-158676
Intron: 158677-161828
Exon: 161829-162013
Intron: 162014-167314
Exon: 167315-167368
Intron: 167369-185990
Exon: 185991-186152
Intron: 186153-188485
Exon: 188486-188653
Intron: 188654-197717
Exon: 197718-197822
Intron: 197823-209669
Exon: 209670-209780
Intron: 209781-210491
Exon: 210492-210803
Stop: 210804

SNPs:

| DNA Position | Major | Minor | Domain | Protein Position | Major | Minor |
|---|---|---|---|---|---|---|
| 177 | T | C | Beyond ORF(5') | | | |
| 2555 | - | T A | Intron | | | |
| 2924 | C | A | Intron | | | |
| 3162 | C | T | Intron | | | |
| 3163 | G | T | Intron | | | |
| 4092 | - | A | Intron | | | |
| 4720 | C | T | Intron | | | |
| 6289 | G | A | Intron | | | |
| 6611 | T | C | Intron | | | |
| 7861 | G | A | Intron | | | |
| 8614 | G | T | Intron | | | |
| 9249 | T | G | Intron | | | |
| 10272 | C | G | Intron | | | |
| 10351 | G | T | Intron | | | |
| 10444 | G | A | Intron | | | |
| 10467 | G | A | Intron | | | |
| 10785 | C | T | Intron | | | |
| 10846 | C | T | Intron | | | |
| 10847 | A | G | Intron | | | |
| 13842 | G | A | Intron | | | |
| 14103 | A | G | Intron | | | |
| 14128 | T | C | Intron | | | |
| 15560 | A | G | Intron | | | |
| 15657 | - | A | Intron | | | |
| 15736 | A | C | Intron | | | |
| 15914 | C | T | Intron | | | |
| 16657 | A | - | Intron | | | |
| 16658 | A | - | Intron | | | |
| 17099 | T | G | Intron | | | |
| 18139 | T | A | Intron | | | |

| | | | |
|---|---|---|---|
| 19303 | C | T | Intron |
| 19501 | C | A | Intron |
| 22852 | G | A | Intron |
| 23210 | A | G | Intron |
| 24040 | G | A | Intron |
| 24536 | C | A | Intron |
| 25125 | - | A T | Intron |
| 25167 | C | T | Intron |
| 25623 | T | C | Intron |
| 27143 | C | T | Intron |
| 27211 | T | G | Intron |
| 27383 | G | A | Intron |
| 27553 | A | T | Intron |
| 29141 | C | G | Intron |
| 30549 | C | T | Intron |
| 30984 | C | T | Intron |
| 31266 | A | T | Intron |
| 31425 | T | C | Intron |
| 32198 | A | G | Intron |
| 33129 | T | C | Intron |
| 33292 | G | C | Intron |
| 34124 | C | T | Intron |
| 34668 | A | G | Intron |
| 34807 | A | T | Intron |
| 36025 | C | T | Intron |
| 36058 | C | G | Intron |
| 36061 | G | C | Intron |
| 36418 | C | T | Intron |
| 36743 | A | G | Intron |
| 36958 | T | C | Intron |
| 37577 | G | A | Intron |
| 38464 | C | T | Intron |
| 38472 | C | G | Intron |
| 38509 | T | G | Intron |
| 38573 | T | C | Intron |
| 38624 | G | A | Intron |
| 38802 | C | T | Intron |
| 38842 | G | A | Intron |
| 39029 | C | G | Intron |
| 39040 | A | G | Intron |
| 39179 | T | C | Intron |
| 39424 | A | G | Intron |
| 39459 | T | G | Intron |
| 39594 | C | T | Intron |
| 40279 | A | G | Intron |
| 40666 | G | C | Intron |
| 40723 | G | C | Intron |
| 41090 | C | T | Intron |
| 41260 | C | T | Intron |
| 41421 | A | G | Intron |
| 42640 | C | G | Intron |
| 42650 | C | G | Intron |
| 43285 | C | T | Intron |
| 44406 | A | G | Intron |
| 44585 | C | T | Intron |
| 44772 | A | G | Intron |
| 45507 | C | T | Intron |
| 46883 | C | T | Intron |
| 47855 | G | T | Intron |
| 47885 | C | G | Intron |
| 47941 | A | G | Intron |
| 48328 | T | A | Intron |
| 48391 | G | A | Intron |
| 48453 | A | G | Intron |
| 48690 | T | C | Intron |
| 49100 | T | C | Intron |
| 50598 | C | A | Intron |
| 50753 | G | A | Intron |
| 54798 | G | C | Intron |
| 55058 | A | G | Intron |
| 55171 | C | T | Intron |

FIGURE 3, page 62 of 122

| | | | |
|---|---|---|---|
| 55801 | G | A | Intron |
| 56324 | A | G | Intron |
| 56557 | G | A | Intron |
| 56716 | T | G | Intron |
| 58247 | C | T | Intron |
| 62318 | T | C | Intron |
| 62429 | C | A | Intron |
| 62449 | A | G | Intron |
| 62450 | T | A | Intron |
| 62554 | G | A | Intron |
| 63688 | T | C | Intron |
| 64921 | G | A | Intron |
| 64934 | T | C | Intron |
| 65150 | T | A | Intron |
| 65198 | A | G | Intron |
| 65674 | A | T | Intron |
| 65720 | C | G | Intron |
| 65820 | T | C | Intron |
| 65948 | T | C | Intron |
| 65978 | G | A | Intron |
| 65988 | C | T | Intron |
| 66089 | G | T | Intron |
| 66332 | C | T | Intron |
| 66361 | T | G | Intron |
| 67130 | G | A | Intron |
| 67148 | T | C | Intron |
| 67541 | G | T | Intron |
| 67608 | G | A | Intron |
| 67670 | T | C | Intron |
| 70638 | C | T | Intron |
| 70767 | T | C | Intron |
| 71275 | G | A | Intron |
| 71401 | C | A | Intron |
| 71656 | C | T | Intron |
| 71969 | C | T | Intron |
| 72194 | A | G | Intron |
| 72292 | A | G | Intron |
| 72351 | A | G | Intron |
| 72382 | A | C | Intron |
| 72424 | G | T | Intron |
| 72466 | G | A | Intron |
| 72829 | G | A | Intron |
| 72913 | G | - | Intron |
| 73395 | C | G | Intron |
| 73961 | T | C | Intron |
| 75749 | T | C | Intron |
| 77275 | C | T | Intron |
| 77282 | G | A | Intron |
| 81236 | T | C | Intron |
| 82536 | C | T | Intron |
| 82954 | A | C | Intron |
| 84157 | G | C | Intron |
| 85443 | T | G | Intron |
| 85674 | T | C | Intron |
| 85850 | G | A | Intron |
| 85905 | T | C | Intron |
| 86535 | - | G | Intron |
| 87371 | C | G | Intron |
| 87392 | G | A | Intron |
| 87423 | T | C | Intron |
| 87627 | T | C | Intron |
| 87637 | G | A | Intron |
| 87777 | A | G | Intron |
| 87810 | C | T | Intron |
| 89812 | G | A | Intron |
| 90137 | G | A | Intron |
| 90400 | G | A | Intron |
| 92359 | A | G | Intron |
| 92555 | - | T C | Intron |
| 92641 | G | C | Intron |
| 93969 | G | C | Intron |

FIGURE 3, page 63 of 122

| | | | |
|---|---|---|---|
| 96601 | A | G | Intron |
| 96865 | T | - | Intron |
| 98448 | A | G | Intron |
| 100137 | T | C | Intron |
| 100264 | A | G | Intron |
| 100873 | T | C | Intron |
| 102673 | C | T | Intron |
| 102807 | T | A | Intron |
| 102938 | A | G | Intron |
| 104061 | C | T | Intron |
| 107552 | - | A | Intron |
| 110789 | T | C | Intron |
| 110884 | T | C | Intron |
| 115075 | C | T | Intron |
| 115286 | C | T | Intron |
| 121154 | G | A | Intron |
| 121250 | T | G | Intron |
| 124478 | G | T | Intron |
| 124841 | C | T | Intron |
| 124842 | A | G | Intron |
| 128941 | G | A | Intron |
| 129471 | C | T | Intron |
| 130568 | T | C | Intron |
| 132179 | G | C | Intron |
| 132792 | C | G | Intron |
| 133502 | A | T | Intron |
| 133661 | A | G | Intron |
| 133768 | G | T | Intron |
| 133837 | A | C | Intron |
| 134003 | A | G | Intron |
| 134098 | C | - | Intron |
| 134530 | G | A | Intron |
| 134746 | T | C | Intron |
| 135854 | G | T | Intron |
| 136893 | G | A | Intron |
| 136945 | C | A | Intron |
| 137997 | - | T | Intron |
| 139348 | G | C | Intron |
| 139437 | A | - | Intron |
| 140321 | C | T | Intron |
| 140570 | G | A | Intron |
| 141441 | T | C | Intron |
| 141639 | C | A | Intron |
| 141796 | A | - | Intron |
| 141797 | - | C T | Intron |
| 141799 | T | - | Intron |
| 142186 | G | T | Intron |
| 142212 | G | A | Intron |
| 142600 | A | T | Intron |
| 142631 | T | C | Intron |
| 145397 | G | A | Intron |
| 145438 | C | T | Intron |
| 145855 | A | - G | Intron |
| 146816 | G | A | Intron |
| 147228 | G | C | Intron |
| 147968 | T | C | Intron |
| 149372 | G | A | Intron |
| 149466 | G | T | Intron |
| 149468 | G | A | Intron |
| 149474 | C | A | Intron |
| 151121 | G | A | Intron |
| 151984 | C | T | Intron |
| 152547 | A | C | Intron |
| 152560 | C | T | Intron |
| 154834 | T | C | Intron |
| 155118 | G | A | Intron |
| 156897 | C | T | Intron |
| 157808 | - | G T | Intron |
| 159171 | A | G | Intron |
| 159465 | G | A | Intron |
| 159505 | C | T | Intron |

FIGURE 3, page 64 of 122

| | | | | | | |
|---|---|---|---|---|---|---|
| 159786 | C | T | Intron | | | |
| 159787 | G | A | Intron | | | |
| 160954 | - | T A | Intron | | | |
| 160955 | - | A T | Intron | | | |
| 160959 | G | T | Intron | | | |
| 161415 | C | T | Intron | | | |
| 161800 | - | T C | Intron | | | |
| 161899 | T | C | Exon | 177 | I | I |
| 162793 | T | C | Intron | | | |
| 162919 | C | A | Intron | | | |
| 162939 | - | A G | Intron | | | |
| 163647 | A | C | Intron | | | |
| 163675 | G | A | Intron | | | |
| 165562 | C | T | Intron | | | |
| 166011 | T | C | Intron | | | |
| 166623 | G | A | Intron | | | |
| 167461 | G | A | Intron | | | |
| 168935 | G | A | Intron | | | |
| 169142 | T | G | Intron | | | |
| 169379 | G | C | Intron | | | |
| 171315 | G | T | Intron | | | |
| 171400 | A | G | Intron | | | |
| 172007 | G | A | Intron | | | |
| 172220 | C | T | Intron | | | |
| 172690 | T | C | Intron | | | |
| 174992 | C | G | Intron | | | |
| 176676 | G | A | Intron | | | |
| 176723 | G | A | Intron | | | |
| 176944 | A | G | Intron | | | |
| 178739 | C | T | Intron | | | |
| 179524 | G | C | Intron | | | |
| 179726 | A | G | Intron | | | |
| 179901 | G | T | Intron | | | |
| 180348 | A | C | Intron | | | |
| 180459 | A | G | Intron | | | |
| 180786 | C | T | Intron | | | |
| 181129 | A | G | Intron | | | |
| 181918 | C | T | Intron | | | |
| 181936 | - | T | Intron | | | |
| 183558 | C | T | Intron | | | |
| 184778 | C | T | Intron | | | |
| 185666 | A | G | Intron | | | |
| 185832 | A | - | Intron | | | |
| 187287 | C | T | Intron | | | |
| 187351 | T | - | Intron | | | |
| 187706 | C | T | Intron | | | |
| 188282 | A | G | Intron | | | |
| 190074 | C | T | Intron | | | |
| 193266 | A | G | Intron | | | |
| 193763 | G | A | Intron | | | |
| 193782 | C | T | Intron | | | |
| 194094 | T | C | Intron | | | |
| 194499 | G | A | Intron | | | |
| 195249 | T | C | Intron | | | |
| 197371 | A | G | Intron | | | |
| 198021 | T | C | Intron | | | |
| 198039 | T | A | Intron | | | |
| 198143 | C | T | Intron | | | |
| 198458 | C | T | Intron | | | |
| 199076 | C | A | Intron | | | |
| 199527 | A | G | Intron | | | |
| 199584 | C | G | Intron | | | |
| 200070 | T | G | Intron | | | |
| 200429 | A | G | Intron | | | |
| 200676 | A | G T | Intron | | | |
| 202325 | T | C | Intron | | | |
| 202550 | C | T | Intron | | | |
| 202609 | G | C | Intron | | | |
| 202714 | C | T | Intron | | | |
| 202809 | A | G | Intron | | | |
| 203159 | G | C | Intron | | | |

FIGURE 3, page 65 of 122

| | | | |
|---|---|---|---|
| 203168 | G | A | Intron |
| 203704 | C | T | Intron |
| 204111 | G | A | Intron |
| 204132 | C | T | Intron |
| 204285 | T | A | Intron |
| 204334 | T | G | Intron |
| 205015 | G | T | Intron |
| 205155 | C | A | Intron |
| 205510 | T | A | Intron |
| 205712 | G | A | Intron |
| 206028 | G | A | Intron |
| 206073 | G | C | Intron |
| 206487 | - | A | Intron |
| 207036 | G | A | Intron |
| 209309 | G | C | Intron |
| 210867 | T | G | Beyond ORF(3') |
| 212386 | A | G | Beyond ORF(3') |

Context:

DNA
Position

177
TTCAAAGTAGTAAGATACAAAAACTGAAAATGGAGAAATTAAAAGATGGAATCATTAAAT
CAGAGACTCTTAATGTTGGCAGAGACCTTAGAAGTGATCTTTCCTGATTCTGTTCTCTCA
TCTTCCTATGCTGATGCTTATTCTTCCTTTAGAAGGTTCCTACCCAGTGCTTGCTG
[T,C]
TATTAGAGCCTAAGAGTTAAGAGCTGGGGCCTGATGGTGGCATTTACTGTGTTTAAATGC
CCAATCTCTTTCATTAGCAGTGAAAACTTGGGGTGAGTTTTTAGACCTCTGTTTCTTCAT
CTATAAAATGGGCATGAGGCTACCTACACAGGTATTGTACAAATAAATGATGCAGGTGCA
TTTCTTAGCATGGTACCTGGCACATTCAAAATAGTGAATAAACATTAGCCTTAAAAATTA
TTTTAGCTAATTAATTAATATATGTGAAAGTGCATAGGAAATCACAAAGCATTTGACCTC

2555
AACAATATCCAGATCGGTGAGTGAGGGGGCAGCCTGGGGAGGGACTTTCTGGGTCTGGCC
AGGGATTTTTTTGGGATAGGGGTTGTGTACCCCCTCCCCGGTACTGACTGTTTTGCTTG
GCTCCCTAAAGCTGTGCTGCGGTAACAGAAGGGAGACTTGGGCTTACAGCCAGAGGAGGG
GGCTTCTCCTGATCGGATGAGGGGCAGAGGGGAAGTGTTCACACACGCACACATACCCTA
CTCGCACTCCAGGCAAGAGCATGTGAAATGGAGGAACCATCGCTTTGGAGGAAAAAAAAA
[-,T,A]
TCAGGCTGGAAAGGGTGGTGGGTGTTTAAGGAGTTAACTCTATTGCTTGGTAGATGGTGC
TTGATTCCATTTTTAATGTAAGTATGTATGGTGTGTGTGTTTTCACGTGTGTGATTATAT
ATTACATATGCACATATATATGTAATTGAAGGAGGCAGTGCTTTCTCTGCTGGGGGACAG
AAAAGAGACCCTCGAGAAGAAGGAGTGAGGGGTGCTGGGTATATTGCAGCCACTGAAATA
ATGCCAGAAGGCCCCCACTCCAAGGCGGGTAGGCTCCCTCTCCTGTTCTGGACTCCTCCA

2924
ATTTTTAATGTAAGTATGTATGGTGTGTGTGTTTTCACGTGTGTGATTATATATTACATA
TGCACATATATATGTAATTGAAGGAGGCAGTGCTTTCTCTGCTGGGGGACAGAAAAGAGA
CCCTCGAGAAGAAGGAGTGAGGGGTGCTGGGTATATTGCAGCCACTGAAATAATGCCAGA
AGGCCCCCACTCCAAGGCGGGTAGGCTCCCTCTCCTGTTCTGGACTCCTCCAGCTCCCTT
CTCTTTGCTGTCTGCCATGCTGCGCTGGTGGTCTCCACTCCCCCGATCCTGGAACTTCCT
[C,A]
GCCTGCCTTTTCTCCGTTCCTTCCTTGCCCCCTCCTCTTAGATTTCCTATCCACAGAGGT
CTACCTTTTACACACACAAACACACACACGTACACATGCTCCTTTCTCCTCCTGTTGGCT
CTCCATTATCCTTGTTACTGGGCTCCATCCTCTCAACTTGGAGGCAGGTTTCAACATGCT
GCATGCTTTTTTGTTCCCCATTTCCCCTTCTTAGTTGTTACACTTCTCAAAGGCCCCGC
CACCCTCCCTGTATTTCTGAGGGGACTGACAGATATTGCTACTCCTGATAATCATGAGGG

3162
TTCTCTTTGCTGTCTGCCATGCTGCGCTGGTGGTCTCCACTCCCCCGATCCTGGAACTTC
CTCGCCTGCCTTTTCTCCGTTCCTTCCTTGCCCCCTCCTCTTAGATTTCCTATCCACAGA
GGTCTACCTTTTACACACACAAACACACACACGTACACATGCTCCTTTCTCCTCCTGTTG
GCTCTCCATTATCCTTGTTACTGGGCTCCATCCTCTCAACTTGGAGGCAGGTTTCAACAT
GCTGCATGCTTTTTTTGTTCCCCATTTCCCCTTCTTAGTTGTTACACTTCTCAAAGGCCC
[C,T]
GCCACCCTCCCTGTATTTCTGAGGGGACTGACAGATATTGCTACTCCTGATAATCATGAG
GGAAAGCAAAACAAACAGAAGCAATAACACCAATCACAAAGCATGTCCACAAGGGCTTGG
GGCTTCCGTGTGACCAGCATGTCAGTGTCGTTTGTGTCCCGGAATGAAGCAAGCTGCTGT
GTTTGGAAGCATCTTCGTTGGTTTGGTTTCTAGTCTCTCTCCCCTGGTAGGGAGATAGCT
CCACTAGGGAAAGTTCGCATTGCTGGGAGTTTGTGCTCTTTTGTGAGTGTGTGTTTGAGG

3163
TCTCTTTGCTGTCTGCCATGCTGCGCTGGTGGTCTCCACTCCCCCGATCCTGGAACTTCC

FIGURE 3, page 66 of 122

TCGCCTGCCTTTTCTCCGTTCCTTCCTTGCCCCCTCCTCTTAGATTTCCTATCCACAGAG
GTCTACCTTTTACACACACAAACACACACACGTACACATGCTCCTTTCTCCTCCTGTTGG
CTCTCCATTATCCTTGTTACTGGGCTCCATCCTCTCAACTTGGAGGCAGGTTTCAACATG
CTGCATGCTTTTTTTGTTCCCCATTTCCCCTTCTTAGTTGTTACACTTCTCAAAGGCCCC
[G,T]
CCACCCTCCCTGTATTTCTGAGGGGACTGACAGATATTGCTACTCCTGATAATCATGAGG
GAAAGCAAAACAAACAGAAGCAATAACACCAATCACAAAGCATGTCCACAAGGGCTTGGG
GCTTCCGTGTGACCAGCATGTCAGTGTCGTTTGTGTCCCGGAATGAAGCAAGCTGCTGTG
TTTGGAAGCATCTTCGTTGGTTTGGTTTCTAGTCTCTCTCCCCTGGTAGGGAGATAGCTC
CACTAGGGAAAGTTCGCATTGCTGGGAGTTTGTGCTCTTTTGTGAGTGTGTGTTTGAGGG

4092 GGGAGCATCATAATCAAGAATTTTTTTTGTTTTCATTCTTTAAAATGGGAGCACTTGTAC
ATGTGGAAATCACTGGCTCTTACATGTGGCATTGTTTACATTTGTGCTTATATACTACCT
ATCCTTTGTGGCTTGGAAGTGTTTGTCTAGTATATTTGTGTATATAGTAAATGGTATAAA
TGCATGAGGATGTTTCATGTATGTGCTATGTTTTCTCATGTATCTCTGCATATTTTTAAA
ATTATATTTAGCCCTAACTTGGTTGTTCAACTGATAAAGCCATTGCTACTGTTTTCAAAA
[-,A]
AAAAAGAGATTGAAGCATTAAATTGTAGAACAAAATGCTGAAAATATCACTGCCATCAGG
TAGTACTTGATTCTATTTGTGTGATCTGTAACAAAAGGCTTGCAATCCATTTATTGGTTC
TTAAAAACAGACACCCACTCTACAAGAAGTTAGAAGTGCATTATGTTTGGACTGTGATTA
CTGTCAGATTTGAGATAAACTTCTATGTAAACATCATTATAGTTCAGTCTCTAGAAATGG
CTGATTTTAATTCACAGAAATGTAATTGATTTACATGTTGACAGTAAATACAAAGGTAAG

4720 CATCCCATCAGGCACCTTTACTATACCTTTTACTAGAATAGAATGTTTGTATCCTCTTGA
GATGCCTAAGATCCCACATCTTTGAAGCACAAGGTTCCACCATGCAAACACACAATGGCA
ATCCCTTATGTAACAAGTCATTCCTAGGTAACTGGGATCATGTGTGGTGAAAGAGTAAGC
AAAACATTGTTTGCAGAAAAGCAAGAGTTTTTAGAGAAAATGAATAATAAACCTTAGGGG
CAATAGAATAGTTAAATTGCATGCAGGTCTTGCTAGGCCAAAGACTAAAAACTGTCCATG
[C,T]
AAACAGTTATAGTAGTGGAGAAGCCCACAGGGTCCCAGAGCTAGATTTCAATCACCCTGC
AGCACTGATTAGTACCTACTTCCCGTAAGGCTCTCTGGTGAGAGATGAGGCTGATGTAAG
AAAAATTAGACATGACTAGAGGGTGAGGGGGCTTATGTGTATGTTTATATAAGAGAATAG
CAGCTCCTAGGTGGTTTGCACAAGGGAGGAAGAAGAGAAATGGCACAAGTCTCCTGTTTT
CTCTGACTTTAGCTGAGTTGAGGGGTACACAATCAAATGTTTGAGCAAAGTAATAGATAT

6289 CATCTGAATTGAATGCATTGTAAAATGTGGGCAACAAACACCATTCTGAGTTTTCCTGGC
AACTAGGAATGAAAAGGAAGCCTGTGCTCACATGATTGGCTTTTCATGACAGATGAAAGC
ATAAAAATTAATCAGGAAACATATTTTCCCTTCAGGGATTAAGCTCAAGTAAAAATTTAT
GGCAGGGAAATGTGAGCTGAATTCACAAGAACAATTTGAGACCCCAAACTGGATTGAATT
GGCACGATAGTCTTGGTGTGTCACTATTGACTTGGTGACTTCTGCTGAGCTGTCTCTGGT
[G,A]
GAAGTCATGGACCATATTTCCTTTGTGTCTTTCTCATAGTCCCACTGGTGAGTTCTCAAT
GATTTGAATAGGCTATGCTTTGAAGTCTCAAAATGAGAAGTCAGAATTCTTTCTATCCCA
AAGACCACTCCTAAAATAATGTTGTTACAAATTCCAAGAACTATAATTATAGCAGATTTC
ATTTATTGAGAACTTACTGTGCATCAGAACTATGATAAATACTTTATAGTCATTTATAGT
CACATTCATTACCATGTATTAAGCACTGACTACAGCCCATGTAATGCACTAATTGCTTTT

6611 TTTGTGTCTTTCTCATAGTCCCACTGGTGAGTTCTCAATGATTTGAATAGGCTATGCTTT
GAAGTCTCAAAATGAGAAGTCAGAATTCTTTCTATCCCAAAGACCACTCCTAAAATAATG
TTGTTACAAATTCCAAGAACTATAATTATAGCAGATTTCATTTATTGAGAACTTACTGTG
CATCAGAACTATGATAAATACTTTATAGTCATTTATAGTCACATTCATTACCATGTATTA
AGCACTGACTACAGCCCATGTAATGCACTAATTGCTTTTTATGTGTTAGCTCATTTAATC
[T,C]
TCACAGGAGCTTTGCAGAGTACTAGACATTATCTTCCTTTTAGAGATGAGAAAACTGAGG
CTACAACAGATTATATAACTTGCCCAAGGTTACTCAGGAAGCAAATGGTGGTTTTGAGAC
CTGAAGGTCCATGTTCCTGGATACTGTGACAGATACACTGATTCTTATGGTACCCTAATC
AACTAGTCGGATTACCCAAGAAATGAAAGGGAATTTTCAGGGTCTTGTAAGGCAGAGGTC
TAATAAAGTACCTAAGGAGAAAAACTTACAGTGTTTCAAACTGTAGCTATGATTTGCACA

7861 AGGCCTGGAGTGGATGAATCTGAGTTCTTGAACTTGATGCTGCCATCCATGAACTAGTGT
ACAGGTTTCCATGAATTCCTGTCTTGTTCGTTCAGTTAATTCTTTAAGTGTTTCTTCAAA
GCTATAAACTGAAATAGATATTGGAAATACAGAGATGATAAAATGCCCTTGCTCTCAGGT
AGCTTACAGTCTAGTGGGAAACATTGTTATGGGGATTATCTGAGAAGCAATAATCTTATT
TTGTGCTTAGACTTTGTGTTTCTTTTCTTTAGCTCCCAGATCCCAAAGGGGGTACTGGGC
[G,A]
AGTTAGGTGGAAATCCTGGCCTGGCTGGAGGAGCCTCTCTTAAATTTCATGTAAGGCTAG
GAATACTTTAGGGCTGTGTTCACTGTGGTCCATTGGTTTGGGAAAACTTTACATCTGTCC
CAATTTTAATTGAGTAAAAAATGTCAGTGGGAGCAAAGCAGTTTTAGGAAGAATGTACTC
ATTACTGATACATGGAAAAGCAAGAAAAGCATCTTATTCAGACTAATTTTCTGTGCTGTG
TTTTTTGAAATCTGAATTAGTAGTTGCCTTAAATTAACTGCCCAATAAGTCTTAGATCTA

FIGURE 3, page 67 of 122

8614 TAGCAGCAGGGGACTAAAAATGAGGAGAGGTGGTTATATGGTAGGGAAGGTGGGGAAGAT
AGAAGAGGACTATGGCTACTACTACTGGCCAAGGTGAGAGTTTGGTGCCTTCTTCGTGTT
CAATCTTTCTTGCTTCCCTGGTCTGCCATTGTTAAAGAGTAAAGCCATTGAATCAGCAAC
CCAATGCCTTGGGATCTCCTTTAAGCACTTTTCCAAGCTTACAGGGGTAGAGTTTGGGGA
GATTGTGCATAGAGAAGATATTTACTGATCAGCTACCCAGCTTATTTTGGTGCCTTTGTG
[G,T]
TAAGTGTAAATAAAGGAATAAATGAAATGCTGATTGAGATTATTACTATTAGAGGTCTGA
GTAGCATAGTTGCAGCTTAATTCTTACCTTTTAATTTATTCACCTATTTATTCATTCATT
CATTCAGCAAGTATATACTGAATGCCTACTTCATGCCAAACACTGGGCCAGACGCTAGGA
ATATAGGGGCCAGGAAAGAAGGCACAGCCTCTTTCCTTGTGGAGCTAACAGTTTAGCCCA
GAGGTTCACAAACTTCAGTGCACTTAAAATTCACTCAGGGAGCTTGTTTAAAGCAAGACT

9249 TCAAGAGTAGGCCCTGGAGGAATTCTATAGCAATTATTATGGGGATTACACTTTAAGAAT
CTCTTTAATCTAAAAAGTCTTCCATCCCTTTAGTAAGCATTTTTGAGCCCTCAACCAAAC
CTAGGCATGACATAAAGTGCTACAAATGCAGACAACAGTAAGTTGCATTCCCCACCCTGG
AGTACTTTATCCATAGTAAGACATTTTCTATCCTGTAAAGAGAAAATTAAAATGTAATGT
TGTAAGTGCTATAGCAGCAATTTGTATGGAGTATTGAAGATTCCTTGAAGAGTGGAGTTT
[T,G]
TCTCTAGGAGGTGGTGATTGAATTGAGCCTCAACGATAAATAGGGTTATCTATCTGCAGA
AGGGGTCACCAAATATAGCCATCCACAAGCCAGTTCCAGCACAGAGACTGAGTTCTGGGC
CCATACACTGTGTAAGAACCATGGAATTTCACATTAGAACTTGGACATCTTGTCTTGACT
AATATTTTTAAATATTAAAATATCTGGCAACACTAGGGCCCAGGTCTATGCAGCCTCAAT
TTGCTGAGATGGGACAGAGTAAACCCCATCTACATGGCCTCTTTCCCAATCAGCCCATTC

10272 TTTCTTGACCTACACAATGCTTTTTCATATTTGGCATAAAAATCCAGATTTCTGGCATCT
TTAAAAAAAAACTTAGGGCATTAAGCAACCCTAGGCCCACATTCCTGCTTAACTTCTAT
TTTCTAGAGCTGAGAAGTGCTGCCCCTTTTTAAATACATAAACTCCCAAGTTAACCAAAGT
TTCCATTACTTCCTGTTTGATTGCTAGAGTAATCAAATTATGTTGTTTGGGCAGGCCTGT
AAGTAGGCCAATCTACTCATACCTGATTTATATCGTCAGCATTCATCATTTTATTATTTT
[C,G]
TTCTAATAATATCTATTACTTACCCTGTCAAAAATAATAAAAGACACAAAAGATGTATAA
CTCCTACTCTCAAAAAAAGTAGTGTGTATACAGTAATGAAGAGAATGGTGGCTGATGGTG
GGATAAACAAGAATTATTTTGAAGACCTACTATGTGCCAAATACTTTGCAGGTGTTGTCT
TAAGTTTTATAACTGTCTTGAAAGGTGATTATCCCCATTTCATTGATGATGGTACTGAGA
CTGAGAGAGATTGTGTCTTCTTTATATTATGCAACAAATAAAAACCTAAGCTAGTATTTA

10351 CATTAAGCAACCCTAGGCCCACATTCCTGCTTAACTTCTATTTTCTAGAGCTGAGAAGTG
CTGCCCTTTTTAAATACATAAACTCCCAAGTTAACCAAAGTTTCCATTACTTCCTGTTTG
ATTGCTAGAGTAATCAAATTATGTTGTTTGGGCAGGCCTGTAAGTAGGCCAATCTACTCA
TACCTGATTTATATCGTCAGCATTCATCATTTTATTATTTTGTTCTAATAATATCTATTA
CTTACCCTGTCAAAAATAATAAAAGACACAAAAGATGTATAACTCCTACTCTCAAAAAAA
[G,T]
TAGTGTGTATACAGTAATGAAGAGAATGGTGGCTGATGGTGGGATAAACAAGAATTATTT
TGAAGACCTACTATGTGCCAAATACTTTGCAGGTGTTGTCTTAAGTTTTATAACTGTCTT
GAAAGGTGATTATCCCCATTTCATTGATGATGGTACTGAGACTGAGAGAGATTGTGTCTT
CTTTATATTATGCAACAAATAAAAACCTAAGCTAGTATTTAAAGCCAGTTTGGGGGGCTC
CAAAACTCAATGAGCATTCTCCTTTTAAAGATCTATGAATATGGCCAGGGGCAGTGGCTC

10444 ACCAAAGTTTCCATTACTTCCTGTTTGATTGCTAGAGTAATCAAATTATGTTGTTTGGGC
AGGCCTGTAAGTAGGCCAATCTACTCATACCTGATTTATATCGTCAGCATTCATCATTTT
ATTATTTTGTTCTAATAATATCTATTACTTACCCTGTCAAAAATAATAAAAGACACAAAA
GATGTATAACTCCTACTCTCAAAAAAAGTAGTGTGTATACAGTAATGAAGAGAATGGTGG
CTGATGGTGGGATAAACAAGAATTATTTTGAAGACCTACTATGTGCCAAATACTTTGCAG
[G,A]
TGTTGTCTTAAGTTTTATAACTGTCTTGAAAGGTGATTATCCCCATTTCATTGATGATGG
TACTGAGACTGAGAGAGATTGTGTCTTCTTTATATTATGCAACAAATAAAAACCTAAGCT
AGTATTTAAAGCCAGTTTGGGGGGCTCCAAAACTCAATGAGCATTCTCCTTTTAAAGATC
TATGAATATGGCCAGGGGCAGTGGCTCACACTTGTAATCCCAGCACTTTGGAAGGCCGAG
GTGGGCAGATCATGAGGTCAGGAGATTGACACCATCCTGGCTAATACAGTGAAACCCCAT

10467 TTTGATTGCTAGAGTAATCAAATTATGTTGTTTGGGCAGGCCTGTAAGTAGGCCAATCTA
CTCATACCTGATTTATATCGTCAGCATTCATCATTTTATTATTTTGTTCTAATAATATCT
ATTACTTACCCTGTCAAAAATAATAAAAGACACAAAAGATGTATAACTCCTACTCTCAAA
AAAAGTAGTGTGTATACAGTAATGAAGAGAATGGTGGCTGATGGTGGGATAAACAAGAAT
TATTTTGAAGACCTACTATGTGCCAAATACTTTGCAGGTGTTGTCTTAAGTTTTATAACT
[G,A]
TCTTGAAAGGTGATTATCCCCATTTCATTGATGATGGTACTGAGACTGAGAGAGATTGTG
TCTTCTTTATATTATGCAACAAATAAAAACCTAAGCTAGTATTTAAAGCCAGTTTGGGGG
GCTCCAAAACTCAATGAGCATTCTCCTTTTAAAGATCTATGAATATGGCCAGGGGCAGTG
GCTCACACTTGTAATCCCAGCACTTTGGAAGGCCGAGGTGGGCAGATCATGAGGTCAGGA
GATTGACACCATCCTGGCTAATACAGTGAAACCCCATCTCTACTAAAAATACAAAAACTT

FIGURE 3, page 68 of 122

10785  CCCCATTTCATTGATGATGGTACTGAGACTGAGAGAGATTGTGTCTTCTTTATATTATGC
AACAAATAAAAACCTAAGCTAGTATTTAAAGCCAGTTTGGGGGGCTCCAAAACTCAATGA
GCATTCTCCTTTTAAAGATCTATGAATATGGCCAGGGGCAGTGGCTCACACTTGTAATCC
CAGCACTTTGGAAGGCCGAGGTGGGCAGATCATGAGGTCAGGAGATTGACACCATCCTGG
CTAATACAGTGAAACCCCATCTCTACTAAAAATACAAAAACTTAGCTGGGCGTGGTGGCA
[C,T]
GCACCTGTAGTCCCAGCTACTCAGGAGGCTGAGGCAGGAGAATTGCTTGAACTCAGGAGG
CAGAGGTTGCATTGAGCCAAGATCACGCCACTGCACTCCAGCCTGGCAACAGAGCGAGAA
TTTGTCTCAAAAAAAAAAAAAAAAAAAAAAAAAAACCTATGAATATATGGACAGAGAAAA
GTACCATAGCAGTGAAATAGCCCAACGGTAGAAGTGTCACAGTGGAATTTATGATTCAAG
CTTAAGAGCTAAGTCTTCCAAGGCAGAAGCTATGACTGTGGATGATGAAAACTTCTTGGG

10846  ACAAATAAAAACCTAAGCTAGTATTTAAAGCCAGTTTGGGGGGCTCCAAAACTCAATGAG
CATTCTCCTTTTAAAGATCTATGAATATGGCCAGGGGCAGTGGCTCACACTTGTAATCCC
AGCACTTTGGAAGGCCGAGGTGGGCAGATCATGAGGTCAGGAGATTGACACCATCCTGGC
TAATACAGTGAAACCCCATCTCTACTAAAAATACAAAAACTTAGCTGGGCGTGGTGGCAC
GCACCTGTAGTCCCAGCTACTCAGGAGGCTGAGGCAGGAGAATTGCTTGAACTCAGGAGG
[C,T]
AGAGGTTGCATTGAGCCAAGATCACGCCACTGCACTCCAGCCTGGCAACAGAGCGAGAAT
TTGTCTCAAAAAAAAAAAAAAAAAAAAAAAAAAAACCTATGAATATATGGACAGAGAAAAG
TACCATAGCAGTGAAATAGCCCAACGGTAGAAGTGTCACAGTGGAATTTATGATTCAAGC
TTAAGAGCTAAGTCTTCCAAGGCAGAAGCTATGACTGTGGATGATGAAAACTTCTTGGGG
AAGGTGGAACTTTAGCAGGCATTAAAGGGTGGAGCAGATTTTGGTTGTGGAGTGGGAGGA

10847  CAAATAAAAACCTAAGCTAGTATTTAAAGCCAGTTTGGGGGGCTCCAAAACTCAATGAGC
ATTCTCCTTTTAAAGATCTATGAATATGGCCAGGGGCAGTGGCTCACACTTGTAATCCCA
GCACTTTGGAAGGCCGAGGTGGGCAGATCATGAGGTCAGGAGATTGACACCATCCTGGCT
AATACAGTGAAACCCCATCTCTACTAAAAATACAAAAACTTAGCTGGGCGTGGTGGCACG
CACCTGTAGTCCCAGCTACTCAGGAGGCTGAGGCAGGAGAATTGCTTGAACTCAGGAGGC
[A,G]
GAGGTTGCATTGAGCCAAGATCACGCCACTGCACTCCAGCCTGGCAACAGAGCGAGAATT
TGTCTCAAAAAAAAAAAAAAAAAAAAAAAAAAAACCTATGAATATATGGACAGAGAAAAGT
ACCATAGCAGTGAAATAGCCCAACGGTAGAAGTGTCACAGTGGAATTTATGATTCAAGCT
TAAGAGCTAAGTCTTCCAAGGCAGAAGCTATGACTGTGGATGATGAAAACTTCTTGGGGA
AGGTGGAACTTTAGCAGGCATTAAAGGGTGGAGCAGATTTTGGTTGTGGAGTGGGAGGAG

13842  ATGACCTTGTTTACTTTAGCTTCCCATCACAGTCTCCACCACAGTATAGTGTTCAGTGGT
GCTAGATGAATGAAAGAATAGATGGCAGTGACAAGAATAAGCCTGAATCATTGCTGCTTA
GGGTAATGCTTTTGATATTATGAGTTTTGAGAGTTCCAACAGGCTGTGCTGTAAATACCT
ATGGATGGTTATTACTGTGTAGCTCCAAAGTTATGGGGGTGAAAATCAGGTGTAAGTCCA
ATTGAAAGCTCATTTTAGCTCCCGCTGGACTATTGTCATGAGGGGTCCTAAATAAGGTAT
[G,A]
AGGTTCCATCTTCTAAATAAAGAATTTCTGATTCAAGCCCTGGGTTTGCCATTGATGTAT
GAGCCTTGTATGCATCTTACGACTTTGGTGTGTCCCAGCCTGCTGTCCAGAAAGCACAGG
GGAGCCCAGGGCCATGGGAGGTCCAGGTTGAGGAGGCAGGCAAAACTGGGGCAAATGAGG
CAGTTGGAGGCTAATGAAATTGATACCCTATGGTTAGGCGTGTTTCCATGTGTTCATTGT
TTGGAACCTCTAGGATGAAAATAAAGTTTGAGAATAGCCTTTAGTTTGTCTACAAAAGTA

14103  CCGCTGGACTATTGTCATGAGGGGTCCTAAATAAGGTATAAGGTTCCATCTTCTAAATAA
AGAATTTCTGATTCAAGCCCTGGGTTTGCCATTGATGTATGAGCCTTGTATGCATCTTAC
GACTTTGGTGTGTCCCAGCCTGCTGTCCAGAAAGCACAGGGGAGCCCAGGGCCATGGGAG
GTCCAGGTTGAGGAGGCAGGCAAAACTGGGGCAAATGAGGCAGTTGGAGGCTAATGAAAT
TGATACCCTATGGTTAGGCGTGTTTCCATGTGTTCATTGTTTGGAACCTCTAGGATGAAA
[A,G]
TAAAGTTTGAGAATAGCCTTTAGTTTGTCTACAAAAGTAATATATACATTACAGAAAGCT
ATAGGAACAGAGACAGCAAACACAATAAAACTTGTATAATTATAGTACTAAGGATACATT
TTCCATCCTTTTTTGAACCTAACAATTTAAACATTAATAGATTTATCTTACTGTCTTATA
ACATGATTTTTTGCATATTACAACCTTTAGGCTACTTTTATTATTGCACATTCATTTTTA
ATGGTTTCATAAAAGCCCACTGTACATATGTACCCTAATTTATTTAAGCTGTCTCCTTTT

14128  CCTAAATAAGGTATAAGGTTCCATCTTCTAAATAAAGAATTTCTGATTCAAGCCCTGGGT
TTGCCATTGATGTATGAGCCTTGTATGCATCTTACGACTTTGGTGTGTCCCAGCCTGCTG
TCCAGAAAGCACAGGGGAGCCCAGGGCCATGGGAGGTCCAGGTTGAGGAGGCAGGCAAAA
CTGGGGCAAATGAGGCAGTTGGAGGCTAATGAAATTGATACCCTATGGTTAGGCGTGTTT
CCATGTGTTCATTGTTTGGAACCTCTAGGATGAAAATAAAGTTTGAGAATAGCCTTTAGT
[T,C]
TGTCTACAAAAGTAATATATACATTACAGAAAGCTATAGGAACAGAGACAGCAAACACAA
TAAAACTTGTATAATTATAGTACTAAGGATACATTTTCCATCCTTTTTTTGAACCTAACAA
TTTAAACATTAATAGATTTATCTTACTGTCTTATAACATGATTTTTTGCATATTACAACC
TTTAGGCTACTTTTATTATTGCACATTCATTTTTAATGGTTTCATAAAAGCCCACTGTAC

FIGURE 3, page 69 of 122

ATATGTACCCTAATTTATTTAAGCTGTCTCCTTTTATGGGATATCTAGTTTATTTCCCTT

15560 TCAGATCCCAGCACTGGCAGCCTTCACCTGCCCAGCTACAAGTCCAGTGGAAAGGAAACT
TCTCTTTTCTCATCAGTTCCACAAAAGTCCTGGGCCTGATGTCATTGGATAAAACTTAGG
ACACATGCTCATTTCTGAATATGACACAGTGGCCAGGATATTGTAGTCTTTTGCTTGACA
TGGGCCTAGTGAAATCATCATTTTTAGAGCTTGGGGTAGTGAGAAGAACCAAAAGATTGT
GGATTTAAGCCAGCCCACCAAAACCATACGGACATGGGGGAGGAATAATTCCCTCAAAGG
[A,G]
AATCAGGATGCTATTACCAAAAGAATGGAGATTGAATGCTTGAGAGGCAAAATAGATATA
TATATATATTTTTGTCTATTAAGCATATATATATATACACTATCTATATATAGATGTAAA
TGTATTTATTGTCTATTTTATGTATTTATTGTAAATAAATACATTTACTCTCTCTATATA
TATATTCTATCTATATATAGATGTCCCCCATTGCACATCTTTTCAGAAAAGAAAATTCAG
ACAGGCTGGAGCTGAACCAATGCAGACAAAAAGTCAACATGCTAAAGTCAGAAGAGCCAC

15657 GATGTCATTGGATAAAACTTAGGACACATGCTCATTTCTGAATATGACACAGTGGCCAGG
ATATTGTAGTCTTTTGCTTGACATGGGCCTAGTGAAATCATCATTTTTAGAGCTTGGGGT
AGTGAGAAGAACCAAAAGATTGTGGATTTAAGCCAGCCCACCAAAACCATACGGACATGG
GGGAGGAATAATTCCCTCAAAGGGAATCAGGATGCTATTACCAAAAGAATGGAGATTGAA
TGCTTGAGAGGCAAAATAGATATATATATATATATTTTTGTCTATTAAGCATATATATATAT
[-,A]
CACTATCTATATATAGATGTAAATGTATTTATTGTCTATTTTATGTATTTATTGTAAATA
AATACATTTACTCTCTCTATATATATATTCTATCTATATATAGATGTCCCCCATTGCACA
TCTTTTCAGAAAAGAAAATTCAGACAGGCTGGAGCTGAACCAATGCAGACAAAAAGTCAA
CATGCTAAAGTCAGAAGAGCCACCAATGAGACAAGCACATACAAGGGATTCTGGTGGGTA
AGTCAAGATCAGAAGTCAGGACAGGCAAAAGGTCTGAAATTCAGGCTTCTGAGTTAATCA

15736 GACATGGGCCTAGTGAAATCATCATTTTTAGAGCTTGGGGTAGTGAGAAGAACCAAAAGA
TTGTGGATTTAAGCCAGCCCACCAAAACCATACGGACATGGGGGAGGAATAATTCCCTCA
AAGGGAATCAGGATGCTATTACCAAAAGAATGGAGATTGAATGCTTGAGAGGCAAAATAG
ATATATATATATATTTTTGTCTATTAAGCATATATATATATACACTATCTATATATAGAT
GTAAATGTATTTATTGTCTATTTTATGTATTTATTGTAAATAAATACATTTACTCTCTCT
[A,C]
TATATATATTCTATCTATATATAGATGTCCCCCATTGCACATCTTTTCAGAAAAGAAAAT
TCAGACAGGCTGGAGCTGAACCAATGCAGACAAAAAGTCAACATGCTAAAGTCAGAAGAG
CCACCAATGAGACAAGCACATACAAGGGATTCTGGTGGGTAAGTCAAGATCAGAAGTCAG
GACAGGCAAAAGGTCTGAAATTCAGGCTTCTGAGTTAATCAAAGCTGTAGGGGTCTTTGG
TAATCCTTGTCCAGCCACGAGCAAACCTGTGTTCACAGAACAGTTAGAAAGTGCTAGCCA

15914 AGATATATATATATATTTTTGTCTATTAAGCATATATATATATACACTATCTATATATAG
ATGTAAATGTATTTATTGTCTATTTTATGTATTTATTGTAAATAAATACATTTACTCTCT
CTATATATATATTCTATCTATATATAGATGTCCCCCATTGCACATCTTTTCAGAAAAGAA
AATTCAGACAGGCTGGAGCTGAACCAATGCAGACAAAAAGTCAACATGCTAAAGTCAGAA
GAGCCACCAATGAGACAAGCACATACAAGGGATTCTGGTGGGTAAGTCAAGATCAGAAGT
[C,T]
AGGACAGGCAAAAGGTCTGAAATTCAGGCTTCTGAGTTAATCAAAGCTGTAGGGGTCTTT
GGTAATCCTTGTCCAGCCACGAGCAAACCTGTGTTCACAGAACAGTTAGAAAGTGCTAGC
CATTCACCCACATAGAAGCGACTGGGAGGTGGCTCTCCAGGCCACTCTGATAATAAGTT
GAGGTTGTCGGCTGTAAAATGTTTGGTGATCCTGAGGCACCAATACTCTGTCCCAGTGAC
CAGGACATTTCCTGCTCTACTCAAACACTCAAGCTATTGTGCACAAACTCTTTAACAGTC

16657 ATGAAGGAGGCTTTAACCTCTGTTAAACAAGCAGAGATCTCAAGCTGGCTCCTGTCCAAG
GCAAACAGGGCAGTATGGTTCTTTTACATAGGTCATGGATTTACAGGGGACTGATATCCT
AAGACTAACACTGATGAGGCACAAGACTGTAATGATTGAAAAGTGGTTTAGCTACAAAGG
TCAACTGATTTGGGGGAAGGTGCACTTGTTTATTCAATAATTGATATTTGTGGAGCATCG
TGGTAGATGAGATTATTATTTGGCAATTATTTCTCTCTCCCTCAAACTCCTTGGGAAAAA
[A,-]
ATATAACTTCCTGCTTCATTAATGTCACATTTGGTCATTTGACATGCTCTGGCAACTTAG
ATATTAGTAGATATGTTTGAAGCAGAGATTATGAGAAGAACATGCCCCAGAGAGCCTGCT
CGTCTCATAGGAAAGGTAAATACAGTAAGTAGAAGTGTCCCAGTCAACCCACAGCCCACA
GACTAAAGTTTGAAGCAGAGCTATCCCAGCTGACCTGAAAATCTGTGAGCATTGTAGGAA
ATGCTCAATGTTATATACCACTGAAATTGGAAATCCTTTGTTTTGCAGCAATAGCTGGCC

16658 TGAAGGAGGCTTTAACCTCTGTTAAACAAGCAGAGATCTCAAGCTGGCTCCTGTCCAAGG
CAAACAGGGCAGTATGGTTCTTTTACATAGGTCATGGATTTACAGGGGACTGATATCCTA
AGACTAACACTGATGAGGCACAAGACTGTAATGATTGAAAAGTGGTTTAGCTACAAAGGT
CAACTGATTTGGGGGAAGGTGCACTTGTTTATTCAATAATTGATATTTGTGGAGCATCGT
GGTAGATGAGATTATTATTTGGCAATTATTTCTCTCTCCCTCAAACTCCTTGGGAAAAAA
[A,-]
TATAACTTCCTGCTTCATTAATGTCACATTTGGTCATTTGACATGCTCTGGCAACTTAGA
TATTAGTAGATATGTTTGAAGCAGAGATTATGAGAAGAACATGCCCCAGAGAGCCTGCTC
GTCTCATAGGAAAGGTAAATACAGTAAGTAGAAGTGTCCCAGTCAACCCACAGCCCACAG

FIGURE 3, page 70 of 122

ACTAAAGTTTGAAGCAGAGCTATCCCAGCTGACCTGAAAATCTGTGAGCATTGTAGGAAA
TGCTCAATGTTATATACCACTGAAATTGGAAATGGTTTGTTTTGCAGCAATAGCTGGCCA

17099 ACAGTAAGTAGAAGTGTCCCAGTCAACCCACAGCCCACAGACTAAAGTTTGAAGCAGAGC
TATCCCAGCTGACCTGAAAATCTGTGAGCATTGTAGGAAATGCTCAATGTTATATACCAC
TGAAATTGGAAATGGTTTGTTTTGCAGCAATAGCTGGCCAATAGAAGCAACCAGCGTGTG
TTCCACACTTTGCTAGGCACTGAGGGAACATTGGAAATGACAGACATAGTCCTGGTCTCC
ATGGAGCACTATTGTAGCTAGGAAGATAGACAATGAATACATTTACAAATAAAATATATA
[T,G]
AGAGAGATCATTACTAGGGTCATAAAGAAAATAGGATGTAGTGACATCACCACTATGGTA
GAGAAGAACACCTTTAAAGTAAGTGGTCAAAGAAGGCATTTCAAAGGAGGTGACTTCTGA
GCTCAGATATAAAAGTTGGAAGAGAGCCAAATGAGAGTAAATTCCCCTGTGGAATGTCGA
AATCCAGCCCCATGGCAACTTGGATTGAGAATCTTGGTCTAGGCAGAGGAGAATGAGGT
GCCCTGGAAAAATCTCCTGCAAACTAGGTCACTCACTTGTCTTAGGGCAGATACTAGCTT

18139 TAGAAAGGAGTCTCCCTTGAGCAAGCAGGATAAGCTCCAGCATCCCTAATCTATCTGGTA
AAGGCTATAGAGGTGTCACACCTACAAGGGAGAACAAAGAACATCTAATGCAAGCCCTCT
GTTTAATCTTCACTCCAGACACTGAAAAGCAAGAATGTTGGGGGACAGGAAGCTCACAGC
GCCCGCATGGAATTTAGACTCCAAGTAGTTTATTAGCTTTGGGAAAATTATTTAACTTAC
ACTGCACTTACTAGCTCTTCTTCCTTACTCCAAGATCACTCTGAATACTTTAAAATATGG
[T,A]
TGGACATGGTGGCTCACACCTGTAATCCCAGCACTTTGGGAGGCCAAGGCGGGCAGATCA
CTTGAGGCCAGGAGTTCGAGATCAGTCGGGCCAACATGGCAAAACCCTGCCTCTACTAAA
AAATACAAAAAATAGCTGGCATGGTGGCACACACCTGGAATCTCAGCTACTTGGGAGGCT
GAGGCACGAGAATTACTTGAATATGGGAGGTGGAGGTTGCAGTGAGCCAAGATCAAGCCA
CTGCACTCCAGCCTGGGAGAAAGAGTGAGACTCCTTCTCAAAAAATAATAATAATAAATA

19303 ATTTATTGAAGACTATTTCTGATCATCAAGCTTCTTGTCTCAAAAAAATATCAGTGGCTT
CCCATCTTATTTTAAGTTCAAACTCAGACTAAAATATGAGTCTCTCCATAATGGGTCTCT
GCCTGCCTTCCTTTTGAGACTTACCTAAACCCTACACTCTATGTTCCAGCCAAACTAGAC
TACCTAGTGTTGCCACAAACATGCCTCTCAGTCTTTCACTGCTTTGGTCATACTACTGAT
TCCATCTGAAATAGTCTCTACCACATTGAGCACCCACTCTCTACTAAACCCTGGAGATAC
[C,T]
GCAGAAAACAAAACCAGCAAACTCCCTGTACCCTTGGGGTTTACGTCCTGGGAAACAAAT
ACATATAATGATTTCAAATACTAGTTAAATGATACAAACATAGCCAAATAGAGTCATGGG
ACAGAGAGTGAGCTGTAGTGCTACATTAGATGGGTGGTCAGGGAGGACAGGCATCACCTG
AAGAGATGATATTTTAACTGAGCCTTGTTGCAATCCATAGAACTTTCTGCAGTGTTGGGA
GACATTCTATATCTGTGCTGTCTAATATGTAGGCACTAGCAACATCTGCCCCTATTACAC

19501 ACATGCCTCTCAGTCTTTCACTGCTTTGGTCATACTACTGATTCCATCTGAAATAGTCTC
TACCACATTGAGCACCCACTCTCTACTAAACCCTGGAGATACCGCAGAAAACAAAACCAG
CAAACTCCCTGTACCCTTGGGGTTTACGTCCTGGGAAACAAATACATATAATGATTTCAA
ATACTAGTTAAATGATACAAACATAGCCAAATAGAGTCATGGGACAGAGAGTGAGCTGTA
GTGCTACATTAGATGGGTGGTCAGGGAGGACAGGCATCACCTGAAGAGATGATATTTTAA
[C,A]
TGAGCCTTGTTGCAATCCATAGAACTTTCTGCAGTGTTGGGAGACATTCTATATCTGTGC
TGTCTAATATGTAGGCACTAGCAACATCTGCCCCTATTACACATTAGAAATGTAGTGAGC
ATGACTGAGGAACCAAATCTTTCATGTAATTTAATTTTTATTAATTGTAATTTAAAAAGT
CACATGTGGCTAGTGACTGTCATATTAGACAGTGCTAATCTAGATTCTAGAATATTTCAG
ACAAGAAAAAAAAAAACAGTAAGCATAAAGGCTTTAAATGAGAGTGAGTGTATATTCAAAG

22852 GAACCCAGGGCTTTTATTGACCTGGTTGGCTGAATCATTGTATGTAGAGGTGAAGTAAAG
GCAGTGCAGGTGCAGGTGCAGTCACAGATCATGCTTTTATACTTGTGGCATGTATAGGAA
ATGTTGAATAAGCTCATCTCTGGATGGGGATTTTAGTACGTTAATAAAGGGAGTTCACCA
AAGTTCATCTCCAACTCAGGCATCTCAACCAGTTTTTGTTTTTTGGGCTTCTTCCTGGAA
TTTTTTTTGAAACAAGAACTCAAGGTGCAACAGTTACAAGTGTGTAATTTCTCATTGTGT
[G,A]
TACCCAACAATCTGGGGACCCTGAGTTATAACTCTTTTTGCTGAATTTGTGAATAATGTC
TTGTGATGTTTAATCCTGTTTTACATATGGTGAAACTAAGGCTGAGAGCATACACAGGGA
TTTATCTGCAGTCAGGTAGCAGCCAGGTCACGATGCTAACACAGAACTTTTGACCGTCAC
CCAAGGCCTCCTACTCTTCCAGGCTCCCTGTCAATTTTTGGAGCCAGTCCTCTAAACAGT
TTTACCCAGAACAAGGAATTGCCGGTGATTTCAGAAAGAACTGGCAGACTCGGGGGAGGC

23210 GTCTTGTGATGTTTAATCCTGTTTTACATATGGTGAAACTAAGGCTGAGAGCATACACAG
GGATTTATCTGCAGTCAGGTAGCAGCCAGGTCACGATGCTAACACAGAACTTTTGACCGT
CACCCAAGGCCTCCTACTCTTCCAGGCTCCCTGTCAATTTTTGGAGCCAGTCCTCTAAAC
AGTTTTACCCAGAACAAGGAATTGCCGGTGATTTCAGAAAGAACTGGCAGACTCGGGGGA
GGCACTTGCCAAATTGGCTCAGGCTGGCCTTGCTGCCATGCTTCTTTTCCTCGTTCCTGC
[A,G]
AAGCCAGTTCTAGGTAACCTACCTGCAGATGTCTACCCTGAAATAACACCCAGCCTCTGT
TACACTGCTGTTACACACAAACAAACAAAGCAAATCTGCTGCAAAAAGAGGCAGGTTGAA

FIGURE 3, page 71 of 122

ATAAATTATTTTTAGTGCAACATATAACGTCAATGTCAAAAATACGAAAGAGGCAGGTTG
CATAGGGAGGCTGAGGAGGAGATGCTGAGATTCAGTGTGGAAGGTGACAAGATAAGAGGA
GGAAAGTTTGCCCTGGCCCTGAGGCAGCAAAATTAATTTTGCCCCAGGCCTTTAACTGAG

24040 ATTTGGAAAGGTACTGCATTTTCTATGGCCCAAGAGGCCAAAACACAGACAAAGTGAGTA
CAACATTTGGTCTGGCAGATTTTGACTCCACACGACAGAGCCCATTCTAAGTGTGTGGAC
TGGCTAGCAGTGGCGAGGGTTCCCTTTCTCTAGTCTGCAAACCTCCCAATCAACATGGCT
GTTAGAAACCTGGTCCTTTTGCAGAATTGCTTTACCACTTCTACCTTGATGACCCAGTGC
CTGTGATACCACCGTTAGAAAGTCATCTAATTGCGTTTAAACTTGTTCTCTCCAGCATCC
[G,A]
TTGAATAGCAAAGACAAATCCTTCTGACCATAGTTCTAATTCTGTGGGCTGGCACTATGG
ATTTAATTGTGCCCTCCCAAAATCCGTTTGTTAAAGCCCTAACCTCCAGCATGATGGTAG
TGGGTTTAGCTGTCGTCATGAGGATGTCATCCTCATAATGGATTAATACTCTATAAGAGA
CACCAGAATACTTGCTCTTTCTCTTTTTCTGTGCACATGCACCAAAGTAAGGTCATGAGA
ACACACAGCAAGATGGCGGCCATTGGCAAGTCAGGAAGAGAACCTCACCATAGTGGCACC

24536 TCTTTCTCTTTTTCTGTGCACATGCACCAAAGTAAGGTCATGAGAACACACAGCAAGATG
GCGGCCATTGGCAAGTCAGGAAGAGAACCTCACCATAGTGGCACCATGATCTCGCACTTC
CAGTTTCCAGAACTGTGAAAAAAGAAATTTTTGTTGTTTAAGTCACCATTCCATAGTATT
TGGTTATGGCATCCTGAGCTGACTAACACCACTGGTAATTAAGGTGTTTCTTCCATGAAA
AATGAAATGATGGTCAATAGGAAGCAAACAGAAGCTTAAGCAGAAGGGCAGAAAGGAGTG
[C,A]
ATTTGGGAACCAGAGGGAGTCCTATAGAGACTAGACCTGGGATTTTGACAGTTCTGCTGA
GGGCTGGCCCTGTGCCCAGCCTCCTTCCACTTCTCTTCATCTCACTAGACCAAGAAAATA
TGCACATCTGTTATCCACAAATACTCTGAATTCCCCCGCCAACGCAGATCCCCGGGAAAA
CCTAACACAAGCAGAACAGTGGAGGAGATGCACGGGGTATTTGGTGTTTCTCAGGAAAAA
GGCTTGATTTTTTGACACCCTCTATCTTGGTCTCTTAATTTGTCCTGAGTCAGTGAGCCA

25125 GTCAGTGAGCCACAGTGAAGTCCAGAGAAAAAAATGGAAATAGGAGAATCGGGCTTAAAC
CTCAGTTTTGTCGCTGATTAACCTGTGATCTTGGGCAACCCACTGATCTGTTCTTTGTTT
CAGTTTCCCTCCATGACCCTGAGTACTTTAATAGCCTCTATTCTCCCATGTATCTCTGTT
GAACAGATCATAAAGAGTAGTGATTATGAATCCAGACTTTACTGTTACTGTCAAATATCA
CATTAATTTCCTCAGCCACTTTACACCTGTGCAACCTGAGGCAAAATTTTGTAATATCTC
[-,A,T]
GTTTCAGTTTTTATAGCTGTCAAATGGGGTTAATAACAATCCCTATCACAAGCAGTCTTT
ACAGGCATGGAATGAAAAATTGCTTGTGAAATGCTGAGTGTAAGGCCTATTATATTCAGT
AACTATTACCTCTATTTGGTTCAACACCATTTTGCAGTCTCCCCCAAACACCCTGCTGC
AACACACCTCTAAGCCTTGGCTATGCTGGCCTAAAAAACTTCTAGACACCCTTGATGACC
CAAATGAAAATCTTCTGAACCCAAGGAATGCTTTCCTGGCTGTGTAGGTGGCAAGCATCA

25167 GGAGAATCGGGCTTAAACCTCAGTTTTGTCGCTGATTAACCTGTGATCTTGGGCAACCCA
CTGATCTGTTCTTTGTTTCAGTTTCCCTCCATGACCCTGAGTACTTTAATAGCCTCTATT
CTCCCATGTATCTCTGTTGAACAGATCATAAAGAGTAGTGATTATGAATCCAGACTTTAC
TGTTACTGTCAAATATCACATTAATTTCCTCAGCCACTTTACACCTGTGCAACCTGAGGC
AAAATTTTGTAATATCTCTGTTTCAGTTTTTATAGCTGTCAAATGGGGTTAATAACAATC
[C,T]
CTATCACAAGCAGTCTTTACAGGCATGGAATGAAAAATTGCTTGTGAAATGCTGAGTGTA
AGGCCTATTATATTCAGTAACTATTACCTCTATTTGGTTCAACACCATTTTGCAGTCTC
CCCCAAACACCCTGCTGCAACACACCTCTAAGCCTTGGCTATGCTGGCCTAAAAAACTTC
TAGACACCCTTGATGACCCAAATGAAAATCTTCTGAACCCAAGGAATGCTTTCCTGGCTG
TGTAGGTGGCAAGCATCACACTCTCAAGGGAGTAAAACTGTGCCTTTCTGCAACCATTAT

25623 TGGCTATGCTGGCCTAAAAAACTTCTAGACACCCTTGATGACCCAAATGAAAATCTTCTG
AACCCAAGGAATGCTTTCCTGGCTGTGTAGGTGGCAAGCATCACACTCTCAAGGGAGTAA
AACTGTGCCTTTCTGCAACCATTATTGCCCATAACCCATCATGTTGTGATGCGTTTTTA
CAAGATTGTCTTTTGTTGTCTATGCTTTTGGGGTTATATGCAAGAAATCATTATCCAGAC
CAATGTCACATGGTTTTTCCCCTATGTTTTTCTCCAGTCGTTTTACAATTTCAGGACTTA
[T,C]
ATTTAAGTATTTAATTCATTTTGAGTTGATTCTTGTGTAAGGGATGAGAAAACGGTCCAA
TTCAATTCTTCTGCATGTGAATAGCCAGCTTTTCCGGCACCATTTATTGAAGAGACTATC
CTTTTCCCCTTGTGTGCTCTTGGCACCTTTGTAGAAAATCAGTTGATCATAGACTTGTAG
GTTTATTTCTCAGCTGTCTATCCTATTCCATTGGTCTACATATCTGCTTTTATGCTAGTA
CCATGCTGTTTTGATTAGTATAGCTTTGCAATATATTTTGAAATCAGATCATGTGATGCC

27143 CAACAAAGTGACTGTAGTTAATAATATATTATGTATTTCAAAATTTCTAAAAGACTGGAT
TTTAAATGTTCTCACCACAAAGAAATGACAAGTATGTGAGGTTATGAATACGTTAATTAG
CCTGATTTGTTCATGCCACAATGTATATGTCTATCAAAAGATCACACTGTAACACAGAAA
TAGATATTATTTGTCAATTAAAAACAAATTTTTTAAAAAGGCTATTTTTCTTGCTGAATC
CCACATGTCTCTGGGGCTAGGGTAGATGTCTTTTTTAACCAGATTGTGTCCAGCTTAGTC
[C,T]
GGTGTTCAATAAGCATTAAGTGTCTGAAGGGTGGTCAATGGACAAACAGATGAAGGGTTG

FIGURE 3, page 72 of 122

```
            CATAGATTAATAGAAGTCTACCATATCTAGGCTGGGAGTGGTGGCTCACACCTGTAATCC
            CAGCACTTTGGGAGGCCAAGGTGGGCGGATCATGAGGTCAGGAGATTGAGACCATCCTGG
            CTAACACGGTGAAACCCTGTCTCTACTAAAAATACAAAAAATCAGCCTGACGTGGTGGCG
            GGCGCCTGTAATCCCAGCTGCTCAGAAGGCTAAGGCAGGAGAATCACTTGAACCTGGGAG

27211       TTCTCACCACAAAGAAATGACAAGTATGTGAGGTTATGAATACGTTAATTAGCCTGATTT
            GTTCATGCCACAATGTATATGTCTATCAAAAGATCACACTGTAACACAGAAATAGATATT
            ATTTGTCAATTAAAAACAAATTTTTTAAAAAGGCTATTTTTCTTGCTGAATCCCACATGT
            CTCTGGGGCTAGGGTAGATGTCTTTTTTAACCAGATTGTGTCCAGCTTAGTCCGGTGTTC
            AATAAGCATTAAGTGTCTGAAGGGTGGTCAATGGACAAACAGATGAAGGGTTGCATAGAT
            [T,G]
            AATAGAAGTCTACCATATCTAGGCTGGGAGTGGTGGCTCACACCTGTAATCCCAGCACTT
            TGGGAGGCCAAGGTGGGCGGATCATGAGGTCAGGAGATTGAGACCATCCTGGCTAACACG
            GTGAAACCCTGTCTCTACTAAAAATACAAAAAATCAGCCTGACGTGGTGGCGGGCGCCTG
            TAATCCCAGCTGCTCAGAAGGCTAAGGCAGGAGAATCACTTGAACCTGGGAGGCAGAGAT
            TTCAGTGAGCCAAGATCACACCACTGCACTCCAGCCTGGGCAACCGAGTGAGACTCTGTC

27383       CCACATGTCTCTGGGGCTAGGGTAGATGTCTTTTTTAACCAGATTGTGTCCAGCTTAGTC
            CGGTGTTCAATAAGCATTAAGTGTCTGAAGGGTGGTCAATGGACAAACAGATGAAGGGTT
            GCATAGATTAATAGAAGTCTACCATATCTAGGCTGGGAGTGGTGGCTCACACCTGTAATC
            CCAGCACTTTGGGAGGCCAAGGTGGGCGGATCATGAGGTCAGGAGATTGAGACCATCCTG
            GCTAACACGGTGAAACCCTGTCTCTACTAAAAATACAAAAAATCAGCCTGACGTGGTGGC
            [G,A]
            GGCGCCTGTAATCCCAGCTGCTCAGAAGGCTAAGGCAGGAGAATCACTTGAACCTGGGAG
            GCAGAGATTTCAGTGAGCCAAGATCACACCACTGCACTCCAGCCTGGGCAACCGAGTGAG
            ACTCTGTCTCAAAAAAATAAAAATAAGAAATCTACCATATCTACTTCTCAGGCATAAATA
            TGATAACTATTTCCTTTAATTTCCCATTGGATAAATAACTGTTTATAAACATCTAGTTGC
            CAGACCCATGCTTGGAGTCTCAGGGCTAAAAGAAATGCTCCCCATTTGCTCTATGTGCTA

27553       ACCTGTAATCCCAGCACTTTGGGAGGCCAAGGTGGGCGGATCATGAGGTCAGGAGATTGA
            GACCATCCTGGCTAACACGGTGAAACCCTGTCTCTACTAAAAATACAAAAAATCAGCCTG
            ACGTGGTGGCGGGCGCCTGTAATCCCAGCTGCTCAGAAGGCTAAGGCAGGAGAATCACTT
            GAACCTGGGAGGCAGAGATTTCAGTGAGCCAAGATCACACCACTGCACTCCAGCCTGGGC
            AACCGAGTGAGACTCTGTCTCAAAAAAATAAAAATAAGAAATCTACCATATCTACTTCTC
            [A,T]
            GGCATAAATATGATAACTATTTCCTTTAATTTCCCATTGGATAAATAACTGTTTATAAAC
            ATCTAGTTGCCAGACCCATGCTTGGAGTCTCAGGGCTAAAAGAAATGCTCCCCATTTGCT
            CTATGTGCTAGTCACATCAATCCCACTTGATCCCCACAGCACCCTTTGGGGGAAAGAGAG
            TAGTTGATAATCTGATTTTACCAATGAACAAAGGCTCAGAAAAGACTAGTTGATCCTAAA
            AACACCACACAGCATTCTAATGTTGTAAAAATACCTGGATTTGAGTCCCCTGTACACTGA

29141       AAGTAGCTGTGGCAGCTCCTTATAAAGAGATCACAGCTGGAGATGCGTTCACTAATCCCA
            CAGAATAATCCTCTGTTTCTCTTTCCTGAACCCCCACATCTAGTTCATCAGCAAGTCTGT
            CAGTGCTAGTTACAAAATATATTTTGAATCCACACACTTTTTTCAAAAAAAATCTCTACC
            ATAACCCCGTATCCCTCACACTGTGATCTTTTTCCCATATCACTACATTAACCTCCTAAC
            CTGTCTTCTTGCCTCCTTCCAGACAATGTTCCACCTGGAGGCTAAAGTGACTTTTTAAAC
            [C,G]
            TATTGAGCTGAACATTCCATTCCTCTGCTTAAGTAAATGTAGACTCCCTTCCTTGGCCTA
            CAAGGCCCTCCATGAACCTGTCCCTCCCTAACCTTACCTCTTGCCCCTCTCTCATGTAAC
            TGGATTTCAGCCTTCCAGGCCTTCCTTCAGTTCCTTAAACAGGCCAAGCTGCCAGGGCCT
            TTGCACTGGCTGTTCCCTTTGCCTGGGATGCCGTTAAATCTCATCATGGCTGGCTCTAGT
            TCACTATTCAGGTCCCAATTCCCACGTTACTTTCTCAGAGAGTGTTCCCTGAACACTTAA

30549       TGGCAGCCTGTTAGAAATGCCAGTTCAAGGCCAGGCACGGTGGCTTACGCCTGTAATCCC
            AGCACTTTGGGAGGCCGAGGTGGGCAGATCACAAGGTCAGGAGATCGAGACCATCCTGGC
            TAACACCGTGAAACCCCGTCTCTACCAAAAATACAAAAATTAGCCGGGCATGATGGCAC
            GCACCTGTAGTCCAGCTCCTCAGGAGGCTGAGGCAGGAGAATCGCTGGAATCGGGAGGTG
            GCAGCTGCAGTGAGCCAAGATCACGCCACTGCACTCCAGCCTGGACGACAGAGCGAGACT
            [C,T]
            CATCTCAAAAAAAAAGGAAAGAAAAGAAATGCCAATTCGAGGGTCTCAGGCCGGACCTCC
            TGAATCAGAAACTTTGGAGTTGGGGCTCAGCACTCTGTTTTAACAGGCCCCGCAGATGAT
            TCTGAAGATGCTCACCAAAGTTTGACAACCACTACCTATTGAATGACTTAATTTTATGGG
            ATACTAGATCAGACTAGATCAGAGTCTGAAGTTTTTCTGTAACTCAGTTCTCATCTTAAC
            GCTGTGAGTGTAGATTGCTCTCAATCCACGGCTGAAGAAGCCAGATTGTGACTGAATAAA

30984       CCAAAGTTTGACAACCACTACCTATTGAATGACTTAATTTTATGGGATACTAGATCAGAC
            TAGATCAGAGTCTGAAGTTTTTCTGTAACTCAGTTCTCATCTTAACGCTGTGAGTGTAGA
            TTGCTCTCAATCCACGGCTGAAGAAGCCAGATTGTGACTGAATAAAGCCAGTTACCCTGC
            CTGACCCTGGCTCCAGGACCTGCAGCATGTAAAACATCATCCAGGAGTGCAGCCCCTGTG
            AAGACAGCTGACCTGAAGGGCATGGAGTCTGTGACCCCATCCACCTTGAGAAGCATGCTT
            [C,T]
```

FIGURE 3, page 73 of 122

AACCAGCAAAGGAAAGACAGTCCTAGACAAGGAAACATCATCAAGTCTCTCTGTAGGAAT
ACTTCATATCAGACCATATTGCCATGTGTTGAAGATTATTATATAATGATAATAATTAGT
ACAATAGTAATACCATACATTTTGATTACATTTTTGACATTTTCAAGGCATGTTTATATT
CTAATAATCTATTTTCCCTCTTGATAATTTTATTTTCTCCCTTAAAAATCTCTCCAGTTA
CACAAAGTAGAGTAGGAGTGAAAGGATTGTTAATCTGTTAATCTGCCTGTCCAGGGGAGA

31266 ACCTTGAGAAGCATGCTTCAACCAGCAAAGGAAAGACAGTCCTAGACAAGGAAACATCAT
CAAGTCTCTCTGTAGGAATACTTCATATCAGACCATATTGCCATGTGTTGAAGATTATTA
TATAATGATAATAATTAGTACAATAGTAATACCATACATTTTGATTACATTTTTGACATT
TTCAAGGCATGTTTATATTCTAATAATCTATTTTCCCTCTTGATAATTTTATTTTCTCCC
TTAAAAATCTCTCCAGTTACACAAAGTAGAGTAGGAGTGAAAGGATTGTTAATCTGTTAA
[A,T]
CTGCCTGTCCAGGGGAGAGGCAAAGTAAAGAGATGTATCTGTGATTTCATGGCCTGTTAG
GTTCGTAGTAACAATAGCTAATGTGTGTTAGGGAGCTTAAGTGGGCCAGGCTCTTTGCTA
GATATGTCAGTGCTTATTAATTTAATAAAACCTCTAGATCCAAGGCTTCCAGACTCCCAA
CTGGTCTCCTTCAGCAAGCAGCGTTTCTTTTCTTTCACCTCACTCTGAATTCTTCAGACT
CTCTAGTCATTCATTTATTTTATTCATTCAACTTTTATTTAGCTTATACATCCTACAGAG

31425 TTTGATTACATTTTTGACATTTTCAAGGCATGTTTATATTCTAATAATCTATTTTCCCTC
TTGATAATTTTATTTTCTCCCTTAAAAATCTCTCCAGTTACACAAAGTAGAGTAGGAGTG
AAAGGATTGTTAATCTGTTAATCTGCCTGTCCAGGGGAGAGGCAAAGTAAAGAGATGTAT
CTGTGATTTCATGGCCTGTTAGGTTCGTAGTAACAATAGCTAATGTGTGTTAGGGAGCTT
AAGTGGGCCAGGCTCTTTGCTAGATATGTCAGTGCTTATTAATTTAATAAAACCTCTAGA
[T,C]
CCAAGGCTTCCAGACTCCCAACTGGTCTCCTTCAGCAAGCAGCGTTTCTTTTCTTTCACC
TCACTCTGAATTCTTCAGACTCTCTAGTCATTCATTTATTTTATTCATTCAACTTTTATT
TAGCTTATACATCCTACAGAGAAGGTGAAGGGCACAGAGGTGAATGTGCTGGCCCACAAA
TTGCTAGCTCTCTCAGGGGAATCCAGAACAATGCAGTGCCACCCCACAGTGGAGCCTTGAA
GGACAAAGGCAAATTATTTACCAAATCAAAAGTTGCCAGATTCAAGATTCTCTGCAGTTC

32198 GAAGGAATAAAAGACAGAAGACTTCCTAGATCTAGTGCTAGAGGCTCCATAGTTCTGTTC
CTTACAAATGCTGTAACTTTGGGCCAGCCTCCCAACCTATTCAACCTTCTGCTTCCTTCT
CCATGAAATAAGAACCTGGATTTCTTACTCACCTGATTCACAGGGAACCTCTGAAAATCA
AACGTAAGAATTAGTAATAGTAATAATAACAATATAAATAGCTAACATCTATTGAGCAAT
TATATTTCTTACTTTCACTGGCTTATTTCATTTAATCATGAAAGCATTTCCATGAAGCAG
[A,G]
TAATGTTTTAGGCCCCAGTTTATAGATTATAAAAACAGAGGTTTAGTAAATTACTAAGTT
CACCCACCCTTAACAAGCAGTGGAACAAGGATTTGAATTCAGATCTGTCTGATCTTTGAA
CCTATTACTATTAAATCACTACCCCAGAATTCAAAAACAAATGAGGAAAACTCTGCGAGT
CATGCTGATGAAATGAGCGGAATCAAAAGAGGGAACAAAAGTGAGGGCCTGGGGTCAGAG
GCTGTTAGCTTGGCATGAAGGATGGAAAGCATTTCCAGATACCATGTCCTGAGTGAGCAC

33129 CTCAGTCTTGCTGCCTTCCCTTGAGTCTGGACAGAACCATCCTCGGTGGTGAGCTTCCCA
GAGCCTTTTGGGAGTGGCTCAGGGGACCAATTTGCTTCCTTGAAGAATTTTGAATAGCTT
CAGATGTAGCTCTGGTGGTTGAAGCTAAGGACAATAATGAAAATAATATGATAGCTGACA
TTCATTGAACTCTAATCAGGGGCTTGTTTTAAGGCATATTTTAGGCTCTATGCACTGTTG
TGTGTCTTGCTGCTCTCATTACACCAAAGATATTATAGCACACCCACATCTCACATTGAA
[T,C]
CTGATTTATGTGTGAGTTGAGTGGCATTGCTGCACACTAGTTGGTGCAATGACATGTTTT
ATAGATATTTAAATATTTATTAATTTGATTTTACAGTTTGCTTTTAATATTTCAGAGTCA
ATATATTTATTTTTCTGGTCAGACATACTTTTTAGGCCCACCCCTTCAAAAGACTGTAGGA
CCCAGACACTGAGTTTTCTCATGCCACCTGGAGAAAGTGATCCTGTAATTATTGTGTTGG
GAGCTGAGTGCTCCCACACATTGCCTGTGGATAAGTGTAAGACTCTGGAATTAAACTGCC

33292 TAATATGATAGCTGACATTCATTGAACTCTAATCAGGGGCTTGTTTTAAGGCATATTTTA
GGCTCTATGCACTGTTGTGTGTCTTGCTGCTCTCATTACACCAAAGATATTATAGCACAC
CCACATCTCACATTGAATCTGATTTATGTGTGAGTTGAGTGGCATTGCTGCACACTAGTT
GGTGCAATGACATGTTTTATAGATATTTAAATATTTATTAATTTGATTTTACAGTTTGCT
TTTAATATTTCAGAGTCAATATATTTATTTTTCTGGTCAGACATACTTTTTAGGCCCACC
[G,C]
TTCAAAAGACTGTAGGACCCAGACACTGAGTTTTCTCATGCCACCTGGAGAAAGTGATCC
TGTAATTATTGTGTTGGGAGCTGAGTGCTCCCACACATTGCCTGTGGATAAGTGTAAGAC
TCTGGAATTAAACTGCCTTAGGTTTGAATCCTGAACCCACTACTTTCTAGCTGTGTAATC
TTTGGCAAGTGCCATATCCTATTTGTGCCTCAGTTTTCTCATTTGCAAGATGGTTATTGT
AAGGACTGAATCAGAGAACACATAAACAGTTTAAAATACTACCTGTAACCTGTATCATGG

34124 ATGAGTTTATTTCTTGGTCATGCTGCAAGTCCAACACAAAATGGTGGGGGAGTGGGGAGA
GGCATTGCTCCTCATGCTTCCTTAGGGACCCAAGCTGAAAGAGGGACCATCCTAACATGA
TCACAGTGTCAAAGGAACTTATGTAATAAGCCACACCCTGGCTCTAAAGCCTTATTCCCA
AGGTCACGGACATCATTTCCACACACAGTTCATTGGATCAAGCAAGTTGATGGCCAGGCT
TAACTTTAAAGGAGGTAGAAAAGTGAAATCTTACCATGTAACTGCAAAATTGGGAATAGC

FIGURE 3, page 74 of 122

```
         [C,T]
         AAATGTTATCTCAGAGGAAGGTTTTGAGGATCAAATTAATTAATCTATGAAATTATCAAA
         AATAGGGCCTAGAACATAGAAAAATCTTCTTTAATGTTAGGTATGAATTCTTATTAATTA
         ATGAATTGCCTCTTGTAGCAGCTCTCCTGTATAAATATCTTCCACCTGATTCTCTTGTTC
         CTGATATCTCTCTCTCTCTCTCTCTCTCTCTCTCAATGATCCATCTTGCAGACCTG
         ATCCATTTTATTATTAGACCTCTCTCTTATCATGTCATCTCTCTTGTTCTCCCTTGTCTG

34668    CATTTTATTATTAGACCTCTCTCTTATCATGTCATCTCTCTTGTTCTCCCTTGTCTGATT
         GGGTAAGTTCAGAGTCCTAAGCAAGATATCTGAGGGCAATCCGTAATTCACTTCTAACCT
         ACTCTGGAATTTTTTCTCCCACTTTTCTCTAAGGCTGTGTTCTAACTGGAAGGACTCATT
         CACTGTTCCCAAATTAGACTGGCACATTCCTACCCCATCCCTTGATATTCTTCATTCTTA
         TTGTATAATCTCCCTTCTCAAATGCCTCTTGCCTTTCTGCAATTTTATATCCCTCATTAT
         [A,G]
         CAGTTTACCACTTCCTCCAAGAAGCCTCATTTTTCACCACAGCCTGAAATGATTTCATTC
         AGGGCTGAACTTCCACAGTACTACTCATTTGGCTGAACTTTACTACTCATTTGACCCTGA
         ACTCAGACTGCTTTGAACATTTTTTTTTTTATTTATGCTTATGTTGTTACTGTTGTGGAA
         AGAACACAGAGCACAGCATCAGACTCATATTGATCTAAATTTCAGGTCTGTCATTGACTG
         GCCTTGACACCCTGTGCAGGTCAGCCATGTTCTCGAGCTCCTTGCCCCTTTCCTGTGACA

34807    CACTTTTCTCTAAGGCTGTGTTCTAACTGGAAGGACTCATTCACTGTTCCCAAATTAGAC
         TGGCACATTCCTACCCCATCCCTTGATATTCTTCATTCTTATTGTATAATCTCCCTTCTC
         AAATGCCTCTTGCCTTTCTGCAATTTTATATCCCTCATTATGCAGTTTACCACTTCCTCC
         AAGAAGCCTCATTTTTCACCACAGCCTGAAATGATTTCATTCAGGGCTGAACTTCCACAG
         TACTACTCATTTGGCTGAACTTTACTACTCATTTGACCCTGAACTCAGACTGCTTTGAAC
         [A,T]
         TTTTTTTTTTTATTTATGCTTATGTTGTTACTGTTGTGGAAAGAACACAGAGCACAGCAT
         CAGACTCATATTGATCTAAATTTCAGGTCTGTCATTGACTGGCCTTGACACCCTGTGCAG
         GTCAGCCATGTTCTCGAGCTCCTTGCCCCTTTCCTGTGACATGAAAGTGATTATACCTAT
         TTCATAAGAATGCTGCGAGGATAGAATTGAAAACAAGTTATAGTGACCTACATATAGGAG
         ATGACTGTCCTCATCATAGCTGTGTCCCTAGTATCAAGAACAGTACCTGGCAAATAATAG

36025    GAAGAGCTCCTCTTGACTGGATACAAATCTTTTCCTGGTAGGGCTTTGTAAGACAACTCA
         TCTATAAGGATGAATAAACTTTCTATCCTTCTGGACTAGCTTTCCTGCATAGCTAACTCA
         TTTAATTCCAGGCTAGATCACTTCTAAAAAATCAATGCATTAGAATTGAATTAATTTGTG
         TTCACTTAATTGATATAGTGTGTGCTTTTCTAAATGGCACTAGGTTTGAAAGTGAAGCTG
         GTCACACTTTTTTACAGTAGGCTTCTCTAATAACACTTGATTCTGTCTTTGTACCCAGTG
         [C,T]
         CTTCTGTATAGTATTAGCTCAGGGATTTGTACGTTGTTGGCCAACAAACTTTGTTGATGC
         ATTGAAAAATACAGTTTCCTAATTGCAACTCCAGTGAACCTGTAATATAGTAAGATCCTA
         CAGGTCTCTGTAGGAAATATTGCTACTGAAAGTCAAAGATCACTCATTAAGTCCATCTCA
         TAGTTGATTGTAGTCCAGTGGAAATATTTGCTATATTTGGCAGAACTGTCTTTGTATAAA
         TAGTGAACAGATACATTCCATCTTAGCACTGCCAGCTTAGGATCTCTTAAGGATTCGACT

36058    CCTGGTAGGGCTTTGTAAGACAACTCATCTATAAGGATGAATAAACTTTCTATCCTTCTG
         GACTAGCTTTCCTGCATAGCTAACTCATTTAATTCCAGGCTAGATCACTTCTAAAAAATC
         AATGCATTAGAATTGAATTAATTTGTGTTCACTTAATTGATATAGTGTGTGCTTTTCTAA
         ATGGCACTAGGTTTGAAAGTGAAGCTGGTCACACTTTTTTACAGTAGGCTTCTCTAATAA
         CACTTGATTCTGTCTTTGTACCCAGTGTCTTCTGTATAGTATTAGCTCAGGGATTTGTAC
         [C,G]
         TTGTTGGCCAACAAACTTTGTTGATGCATTGAAAAATACAGTTTCCTAATTGCAACTCCA
         GTGAACCTGTAATATAGTAAGATCCTACAGGTCTCTGTAGGAAATATTGCTACTGAAAGT
         CAAAGATCACTCATTAAGTCCATCTCATAGTTGATTGTAGTCCAGTGGAAATATTTGCTA
         TATTTGGCAGAACTGTCTTTGTATAAATAGTGAACAGATACATTCCATCTTAGCACTGCC
         AGCTTAGGATCTCTTAAGGATTCGACTATTTACTTAACTGAGGTACAGCCCATGGGACAC

36061    GGTAGGGCTTTGTAAGACAACTCATCTATAAGGATGAATAAACTTTCTATCCTTCTGGAC
         TAGCTTTCCTGCATAGCTAACTCATTTAATTCCAGGCTAGATCACTTCTAAAAAATCAAT
         GCATTAGAATTGAATTAATTTGTGTTCACTTAATTGATATAGTGTGTGCTTTTCTAAATG
         GCACTAGGTTTGAAAGTGAAGCTGGTCACACTTTTTTACAGTAGGCTTCTCTAATAACAC
         TTGATTCTGTCTTTGTACCCAGTGTCTTCTGTATAGTATTAGCTCAGGGATTTGTACGTT
         [G,C]
         TTGGCCAACAAACTTTGTTGATGCATTGAAAAATACAGTTTCCTAATTGCAACTCCAGTG
         AACCTGTAATATAGTAAGATCCTACAGGTCTCTGTAGGAAATATTGCTACTGAAAGTCAA
         AGATCACTCATTAAGTCCATCTCATAGTTGATTGTAGTCCAGTGGAAATATTTGCTATAT
         TTGGCAGAACTGTCTTTGTATAAATAGTGAACAGATACATTCCATCTTAGCACTGCCAGC
         TTAGGATCTCTTAAGGATTCGACTATTTACTTAACTGAGGTACAGCCCATGGGACACACA

36418    AGTGAACCTGTAATATAGTAAGATCCTACAGGTCTCTGTAGGAAATATTGCTACTGAAAG
         TCAAAGATCACTCATTAAGTCCATCTCATAGTTGATTGTAGTCCAGTGGAAATATTTGCT
         ATATTTGGCAGAACTGTCTTTGTATAAATAGTGAACAGATACATTCCATCTTAGCACTGC
         CAGCTTAGGATCTCTTAAGGATTCGACTATTTACTTAACTGAGGTACAGCCCATGGGACA
```

FIGURE 3, page 75 of 122

```
              CACATCACCTATTGAATTCCAGGTCTTAGCAGTTTATTAGAAGTGTAAACAATGCTTCCA
              [C,T]
              TCAAAAAGTCAACTCATCCAATTGTTAAGACGATTTATCTTTTTTCTTTCATTTCAGCC
              TAGTGCAGTGATTCTCAGCTGGGAGTGATTTTGCCCCTTTCCCTTCCTGGGGGACATGTG
              GCAATGTCTGGAGACACTTTTAAGTGTCACAACTCAGGACTGGAGAACTACTATTGACAT
              TTAGGTAAAAGCAATGGATGTGCTAACCATCCTGTAATGCACAGAACAAACCCCTACAAC
              AAATAATTATCTGGGCTAAAATGTCAATAATGCTGAGGTTAAGAAACCTCATTCTATTTT

    36743     GTTAAGACGATTTATCTTTTTTCTTTCATTTCAGCCTAGTGCAGTGATTCTCAGCTGGGA
              GTGATTTTGCCCCTTTCCCTTCCTGGGGGACATGTGGCAATGTCTGGAGACACTTTTAAG
              TGTCACAACTCAGGACTGGAGAACTACTATTGACATTTAGGTAAAAGCAATGGATGTGCT
              AACCATCCTGTAATGCACAGAACAAACCCCTACAACAAATAATTATCTGGGCTAAAATGT
              CAATAATGCTGAGGTTAAGAAACCTCATTCTATTTTTTGTACTCATTAACTATCCCCCTC
              [A,G]
              AAACATCTCATGTACCCCATAAATATATATACCTACTATGTACCACAAAATTAAAAATAA
              AAAAGAGTATAAAATTAAAAAAAAAAACCACCTAGTCTAGTTCTTTTTTTGGCCAAGTGC
              TGGGCACTGGTTCCCTCTGCTATTTCATTGTGTGGAACCTGGATGGGCTACTCAGAGTGT
              TCCTTGTTCAGAATCAACTTCAGCTGGCTTACTCTTAGTGGGAAGGCAAAACTTGGGAGA
              TAAGGGTCATCTCAATTTCTCCTTTCTTTAAGCACTAGTGGTTAGCCCTGTAGCTGGAAT

    36958     CAAATAATTATCTGGGCTAAAATGTCAATAATGCTGAGGTTAAGAAACCTCATTCTATTT
              TTTGTACTCATTAACTATCCCCCTCAAAACATCTCATGTACCCCATAAATATATATACCT
              ACTATGTACCACAAAATTAAAAATAAAAAGAGTATAAAATTAAAAAAAAAAACCACCTA
              GTCTAGTTCTTTTTTTGGCCAAGTGCTGGGCACTGGTTCCCTCTGCTATTTCATTGTGTG
              GAACCTGGATGGGCTACTCAGAGTGTTCCTTGTTCAGAATCAACTTCAGCTGGCTTACTC
              [T,C]
              TAGTGGGAAGGCAAAACTTGGGAGATAAGGGTCATCTCAATTTCTCCTTTCTTTAAGCAC
              TAGTGGTTAGCCCTGTAGCTGGAATACAAACCACAACCCTCTCTCCTGATTCACTATAAG
              AACCTGGCTTGGACTTCTCAAGATAGTTTTCCCTCCTCATTTCCCTGGCTTGGTTGGAAC
              ACACTCCACTCAGTAAGTTGGAGAGTCTCTGTGGGTATACAACTGGCACTTTGATTGCCG
              CAACTTTGTTATCTGTGATCATGGTATATAATAATCAGGATGAAAGTCAAGTTTCCTATT

    37577     ACTCAACACTGTAAAAGAAAACTACTCCTGTGGAAATTAAACAGAGTCATTTTCTTGTGG
              TGAAAAGGTCCTGGGTTTGCCTCAGTGGGTCTAGATTTCAGCCTTGGCTACTAAACTTGC
              TCATGGGCCTCTGTTTCTTTATCTGTATGATGGGAATAATAATTTCTGCCCTGATTACAT
              TAATGATGGAGAGGATCTATAAGATGGCTCCTAAGTTCTGTAAAATGTACCGCAGTTGCT
              CCCCAAAAGTGAAACTTGGGATTGGGAAAACTTCTACACAATCCCAGTCTATGAATTAAC
              [G,A]
              CTTAGGAATCACTGCATTATTATTTGAAGAAGTATATTTATAACTGCAGCATATCAGCAA
              AATGAGGCCAATATAGTAAAGCAAAATGTATATTTTAAAGGACTCATATTCTAAGCTTAT
              ACTCTTTTTTTGTTCAAATACCTTTTCTATTATGCAATGTTATGTGATAGATTGCAGAA
              TGTTTGGTTGTGTTTTAAAACAACTTACATGAAAATATCAAACATTAACAACCTGTATCA
              GTCCCAGAAATGTCTTTAAATATTTTTCTGATCTTTGAAACTGAATCCAAAGGAACTCTG

    38464     CTAAATTTTAAGAGCCTCAGTTTCTTCATCTGCAAAAATGGAAATAGTAATACTACCCCA
              CAGGGTTGTTTGTGTGACTAAGTGAGCCAATATAGGGAAGAGGCTAGATAGAGAGACTAG
              CACTTGGTGGGTGCTCAGGGTTGTTTGTTTCATTCATTTAAATTATTTCCAGTATCCCCT
              AGTGTGTAAATAGTGAATCTGTGACATGGAGGCTCTTCCAAATTTAATCCAGTGCCATAT
              GCCTTCGTGATGCTGATCATAATCTTGAGAACACAATCCTGAACTCCGCAATCTTGAATA
              [C,T]
              TGAAATCGCAAAAATTCAAAATCCCTAAAGTCTAAAATTTCCAATAGCTAAATTCCTGAA
              AAACACAATTTTGAAAGATTAAAATTGCAAATCTTGAAATCTTGCAAATCAAATCCTGGG
              GAAGGGATTAGTGTATTTTTGGTTGTACACAGGATAGGTGCATCGTGTTAGTTACATCAT
              ATTAGGCAGAACTCTTATCCTGTTATTGTCTTCATTTGGAAATTAATTATGGTTTAAGGA
              GATGCATATTGGAGCTGACAAGGGGCAGACATGTGGGCTTAATTTTAGGTGTACACTTGA

    38472     TAAGAGCCTCAGTTTCTTCATCTGCAAAAATGGAAATAGTAATACTACCCCACAGGGTTG
              TTTGTGTGACTAAGTGAGCCAATATAGGGAAGAGGCTAGATAGAGAGACTAGCACTTGGT
              GGGTGCTCAGGGTTGTTTGTTTCATTCATTTAAATTATTTCCAGTATCCCCTAGTGTGTA
              AATAGTGAATCTGTGACATGGAGGCTCTTCCAAATTTAATCCAGTGCCATATGCCTTCGT
              GATGCTGATCATAATCTTGAGAACACAATCCTGAACTCCGCAATCTTGAATACTGAAATC
              [C,G]
              CAAAAATTCAAAATCCCTAAAGTCTAAAATTTCCAATAGCTAAATTCCTGAAAAACACAA
              TTTTGAAAGATTAAAATTGCAAATCTTGAAATCTTGCAAATCAAATCCTGGGGAAGGGAT
              TAGTGTATTTTTGGTTGTACACAGGATAGGTGCATCGTGTTAGTTACATCATATTAGGCA
              GAACTCTTATCCTGTTATTGTCTTCATTTGGAAATTAATTATGGTTTAAGGAGATGCATA
              TTGGAGCTGACAAGGGGCAGACATGTGGGCTTAATTTTAGGTGTACACTTGACTGGATTA

    38509     AGTAATACTACCCCACAGGGTTGTTTGTGTGACTAAGTGAGCCAATATAGGGAAGAGGCT
              AGATAGAGAGACTAGCACTTGGTGGGTGCTCAGGGTTGTTTGTTTCATTCATTTAAATTA
              TTTCCAGTATCCCCTAGTGTGTAAATAGTGAATCTGTGACATGGAGGCTCTTCCAAATTT
```

FIGURE 3, page 76 of 122

AATCCAGTGCCATATGCCTTCGTGATGCTGATCATAATCTTGAGAACACAATCCTGAACT
CCGCAATCTTGAATACTGAAATCGCAAAAATTCAAAATCCCTAAAGTCTAAAATTTCCAA
[T,G]
AGCTAAATTCCTGAAAAACACAATTTTGAAAGATTAAAATTGCAAATCTTGAAATCTTGC
AAATCAAATCCTGGGGAAGGGATTAGTGTATTTTTGGTTGTACACAGGATAGGTGCATCG
TGTTAGTTACATCATATTAGGCAGAACTCTTATCCTGTTATTGTCTTCATTTGGAAATTA
ATTATGGTTTAAGGAGATGCATATTGGAGCTGACAAGGGGCAGACATGTGGGCTTAATTT
TAGGTGTACACTTGACTGGATTAAGGAATATCTAAAACCTGGTAAAACATTACTTTTGGT

38573 AGAGAGACTAGCACTTGGTGGGTGCTCAGGGTTGTTTGTTTCATTCATTTAAATTATTTC
CAGTATCCCCTAGTGTGTAAATAGTGAATCTGTGACATGGAGGCTCTTCCAAATTTAATC
CAGTGCCATATGCCTTCGTGATGCTGATCATAATCTTGAGAACACAATCCTGAACTCCGC
AATCTTGAATACTGAAATCGCAAAAATTCAAAATCCCTAAAGTCTAAAATTTCCAATAGC
TAAATTCCTGAAAAACACAATTTTGAAAGATTAAAATTGCAAATCTTGAAATCTTGCAAA
[T,C]
CAAATCCTGGGGAAGGGATTAGTGTATTTTTGGTTGTACACAGGATAGGTGCATCGTGTT
AGTTACATCATATTAGGCAGAACTCTTATCCTGTTATTGTCTTCATTTGGAAATTAATTA
TGGTTTAAGGAGATGCATATTGGAGCTGACAAGGGGCAGACATGTGGGCTTAATTTTAGG
TGTACACTTGACTGGATTAAGGAATATCTAAAACCTGGTAAAACATTACTTTTGGTGTGT
CTGTGAGTGTGTTTCCAGAGGAGTGTGTGACCTAAGTGGATTAGGCGGGGAAGATCTGCC

38624 AATTATTTCCAGTATCCCCTAGTGTGTAAATAGTGAATCTGTGACATGGAGGCTCTTCCA
AATTTAATCCAGTGCCATATGCCTTCGTGATGCTGATCATAATCTTGAGAACACAATCCT
GAACTCCGCAATCTTGAATACTGAAATCGCAAAAATTCAAAATCCCTAAAGTCTAAAATT
TCCAATAGCTAAATTCCTGAAAAACACAATTTTGAAAGATTAAAATTGCAAATCTTGAAA
TCTTGCAAATCAAATCCTGGGGAAGGGATTAGTGTATTTTTGGTTGTACACAGGATAGGT
[G,A]
CATCGTGTTAGTTACATCATATTAGGCAGAACTCTTATCCTGTTATTGTCTTCATTTGGA
AATTAATTATGGTTTAAGGAGATGCATATTGGAGCTGACAAGGGGCAGACATGTGGGCTT
AATTTTAGGTGTACACTTGACTGGATTAAGGAATATCTAAAACCTGGTAAAACATTACTT
TTGGTGTGTCTGTGAGTGTGTTTCCAGAGGAGTGTGTGACCTAAGTGGATTAGGCGGGGA
AGATCTGCCCTCAGTGGTGGCAGGCACCCTTCAATCAGCAGAGGCCACAGGAAGAACAAA

38802 TTTCCAATAGCTAAATTCCTGAAAAACACAATTTTGAAAGATTAAAATTGCAAATCTTGA
AATCTTGCAAATCAAATCCTGGGGAAGGGATTAGTGTATTTTTGGTTGTACACAGGATAG
GTGCATCGTGTTAGTTACATCATATTAGGCAGAACTCTTATCCTGTTATTGTCTTCATTT
GGAAATTAATTATGGTTTAAGGAGATGCATATTGGAGCTGACAAGGGGCAGACATGTGGG
CTTAATTTTAGGTGTACACTTGACTGGATTAAGGAATATCTAAAACCTGGTAAAACATTA
[C,T]
TTTTGGTGTGTCTGTGAGTGTGTTTCCAGAGGAGTGTGTGACCTAAGTGGATTAGGCGGG
GAAGATCTGCCCTCAGTGGTGGCAGGCACCCTTCAATCAGCAGAGGGCACAGGAAGAACA
AATACAGAAGTCAAATTGGTCTCTCTGGCAGCTGGCTGGCTTTTCTTCTACTGCACTGGA
CATCAGAAATATTCCAAAAAGTGTAGTTTCACAATGTTCACTTTCTCCATAAGCATCATG
TGTGTACATGAAAACATGGAAACTTCCTTAATAAATGTAGAGATGTCTTTTTGTATATCT

38842 ATTAAAATTGCAAATCTTGAAATCTTGCAAATCAAATCCTGGGGAAGGGATTAGTGTATT
TTTGGTTGTACACAGGATAGGTGCATCGTGTTAGTTACATCATATTAGGCAGAACTCTTA
TCCTGTTATTGTCTTCATTTGGAAATTAATTATGGTTTAAGGAGATGCATATTGGAGCTG
ACAAGGGGCAGACATGTGGGCTTAATTTTAGGTGTACACTTGACTGGATTAAGGAATATC
TAAAACCTGGTAAAACATTACTTTTGGTGTGTCTGTGAGTGTGTTTCCAGAGGAGTGTGT
[G,A]
ACCTAAGTGGATTAGGCGGGGAAGATCTGCCCTCAGTGGTGGCAGGCACCCTTCAATCAG
CAGAGGGCACAGGAAGAACAAATACAGAAGTCAAATTGGTCTCTCTGGCAGCTGGCTGGC
TTTTCTTCTACTGCACTGGACATCAGAAATATTCCAAAAAGTGTAGTTTCACAATGTTCA
CTTTCTCCATAAGCATCATGTGTGTACATGAAAACATGGAAACTTCCTTAATAAATGTAG
AGATGTCTTTTTGTATATCTTCGTTGGTGAAATGGAACATTTCTTGAGATCTCAGTTCTG

39029 GCAGACATGTGGGCTTAATTTTAGGTGTACACTTGACTGGATTAAGGAATATCTAAAACC
TGGTAAAACATTACTTTTGGTGTGTCTGTGAGTGTGTTTCCAGAGGAGTGTGTGACCTAA
GTGGATTAGGCGGGGAAGATCTGCCCTCAGTGGTGGCAGGCACCCTTCAATCAGCAGAGG
GCACAGGAAGAACAAATACAGAAGTCAAATTGGTCTCTCTGGCAGCTGGCTGGCTTTTCT
TCTACTGCACTGGACATCAGAAATATTCCAAAAAGTGTAGTTTCACAATGTTCACTTTCT
[C,G]
CATAAGCATCATGTGTGTACATGAAAACATGGAAACTTCCTTAATAAATGTAGAGATGTC
TTTTTGTATATCTTCGTTGGTGAAATGGAACATTTCTTGAGATCTCAGTTCTGTGAGCAA
TTGCAAGTGTGGTGATGACCCATTGCAGTTCTTGATCAATTTCGTCAAAAGATTTAGGTT
GTCCATCATGTATTTCAGATGATTGCAGTAGTAAAGCTTAGTGCACACAATTACCAACCA
TAGTTATATACATTTGTAAATTTTACTTTTTGACTTATTACTTTATGAGTACAGTTCATT

39040 GGCTTAATTTTAGGTGTACACTTGACTGGATTAAGGAATATCTAAAACCTGGTAAAACAT
TACTTTTGGTGTGTCTGTGAGTGTGTTTCCAGAGGAGTGTGTGACCTAAGTGGATTAGGC

FIGURE 3, page 77 of 122

GGGGAAGATCTGCCCTCAGTGGTGGCAGGCACCCTTCAATCAGCAGAGGGCACAGGAAGA
ACAAATACAGAAGTCAAATTGGTCTCTCTGGCAGCTGGCTGGCTTTTCTTCTACTGCACT
GGACATCAGAAATATTCCAAAAAGTGTAGTTTCACAATGTTCACTTTCTCCATAAGCATC
[A,G]
TGTGTGTACATGAAAACATGGAAACTTCCTTAATAAATGTAGAGATGTCTTTTTGTATAT
CTTCGTTGGTGAAATGGAACATTTCTTGAGATCTCAGTTCTGTGAGCAATTGCAAGTGTG
GTGATGACCCATTGCAGTTCTTGATCAATTTCGTCAAAAGATTTAGGTTGTCCATCATGT
ATTTCAGATGATTGCAGTAGTAAAGCTTAGTGCACACAATTACCAACCATAGTTATATAC
ATTTGTAAATTTTACTTTTTGACTTATTACTTTATGAGTACAGTTCATTTGCACATCTTT

39179 TGGTGGCAGGCACCCTTCAATCAGCAGAGGGCACAGGAAGAACAAATACAGAAGTCAAAT
TGGTCTCTCTGGCAGCTGGCTGGCTTTTCTTCTACTGCACTGGACATCAGAAATATTCCA
AAAAGTGTAGTTTCACAATGTTCACTTTCTCCATAAGCATCATGTGTGTACATGAAAACA
TGGAAACTTCCTTAATAAATGTAGAGATGTCTTTTTGTATATCTTCGTTGGTGAAATGGA
ACATTTCTTGAGATCTCAGTTCTGTGAGCAATTGCAAGTGTGGTGATGACCCATTGCAGT
[T,C]
CTTGATCAATTTCGTCAAAAGATTTAGGTTGTCCATCATGTATTTCAGATGATTGCAGTA
GTAAAGCTTAGTGCACACAATTACCAACCATAGTTATATACATTTGTAAATTTTACTTTT
TGACTTATTACTTTATGAGTACAGTTCATTTGCACATCTTTGTTGTAACCATGAAACTGC
CATTAGTACACCTGAGTGTTTATGCTTGCGAAAATGTGTATGTTATTATTGAATATTTTA
TTGTATAGAGTGGACTATGTGTGTTCTTTGCATTTTTATTTTTCTCAAAACATATAGACA

39424 TCTTGAGATCTCAGTTCTGTGAGCAATTGCAAGTGTGGTGATGACCCATTGCAGTTCTTG
ATCAATTTCGTCAAAAGATTTAGGTTGTCCATCATGTATTTCAGATGATTGCAGTAGTAA
AGCTTAGTGCACACAATTACCAACCATAGTTATATACATTTGTAAATTTTACTTTTTGAC
TTATTACTTTATGAGTACAGTTCATTTGCACATCTTTGTTGTAACCATGAAACTGCCATT
AGTACACCTGAGTGTTTATGCTTGCGAAAATGTGTATGTTATTATTGAATATTTTATTGT
[A,G]
TAGAGTGGACTATGTGTGTTCTTTGCATTTTTATTTTTCTCAAAACATATAGACATTATT
TTATGTTTCTCAAATAAAAGAAACATTGCCCTTTTAAAATGTGAATAAATGTCTTTTAAA
TTTTCTTTTTATTATTTTTTCCAGAATATGTTTTTGGGTTTTTGATCTTTTGAGATTTCA
ACATTTGGGATTATGGTGTTTGGGATTGTGTCTTTCAGGATTATAGCCAAACCCATTTCT
TCTCTGCCTCTGAACATCTGCAAACCCACTATTCTAGTCCTCACTTTTAAGGGTACAGGC

39459 TGGTGATGACCCATTGCAGTTCTTGATCAATTTCGTCAAAAGATTTAGGTTGTCCATCAT
GTATTTCAGATGATTGCAGTAGTAAAGCTTAGTGCACACAATTACCAACCATAGTTATAT
ACATTTGTAAATTTTACTTTTTGACTTATTACTTTATGAGTACAGTTCATTTGCACATCT
TTGTTGTAACCATGAAACTGCCATTAGTACACCTGAGTGTTTATGCTTGCGAAAATGTGT
ATGTTATTATTGAATATTTTATTGTATAGAGTGGACTATGTGTGTTCTTTGCATTTTTAT
[T,G]
TTTCTCAAAACATATAGACATTATTTTATGTTTCTCAAATAAAAGAAACATTGCCCTTTT
AAAATGTGAATAAATGTCTTTTAAATTTTCTTTTTATTATTTTTTCCAGAATATGTTTTT
GGGTTTTTGATCTTTTGAGATTTCAACATTTGGGATTATGGTGTTTGGGATTGTGTCTTT
CAGGATTATAGCCAAACCCATTTCTTCTCTGCCTCTGAACATCTGCAAACCCACTATTCT
AGTCCTCACTTTTAAGGGTACAGGCTCAGAGGACTAAACTGAGGTTCTCAAGCTTTTATG

39594 ACTTTTTGACTTATTACTTTATGAGTACAGTTCATTTGCACATCTTTGTTGTAACCATGA
AACTGCCATTAGTACACCTGAGTGTTTATGCTTGCGAAAATGTGTATGTTATTATTGAAT
ATTTTATTGTATAGAGTGGACTATGTGTGTTCTTTGCATTTTTATTTTTCTCAAAACATA
TAGACATTATTTTATGTTTCTCAAATAAAAGAAACATTGCCCTTTTAAAATGTGAATAAA
TGTCTTTTAAATTTTCTTTTTATTATTTTTTCCAGAATATGTTTTTGGGTTTTTGATCTT
[C,T]
TGAGATTTCAACATTTGGGATTATGGTGTTTGGGATTGTGTCTTTCAGGATTATAGCCAA
ACCCATTTCTTCTCTGCCTCTGAACATCTGCAAACCCACTATTCTAGTCCTCACTTTTAA
GGGTACAGGCTCAGAGGACTAAACTGAGGTTCTCAAGCTTTTATGTGCATCAGACTCACC
TGGAAAACTTGTTAAAACACAGCTTGCAAGGCCAACCCCAGAATTTCTGATTTGGGAGGT
CTGGTGTGAGGACAAGAATTTACATTTCTACCAAGTTCCAGGTGATGCTGATGCTGCTGG

40279 TGTTGGCAGTTTTCCCACAATTTTCCAAAACTGGTCTTCATCCAGTGTCTCCTCTCATAG
TAGACATCACATTCATCCAGAAAATAAGGCATTCTCCTATATGCCTTCTTCTCTCTTCCT
CCACGTTCCTTCTGTCTTCAGGCATTGTCTCACTGGTCCCTGGCCCAGTCTGTCAATCAG
CTGACATCACTGCCCCCACTTGCTTTGAATCATGCCTCCTCCCTTAATGTCTATGTGTCC
TTGCATAGGTTGGTTACCAGAGTAGATATACAAAGAATGAATGAGTCTCCCCATCTTTCC
[A,G]
ACCTCAAGAACTTGATTAGTGGTATCCTGACTGGAACAATGGAATATGGCCTTTTGTCTG
CAAACAGAAACAATTATAGCAGGTTTTCTCACTAGGGTCATGTTTGCCTATTTTATGTTA
ATAAGAGCTGTTGTATTGACTTAGCTGTCTTTATTCTAGTCACTTCTGCTTCACAATAAG
AGGCTATCTGTGCTTGCGTTCCAGGGGGTGAGTTACTGTCTTATATTGTCTGACAGGGCT
GTCCCTTGAGGAATATCTTTCCCCAATGCCAGTTCTTGTAGAGGGGCCAGGAGGTCAGAA

40666 TCTCACTAGGGTCATGTTTGCCTATTTTATGTTAATAAGAGCTGTTGTATTGACTTAGCT

```
        GTCTTTATTCTAGTCACTTCTGCTTCACAATAAGAGGCTATCTGTGCTTGCGTTCCAGGG
        GGTGAGTTACTGTCTTATATTGTCTGACAGGGCTGTCCCTTGAGGAATATCTTTCCCCAA
        TGCCAGTTCTTGTAGAGGGGCCAGGAGGTCAGAACTTAAGCTAACAAATGATTATCTTTC
        TCAGCAGAATTACCAGAGGACCTCAGACTCCTGGGTTCCTCCTTAAGGGACTCAGGTTCA
        [G,C]
        ATCTTTGGCCCAGAACACACTGTAACCTCTGAGTTCAGGCTTTAGATGAGGCACCTGTCA
        ATTCCTATGGGACCTCAACCCAGTCTCAAATACTTGGTCAAAAGGTGAGTTGAAACTTAA
        AACAGTACCAGCCCCTGGACAGTATAAGTTGGTCTCATCACATCGAAGTATTCATGATGA
        GCATCATAAAATCTTCTGAGAGTTGGTTTTGATGAACAGATAAGGAAGAATACCAACACC
        CTAAAAGTTGAGGGCAATTCAAGTCCAGATGAGAAGAAACGTGCAGGATTGCAGACTTGG

40723   GCTGTCTTTATTCTAGTCACTTCTGCTTCACAATAAGAGGCTATCTGTGCTTGCGTTCCA
        GGGGGTGAGTTACTGTCTTATATTGTCTGACAGGGCTGTCCCTTGAGGAATATCTTTCCC
        CAATGCCAGTTCTTGTAGAGGGGCCAGGAGGTCAGAACTTAAGCTAACAAATGATTATCT
        TTCTCAGCAGAATTACCAGAGGACCTCAGACTCCTGGGTTCCTCCTTAAGGGACTCAGGT
        TCAGATCTTTGGCCCAGAACACACTGTAACCTCTGAGTTCAGGCTTTAGATGAGGCACCT
        [G,C]
        TCAATTCCTATGGGACCTCAACCCAGTCTCAAATACTTGGTCAAAAGGTGACTTGAAACT
        TAAAACAGTACCAGCCCCTGGACAGTATAAGTTGGTCTCATCACATCGAAGTATTCATGA
        TGAGCATCATAAAATCTTCTGAGAGTTGGTTTTGATGAACAGATAAGGAAGAATACCAAC
        ACCCTAAAAGTTGAGGGCAATTCAAGTCCAGATGAGAAGAAACGTGCAGGATTGCAGACT
        TGGAATCCCAAAGAGGCACTTAGTAATGGTTATAAACTCTGAGGGTTATTCGTAACTGAT

41090   AGTACCAGCCCCTGGACAGTATAAGTTGGTCTCATCACATCGAAGTATTCATGATGAGCA
        TCATAAAATCTTCTGAGAGTTGGTTTTGATGAACAGATAAGGAAGAATACCAACACCCTA
        AAAGTTGAGGGCAATTCAAGTCCAGATGAGAAGAAACGTGCAGGATTGCAGACTTGGAAT
        CCCAAAGAGGCACTTAGTAATGGTTATAAACTCTGAGGGTTATTCGTAACTGATGCCTGG
        CCTTGGGGTAAATGGATATCCTGAGGCTTTGGGCAGAACAGTTGCAAACTCCCCAACCTT
        [C,T]
        TGCTTTTCTTGGAGGTGATGTTTGTATGAAAAGAGCAGTTTTCTGGAATTCACACAATAA
        AATGAGCCCTCTCATTTCAGGCCCTCTGCTGGGTAATCTTGGGCAATATGCTTCCCCTCT
        CTGAGCCTTATTACCCTGTTCCCTCATTTTCGAAGCAGATTCTAACCTCCGATCTGCTTC
        TGTGGTGGCCTCACTGGGATATTCTGAAGCTCAAGTGCTGCTGCTGCTAATAATAATAAT
        ACCAATTACTATAGCAACAGCAACAACTCTAACTGTGAGCACTTGTGCTGTGCCCAGCTC

41260   GACTTGGAATCCCAAAGAGCCACTTAGTAATGGTTATAAACTCTGAGGGTTATTCGTAAC
        TGATGCCTGGCCTTGGGGTAAATGGATATCCTGAGGCTTTGGGCAGAACAGTTGCAAACT
        CCCCAACCTTCTGCTTTTCTTGGAGGTGATGTTTGTATGAAAAGAGCAGTTTTCTGGAAT
        TCACACAATAAAATGAGCCCTCTCATTTCAGGCCCTCTGCTGGGTAATCTTGGGCAATAT
        GCTTCCCCTCTCTGAGCCTTATTACCCTGTTCCCTCATTTTCGAAGCAGATTCTAACCTC
        [C,T]
        GATCTGCTTCTGTGGTGGCCTCACTGGGATATTCTGAAGCTCAAGTGCTGCTGCTGCTAA
        TAATAATAATACCAATTACTATAGCAACAGCAACAACTCTAACTGTGAGCACTTGTGCTG
        TGCCCAGCTCTGCGGATGGTCTCATGTGTTCCATCAGCCCGTTCTTACAGAAGTTCTGGT
        AGGTAGTTACTATCATTATACCCATCCCATAGGCAAAAAAACTCAGCCACAGAAAGGTTA
        AATAGCTTGTCTCAGGTCACATAGCTAATAGTGGTAGAGTCTGTACTGGAACCCAGCACT

41421   AAGAGCAGTTTTCTGGAATTCACACAATAAAATGAGCCCTCTCATTTCAGGCCCTCTGCT
        GGGTAATCTTGGGCAATATGCTTCCCCTCTCTGAGCCTTATTACCCTGTTCCCTCATTTT
        CGAAGCAGATTCTAACCTCCGATCTGCTTCTGTGGTGGCCTCACTGGGATATTCTGAAGC
        TCAAGTGCTGCTGCTGCTAATAATAATAATACCAATTACTATAGCAACAGCAACAACTCT
        AACTGTGAGCACTTGTCCTGTGCCCAGCTCTGCGGATGGTCTCATGTGTTCCATCAGCCC
        [A,G]
        TTCTTACAGAAGTTCTGGTAGGTAGTTACTATCATTATACCCATCCCATAGGCAAAAAAA
        CTCAGCCACAGAAAGGTTAAATAGCTTGTCTCAGGTCACATAGCTAATAGTGGTAGAGTC
        TGTACTGGAACCCAGCACTGTCCTGCATTTAACTGCTATGGTACACTGCTCTGTAGATGT
        TAAAATTACTTTTGGTGAACTTTAAGTAACTATCAATGGAAGATGATTTCTTTGCCATGC
        GACAGTTTGCTCTCCAAGCTTTAAGCGGATCACCAAGGAGTCTAACTCCTCTGGCCCTGA

42640   ACAGGGACAGAGAGGGATGGTTGAAGAAGACATACATGAGCTAAGATGAGAATGGTAAGT
        GAGAGTTGGCTGTGGGATAATAGTGGGGAAAAATATTCTAGGCAGAGGGAACTTCAAGTA
        CAAAAGTTTTTAGGTGGGTACAAGTTGAGATGGTTCAAGTAATAGAAAGGAAGCCCACAT
        GGGGGTTGGGAGGTGGTGAGCCCTAGAGGTAGAGTGCTAGGAGAGGTGGTTGTAGGGTCA
        GTCAGGGACAAATGATGCAGGGCCTTCTAGACCATGGGCCTTCCTGGGGATCTTCTCTTT
        [C,G]
        AGCCCTCTACGGGCCCAGCCAACCAAGGCAGGAACTGCCTTCTGTGTATTCATCATATCT
        CTGAAGTCCAACCCCAAACCTCTCCAAGGCCAAGTCTGTGTCTTTTTCTTTCTAAATATC
        CTCACCCAAATCTTACACAGTTCTTGACACATAGCAGATTCTCAGGATAGCCTGATGACT
        TCAAGGTATAAGTTAAGGAAGATATTGCAGACCACAGATATATTTTATTTATAACCAAGG
        AAGAGCTTATATTTAGCAAAAGTCTGCACTTCCTCAGTAGGTACTAAGCTCCCTGTTACT
```

42650 AGAGGGATGGTTGAAGAAGAGATACATGAGCTAAGATGAGAATGGTAAGTGAGAGTTGGC
TGTGGGATAATAGTGGGGAAAAATATTCTAGGCAGAGGGAACTTCAAGTACAAAAGTTTT
TAGGTGGGTACAAGTTGAGATGGTTCAAGTAATAGAAAGGAAGCCCACATGGGGGTTGGG
AGGTGGTGAGCCCTAGAGGTAGAGTGCTAGGAGAGGTGGTTCTAGGGTCAGTCAGGGACA
AATGATGCAGGGCCTTCTAGACCATGGGCCTTCCTGGGGATCTTCTCTTTCAGCCCCTCTA
[C,G]
GGGCCCAGCCAACCAAGGCAGGAACTGCCTTCTGTGTATTCATCATATCTCTGAAGTCCA
ACCCCAAACCTCTCCAAGGCCAAGTCTGTGTCTTTTTCTTTCTAAATATCCTCACCCAAA
TCTTACACAGTTCTTGACACATAGCAGATTCTCAGGATAGCCTGATGACTTCAAGGTATA
AGTTAAGGAAGATATTGCAGACCACAGATATATTTTATTTATAACCAAGGAAGAGCTTAT
ATTTAGCAAAAGTCTGCACTTCCTCAGTAGGTACTAAGCTCCCTGTTACTAGAGGTACAT

43285 ATTGAATAGAGGTAGTAGTCATGGTGTTTTGCAATAGAGATAGCAGTAGTGGTCACAATG
ATAAAAATAGTAATATTCCTATGTATTAAACAGTCAATATATGCCAGACCCTAGATGTAT
ATTATCTCATTTAAGCTTCCTAAAACAACCTCATAAGGAAATACCATTATTATTTCCACT
TCCAGTCACAGAGACTGAAACCTCTCACATTTAAGGACTGTGCACCTGGGGTCAGGTAGT
GAGTAAGTGGTAGGGTCCACTTGAAAACCCATACTTCCAGTCCATACTTGAAAACCCCTCT
[C,T]
TAGGGAAACTTAATGATTGGAGTCCATATTTTGACTTCATGTATCTTGGCTTTTTATTTC
TATCCAGAGCTTTATTGCAGGGTGTAGGGGGTGTCACTCTTTTACAGCCTTTACAGCCCT
TTTACATATATTAGGTAATAATATAGAATTGAATTCTAAAATAGCTGAAAGTATGTTTTT
TCCTCCAGCAAAATCATTCCCCAAAGATCATCCCCAAACTGATGAGTATCTTGTTCCTGT
GAGCATTACTGTACTGATCTTTCTCCCGTCATGTAGTACTTTGTTATTTGAGTCATTTCA

44406 AATTGTGTGACCTTGAGCAAGCCCCTTTACTTCATCTAGCTAATAAAAAATAAATAAATA
AATAAAACAGTCACCTCTGCATAGGTGTATGCCAAGGACTGAGTCAAGAAATTTTTAAGA
ACACTTAGCCCAGGACCTAGAAGATTCTAGTAAGGGTTTAGTAAATGTTAATTATGGTTG
TTAGTAACATCATCAAATTTTTAAAATATTATCACACTGACTTTTTGTGAATCTAGACTT
GCTAGCTCTGGTGTGCATCCAATGATACAAACCCCCATATTCAACATTCCTCTTTGAAAG
[A,G]
TTTCACAGAATGTTGTCTGAGCTGACCTTAAAGATACCTTGCAGCTCCAAAGTTCTGTGA
CTTTCACCAGGAGTCTCAAGGCAAATGCACAGAAGGGTCAGGCAAGTATCGTGAATGGAG
GCTGGACCAGGGAGCCCATGCATTCTTCCAAAGGCATTTCAATTCAGTCTTGTTAAAGCA
CTGAGTTGCACAAAAGAAACGTCACTGTTGGCCAGCCTCGGTTCTTCGGCTAGCTCCTTC
AACCCAAGTGTATCATCTAGGATGGAGGAGGCTTCTGAGGGACTGAGGGAGGACAAATCT

44585 GTTAGTAACATCATCAAATTTTTAAAATATTATCACACTGACTTTTTGTGAATCTAGACT
TGCTAGCTCTGGTGTGCATCCAATGATACAAACCCCCATATTCAACATTCCTCTTTGAAA
GGTTTCACAGAATGTTGTCTGAGCTGACCTTAAAGATACCTTGCAGCTCCAAAGTTCTGT
GACTTTCACCAGGAGTCTCAAGGCAAATGCACAGAAGGGTCAGGCAAGTATCGTGAATGG
AGGCTGGACCAGGGAGCCCATGCATTCTTCCAAAGGCATTTCAATTCAGTCTTGTTAAAG
[C,T]
ACTGAGTTGCACAAAAGAAACGTCACTCTTGGCCAGCCTCGGTTCTTCGGCTAGCTCCTT
CAACCCAAGTGTATCATCTAGGATGGAGGAGGCTTCTGAGGGACTGAGGGAGGACAAATC
TTGGAAAGAGAGGTACAAGGAAGAGATGGGATTTGGATAAGGCAAGGAAGAGCCAGCACG
CTTTGGATGAACTGACCTCTAGATACATTCATTTTTATGCCAAAAGTCCATTTCCCACTC
TTTAAACCCCTTCACCTCTTCTCAAGAAACTTGTGTCTCAGCTTCAGAGAGCCATGGCCT

44772 ACCAGGAGTCTCAAGGCAAATGCACAGAAGGGTCAGGCAAGTATCGTGAATGGAGGCTGG
ACCAGGGAGCCCATGCATTCTTCCAAAGGCATTTCAATTCAGTCTTGTTAAAGCACTGAG
TTGCACAAAAGAAACGTCACTGTTGGCCAGCCTCGGTTCTTCGGCTAGCTCCTTCAACCC
AAGTGTATCATCTAGGATGGAGGAGGCTTCTGAGGGACTGAGGGAGGACAAATCTTGGAA
AGAGAGGTACAAGGAAGAGATGGGATTTGGATAAGGCAAGGAAGAGCCAGGAGGCTTTGG
[A,G]
TGAACTGACCTCTAGATACATTCATTTTTATGCCAAAAGTCCATTTCCCACTCTTTAAAC
CCCTTCACCTCTTCTCAAGAAACTTGTGTCTCAGCTTCAGAGAGCCATGGCCTCATTTAA
AATGTTGTGAAAGAAGGTGATGGAAGCATCAGGTTCCTAGGCTGGTGAATTTTTATTTTT
ATTTCTCCATTGACACAGTTTAACCTTTGCTTTTGGCAGCTAGCATATTGCTCAAATAAA
GTGAAGAGAAGGGTGTGGGGGAGAAGGCAAGAGATATTTGGCTAGAAGGTTATGAGAATC

45507 ATAACTCACCCATGGTCACCTATGTGAAAAAAGTGCAGAGCTAAGAATGGAATTGAAATC
TGTCAAACTCCAGAGTGTAGAGACTGACCAAGTAGACCCCCCACTTCCAGGCCAATGCAT
TTCGGCACTTGATTTGTGGCAAGGAGTCCTCTCAGGGTTTTGGGGCTATGCTGGTGCTTG
CTATGCTGCCTCGGAAATGTCACCTAACCTAGAAATAGTGTTTATTCTGTTACAAAGCAA
GTTGGAAGAAAAGAAAACACTCCTTTTTTCTTTTTTCTGTGCCTCCTCTCCTTACTTTCC
[C,T]
CTGAAACTTAAGTTCCAAGGAGTGCAATTAGCAGGTCAGCTTGTCTTGCTGAACAGTCAG
GTTACTTTCCCTCAGTATTTGATGCCAAGTGAATGTTGAGCTGAAAGGCTGGCTGATAAA
TGCCCCTCTGGGGAGAAGGAACTGTGAAATAGCCTGGATCTATTGGCAGATACTAGGGCC
AAAAAGTCCTTAGAAACTCAACCTGAAAAAAATGTCTAGGGAAAGCAAAACGGCCAACTA
AGGTAGTAAACACTTCAGAAAACCTTGATAATAGCAATTTGGAAAATCTTGCATGTACAG

FIGURE 3, page 80 of 122

46883 GTAAATTTAGAATGTCAAACACGTACAGACTAATGCTATTTACCCACCATCCACCACCAT
TGTTTATCCAGTTGTTTATTCAATTGCAAATGGCTTCTTAGCCTGTTGGAGAAATGATCT
GAGGTGGTCAGAGGTATGGCCCATATCTGTCAAATAAAGCAACCTCCTGGCACATATGAT
AGGCCAAAACCCTATCACTTGGGATTTGTGAACAACATTCTCCAGTCAGCTGAACAAGCA
GGTGCTAGAAAAGAGTGTAAATAATTCAACTTGTTTCAGGACATGTGTTTAGGTGAGTAA
[C,T]
GTGAATGTGAACAGTTTTTATCTTTTATTTCTTGGTCTCAAGTTGGCACTATTAGGCATC
CATTCCTAACATAAAATAGTGTCTATGAATGGCAGCTGGTCATTAGATGTACATATCCAA
ATCCAAGATCAGTACAATTTTCACCTCCACCTTGTCTTACCTCTTGCACTCCCTAACTCA
GTGGCAGTGCCACAATCCACCTAATCACCCAGAAAGAGACCAAGAGACTTTTGATTCTTT
TTCCCTTATCCATGTCTTTGATCTGCCACCAAGTTCTGGAGCTGTTACCTCTACTGTCTC

47855 CTTTCTTCATCCCTGTCTCCTCTCAAGACTTTTAATCGTCCCTCAGGGCCAAGTTTAGAT
CTAACCCCTACCAATAAGCTTTCCTCAATCTCCCACCCCTACCTCCACAAGAATTAGCCT
TCCCCCATTATATCCCTTATCATTCTGCCGTACATTAGCAAGATTTGTATGCATGACTGT
TAGACTGACAGCTCCCTTTGGGGGAAAGGGCCTTCTTGTGCTCATCTGTCCATCTCCTTT
CTCTCTTCTTCCTCTTGCCTCCTCCCTCCTAACCTCCTCCAGCCCAGCATCTAAGTGCAG
[G,T]
ACATTTCACATAAGAGACACCCCAGCAAAGTGTGTTGAATAGAATCCATTAATTTGCATT
CCATTTCTTTGGAAATAGCTTTTGGGATCCATTGGGCAGATAGTGAAAATTTCAACTAAC
ATGATGGTGGAGAAAAACCTTAACTTTTGTGCTCATGTTAAATTTAGAAACATTTTGTTT
CATTCTATCACCTCTGCTAACCTCTTAACTAACTTGAGGTTATGGAGAAAGGGCAGAAGA
CTTATTTTTCTACTTCTTTAATATTTCCGGTCAATTCTCTCTTCTCCATCAGTATTGCCA

47885 TTTAATCGTCCCTCAGGGCCAAGTTTAGATCTAACCCCTACCAATAAGCTTTCCTCAATC
TCCCACCCCTACCTCCACAAGAATTAGCCTTCCCCCATTATATCCCTTATCATTCTGCCG
TACATTAGCAAGATTTGTATGCATGACTGTTAGACTGACAGCTCCCTTTGGGGGAAAGGG
CCTTCTTGTGCTCATCTGTCCATCTCCTTTCTCTCTTCTTCCTCTTGCCTCCTCCCTCCT
AACCTCCTCCAGCCCAGCATCTAAGTGCAGTACATTTCACATAAGAGACACCCCAGCAAA
[C,G]
TGTGTTGAATAGAATCCATTAATTTGCATTCCATTTCTTTGGAAATAGCTTTTGGGATCC
ATTGGGCAGATAGTGAAAATTTCAACTAACATGATGGTGGAGAAAAACCTTAACTTTTGT
GCTCATGTTAAATTTAGAAACATTTTGTTTCATTCTATCACCTCTGCTAACCTCTTAACT
AACTTGAGGTTATGGAGAAAGGGCAGAAGACTTATTTTTCTACTTCTTTAATATTTCCGG
TCAATTCTCTCTTCTCCATCAGTATTGCCAGTGCCTTCGTTGAGACAGGTCATCTTTGTG

47941 AATCTCCCACCCCTACCTCCACAAGAATTAGCCTTCCCCCATTATATCCCTTATCATTCT
GCCGTACATTAGCAAGATTTGTATGCATGACTGTTAGACTGACAGCTCCCTTTGGGGGAA
AGGGCCTTCTTGTGCTCATCTGTCCATCTCCTTTCTCTCTTCTTCCTCTTGCCTCCTCCC
TCCTAACCTCCTCCAGCCCAGCATCTAAGTGCAGTACATTTCACATAAGAGACACCCCAG
CAAAGTGTGTTGAATAGAATCCATTAATTTGCATTCCATTTCTTTGGAAATAGCTTTTGG
[A,G]
ATCCATTGGGCAGATAGTGAAAATTTCAACTAACATGATGGTGGAGAAAAACCTTAACTT
TTGTGCTCATGTTAAATTTAGAAACATTTTGTTTCATTCTATCACCTCTGCTAACCTCTT
AACTAACTTGAGGTTATGGAGAAAGGGCAGAAGACTTATTTTTCTACTTCTTTAATATTT
CCGGTCAATTCTCTCTTCTCCATCAGTATTGCCAGTGCCTTCGTTGAGACAGGTCATCTT
TGTGGTTAAAGTTTGAAGTCCCTGAGATAAGACTATCTGGGTTTTAATACTAGTTATGCT

48328 TTTTGTTTCATTCTATCACCTCTGCTAACCTCTTAACTAACTTGAGGTTATGGAGAAAGG
GCAGAAGACTTATTTTTCTACTTCTTTAATATTTCCGGTCAATTCTCTCTTCTCCATCAG
TATTGCCAGTGCCTTCGTTGAGACAGGTCATCTTTGTGGTTAAAGTTTGAAGTCCCTGAG
ATAAGACTATCTGGGTTTTAATACTAGTTATGCTAACAGACAGACCTTGGGTGAGTTAGT
TACTCTTTCTGGGCCTCAGTTTCCTCAACCATAAAATGAAAATATTAATGCTACCCATTT
[T,A]
GTAGAGAGAGATTCCACAGGCCTAGTTGGTGGCCAGGGAACCCTGGGATAATAAAAGCAA
TCGGACATCTTGGGAACCAGGTAATCTCCTAACATTCCAAAGATACCTGCTGTCCCCTCT
CAACGCCATACAGTGTGTGCCAGTAGATTATAAACTGCATAAGGAAAGAGATGATGTCTG
CTCTCCTCCATATCCCTGGCTCCTGACACATAAGAGGATCATAAACGCACTTTGCAAAGC
AAATGCCAGCTCTGGAATTCTGCAGCAGCCTGGAGACCAGACCCTGCACATCAAGGCCCA

48391 GAAGACTTATTTTTCTACTTCTTTAATATTTCCGGTCAATTCTCTCTTCTCCATCAGTAT
TGCCAGTGCCTTCGTTGAGACAGGTCATCTTTGTGGTTAAAGTTTGAAGTCCCTGAGATA
AGACTATCTGGGTTTTAATACTAGTTATGCTAACAGACAGACCTTGGGTGAGTTAGTTAC
TCTTTCTGGGCCTCAGTTTCCTCAACCATAAAATGAAAATATTAATGCTACCCATTTTGT
AGAGAGAGATTCCACAGGCCTAGTTGGTGGCCAGGGAACCCTGGGATAATAAAAGCAATC
[G,A]
GACATCTTGGGAACCAGGTAATCTCCTAACATTCCAAAGATACCTGCTGTCCCCTCTCAA
CGCCATACAGTGTGTGCCAGTAGATTATAAACTGCATAAGGAAAGAGATGATGTCTGCTC
TCCTCCATATCCCTGGCTCCTGACACATAAGAGGATCATAAACGCACTTTGCAAAGCAAA
TGCCAGCTCTGGAATTCTGCAGCAGCCTGGAGACCAGACCCTGCACATCAAGGCCCAGTG

FIGURE 3, page 81 of 122

```
       GAAAACTAATGATTTCTCCCCCGCAGACCTGCCTAGCGAAGGGCCCCGTGGAGCTTGGCT
48453  CCAGTGCCTTCGTTGAGACAGGTCATCTTTGTGGTTAAAGTTTGAAGTCCCTGAGATAAG
       ACTATCTGGGTTTTAATACTAGTTATGCTAACAGACAGACCTTGGGTGAGTTAGTTACTC
       TTTCTGGGCCTCAGTTTCCTCAACCATAAAATGAAAATATTAATGCTACCCATTTTGTAG
       AGAGAGATTCCACAGGCCTAGTTGGTGGCCAGGGAACCCTGGGATAATAAAAGCAATCGG
       ACATCTTGGGAACCAGGTAATCTCCTAACATTCCAAAGATACCTGCTGTCCCCTCTCAAC
       [A,G]
       CCATACAGTGTGTGCCAGTAGATTATAAACTGCATAAGGAAAGAGATGATGTCTGCTCTC
       CTCCATATCCCTGGCTCCTGACACATAAGAGGATCATAAACGCACTTTGCAAAGCAAATG
       CCAGCTCTGGAATTCTGCAGCAGCCTGGAGACCAGACCCTGCACATCAAGGCCCAGTGGA
       AAACTAATGATTTCTCCCCCGCAGACCTGCCTAGCGAAGGGCCCCGTGGAGCTTGGCTGG
       TGAGAGCATTCTTCATTCTCCGCATGTCCCTGGCTCTCCCTCTCTCTCCCCACCTCCGCA
48690  CGGACATCTTGGGAACCAGGTAATCTCCTAACATTCCAAAGATACCTGCTGTCCCCTCTC
       AACGCCATACAGTGTGTGCCAGTAGATTATAAACTGCATAAGGAAAGAGATGATGTCTGC
       TCTCCTCCATATCCCTGGCTCCTGACACATAAGAGGATCATAAACGCACTTTGCAAAGCA
       AATGCCAGCTCTGGAATTCTGCAGCAGCCTGGAGACCAGACCCTGCACATCAAGGCCCAG
       TGGAAAACTAATGATTTCTCCCCCGCAGACCTGCCTAGCGAAGGGCCCCGTGGAGCTTGG
       [T,C]
       TGGTGAGAGCATTCTTCATTCTCCGCATGTCCCTGGCTCTCCCTCTCTCTCCCCACCTCC
       GCAGCCTCCCAGTCAAGCTATTGTGCATCTCCTGCTCTCTGTGTCTCGCTGCCTGGGTCC
       CTTTCTGCGCTGCTGCCTAAGCATTGTCTGTGATGTCTTTAGTGTGAAAGGTGATTCACA
       GAAATAAATTGCATTGTGTTTTAGGTCCATAGCAATCTACCTCTGTAATCATGTCTGTAA
       GGGACTTCATAATAGTGTGAGGGCCTTGGTGTCAGAACCAGGGTCTCCAGTGGCTTCAAG
49100  TGCCTGGGTCCCTTTCTGCGCTGCTGCCTAAGCATTGTCTGTGATGTCTTTAGTGTGAAA
       GGTGATTCACAGAAATAAATTGCATTGTGTTTTAGGTCCATAGCAATCTACCTCTGTAAT
       CATGTCTGTAAGGGACTTCATAATAGTGTGAGGGCCTTGGTGTCAGAACCAGGGTCTCCA
       GTGGCTTCAAGATAGATAAGTGCTGCAACCAAATGCACATTCAGCCAGTGAAGTTGCAAG
       TTAGAGGTGAAGATGGAGGTGCTGCTGCTATGAAGCAACCATACTCTCAGCCCTTTTATC
       [T,C]
       GCAGGTTGATAAAAATCAATCAAAACATGAGATGTGGTTTTTTGTTTGTTTTTAATAACC
       ACTGGAAAACTAAGACTTGTTTAATAGAGTCTCAGCCAACAGCTTGTGCTCTTACCAGCC
       CTGTGATTAGACGAAAGGGAAAGTTCAAAGTGTCACCTAGAAGGGGGAGGCACCAAAGAA
       GAAGAGGCAGGGAGGTGATACAGTGAAAGGCAAGGAGGAGCTGGGCTGGAATCTGAGAAA
       CCTGAGACTGATTTGTTCTAATCATCATCCTATGTGATGGTGGAAGATAAGAACCACAGA
50598  TGGAATGACACTGGCTGGGTTTGTGAACTAATCAAACCTCATGAAGGGGTAACTAGCTGG
       CCAGGGCTGAGAGAATGATTAAATTAGGTCACTGTTTCCTAAACACAACCCTTCTCCTAT
       CTTCATGTATTTATCATATCTGTGCATTTACTTATATTTTCCTTTAACAAACATATTTA
       ATTAAAGTTATTTAAAAAGGAAACATATCAACTATTGCAAATAGAAAAACCAGTATCACT
       ATTAATAGGTAGAAGCTATAAAATTAAAACAAAGCATTGTTATTATATTCTAGCCATATG
       [C,A]
       CATTGCATTCATAGCGTTCTGAGCCTGATTCTTGCCTCTTTTTGTTTAAAATAAAAGGGA
       AATGGCAAGGTATGGAGATAAATAATTTACCAAACAGATTTTCTTTTTCACTTAATAGCA
       GGAATAAAAGGAAATTTAAAATGAATGTGCATACGCATTGTGAGTCTGTTGTTTAATGCC
       ATTCTCACATTGGGAAATTCCACTCACCATACCTGGGTTCTAGTCTTTACTGAGCAATTA
       AATTGCTATATGGCTAGCTCACCTTCTTGTACCTCAATTTGTACATATGTAGAATGAGGT
50753  ATTTTCCTTTAACAAACATATTTTAATTAAAGTTATTTAAAAAGGAAACATATCAACTAT
       TGCAAATAGAAAAACCAGTATCACTATTAATAGGTAGAAGCTATAAAATTAAAACAAAGC
       ATTGTTATTATATTCTAGCCATATGCCATTGCATTCATAGCGTTCTGAGCCTGATTCTTG
       CCTCTTTTTGTTTAAAATAAAAGGGAAATGGCAAGGTATGGAGATAAATAATTTACCAAA
       CAGATTTTCTTTTTCACTTAATAGCAGGAATAAAAGGAAATTTAAAATGAATGTGCATAC
       [G,A]
       CATTGTGAGTCTGTTGTTTAATGCCATTCTCACATTGGGAAATTCCACTCACCATACCTG
       GGTTCTAGTCTTTACTGAGCAATTAAATTGCTATATGGCTAGCTCACCTTCTTGTACCTC
       AATTTGTACATATGTAGAATGAGGTTGGTGAGTTGAAATACAGAATTCCTTTAAACCCAA
       GTTTCTCAATGTTGCTCACGGGCAAGCTGCACCTGAATTTTCTGTGTAGGTATACTTGTT
       GAAAAATGTTAATTCTAAGCTCCATCCAAGATATTCTGAAAAAGAATTTCTGGAAATTT
54798  GTGGCAATGTTGGAATGGTGACAATGTTGTAATCCCAGTGGTAATATTATAATGGTGGCA
       GTTGTGGTGGTGGTGATGATGATGATACTAACAAATGAGGATGATAAGAATCAACAG
       CTAACATTTGTAGAGAGTTTACTATTGTATATACAAGGCATGGTACTAAGTACTTGCATA
       TATCTAATTTCATCCTTTTGACTTCTTTTAGATATGGCCAGTACTCCACATCTTTCAAGT
       GGGTGAACTGAGGTTTCAGAAGTTGAGTAATTTCCTGAGAGCCTACATTTAGTAAACTAA
       [G,C]
       ACAAAGTCAGAATTTGATACAGGCCATATGATGTCATCATATATATGTAAAGTGCTCAAC
       TGTTGGTTACTTGAATGAGGAAGGAAAGAAGGAAGAAAGAGAAGGAGTGAGGGAGGGAGG
       AATTTACTTGTTTTCTAATCTTAAGATTCCTTTTCTGAAAATAGAGATAATTCTAGCATT
```

FIGURE 3, page 82 of 122

TATGGAAATCAAATGAGATTAAAAAAAGTCAAAGCTCTTTGAAAACTGTCAAGTCTTCTC
TATGTACGAGGGCTAAACCATCAGAGGCAGCTTCATAATTACTCATTCATTCATTCAATA

55058 AGTTGAGTAATTTCCTGAGAGCCTACATTTAGTAAACTAAGACAAAGTCAGAATTTGATA
CAGGCCATATGATGTCATCATATATATGTAAAGTGCTCAACTGTTGGTTACTTGAATGAG
GAAGGAAAGAAGGAAGAAAGAGAAGGAGTGAGGGAGGGAGGAATTTACTTGTTTTCTAAT
CTTAAGATTCCTTTTCTGAAAATAGAGATAATTCTAGCATTTATGGAAATCAAATGAGAT
TAAAAAAAGTCAAAGCTCTTTGAAAACTGTCAAGTCTTCTCTATGTACGAGGGCTAAACC
[A,G]
TCAGAGGCAGCTTCATAATTACTCATTCATTCATTCAATAGATATTTGGTTTTCTGTTTT
AGGCACTAGAATATAGTGGGCAAAACAAACTAAAGTGCCTGCCCTCAGTGAGCTTTCAGT
CGAGTCTAGTGACAGACAAGCAAATGCCAGGTGAAATATATAGTCCTGTGGGAAAAAATA
AAGCATGGAGGGGGTGAGGGAATATGTGTGTATGTTGGGGGTGGGGTCACTCTTTAAATA
GGGTGGTGAGGGAAGGCCTCTGATAAGGTGATATCTGAGCAGGGCCTGAAAAAGGTAAGC

55171 GAATGAGGAAGGAAAGAAGGAAGAAAGAGAAGGAGTGAGGGAGGGAGGAATTTACTTGTT
TTCTAATCTTAAGATTCCTTTTCTGAAAATAGAGATAATTCTAGCATTTATGGAAATCAA
ATGAGATTAAAAAAAGTCAAAGCTCTTTGAAAACTGTCAAGTCTTCTCTATGTACGAGGG
CTAAACCATCAGAGGCAGCTTCATAATTACTCATTCATTCATTCAATAGATATTTGGTTT
TCTGTTTTAGGCACTAGAATATAGTGGGCAAAACAAACTAAAGTGCCTGCCCTCAGTGAG
[C,T]
TTTCAGTCGAGTCTAGTGACAGACAAGCAAATGCCAGGTGAAATATATAGTCCTGTGGGA
AAAAATAAAGCATGGAGGGGGTGAGGGAATATGTGTGTATGTTGGGGGTGGGGTCACTCT
TTAAATAGGGTGGTGAGGGAAGGCCTCTGATAAGGTGATATCTGAGCAGGGCCTGAAAAA
GGTAAGCCAGGGAGTCACACAGAATCTGGGAAAAAAGTGTTTTATATCCCACAGGGGAGT
TTAAAAGTCAAATGAGGAATGATATCACTGTGATAAGAATGCTAGGAATGGGATTATGCA

55801 TGCAGTCAAGTCAGTCTTTTCCTTGGTAACCTCCTCTGGTGGGGTCTCTGAAGGCTCAGT
CAAGGTGTGATGTCCCAGGGGAGATACTATTATCTGAAAGCATGGTTCCTCTGGCAACAG
GCAATGGGTCTGAGGGAGATATCTTCTATTCTCCATTCAACCATCCATGAGCATGATGAC
ACTAGGCAGGTCATCTGTGCTCATGGCATCACCCCTTCCAGCTGGGAAAGACAAAGGAAA
GTCAGGGAGGTTCTCCCCACATCAAATGGAAAAGTCCTGCTCCACCAGGGTCTATAATGA
[G,A]
ATGGTTTATTTAAGTCTATAATGACCTAAGATAAAGTTAATTTACTTTATTCAGATTTAC
AGACATTACCAAATTACATAGGATTGCAAACACAGGAGAAGATAAAATAAATTACCAACC
AGATTGAAGAGCTTAGAGAAATAGGTAAATAGTCATGGGAAGAGATTTAATTTAGATAAA
CCAAAGGCAGGATATCTGGAAAATGCCAAGGTCAGGGAAAAGCCGAGAGGAAAAGATAGC
TAGTAAGATGGAAGAGACATGGAAAGGATTCAGAAAATGACGTTGGTGATAGTGAGTGTG

56324 CCGAGAGGAAAAGATAGCTAGTAAGATGGAAGAGACATGGAAAGGATTCAGAAAATGACG
TTGGTGATAGTGAGTGTGGCCAGTATTATGATAAAGATAGAGGAAATGGGAAAGATATTA
CTGAAAAATATGGCTTCTCCTTAGAATCCCAAAATAAATGAGGTAATTTGTGGAAAGCAG
TGCCAGACTGGATTCTGTGGTCTTAGTTCCAAGTCTGCTAGGAACTGCCTCTGCAACTTG
GGAAAGCTTTTTGATTTTTTTCTAACCTTTAGCTTCCTCTTCTGTTATGACATACAATAC
[A,G]
GTTCTAAGTCTAAATGTTTCTAGTTCTCTTGTGTTTAAGGAAGGCGCCATGTGCTCTGAG
GAGACCCTGAATCCATCCCTGGTCCTCCTGGCTGACCTTAATAGAAACATTGAAAGATGG
AGATTCATGACAAGTAGTCAAACGGAAAGGCATTCATTTTGGAGATGGATCAAGGGTCCA
GGCTCATCGGAGACACTGAAAAAGTTGAAAGGTTGCAAAATTGAGGGAGAACGACAGTTA
TGATAGTTCAGTATAACTGGGTTTTGCCAGAGGTTGTAGAAAAAAGTTAAAGATTGATTT

56557 CAACTTGGGAAAGCTTTTTGATTTTTTTCTAACCTTTAGCTTCCTCTTCTGTTATGACAT
ACAATACGGTTCTAAGTCTAAATGTTTCTAGTTCTCTTGTGTTTAAGGAAGGCGCCATGT
GCTCTGAGGAGACCCTGAATCCATCCCTGGTCCTCCTGGCTGACCTTAATAGAAACATTG
AAAGATGGAGATTCATGACAAGTAGTCAAACGGAAAGGCATTCATTTTGGAGATGGATCA
AGGGTCCAGGCTCATCGGAGACACTGAAAAAGTTGAAAGGTTGCAAAATTGAGGGAGAAC
[G,A]
ACAGTTATGATAGTTCAGTATAACTGGGTTTTGCCAGAGGTTGTAGAAAAAAGTTAAAGA
TTGATTTGAAATGGTTGAGGGGTATGTACAATGCAGAAGGAGGGGTGAGTTAAATAAGAC
AATTTATAGGCTGGATGTCTTCAGGGACTGGGGGGAAGTTTGGGTATCTTTAAGATGGCA
TGGCAGTCTGACATACAGGAATAGTTGTATCCACTGCAAATCATAACCTTCTATGCATTT
CAGGGTCGGCTTAAGGATATTTGCAAAGAACATACTGGAGGGAGAACATCAGACTTGTCC

56716 CTGACCTTAATAGAAACATTGAAAGATGGAGATTCATGACAAGTAGTCAAACGGAAAGGC
ATTCATTTTGGAGATGGATCAAGGGTCCAGGCTCATCGGAGACACTGAAAAAGTTGAAAG
GTTGCAAAATTGAGGGAGAACGACAGTTATGATAGTTCAGTATAACTGGGTTTTGCCAGA
GGTTGTAGAAAAAAGTTAAAGATTGATTTGAAATGGTTGAGGGGTATGTACAATGCAGAA
GGAGGGGTGAGTTAAATAAGACAATTTATAGGCTGGATGTCTTCAGGGACTGGGGGGAAG
[T,G]
TTGGGTATCTTTAAGATGGCATGGCAGTCTGACATACAGGAATAGTTGTATCCACTGCAA
ATCATAACCTTCTATGCATTTCAGGGTCGGCTTAAGGATATTTGCAAAGAACATACTGGA

FIGURE 3, page 83 of 122

GGGAGAACATCAGACTTGTCCTAGTTGCTTGGGTCCCGGGTTAGTTCACCACTACAGCAA
TGTGGGAGCTAACTGCATGCTAAGCTTGGCATGCAGGGATTGGCAAACCTTTTCTGTAAA
AACCCAGATAGTAAATGTTTTAGATTTTGTGAGCCATACGGTCTCTGTCACAATTACTCA

58247 CCAAGGAAACACAGTTTATTATAAGTGCCAAAGTCAGGCCTCAAACTCAGCTCTGCTCCC
ACAGCTGACACTCCTAACCAACACATTGTCCTATTGCACAACTGCAGCATTCTTTCATTA
GTGGGTATGTTAATGTGAAGAACCAGCACTTGGACCAGTGCCTTATAAGGATCCTTTGAA
ACCAAGATTTTATTGTGGTTGAAGGGCAGAGAGCTAAATCACCAAAATGTGTAAGTAGAG
ACAGACCAGAATGTAATCTCCATGAAAGCAATGTCCTTCTCTGTTTTTAATTTTTTCAC
[C,T]
ATGTTATCCCTAGCACTTAGTTGTGTCTGATAAATATTTGAATAAATGCATCAGTATGTG
AACATTATTTGGAATTATTTTTTCTTTTTAATATCAAAAATCTCATAACCACCTAGGCCA
AGCTTAACCCGTGGGCCTCAGGCCGCATGCAGCCCAACACGGCTTTGAATGAGGCCCAAT
ACAAATTTGTAAAGTTTCTTAAAACATTTTGAGACTTTTTGTGTGATTTTTTTTTTAGCT
CATCAGCTATTGTTAGTGTTAGTGTATGTGATGTGTGGTCCAAGACAATGCTTCTTCTTT

62318 CTAACCTGTCTATCTTAATAGGATGTTGTAAGAATTAACTGAAATAATGTACAGTCTGCC
TCACAATCATCTGGACGGCTTGAGAAAGCACAGATTGCCAGATCCCACCCCCAGAGGTTC
TAATTCAGTAGGTCTGGGGTTGGACCCAAGAATTTATATTCTTTTTTATTATGATGATGA
TTATTATACTTTAAGTTTTAGGGTACATGTGCACAATGTGCAGGTTAGTTACATATGTAT
ACAATGAATTTATATTCTTAACAAGCTCTCAAGTGATGCTGATATAGCTGGTCTGGGGAT
[T,C]
ACAGTAAGAAAACCACTGCTTTAGGTCAATGCAGTTTTTTTTAAAAGCTATTATTCATAA
CTGGCTCAAGAGTCATGTAAGTGTTGATTATGTTTTATTATGTGTCTAGACCCTTAATAG
ACTACTCAGGATATGCACAAATAGAAGATGTAATATTTTCTGTAGCATTCCCTACACCAA
ATCGGCCTTGCTCGGTCATGCATAGTTAATGTATGTGTTGATTTTATTTGTCTTCGTGTG
GCTTCTAGTCTCACTAGAAAGACATACATTTATTTGAATGTTGTAGAATGATATTATTCA

62429 CAGAGGTTCTAATTCAGTAGGTCTGGGGTTGGACCCAAGAATTTATATTCTTTTTTATTA
TGATGATGATTATTATACTTTAAGTTTTAGGGTACATGTGCACAATGTGCAGGTTAGTTA
CATATGTATACAATGAATTTATATTCTTAACAAGCTCTCAAGTGATGCTGATATAGCTGG
TCTGGGGATTACAGTAAGAAAACCACTGCTTTAGGTCAATGCAGTTTTTTTTAAAAGCTA
TTATTCATAACTGGCTCAAGAGTCATGTAAGTGTTGATTATGTTTTATTATGTGTCTAGA
[C,A]
CCTTAATAGACTACTCAGGATATGCACAAATAGAAGATGTAATATTTTCTGTAGCATTCC
CTACACCAAATCGGCCTTGCTCGGTCATGCATAGTTAATGTATGTGTTGATTTTATTTGT
CTTCGTGTGGCTTCTAGTCTCACTAGAAAGACATACATTTATTTGAATGTTGTAGAATGA
TATTATTCATTGGAATAAAATCGGATCTTTTTACAGTTTTTTTTGTTTGTTTGTTTCTTA
ATGAGCAGGCCTATGATTCCTAAAGGACTTTTTATTTTATTTCATTTGAACCTTTGATAG

62449 GTCTGGGGTTGGACCCAAGAATTTATATTCTTTTTTATTATGATGATGATTATTATACTT
TAAGTTTTAGGGTACATGTGCACAATGTGCAGGTTAGTTACATATGTATACAATGAATTT
ATATTCTTAACAAGCTCTCAAGTGATGCTGATATAGCTGGTCTGGGGATTACAGTAAGAA
AACCACTGCTTTAGGTCAATGCAGTTTTTTTTAAAAGCTATTATTCATAACTGGCTCAAG
AGTCATGTAAGTGTTGATTATGTTTTATTATGTGTCTAGACCCTTAATAGACTACTCAGG
[A,G]
TATGCACAAATAGAAGATGTAATATTTTCTGTAGCATTCCCTACACCAAATCGGCCTTGC
TCGGTCATGCATAGTTAATGTATGTGTTGATTTTATTTGTCTTCGTGTGGCTTCTAGTCT
CACTAGAAAGACATACATTTATTTGAATGTTGTAGAATGATATTATTCATTGGAATAAAA
TCGGATCTTTTTACAGTTTTTTTTGTTTGTTTGTTTCTTAATGAGCAGGCCTATGATTCC
TAAAGGACTTTTTATTTTATTTCATTTGAACCTTTGATAGAAACTGCATCTTTCATGTGA

62450 TCTGGGGTTGGACCCAAGAATTTATATTCTTTTTTATTATGATGATGATTATTATACTTT
AAGTTTTAGGGTACATGTGCACAATGTGCAGGTTAGTTACATATGTATACAATGAATTTA
TATTCTTAACAAGCTCTCAAGTGATGCTGATATAGCTGGTCTGGGGATTACAGTAAGAAA
ACCACTGCTTTAGGTCAATGCAGTTTTTTTTAAAAGCTATTATTCATAACTGGCTCAAGA
GTCATGTAAGTGTTGATTATGTTTTATTATGTGTCTAGACCCTTAATAGACTACTCAGGA
[T,A]
ATGCACAAATAGAAGATGTAATATTTTCTGTAGCATTCCCTACACCAAATCGGCCTTGCT
CGGTCATGCATAGTTAATGTATGTGTTGATTTTATTTGTCTTCGTGTGGCTTCTAGTCTC
ACTAGAAAGACATACATTTATTTGAATGTTGTAGAATGATATTATTCATTGGAATAAAAT
CGGATCTTTTTACAGTTTTTTTTGTTTGTTTGTTTCTTAATGAGCAGGCCTATGATTCCT
AAAGGACTTTTTATTTTATTTCATTTGAACCTTTGATAGAAACTGCATCTTTCATGTGAC

62554 GTATACAATGAATTTATATTCTTAACAAGCTCTCAAGTGATGCTGATATAGCTGGTCTGG
GGATTACAGTAAGAAAACCACTGCTTTAGGTCAATGCAGTTTTTTTTAAAAGCTATTATT
CATAACTGGCTCAAGAGTCATGTAAGTGTTGATTATGTTTTATTATGTGTCTAGACCCTT
AATAGACTACTCAGGATATGCACAAATAGAAGATGTAATATTTTCTGTAGCATTCCCTAC
ACCAAATCGGCCTTGCTCGGTCATGCATAGTTAATGTATGTGTTGATTTTATTTGTCTTC
[G,A]
TGTGGCTTCTAGTCTCACTAGAAAGACATACATTTATTTGAATGTTGTAGAATGATATTA

FIGURE 3, page 84 of 122

TTCATTGGAATAAAATCGGATCTTTTTACAGTTTTTTTTGTTTGTTTGTTTCTTAATGAG
CAGGCCTATGATTCCTAAAGGACTTTTTATTTTATTTCATTTGAACCTTTGATAGAAACT
GCATCTTTCATGTGACCACTCTCCATTTTTCTGCTCATATGACCACATTTCCCAGTAGTC
TTTAAAGGCTCCAGTTTGGATGGGATTTCGATTAATGGAAGAGAACAGATAGCTCTGTAA

63688 AGAGGTCCCAAACTGGTGTTCTATGGATTGCATCCAGTGATTTTATGTGTAGCATAACTT
TTTAAGAGGAAGAGAGAAGAAAATTGACTTTGCGATCAACATTACAAAAAAACATCATGA
GACTTTGAATAGAAATTTGGATTTTCAGCAAAAAAAAAGAAAAAAAAAAAGAAGAAGGTT
TGGCAGTACTGGACTCCCATCTTTAAGGGTAACAGCCGAATGCTGGCCACGTCCTGTAAG
AACCCACACTCTCCAGTTTGCTGCTGTCCATACCAGCTTGTGTGACTCCTTTACATTACC
[T,C]
GCTTGACTCCTAAAGGTATTTCAATTAGTGGCCTGTTTTTGCTCTTTTTGGCAAGTTCAC
AGACTTACAGAGTTTGAAAGCTAAAGGAGTCCCTGAGAACAAGGATTTTCTAATGTTACT
TCACATCAAAATCACCTATACCCTATAACCAGGCTGCATCCAGTACCAATTAAATAAGAA
TCTCTGGGGAGGACCAAGCTGTCAGGATTTTTTTTTTTAATTCCCCAGATGATTCCAGTA
TACAGATCAGTTCATCTAAGAACCAGTACCTTGGAAGAATACTACTCAGAATTTATTGTG

64921 CGAATGAGAGGCATAAGACAGAGTGAAAGACTGAGGCAGGTTTCAGAGCAGGAGTGAATG
TTTATTAAAAAGCTTTAGAACAGGAATGAAAGAAAGTAAAGTACACTTGGAAGAGGGTTA
ACGGGGAGACTTGAGAGACCAAGTGCATGGTTTGACCTCTGACTTGGGGTTTTATGTGCT
GGTGTGCTTCGGGGGTCTTACATTACTTCTCCACTGATTCTTCCATTGGGATGGACTGTC
CATATGCACAGTGGCCTGTTAGTGCTTGTGAGGAGCCGCATGCACAGTGTGTTTACTGAA
[G,A]
TTGTATCCATGCTCACGTGAGGCATTCTTCCCTTACCAGTATTCGTAGAACCATATGCCA
GTTAAACTCCACCATTTTGCCTCTTAGTGTGCATGCTTGAGCTCATTCACCCAGTTTCTG
AGATATTGGGAAAATGCGATCACCAGTTTCAGGTTTTTCTATCCATTGGGAAACTGCCTT
TCCCTGGCACTGGCTGCAACCAATTATTATTTTAGAGAGACAGTTTAATAATCGCCTATC
ATCTGATGGTTGCCTGACATTTCTTGTGGTGGCAGCAGGGGGGACCCTCTCCTGTCCTGC

64934 TAAGACAGAGTGAAAGACTGAGGCAGGTTTCAGAGCAGGAGTGAATGTTTATTAAAAAGC
TTTAGAACAGGAATGAAAGAAAGTAAAGTACACTTGGAAGAGGGTTAACGGGGAGACTTG
AGAGACCAAGTGCATGGTTTGACCTCTGACTTGGGGTTTTATGTGCTGGTGTGCTTCGGG
GGTCTTACATTACTTCTCCACTGATTCTTCCATTGGGATGGACTGTCCATATGCACAGTG
GCCTGTTAGTGCTTGTGAGGAGCCGCATGCACAGTGTGTTTACTGAAGTTGTATCCATGC
[T,C]
CACGTGAGGCATTCTTCCCTTACCAGTATTCGTAGAACCATATGCCAGTTAAACTCCACC
ATTTTGCCTCTTAGTGTGCATGCTTGAGCTCATTCACCCAGTTTCTGAGATATTGGGAAA
ATGCGATCACCAGTTTCAGGTTTTTCTATCCATTGGGAAACTGCCTTTCCCTGGCACTGG
CTGCAACCAATTATTATTTTAGAGAGACAGTTTAATAATCGCCTATCATCTGATGGTTGC
CTGACATTTCTTGTGGTGGCAGCAGGGGGGACCCTCTCCTGTCCTGCTCGTGTCTGACTA

65150 GATGGACTGTCCATATGCACAGTGGCCTGTTAGTGCTTGTGAGGAGCCGCATGCACAGTG
TGTTTACTGAAGTTGTATCCATGCTCACGTGAGGCATTCTTCCCTTACCAGTATTCGTAG
AACCATATGCCAGTTAAACTCCACCATTTTGCCTCTTAGTGTGCATGCTTGAGCTCATTC
ACCCAGTTTCTGAGATATTGGGAAAATGCGATCACCAGTTTCAGGTTTTTCTATCCATTG
GGAAACTGCCTTTCCCTGGCACTGGCTGCAACCAATTATTATTTTAGAGAGACAGTTTAA
[T,A]
AATCGCCTATCATCTGATGGTTGCCTGACATTTCTTGTGGTGGCAGCAGGGGGGACCCTC
TCCTGTCCTGCTCGTGTCTGACTAGCTACCTACTGTAATAAATGGGGTGCAGATTAGAAA
ACAGGTCCTTACCCTCCCCCTTCCCCACCCAGTTATTGCTCAAGATCACATAATTATGAA
ATAGAAGAGCTGATACATAGAGAAAAATAGTTCCAGTTGTCTTTATAAGTGGTTCAAAAC
TCTGTGAGCTTCTTTGATGGGTTGAGTTGTAAGTTATGTGGCAGCCTCTCCTTTCAGGTG

65198 GCATGCACAGTGTGTTTACTGAAGTTGTATCCATGCTCACGTGAGGCATTCTTCCCTTAC
CAGTATTCGTAGAACCATATGCCAGTTAAACTCCACCATTTTGCCTCTTAGTGTGCATGC
TTGAGCTCATTCACCCAGTTTCTGAGATATTGGGAAAATGCGATCACCAGTTTCAGGTTT
TTCTATCCATTGGGAAACTGCCTTTCCCTGGCACTGGCTGCAACCAATTATTATTTTAGA
GAGACAGTTTAATAATCGCCTATCATCTGATGGTTGCCTGACATTTCTTGTGGTGGCAGC
[A,G]
GGGGGACCCTCTCCTGTCCTGCTCGTGTCTGACTAGCTACCTACTGTAATAAATGGGGT
GCAGATTAGAAAACAGGTCCTTACCCTCCCCCTTCCCCACCCAGTTATTGCTCAAGATCA
CATAATTATGAAATAGAAGAGCTGATACATAGAGAAAAATAGTTCCAGTTGTCTTTATAA
GTGGTTCAAAACTCTGTGAGCTTCTTTGATGGGTTGAGTTGTAAGTTATGTGGCAGCCTC
TCCTTTCAGGTGAGAATGAAGCAGTCAGCCAGGTCTAATTGCCTAGTTATATGAGTGTAC

65674 TATAAGTGGTTCAAAACTCTGTGAGCTTCTTTGATGGGTTGAGTTGTAAGTTATGTGGCA
GCCTCTCCTTTCAGGTGAGAATGAAGCAGTCAGCCAGGTCTAATTGCCTAGTTATATGAG
TGTACTGAGTAGGTAACTCTCTCAATAGTTTAATTTGAGGTCTGCAATTGGAGAGTTGAT
GCTGAAACATTTCTCAGGACCAGAAATTTCCTTTCAGGCTAGCCACTTCTCTGAGCTGAA
AATGCTGTCATGGTGAATTCATTCTTCTAGATCCATGTTTTTAAGTATATTATCAAAGG
[A,T]

CTATGTGTATCGGAATCCCTTGAGACTCTAGTTAATGACTGTCCACGTCCCACTCCCAGA
GATTCCGAGTCAGTAAATCTGGGGTGGGGCTCAGGAAGTGGTTTTTTGTTGTTGTTGCTG
CTTTGTTTTGTTTTTGAGATGGAGTTTTACTCTGTTGCCCAGGCTGGAATGCAGTGGCGT
GATCTTGGCTCACTGCAACCTCTGCCTCCCAGGTTCAAGCGATTCTCCTGCCTCAGCCTC
CCAAGTAGCTGGGATTACAGGTGCCCACCAGCATGCCAGGCTAATTTTTATATTTTTAGT

65720 TAAGTTATGTGGCAGCCTCTCCTTTCAGGTGAGAATGAAGCAGTCAGCCAGGTCTAATTG
CCTAGTTATATGAGTGTACTGAGTAGGTAACTCTCTCAATAGTTTAATTTGAGGTCTGCA
ATTGGAGAGTTGATGCTGAAACATTTCTCAGGACCAGAAATTTCCTTTCAGGCTAGCCAC
TTCTCTGAGCTGAAAATGCTGTCATGGTGAATTCATTCTTCTAGATCCATGTTTTTTAAG
TATATTATCAAAGGACTATGTGTATCGGAATCCCTTGAGACTCTAGTTAATGACTGTCCA
[C,G]
GTCCCACTCCCAGAGATTCCGAGTCAGTAAATCTGGGGTGGGGCTCAGGAAGTGGTTTTT
TGTTGTTGTTGCTGCTTTGTTTTGTTTTTGAGATGGAGTTTTACTCTGTTGCCCAGGCTG
GAATGCAGTGGCGTGATCTTGGCTCACTGCAACCTCTGCCTCCCAGGTTCAAGCGATTCT
CCTGCCTCAGCCTCCCAAGTAGCTGGGATTACAGGTGCCCACCAGCATGCCAGGCTAATT
TTTATATTTTTAGTAGAGACGGGGTTCCCCCATGTTGGCCAGGCTGGTCACAAACTGCTG

65820 AGTTTAATTTGAGGTCTGCAATTGGAGAGTTGATGCTGAAACATTTCTCAGGACCAGAAA
TTTCCTTTCAGGCTAGCCACTTCTCTGAGCTGAAAATGCTGTCATGGTGAATTCATTCTT
CTAGATCCATGTTTTTTAAGTATATTATCAAAGGACTATGTGTATCGGAATCCCTTGAGA
CTCTAGTTAATGACTGTCCACGTCCCACTCCCAGAGATTCCGAGTCAGTAAATCTGGGGT
GGGGCTCAGGAAGTGGTTTTTTGTTGTTGTTGCTGCTTTGTTTTGTTTTTGAGATGGAGT
[T,C]
TTACTCTGTTGCCCAGGCTGGAATGCAGTGGCGTGATCTTGGCTCACTGCAACCTCTGCC
TCCCAGGTTCAAGCGATTCTCCTGCCTCAGCCTCCCAAGTAGCTGGGATTACAGGTGCCC
ACCAGCATGCCAGGCTAATTTTTATATTTTTAGTAGAGACGGGGTTCCCCCATGTTGGCC
AGGCTGGTCACAAACTGCTGACCTCACATGATCTGCCCACCTCAGCCTCCCAAAGTGCTG
GAATTACAGGCATGAGCCACTGCACCTGGCCAGGAAGTGGCATTTTTCAGAAAACTCATC

65948 ATGTTTTTTAAGTATATTATCAAAGGACTATGTGTATCGGAATCCCTTGAGACTCTAGTT
AATGACTGTCCACGTCCCACTCCCAGAGATTCCGAGTCAGTAAATCTGGGGTGGGGCTCA
GGAAGTGGTTTTTTGTTGTTGTTGCTGCTTTGTTTTGTTTTTGAGATGGAGTTTTACTCT
GTTGCCCAGGCTGGAATGCAGTGGCGTGATCTTGGCTCACTGCAACCTCTGCCTCCCAGG
TTCAAGCGATTCTCCTGCCTCAGCCTCCCAAGTAGCTGGGATTACAGGTGCCCACCAGCA
[T,C]
GCCAGGCTAATTTTTATATTTTTAGTAGAGACGGGGTTCCCCCATGTTGGCCAGGCTGGT
CACAAACTGCTGACCTCACATGATCTGCCCACCTCAGCCTCCCAAAGTGCTGGAATTACA
GGCATGAGCCACTGCACCTGGCCAGGAAGTGGCATTTTTCAGAAAACTCATCCAAGTGAT
TTTGATGCAGGTAGTAGGCCAGATGCAGAGAAATATGATATAAAGGTAAATGTCCTTTCT
TCCCTGTCTACTAGTATAGTGACCATTTTCTCCTGAATCAAATACTGCAGCCTTGAAACT

65978 TGTGTATCGGAATCCCTTGAGACTCTAGTTAATGACTGTCCACGTCCCACTCCCAGAGAT
TCCGAGTCAGTAAATCTGGGGTGGGGCTCAGGAAGTGGTTTTTTGTTGTTGTTGCTGCTT
TGTTTTGTTTTTGAGATGGAGTTTTACTCTGTTGCCCAGGCTGGAATGCAGTGGCGTGAT
CTTGGCTCACTGCAACCTCTGCCTCCCAGGTTCAAGCGATTCTCCTGCCTCAGCCTCCCA
AGTAGCTGGGATTACAGGTGCCCACCAGCATGCCAGGCTAATTTTTATATTTTTAGTAGA
[G,A]
ACGGGGTTCCCCCATGTTGGCCAGGCTGGTCACAAACTGCTGACCTCACATGATCTGCCC
ACCTCAGCCTCCCAAAGTGCTGGAATTACAGGCATGAGCCACTGCACCTGGCCAGGAAGT
GGCATTTTTCAGAAAACTCATCCAAGTGATTTTGATGCAGGTAGTAGGCCAGATGCAGAG
AAATATGATATAAAGGTAAATGTCCTTTCTTCCCTGTCTACTAGTATAGTGACCATTTTC
TCCTGAATCAAATACTGCAGCCTTGAAACTAGTTAAAACCAGGGTTGTGCCATACTTCTA

65988 AATCCCTTGAGACTCTAGTTAATGACTGTCCACGTCCCACTCCCAGAGATTCCGAGTCAG
TAAATCTGGGGTGGGGCTCAGGAAGTGGTTTTTTGTTGTTGTTGCTGCTTTGTTTTGTTT
TTGAGATGGAGTTTTACTCTGTTGCCCAGGCTGGAATGCAGTGGCGTGATCTTGGCTCAC
TGCAACCTCTGCCTCCCAGGTTCAAGCGATTCTCCTGCCTCAGCCTCCCAAGTAGCTGGG
ATTACAGGTGCCCACCAGCATGCCAGGCTAATTTTTATATTTTTAGTAGAGACGGGGTTC
[C,T]
CCCATGTTGGCCAGGCTGGTCACAAACTGCTGACCTCACATGATCTGCCCACCTCAGCCT
CCCAAAGTGCTGGAATTACAGGCATGAGCCACTGCACCTGGCCAGGAAGTGGCATTTTTC
AGAAAACTCATCCAAGTGATTTTGATGCAGGTAGTAGGCCAGATGCAGAGAAATATGATA
TAAAGGTAAATGTCCTTTCTTCCCTGTCTACTAGTATAGTGACCATTTTCTCCTGAATCA
AATACTGCAGCCTTGAAACTAGTTAAAACCAGGGTTGTGCCATACTTCTACTCAGCTCAG

66089 TTGCTGCTTTGTTTTGTTTTTGAGATGGAGTTTTACTCTGTTGCCCAGGCTGGAATGCAG
TGGCGTGATCTTGGCTCACTGCAACCTCTGCCTCCCAGGTTCAAGCGATTCTCCTGCCTC
AGCCTCCCAAGTAGCTGGGATTACAGGTGCCCACCAGCATGCCAGGCTAATTTTTATATT
TTTAGTAGAGACGGGGTTCCCCCATGTTGGCCAGGCTGGTCACAAACTGCTGACCTCACA
TGATCTGCCCACCTCAGCCTCCCAAAGTGCTGGAATTACAGGCATGAGCCACTGCACCTG

[G,T]
CCAGGAAGTGGCATTTTTCAGAAAACTCATCCAAGTGATTTTGATGCAGGTAGTAGGCCA
GATGCAGAGAAATATGATATAAAGGTAAATGTCCTTTCTTCCCTGTCTACTAGTATAGTG
ACCATTTTCTCCTGAATCAAATACTGCAGCCTTGAAACTAGTTAAAACCAGGGTTGTGCC
ATACTTCTACTCAGCTCAGAAGGAGGCTCTCCATTTGAGAACACATGGGTTCCTTTTGCT
ACCAGGACATGCAGCTTGGAACCTCTGATTCTCAGTGATGTAGGCATTTTCTTAGCATAC

66332 TCTGCCCACCTCAGCCTCCCAAAGTGCTGGAATTACAGGCATGAGCCACTGCACCTGGCC
AGGAAGTGGCATTTTTCAGAAAACTCATCCAAGTGATTTTGATGCAGGTAGTAGGCCAGA
TGCAGAGAAATATGATATAAAGGTAAATGTCCTTTCTTCCCTGTCTACTAGTATAGTGAC
CATTTTCTCCTGAATCAAATACTGCAGCCTTGAAACTAGTTAAAACCAGGGTTGTGCCAT
ACTTCTACTCAGCTCAGAAGGAGGCTCTCCATTTGAGAACACATGGGTTCCTTTTGCTAC
[C,T]
AGGACATGCAGCTTGGAACCTCTGATTCTCAGTGATGTAGGCATTTTCTTAGCATACAGC
AGCCTGGAATTTATCATAATGTACATGTCACAGGAGGATATGAAATAGAGTAAACACCTT
TTTTATAGACTTTAGATTTTGAGGTCTCACTACAGCAGCGTTTTGCAACTTTTTAAAAAA
GAACCAATAATGATCTCTTTGGATGTTCATAAAAGCCTCACACTCTGCTGTCCCATACTA
GATTCTGATATACCTAACTTTGAAGGATGTCCACCATTGAGTGTCACTACATACAGGGAG

66361 GAATTACAGGCATGAGCCACTGCACCTGGCCAGGAAGTGGCATTTTTCAGAAAACTCATC
CAAGTGATTTTGATGCAGGTAGTAGGCCAGATGCAGAGAAATATGATATAAAGGTAAATG
TCCTTTCTTCCCTGTCTACTAGTATAGTGACCATTTTCTCCTGAATCAAATACTGCAGCC
TTGAAACTAGTTAAAACCAGGGTTGTGCCATACTTCTACTCAGCTCAGAAGGAGGCTCTC
CATTTGAGAACACATGGGTTCCTTTTGCTACCAGGACATGCAGCTTGGAACCTCTGATTC
[T,G]
CAGTGATGTAGGCATTTTCTTAGCATACAGCAGCCTGGAATTTATCATAATGTACATGTC
ACAGGAGGATATGAAATAGAGTAAACACCTTTTTTATAGACTTTAGATTTTGAGGTCTCA
CTACAGCAGCGTTTTGCAACTTTTTAAAAAAGAACCAATAATGATCTCTTTGGATGTTCA
TAAAAGCCTCACACTCTGCTGTCCCATACTAGATTCTGATATACCTAACTTTGAAGGATG
TCCACCATTGAGTGTCACTACATACAGGGAGCAAATTCCATTTCATTTTTCGCGCATTCC

67130 CTCCTGGCAGGTATTTTCCCCCTTCCTTATTCCACTAAGACTCACTTGCAACGCAAAGAC
CAGGGCCTCATGGAAGAAGGCAGCTGGGCACAAGCCTGTTGCCATGGAAAGCTTAGGGCG
GGAAGCGATTGATTGGTCTCTGCATACAGAGACTGATCTAGAAGGCTTCAGTGTGTCTGA
ATGGACCTGTCTGGGCTGGAATTTCAGTCAGTCTGACAGACTGCTAAAGGAGACTCAGGT
GTACACTTCAGCAACTTGATAACTCTTCCCCAGCTGAAAGTCGAATCATTTGATCCAACG
[G,A]
GAAAGAAGCTAAAATTGTCCTGACAGCTAAAGAGCGATCTGACCTTTGTGATCAGGAGGA
GAATTTCTTGTGATACAGAAAGTGAAAGTAGAAACTGGAATGATGGTATTGATGATGAAG
GCATTTAGAGCAGCAGGCACTGCCATTCATTAAAAGATTGCACTGTGTCAGGCACATGCT
TTATCCTATTGAACCATCATGCCAAACTTGGGACACTTAGGTATCATTGTTTTTCATTTT
CCATTAAGAACTTGAGGATTAAAGCTGTTAATCTATCTGTTCATGGTGAAATGAGTAGTA

67148 CCCCTTCCTTATTCCACTAAGACTCACTTGCAACGCAAAGACCAGGGCCTCATGGAAGAA
GGCAGCTGGGCACAAGCCTGTTGCCATGGAAAGCTTAGGGCGGGAAGCGATTGATTGGTC
TCTGCATACAGAGACTGATCTAGAAGGCTTCAGTGTGTCTGAATGGACCTGTCTGGGCTG
GAATTTCAGTCAGTCTGACAGACTGCTAAAGGAGACTCAGGTGTACACTTCAGCAACTTG
ATAACTCTTCCCCAGCTGAAAGTCGAATCATTTGATCCAACGGGAAAGAAGCTAAAATTG
[T,C]
CCTGACAGCTAAAGAGCGATCTGACCTTTGTGATCAGGAGGAGAATTTCTTGTGATACAG
AAAGTGAAAGTAGAAACTGGAATGATGGTATTGATGATGAAGGCATTTAGAGCAGCAGGC
ACTGCCATTCATTAAAAGATTGCACTGTGTCAGGCACATGCTTTATCCTATTGAACCATC
ATGCCAAACTTGGGACACTTAGGTATCATTGTTTTTCATTTTCCATTAAGAACTTGAGGA
TTAAAGCTGTTAATCTATCTGTTCATGGTGAAATGAGTAGTATGTGGCCTGGGTTTGAAC

67541 GATGATGAAGGCATTTAGAGCAGCAGGCACTGCCATTCATTAAAAGATTGCACTGTGTCA
GGCACATGCTTTATCCTATTGAACCATCATGCCAAACTTGGGACACTTAGGTATCATTGT
TTTTCATTTTCCATTAAGAACTTGAGGATTAAAGCTGTTAATCTATCTGTTCATGGTGAA
ATGAGTAGTATGTGGCCTGGGTTTGAACCTTTGTTATAGCTGCAATTTTTTCAGAGCTTT
TAATTGTTGAACTACACGGTGTTTCTGGGGCTATTCTTGATCTTTGCACAGTGTGGGGGC
[G,T]
AAAGTTGGTCCTTTTTAGGAATTCAACTATTCTCTCATTTAGTTATGGCCAAGAAAGGAGA
GGCTCAGAGATCAGTTGGTGCCTCAAAAGGTCGCTCTTCCCTGCAGCCGACTTAATATGT
CTCCTAGCTCCCAGTCCAGTGCTCCAGCAAGATCCGGAAGCTAAATATTCCCTGAAGCCT
TTATAATCTATTGAGAATACACAACAGAGTTGCTGGGAGTTTTTCCAAGGCAGTAAGTCT
CATTTTTCTTATTAGTTTGGATCCCCTGAACCCTTAAGGTAGTATCTCAAATGCAGTTAA

67608 GCTTTATCCTATTGAACCATCATGCCAAACTTGGGACACTTAGGTATCATTGTTTTTCAT
TTTCCATTAAGAACTTGAGGATTAAAGCTGTTAATCTATCTGTTCATGGTGAAATGAGTA
GTATGTGCCCTGGGTTTGAACCTTTGTTATAGCTGCAATTTTTTCAGAGCTTTTAATTGT
TGAACTACACGGTGTTTCTGGGGCTATTCTTGATCTTTGCACAGTGTGGGGGCGAAAGTT

GGTCCTTTTAGGAATTCAACTATTCTCTCATTTAGTTATGGCCAAGAAAGGAGAGGCTCA
[G,A]
AGATCAGTTGGTGCCTCAAAAGGTCGCTCTTCCCTGCAGCCGACTTAATATGTCTCCTAG
CTCCCAGTCCAGTGCTCCAGCAAGATCCGGAAGCTAAATATTCCCTGAAGCCTTTATAAT
CTATTGAGAATACACAACAGAGTTGCTGGGAGTTTTTCCAAGGCAGTAAGTCTCATTTTT
CTTATTAGTTTGGATCCCCTGAACCCTTAAGGTAGTATCTCAAATGCAGTTAAGTGTTCA
ACCAATATTTGTTGCAAGAATAAACATTACTAGTAAGAAATGTGATCTTGGAGACAATAT

67670 TCCATTAAGAACTTGAGGATTAAAGCTGTTAATCTATCTGTTCATGGTGAAATGAGTAGT
ATGTGGCCTGGGTTTGAACCTTTGTTATAGCTGCAATTTTTTCAGAGCTTTTAATTGTTG
AACTACACGGTGTTTCTGGGGCTATTCTTGATCTTTGCACAGTGTGGGGGCGAAAGTTGG
TCCTTTTAGGAATTCAACTATTCTCTCATTTAGTTATGGCCAAGAAAGGAGAGGCTCAGA
GATCAGTTGGTGCCTCAAAAGGTCGCTCTTCCCTGCAGCCGACTTAATATGTCTCCTAGC
[T,C]
CCCAGTCCAGTGCTCCAGCAAGATCCGGAAGCTAAATATTCCCTGAAGCCTTTATAATCT
ATTGAGAATACACAACAGAGTTGCTGGGAGTTTTTCCAAGGCAGTAAGTCTCATTTTTCT
TATTAGTTTGGATCCCCTGAACCCTTAAGGTAGTATCTCAAATGCAGTTAAGTGTTCAAC
CAATATTTGTTGCAAGAATAAACATTACTAGTAAGAAATGTGATCTTGGAGACAATATTT
TATGTTCCTAGTCTCTAGTTTTCCTATTTTTGAAATAAGCAGGTGTGTTCTAGATATTTC

70638 GACATTGCCAGCCTTCTTTCCCTTTCCGGGACCTTGGAAACCCTGTCCATTGGTAACCAG
TTTGATGGCTAAGCTCCATTTTTCCATCATGTTTCCTAGACAACGCCATGCAAGCTTCTG
CTCCAGCCCCTTTGGAGCTCTGATTCAGACACTAATCTCAGGCCCTCCAAGGAAGCATCA
TTCAGACCTTCCCTGCTTCCTGCAGAGGCACATGTAGTACAGTACGTGAGGCTTTCTATG
GAGCTGCTCTCATTTTTGTTCATTAACTTCTCTCCCTGGGAGGAGGCATGCCAGGGAGGG
[C,T]
GTTTATCAAGATGAGGCACATGACAATAGGAGCACCAGATTTCCAGTCCCTGTTTTGTTA
TCAGAAGTTCGCTTTCCAGACTTGGGCAAATCACTTTAATGTCTCTTGCTTAAAACCTTG
ACTAGCTTTTCAATGTTTTTGGGGACAAGGACTCAAGGCCTTAGAGATCTTGTGATCTCT
CTACATGTGTAATAAATATATAAACCATAATATAGCTGCTTATTATCAAGTATCATGCAC
TGTACATGACTGTATGTGCTATACTTTTATATGCAACTGGCAGCACAGTAGGTTTCTTTA

70767 CTTTGGAGCTCTGATTCAGACACTAATCTCAGGCCCTCCAAGGAAGCATCATTCAGACCT
TCCCTGCTTCCTGCAGAGGCACATGTAGTACAGTACGTGAGGCTTTCTATGGAGCTGCTC
TCATTTTTGTTCATTAACTTCTCTCCCTGGGAGGAGGCATGCCAGGGAGGGCGTTTATCA
AGATGAGGCACATGACAATAGGAGCACCAGATTTCCAGTCCCTGTTTTGTTATCAGAAGT
TCGCTTTCCAGACTTGGGCAAATCACTTTAATGTCTCTTGCTTAAAACCTTGACTAGCTT
[T,C]
TCAATGTTTTTGGGGACAAGGACTCAAGGCCTTAGAGATCTTGTGATCTCTCTACATGTG
TAATAAATATATAAACCATAATATAGCTGCTTATTATCAAGTATCATGCACTGTACATGA
CTGTATGTGCTATACTTTTATATGCAACTGGCAGCACAGTAGGTTTCTTTAAACCAGCAT
CAACACAAACACATTAGTAATGCATTGTGTTACAACATTACCATGGCAGAGATATTACTA
GACAATAGGAATTTTTCAGCTCTATTATAATCTTATGGGACCACCATCATATAAGCAGGT

71275 TGTTACAACATTACCATGGCAGAGATATTACTAGACAATAGGAATTTTTCAGCTCTATTA
TAATCTTATGGGACCACCATCATATAAGCAGGTCATTGTTAACCAAAACATCATTACATG
GTACATGACTATATTTTGGTATAATTTTATACAAAAAAAAATTGCCTGACTTTTGCCTAC
CTACCCAGCTCCTACTTCCTTGAGTTCACTCCTTTGTGCACTCCAACCCCACTCACCTAT
CTGTTATCCTTCTGACACACCCTATTGCCTCCTTCCATTTGGCTTTATCCTACAAAGTTT
[G,A]
CTGTTTACAAAGTTTACTCTGAAATAGAGGTCATCATTTTGAAGACTAGAAAACCAAGGC
ACAGAGACTTACATGCCTTGCCCAAGTTTGCATAGTTTGTAAATGGAAAAGCTGGGGAAA
ATCCACGGAAACTTGGCTCTGGATTCCATGCTATTGACCAACTCCTGACTTCCTGCCCTG
CTAGACCTTAGTGGGTGGTCATGAAATAAAGGATGTAGGAACAGTGTGCCAAGAGTTCTG
TTGGATTATTTTAGCTGAAATCTCATAATGGCTTTTTATAGAATATTAATGACTTACAGA

71401 GACTATATTTTGGTATAATTTTATACAAAAAAAAATTGCCTGACTTTTGCCTACCTACCC
AGCTCCTACTTCCTTGAGTTCACTCCTTTGTGCACTCCAACCCCACTCACCTATCTGTTA
TCCTTCTGACACACCCTATTGCCTCCTTCCATTTGGCTTTATCCTACAAAGTTTGCTGTT
TACAAAGTTTACTCTGAAATAGAGGTCATCATTTTGAAGACTAGAAAACCAAGGCACAGA
GACTTACATGCCTTGCCCAAGTTTGCATAGTTTGTAAATGGAAAAGCTGGGGAAAATCCA
[C,A]
GGAAACTTGGCTCTGGATTCCATGCTATTGACCAACTCCTGACTTCCTGCCCTGCTAGAC
CTTAGTGGGTGGTCATGAAATAAAGGATGTAGGAACAGTGTGCCAAGAGTTCTGTTGGAT
TATTTTAGCTGAAATCTCATAATGGCTTTTTATAGAATATTAATGACTTACAGAGCTCTT
TGCTCTGGGTTATGGACTTAGGTTTCTAAATTGTCATCTCCTTCTAGATAACTTTTCAGG
AACTTATCAGCACCCACACAGGACTGGATGTGCTTTTGGAAGGTACCATGGAGGCTGATA

71656 CCCAAGTTTGCATAGTTTGTAAATGGAAAAGCTGGGGAAAATCCACGGAAACTTGGCTCT
GGATTCCATGCTATTGACCAACTCCTGACTTCCTGCCCTGCTAGACCTTAGTGGGTGGTC
ATGAAATAAAGGATGTAGGAACAGTGTGCCAAGAGTTCTGTTGGATTATTTTAGCTGAAA

```
        TCTCATAATGGCTTTTTATAGAATATTAATGACTTACAGAGCTCTTTGCTCTGGGTTATG
        GACTTAGGTTTCTAAATTGTCATCTCCTTCTAGATAACTTTTCAGGAACTTATCAGCACC
        [C,T]
        ACACAGGACTGGATGTGCTTTTGGAAGGTACCATGGAGGCTGATATGGTGTGGCTATATC
        AAATCTCATCTTGAATTGTAGCTCCCATAACCCCCACGTGTCAAGGGAGGGACCAGGTGG
        GAGGTAATTAAATCATGGGTGTGTGTTTTTCCGTGCTGTCCTCGTGACAGTGAATAAGTC
        TCATGAGATCTGATGGTTTTATAAAGGGCAGTTCCCCTGCACATGCTTTCTTGCCTGCCA
        CCATGTAAGAAGTGCCTTTGCTCTTCTACCATGATTGTGAGGCCTCCCTAGCTGTGTGCA

71969   ATGTGCTTTTGGAAGGTACCATGGAGGCTGATATGGTGTGGCTATATCAAATCTCATCTT
        GAATTGTAGCTCCCATAACCCCCACGTGTCAAGGGAGGGACCAGGTGGGAGGTAATTAAA
        TCATGGGTGTGTGTTTTTCCGTGCTGTCCTCGTGACAGTGAATAAGTCTCATGAGATCTG
        ATGGTTTTATAAAGGGCAGTTCCCCTGCACATGCTTTCTTGCCTGCCACCATGTAAGAAG
        TGCCTTTGCTCTTCTACCATGATTGTGAGGCCTCCCTAGCTGTGTGCAACTGTGAGTCTA
        [C,T]
        TTAACCTCTTTTTCTTTATAAACTACTCAGTCTTGGGTGTGCTTTTATTAGCAGCATGAC
        AACAGACTAGTCTAATACAGAGGCTTTGGGCATAAGCTATGGGCCTTTGGTTTTGAGGTT
        CTCCAATATTCAGCTGGGAAATTATGTACCACTAAGATGAGTTTTGGAGAAGCCTCCTTG
        AGAGTAATTAAACCAGAGCAGCAAAACAATAGACTCCTACCTGTATGGAAAGGACAGAGT
        CACAAGTCAAAGCTTCAGGCTGAACCTTTCTTAGCAAAGTGAGAAGGGTAGATCTGAGAC

72194   CCACCATGTAAGAAGTGCCTTTGCTCTTCTACCATGATTGTGAGGCCTCCCTAGCTGTGT
        GCAACTGTGAGTCTACTTAACCTCTTTTTCTTTATAAACTACTCAGTCTTGGGTGTGCTT
        TTATTAGCAGCATGACAACAGACTAGTCTAATACAGAGGCTTTGGGCATAAGCTATGGGC
        CTTTGGTTTTGAGGTTCTCCAATATTCAGCTGGGAAATTATGTACCACTAAGATGAGTTT
        TGGAGAAGCCTCCTTGAGAGTAATTAAACCAGAGCAGCAAAACAATAGACTCCTACCTGT
        [A,G]
        TGGAAAGGACAGAGTCACAAGTCAAAGCTTCAGGCTGAACCTTTCTTAGCAAAGTGAGAA
        GGGTAGATCTGAGACAAAGGAGCAGGGATTTTTTTTAGGTTGATTCCTGTATTTATGTAA
        CTTCTTTCTCCTCAACAGTACAGGTTTCTTCATGATACATGTCTTCAAGACAGCATTGGA
        GTAAAGGATTCTCAGTGGCCTTGTTTTATTCAATGGCATTTAGTAAACGTGGGGAAGGGA
        TCAAGAGTCCACATCAGATCCTGGCCCTGGAGCAGCTTTTCTAGTCGGGGGTCATGATAG

72292   CTACTCAGTCTTGGGTGTGCTTTTATTAGCAGCATGACAACAGACTAGTCTAATACAGAG
        GCTTTGGGCATAAGCTATGGGCCTTTGGTTTTGAGGTTCTCCAATATTCAGCTGGGAAAT
        TATGTACCACTAAGATGAGTTTTGGAGAAGCCTCCTTGAGAGTAATTAAACCAGAGCAGC
        AAAACAATAGACTCCTACCTGTATGGAAAGGACAGAGTCACAAGTCAAAGCTTCAGGCTG
        AACCTTTCTTAGCAAAGTGAGAAGGGTAGATCTGAGACAAAGGAGCAGGGATTTTTTTTA
        [A,G]
        GTTGATTCCTGTATTTATGTAACTTCTTTCTCCTCAACAGTACAGGTTTCTTCATGATAC
        ATGTCTTCAAGACAGCATTGGAGTAAAGGATTCTCAGTGGCCTTGTTTTATTCAATGGCA
        TTTAGTAAACGTGGGGAAGGGATCAAGAGTCCACATCAGATCCTGGCCCTGGAGCAGCTT
        TTCTAGTCGGGGGTCATGATAGCTACAGTCTCTCTAGTATCTTCTCTGTGCCATTTAAAT
        AAATAAATCAGAGAATTGGACTCAGAATCTGATTCTCTGATTCCGCTGAGTCAGTTCTTG

72351   GGCTTTGGGCATAAGCTATGGGCCTTTGGTTTTGAGGTTCTCCAATATTCAGCTGGGAAA
        TTATGTACCACTAAGATGAGTTTTGGAGAAGCCTCCTTGAGAGTAATTAAACCAGAGCAG
        CAAAACAATAGACTCCTACCTGTATGGAAAGGACAGAGTCACAAGTCAAAGCTTCAGGCT
        GAACCTTTCTTAGCAAAGTGAGAAGGGTAGATCTGAGACAAAGGAGCAGGGATTTTTTTT
        AGGTTGATTCCTGTATTTATGTAACTTCTTTCTCCTCAACAGTACAGGTTTCTTCATGAT
        [A,G]
        CATGTCTTCAAGACAGCATTGGAGTAAAGGATTCTCAGTGGCCTTGTTTTATTCAATGGC
        ATTTAGTAAACGTGGGGAAGGGATCAAGAGTCCACATCAGATCCTGGCCCTGGAGCAGCT
        TTTCTAGTCGGGGGTCATGATAGCTACAGTCTCTCTAGTATCTTCTCTGTGCCATTTAAA
        TAAATAAATCAGAGAATTGGACTCAGAATCTGATTCTCTGATTCCGCTGAGTCAGTTCTT
        GGCCAGGGTCATGAAACTGGTAACTTGTACAGCCTGGACCCGTACTCAAGGATGTGAGAC

72382   TTGAGGTTCTCCAATATTCAGCTGGGAAATTATGTACCACTAAGATGAGTTTTGGAGAAG
        CCTCCTTGAGAGTAATTAAACCAGAGCAGCAAAACAATAGACTCCTACCTGTATGGAAAG
        GACAGAGTCACAAGTCAAAGCTTCAGGCTGAACCTTTCTTAGCAAAGTGAGAAGGGTAGA
        TCTGAGACAAAGGAGCAGGGATTTTTTTTAGGTTGATTCCTGTATTTATGTAACTTCTTT
        CTCCTCAACAGTACAGGTTTCTTCATGATACATGTCTTCAAGACAGCATTGGAGTAAAGG
        [A,C]
        TTCTCAGTGGCCTTGTTTTATTCAATGGCATTTAGTAAACGTGGGGAAGGGATCAAGAGT
        CCACATCAGATCCTGGCCCTGGAGCAGCTTTTCTAGTCGGGGGTCATGATAGCTACAGTC
        TCTCTAGTATCTTCTCTGTGCCATTTAAATAAATAAATCAGAGAATTGGACTCAGAATCT
        GATTCTCTGATTCCGCTGAGTCAGTTCTTGGCCAGGGTCATGAAACTGGTAACTTGTACA
        GCCTGGACCCGTACTCAAGGATGTGAGACTTGGAGTGGGGTTGAGAGGAGGACAGTTCA

72424   AGATGAGTTTTGGAGAAGCCTCCTTGAGAGTAATTAAACCAGAGCAGCAAAACAATAGAC
        TCCTACCTGTATGGAAAGGACAGAGTCACAAGTCAAAGCTTCAGGCTGAACCTTTCTTAG
```

```
          CAAAGTGAGAAGGGTAGATCTGAGACAAAGGAGCAGGGATTTTTTTTAGGTTGATTCCTG
          TATTTATGTAACTTCTTTCTCCTCAACAGTACAGGTTTCTTCATGATACATGTCTTCAAG
          ACAGCATTGGAGTAAAGGATTCTCAGTGGCCTTGTTTTATTCAATGGCATTTAGTAAACG
          [G,T]
          GGGGAAGGGATCAAGAGTCCACATCAGATCCTGGCCCTGGAGCAGCTTTTCTAGTCGGGG
          GTCATGATAGCTACAGTCTCTCTAGTATCTTCTCTGTGCCATTTAAATAAATAAATCAGA
          GAATTGGACTCAGAATCTGATTCTCTGATTCCGCTGAGTCAGTTCTTGGCCAGGGTCATG
          AAACTGGTAACTTGTACAGCCTGGACCCGTACTCAAGGATGTGAGACTTGGAGTGGGGGT
          TGAGAGGAGGACAGTTCATGACAAGCCTGACCCAACATAGTGCTGTGCCCAATTAGCTAG

72466     AGCAGCAAAACAATAGACTCCTACCTGTATGGAAAGGACAGAGTCACAAGTCAAAGCTTC
          AGGCTGAACCTTTCTTAGCAAAGTGAGAAGGGTAGATCTGAGACAAAGGAGCAGGGATTT
          TTTTTAGGTTGATTCCTGTATTTATGTAACTTCTTTCTCCTCAACAGTACAGGTTTCTTC
          ATGATACATGTCTTCAAGACAGCATTGGAGTAAAGGATTCTCAGTGGCCTTGTTTTATTC
          AATGGCATTTAGTAAACGTGGGGAAGGGATCAAGAGTCCACATCAGATCCTGGCCCTGGA
          [G,A]
          CAGCTTTTCTAGTCGGGGGTCATGATAGCTACAGTCTCTCTAGTATCTTCTCTGTGCCAT
          TTAAATAAATAAATCAGAGAATTGGACTCAGAATCTGATTCTCTGATTCCGCTGAGTCAG
          TTCTTGGCCAGGGTCATGAAACTGGTAACTTGTACAGCCTGGACCCGTACTCAAGGATGT
          GAGACTTGGAGTGGGGGTTGAGAGGAGGACAGTTCATGACAAGCCTGACCCAACATAGTG
          CTGTGCCCAATTAGCTAGCTACACAGATAAGCAAACTGAGGCTACCACTGGGTCAGTTCT

72829     AAATAAATAAATCAGAGAATTGGACTCAGAATCTGATTCTCTGATTCCGCTGAGTCAGTT
          CTTGGCCAGGGTCATGAAACTGGTAACTTGTACAGCCTGGACCCGTACTCAAGGATGTGA
          GACTTGGAGTGGGGGTTGAGAGGAGGACAGTTCATGACAAGCCTGACCCAACATAGTGCT
          GTGCCCAATTAGCTAGCTACACAGATAAGCAAACTGAGGCTACCACTGGGTCAGTTCTTG
          GCAAGGGTCAGGAAGCTGTAACTTGTAGAGCCTGGACAAGTGTCTGTGATGTCAAACCCC
          [G,A]
          TCCATGTAACTGCTAGTTACTATATGGGAACTCAAGTTTATTACTTAACTGTATTAAGCT
          TCCATTTTCTCTAAGAAATGGGGGAAAAAAAGCTTTTACCTTGGCTTAAAGCAGTTGCAA
          GAATTAAAAAGTTAATTCATGTTGTTTATTTATCAGAATGCCTAGCACATTATAAGTCTC
          AGTATAGGAGAATTGTATTATTCTTACCATCATCACCATCACCACCATTATTTGCCAAGA
          GAGAGGTATATGCAAAGTGCTATAGTGGTTCAAAGGAGGGGGCAATCGCTTCCACCAGGA

72913     AACTTGTACAGCCTGGACCCGTACTCAAGGATGTGAGACTTGGAGTGGGGGTTGAGAGGA
          GGACAGTTCATGACAAGCCTGACCCAACATAGTGCTGTGCCCAATTAGCTAGCTACACAG
          ATAAGCAAACTGAGGCTACCACTGGGTCAGTTCTTGGCAAGGGTCAGGAAGCTGTAACTT
          GTAGAGCCTGGACAAGTGTCTGTGATGTCAAACCCCGTCCATGTAACTGCTAGTTACTAT
          ATGGGAACTCAAGTTTATTACTTAACTGTATTAAGCTTCCATTTTCTCTAAGAAATGGGG
          [G,-]
          AAAAAAAGCTTTTACCTTGGCTTAAAGCAGTTGCAAGAATTAAAAAGTTAATTCATGTTG
          TTTATTTATCAGAATGCCTAGCACATTATAAGTCTCAGTATAGGAGAATTGTATTATTCT
          TACCATCATCACCATCACCACCATTATTTGCCAAGAGAGAGGTATATGCAAAGTGCTATA
          GTGGTTCAAAGGAGGGGCAATCGCTTCCACCAGGAAGACAGTGGAGGGTAGTGTGAGGA
          TAAATGTAAAACCTGAAAATTTAAACTTGAACTTGAAAGGAGACTGTGTATGTGGGAATT

73395     TGGTTCAAAGGAGGGGGCAATCGCTTCCACCAGGAAGACAGTGGAGGGTAGTGTGAGGAT
          AAATGTAAAACCTGAAAATTTAAACTTGAACTTGAAAGGAGACTGTGTATGTGGGAATTT
          TGGATCAAAAGGGGATTCCAATAGAAGAAACAGCTGAGTTAAAGCAAAGCGATAGAACAC
          TGATAACGACTATGAATGGTGAATAGAGCATTTTGGCTGATTGCTGTGTACCTAAATGGA
          GATGAGGGTGGAAAGATGCATTGGGGGGTAAGACTTTGAGAACCAAGTTCATTTGAGAAC
          [C,G]
          AAGTTCATTTGAGAACAACTACGAATGGTGAATAGAGCATTTTGGCTGATTGCTGTGTAC
          CTAAATGGAGGTGAGGGTGGAAACATGCATTGGGGGATAACTATGAGAACCAAGTTAAGG
          GAAGTGTCATGAGCAGAGCTATGCTCCAAAAAGATTTAGCAGGCCATCTATACCCATTAT
          GTCTGGGGTGCATATGAGGGAGTTACAGGATGTGAGACTTGGAGTGGGGGTGGAGGGAGG
          GCAGTTCATGACAAGCCTGACCCAACACACTGTTGTGTCCAATTAGCACGACCTATTTTG

73961     CACACTGTTGTGTCCAATTAGCACGACCTATTTTGGCTTTGAATGGGGAAGGAGAATCTG
          TGACCTCTGAGTCAGCCTTTATGGAATGCTCAAGCATTAACAGGTCTTGCAAGATGCATT
          CTCTATCAGTCATAGTACTTTAATAATGGTTCCTTACTCAGCTTCATTCATTCATTGGAA
          ATTCATGCATGTCTTTGTAGTCCATAGGATTCTCAGAATAACCTTGTGACTAGACGAGAG
          AAATATTGACTGTGCGATTACTGAAGGCAAAGACTGTTTGTGATGCTTGATTACTTGATT
          [T,C]
          TTGCATATCCAACAAGTGAATGAGTGAGTAAGTGAGTGAGTGAGTGAATGATTGAATCTC
          CACTTGACTCCTGAGGCAACTGAGATGAGGAGATATTAAAATATCTCAAGGTGTCATTAT
          TGGACACACATATGACTAGGACTTTTGTTACTTTCATACTTCTCCATTTACAATTTCTTA
          AAAGAGTACTTTCCAAAGTATATACAATTTAATGATTTGAAATCCTGCTTGCGGCCAGGC
          ACGGTGGCTCATGCCTGTAATCCCAGCACTTTGGGAGGCTGAGGCGTGTGGATCACGAGA

75749     TGCCAACATCAGGCCAACTGAACCCTTGAGAGATTGCCCTATAAACTGTTATTGGAGCAG
```

FIGURE 3, page 90 of 122

CATCTGTTTGCCAGGGTAAATATTCAGTCATATGGACTGGGCCCTGGAGTCTTCAGATGG
TGCAGCCCTTCCCAGAGGGAAGACTTCATGGGGGTCCAAATGCTGGTAAGAAGTTTTTGT
TTGTCTGTGTCTGCCATCACAGCATAGAGATTAAGAACCTGGTATTTGGAATCAGACAGA
TTTTTGTGTATTATTTACCTGTTGCTGCATAACAAATTGCCCCCAAACTCGGTGACTTTC
[T,C]
ACAACAATCTTTGTTTATTATCTCTTATGGATCCCTGGGCCAAGAATTCACATGGAGCAC
AATGGAGAAGGATGGAAGACCTGAAAACTAAACTGAAATCATCTAAAGACTTATTTACTC
ATGTGAGCTGTGTTGGAGCTGTCAGCTGCAACACTTACACAAGGCCTCTGCATTGGGCCT
GAACTTCCTCACAACATGGTGACTGGGTCTTAAGGATTGGCCTAGATAAAGTCATGGCAG
AGACCACTCATGGAAAGCTATGTCAACAATGGAAGATGAATGGCCAGGATGAAGACAGAG

77275 TTTTCTATATATGAAATCATACTATTTGTGGTCCTTTGTGACTGGCCTCTTTCACTTAGC
ATAATGTTTTCAAGGTTCATTCATGTCTTAGCATGTATCAGTGCTTCATCCCTTTATGGT
ATATCCATAAAATGAAATATTATAGGACTATAGTATTTCATTTTATGGATATACCATATT
TTGTTTATCCATTTATTAGTTGATAGACATTTGAGTTGTTTTTACTTTTTGACTACTATG
ACTAATGCTGCTATGGAAATTCTTTTACAAGTTGTCATGTGGCCATATGTTTTCATTTTT
[C,T]
TTGAGTGTGTACCTAGTGGTGAAATTGCTGTGTTATGTAGTAACTCTATGTTTAGCCTTT
TGAGGAACTGCCAAACTGTTTTCCAAAGTGATTGCACCAGTTTACATTCTCACCAGCAAT
ATATGAGGGTTTCAATTTCTCCACATCCTTACCAACACTTGTTATTGTCTGTCTTTTTCA
TTATAGTCATTCTGTGGGTATGAAGTGGTATCTCATTGTGGTTTTGATTTACATTTTGTA
ACGACTGATGGGTGTTGAACATCTTTTTTATTTCCTATTGGTTATTTTGTATATCTTCTT

77282 TATATGAAATCATACTATTTGTGGTCCTTTGTGACTGGCCTCTTTCACTTAGCATAATGT
TTTCAAGGTTCATTCATGTCTTAGCATGTATCAGTGCTTCATCCCTTTATGGTATATCCA
TAAAATGAAATATTATAGGACTATAGTATTTCATTTTATGGATATACCATATTTTGTTTA
TCCATTTATTAGTTGATAGACATTTGAGTTGTTTTTACTTTTTGACTACTATGACTAATG
CTGCTATGGAAATTCTTTTACAAGTTGTCATGTGGCCATATGTTTTCATTTTTCTTGAGT
[G,A]
TGTACCTAGTGGTGAAATTGCTGTGTTATGTAGTAACTCTATGTTTAGCCTTTTGAGGAA
CTGCCAAACTGTTTTCCAAAGTGATTGCACCAGTTTACATTCTCACCAGCAATATATGAG
GGTTTCAATTTCTCCACATCCTTACCAACACTTGTTATTGTCTGTCTTTTTCATTATAGT
CATTCTGTGGGTATGAAGTGGTATCTCATTGTGGTTTTGATTTACATTTTGTAACGACTG
ATGGGTGTTGAACATCTTTTTTATTTCCTATTGGTTATTTTGTATATCTTCTTTGGAGAA

81236 TTGTGTTTGCTTAGTACTTCTTTCTTAAGGTTGTTGGCAAGAGCATCTGCTGGTAACTTG
GCTCAGTGTGTTGTAGGTTTTTGTATATGGTTTGGGTTTCCTATTCCTGGGCATTGAACT
ATTAAGATTCCTGCAGATAGGCATAACTACTTACAGCCTTTTCTGTGTATATATTAGCTC
TTACGGACCTCATAAACCTAAAGAGGTGCAGAGGAAAAGTGCCATCATTCTCATTTTACA
ACTGGGGAAGCAGAGGCCCAGAAAAGTGATCTAACTTTCCCAAGTTCACAAATGTGTTAT
[T,C]
AGAGCTGCAACCAGAGCTAAGGTTGAGGCTTTATGAACCTTAGGTTACTATTCGGTTAAT
AGGCTCAGTGCAGCCTTACCTTACTAATTATTAAAAATAGACAACATTAGGATTTAAACC
AGATGGTCTTTTCCTGTTGTTCACACTCTTACCCACTGTCAGCAATGGCCCATCAGATAA
TCCACACTGATTCATGAAAAGGCAAATATTTTCTGTTTCTGTTCTAAGCTAGGCTTGCCA
AAACCGAGAGCAATATTCTCTATCCCCGAGATGCATTGCTTCAAGCACCTATCTACTTTC

82536 GCCTGAATGAGTAATTCCTTCTGGATTACTAATATCAAAAGTCCATTTGTATCTGATTGA
GATGAGGAAAGAAATGCAGGATGGAGCAGGGAACCAGTCCTCACACTACATGGTTTACTC
CAGCGATTCTCAACGTTAGCACTACCTATGTTTTGCACAGGGTTAGTCTTTGTTTTGGGG
GGCTGTCCTGCACAATGGAGGATGTTCATCAGTATCCTTGGCCTCTATCCATTATAAGAT
GCCAGCAGCAAACCAACCTCCTCCAAGTTCTGATGACCAAAACTATATCCAGATATTTGC
[C,T]
GACTGGGGGCACTTGCCCCCAGTTGAGAGTCACTAATTACACAGTACATTTGTCCATGAT
GGGGACATGTAGGCTCACGGGGTAGCCAGTGACAGGCAGGCAGACAGGAGTGGGGAATTT
TTTTTCTGTAAAGGCCCCAAGTAGCAAATATTTTAGGCACTGTCTGTCCCAACTACTAAA
CTCTGCCATGTAGCTTGAAAGCAGCCAAAGACAACACATAAATGAACATGTTCCAGCAAA
ACTATTTATGGGCCCTGAAATTTGAATTTCATATAATTTTCATGTGTCACTAAGTAATCT

82954 TTTTTTTTCTGTAAAGGCCCCAAGTAGCAAATATTTTAGGCACTGTCTGTCCCAACTACT
AAACTCTGCCATGTAGCTTGAAAGCAGCCAAAGACAACACATAAATGAACATGTTCCAGC
AAAACTATTTATGGGCCCTGAAATTTGAATTTCATATAATTTTCATGTGTCACTAAGTAA
TCTTTTTAAAATTTTTATTCAACCACCTAAAAATGTTAAAACTATACATGAGTCGTACAA
AATCAGGTGGTGGGCTAGACTTGGCCCATGAGCCATAGTTTTCTGACCTTTGGACTAAGA
[A,C]
ATACATGAAGCCGTAACTTCATATTTATCCCTAAGATAAACATGGGATAAATATGATACT
TCTCCTAACACCATCAAATTTACATATAAATTTTAGAGAAAGCATATTATTTTATTAAAA
TGAGCATTGCTATATTTTGGAATAGGACCCAAGCCAAAATGAATTTTAGAGATAAAACAT
TATATTCCAAAGTTATATCTTGCTTCCCATGGGCTGTTGACCCATGCCTCAGGTCCCCAG
AGGCCTTCATTTCCTGCCTTCATTTTCCCTTGCTTTTAGGCTACCTTGGTAGGAAAACTT

84157 TAGAGCTGTCAGCCGTGGATGGGAGATCAGGGATTGGCTGGCAAAAGTGCCAGGGTGTTG
ACAGGCATAGTCTCAGTCATCTCCACAGTTCTTCCTGGCTGGAAATGCCTCTGGCTATAT
TACCCTTATTGCATGATTTCATGGTACTGATCAGATCCAAAGAAGGAGGATGATTGTGAG
ATGCAAAGCTCAGGGGACGACTACGCGGTGAAGGTGAGAGAATGCCCAGAGCTTTGAAGA
GGCTGCTTCTTCTTCAAAGCTGTGTTCCAGCAGAGCACATTTTGTGCATACTTGAATTTT
[G,C]
GTTGGCTCTAGGCTGAGCGCATTCTATTGTGGCGTTGGCATGGGAAGAGGGAGGCATGCG
AGAAATATTGCATCTCTGCTATTCTCCTGGGCCCTTGTGAATGGGAATGTCTTCTTAATG
AGCCTATCCCAGAGAGTCTGGCCTTTCAGATAAACAAATAAGCATCAGCAGGAGATGCTC
ACAAAAGGACTGGGCAAAATAGGGCCACGTTGAGTGACAACCCAAATAAAGGAGTCCTAA
GAGGTCTGAAGCTGGTGGCTAATGAGCACATCTCCTCATTTGTGATTTCTTGGCCAGGAC

85443 GCTCGTGAGGCCTGGCACGGAATTAGCAAGACTAAAGGCTCTGTCCCAGTCCAACCTTCT
GTGAGTCTATAACTGAAGCATCCAAAGTATAAGCTGGGTGATTAGGGGAAGAAGAAGTCA
CCTAGCTGGCAAGGGGCCTAAAACTCAAGTCCCCTCCTTCTAGGACCAGAGTACTCACCA
ACTACCAAGCTGCCTTAAAATAAAAACATTCAAGAACAAGTGATGTGCAGAGAGGCAACA
CAGTGATAAGTAACTGGGGTCTGGAAATGGGAGACTTCAACTTCAATTTCAGCACTGTTA
[T,G]
TTTGGTAGTTTAATGATTTAGAGTCAGTTGTTTAATCTCTTAGAGACTCAGTTACTTCAT
CAGCAAGGGTGTTACTATAGTAATACCTGCTAGACATTATTATTATATGGAGAGAGAGAG
CTTGGTAAGCTGTGACATATACATTCTAGTTGGTGGTTGTTTCTGTTGTTATTATTAATA
GTAACAACAATAAATATCCTGTTGTTTATTTTTTTGAAGTGTTCAGTGGCTGGTAACTGA
ATTAGAGTGCCTGGAGATATAGGTAAGGGTTTTTTGTTTTAATAATCATTATCTTTGTTC

85674 GAGGCAACACAGTGATAAGTAACTGGGGTCTGGAAATGGGAGACTTCAACTTCAATTTCA
GCACTGTTATTTTGGTAGTTTAATGATTTAGAGTCAGTTGTTTAATCTCTTAGAGACTCA
GTTACTTCATCAGCAAGGGTGTTACTATAGTAATACCTGCTAGACATTATTATTATATGG
AGAGAGAGAGCTTGGTAAGCTGTGACATATACATTCTAGTTGGTGGTTGTTTCTGTTGTT
ATTATTAATAGTAACAACAATAAATATCCTGTTGTTTATTTTTTTGAAGTGTTCAGTGGC
[T,C]
GGTAACTGAATTAGAGTGCCTGGAGATATAGGTAAGGGTTTTTTGTTTTAATAATCATTA
TCTTTGTTCAAGAGAATAGGAAAAATATAAGCCTCTTTTTAACTTTAATGCAAAAAAGTC
TTTATAGCTTGTGTGTGAAAAACAAGAGGAAGGGAGGAAGGGGAGGAAAGAGATTGTCTA
TTTCTACTTAAAGCTAATTAGAGAAGTAATTTTAGGTAAGAGTATTATGACCTGATTTCT
GATTAATTTAAGTATTATTATACTGTTGTAATAGAAATCCCTGAAGTGCTTTATTGATTA

85850 ATGGAGAGAGAGAGCTTGGTAAGCTGTGACATATACATTCTAGTTGGTGGTTGTTTCTGT
TGTTATTATTAATAGTAACAACAATAAATATCCTGTTGTTTATTTTTTTGAAGTGTTCAG
TGGCTGGTAACTGAATTAGAGTGCCTGGAGATATAGGTAAGGGTTTTTTGTTTTAATAAT
CATTATCTTTGTTCAAGAGAATAGGAAAAATATAAGCCTCTTTTTAACTTTAATGCAAAA
AAGTCTTTATAGCTTGTGTGTGAAAAACAAGAGGAAGGGAGGAAGGGGAGGAAAGAGATT
[G,A]
TCTATTTCTACTTAAAGCTAATTAGAGAAGTAATTTTAGGTAAGAGTATTATGACCTGAT
TTCTGATTAATTTAAGTATTATTATACTGTTGTAATAGAAATCCCTGAAGTGCTTTATTG
ATTATCTGTTGGTAGAATGAAAGGGTAAGCAGCTGTAGTAAATAAAATTTTTGTCTGAGG
CAAAGCAAAGGAGAAGTAATATAGGAGAAATTATTATAATAAAGATGGGAGTGAGAGAAG
AAACCTGGGTTCTAGTTCTTTCAGATAGGTGACCTTGAACAAATCTCTTCCCTATACTTG

85905 TCTGTTGTTATTATTAATAGTAACAACAATAAATATCCTGTTGTTTATTTTTTTGAAGTG
TTCAGTGGCTGGTAACTGAATTAGAGTGCCTGGAGATATAGGTAAGGGTTTTTTGTTTTA
ATAATCATTATCTTTGTTCAAGAGAATAGGAAAAATATAAGCCTCTTTTTAACTTTAATG
CAAAAAAGTCTTTATAGCTTGTGTGTGAAAAACAAGAGGAAGGGAGGAAGGGGAGGAAAG
AGATTGTCTATTTCTACTTAAAGCTAATTAGAGAAGTAATTTTAGGTAAGAGTATTATGA
[T,C]
CTGATTTCTGATTAATTTAAGTATTATTATACTGTTGTAATAGAAATCCCTGAAGTGCTT
TATTGATTATCTGTTGGTAGAATGAAAGGGTAAGCAGCTGTAGTAAATAAAATTTTTGTC
TGAGGCAAAGCAAAGGAGAAGTAATATAGGAGAAATTATTATAATAAAGATGGGAGTGAG
AGAAGAAACCTGGGTTCTAGTTCTTTCAGATAGGTGACCTTGAACAAATCTCTTCCCTAT
ACTTGGCCTCGGTTTCCCCATCGGAACAACCTAGGGCATACTCTAGATAATCCCTAAGGT

86535 TCTACCTGTACAATACTGAAACAGTGATTAAGAGGGAGAGACACCCACAAAGAAAGAAAT
AGTTTGTGCTGTGCTCAAATGCCTGACTGATAAAAAAGAGAACAGACTCATAAAACCCAC
TAATTCAAATTAAATGGATAATTCTTGTTGATTTTGAGCTGGCAATCTCAGGCTTCTAAA
TCACAAGGAAACTCCATTTGATCCTGCAATGGTCTCTTGGTCTCTTTCTTAGCTCAGTAG
TGCTAAGCACAGAGGTTTCATGGAAATCAAGAGAGAAAGAGAGAGAGAGAGAGAGACAGA
[-,G]
AGAGAGCTGTTTAAAAAAAGAAGAACAATATACTTGGATGAACTAAAGAGTGGTCCTCAT
GAAAGCCTCATAATGTCCATTGCCTACCTGTTTAACCCCTTTGTGGCCTGATTTTTGGTCC
TCAACTGAAATCAAATTAGGTAGTCTTATGTAGGGAAATGAATAACTTGTACACTGTTGT
TGTTTGCCATCTTTAGGACCACCAAAGGGTAACGAATTCAGCAGACCCACAATCCGGCAC
TTCAGGTTTTTGAAATTTACTCATGAAAATTTAGGAAGTCCTAAAGGCTGTGAAAAATCA

FIGURE 3, page 92 of 122

87371 GAGTTGTAGGTGCACTCTGTTCTCTGGTTCTTTGCAGTGTAATGGCAGAACTGAGGTTAG
AATTCTCCTTGGATGTAAGGATCACCAGCCCACCAGGCTGGCAGTTAGACAAGGGAGTGA
TGGATTTGGGATGCTTTGTGTGACCTTGTATACAACAGGTTCTTAGACACAACCCTAGGA
CATGGAAAAGAATTACATTCATCCTGAGCCCCAGCTACTGTTACCAATTCAAATTAGGAC
AACATATTGATTAAGATACAGGTAGTTATGCTACCCTAAGAACTGGAATCTGAATACCTA
[C,G]
TTTTTATTTCTACTTCTACCGCTTGTTAGTAACCTATTCTTGATCCACCATTTAACTTCT
GTGAGCCTCAGTTTCTCCATCTTTAAGACAGTGATGATAATGACAGTATCTGTAGAACAG
CTTAACTTGAACTAAATGAGAAAAACTAAACAAAACACATAGAATTAAGTATGAATTTCT
GAGGTTAGTTTATACATGTTTTAAGAGCTTAGAGAAAAGGAAAAAACATAAGTATCCTAA
GGAGATTAGGAAATGTTTCCTTGGGGAGGTTGGAAAGCAGCTAAGCCTTGAAGAATAGGA

87392 CTCTGGTTCTTTGCAGTGTAATGGCAGAACTGAGGTTAGAATTCTCCTTGGATGTAAGGA
TCACCAGCCCACCAGGCTGGCAGTTAGACAAGGGAGTGATGGATTTGGGATGCTTTGTGT
GACCTTGTATACAACAGGTTCTTAGACACAACCCTAGGACATGGAAAAGAATTACATTCA
TCCTGAGCCCCAGCTACTGTTACCAATTCAAATTAGGACAACATATTGATTAAGATACAG
GTAGTTATGCTACCCTAAGAACTGGAATCTGAATACCTACTTTTTATTTCTACTTCTACC
[G,A]
CTTGTTAGTAACCTATTCTTGATCCACCATTTAACTTCTGTGAGCCTCAGTTTCTCCATC
TTTAAGACAGTGATGATAATGACAGTATCTGTAGAACAGCTTAACTTGAACTAAATGAGA
AAAACTAAACAAAACACATAGAATTAAGTATGAATTTCTGAGGTTAGTTTATACATGTTT
TAAGAGCTTAGAGAAAAGGAAAAAACATAAGTATCCTAAGGAGATTAGGAAATGTTTCCT
TGGGGAGGTTGGAAAGCAGCTAAGCCTTGAAGAATAGGATGTATTTTGAACACTGGGAGA

87423 GAGGTTAGAATTCTCCTTGGATGTAAGGATCACCAGCCCACCAGGCTGGCAGTTAGACAA
GGGAGTGATGGATTTGGGATGCTTTGTGTGACCTTGTATACAACAGGTTCTTAGACACAA
CCCTAGGACATGGAAAAGAATTACATTCATCCTGAGCCCCAGCTACTGTTACCAATTCAA
ATTAGGACAACATATTGATTAAGATACAGGTAGTTATGCTACCCTAAGAACTGGAATCTG
AATACCTACTTTTTATTTCTACTTCTACCGCTTGTTAGTAACCTATTCTTGATCCACCAT
[T,C]
TAACTTCTGTGAGCCTCAGTTTCTCCATCTTTAAGACAGTGATGATAATGACAGTATCTG
TAGAACAGCTTAACTTGAACTAAATGAGAAAAACTAAACAAAACACATAGAATTAAGTAT
GAATTTCTGAGGTTAGTTTATACATGTTTTAAGAGCTTAGAGAAAAGGAAAAAACATAAG
TATCCTAAGGAGATTAGGAAATGTTTCCTTGGGGAGGTTGGAAAGCAGCTAAGCCTTGAA
GAATAGGATGTATTTTGAACACTGGGAGAAGAGATGAGAAGGTAGTGAAGTGGAGGCAAT

87627 TACAGGTAGTTATGCTACCCTAAGAACTGGAATCTGAATACCTACTTTTTATTTCTACTT
CTACCGCTTGTTAGTAACCTATTCTTGATCCACCATTTAACTTCTGTGAGCCTCAGTTTC
TCCATCTTTAAGACAGTGATGATAATGACAGTATCTGTAGAACAGCTTAACTTGAACTAA
ATGAGAAAAACTAAACAAAACACATAGAATTAAGTATGAATTTCTGAGGTTAGTTTATAC
ATGTTTTAAGAGCTTAGAGAAAAGGAAAAAACATAAGTATCCTAAGGAGATTAGGAAATG
[T,C]
TTCCTTGGGGAGGTTGGAAAGCAGCTAAGCCTTGAAGAATAGGATGTATTTTGAACACTG
GGAGAAGAGATGAGAAGGTAGTGAAGTGGAGGCAATAGCCTGCACTATCCAGAGACAGTT
TCTGATTGTCCTAATGCTATGGGCTCTCTACTTCAGTTTAAGAAATATTCCAATCTTTGA
TACCTTCATTCAACAGTCCTTTCTATTTTTCTAATTTCATTTCCTGAATTGTTTCCCTGC
GGAGGAGTGGGCCTACTTGTTGAAATAAATCACATCACAGATACCTCTTTTCTTCTCTTT

87637 TATGCTACCCTAAGAACTGGAATCTGAATACCTACTTTTTATTTCTACTTCTACCGCTTG
TTAGTAACCTATTCTTGATCCACCATTTAACTTCTGTGAGCCTCAGTTTCTCCATCTTTA
AGACAGTGATGATAATGACAGTATCTGTAGAACAGCTTAACTTGAACTAAATGAGAAAAA
CTAAACAAAACACATAGAATTAAGTATGAATTTCTGAGGTTAGTTTATACATGTTTTAAG
AGCTTAGAGAAAAGGAAAAAACATAAGTATCCTAAGGAGATTAGGAAATGTTTCCTTGGG
[G,A]
AGGTTGGAAAGCAGCTAAGCCTTGAAGAATAGGATGTATTTTGAACACTGGGAGAAGAGA
TGAGAAGGTAGTGAAGTGGAGGCAATAGCCTGCACTATCCAGAGACAGTTTCTGATTGTC
CTAATGCTATGGGCTCTCTACTTCAGTTTAAGAAATATTCCAATCTTTGATACCTTCATT
CAACAGTCCTTTCTATTTTTCTAATTTCATTTCCTGAATTGTTTCCCTGCGGAGGAGTGG
GCCTACTTGTTGAAATAAATCACATCACAGATACCTCTTTTCTTCTCTTTTGTTAAAAGT

87777 GTATCTGTAGAACAGCTTAACTTGAACTAAATGAGAAAAACTAAACAAAACACATAGAAT
TAAGTATGAATTTCTGAGGTTAGTTTATACATGTTTTAAGAGCTTAGAGAAAAGGAAAAA
ACATAAGTATCCTAAGGAGATTAGGAAATGTTTCCTTGGGGAGGTTGGAAAGCAGCTAAG
CCTTGAAGAATAGGATGTATTTTGAACACTGGGAGAAGAGATGAGAAGGTAGTGAAGTGG
AGGCAATAGCCTGCACTATCCAGAGACAGTTTCTGATTGTCCTAATGCTATGGGCTCTCT
[A,G]
CTTCAGTTTAAGAAATATTCCAATCTTTGATACCTTCATTCAACAGTCCTTTCTATTTTT
CTAATTTCATTTCCTGAATTGTTTCCCTGCGGAGGAGTGGGCCTACTTGTTGAAATAAAT
CACATCACAGATACCTCTTTTCTTCTCTTTTGTTAAAAGTTCTGTTAAAATATATATATT
GTTAAAAAATTAAAGGTTATCTCCAGATAATTCCCCAAATGAGTAGGCTTAGGCTTTAAT

```
       CATATTATGTTCCCTTCCTTCTTGCTCTTCACTTGCCAAGTTATACTAATGATCATAATC
87810  AGAAAAACTAAACAAAACACATAGAATTAAGTATGAATTTCTGAGGTTAGTTTATACATG
       TTTTAAGAGCTTAGAGAAAAGGAAAAAACATAAGTATCCTAAGGAGATTAGGAAATGTTT
       CCTTGGGGAGGTTGGAAAGCAGCTAAGCCTTGAAGAATAGGATGTATTTTGAACACTGGG
       AGAAGAGATGAGAAGGTAGTGAAGTGGACGCAATAGCCTGCACTATCCAGAGACAGTTTC
       TGATTGTCCTAATGCTATGGGCTCTCTACTTCAGTTTAAGAAATATTCCAATCTTTGATA
       [C,T]
       CTTCATTCAACAGTCCTTTCTATTTTTCTAATTTCATTTCCTGAATTGTTTCCCTGCGGA
       GGAGTGGGCCTACTTGTTGAAATAAATCACATCACAGATACCTCTTTTCTTCTCTTTTGT
       TAAAAGTTCTGTTAAAATATATATATTGTTAAAAAATTAAAGGTTATCTCCAGATAATTC
       CCCAAATGAGTAGGCTTAGGCTTTAATCATATTATGTTCCCTTCCTTCTTGCTCTTCACT
       TGCCAAGTTATACTAATGATCATAATCTCTTCTATGTGTTTTGGACTTTACAGTGTGTGA
89812  AACCCAGTCTCTACTAAAAATACAACAAATTAGCTGAGCATCATGGTGCGTGCCTGTAAT
       TCTAGCTACTCGGGAGGCTGAGGACATGAAAATCGCTTGAACCTAGGAGGCAGAGGTTGC
       AGTGAGCCAAGATCACACCATTGCGCCCCAGCCTGAGCAGCAGAGAGAGACTCTGTCAAA
       AAAAAAAAAAAAAAAAAAAATGAAAGTAAAGAAGAAAGAAAGAAAAGGAGAAAG
       AAAACACGATTCTCTGAAGAAAAAAGCAATACACTGAGAGAAGGAAACATGAAGGTATTC
       [G,A]
       TTTAAATAGTGGGTCAGTGAATGCCCTTACTGAGTAAAAGTGACATTTAAGCCTAGATTT
       CAATGCTGGATGGTATTCATGCTACAAAACAATTTGGAGAATATTCTAGCCAAAAGGGAA
       TAATTTGTGCAATGATTTGAAAAATGGAAGGACAACCAGGGTAGCTGGAATGTTTATGGC
       AAGGGAGAGAGTGATAGAAGATTAAATCAGGAAAACAGAGAAAGTAACAGATGAGGCAGT
       GCTTGACAGGCCATGAAAAGAAGAGTGACTTTTATTTTAAGTGCATGAGAAGCCACTGGA
90137  CCTTACTGAGTAAAAGTGACATTTAAGCCTAGATTTCAATGCTGGATGGTATTCATGCTA
       CAAAACAATTTGGAGAATATTCTAGCCAAAAGGGAATAATTTGTGCAATGATTTGAAAAA
       TGGAAGGACAACCAGGGTAGCTGGAATGTTTATGGCAAGGGAGAGAGTGATAGAAGATTA
       AATCAGGAAAACAGAGAAAGTAACAGATGAGGCAGTGCTTGACAGGCCATGAAAAGAAGA
       GTGACTTTTATTTTAAGTGCATGAGAAGCCACTGGAAGGTCACAAGTAGAAAGGGATGTG
       [G,A]
       TCTCATCTGTTTTAAGAATTTGGTCCAGTCGGCTGGCCGCGGTGGCTCATGCCTGTAATC
       CCAGCACTTTGGGAGCCCAAGGCGGGTGGATCACGAGGTCAGGAATTCGAGACCAGCCTG
       GCCAGCATGGTGAAACCCCGTCTTTACTAAAAATACAAAAAATTAGCTGGGCATGGTGGC
       GTGCACCTGTAGTCCTAGCTACTTGGGAGGCTGAGGCAGGAGAATTGCTTGAACCCGCCA
       GGTGGAGATTGCAGTGAGCCGAGATAGCACCATTGCACTCCAGCCTGGGTGACAGAGGGA
90400  AGAAGCCACTGGAAGGTCACAAGTAGAAAGGGATGTGGTCTCATCTGTTTTAAGAATTTG
       GTCCAGTCGGCTGGCCGCGGTGGCTCATGCCTGTAATCCCAGCACTTTGGGAGCCCAAGG
       CGGGTGGATCACGAGGTCAGGAATTCGAGACCAGCCTGGCCAGCATGGTGAAACCCCGTC
       TTTACTAAAAATACAAAAAATTAGCTGGGCATGGTGGCGTGCACCTGTAGTCCTAGCTAC
       TTGGGAGGCTGAGGCAGGAGAATTGCTTGAACCCGCCAGGTGGAGATTGCAGTGAGCCGA
       [G,A]
       ATAGCACCATTGCACTCCAGCCTGGGTGACAGAGGGAGACTCCATCTCAAAAATAAATAA
       ATAAATAAATAAAAGAATTTCGCCCAGTCACTGAACTTCTTTGTGACTCCCTTTTCTCTC
       CTGAAAACAAGGATTAAACTACTGATTGTCCTTCCAAGAGGTTGTCTGAGTGTCAGATCA
       TGTTCATTATAATACTTTGCTCCAAGTTGTCCTTGATAAATTTTGAACTGAATTGTTTCA
       TAACAATATGAAAATGCTTTATAAACTGTAAAGGGCCATGCAAGTATAAAGTATTACCAA
92359  TCAAGTGTCTGCCTTAGAGCTAAGCTTCTCTCTTGGTGAAATGGTTTAAAATACCCATCC
       AGTACATGTCCTAAAATGGACATGAGGTTCCTCTGGGATAAAGGATGAGAAGATACTTTG
       TATTTTGTAACATTCTACTCAGATGCAGGATGTTCATCTCATTAATATTACACTCTGGTG
       CCAGTTTCTGGGGGGTCAGCTGCAGAGAAGCTAGTTCAGGCTGCAACATCTCATTAGAAG
       CTGAAATTTGGATTCAGGAAGAGGAGCATGGAGTGGGTGAGAGCCACTGTCTGCTGCTCA
       [A,G]
       GTTCCTGCTGCTATCTGTATTCAGAGAGGCATCCTGGTACCTTAGCAGTGCTGCTCAGTG
       GGACGTCTCTGACTTTGATGTTGCACGTGTCAACATTCTAATAGGGCAGCAGCCGAGATG
       GGGTATGAGTTTGGAAAGACATCTTATGACAGCTTTTTCCTAAAGATGTTTCAAGAGATA
       ACCCTTTAGAAATAACGAAGGTAGTTTATGCATTTCATAGGAAACCCAGCGGCTTACGTA
       GCAGCTCACTTCGAAGTCTGGCATGCGGACGGCTTCCTACTGTCCCGTTTTTGCCCTCCC
92555  CAGCTGCAGAGAAGCTAGTTCAGGCTGCAACATCTCATTAGAAGCTGAAATTTGGATTCA
       GGAAGAGGAGCATGGAGTGGGTGAGAGCCACTGTCTGCTGCTCAAGTTCCTGCTGCTATC
       TGTATTCAGAGAGGCATCCTGGTACCTTAGCAGTGCTGCTCAGTGGGACGTCTCTGACTT
       TGATGTTGCACGTGTCAACATTCTAATAGGGCAGCAGCCGAGATGGGGTATGAGTTTGGA
       AAGACATCTTATGACAGCTTTTTCCTAAAGATGTTTCAAGAGATAACCCTTTAGAAATAA
       [-,T,C]
       GAAGGTAGTTTATGCATTTCATAGGAAACCCAGCGGCTTACGTAGCAGCTCACTTCGAAG
       TCTGGCATGCGGACGGCTTCCTACTGTCCCGTTTTTGCCCTCCCTGCACATCTGTGAGAA
       ATCATCACTTGTCACAGTAACACAGTATTGTATTTAGTTACATTGACAGCAATGGTGAAA
```

FIGURE 3, page 94 of 122

GGACTATAAGCCTATTTCCTTCTAAACTGTTCACATCAAATGAACCTTAAACATTTACTC
CTCTCTTAAAATGTAAATCAGATCACCTCAGCCTACTGTTTAAACATTCTATCATGGCTT

92641 GCCACTGTCTGCTGCTCAAGTTCCTGCTGCTATCTGTATTCAGAGAGGCATCCTGGTACC
TTAGCAGTGCTGCTCAGTGGGACGTCTCTGACTTTGATGTTGCACGTGTCAACATTCTAA
TAGGGCAGCAGCCGAGATGGGGTATGAGTTTGGAAAGACATCTTATGACAGCTTTTTCCT
AAAGATGTTTCAAGAGATAACCCTTTAGAAATAACGAAGGTAGTTTATGCATTTCATAGG
AAACCCAGCGGCTTACGTAGCAGCTCACTTCGAAGTCTGGCATGCGGACGGCTTCCTACT
[G,C]
TCCCGTTTTTGCCCTCCCTGCACATCTGTGAGAAATCATCACTTGTCACAGTAACACAGT
ATTGTATTTAGTTACATTGACAGCAATGGTGAAAGGACTATAAGCCTATTTCCTTCTAAA
CTGTTCACATCAAATGAACCTTAAACATTTACTCCTCTCTTAAAATGTAAATCAGATCAC
CTCAGCCTACTGTTTAAACATTCTATCATGGCTTTCCATCATGAATAGAATCCAAATGCC
TAACACAAGCTGGATGGTAGCCTGATCTGACCTTTGCTGACCTCTCTGACCTCCCCTCAC

93969 GATCTATTATCCAATGAATATTTGTTGGAGGAATGAATCAATCCTCTCTTTTTACAGAGG
GAGAAGTTAGGACCAGAGAAGAGTAGACATCATTGTGTTTCTGAAGGTTTTATGTTAGCA
CCTTTGGGCCATGCTGGGACCTTGGCAAATTATAGCATTCAAGGGTTTTAGGGTAATGTT
CATGGATCCCTAGAAAGTCAGCAAATGGGGATCAGGGTGTCTTGAGCCCCTGTGAAAGTGT
TGGCATATTTCTGGGGAGAAGATTCATAGCTTTTATTAGTACTTCAAATAGATATTTGAT
[G,C]
CATTGGTAGCACCCATCAATTTTTCCTTTTAATTAGCTTAGTTTGGGGCAATGTGGAGCGA
GCCTAAAAGAGGATAGATGTCTCAGCACCACCTTGAAGACCTTTCTTCTTTTTCACTGAC
AGCATGGTTCCATCGTTCTGCCCCTGAATACGGGGACAGCTCCTCTTTTTCTATTACCAG
AGCATATCTTTCTTAAATTCACTATTTCCATGATGAATCTACAGTGCCAGAAGCTAGAGT
CTGGAATCAAAGAATTCCAGAGTTGGGAGAGCACTTAATTCAGTGTTCATAAACCAAAGT

96601 GATGACTACAATGTGGTATTTTATGTTTGTTTGAGAATATTAGCTGTTAGGGCTGTGGTA
ACCTCTACCAGATTGGGTTAAACAAAAGCAGTCTGCAGTCCATGATAATACAATGGAAAA
GCATAGGGAACACAAGAAACCTGGGTGAACTTTTTCACAAACAATTCATTTTTCTAATGA
GGCAACTAAAGCTCAGAAAAGGAAAGGGTCTTCCTTGTGATCATACATTCATTTTATCAT
TCAACAAACCTTAACTGAATACCTCCTATTCAACAGTGCACGAGCTGCCAGGAACAATGA
[A,G]
GTAAGTATTAACAGAAATGCCTAACATTTACTGAGCACTTCTTAGGTGCTGGGTACACAC
TAAGTCCTTCAAGTAGTCTCTCCTGCTGAAAGTGCTATTCCAAGTGCAAGTTGGAACAGC
AGGTGCCTTGGCACCAAAGCTCTATGTGACCGACCTTTCTGACCTGGCCTCACTTCCTTC
CCCCTCCCCTCATTTCTCTCTCTTCTCTCCCTTTATTTTTCTTTTCTTTCTCTCTCTCTT
TTTTTTTTTTTTTTTTTTTTTTTGAGACAGACTCTTGCTCTGTCGCCCAGGCTGGAGTA

96865 CCTATTCAACAGTGCACGAGCTGCCAGGAACAATGAAGTAAGTATTAACAGAAATGCCTA
ACATTTACTGAGCACTTCTTAGGTGCTGGGTACACACTAAGTCCTTCAAGTAGTCTCTCC
TGCTGAAAGTGCTATTCCAAGTGCAAGTTGGAACAGCAGGTGCCTTGGCACCAAAGCTCT
ATGTGACCGACCTTTCTGACCTGGCCTCACTTCCTTCCCCCTCCCCTCATTTCTCTCTCT
TCTCTCCCTTTATTTTTCTTTTCTTTCTCTCTCTCTTTTTTTTTTTTTTTTTTTTTTTTT
[T,-]
GAGACAGACTCTTGCTCTGTCGCCCAGGCTGGAGTACACTGTCGCGATCTCAGCTCACTG
CAACCTCCACCTCCCGGGTCCAAGCAATTTTCCTGTCTCACCCTCCCAAGTAGCTGGGAC
TACAGGCACCCACAACCATGCCCAGCTAATTTTTGTGTTTTTAGTAGAGACAGGGTTTCA
CCATATTGGTCAGGCTGGTCGTGAAATCCTGACCTCAGGTGATCCGCCCTCCTCGGCCTC
CCAAAGTGCTGGGATTACAGGTGTGAGCCACTGTGCCCGGCCCCTGTCCTCATTTCTTAT

98448 TTCAGTACACAAGAAAACTGATAGTCCACTTGAGGCAC
[A,G]
TTTCCAGACAGGGTCTTAACTTCTCCTCACTGCTGATC

100137 CTTTCTAAAGCACTGGGTTTGTGTGTATGTGTATGCACGCACTTCCCCCAACCCCCATGC
CTCCATTACTCCTCTACTCCAAAAAATGTCAGTTGTTTTTCTAGTGCCTGCAATGTAAGG
CCTAAGCCCACTGGCATCAAAGACTTCTGTAATTTAGCATCAACTAAACTTTCAGCTGTC
ACTTCCCACTGTTGGGAAACCATATAACATGATGTTAGAACATAGTGACAGAAGGAGCTT
TGGAGTCAAATAGCTGATGTAAATCTTGTTTCTTCCATTTTCTGCCTTTGTGACCTAGGA
[T,C]
AGATTGCTTAATCCTGCTGAGCCTATGGTTTTATACTTTTAAATTGAAATTATAGTGTAA
AGTTTAAATCAGATAATTAAATAAAGCCTTGAGCATAATCCATGATGTACTGAAAGTAAT
GATTAAATAATAGTCTATTAGACTATACAGCCTACTCACTATCTCTCATTCTTATCTAGT
ATTTACTAGCTAGTTAGGCACTATTTCTATTGCTTAGAACAACTTCTTTCGCATCTATCC
AAAATGTATAACCCTTTGGTCACCAGATCAATATCTTCAGCTCCTTCCTTTCAGGTACTA

100264 CCACTGGCATCAAAGACTTCTGTAATTTAGCATCAACTAAACTTTCAGCTGTCACTTCCC
ACTGTTGGGAAACCATATAACATGATGTTAGAACATAGTGACAGAAGGAGCTTTGGAGTC
AAATAGCTGATGTAAATCTTGTTTCTTCCATTTTCTGCCTTTGTGACCTAGGATAGATTG
CTTAATCCTGCTGAGCCTATGGTTTTATACTTTTAAATTGAAATTATAGTGTAAAGTTTA

FIGURE 3, page 95 of 122

AATCAGATAATTAAATAAAGCCTTGAGCATAATCCATGATGTACTGAAAGTAATGATTAA
[A,G]
TAATAGTCTATTAGACTATACAGCCTACTCACTATCTCTCATTCTTATCTAGTATTTACT
AGCTAGTTAGGCACTATTTCTATTGCTTAGAACAACTTCTTTCGCATCTATCCAAAATGT
ATAACCCTTTGGTCACCAGATCAATATCTTCAGCTCCTTCCTTTCAGGTACTATATATTG
CATTTGCTTCATAACACCTAATACAATGCATGAAGCATGCTTTTAATAAACATTCCTTGG
ATGGATGAATAAATAAATGAATAAAGAAATGAAGTAAAAGAAAGTCAATTTTTATATTAT

100873 AGGGAAAAAAGAGAAACGAATCAAAATATCTTGGAAATAAAATTCTGTTCCTCTCTGAGC
TTTTGATTTGTTTATAAGCTGGGGAGCATGTTGCTTACCATTTATTTAGTCTCACAAGTA
TGTTAACATCATCAACATAAGGTTTATGAAGTACTTTATACTGCCTGGAGGAAGGATGGT
ATAGAAATTTAAAATATTATATATATGATCCTTCCAGGAAGAAAAAAAGAAGCAATATCTAT
TCTGTGAGGTGCATCAATTTTGGATCACTCTAATGGAAGTGCCCCGAGCAGTTGGTTTAT
[T,C]
TCTTCAAATGTGAATTAATTTATACATTTCAAAGCTCCTGATGGATACTTTTCATTTTAA
TTAAGTACATTTTTGCCAAATTTCAACTTTAAAAACTCAACAAATTTGTTCCCACACTTG
CTTTGTAGAATTTGCAATATTAGATATAAATTTATTATAAAAGGGTATGTTAGAAACTTC
TCATACTGAAATCGGCCACCCAGCAACTTTTTCTTAGGATTCAAGTGCTCTAACATGTGC
TTGCTTGTTTGTCTGTGTGATTCGGTGGTTTTATTTTGATTTTCATAGAAAATAATAAAT

102673 GAAGAATACCACCTTTTTTTCTTACCCTTTTAAAGTTGAGAAGATTATTTGTAAGAGTGT
GAAATGGTCTAAGCATTGCCCCTTTAAATGGGGGTATTGTGTTAATTGTAAGCACTGCAA
AGTGGGTTGCTATATTGTGGCTGTTGTACTCAGTGTCAAAAGATTTAGTTCCTTCTTGAC
CCAGTCCTAGTTATTCAAGAGTCATCAAACAGAGATACACAATTTTAAATTGTTTTTCAG
AATGAATCTGAAGAGAGCGAAGAGTTGAGTGGAGAAGTCAGCTAGATCATCCTTGTCTAT
[C,T]
TATGCAGACTCCTTCCCATAATTTTTCCCCAATCTAGTTTATGCCTAATTTTATACCAGG
AATTTCTTCCTGACCTTTTAATTGCCTGTCCTTAGGGCATGAAAATTATGAGTGTAATTT
TACAGACCATTCTTAACTTTTCAAAACCATTCCAACGATATTCATCTAAGAAATGGCCAG
TGTTTGTGGAGCACTAATTTGTCACGCAGCATTGTGCTAGACATTCAAGATATCCCATTG
AGTATCGCACGAAAACCCTGACCAACACATCCCTATACCAACTAGGTCAGATCCTCATTC

102807 TTGTGGCTGTTGTACTCAGTGTCAAAAGATTTAGTTCCTTCTTGACCCAGTCCTAGTTAT
TCAAGAGTCATCAAACAGAGATACACAATTTTAAATTGTTTTTCAGAATGAATCTGAAGA
GAGCGAAGAGTTGAGTGGAGAAGTCAGCTAGATCATCCTTGTCTATCTATGCAGACTCCT
TCCCATAATTTTTCCCCAATCTAGTTTATGCCTAATTTTATACCAGGAATTTCTTCCTGA
CCTTTTAATTGCCTGTCCTTAGGGCATGAAAATTATGAGTGTAATTTTACAGACCATTCT
[T,A]
AACTTTTCAAAACCATTCCAACGATATTCATCTAAGAAATGGCCAGTGTTTGTGGAGCAC
TAATTTGTCACGCAGCATTGTGCTAGACATTCAAGATATCCCATTGAGTATCGCACGAAA
ACCCTGACCAACACATCCCTATACCAACTAGGTCAGATCCTCATTCACAGGTATTCATAA
TACATAAAATTCCCCTGCATAGCACTAGGTCACATGTAGGCAATAATTATTTATCTTGTA
TATGCCTTTTCACTCAACTGTGAGCTCCTAGAGGACATAGGTAAAATCTGTTTTGTTCAC

102938 TGAGTGGAGAAGTCAGCTAGATCATCCTTGTCTATCTATGCAGACTCCTTCCCATAATTT
TTCCCCAATCTAGTTTATGCCTAATTTTATACCAGGAATTTCTTCCTGACCTTTTAATTG
CCTGTCCTTAGGGCATGAAAATTATGAGTGTAATTTTACAGACCATTCTTAACTTTTCAA
AACCATTCCAACGATATTCATCTAAGAAATGGCCAGTGTTTGTGGAGCACTAATTTGTCA
CGCAGCATTGTGCTAGACATTCAAGATATCCCATTGAGTATCGCACGAAAACCCTGACCA
[A,G]
CACATCCCTATACCAACTAGGTCAGATCCTCATTCACAGGTATTCATAATACATAAAATT
CCCCTGCATAGCACTAGGTCACATGTAGGCAATAATTATTTATCTTGTATATGCCTTTTC
ACTCAACTGTGAGCTCCTAGAGGACATAGGTAAAATCTGTTTTGTTCACTGCTGAATTCC
TAGAACCCAACATAGTATCTAGCACCAAGAAGCACTCAATAGAAGTTGGATGAACTAAAG
AAGAAATGGTTGGTCTAGGAAGGGGTTGGGACCATAAGAAGCATACTGTTATTTAAGAAG

104061 GAGAGTGTCCCTGAAACTAGTAGATGGCTCTAGATTCCATTGAATTCCTGCCAAGGGGCC
TGACAGCATAGATGAATTCTACTACTTCCAGCTTCCTCTAGAGTTAGCAGAGTCCAGGTT
TGGGAGTCAGGAGACCCAGATTCTAGTCCTGTCTGTGCCGTGGTCTCTTTGTGGTTTTGA
GCATATCACTTTATCTCTTGTATCCTCAGTTTCCTCTTGTGTAAAAAGGAGATTTTTCTC
ATCACTAGTTGGTAGGACAAGGACATTTTTAATTTATTTTTTCTCCCTAAATAATGCATG
[C,T]
ATAACTTACAAAATCAAATGTTACTTCAAGTCATAAGACAAAATTCAACATTCTCTTCCC
TCCTCCCTTTCTATCTTGGATTCCAGCTCTCATAGGGGATCACTTTAGGCTCTCTTAGCT
GTTTCTTCTGATATTTTACCTTTGTATCTCTTGTATTGCCTGTTCTGGTTTGGGCTGCTA
TAACAAATACTATAGACTGGGTGGCTTAAACAAAAGATGTTTATTTCTCAGTTCTGGAGG
CTGGGAAGTACAAGATCAATGTGAGGCCAATTTGGGTCTTGGCAAAGACCTGCTTCCTAG

107552 TATAATATAATATATATATAATTAATATATATAATATAATGTAAATACGGTCTACATCTT
AGAAATAGTTCTTTAGTCCTTTACTAACTAACAAAGTGCTAGACACAGAATGCTGGGCAG
GCACATAGGATTGGAACACTAAATACTTCTTTGGCTAACTTAGTGCTTTTAAATATATAT

FIGURE 3, page 96 of 122

TCAGTCATTTCTAAATTCCCAGTGTCATGTTCCATGAGAGGTCACATAGATGCATAAAAG
CTCCCTCAAGGACTGTAACCTTATTAGGGAAATACACATATATAGACAATAAAAAAAAAA
[-,A]
CAGGTCAACACTGTCACTAAGTAGCAAATTATGTCATTTTCATAGTTTAAGAGTGACAGA
TTTCATGGCCTGAGTGATCAATTTGGATGCATCCATCATGGCTGGCATCCCAGAAAAGGC
TGGGAATGATTTAGACAGAGTGAAATGAGAGAGTCTTTTAACCACACAGGGTATAACAAG
TATGCATCTATTCTTTTTGGAATGTTTAAAAATTATCAAATCAGAAGCATCTTAAAATTC
ACTTTTCTTTGAAAAATGTATGCAAGATCCAGCCACTTTATTTTTGTTCATATTTGGTTT

110789 CATGCCATTCTCCTGCCTCAGCCTCCCGAGCAGCTGGAACTGCAGGCGCCCGCCACCACG
CCTGGCTAGTTTTTTTGTATTTTTAGTAGAGATGGGGTTTCACCCTGTTAGCCAGGATGG
TCTCGATCTCCTGACCTCATGATCCACCCACCTCAGCCTGCCAAAGTGCTGGGATTACAG
GCATGAGCCACTGTACCCGGCCAGGGCTGTTGATTTTATATAATTTCCTTCCTTTTTGGC
TGATTGAAGTCCATTGCTAATTCTAGTTTGACACTTTTTATTACCTCAACTAGATTATTT
[T,C]
GTCCAGAAAGTTTACTGAGCATCTTCTAGGCTAAGCACTTTAGAAAGTATGAAAGAAGTT
TAATTCACAATACTTATCCTAAAAGATCACAATCTTGCTGATGGCACTTAGACAGTACAG
CAATCCCTTGATATCCACAGGGGTTTGGTACCAGGACTCCTACAGATACCAACATCTAGG
TATGTTTAAGTCCTTTATATAACATGGCGTGGTGTTTGCACATAACCTAGGCACATCCTC
TCACATACTTTAAATCATCTCTATATTACTTATAATACCTAATACAATGTAAATACTATG

110884 GGTTTCACCCTGTTAGCCAGGATGGTCTCGATCTCCTGACCTCATGATCCACCCACCTCA
GCCTGCCAAAGTGCTGGGATTACAGGCATGAGCCACTGTACCCGGCCAGGGCTGTTGATT
TTATATAATTTCCTTCCTTTTTGGCTGATTGAAGTCCATTGCTAATTCTAGTTTGACACT
TTTTATTACCTCAACTAGATTATTTGTCCAGAAAGTTTACTGAGCATCTTCTAGGCTAA
GCACTTTAGAAAGTATGAAAGAAGTTTAATTCACAATACTTATCCTAAAAGATCACAATC
[T,C]
TGCTGATGGCACTTAGACAGTACAGCAATCCCTTGATATCCACAGGGGTTTGGTACCAGG
ACTCCTACAGATACCAACATCTAGGTATGTTTAAGTCCTTTATATAACATGGCGTGGTGT
TTGCACATAACCTAGGCACATCCTCTCACATACTTTAAATCATCTCTATATTACTTATAA
TACCTAATACAATGTAAATACTATGTAAATAGCTGCCACACTTTATTATTTTGATTGTTA
TGTTGTTAATTTTATTTTTAATATTTTCAATCTGCAGTTGTGAATCTGCAAACGTAGAAC

115075 AGGCTGCATAGTATTCCATGGTGTATATGTGCCACATTTTCTTAATCCAGTCTATCATTG
TTGGACATTTGGGTTGGTTCCAAGTCTTTGCTATTGTGAATAGTGCCACAATAAACATAA
CGTGTGCATGTGTCTTTATAGCAGCATGATTTATAGCCCTTTGGCTATATACCCAGTAAT
GGGATGGCTGGGTCAAATGGTATTTCTAGTTCTAGATCCCTGAGGAATCGCCACATGTGC
CCTAAAACTTAAAGTATAATAATAATTAAAAAAAAACAGTTACCAGTATTTATTGAGTGC
[C,T]
TAAGGTAGTAAAGGCTTGAGAAGCTGGAGCCTATTTTCATACCGAATATGTAAATATCGA
CATCTCTGCTCTAGAAGATCTAGGACACTCTGGAAAAGTGTCTGTATATCTTATATTAGG
AGTAGTGGCCTCACCAATGTGGTGTCATGGTTAGTAAAGGACAGGCTGAGTGAACAAGAA
GGGACTGATCATGTCTTTGCCAGTTGCCACCGCCTAGCTACGTTCTTGGGCATGGGACCT
AATTTGTCCAGCCTCAACTTTCATCTGTGTGACAGGTCCAATAATTCCCCATACCACAGG

115286 CTAGATCCCTGAGGAATCGCCACATGTGCCCTAAAACTTAAAGTATAATAATAATTAAAA
AAAAACAGTTACCAGTATTTATTGAGTGCCTAAGGTAGTAAAGGCTTGAGAAGCTGGAGC
CTATTTTCATACCGAATATGTAAATATCGACATCTCTGCTCTAGAAGATCTAGGACACTC
TGGAAAAGTGTCTGTATATCTTATATTAGGAGTAGTGGCCTCACCAATGTGGTGTCATGG
TTAGTAAAGGACAGGCTGAGTGAACAAGAAGGGACTGATCATGTCTTTGCCAGTTGCCAC
[C,T]
GCCTAGCTACGTTCTTGGGCATGGGACCTAATTTGTCCAGCCTCAACTTTCATCTGTGTG
ACAGGTCCAATAATTCCCCATACCACAGGGATGTTGTGATGATTAAATGATAAGCAGAGA
TTTTAGTACAGGATTGGATATATAGTAAGCTCTCCATAAATGGTAATACTATTACTATAC
ATATACATGTATTTTACATACCTATATATATTTACATACATTTATGATCTAGTTTATAAT
CTCCAATATGCCTTGGAAGCTTCAGAATGAGTCTTATTTCATTTTTGTAATGTTACTATC

121154 GAGTATTCGTCCAAATTACATAGTCTTTCATTAACACAAGAGGAAGTCCTGTTCCTGATC
TTGAAAAAAATGATAGATATGTCCACAATAGGCTGAAACAAGGCAGTGATTTCTCCCTTC
ATATGAGGAATACATTCTCCCACAATGTCCAGCTAGCCTCCTTCTCATTCACCTTAGCCC
AGTGACTTTGGCATTTGGGATTCAGACTCTTTTCCTTTTTTTTTTTTTTTTTTTTTTTGA
GATGGAGTCTTGCTCTGTCACCCAGGCTGGAGTGCAGTGGAGCAATCTTGGCTCACTGCA
[G,A]
GCTCCACCTTCCGGGTTCAGGTCATTCTCCTGCCTCAGCCTTCCGAGTAGCTGGGATTAC
ATGGCCCACCACCACACCCAGCTAATTTTTGTATTTTTAGTAGAGACGAGGTTTCACCAT
GTTAGCCAGGATGGTCTCGATCTCCTGACCTTGTGATCTGCCGGCCTCGGCCTCCCAAAG
TGCTGGGATTACAGGCATGAGCCACCGAGCCCAGCCCAGACTCTTTTCTTAAATATTCCA
ATAAGGTACAATTTGATCATCCTAGGTTTCTTTCCTCTAAGTCTGGCATGATATGGTTGG

121250 AACAAGGCAGTGATTTCTCCCTTCATATGAGGAATACATTCTCCCACAATGTCCAGCTAG
CCTCCTTCTCATTCACCTTAGCCCAGTGACTTTGGCATTTCGGATTCAGACTCTTTTCCT

TTTTTTTTTTTTTTTTTTTTTTTGACATGGAGTCTTGCTCTGTCACCCAGGCTGGAGTGCA
GTGGAGCAATCTTGGCTCACTGCAGGCTCCACCTTCCGGGTTCAGGTCATTCTCCTGCCT
CAGCCTTCCGAGTAGCTGGGATTACATGGCCCACCACCACACCCAGCTAATTTTTGTATT
[T,G]
TTAGTAGAGACGAGGTTTCACCATGTTAGCCAGGATGGTCTCGATCTCCTGACCTTGTGA
TCTGCCGGCCTCGGCCTCCCAAAGTGCTGGGATTACAGGCATGAGCCACCGAGCCCAGCC
CAGACTCTTTTCTTAAATATTCCAATAAGGTACAATTTGATCATCCTAGGTTTCTTTCCT
CTAAGTCTGGCATCATATGGTTGGTAAATGGAGGTTAACTATTTTATTATTTTGCTAGAG
AAGAACTCCTAAAGCCCCTATGGGGTTGGCATCATTCTACTGTCTGCATGCCTGGAAGAT

124478 TATTTCCTTATCAGAAAAGAACTTTGCATAATCCGTAAGGGACTTCTTCTACTTCCCATT
CCACTGAAGAACTTCAATTTAGTATTTTACCCAGCATTTGCTGCAAGCTTCGTAGGATAC
CCAGCCACACATACCCATATCAGCAGCAAGTTCTGAGAGCCAGCGGCAGTATTAGCATTA
TAAAGTGTTTCCAGAGTTGGACCAGTGTGTGCTTCCCCTTCATAAATCCTTAAATCTTAG
GCTCACTCAGCTGGAAAAAAAAAAAAAGAAATCTGGGTTTGAAGAACACTTATTTATTTTT
[G,T]
ATTTTCTCTGCCTTGTGTGCTTCTTTTGACTGCGCATCTGAATATCAAGGCAAGAAGTGC
TCAAGTTCCTCTGGGCTCTGGAAGGCTGGAACCAATTGGTATTCTTGGAGTCGGTCCTTT
TTGGACTAAAGCTCCTTTTTCTTTTCCTCCCCCCAATAAAAATTTCTGTTCCAGGGAGTA
CTTTCTCAGTCACTCCTTTCCTAATGTAATTCTGTTTGATTTCCACTGAACGGCTCCTGA
AAGGAGACACTGAACCATGCCTCCACAAGCATTTCAATTCCTCAACACCAGCTTTCAGGC

124841 AAGTTCCTCTGGGCTCTGGAAGGCTGGAACCAATTGGTATTCTTGGAGTCGGTCCTTTTT
GGACTAAAGCTCCTTTTTCTTTTCCTCCCCCCAATAAAAATTTCTGTTCCAGGGAGTACT
TTCTCAGTCACTCCTTTCCTAATGTAATTCTGTTTGATTTCCACTGAACGGCTCCTGAAA
GGAGACACTGAACCATGCCTCCACAAGCATTTCAATTCCTCAACACCAGCTTTCAGGCAG
GAGCAGTTCCAGATGCATTTTTATATCCAGTAATCATGCATTTAACCAAAATGATTGATG
[C,T]
AGCATTTTTTCCCCTCTCTATCATTTCCAGTCCATTAGTCTTATTTGTTTTCCATGGTTT
GGGTTCCTGCCAAATCAGTGAATATACAAATACTTGCATAAGTCATGCACATCTACACAC
ACATACATGTAATAGGTACTGGGTCTGTATCTGAGTTGAATATTCAACATTTTATTTCCA
GGCTTCATGTCTCCACTGAAGTTTTAGCCGCTTCTTTCCTTCTTTCTTACTTCCCTCTCT
CCCTTCTTTTTTTCCCTCTCTTCCTCTCCTTTATAGTCTATTAAGTTGGTGCAAAAGTAA

124842 AGTTCCTCTGGGCTCTGGAAGGCTGGAACCAATTGGTATTCTTGGAGTCGGTCCTTTTTG
GACTAAAGCTCCTTTTTCTTTTCCTCCCCCCAATAAAAATTTCTGTTCCAGGGAGTACTT
TCTCAGTCACTCCTTTCCTAATGTAATTCTGTTTGATTTCCACTGAACGGCTCCTGAAAG
GAGACACTGAACCATGCCTCCACAAGCATTTCAATTCCTCAACACCAGCTTTCAGGCAGG
AGCAGTTCCAGATGCATTTTTATATCCAGTAATCATGCATTTAACCAAAATGATTGATGC
[A,G]
GCATTTTTTCCCCTCTCTATCATTTCCAGTCCATTAGTCTTATTTGTTTTCCATGGTTTG
GGTTCCTGCCAAATCAGTGAATATACAAATACTTGCATAAGTCATGCACATCTACACACA
CATACATGTAATAGGTACTGGGTCTGTATCTGAGTTGAATATTCAACATTTTATTTCCAG
GCTTCATGTCTCCACTGAAGTTTTAGCCGCTTCTTTCCTTCTTTCTTACTTCCCTCTCTC
CCTTCTTTTTTTCCCTCTCTTCCTCTCCTTTATAGTCTATTAAGTTGGTGCAAAAGTAAT

128941 CAATTCACAGCATTGCCAAGAAAGACTGTAGATATTCAGGGATCAGAGTGAGATTCCTAT
GAGCCAGAGAATCAAAAGCTCTGTAAATTAGTGAGTTCGTGATATCATGCTACGCTCCTG
TTTTTAAGAGCTAGATATCAAAATAAATGGTCCAGTGTATGTGCCTGATGGCTATGTCTT
TTCCACTGTACACACAAGTAAGATTCTGCATGGTGACTATCATTTTGTTTTCAGGAAGTA
GATGAATCAGCCGTTTGGTTCCCTGGGAATGTGGGCTGCTGGCTTTTAATTCTTTTTGGG
[G,A]
AAGATTTCTATGTCATCAGCCATCTTGTTTATCTGGAAACATGGGACAAACGTTGGCTCT
CTTTCTACCTATGTAGTCCTTTGCTAGGGTTGTACAGCTTGAGTAGAATTGGGAAAAGTG
ATTTGGATCCTTGTGACTGGGATTAGGGAGAATTGGTACATGAGTATACAGAATCTTTTC
ATTGATCTCCTTGCCTCTGACCTTGATTTAGCCACCTACTTTCAGTGGATAAGGCCCTAC
AGAACAAACCAACTGAAGCATACTTTAGGATAGGCCACACCTCTAATCTCATATTTATTA

129471 TAAGGCCCTACAGAACAAACCAACTGAAGCATACTTTAGGATAGGCCACACCTCTAATCT
CATATTTATTATGACCAACTAAAAACTGCTTATCCTTCTCTTTATGTCTATTATTTAACT
TTCCCCTCCTCTCTACCTTCTTTCCCTTAAGTCCTTCTGATACACTACATGCTCCTGCCA
TTGTGACTATGAGTCTAAAAAGCTGGTGGCATTACCCACCTTCCCCTCCACCTTCAAAAC
TCACATGTACACCATGCTTTGGGCTTCTCTGATTTGGCTCACTATTTCTTCAACTTAGAA
[C,T]
GCCCACTTTCTATTATGATCATTAAAAGATCCTGGATTTATGTGTGGGGTGGATGTAGTA
ACAACTGGGAAATAGCATAAAATTATTTGGTTTCTTGTATGCTGGTTTTCTTCCCAGAGG
TAACCTGTTTGGTTTGACGTTTGGCTTAATGTTGTTAATTTGACGAAGGTGGAAATGGAT
GGGCTAGAAATCTTTGTGGGACTAGGATAAGGCTTGAATGGTCTAATCTAGGGATTCAAA
CTTTCTAGTTAAGAATGTACAACCTGTGAGGATAATTTGCATTTTATTCTACATATATCC

130568 AATAGAAAGAAGTATAAAATACAGTGCCTAGGTCTGCAAGTATTTATTACCTGTGACACT

FIGURE 3, page 98 of 122

```
          ACTATGTTGGCCAAGGAGAAGTTCTGTATATTATGCTCTTTTTATAAAAGCAGAAGCATG
          TATAGAAACTATTAGGATATTTTTCTTCAAAATGTTTAAAATTCTTTAGCTGCTTACAAG
          AGAAATTTATTTAGTACTACTTTCTCAAAGATCCCATTTCCTGACAATGCTAATAATGGA
          GGCATTTCAAGATAATGACCTCATAAAATTCACACAACTGTCTGTCTGTGCAGACTTAGA
          [T,C]
          AGCACAGTCATGACCTCACTTAGGTCAGGGACAGATCTTAGCTTGATAGGGCAATGGTCA
          GAAATGCAGTTTGGTTTAAACAGTTTTTTCCTCTTCTCTGTTGACTCATTTAATGAAAGA
          AAGTGTCTCATTCAACCTGCATATTTTTTTCAAAGATTCCACAATGATGGGGCCATGTCT
          CCTATGAGTTATTATACAAAATGGACACTGAGTCCTGAGGTACATTAGGAAGCCCCAAAC
          TTATCCTTGTATTTAATTCATTTGAACATTTTGGATATTTTATTTTATCAAGCCAGTCAT

132179    CACTTAAAGGAACACCAAATCATTTGAGTGCACAGGCAATGACACCATCTGTAGACTTAT
          CTGATCCAGAGAACCTGAGGTGGAGCCTATAGCCTCTGGTCAGTTGGAAGCGGTGGGGAA
          ATCTCAAGAACACTTGTCCTGAGAGAAAGAAAACTTTATCTGCTTGTTACACATGAGCCT
          GAGCTGAGGAAATAGACCTGGATCCAGGGAATTCGTGTTTACTGGGTGCCACAACTTGTG
          TTAGCACTTGACATGATTTCTTCTATTTAAATATTAGACTAAAAACACTCTATCAGACTA
          [G,C]
          GGTTTTAAAATACTATTTCATTTTTTTGGTACCTATTTATAAAATGGGGAAACTGAGTCT
          TGGGGGATATTAAGGTCTTATAGACTGTAAATGGTATAATCCAAGGTTGAAAGGTTTCCT
          GACTCTAATGCTGGTTCTCTTTCACAATACCTCATTGCCTTCTGGAAGTTGTAGTTCCTA
          CCCTAGTTCTGCCTTTATTTGGCTGTGGTAATCAAAACAAATCACTTAAGTTCTTGAATC
          TCATTTTGTTCTTCTGTTAAATATCACAAAACCAACCAACCAACCAAAACAGTGAGAATA

132792    GCTTCCATGATTTGTGGATGGTCTTCACAGGCAACAATTAATTCATGAGGAATGATGCCC
          ACTGCTGTCATGCAACATAGTGGCCCTGGATTTTAAGGAATCCATGTATTAATACATGCA
          ACCTGAAATCACATATGTAAATTGTATTATATACTTGCATATCTATATTGTTTTAGAGAA
          GAGGCTAAAGCTTTCTTGAGAGGCTTTCTGTGGCATCTATATCCCCAAATTCCTAAAAAT
          CATTAGGTTCTTGGCAGCTCATTAAGTGATTAGTAGGTCTCCTTATGATGTGTTATAACT
          [C,G]
          AAAACATCAGTAACCATCTGAAAGAAATTAAGGTTTAGGACAGGCATGGTGGTACACACC
          TGTAATCCCAGCATTTGGGGAGGTAAAGATGGCAGTATCGCTTGAGGCCAAGAGTTTAAG
          AACAGCCTGAGCAACACAGTGAGACCCTATCTTTACAAAAAATTTAAAATTGTTATTAAA
          AGAAATTAAAGTTTAGTACATGAAAGCAGCTGAAACTCAGAACTGACCCTTACATCAGAA
          ACCATGTGGTATCATGGAAAGAAATCTGGCAAAGAATCAAAGATTCTGGGTCCTACTTTA

133502    AAAAGAATCAAATGTGATAATATGGATGAAGGCACTTTGGCAAAATATGAAGTACCCTGC
          AAAAGTCTGATATTAACCATGAGATATTAAAGTATCAAGTCATTTCACTAGTTGTCAACT
          GAGAAAAAGGGAAAATTGCAAGTTCCATCAGCAAAATTTAGAAGCCTTGCTTTTTCATTC
          CTTCAGCAAGGTCCTACAGCTGATATTTATGCCATAAATTTTCTTGACTTTAATGAGAATT
          GGTTGCAAATACACCTTACAGGATTCAAATGGAGATCATCACCATTCTAGGAGCTGCTAA
          [A,T]
          CAGAACATGTGGCTTCTTCTCTAGCCAAGAGTTCTCCTCTTTTATCACCTTTATTTTATG
          ATCAGTGGTTCTCAAGGAATGGTCAAGCACCAGCAGCGTGAGCATCTTCTGGGAATATGT
          TAGAAATGAAAATTCTCGAGCCCCATCCCAGACCTACTAAATCAGAAATCCTGGAGGTGG
          AGCCCAGCAGGCTGTGTTTTAACAAACCCTTAAGAGGATTCTGATGCCCTGCACACTTAA
          GTGTGAGAACCACTGCCATAAGTGAGTATCCTTGGAGAGACCTACTTTGGTCCTGGGTAC

133661    AGAAGCCTTGCTTTTTCATTCCTTCAGCAAGGTCCTACAGCTGATATTTATGCATAAATT
          TTCTTGACTTTAATGAGAATTGGTTGCAAATACACCTTACAGGATTCAAATGGAGATCAT
          CACCATTCTAGGAGCTGCTAAACAGAACATGTGGCTTCTTCTCTAGCCAAGAGTTCTCCT
          CTTTTATCACCTTTATTTTATGATCAGTGGTTCTCAAGGAATGGTCAAGCACCAGCAGCG
          TGAGCATCTTCTGGGAATATGTTAGAAATGAAAATTCTCGAGCCCCATCCCAGACCTACT
          [A,G]
          AATCAGAAATCCTGGAGGTGGAGCCCAGCAGGCTGTGTTTTAACAAACCCTTAAGAGGAT
          TCTGATGCCCTGCACACTTAAGTGTGAGAACCACTGCCATAAGTGAGTATCCTTGGAGAG
          ACCTACTTTGGTCCTGGGTACTTTAAGGAAAATCGTGGGGCCCCAGTAATCCAAAAGAGT
          ACCTCATCTAAGTCTCTGAAGGGCTGATGTTAGAGCAAAGGTTGGGCTAGTGAATGTCAA
          TGTTAGCAAACATGGTGGGTGTGACCCAAAACATAATCAAATAGGCCTCTTAGGTTAAAG

133768    AAATGGAGATCATCACCATTCTAGGAGCTGCTAAACAGAACATGTGGCTTCTTCTCTAGC
          CAAGAGTTCTCCTCTTTTATCACCTTTATTTTATGATCAGTGGTTCTCAAGGAATGGTCA
          AGCACCAGCAGCGTGAGCATCTTCTGGGAATATGTTAGAAATGAAAATTCTCGAGCCCCA
          TCCCAGACCTACTAAATCAGAAATCCTGGAGGTGGAGCCCAGCAGGCTGTGTTTTAACAA
          ACCCTTAAGAGGATTCTGATGCCCTGCACACTTAAGTGTGAGAACCACTGCCATAAGTGA
          [G,T]
          TATCCTTGGAGAGACCTACTTTGGTCCTGGGTACTTTAAGGAAAATCGTGGGGCCCCAGT
          AATCCAAAAGAGTACCTCATCTAAGTCTCTGAAGGGCTGATGTTAGAGCAAAGGTTGGGC
          TAGTGAATGTCAATGTTAGCAAACATGGTGGGTGTGACCCAAAACATAATCAAATAGGCC
          TCTTAGGTTAAAGTCCTGATGTTAGGTTTGCTGGTTGAGAACGAATACAAATGTATCTCA
          AGGAATGCAGTTCTCTCAAGATTCAGAAAGTATGGATACCTTTGCCATGCCTGGCAGCTT
```

FIGURE 3, page 99 of 122

133837 TCCTCTTTTATCACCTTTATTTTATGATCAGTGGTTCTCAAGGAATGGTCAAGCACCAGC
AGCGTGAGCATCTTCTGGGAATATGTTAGAAATGAAAATTCTCGAGCCCCATCCCAGACC
TACTAAATCAGAAATCCTGGAGGTGGAGCCCAGCAGGCTGTGTTTTAACAAACCCTTAAG
AGGATTCTGATGCCCTGCACACTTAAGTGTGAGAACCACTGCCATAAGTGAGTATCCTTG
GAGAGACCTACTTTGGTCCTGGGTACTTTAAGGAAAATCGTGGGGCCCCAGTAATCCAAA
[A,C]
GAGTACCTCATCTAAGTCTCTGAAGGGCTGATGTTAGAGCAAAGGTTGGGCTAGTGAATG
TCAATGTTAGCAAACATGGTGGGTGTGACCCAAAACATAATCAAATAGGCCTCTTAGGTT
AAAGTCCTGATGTTAGGTTTGCTGGTTGAGAAGGAATACAAATGTATCTCAAGGAATGCA
GTTCTCTCAAGATTCAGAAAGTATGGATACCTTTGCCATGCCTGGCAGCTTGAAAGAAAT
AGCAATGTAAAGTTAAACCACGCCTATGTGAAAGTTAGCTCCATAGCAGGCTTTCTTCTC

134003 AACAAACCCTTAAGAGGATTCTGATGCCCTGCACACTTAAGTGTGAGAACCACTGCCATA
AGTGAGTATCCTTGGAGAGACCTACTTTGGTCCTGGGTACTTTAAGGAAAATCGTGGGGC
CCCAGTAATCCAAAAGAGTACCTCATCTAAGTCTCTGAAGGGCTGATGTTAGAGCAAAGG
TTGGGCTAGTGAATGTCAATGTTAGCAAACATGGTGGGTGTGACCCAAAACATAATCAAA
TAGGCCTCTTAGGTTAAAGTCCTGATGTTAGGTTTGCTGGTTGAGAAGGAATACAAATGT
[A,G]
TCTCAAGGAATGCAGTTCTCTCAAGATTCAGAAAGTATGGATACCTTTGCCATGCCTGGC
AGCTTGAAAGAAATAGCAATGTAAAGTTAAACCACGCCTATGTGAAAGTTAGCTCCATAG
CAGGCTTTCTTCTCTGAGATTTGAATTTATGGAACATGATAACAAATATGAAAATAGATA
ATTTTTATTGAATATCATATCACTACCACTATTTTAAGTGATTTGTATGTATTAATGGCT
AACCTTTTTTCAGGTAGTTACTCCACCAAGCTCTTTGCTGGGCCCTGAAAATGTAACAGT

134098 GGTACTTTAAGGAAAATCGTGGGGCCCCAGTAATCCAAAAGAGTACCTCATCTAAGTCTC
TGAAGGGCTGATGTTAGAGCAAAGGTTGGGCTAGTGAATGTCAATGTTAGCAAACATGGT
GGGTGTGACCCAAAACATAATCAAATAGGCCTCTTAGGTTAAAGTCCTGATGTTAGGTTT
GCTGGTTGAGAAGGAATACAAATGTATCTCAAGGAATGCAGTTCTCTCAAGATTCAGAAA
GTATGGATACCTTTGCCATGCCTGGCAGCTTGAAAGAAATAGCAATGTAAAGTTAAACCA
[C,-]
GCCTATGTGAAAGTTAGCTCCATAGCAGGCTTTCTTCTCTGAGATTTGAATTTATGGAAC
ATGATAACAAATATGAAAATAGATAATTTTTATTGAATATCATATCACTACCACTATTTT
AAGTGATTTGTATGTATTAATGGCTAACCTTTTTTCAGGTAGTTACTCCACCAAGCTCTT
TGCTGGGCCCTGAAAATGTAACAGTGAACAAGAAAAAAATCTCTTTCCTCAAGGAACTCA
CACTTCAATGAAGGGAAATTAGAAGAAATTAGCCTATTACTGTTCAAGTTCAGGGTGTTT

134530 ATGTATTAATGGCTAACCTTTTTTCAGGTAGTTACTCCACCAAGCTCTTTGCTGGGCCCT
GAAAATGTAACAGTGAACAAGAAAAAAATCTCTTTCCTCAAGGAACTCACACTTCAATGA
AGGGAAATTAGAAGAAATTAGCCTATTACTGTTCAAGTTCAGGGTGTTTGCAGAGGCCTA
GATGCGGCACCTACACTCAGTCTTATGTAAATAGAGGTTTCTCAAAGGAAGAAATGTATA
AATTTAGACCTCTGTAGAGTGAGAGGAGTTGATCACTTTAGAGTGGAGAAACAGATTTAG
[G,A]
ATAACTATACTCTAGATCACACAGCAAGTAAGTGATAGTGTTGGGATTTGAACTCAGGTT
GGTTTCATCCAAAGCCATTGCTTTCAACCATTAAGGCAAGGGCAGAAAATGGGTTTTATC
AAGCCTGTCAATTCTGACAAATTAATAATGGCTTCCAAGAATGTGGATGGTGAATACTCG
GTGAGCACTGGGCTCAATTGGAAAAAAAAATGCCATGATTAATTAATAATGTCTTCCCTG
GGTTCAGAGAGGAGGGTGTATGTGTCATGCATTTGCCTACCCTGCAGTACAGAGTACTGC

134746 GTTTCTCAAAGGAAGAAATGTATAAATTTAGACCTCTGTAGAGTGAGAGGAGTTGATCAC
TTTAGAGTGGAGAAACAGATTTAGGATAACTATACTCTAGATCACACAGCAAGTAAGTGA
TAGTGTTGGGATTTGAACTCAGGTTGGTTTCATCCAAAGCCATTGCTTTCAACCATTAAG
GCAAGGGCAGAAAATGGGTTTTATCAAGCCTGTCAATTCTGACAAATTAATAATGGCTTC
CAAGAATGTGGATGGTGAATACTCGGTGAGCACTGGGCTCAATTGGAAAAAAAAATGCCA
[T,C]
GATTAATTAATAATGTCTTCCCTGGGTTCAGAGAGGAGGGTGTATGTGTCATGCATTTGC
CTACCCTGCAGTACAGAGTACTGCCCTCCAGGACTTAGCACGAGAGGATGAAATCTGCGGT
TGTTTCTTATTCATGTAAGAGTGTCTATGACTTCAAGGAACCTTAGAGCTCAATGGCATC
AGCAGGGGCTTATTATATGTTAGCAAAGGTAGCAAGTGACAGCCCAGGATGGAGCATTCA
GTAAAAAAGAGAATAAAGTTTCCTGTCAAAAGAGAAGACACTAATTAAGTTTAACAGTGA

135854 TGCTTGGAAATGGCTTCTGGATGAATTTCCTTTGCAAAAAGTCTCTTTCACTTTCCCCAG
CTCACCTTCACATTTAACCGTAATAAGCACTCTTTACTCTAGACATTTAACAGATGTTTT
TAAATAACTCAGTTATTGGGTATATAAAAAGAAGAAGATGACCTCCCCAAAAGTCCCAAG
GTCAGAGCTATTTGCCATCTGAGCAATTGTCCCCAGGAAGAATGTTGTGAATGATCACTT
CTCTCTAACCGTGACTCAGCACAGCACACCAACCTGCACCCATTTTCAGAGGCTCACCTT
[G,T]
GGTTGAGGGTGACTTTGAGTATATGGGCCTCAGCAGTCACCGCCCCAAGGGCTGTGCCTGC
TTGTCATGCTTCTCTATCACCCCACCCACCTGCAGCCATCAGAGAGGACCAGTTTCTCAC
TGATCCTCCTCCCCTGATGCATTTACATGAGAGATGGGGGAGGAGCTTTCCCCCTTGAGA
CTTGTTCACCTTGTTTTACTTTGGAAGACAAGATTTTACAGTACCAGGAATCAAAACATT
TCTCTGATCACGTCATGCTGACCAGTGCTAAATTATCTCTGATTCATTGTACATTTTACA

FIGURE 3, page 100 of 122

136893 ATATAAGTCCCTAGTACATCTCTATTTTTTTTTTAGCAATATTGCTGCTGAAGCTTAGCT
GTGTGCTCTCGTGTGTCCCATCCTGCTCTTTCTGCCTCAGGTGTGTGGTCTAGTTAATCC
TCCATTCCATGGGAGAAACATAGCCCAGGAATGCTGGTTGTGAGGAGATTTGATTTCTAC
TCCTACTTCTGCCATTAACTGTATGACTTTGGGCAAGGCTCTTTCCTGGTCCCAGCCCAG
CCCCAGCTATTCAGCATCCATTTAGGATAGGTTGGTCTCTAAGGAGCCTTTCTAGCCCCA
[G,A]
CATTCAAGGACTTAGTGGAAACTAGAATTCTGGGTTCAGTTGAGTTCAGTGCCACCGGCA
TTTGCCGACTGACTTCCTCTTTGTCATCAAGCACCATACGGGGCACTGCAGGGGATATGT
TTATATCAGAGCTCTCTCTGATACCACGGCACTCACGGGCAAAGGGAGAGTGGGATGAGA
AAAACAAGTGTATTGATATACCAGTGCAGAGCAGACTATGTTGTATGCTGGAAGCAAAGT
ACAAATGATTATAGGGTCCAAAGGAAGCAGAAATTTCATTTATTTATGAAAAGTCAGAAT

136945 GCTTAGCTGTGTGCTCTCGTGTGTCCCATCCTGCTCTTTCTGCCTCAGGTGTGTGGTCTA
GTTAATCCTCCATTCCATGGGAGAAACATAGCCCAGGAATGCTGGTTGTGAGGAGATTTG
ATTTCTACTCCTACTTCTGCCATTAACTGTATGACTTTGGGCAAGGCTCTTTCCTGGTCC
CAGCCCAGCCCCAGCTATTCAGCATCCATTTAGGATAGGTTGGTCTCTAAGGAGCCTTTC
TAGCCCCAGCATTCAAGGACTTAGTGGAAACTAGAATTCTGGGTTCAGTTGAGTTCAGTG
[C,A]
CACCGGCATTTGCCGACTGACTTCCTCTTTGTCATCAAGCACCATACGGGGCACTGCAGG
GGATATGTTTATATCAGAGCTCTCTCTGATACCACGGCACTCACGGGCAAAGGGAGAGTG
GGATGAGAAAAACAAGTGTATTGATATACCAGTGCAGAGCAGACTATGTTGTATGCTGGA
AGCAAAGTACAAATGATTATAGGGTCCAAAGGAAGCAGAAATTTCATTTATTTATGAAAA
GTCAGAATAAAACTTCATGGCATTTCAGATCAGCCTTGAAAGAGAAAATTCAAACAGGAT

137997 TTTTAAATGATTAAAAGTTCTAGATGATTTTAAATAGGAGAGAAAAGCAGAGGAGCTGAT
TGAGCAAATGCTGAGAGGAGGTAAAGTGTGGGACATATTTAGGGCAGAGTGATTATTCAG
TATTAGGGTCTCTTCTCCACAGTTTGAGAGGTTCCCACCTGAAGTCTTCTTCCATCTCAT
CTCTTCCAGCTATGCCAGGCCTTGACTCTGCTCTCTCTATGTGGAGAATGACAAATCTAG
TCTCTGTGTGTGTGTGTCTGTGTGTGTGTGTGTGTGTGTGTGTGTGTGTGTGTGTGTGTG
[-,T]
ATGTGTTGTGCTGTTGAAGCTGAATGCCAGCACAATTCTCATCAGCATTTGAGTTCATTG
GCAGCATTTGAAAGAAAGTATAGACCCTTAGCTCTCAGTGCTAATATAGACATTGGCACA
TTAGTTTCAGCTGAATTAACTCATGTAGGACTGACGCTAAGGGACAGTTAGAGTGGAGTG
GAAACTTCTCTGCATACAGAAATAACATCTCAGCACTGTCTGTGTAGCAAGATGTATTAT
CATCATCTTATTGGTACTGGACAAAGCAGGATCTTCAGATGGTGCCCAGCGACTATAGGG

139348 CCCCAGTCAGAATGAAGTCACTAACTCCAGAGTAAAAGAATGGGGCAACCCATGCTCTCT
GTAAAGTGAATTCTAATGAGGTAAAAGTGGGCAGGTCTCTACTGGAGGAGAGAGGACAGC
AGCGAGGAGAGTGGCATGGGAAGTGGAGAGAGCTGCATATGCCCCCACCTCCCCAGTTCT
CTGAGAGATATTCCACACAGGAATTCCTGACCCTTGCCCAGCAATTGTTCAATGACTCTG
ACCATGGAAAGCATACGAGAAAAAGTACGCCAGAAAAGTTGTATCATGGTCGGTAGACCA
[G,C]
AGACAACAGAGAAACTGGCTGCAAGTCTCAGCATCACTCAGAAAGCCTTTGTTCCCAAGG
CACTATTAAGTATCAGGCAGACAGAGAGATTCCTGAGACACAGCTCCTGTCCTCACAGGA
AGGACTCACTGGATAAGATGGGAGGCAAACCCAGGCAGGCTAGCATTGATGCAAGATGCT
GAGTGCCATAACAAACGTCTAAGCAGCTTGCTTTAGGTGTAGTGTGAAGGGAGGATCAGA
CATAGTTAATTCTAACACGAGGTAGGAAGTGTTAAGTGTGCTAATAGCAATACAAGCCAA

139437 GGCAGGTCTCTACTGGAGGAGAGAGGACAGCAGCGAGGAGAGTGGCATGGGAAGTGGAGA
GAGCTGCATATGCCCCCACCTCCCCAGTTCTCTGAGAGATATTCCACACAGGAATTCCTG
ACCCTTGCCCAGCAATTGTTCAATGACTCTGACCATGGAAAGCATACGAGAAAAAGTACG
CCAGAAAAGTTGTATCATGGTCGGTAGACCAGAGACAACAGAGAAACTGGCTGCAAGTCT
CAGCATCACTCAGAAAGCCTTTGTTCCCAAGGCACTATTAAGTATCAGGCAGACAGAGAG
[A,-]
TTCCTGAGACACAGCTCCTGTCCTCACAGGAAGGACTCACTGGATAAGATGGGAGGCAAA
CCCAGGCAGGCTAGCATTGATGCAAGATGCTGAGTGCCATAACAAACGTCTAAGCAGCTT
GCTTTAGGTGTAGTGTGAAGGGAGGATCAGACATAGTTAATTCTAACACGAGGTAGGAAG
TGTTAAGTGTGCTAATAGCAATACAAGCCAAGAACTATGAGAGCCCAGCGAAGGATGGAT
TAATTCTGACTGGGACTCTCACAGAAGAGGTGGTGTCTAAGTGGGACCTTGAAGGATTGG

140321 GTTCAATAAATGATAGTTTTTATTGTCTGTGCTATGACTATTTCAGTGAACATTATCTCA
GTCTTCTGGGTAGCATCTGAGGCTAATTGGCCACTGTTAGGCAATTTTAAAAGTTAACGA
AATGCACCTACAACTTCATCTGCATTTGTCCTCTCTTCAGATCCTTGTATATGAGCATCT
TTGCCTATTCTTGGATCATAGTCTTGCTTTTTTGTTTTTGATTTGTTTGTGGGTTTTTTT
TCTATACAATAGAGCAAATTATTGATTCCTTTTTATAATTTCCTCTTCCTGTTCTAAAGT
[C,T]
CTACCTTGGATGGTCCACTCTTTGTTGTGTGTTCAGATCCAGTAGTGAGTGCAGAAGGAC
AGTTACCATAGTCAGCCTCTCAGTTAGAATTCTGTCGTGTCTACAGACCAGCTTTGTTCC
TCTCCTAGTCACCACTATGCTGCTGAGAATCATCATAGAATATGGGAACTGCAGGCAACT
GCAGCCAAATCTTTTGTTTTACCAATGAGAACCTCCAGCCCAGGGACAGGAAGAAAATTG

TCAAGTTTGTACAGAGAGACAGGCAGGGGTGGGCCTGTGTACTAGTCCTCAAGTGTGCTG

140570 TAGAGCAAATTATTGATTCCTTTTATAATTTCCTCTTCCTGTTCTAAAGTCCTACCTTG
GATGGTCCACTCTTTGTTGTGTGTTCAGATCCAGTAGTGAGTGCAGAAGGACAGTTACCA
TAGTCAGCCTCTCAGTTAGAATTCTGTCGTGTCTACAGACCAGCTTTGTTCCTCTCCTAG
TCACCACTATGCTGCTGAGAATCATCATAGAATATGGGAACTGCAGGCAACTGCAGCCAA
ATCTTTTGTTTTACCAATGAGAACCTCCAGCCCAGGGACAGGAAGAAAATTGTCAAGTTT
[G,A]
TACAGAGAGACAGGCAGGGGTGGGCCTGTGTACTAGTCCTCAAGTGTGCTGACTCACAGG
CCAGTGCCCTGGATGGTTTGCATGCCCTTTCTGCTTTTCTTCCGCAGACTTAGGCTGTGA
GGAGGGCAAAAATGCCTTTCCTCCTCCTCATTTCCTCTTCCCTCCCCCTTCCTCCCTGCT
TTGGGTAAAGCTGAAACATGCAGCTCGTGCTTCCACAAGGCATCCTCAGCATGCTTTTCA
CAGCACCCTCTGCTGACTCCGGGGCCTTCACAGCTTGCAGCCCAGTTGACAGCCAGTGAA

141441 CACGCATTTATGCATTTGCACTATGTAGTAGGCATTTCTGCCTTGGACTTTTAAAAACAT
GCTTGCCCTTTAGGATCCTCATCTTGGAAATCTGCCCTCTTCTCCCTCTTTAAGGGATTG
CCCTTCCCTCTGAATGTGCAGAACATGCTGTTCTTCTACTGCAGAATTTATTTCATTTTC
TCATGCAATTTTTATTAGTGGCTCATAAGTGTGTCTTTCATCGCATTGGAATGACCCCTCT
TAGAGGCAAGGGTCTTGACTGTTGTTTTCCCCATACTATACCACATACACTATGTTGAAT
[T,C]
GATAAATTTACTTATTCAGTGAATGTTTTGGTATTATAATAGACATGTTGCAAGGTAGTT
TAGCAAAGTGATAAGGACTCATGTGGAATCAGACATACAGGGGTTTGAATTGTAGCTCCA
CTATTATCAGTTCTGTGACCCCTGCCTACCTATGTTTTAGTCCCTCTTTTGTTAAATGGC
AATAATAATAAAGTACACCCTCTTAAGCTGTTACAGAGATTAAAAGAATTGATGAAAGTA
AAATGTGTAGTCTATTTTCTAGCATTAAAGTGCTCAGTATATGCAAGCACCTATTAGTAA

141639 TGGCTCATAAGTGTGTCTTTCATCGCATTGGAATGACCCCTCTTAGAGGCAAGGGTCTTGA
CTGTTGTTTTCCCCATACTATACCACATACACTATGTTGAATTGATAAATTTACTTATTC
AGTGAATGTTTTGGTATTATAATAGACATGTTGCAAGGTAGTTTAGCAAAGTGATAAGGA
CTCATGTGGAATCAGACATACAGGGGTTTGAATTGTAGCTCCACTATTATCAGTTCTGTG
ACCCCTGCCTACCTATGTTTTAGTCCCTCTTTTGTTAAATGGCAATAATAATAAAGTACA
[C,A]
CCTCTTAAGCTGTTACAGAGATTAAAAGAATTGATGAAAGTAAAATGTGTAGTCTATTTT
CTAGCATTAAAGTGCTCAGTATATGCAAGCACCTATTAGTAATTAATGTTAGAAATAATA
ATGATAATTATCATCATCATCATCATCATCATCATCATTTGTTGCCACTGTGGCTGTGCC
AGGTTCTCCAGATCCTCAATGATCCCCTTTCTTTTCTTAGATATGTGAGGGAGATAAGCA
AAGGAATATATTGAAGAGAAAAAGCCCAATGTTTATTACTGCGTGGCTGTTGCTATGCTG

141796 GTAGTTTAGCAAAGTGATAAGGACTCATGTGGAATCAGACATACAGGGGTTTGAATTGTA
GCTCCACTATTATCAGTTCTGTGACCCCTGCCTACCTATGTTTTAGTCCCTCTTTTGTTA
AATGGCAATAATAATAAAGTACACCCTCTTAAGCTGTTACAGAGATTAAAAGAATTGATG
AAAGTAAAATGTGTAGTCTATTTTCTAGCATTAAAGTGCTCAGTATATGCAAGCACCTAT
TAGTAATTAATGTTAGAAATAATAATGATAATTATCATCATCATCATCATCATCATCATC
[A,-]
TTTGTTGCCACTGTGGCTGTGCCAGGTTCTCCAGATCCTCAATGATCCCCTTTCTTTTCT
TAGATATGTGAGGGAGATAAGCAAAGGAATATATTGAAGAGAAAAAGCCCAATGTTTATT
ACTGCGTGGCTGTTGCTATGCTGTGGGCTTCTATGAGCTGGAGGACCCAAGAAAGCTACT
TTCCCTGTGGCCCTCACCTATTCTTGGCTGTCTGGATCTCAGCACTATGGGGATCAGAAG
AGGCCACCCCAAAACAATAGGAAATAAAAAGGAATTTTTGCCCAATGCTTTGAACAAGGC

141797 TAGTTTAGCAAAGTGATAAGGACTCATGTGGAATCAGACATACAGGGGTTTGAATTGTAG
CTCCACTATTATCAGTTCTGTGACCCCTGCCTACCTATGTTTTAGTCCCTCTTTTGTTAA
ATGGCAATAATAATAAAGTACACCCTCTTAAGCTGTTACAGAGATTAAAAGAATTGATGA
AAGTAAAATGTGTAGTCTATTTTCTAGCATTAAAGTGCTCAGTATATGCAAGCACCTATT
AGTAATTAATGTTAGAAATAATAATGATAATTATCATCATCATCATCATCATCATCATCA
[-,C,T]
TTGTTGCCACTGTGGCTGTGCCAGGTTCTCCAGATCCTCAATGATCCCCTTTCTTTTCTT
AGATATGTGAGGGAGATAAGCAAAGGAATATATTGAAGAGAAAAAGCCCAATGTTTATTA
CTGCGTGGCTGTTGCTATGCTGTGGGCTTCTATGAGCTGGAGGACCCAAGAAAGCTACTT
TCCCTGTGGCCCTCACCTATTCTTGGCTGTCTGGATCTCAGCACTATGGGGATCAGAAGA
GGCCACCCCAAAACAATAGGAAATAAAAAGGAATTTTTGCCCAATGCTTTGAACAAGGCA

141799 GTTTAGCAAAGTGATAAGGACTCATGTGGAATCAGACATACAGGGGTTTGAATTGTAGCT
CCACTATTATCAGTTCTGTGACCCCTGCCTACCTATGTTTTAGTCCCTCTTTTGTTAAAT
GGCAATAATAATAAAGTACACCCTCTTAAGCTGTTACAGAGATTAAAAGAATTGATGAAA
GTAAAATGTGTAGTCTATTTTCTAGCATTAAAGTGCTCAGTATATGCAAGCACCTATTAG
TAATTAATGTTAGAAATAATAATGATAATTATCATCATCATCATCATCATCATCATCATT
[T,-]
GTTGCCACTGTGGCTGTGCCAGGTTCTCCAGATCCTCAATGATCCCCTTTCTTTTCTTAG
ATATGTGAGGGAGATAAGCAAAGGAATATATTGAAGAGAAAAAGCCCAATGTTTATTACT
GCGTGGCTGTTGCTATGCTGTGGGCTTCTATGAGCTGGAGGACCCAAGAAAGCTACTTTC

```
          CCTGTGGCCCTCACCTATTCTTGGCTGTCTGGATCTCAGCACTATGGGGATCAGAAGAGG
          CCACCCCAAAACAATAGGAAATAAAAAGGAATTTTTGCCCAATGCTTTGAACAAGGCAGG

142186    TATATTGAAGAGAAAAAGCCCAATGTTTATTACTGCGTGGCTGTTGCTATGCTGTGGGCT
          TCTATGAGCTGGAGGACCCAAGAAAGCTACTTTCCCTGTGGCCCTCACCTATTCTTGGCT
          GTCTGGATCTCAGCACTATGGGGATCAGAAGAGGCCACCCCAAAACAATAGGAAATAAAA
          AGGAATTTTTGCCCAATGCTTTGAACAAGGCAGGTCCAAGCTTCCCACCTCAGATCTTCA
          GAGTGAAGTCCCCTCCCTCCCATGCTCAAAGCAGCTCTAGACCTGCACAGCACCCTCAAA
          [G,T]
          AAGCAAATCCAGCAGAGATTTTATGGCTTTAGCACCATCTGGCCTTATCTCCTTAGCTGT
          CTTGAAGGAGACAATAGAGGGTGGAGGAGAAGTAATCATCCTAAAACCAACAGGTGGCCC
          CAGTTGTAGGCTATGTAGCAGCATGGCTGTGGTGGTGGTGGTTGCTTGGTGTATGTGTGG
          AAGTGCAAGGGAAGTCTATAATGCAGTGTTCTGAGTGTGTGCAGAACCTATGGAGGAAAT
          CAGAACTTGAGATAGAGAAACAAGTCCTGTTAATGGTAACGCCATTTGGATCTGGAAATA

142212    TTATTACTGCGTGGCTGTTGCTATGCTGTGGGCTTCTATGAGCTGGAGGACCCAAGAAAG
          CTACTTTCCCTGTGGCCCTCACCTATTCTTGGCTGTCTGGATCTCAGCACTATGGGGATC
          AGAAGAGGCCACCCCAAAACAATAGGAAATAAAAAGGAATTTTTGCCCAATGCTTTGAAC
          AAGGCAGGTCCAAGCTTCCCACCTCAGATCTTCAGAGTGAAGTCCCCTCCCTCCCATGCT
          CAAAGCAGCTCTAGACCTGCACAGCACCCTCAAAGAAGCAAATCCAGCAGAGATTTTATG
          [G,A]
          CTTTAGCACCATCTGGCCTTATCTCCTTAGCTGTCTTGAAGGAGACAATAGAGGGTGGAG
          GAGAAGTAATCATCCTAAAACCAACAGGTGGCCCCAGTTGTAGGCTATGTAGCAGCATGG
          CTGTGGTGGTGGTGGTTGCTTGGTGTATGTGTGGAAGTGCAAGGGAAGTCTATAATGCAG
          TGTTCTGAGTGTGTGCAGAACCTATGGAGGAAATCAGAACTTGAGATAGAGAAACAAGTC
          CTGTTAATGGTAACGCCATTTGGATCTGGAAATAACTGTGTTTGCATAGTCCATGTCTGT

142600    GTGGCCCCAGTTGTAGGCTATGTAGCAGCATGGCTGTGGTGGTGGTGGTTGCTTGGTGTA
          TGTGTGGAAGTGCAAGGGAAGTCTATAATGCAGTGTTCTGAGTGTGTGCAGAACCTATGG
          AGGAAATCAGAACTTGAGATAGAGAAACAAGTCCTGTTAATGGTAACGCCATTTGGATCT
          GGAAATAACTGTGTTTGCATAGTCCATGTCTGTTCTCTTACAGATGAGCAAACAAAAGCT
          CTTCATTTAAGGAGAGAAATAGTCCACTCTCTTGTTTACTCTTTTACTTGACATTGATTG
          [A,T]
          ACCTCTCAATGGCAAAGACTGTGTTGTGCATTAGATAGATATGCTGAGAAATGAGAAAGA
          GGCTGTGCCCTCAAAAATTTGTCCTAAAAGGGGAACATCTAGATAATCAATGAGCTAATA
          AATGATTAGATACAGTGTTGTCCCTTCAACCATCTCTTTGGATTCACCACATTCTCCACA
          CTCTCTCTAAAGACTCCCACTCATGCCCCTGGTGAGTCAAAAGCTCCTGGCCAGTAGCCT
          CTTCTCTGATCAACTCATATATTTCTGCTCATATCACCTTTGCTGGTGGCATACCAGAAT

142631    GGCTGTGGTGGTGGTGGTTGCTTGGTGTATGTGTGGAAGTGCAAGGGAAGTCTATAATGC
          AGTGTTCTGAGTGTGTGCAGAACCTATGGAGGAAATCAGAACTTGAGATAGAGAAACAAG
          TCCTGTTAATGGTAACGCCATTTGGATCTGGAAATAACTGTGTTTGCATAGTCCATGTCT
          GTTCTCTTACAGATGAGGAAACAAAAGCTCTTCATTTAAGGAGAGAAATAGTCCACTCTC
          TTGTTTACTCTTTTACTTGACATTGATTGAACCTCTCAATGGCAAAGACTGTGTTGTGCA
          [T,C]
          TAGATAGATATGCTGAGAAATGAGAAAGAGGCTGTGCCCTCAAAAATTTGTCCTAAAAGG
          GGAACATCTAGATAATCAATGAGCTAATAAATGATTAGATACAGTGTTGTCCCTTCAACC
          ATCTCTTTGGATTCACCACATTCTCCACACTCTCTCTAAAGACTCCCACTCATGCCCCTG
          GTGAGTCAAAAGCTCCTGGCCAGTAGCCTCTTCTCTGATCAACTCATATATTTCTGCTCA
          TATCACCTTTGCTGGTGGCATACCAGAATCAAGAATCAATTCTGTTTGTTTTCAAACCTG

145397    GGCAGCATGTGCTCTTGGTTGTCATGCCTCCATTCCTCCTTCTGGAAAATAGTAAAGAAG
          AAAATGTATAAGTTAGAGAGGTGAAAGAGTGTTAGAGCTAATTAAATCTCACTTATTTTA
          CTTATGAGGAAATAACTCCCAAAGAGGAGAAATGACTAAGTTCATATAAAGAACCTGCAG
          CTAACTTGGTCATTTAGTCATATAAAGAACCTGCAGCTTACTTGGTCATTTATGCATTTA
          TTCCATTCAGCAGACATGTTTCAGTGCCTCCCATGTGCCAGGCACTGTGGTAGATGCTAG
          [G,A]
          ACAATAGTGATAAGTAAATAAACATGATTCTTGCCCTAATCAGGGAGATGAAATTAAACA
          AATAAACCAAAAGTTAAACAAAATAATTAAAGATAGAGATAAGGTATGATGGAAAGAAAC
          AAGGTACCGCAATAGAGAATAAAGAGTAGGGACCGGGCACGGTGGCTCACTCCTGTAATC
          CCAGCATTTTGGGAGGCCGAGGCGGGTGGATCACAAGGTCAGGACATCGAGACCATCCTG
          GCTAACACGGTGAAACCCCATCTCTACTAAAAATACAAAAAAAATTAGCCAGTCGTGATG

145438    CTGGAAAATAGTAAAGAAGAAAATGTATAAGTTAGAGAGGTGAAAGAGTGTTAGAGCTAA
          TTAAATCTCACTTATTTTACTTATGAGGAAATAACTCCCAAAGAGGAGAAATGACTAAGT
          TCATATAAAGAACCTGCAGCTAACTTGGTCATTTAGTCATATAAAGAACCTGCAGCTTAC
          TTGGTCATTTATGCATTTATTCCATTCAGCAGACATGTTTCAGTGCCTCCCATGTGCCAG
          GCACTGTGGTAGATGCTAGGACAATAGTGATAAGTAAATAAACATGATTCTTGCCCTAAT
          [C,T]
          AGGGAGATGAAATTAAACAAATAAACCAAAAGTTAAACAAAATAATTAAAGATAGAGATA
          AGGTATGATGGAAAGAAACAAGGTACCGCAATAGAGAATAAAGAGTAGGGACCGGGCACG
```

GTGGCTCACTCCTGTAATCCCAGCATTTTGGGAGGCCGAGGCGGGTGGATCACAAGGTCA
GGACATCGAGACCATCCTGGCTAACACGGTGAAACCCCATCTCTACTAAAAATACAAAAA
AAATTAGCCAGTCGTGATGGCAGGCACCTGTAGTCCCAGCTACTCGGGAGGCTGAGGCAG

145855 CACGGTGGCTCACTCCTGTAATCCCAGCATTTTGGGAGGCCGAGGCGGGTGGATCACAAG
GTCAGGACATCGAGACCATCCTGGCTAACACGGTGAAACCCCATCTCTACTAAAAATACA
AAAAAAATTAGCCAGTCGTGATGGCAGGCACCTGTAGTCCCAGCTACTCGGGAGGCTGAG
GCAGGAGAATGGCGTGAACCCGGGAGGTGGAGCTTGCAGTGAGCCGAGATCGCGCCACTG
CAATCCAGTCTGGGCAACAGAGTGAGACTCCATCTCAAAAAAAAAAAAGAAAAAAAAAAA
[A,-,G]
AGTAGGATGAGTATTTTAGAGAAGGCCTCTATGAAGAGAGAACATTTTAAGCTGAGATCT
GAAGAATGCGAAGGGGTCAGCCACTTAAAGAGGGTTGGAAGAGCTTTCTAGGAGATAACA
GCTTGTGTAAAACCTCAAGGCAAGAAAGTCGGGACTGTCCTGAAAGGTAAGAGAAAGACC
AGCATGAAGCCCAGGCAGAGGTGTCATGGCCTGGAAGCAGATGTGGTGGGAGAGATAGGC
AGGGCCAGAACTCAGAGCCTCAGAGTTCAAAGTGCCCTTATTGGCAGACTCTTGATTGAT

146816 GATGAATTTTGCTGATTTAGGGCACCCTCGGGCTGTCCTCTGTAGCTTTCAGTAAAGCTT
TGTCTTGATTGACAGATGCTGATCAAGTTCATGGGTATGCATTACAGTGTACGTTTGCTG
GTTGGCCTAGGAAAACCCATTTGCACGTATGACTTTCATAGGAAAAGAATGGCAAATAAG
AAACAAAAGATTTTTTTCTGCCACTCACCCAAGGAACAGAAATTAAGACAGCCAAAGGA
AGAGTCTGCCTTCATTTAACGGATGATTTACCTGGTGTTCCTTGCGGTAGTGGTTCATTC
[G,A]
TGAACCAGCAGAAGGTATTTTGTGACTATGGGGATTGCGGAGATGACTGGGCCAGGAGGG
GAAGCTGTAAAGCTAATCTCTCCCACAACCCACTTCTCTTTGGCTAATGGCTTTGCTTTT
GTTTGTTCTGCTTTGGCTGGTTCATGTGCTAGTTCCCAAAGGCTGCACAAAGGCAGAGCT
AGGTAGATGTACTCCCTACCAGGGCTCTTTAGTGAATCCCACCTCCTAGCCCCAGATGAG
GCTGAGTGAACACTCACTCCAGCCTTGGACTGTAGCCTTTACTGTGGCCCCTGAACCTAA

147228 TTTGCTTTTGTTTGTTCTGCTTTGGCTGGTTCATGTGCTAGTTCCCAAAGGCTGCACAAA
GGCAGAGCTAGGTAGATGTACTCCCTACCAGGGCTCTTTAGTGAATCCCACCTCCTAGCC
CCAGATGAGGCTGAGTGAACACTCACTCCAGCCTTGGACTGTAGCCTTTACTGTGGCCCC
TGAACCTAACCCAAGAATGAGACTTGTTGACCCAAGGCTCAGACCCCAAGTCTCAGATCC
CTTATTTCAAAGAGAGCTCCTCACCCCAGCTCCAGACTGAGCCCCTGGCCCAGCATTCCT
[G,C]
GCTGAGTCCCCACACGTGGTAGAGCCTTGGCCTCAAAGGGTCCATCCACAATGTTGTGAG
TCCCTTGCTACATATTCACTTTTTGAATGAACCTCTGAGGACCCCTGCCCTCTCAAGACT
GGCGTCTCCTCTGCCATCTCATCAGAGTGGCTTTTAGCCATGGAGCAGTGTCATAGCCTC
CTCTAGTCCAAAGCTGGCCGGTGCTAAGAAGAGGAAGCCTGGAACTCAGAACCTCTGTCC
TTGTGCCAACATGTTAGTTGCAGTCTATCTGTGAGCTTCACAGTCCCATTGACTCTTGTA

147968 TGGGCTCAGACGTGTGTCCATCCTTGCATGACCCTTGGCTCCTCATCTGTTCATGGGTTT
AAAGGTCATCCTTCCTGCCCTGCCTACCTTATTGAGTATTCACAACAGAAAATGAATGTA
GGAGATTGAAAATTGTATAATGCACTCTAAGTTATTATTACCTCTCCCAAATTGTCAGCA
TTTCATCCTTGCTATCTAGCAGCAGAATAGTGTAGGGTAGGAGTTTACAAACTACAGCCC
ACAGGCCAAAGCCAGCCCAAGGCCAGATTTTCTAAATAAAGTTTTATTGAAACACAGCAA
[T,C]
GTAAATATGTAAACTCATTTGTTTACATATTGTCTTTGGCTGCCTTCATGCTATAAAAGT
AGCACTGAGTAGTGCAGCAGAGACCACATGGCCCGCAAAACCTAAGATATTTACTATTTG
GCTTTTTGCAGAAAAAGTTTGCCTATACCTGGCATAGAGGAGCAAAGTGAGGACTCTGAA
GTTGGAATGCCTGTGTTTGGATTCTGAATCTTCTACTTAATGGCTATATGACCTTGTGCA
AGTTAATTAGCTTCACTTTTCTCTCTATGAAATAAAAATAAACATTGTATCCCCACCCTG

149372 AAATGCTCTCATTTTGAACCCATTCAACATCTTCAGGGTTGAGTTCTGTAATGGGATGTA
AATCTTCTTTCCTGGGGAGAAACGGCTGAGGAGACTGGGTGTTGTAGGTGGAATACATTA
AGGCTGGTGGGGTTTGAGTGCCAGCCCAAGAGCACAGCTCTCATTCTCAGTTGGCCTAAG
CTAACAGGGAGTGATCAAGTTCAGTGGACTGAAGCACAGGGGAGTATTACGTATCTTCCA
GACCTGTGGATGCTAGATGGGCAACCTAATTTAGAGGAATATGAAACAAGTAACAGCACC
[G,A]
TGCAATTTTCGTTATTCCCTACCTAGCTCTTTATGAGTTATTGTTCATTATATTAGCAGA
AAAATGAGGATTTGGAGAGCCTCTTCCTTCAAGGGGGCTTACATCTCAATTGCAGGTGAA
AAGGCATAAATACACAAAAAGTTACTTGATAATATAAAATAAAATAATCAATTCATTCAG
TGCAAGACATGTCATGAAAGAAAGATGGGTCAACTTAGTATCCAGAGATTAAAATAGGTA
AATGACTTGCATTCATTCATTTATTCTCATATTCATTCATGTCCAAAAATATTGTGTAGT

149466 CTGGGTGTTGTAGGTGGAATACATTAAGGCTGGTGGGGTTTGAGTGCCAGCCCAAGAGCA
CAGCTCTCATTCTCAGTTGGCCTAAGCTAACAGGGAGTGATCAAGTTCAGTGGACTGAAG
CACAGGGGAGTATTACGTATCTTCCAGACCTGTGGATGCTAGATGGGCAACCTAATTTAG
AGGAATATGAAACAAGTAACAGCACCGTGCAATTTTCGTTATTCCCTACCTAGCTCTTTA
TGAGTTATTGTTCATTATATTAGCAGAAAAATGAGGATTTGGAGAGCCTCTTCCTTCAAG
[G,T]
GGGCTTACATCTCAATTGCAGGTGAAAAGGCATAAATACACAAAAAGTTACTTGATAATA

TAAAATAAAATAATCAATTCATTCAGTGCAAGACATGTCATGAAAGAAAGATGGGTCAAC
TTAGTATCCAGAGATTAAAATAGGTAAATGACTTGCATTCATTCATTTATTCTCATATTC
ATTCATGTCCAAAAATATTGTGTAGTCATTATGGGAACCCTTCAAAGGGATATGAATAAT
AATATAAGCTTTATGAGGGCAAAGGCATCATCTGTCTTATTTACCACTCTATTCCACAGT

149468 GGGTGTTGTAGGTGGAATACATTAAGGCTGGTGGGGTTTGAGTGCCAGCCCAAGAGCACA
GCTCTCATTCTCAGTTGGCCTAAGCTAACAGGGAGTGATCAAGTTCAGTGGACTGAAGCA
CAGGGGAGTATTACGTATCTTCCAGACCTGTGGATGCTAGATGGGCAACCTAATTTAGAG
GAATATGAAACAAGTAACAGCACCGTGCAATTTTCGTTATTCCCTACCTAGCTCTTTATG
AGTTATTGTTCATTATATTAGCAGAAAAATGAGGATTTGGAGAGCCTCTTCCTTCAAGGG
[C,A]
GCTTACATCTCAATTGCAGGTGAAAAGGCATAAATACACAAAAAGTTACTTGATAATATA
AAATAAAATAATCAATTCATTCAGTGCAAGACATGTCATGAAAGAAAGATGGGTCAACTT
AGTATCCAGAGATTAAAATAGGTAAATGACTTGCATTCATTCATTTATTCTCATATTCAT
TCATGTCCAAAAATATTGTGTAGTCATTATGGGAACCCTTCAAAGGGATATGAATAATAA
TATAAGCTTTATGAGGGCAAAGGCATCATCTGTCTTATTTACCACTCTATTCCACAGTGT

149474 TGTAGGTGGAATACATTAAGGCTGGTGGGGTTTGAGTGCCAGCCCAAGAGCACAGCTCTC
ATTCTCAGTTGGCCTAAGCTAACAGGGAGTGATCAAGTTCAGTGGACTGAAGCACAGGGG
AGTATTACGTATCTTCCAGACCTGTGGATGCTAGATGGGCAACCTAATTTAGAGGAATAT
GAAACAAGTAACAGCACCGTGCAATTTTCGTTATTCCCTACCTAGCTCTTTATGAGTTAT
TGTTCATTATATTAGCAGAAAAATGAGGATTTGGAGAGCCTCTTCCTTCAAGGGGGCTTA
[C,A]
ATCTCAATTGCAGGTGAAAAGGCATAAATACACAAAAAGTTACTTGATAATATAAAATAA
AATAATCAATTCATTCAGTGCAAGACATGTCATGAAAGAAAGATGGGTCAACTTAGTATC
CAGAGATTAAAATAGGTAAATGACTTGCATTCATTCATTTATTCTCATATTCATTCATGT
CCAAAAATATTGTGTAGTCATTATGGGAACCCTTCAAAGGGATATGAATAATAATATAAG
CTTTATGAGGGCAAAGGCATCATCTGTCTTATTTACCACTCTATTCCACAGTGTCTAGCC

151121 CTCAGTTTTACTCAGAGAGCTATGTGATCTCTTTCTCCTCACCTGCATCTCTACTGCTTT
CCTCCTTTCCCCCTATACTGTGTCCACATGGGCCTTCTGTTTCTCAAGCTCTTCAGTCTT
GTTCCTGAGCCTCATTCAGAGCCTCTGTTCCATTCCTTCTGCCTGAGACTGCTTCTTTAG
CCTTTAGCCTGGCTGGCTCCTTCTTAGGGTTCATTTCTCAGCTCCAATGCTAGTGACACA
GAGAGGTCTCCCTGACCATCCTGTCTAAAATAGTCCTGCCAGTCACTCTCACATCATCCC
[G,A]
TTTTATTTTCTTTGTAATATTCGCAGCATCCAAAATGGCCTTGTTTATTCACATGTCATC
TCTCTCCCTCTCTAGAGCCTAAGCTCCAAGAGAGCAGAGACTTATCTTTTTATCCAGTGA
TGTATACCCCTAGCACCAGCTTGCTGCCTAGCATACACTACACATTCAGGAAACTTGTTG
GATGGGTGAATGATTAGGCAGAAGAAAGATGGAGAGAAGAAACAGAAAATTTCAATCTGT
AGGACCTCACATCCCCAGTGAGTACAAAAGTTCTATTACAGGTACTTCACCAAAACAAAA

151984 TAGCCTCGTATGCAGTACCACATCTCATTGGCTTTCAATGCCTAGTAATTAAGACCCATG
CTTAATAATAAATACACAAATATGACCTGGGAGGATGGCTTTTCTTCCACATCTCCTTTT
GCAGCCATCTTCCAACTGGGCATCAGGGCCTGGATGAAGAAAGTTCTTGTGAGTCTCAAA
TGAATCCAAAACCAAAGTGAAATGCTACATTGACACATGACACAATGACCTAACTTCTCC
AGCCCGGGCAAGGCCCTTGGCAACCTAGTCCCCACCCATCTCCAACTCTGTGCCATACCC
[C,T]
GACCCCAGTCATACTGGTGTTTCTGGAGTTTTTCTGTTGTGCCCTTCTCTTTTATCTTGG
TGCTTTGGATAAAGTGGTCCCTCTATCTAGACACAGGAACAAGGTGCTTAACACTGTGCC
CGGCCTCTGCTAAAGGACCCAGTTAACACTGACTATAATAGCAGTTATGATCATTTATCC
TGTGGCTGATCCCTTTATTACTCTCTCAAATCACCCTTTATTTTCCTTAATGTAAAACTC
ACTGAACACTTGCTTAAGCTCTGTGAAGGTAGAAAACATGTCTGTCTTGTGTAATTGTGG

152547 GTGAAGGTAGAAAACATGTCTGTCTTGTGTAATTGTGGTACCCCAATTTTCTGGCAATAT
TAGTTTCTGGTGCCAATAAATATCTGTTGAATTTACTAAATAAATGATAACATTGTATCT
AGTAAATGACAGACACCCTGGATGTGTCTCAGAATCCTAAGTAAATGTGATATTGTTTAA
GGGCTTTGGGATGATTTATATCTATTATGGTAATTCTTTGCATGTCAGCATTATATCTAC
GATACAAGAGAATATAAAAAGGGATGGACAGGCACTCTTATTGTCCTCTGAGTGATGGAA
[A,C]
TGAAGCACATCCCTTGATGTTACAACGTTAGAGTAAGATGATGAAGAATGTGATTCCCAC
CAATAAGGATAGAATTATTCCAGGAGGGGAATGAGTGCCTGAAAGTCCCCCCATTCACAC
ATACTTTTGATCTCCCTCCCCTAAAATGAAGCTGTCCTGTCACCTCATTATCTGCTATTT
ACAATGAGGCTGCCACATTCCCAGGGACAGGAGCCAAGGAGAAATGTCGGTGTGAGAGGC
CTTAAATGAAGTGACAATAAAAAAGGAGTTGTTAATGCCAGGAGTTCCCTCCCTGGGAGA

152560 ACATGTCTGTCTTGTGTAATTGTGGTACCCCAATTTTCTGGCAATATTAGTTTCTGGTGC
CAATAAATATCTGTTGAATTTACTAAATAAATGATAACATTGTATCTAGTAAATGACAGA
CACCCTGGATGTGTCTCAGAATCCTAAGTAAATGTGATATTGTTTAAGGGCTTTGGGATG
ATTTATATCTATTATGGTAATTCTTTGCATGTCAGCATTATATCTACGATACAAGAGAAT
ATAAAAAGGGATGGACAGGCACTCTTATTGTCCTCTGAGTGATGGAAATGAAGCACATCC
[C,T]

FIGURE 3, page 105 of 122

TTGATGTTACAACGTTAGAGTAAGATGATGAAGAATGTGATTCCCACCAATAAGGATAGA
ATTATTCCAGGAGGGGAATGAGTGCCTGAAAGTCCCCCCATTCACACATACTTTTGATCT
CCCTCCCCTAAAATGAAGCTGTCCTGTCACCTCATTATCTGCTATTTACAATGAGGCTGC
CACATTCCCAGGGACAGGAGCCAAGGAGAAATGTCGGTGTGAGAGGCCTTAAATGAAGTG
ACAATAAAAAAGGAGTTGTTAATGCCAGGAGTTCCCTCCCTGGGAGACAGCTGTCAGGGC

154834 TTGCAAAGAGGTAAGAAAAGCAGGCTGCAGGCAGGAGGGGACAGTGCAGGATCCCAGGA
TTTTGTTACAAGGGAATCCAAGAACTCAGAGACTTACCTGCTTACTGGATTTGAAAAAGT
GCACTGGGGGTTGCTAGAATTTGACTAAATAACTAAAATATTGTCGAATCAGTAAACATT
TTCCAATCAATTAGACTAGACTCTAGAATGTCAGAGTCTGAAAGGGCATTAAGCATTATA
GAGATCAAACAATCATTTCACAGATGGGAAAGCTGAGGCCTAGGAGAGCGTGGGATTTAC
[T,C]
TAAAGTCATACAAGTACTCTGTAATGATAAAACCAAAAAGAGAATCGTCCAGGTCTTCTG
ACAGCTAGCCTAGTACTTTGTCTACAGAACCATGTTATCTCTTCTGATTGAATATTGGTT
GTGACAGATTCAAAGTAGATATAATACCTCACAACTACTAATTATATTTATCAACATTTA
ACCAATGACTGCCTTCTCCCACAGGCCTTCGGCCTATAGGGTCTGTCTGTCTGTTTCTGT
CTCTCTCTCTTTCTTTTACTTCCTCTCTCTCTGCTGTTGCTTAGGTTTGGCTGAAGTGTA

155118 AGAGCGTGGGATTTACTTAAAGTCATACAAGTACTCTGTAATGATAAAACCAAAAAGAGA
ATCGTCCAGGTCTTCTGACAGCTAGCCTAGTACTTTGTCTACAGAACCATGTTATCTCTT
CTGATTGAATATTGGTTGTGACAGATTCAAAGTAGATATAATACCTCACAACTACTAATT
ATATTTATCAACATTTAACCAATGACTGCCTTCTCCCACAGGCCTTGGGCCTATAGGGTC
TGTCTGTCTGTTTCTGTCTCTCTCTCTCTTTCTTTTACTTCCTCTCTCTCTGCTGTTGCTTA
[G,A]
GTTTGGCTGAAGTGTAGAAATGGTCTGACAGTCAGGCACTGAGCAACTCTGGGAGCCAGG
GTTCACTCAAGTAAATCCAGGCCAGGCTACCTCCAAGCCATGCTCTTTTAGGGAGTAGTG
CGTAAATGCACCCTCTTAGCCTTAGAGGAGAAAGCACTCTGTTTAAGGTAAGAGATGTTT
GCAGAAGGGGAAAATGAGGAGATAATTTGAAGGGGAAAATGTCCTGGCCTCCTGTGTGTC
TAAGGATTTGTTGTGTCTGCCTGCTCCCATTTCGTCCACCCCCATCTCACCCTTTCCTAC

156897 GGCTTCTGGGTAGAGAAGTGATTTTGTCACTGAAAACCAAATGTCCTAAAGCTCAAGGCC
ATGAACACCACCTTCAGATACCAGGAGGGCTATAGAGTGGGTCAAGAGCAAGAATTGTGT
GAAACCAGAATCTCAGTAACTAGAAGTATGCAAGCAGATGTTAATGATCACCTGCCAGGT
TTCCTGCAGATGGTATGCTGGTTTTCAGTGGGAGTAGGACAGATGGGTTATATGGTTCAG
CTGCAATCTTTAAGAGATTATGACCTTTAAAGCCCATTTTCTCTAGGGACTAACAGAAAA
[C,T]
GGAGACTCACAGTAGACAATTAGGTACCACTGGTTAATTGCATTCTTTATTGCAGCATGG
GCCAAAAGATTTTCAATAACATTTCAAAAGTATTCACCAAAAAAAGGTCTTGGAGGCAAA
TAGATTTGACAAAATCTGGGATAAAAATGGGTAGAATTCCTCACAATCTTTTATGCAGCT
AATGTGAAGTATGAAACTCTAAAACAGGGACAAAGTATGCACCATTTCCCAAATGTATTT
GACCAAAGAAGACTTATTTTTTAAGGAGCATCTTGTGGGGCTATAGTTTCATGAAACCTT

157808 GCAAAGATTATGAACTCTCATCCTATATCATATAGTAAAACAAAGTTTAGGAGCTGACTG
ACTTGGAGTTTAATCCCATGACCTTGGTCTTATTAGCATCGTATTTTAATTAGAAGTATA
ATCAACCACAAACCAGGATTGGCAACTGCATTGGGATTCTACAGAATCGGTCCTGTGGGT
ATGTTCTCACAGCTAAGCTATTACTATGGCTGATACACTGGGGGGTCTGAAAATCAGCTA
GCAAGATGTACAAGCACAAAGTGAACATTAGCAGACAAATGAACACTGAGAGTTAAGGGC
[-,G,T]
AGACTGGGAAAATCGACACTTGTTTTCTTAAACGTGTATTAGCAGCAATAGCTGGATTCT
TCCTGTAGCACCTTTTTATGCTTTGCCTTTAATTGATAGACAATGTGAGGGGAAGATCGT
TAGATTAAGAGTCAAGAATATCTGCCCAAGTCATATGTCCTAGCTGTGCTACCTTGAATA
TGTTCATTAAATTTCTGAGCCTTGGTTTCTCCCCTTTAAAAAAATGACCCAGTCATCCCT
TTCTAGCCTCAATAGGGTCATTGTAGAGACCAAGTAAGGTAATAGATGAAAGTGTCTTAT

159171 TCTTAATGCACCATGTCACTCTACAGCTCACTAAGCTTTCATGGCTCCTGAGTCCAAACT
CAATGCAAAAGGACCTCAGACTTTGGAGTCAGGCAGATCTGGATCTGAAACCTAGGTTCT
GTCCTCTCCAGCTGTTTGACTTTGGACAAACTCTCTCTGCCTCAATTTCAGCACTTATAT
AATGGGGATAAAATTCTCTATGCCTTCATTTTCTCATGTCTATAATGAGGATAAAAACAA
TGTCTATCTTATAAAGGTTTTGTGAAACTGAATGAGATGACTATGAAGTGTTCAGTGCCT
[A,G]
CAACATAGTAAAAACTCAAAATTCTTTCTCTGTTTTAGATGTTATCATCATCATCATCCT
CCTCATCATAATCTTCATCCTTCTCTGGGCTTTCTAATTCTTCCTCCTTTGAATTTAACA
TCACATTTTCCAAATGTTTTCTATACTTTTTCTTCTCTATGTCTTTACTCATGTTATTCC
AGTTTTCTGGAATGCACTTCCCTTCTCCAATTTACATCTGTAAATCCTTCTCCTCTTTTG
CAGGATGTCCCTATTCCCCAATTCTGTGGATGGGAGCACTCTCTCCAACTCCCATGATGT

159465 GTGCCTGCAACATAGTAAAAACTCAAAATTCTTTCTCTGTTTTAGATGTTATCATCATCA
TCATCCTCCTCATCATAATCTTCATCCTTCTCTGGGCTTTCTAATTCTTCCTCCTTTGAA
TTTAACATCACATTTTCCAAATGTTTTCTATACTTTTTCTTCTCTATGTCTTTACTCATG
TTATTCCAGTTTTCTGGAATGCACTTCCCTTCTCCAATTTACATCTGTAAATCCTTCTCC
TCTTTTGCAGGATGTCCCTATTCCCCAATTCTGTGGATGGGAGCACTCTCTCCAACTCCC

[G,A]
TGATGTTTGTCTTGTACTGTCCTACCTTCTCATTGTATACTAAATAGTCTTGTAATAATT
TATTCACTACTGGTGTAAACAAATAAATGGGTCACGCAAGACCTGAAAGGTGAGACAGAG
GAGTACAGTACTGATGTGGTTGCCTGCAGGGAGTCTTAGAAAACTTTTGAGTTGGAGAGA
GGTTTGTGAAAGTGATTTTTCAGGCAGTTAGGCAGGCGTCGTTCAGATGGGAAGGAGCCA
ACAGAAGAAACCAGGAACACCCTATTTTCTTTGATTTTCTCTTCACTGTCCCCACTTTGA

159505 TTTAGATGTTATCATCATCATCATCCTCCTCATCATAATCTTCATCCTTCTCTGGGCTTT
CTAATTCTTCCTCCTTTGAATTTAACATCACATTTTCCAAATGTTTTCTATACTTTTTCT
TCTCTATGTCTTTACTCATGTTATTCCAGTTTTCTGGAATGCACTTCCCTTCTCCAATTT
ACATCTGTAAATCCTTCTCCTCTTTTGCAGGATGTCCCTATTCCCCAATTCTGTGGATGG
GAGCACTCTCTCCAACTCCCATGATGTTTGTCTTGTACTGTCCTACCTTCTCATTGTATA
[C,T]
TAAATAGTCTTGTAATAATTTATTCACTACTGGTGTAAACAAATAAATGGGTCACGCAAG
ACCTGAAAGGTGAGACAGAGGAGTACAGTACTGATGTGGTTGCCTGCAGGGAGTCTTAGA
AAACTTTTGAGTTGGAGAGAGGTTTGTGAAAGTGATTTTTCAGGCAGTTAGGCAGGCGTC
GTTCAGATGGGAAGGAGCCAACAGAAGAAACCAGGAACACCCTATTTTCTTTGATTTTCT
CTTCACTGTCCCCACTTTGATGACTTCCCTTCTCAGACTGCGACTATTGCAGGGGTCACC

159786 CCTACCTTCTCATTGTATACTAAATAGTCTTGTAATAATTTATTCACTACTGGTGTAAAC
AAATAAATGGGTCACGCAAGACCTGAAAGGTGAGACAGAGGAGTACAGTACTGATGTGGT
TGCCTGCAGGGAGTCTTAGAAAACTTTTGAGTTGGAGAGAGGTTTGTGAAAGTGATTTTT
CAGGCAGTTAGGCAGGCGTCGTTCAGATGGGAAGGAGCCAACAGAAGAAACCAGGAACAC
CCTATTTTCTTTGATTTTCTCTTCACTGTCCCCACTTTGATGACTTCCCTTCTCAGACTG
[C,T]
GACTATTGCAGGGGTCACCTGGAAGTCTATTTCAGGACAGCTTTGCAGCATAATGTAGCT
GGAGGCCTGGAAGTAATAAAGCCAGAAAAATGTACCTTTGCTTGTGGGAGATCATCTCTG
GGGTCAGCAGAAGCACCCACACTCTCAAAAGAGCTCCACCTACCTCAGAACTCAGAGCTC
AGAGCCCTGCCGTTTGTCAGCTGTGTGACCTTGGACTAATGACTAAATCTCTCTAAGCCT
CAATTTCCACACTATAAAATAGGGATAATAATAGTATCTACCTTGAAAGATTAAGTGGAT

159787 CTACCTTCTCATTGTATACTAAATAGTCTTGTAATAATTTATTCACTACTGGTGTAAACA
AATAAATGGGTCACGCAAGACCTGAAAGGTGAGACAGAGGAGTACAGTACTGATGTGGTT
GCCTGCAGGGAGTCTTAGAAAACTTTTGAGTTGGAGAGAGGTTTGTGAAAGTGATTTTTC
AGGCAGTTAGGCAGGCGTCGTTCAGATGGGAAGGAGCCAACAGAAGAAACCAGGAACACC
CTATTTTCTTTGATTTTCTCTTCACTGTCCCCACTTTGATGACTTCCCTTCTCAGACTGC
[G,A]
ACTATTGCAGGGGTCACCTGGAAGTCTATTTCAGGACAGCTTTGCAGCATAATGTAGCTG
GAGGCCTGGAAGTAATAAAGCCAGAAAAATGTACCTTTGCTTGTGGGAGATCATCTCTGG
GGTCAGCAGAAGCACCCACACTCTCAAAAGAGCTCCACCTACCTCAGAACTCAGAGCTCA
GAGCCCTGCCGTTTGTCAGCTGTGTGACCTTGGACTAATGACTAAATCTCTCTAAGCCTC
AATTTCCACACTATAAAATAGGGATAATAATAGTATCTACCTTGAAAGATTAAGTGGATT

160954 AGGCAAGAGAGTGGATTCTTCCCTAGAACCTTTAGACACCAACACAGCCCTGCTGACACC
TTGATTTTAGCCTGGGACACCTATCTCATGCATCTTACCTCAAGAACTGTAAGATAGTAC
ATTTGTGTTGTTTTAAGCCAGTAAGTGTGTGATAACTTGTTACAGCAGCAGTAGGAAACT
AATACACCATCTAATTCTCCAAGAAGAAACAAAGCAGCATTGAGTAATGGCCTCTCTACT
CATTTAGCTATAGATCAGAAGAGAGTAGTTTAATTCAGGACACATTTTATTTATTTATTT
[-,T,A]
TTTATTTAGTTAGTTAGTTAGTTGAGACAGAGTTTCACTCTTGTCACCCAGGCTGGAGTG
CAATGGCACGATGTGGGCTCACTGCAACCTCTGCCTCCCAGGTTCAAGCAATTCTCCTGC
CTCAGCCTACCAGGTAGCTGGGATTACAGGTACCTGCCACCATGCCTGGCTAATTTTTGT
AATTTTTTTTAGTAGAGATGGGGTTTCATCATGTTTGCCAGGCTGGTCTCAAACTCCTGA
CCTCAGGTGATCCACCCACCTCGACCTCCCAAAGTGCTGGGATTACAGGCGTGAGCCACT

160955 GGCAAGAGAGTGGATTCTTCCCTAGAACCTTTAGACACCAACACAGCCCTGCTGACACCT
TGATTTTAGCCTGGGACACCTATCTCATGCATCTTACCTCAAGAACTGTAAGATAGTACA
TTTGTGTTGTTTTAAGCCAGTAAGTGTGTGATAACTTGTTACAGCAGCAGTAGGAAACTA
ATACACCATCTAATTCTCCAAGAAGAAACAAAGCAGCATTGAGTAATGGCCTCTCTACTC
ATTTAGCTATAGATCAGAAGAGAGTAGTTTAATTCAGGACACATTTTATTTATTTATTTA
[-,A,T]
TTATTTAGTTAGTTAGTTAGTTGAGACAGAGTTTCACTCTTGTCACCCAGGCTGGAGTGC
AATGGCACGATGTGGGCTCACTGCAACCTCTGCCTCCCAGGTTCAAGCAATTCTCCTGCC
TCAGCCTACCAGGTAGCTGGGATTACAGGTACCTGCCACCATGCCTGGCTAATTTTTGTA
ATTTTTTTTAGTAGAGATGGGGTTTCATCATGTTTGCCAGGCTGGTCTCAAACTCCTGAC
CTCAGGTGATCCACCCACCTCGACCTCCCAAAGTGCTGGGATTACAGGCGTGAGCCACTG

160959 AGAGAGTGGATTCTTCCCTAGAACCTTTAGACACCAACACAGCCCTGCTGACACCTTGAT
TTTAGCCTGGGACACCTATCTCATGCATCTTACCTCAAGAACTGTAAGATAGTACATTTG
TGTTGTTTTAAGCCAGTAAGTGTGTGATAACTTGTTACAGCAGCAGTAGGAAACTAATAC
ACCATCTAATTCTCCAAGAAGAAACAAAGCAGCATTGAGTAATGGCCTCTCTACTCATTT

FIGURE 3, page 107 of 122

AGCTATAGATCAGAAGAGAGTAGTTTAATTCAGGACACATTTTATTTATTTATTTATTTA
[G,T]
TTAGTTAGTTAGTTAGTTGAGACAGAGTTTCACTCTTGTCACCCAGGCTGGAGTGCAATG
GCACGATGTGGGCTCACTGCAACCTCTGCCTCCCAGGTTCAAGCAATTCTCCTGCCTCAG
CCTACCAGGTAGCTGGGATTACAGGTACCTGCCACCATGCCTGGCTAATTTTTGTAATTT
TTTTTAGTAGAGATGGGGTTTCATCATGTTTGCCAGGCTGGTCTCAAACTCCTGACCTCA
GGTGATCCACCCACCTCGACCTCCCAAAGTGCTGGGATTACAGGCGTGAGCCACTGGGCC

161415 CATGCCTGGCTAATTTTTGTAATTTTTTTTAGTAGAGATGGGGTTTCATCATGTTTGCCA
GGCTGGTCTCAAACTCCTGACCTCAGGTGATCCACCCACCTCGACCTCCCAAAGTGCTGG
GATTACAGGCGTGAGCCACTGGGCCTGGCCTGCCAGGACACATATTAAACACCTACTGTG
TGAGAGACAAAGTATTAGGTATTAAAGATACTATATTGAACATTCACAAATTTGATCAGC
AGTTATTAGGTGACCATTTAGATGCTAGGTTGGCACATTTAATAAGCAGTTACTGAGTGC
[C,T]
GAATAAAACTAACAGCTAATATTTATAAAACCCTTGCAGGTGTCAGGCTCTGCTATGTAT
CAAACATTCTCACTTAATCCTCATAATGACATTATGAGGTGAGCATTATTTACACCACAC
TTTACCTTTGAAGAAACTAAAGTTTGAAGAGGCTAATGAGCCTGCACAAGGCCATTTAGC
CATATGTTGGATTTGAGCCTCAGATTGTTTTTTAATCACTAGTTCTACCATCTATGTTCA
GAAACACAGTGTCTGATCTCACAGAGTTCAGAGTTTTGCAGCCAGAGAAAACTAGAACTG

161800 AATGACATTATGAGGTGAGCATTATTTACACCACACTTTACCTTTGAAGAAACTAAAGTT
TGAAGAGGCTAATGAGCCTGCACAAGGCCATTTAGCCATATGTTGGATTTGAGCCTCAGA
TTGTTTTTTAATCACTAGTTCTACCATCTATGTTCAGAAACACAGTGTCTGATCTCACAG
AGTTCAGAGTTTTGCAGCCAGAGAAAACTAGAACTGAGTTTGGCAGAAGAGTGGGTTTGG
GGGTAGCCAGGGGAGGTAGGTGCCTGATGGGAGTGGGTGGTGCCCACAAATCCTGACTGT
[-,T,C]
ATTTCTCTTCTACTCATCTGAACTTTAGGCTTATCCGTCCTGCAGAAAGTCCTGGATACA
GCTGCTGAGAAGAACTGGCAGGTGACAGCAGTCAACATCTTGACAACCACAGAGGAGGGA
TACCGGATGCTCTTTCAGGACCTGGAGAAGAAAAAGGAGCGGCTGGTGGTGGTGGACTGT
GAATCAGAACGCCTCAATGCTATCTTGGGCCAGGTAGTGAAAGCAGCAAGGGCTCAGGGT
GGGTGCGGGAGGTGATTCAGGAATAGCCAGACACACTTTTGCCTTGGGTGTTATAAAGAG

161899 ATGTTGGATTTGAGCCTCAGATTGTTTTTTAATCACTAGTTCTACCATCTATGTTCAGAA
ACACAGTGTCTGATCTCACAGAGTTCAGAGTTTTGCAGCCAGAGAAAACTAGAACTGAGT
TTGGCAGAAGAGTGGGTTTGGGGGTAGCCAGGGGAGGTAGGTGCCTGATGGGAGTGGGTG
GTGCCCACAAATCCTGACTGTCATTTCTCTTCTACTCATCTGAACTTTAGGCTTATCCGT
CCTGCAGAAAGTCCTGGATACAGCTGCTGAGAAGAACTGGCAGGTGACAGCAGTCAACAT
[T,C]
TTGACAACCACAGAGGAGGGATACCGGATGCTCTTTCAGGACCTGGAGAAGAAAAAGGAG
CGGCTGGTGGTGGTGGACTGTGAATCAGAACGCCTCAATGCTATCTTGGGCCAGGTAGTG
AAAGCAGCAAGGGCTCAGGGTGGGTGCGGGAGGTGATTCAGGAATAGCCAGACACACTTT
TGCCTTGGGTGTTATAAAGAGGGTTATAAAGAGGGTTCTTCACTAGGTGAGACTAAAAGA
CCTCTATCTCATTTTCTATAATTCACAAAATTTAATTCTGAAATAGCACAAACAATGGGA

162793 CCTTGAACCTGGGAGGTGGAGGTTGCAGTGAGCCAAGATTGTGCTACTGCACTCCAGCCT
AGGCAACAGAGCAAGACTCCATCTCGAAAAATAATAAAAAATAATAATGATAAATTACAT
TCCATTTTAGAGTTTATGAAATGTTATCATATTAGGAACACAGCTTATAGGGCCAAATTT
CTGGGTTCGACTCTGGACTCTGTCACTCATGATCCAGGGTTTGGCATCTCATTCCTTTCA
CCTTCTTAACTGTTTTGAAAGGCTAAGGAAGCAGCAGCCACCTTTATTTCCATTGTTTCC
[T,C]
TGAACATGCCCTTCCCTTTGAGAAATCAATTGACAGTACATTCTTCTATAAACAGGCATT
GTAACTTCAACAGTCTTGAGCTAGATCTCTCTAAACTGTGCTTCCCCTGGTCTCAAAACA
AAAGCCCATGCCCACCACAGAATTAGGATTTTTTGTAGATTCCTTATCTTTTTAAACTAC
ATTTATGTATTCAGATTCAGAGCTAGCAAGGTAGCAGACGTTGCAATAACTTTTGAACAA
TGTCATACAATAAAATTGATAGTTTTAGGTACTTGACAACATGACAAAGTTTGTTAATGG

162919 TTAGAGTTTATGAAATGTTATCATATTAGGAACACAGCTTATAGGGCCAAATTTCTGGGT
TCGACTCTGGACTCTGTCACTCATGATCCAGGGTTTGGCATCTCATTCCTTTCACCTTCT
TAACTGTTTTGAAAGGCTAAGGAAGCAGCAGCCACCTTTATTTCCATTGTTTCCCTGAAC
ATGCCCTTCCCTTTGAGAAATCAATTGACAGTACATTCTTCTATAAACAGGCATTGTAAC
TTCAACAGTCTTGAGCTAGATCTCTCTAAACTGTGCTTCCCCTGGTCTCAAAACAAAAGC
[C,A]
CATGCCCACCACAGAATTAGGATTTTTTGTAGATTCCTTATCTTTTTAAACTACATTTAT
GTATTCAGATTCAGAGCTAGCAAGGTAGCAGACGTTGCAATAACTTTTGAACAATGTCAT
ACAATAAAATTGATAGTTTTAGGTACTTGACAACATGACAAAGTTTGTTAATGGCCTTCA
AGACCCCTGGGGCCCTCACAGAGAATCTTGGTACTAGGACAGCTATTACTCAGAGGCCTC
AGCAATAGAACACAGACAGAGTTTGAATGTTATGGATTCTTTAAGGCACTAACTGTTCTA

162939 TCATATTAGGAACACAGCTTATAGGGCCAAATTTCTGGGTTCGACTCTGGACTCTGTCAC
TCATGATCCAGGGTTTGGCATCTCATTCCTTTCACCTTCTTAACTGTTTTGAAAGGCTAA
GGAAGCAGCAGCCACCTTTATTTCCATTGTTTCCCTGAACATGCCCTTCCCTTTGAGAAA

FIGURE 3, page 108 of 122

TCAATTGACAGTACATTCTTCTATAAACAGGCATTGTAACTTCAACAGTCTTGAGCTAGA
TCTCTCTAAACTGTGCTTCCCCTGGTCTCAAAACAAAAGCCCATGCCCACCACAGAATTA
[-,A,G]
GATTTTTTGTAGATTCCTTATCTTTTTAAACTACATTTATGTATTCAGATTCAGAGCTAG
CAAGGTAGCAGACGTTGCAATAACTTTTGAACAATGTCATACAATAAAATTGATAGTTTT
AGGTACTTGACAACATGACAAAGTTTGTTAATGGCCTTCAAGACCCCTGGGGCCCTCACA
GAGAATCTTGGTACTAGGACAGCTATTACTCAGAGGCCTCAGCAATAGAACACAGACAGA
GTTTGAATGTTATGGATTCTTTAAGGCACTAACTGTTCTACTTTATGAAGTACAAATTTG

163647 AAGATAATAGTTAAGAGCAGAGATAAAACCACACTGGCTAGGGTTCAAATCCCAGCTCTA
GTATTTACTGGCTTTGTGACCTTGACCAGGTTTTTAATCTTTCTACATCTCAAGTTCTTG
ATCTGTAAAATGGGCATCATCATCATAATAATAGCCACTTTTAGAGGGCTCTTGTGAGAA
TTAAAAGAATCAATATATGTGAAGCACTTAGAACAGAGTCTGCCCCACAGTAAGTGGTAC
AAGCAAGCATTTGCCTATTTTTGCTATTCCTAGTGCCTACTAGGACCAGCTTCTTGAGTC
[A,C]
CTTTCTTCCTTGGGCATAAGTGAATCCGTCTGTAAAATGTGAATGAAGGCCTCTGTTCTA
TAAAACTGATAAAAAGGCAAGATAACATAGTCGATGGAAAAAGTGCCAAATGATAATGAC
ATATTAATAGACAGATGACCTATTGTATATTGTTCTATGGTACAGACAGTAGCTATTACT
ACTATTTTTTTAGTGTGTATGGTATACCAGATACTATGCCAAGACCTTCCCATGCATAAT
CCTACTTCATTCCCACATCAACTTTGTAAAACAGCTTTTTTCAATTCCCCTATTTTATAG

163675 CCAGACTGGCTAGGGTTCAAATCCCAGCTCTAGTATTTACTGGCTTTGTGACCTTGACCA
GGTTTTTAATCTTTCTACATCTCAAGTTCTTGATCTGTAAAATGGGCATCATCATCATAA
TAATAGCCACTTTTAGAGGGCTCTTGTGAGAATTAAAAGAATCAATATATGTGAAGCACT
TAGAACAGAGTCTGCCCCACAGTAAGTGGTACAAGCAAGCATTTGCCTATTTTTGCTATT
CCTAGTGCCTACTAGGACCAGCTTCTTGAGTCACTTTCTTCCTTGGGCATAAGTGAATCC
[G,A]
TCTGTAAAATGTGAATGAAGGCCTCTGTTCTATAAAACTGATAAAAAGGCAAGATAACAT
AGTCGATGGAAAAAGTGCCAAATGATAATGACATATTAATAGACAGATGACCTATTGTAT
ATTGTTCTATGGTACAGACAGTAGCTATTACTACTATTTTTTTAGTGTGTATGGTATACC
AGATACTATGCCAAGACCTTCCCATGCATAATCCTACTTCATTCCCACATCAACTTTGTA
AAACAGCTTTTTTCAATTCCCCTATTTTATAGATGAAGAAAAGAGAGATTATACTTGCCC

165562 CCCCAGCACATAGCATAGTGCTTGGCATATAATTTATGTTAAATAAATGTTTGTTGAATG
GATTAATTAGTTAATCATAGAGGGTTTTACAGAGGAGTTGAGATTGGAGCTCAGCCATTA
AGGATACGAACAATCAGAGAGAATGGGAGAGGCCATTCAGACACAAATATTGTGAATGAA
GGCAATGCATTGGGAATGAGCTTTGAAGTAATGGGGGTCAGTGAGGTGATGGACCCCCTTG
TGAAATTGCTTCTTACATTTATAACACCTTTCTCAGTTTGTTACCCTGTATATATTTATC
[C,T]
GTTCACCTATTTATTATGGATCTCCTCTCAATGAAGTGTAACCTCCAAGAGGGCAAGCAC
CATGCTTCTTTCACCTTTCCACTGTGTTGCCAATAGTGCTTCACCCATAGCAAGCTCTTA
ATACATATTTGTGAAAGGAAGGTATTAGAGGAGGGAAGGTCAATGTATAGGTTGGGGAAT
AGATAGATGGGAAGGTTGGTATCAGGTTGGATCATATGAAATTGCCAGTTTTTATAAGTC
AAAAGTCATCAGTTATCAGCTGTTTCCTTTGTTTCAATTTGTACTTTCATCTTGTGGGGA

166011 AGGAGGGAAGGTCAATGTATAGGTTGGGGAATAGATAGATGGGAAGGTTGGTATCAGGTT
GGATCATATGAAATTGCCAGTTTTTATAAGTCAAAAGTCATCAGTTATCAGCTGTTTCCT
TTGTTTCAATTTGTACTTTCATCTTGTGGGGACAATATTTCTCCATTGCCTGAATGTGGT
TGGTTTTAAAATATCATGTCTTTGCTGTTTTGTGTTTATTAGAAGCTGAATAGGTTCTTG
ATAAAGGTGTCTCATTGTTGAAAAGGCAGCAAACCATTTGACAAGCAGATGAAAAAGTAA
[T,C]
GAAGAATTATTAATAAAACTATCATCCCAATAGTATTTGAGCTCCGTGGTCTGGAATTTC
ACAATCTAACCACTATTTCAAAGAATTCATTGTGTGTGCTTGCATTTAATTATTCCCCAC
ATAAAAAAACATGAGTCACTATGCACATACATCCAATTAAGTAGATGTCTGAATGTGGAT
TTTAATAACCTTGAAAATTTATTCAGTTAGAGAAGAAGCCCAAGTGCTTATCATCTGTTA
TATGTCTCCTTGCAACAGTGCAGGGAGAGAGACACCGAGCAGAGTACACTAACCCCAATT

166623 AAAAATAGGGAATTAGATCTAGTTAATCTGCAGGCTGAGCTAGATCTAAAACCAAGGTCT
GTAGTCTTAACCATTCATTATTAGGTGTGTCTCCTGCCCAAGCAAACTTCTGGGCAGTTC
TTTCCACAAATATTTTTTCTACCTGTGATGATTAGGGATAGTCTGCATTTTGGGATAAAA
GGGTATTCATTGACACTGGTTCTTAATGATTAACCATAATCAAACATCAAATGGAAAAGT
TCACAGGAGTCAGGTCCCTGTCCTGATACTGCCACCAGGCTACTATCAGATCTGGGCAAA
[G,A]
CATTTTCCCTCTGTGGGTCTTGACTTCCTATCTGTACAGTGAGAGTTTGGACCAGATGAT
CCTAACTTTCCCTTCCAGCTTCTAAGTTGGGCAATCCATTAATGTCTGAGTACCTAACTG
ATTCGGGGAGGAAGGCACAAAATTCAGAAAAAGAAAGAAGAGCATCTATATATGGTTCAT
GCAAGGAATTGAAGGTGAAGTCATCCACATACCCATCTGACCATTCATCCACCATCCATC
TATTAACTCATCTGTTTTTCCAATCAGCGAATATTGTCATGACAGATTTCATGCAACATA

167461 ATGCCACCATCATTGGATGGTTGGGATATTGTAGTTCTAGTACTTAGGGTAGGGCACATT
GTAAGCACTCGATATCAGCTGCCGTTATTACTGTTGTTGTCGTGGCTTTAACTGTTAGTA

FIGURE 3, page 109 of 122

TGATTAATGAGTCTCCACCTATTATGTTTTGTAGATTATAAAGCTAGAGAAGAATGGCAT
CGGCTACCACTACATTCTTGCAAATCTGGTGAGTAGAGCACTGCAGGCTCTCAGCTCAAG
TCCTTTCCAGGTTTGGGGCCCTACCTTGCTTCTGTTGTCCCTGGCTGATGTGAACTGAGT
[G,A]
GGTGGAAGGGGCAATTCAGGGCTGTAATAATGAGTCTTGGCAATACTACATTTTTATCTT
CTCCACATCCCACTCATCAAACCACAACACACTATTCATGAACCTCTAACCTTCCTTGGA
AGAGAGCATACTGGTGGGCACGGCTTTATCATCTTCACAATTCCAGCTTTAATTGGCTCT
GCCCCTTGGCAATAGGGACAAAATCACCACATCTTTGAATTAATGCAAGATGTCTTGATC
TTACTGGTTTGGGTCCTCCATTTTGACCCCAGTGATAGTTTTACTTCTTATAAATACATT

168935 GAATAATGCTGCTATAAAATATTAGTGTACAAGATTTTCACTTTAATATATACCTAGGCA
TGGAATTACTGGGTTATATGATAACTCTATGTTTAACATTTTGAGGAACTCCAAAATTAT
TTTCCAAAGTGGCTGCATCACCCATCAAATTTTAATCAATAACAAATTTTTCCATGTGAC
AGTTTGAATGATGGCAAGTGTCTCTTAATGATAACTATTTCTACAGTTTATTATCCTGTT
CTGTCTTTGCAATTTTCCATGTTTCCATTAAGAAGTGGTTTCTAGCTTTTTATCTATAAC
[G,A]
AATTTTCAGGTTTTAACTTACTTAACTGAACATATAACTGGCTTCAGTTTTAACCATGTT
ATTTTGTGTTGATTATCTCTATGAGCAATAGTAATTGAACAAAGGATTAATATTTGTTAC
TCATTTCTGGAGTAAAGTCTGTTAGTAGAAATAAGGCACAGGGTGCATGAATCTAAAAAT
GTGACCAAAGCATCCTGCCTAATCCATAAATTCTGTCCTTCTTTCTGACCTGGTATCCAG
CCTTAGATAGATCCCTGCCTTACTCTTCTTTCCCCTTCTTCAACTAACTTGTCTTGGCAA

169142 ATGATAACTATTTCTACAGTTTATTATCCTGTTCTGTCTTTGCAATTTTCCATGTTTCCA
TTAAGAAGTGGTTTCTAGCTTTTTATCTATAACGAATTTTCAGGTTTTAACTTACTTAAC
TGAACATATAACTGGCTTCAGTTTTAACCATGTTATTTTGTGTTGATTATCTCTATGAGC
AATAGTAATTGAACAAAGGATTAATATTTGTTACTCATTTCTGGAGTAAAGTCTGTTAGT
AGAAATAAGGCACAGGGTGCATGAATCTAAAAATGTGACCAAAGCATCCTGCCTAATCCA
[T,G]
AAATTCTGTCCTTCTTTCTGACCTGGTATCCAGCCTTAGATAGATCCCTGCCTTACTCTT
CTTTCCCCTTCTTCAACTAACTTGTCTTGGCAATATTTCGGAGTGAGGACTTGAAATAAG
AAGGGCTTAGAGAAGTAGGTTAATTTAGGCCCAGCTGTTAATGGCTAAATATATTACCTT
TCTCAGAGGTATTTGCATTTTAAATGAGGGTGGCTCTCCAGACACTTTTGGGGAACGAAG
AGTCTCACCCTCCAAAGACCATTTGCAAAAATGGAATTTTTGACTTCGGAGTGAGGAAAG

169379 AGTAGAAATAAGGCACAGGGTGCATGAATCTAAAAATGTGACCAAAGCATCCTGCCTAAT
CCATAAATTCTGTCCTTCTTTCTGACCTGGTATCCAGCCTTAGATAGATCCCTGCCTTAC
TCTTCTTTCCCCTTCTTCAACTAACTTGTCTTGGCAATATTTCGGAGTGAGGACTTGAAA
TAAGAAGGGCTTAGAGAAGTAGGTTAATTTAGGCCCAGCTGTTAATGGCTAAATATATTA
CCTTTCTCAGAGGTATTTGCATTTTAAATGAGGGTGGCTCTCCAGACACTTTTGGGGAAC
[G,C]
AAGAGTCTCACCCTCCAAAGACCATTTGCAAAAATGGAATTTTTGACTTCGGAGTGAGGA
AAGCCCTTAACATCCCTTGACTCCCAGATCCTTAGTGCTAGAGCGGACTTAGGAAGTCAA
CTCCACTTAAACCTCACTTGTTTATAGGGAAACAACCAGCAAAGGGGTGTGACTTGGCCA
AGGTCACACAGTGAGGCAGCACTAGAGCTAGGCCTGTCACCAAGGGTAGCAGGCAGTATT
CAGGCCTTTTCTATAACTCCAGGTCATCTCTCAGTGAAACTTTGTAGGCACCCTGCTGCT

171315 CAGAGTCCTTCAGAGTTGTAGTTCTTATCTTTGTGACTCACCAGAAGCAAATCTTAGACC
AAATGAGTGTTTCTCAAAACAGAGGACCTGTGGACCTCTGTAGTGTTTCTGTAGAGCCAG
TTTGGAAAATGTGGCACCAACAAGCGAATGCTTCAGTGCCACTGCAATTGCCAATATGAG
TACCTAAACCATGGAGTAAATGGTCAGATTGTTATACTGGTATTTAGAATTTTACTGGAA
TGAAAGCACATATTTTAAAATTCTCATAGAGAACTAGAAGATTGGGAGAATTTACACAGG
[G,T]
TTCAGCAGACTCCTGTCTGAAAAATATTGAATTTGTTGGACAACATTGACCAGTGTGAAC
AATATGGTGCCTTCTAGAGGAGTAATAACAATAGTAATATCAACAATCTCTCTCATTTTT
ATACCATATTATAGTTTATGTGATATTTCTGTATGAATCATACTACCGGGTTTTGGATGT
CATAATACTCCTATGAAGTAAACAAGGTGGAATTCATCATCCCCATTTTACAGATGTGGG
AACTGAGGCTGAGACATTACATGACTGAGCTGCAGAGCACAAAGACAGGAACCTAATTAA

171400 ACCTGTGGACCTCTGTAGTGTTTCTGTAGAGCCAGTTTGGAAAATGTGGCACCAACAAGC
GAATGCTTCAGTGCCACTGCAATTGCCAATATGAGTACCTAAACCATGGAGTAAATGGTC
AGATTGTTATACTGGTATTTAGAATTTTACTGGAATGAAAGCACATATTTTAAAATTCTC
ATAGAGAACTAGAAGATTGGGAGAATTTACACAGGGTTCAGCAGACTCCTGTCTGAAAAA
TATTGAATTTGTTGGACAACATTGACCAGTGTGAACAATATGGTGCCTTCTAGAGGACTA
[A,G]
TAACAATAGTAATATCAACAATCTCTCTCATTTTTATACCATATTATAGTTTATGTGATA
TTTCTGTATGAATCATACTACCGGGTTTTGGATGTCATAATACTCCTATGAAGTAAACAA
GGTGGAATTCATCATCCCCATTTTACAGATGTGGGAACTGAGGCTGAGACATTACATGAC
TGAGCTGCAGAGGAGAAAGACAGGAACCTAATTAATGGAGTTTGGCTGTCAGGAATATGA
CAAAAACCAAGAGATGTGGGCATAAGAATAAGATGATCAGGCTAACCTGATGCTGAGACA

172007 TCACTGAATTAGAATTCCTTAAACCCCTAATAAATTACAACAATAATAACAATGGCAATA

FIGURE 3, page 110 of 122

ACTTCCACAATTGACTGATTGCTACATTCTAGACACTATGATAAACACTTAAATGCATGT
CAATTAAACCTTCCCAATAGCCCTTGAGGTTGATATTATCCTCAGATGAAGAAACAGAGC
TTCAGAAAGGTTGACTTTTCCACAGTCACAAAACATATAAAGTGATGGAGCTGCACTTCT
CCTCAAGGGCCATGGAATCCCAAAATTTGTGTTCTTATTACCGTGCCATGTGAGTGCTGG
[G,A]
CAGGGAGAGTTGGGGAAAGAGTCAGGAAAGAGAGGGGGTTGTCCTGGACAAGACAGCTTG
AGTTTAAATCTTGTCTACAGTAGCAGCAATAGATCTGACATTCCAACCCAGGCTCTCAAA
TTCCCATTGGACATCTGTCTCACCATTTACTCCATGGTTTAGGTACTCATATTGGCAATC
GCAGTGGCACTGAAGCATTCACTTGTTAGTGCCGCATTTTCCAAACTGGCTCTACAGACA
CACCACAGAGGTCCACAGGTCCTCTGTTTTGAGAAACACTCATTTGGTCTAAGATTTGCT

172220 CATATAAAGTGATGGAGCTGCACTTCTCCTCAAGGGCCATGGAATCCCAAAATTTGTGTT
CTTATTACCGTGCCATGTGAGTGCTGGGCAGGGAGAGTTGGGGAAAGAGTCAGGAAAGAG
AGGGGGTTGTCCTGGACAAGACAGCTTGAGTTTAAATCTTGTCTACAGTAGCAGCAATAG
ATCTGACATTCCAACCCAGGCTCTCAAATTCCCATTGGACATCTGTCTCACCATTTACTC
CATGGTTTAGGTACTCATATTGGCAATCGCAGTGGCACTGAAGCATTCACTTGTTAGTGC
[C,T]
GCATTTTCCAAACTGGCTCTACAGACACACCACAGAGGTCCACAGGTCCTCTGTTTTGAG
AAACACTCATTTGGTCTAAGATTTGCTTCTGGTGAGTCACAAAGGTAAGAACTACAACTA
CATTGATGGAATTTTATTAAAATTATTATTTCTAGTGTGACAGAAGCTGAGGAAGAGATG
ACGGAGTTAGCCCATTCCAGGTCTTATCGGGGTACTTGGGAACCAGGACAGTTGGCCATT
TCTGCCATGTGCTTGCAGATTAACTCCTGTAGAATGTTAGATTGGAAGTTTTAGTCTATT

172690 AGGAAGAGATGACGGAGTTAGCCCATTCCAGGTCTTATCGGGGTACTTGGGAACCAGGAC
AGTTGGCCATTTCTGCCATGTGCTTGCAGATTAACTCCTGTAGAATGTTAGATTGGAAGT
TTTAGTCTATTTGGCAGCTATTCCAAGCCCCCAGCCCCATGCTGCTGCTCCTCTGCGGGA
TCAGCCCTGAGCAGAAACTGTTCTTTAGTCTCCTTGCTCCCCTGTGGTGATAAATCTGTC
AGCTCCTTCTGCAAAGCTGAGCTCATCCACTTTCTTCAGTGCCTCTCTTCCTGTTGGCTC
[T,C]
GTACCTCACAGTTATGTTTAGTTTCTGCAGCTTCTGGTTAGGCAGGTGGTATAGTAGTTG
GGAAGGGTGGCTTTGGAGCCAGTTCTGGGTTTGAATTCTGACTTTTATACTTATTAGCTA
TGTAACATTAGTCAATTTATCTACCTTTTCTGAGTTTTTGTTGCCTTATCTTTAAAAAAG
AGAATGATATTATGTACATTCTTATAGGGTTTTATGAGAACTAACTGAGATCCCCTCAACG
CTCTCGGAAATGAAATCACATCTACCTGTTTTATGCTGCCATAGCCCCAGATATTTTTTC

174992 AAGTAAGATTCTGGTCCCATTTTATAAGGAGAAAAATGAAGTTCAAGTTGTTGAAAAACC
TTTTGTAAAGTCATTTGACTAAAACTGGAATTCAAACTTAAAACCTTTCCCATTCTAAGG
ATTAGGCTTGTTCTCCATTGGGCCACACTGCCCAAACTGGGGAAACCTTTGCAATTCTTA
GGACTGGTATTATAATTGAGCAAAGCCAAGAAATAAACTCCTTTCTTCCTTAAACTGCCT
GGGTTTGAAATCTGGCTCAGCTACTTACTAGCTGTTTGTCCATTGCAAGTCACTTCTCCT
[C,G]
TTTGTACCTCAGCTGTCTCACCTATGAGTGGGAATATTAATGTGGATCTCATAAGATAAA
GATAAAATGAGTTAATGTATGTAAAGTTTTAGAACACAGAGTGCAACAGAAGCCCAGGGT
CTCATCCTAACTCTGTCACTTACTCATGACCATTTATGCAAATCATATTTTTCTGTAAGA
TCTCAATTTGTTCTAGAATTGGCATAATGTTTTCAAAAGGAAAAAAATCAGCAAAACAAT
CTTCCTGCCTGTGTGATTTAGGGTTCTAGTTTTCCTGATTGTCTTCAGTTCAGAGGTATC

176676 TTTTCATCAAAAGATGGGCATGCTATGAGTATTTGCTTGGCCTTTTCTAGATAGGAAGGT
TTTGATCATGTAAAGGGTAGATGCAATTGGTTTTAAGTCCACTGGGAACTGTAGCCATAA
GGGCCCACCTCATACCAGGAAATTTGCTCTTGCTCTGAAATGGCCTTGGCCAGGTGTCAT
TCCTGACCACAACAGTTGGGGCAGAGTAAAGATGAAGGGACTCTCTGGAAGACCAACTAT
TCCCAGGCCAGGTAGTACACCCATGCAGCCTTGCACTCAATAGCCCAACCTGGAGTCCCT
[G,A]
ACCTTCTGCCAGAAAGTGCCAGCATTTTATCCTAAATCCCAGGGCTGAGAGAAATTAGTT
TGTGAGACCCTGACTGACATTTACAATGCTTTGTCAATACTGGATACTTGTATGAGGTAT
GTCTGTTGGTGTGTTTGCAGATATCCAAGTGTGCCTCCCTGGTTCCAAATGTAACTGGAT
AAGTCAACACGAATGCTTTTTTCTTCTCAATATTTATGGTGTTTTCACTGATTTAAGCAC
AGCTACAATACCTTGTTTAATTAGAGGAAACCAGACTACCCTCTGTGTTACCAGAGATTA

176723 TAGATAGGAAGGTTTTGATCATGTAAAGGGTAGATGCAATTGGTTTTAAGTCCACTGGGA
ACTGTAGCCATAAGGGCCCACCTCATACCAGGAAATTTGCTCTTGCTCTGAAATGGCCTT
GGCCAGGTGTCATTCCTGACCACAACAGTTGGGGCAGAGTAAAGATGAAGGGACTCTCTG
GAAGACCAACTATTCCCAGGCCAGGTAGTACACCCATGCAGCCTTGCACTCAATAGCCCA
ACCTGGAGTCCCTGACCTTCTGCCAGAAAGTGCCAGCATTTTATCCTAAATCCCAGGGCT
[G,A]
AGAGAAATTAGTTTGTGAGACCCTGACTGACATTTACAATGCTTTGTCAATACTGGATAC
TTGTATGAGGTATGTCTGTTGGTGTGTTTGCAGATATCCAAGTGTGCCTCCCTGGTTCCA
AATGTAACTGGATAAGTCAACACGAATGCTTTTTTCTTCTCAATATTTATGGTGTTTTCA
CTGATTTAAGCACAGCTACAATACCTTGTTTAATTAGAGGAAACCAGACTACCCTCTGTG
TTACCAGAGATTATATAGGGAGAGGACACCTTAAAGGTTTGGTTGGTTAAAGTGGCTAAA

```
176944   CCTTGCACTCAATAGCCCAACCTGGAGTCCCTGACCTTCTGCCAGAAAGTGCCAGCATTT
         TATCCTAAATCCCAGGGCTGAGAGAAATTAGTTTGTGAGACCCTGACTGACATTTACAAT
         GCTTTGTCAATACTGGATACTTGTATGAGGTATGTCTGTTGGTGTGTTTGCAGATATCCA
         AGTGTGCCTCCCTGGTTCCAAATGTAACTGGATAAGTCAACACGAATGCTTTTTTCTTCT
         CAATATTTATGGTGTTTTCACTGATTTAAGCACAGCTACAATACCTTGTTTAATTAGAGG
         [A,G]
         AACCAGACTACCCTCTGTGTTACCAGAGATTATATAGGGAGAGGACACCTTAAAGGTTTG
         GTTGGTTAAAGTGGCTAAAATAGGAAAATGTGAAGACTTTTATGCAGAGACATGGGTATT
         TGAGGACACAATTAAGTCTTCAGCCCAGGAGTATTCCACAAATTCACACATATCCATATT
         CATGCGCACATACCTGTGTGATCATAGAATTGTAGATCAAAGCTGGAAGAGCCCTTAAGA
         GAGAAATCAAGTGGCTCAGAACTTTCCAAACTTTTTAGTTTGAGGCTCTATTTTCAAATG

178739   CTTACTTTCTTGGTCTTCTATACTTTTTTAGGCTGATAATTCCCACTTTTAAAAAAATAC
         TTCTAATATAAGACTTTTCAAACCACAGTTTCCTATAACTACTCTCTCAATGGAGCTGTC
         ATCTAAGATTTTATCTGACAATTTGGGGAAACTTGGCATGTTCAACCTGTGCCATTCAGA
         GTATACAGTACAAGTTCTTTGATTTTTCTCTCAACTTACCTCCTGTGGATCTCAAGGGGA
         TGGGATGGAGGAAGTGCTCTTTCCAGTGTCCCAGGATTTGTTTAATAAACCTTACTTGCC
         [C,T]
         GTTTCCTTGAACAATGTTAGATGCTCCTTCTTCCTTCTGACTGGTGTGGTGTCAGCACAG
         GCAGGATGATGAGGGCTGAACAGCTCGTATGTGACCCCTTGAAAGAATCCCAGAGCAAAG
         GAAATCCAGCTTTGAAGATAAAGCCTTTCATCCTTCGATAGCTATGTTCCTATACACCTG
         CTTCATGTTCTCTCAGGCTTCTTGCCTGACCCAGTCCCTGTATTTGAAGCAGTTCTAACA
         CCTAACCTCTTTTGACCCAATGATAATGATAATGGTGAATGTGATGATCATAATAATAGC

179524   ATTGCACGTGATAATTAATAGTCATAATGATGGCCCAGAGCCTCTTCAAGATTCTTAAAG
         CATTCTCCAAATCTTCACAGCAAGATGAAAGCATGTCCAATGTAGTTGTAGTGTTAAACA
         CCTCTTTAGGATATCATAATTACTTGAAATGCCTTTTCATTCTAATCCTTTGAAAATTAT
         AATTGGCATATGATAGATGGAGTGACTATATTAACTAGTTTACTTAATTGAGCGCATTTA
         CTCCCCATCATTGTACTCAAATGCCTTTTCAACATTGTGTTACCTCCTACAGTGGATATA
         [G,C]
         AGAGGAGACAGATTCTGTTCTCAACTAATCCTCTCACCAGCCATATAACCTTAAGCCACT
         ATTCCCCTCTTTGGGCCTCAGTTTCCCTATCTGAACAATATGAGGGGTTTGTTTTACCTC
         CTACAGTGGATATAGAGAGGAGACAGATTCTATTCTCAACCAATCCTCTAACTGGCCATA
         TAACCTTAAGCCACTATTCCCATCTCTGGGCCTCAGTTTCCCTATCTGTACAATATGAAG
         GGTTTGGTCTTCTCTCCAAAATCTTTGCTCCTGTATAGGTCAAAAGTCAGCAAACTATGG

179726   TGACTATATTAACTAGTTTACTTAATTGAGCGCATTTACTCCCCATCATTGTACTCAAAT
         GCCTTTTCAACATTGTGTTACCTCCTACAGTGGATATACAGAGGAGACAGATTCTGTTCT
         CAACTAATCCTCTCACCAGCCATATAACCTTAAGCCACTATTCCCCTCTTTGGGCCTCAG
         TTTCCCTATCTGAACAATATGAGGGGTTTGTTTTACCTCCTACAGTGGATATAGAGAGGA
         GACAGATTCTATTCTCAACCAATCCTCTAACTGGCCATATAACCTTAAGCCACTATTCCC
         [A,G]
         TCTCTGGGCCTCAGTTTCCCTATCTGTACAATATGAAGGGTTTGGTCTTCTCTCCAAAAT
         CTTTGCTCCTGTATAGGTCAAAAGTCAGCAAACTATGGTCCCTGTGTCAAATCCAGCCAT
         CACCTGATTTTATATGGCTCATGAGCTAAGAATGATTTTTTACATTTTTTAATTGTTGGG
         AAAAAAATCAAAAGAATGATATTTTATAATATGTGGAACTATATGACATTAAATTACCAT
         GCCCAAAAATATTGGGACAGCCATGCTCTTCCAATTACTATATGCTAAATAGTAATAGTA

179901   CTCAGTTTCCCTATCTGAACAATATGAGGGGTTTGTTTTACCTCCTACAGTGGATATAGA
         GAGGAGACAGATTCTATTCTCAACCAATCCTCTAACTGGCCATATAACCTTAAGCCACTA
         TTCCCATCTCTGGGCCTCAGTTTCCCTATCTGTACAATATGAAGGGTTTGGTCTTCTCTC
         CAAAATCTTTGCTCCTGTATAGGTCAAAAGTCAGCAAACTATGGTCCCTGTGTCAAATCC
         AGCCATCACCTGATTTTATATGGCTCATGAGCTAAGAATGATTTTTTACATTTTTTAATT
         [G,T]
         TTGGGAAAAAAATCAAAAGAATGATATTTTATAATATGTGGAACTATATGACATTAAATT
         ACCATGCCCAAAAATATTGGGACAGCCATGCTCTTCCAATTACTATATGCTAAATAGTAA
         TAGTAAATTACTATTTTCTATATATGGCTACTTTCATGCTGCAATGGCAGAGCTGACTAG
         TTGTGACAAGAACCATATGGTTTGCAAAGCCTAAAATATTTATAATCTGGCCCTTTACAT
         AAAAAGTTTGCTGACCCCTTGCATAGATGTGGAATAGGGGGACACTAATAGGCTTCAGAT

180348   GCTACTTTCATGCTGCAATGGCAGAGCTGACTAGTTGTGACAAGAACCATATGGTTTGCA
         AAGCCTAAAATATTTATAATCTGGCCCTTTACATAAAAAGTTTGCTGACCCCTTGCATAG
         ATGTGGAATAGGGGGACACTAATAGGCTTCAGATAAACTAGACACTTTGGAAGCATCTAA
         AGACCCTTAGGAGGTTAGTGTCAAGGAGAGGAACCTAGCGCAGTCCCACAAATATTCGTT
         CAAGAAAGACAGCTACATTTGAAGGCCCCTGCTCTGGCAGGGTGACATATTCTGGCTATT
         [A,C]
         ACTGTGCCAGCCACAGTCTGAGGTTCATTGTCCCTCTTTGTCTGGAGCAATCTTGACACA
         CCATCCTAAAGCTAAAGTCATATGTTTCTCCACTGGTGGAGCAGTAGAACACATTTGTGA
         AGAAGACAGATTTTATAGTTGGACCACAGTTTGAATTCTTGCTTGCTGTGTGATCTCAGG
         GAAATTTCCAAAGGTCTCTTAACCATAGCTCCTTAACAGAAAATTAGGATGGATACTCAC
         TCACTCATTTATGCAAATAAGTATTGGGTGTCTACTGTGCACATTTACCTCTTGGAATTG
```

FIGURE 3, page 112 of 122

180459 CTTGCATAGATGTGGAATAGGGGGACACTAATAGGCTTCAGATAAACTAGACACTTTGGA
AGCATCTAAAGACCCTTAGGAGGTTAGTGTCAAGGAGAGGAACCTAGCGCAGTCCCACAA
ATATTCGTTCAAGAAAGACAGCTACATTTGAAGGCCCCTGCTCTGGCAGGGTGACATATT
CTGGCTATTAACTGTGCCAGCCACAGTCTGAGGTTCATTGTCCCTCTTTGTCTGGAGCAA
TCTTGACACACCATCCTAAAGCTAAAGTCATATGTTTCTCCACTGGTGGAGCAGTAGAAC
[A,G]
CATTTGTGAAGAAGACAGATTTTATAGTTGGACCACAGTTTGAATTCTTGCTTGCTGTGT
GATCTCAGGGAAATTTCCAAAGGTCTCTTAACCATAGCTCCTTAACAGAAAATTAGGATG
GATACTCACTCACTCATTTATGCAAATAAGTATTGGGTGTCTACTGTGCACATTTACCTC
TTGGAATTGTTTAAGTAATTAAAGGATTATGTATATAAAGCATTTAACAGAATGCCTGAC
TCAGGAATAGAGCTTGGAAAATGTTTAAAATACATCTCAAACAATTATTATTCTTTTGTT

180786 GTTGGACCACAGTTTGAATTCTTGCTTGCTGTGTGATCTCAGGGAAATTTCCAAAGGTCT
CTTAACCATAGCTCCTTAACAGAAAATTAGGATGGATACTCACTCACTCATTTATGCAAA
TAAGTATTGGGTGTCTACTGTGCACATTTACCTCTTGGAATTGTTTAAGTAATTAAAGGA
TTATGTATATAAAGCATTTAACAGAATGCCTGACTCAGGAATAGAGCTTGGAAAATGTTT
AAAATACATCTCAAACAATTATTATTCTTTTGTTTTAAATTACAGTAACCTCAAAACTC
[C,T]
TAAAAAGCTGTTTGAATAAAGTTATATAATGCATACAAAGGGGCATTTTTAGCCATTATT
GTCATTTTTGTTCTTATAAGCAATGCTTCTGAAGCCGTTTTCAGTGGAGCACTTAACAGC
ACCAGTGTGCTTTAATTTCAGGCCAGGAGATAAAAAATTAAGCAGGCTCTCTTAAAAGA
CCATAACAAAGCTTCAACAAATGCAACAACTTCTCTCCCCTGTCTTGCCACTGCTACTCT
GTCCCCCACTTTCCAGTGACTAATGGATGATATCTAAGATACATTAGAGCTATCTGAGGA

181129 GCATTTTTAGCCATTATTGTCATTTTTGTTCTTATAAGCAATGCTTCTGAAGCCGTTTTC
AGTGGAGCACTTAACAGCACCAGTGTGCTTTAATTTCAGGCCAGGAGATAAAAAATTAAG
CAGGCTCTCTTAAAAGACCATAACAAAGCTTCAACAAATGCAACAACTTCTCTCCCCTG
TCTTGCCACTGCTACTCTGTCCCCCACTTTCCAGTGACTAATGGATGATATCTAAGATAC
ATTAGAGCTATCTGAGGATCGATTTTTATTTTTTAATAGTATTAAAAATACAATATATTC
[A,G]
CATGATAAAACAGATATTACAGAAGGGTATAAAGTAAAAGATAAATGCCCATTCTTTCCA
ATTCTATACTTCATAGAACTAACTATTTTAAACCCTTTTCCTGCATTTGGTTATTTAATG
GTTTCCTTTACACTTCTACATCATATATTTATGTTTCTTTTTCTTGCTTTATCAACTTTA
ACTCCATATCTGACTTCCCATTAGAAAGATGACAAATCAGCTCATATTACACCCCCAACA
TCCCCTTCTCAATGTTTGTTAGCCTATATGCTATTATTTGGAATTCTTCTGATGATTACC

181918 GGTCAATTTCTTTGCATTTAATAATGACAGTAGACACAGCATTCTTTCTCACCGATTTAT
TAGTCACACATGGGGCAATGTGAAATGCTACATAGGTGCAGAAGAAGCAGACAAGAACAC
AGTGACCTAATAGCCCTAGGAACTCACTCATCACCAAGCTTCACTTTAGGTGAGAAACAG
TCACTCAAAGAGAAGCATCTGGTACCAGTGCTGGGAGGTCAGTGGAAGGAGAGTGGGTTT
AGACCTGCATTCTTGTGCTGAATAGCTGGAAAAACACTTGACTAACCTGAAAAACAAGTA
[C,T]
TCTGTAGATTAATTTCATTTTTTTTTTGTCAGTAGTAACAGTATATAGAGCAATGGTCCC
AGCATTTGGGAACATGTTGTAAATAGGCAAAGTGGCTCAAAGAGAGTAGTAATCAAACTT
CGTAGTTAAAATTTTTAATAGAATATAATTAGCAATGTAGTATTTTTATATAATACTATA
TAATTAATAGCACAAATAAAGCACATAAAGAAAAATGTTCTAATTACCAAATATTACCCT
CTAAGGTTTTTTTTAATAAAATGGCAAAGAAAATTAGAAAATTATTTAATTAAACCTTAT

181936 TAATAATGACAGTAGACACAGCATTCTTTCTCACCGATTTATTAGTCACACATGGGGCAA
TGTGAAATGCTACATAGGTGCAGAAGAAGCAGACAAGAACACAGTGACCTAATAGCCCTA
GGAACTCACTCATCACCAAGCTTCACTTTAGGTGAGAAACAGTCACTCAAAGAGAAGCAT
CTGGTACCAGTGCTGGGAGGTCAGTGGAAGGAGAGTGGGTTTAGACCTGCATTCTTGTGC
TGAATAGCTGGAAAAACACTTGACTAACCTGAAAAACAAGTACTCTGTAGATTAATTTCA
[-,T]
TTTTTTTTTGTCAGTAGTAACAGTATATAGAGCAATGGTCCCAGCATTTGGGAACATGTT
GTAAATAGGCAAAGTGGCTCAAAGAGAGTAGTAATCAAACTTCGTAGTTAAAATTTTTAA
TAGAATATAATTAGCAATGTAGTATTTTTATATAATACTATATAATTAATAGCACAAATA
AAGCACATAAAGAAAAATGTTCTAATTACCAAATATTACCCTCTAAGGTTTTTTTTAATA
AAATGGCAAAGAAAATTAGAAAATTATTTAATTAAACCTTATTTAATGAGAGTTCCCAGG

183558 GCATTGCTCTAGGAGCAGGTTCTAGGACACATCAGTGACCAAGACAAAAAAGGTTCCTGC
TCTTAGGAAACTGACATTTCAATAGGAGGAAAGAGGCTATGGGAACACATGAGTAAACAA
GATAATCTCAAATGGTGATAAAAACTCTGGAGAAGCTCTAACAGGGCACTGAGATAGAGC
AGACTGGATAGGGTGCTGGGGGTAACTCTACTATGTTCTTCCAGAAGCAGTTCCCTGAAA
CAAGGATTCAAGTACAAGGGGCTTCTTGGGTGCCAATCCTAAAAAACCAGGGAAGGGAGG
[C,T]
AGAGAAGGGAAGTCTGCCTACAAAGTTTCATAAACAAGATGCCTACACTGCAGGCTACTG
AAGGAGAACAGTCCCTGAGGGGATCCCAACATGTCAGTGTAGAACTCACCTCAGGGTCAT
GCCATGCAGGGGAGAGGATTCTGGGGCACTTATCTACTGACTCTTCATCTGTCATTGATT
GAAAGCTGCTTCTGGGCATATTAACTCCTTAACATGTCTAACTTAGCCTGCAGGTAGGCG

FIGURE 3, page 113 of 122

```
          GAGTAGCCAGGTGTTTGCAGTTGGTACGTAAAGTAGAATACCCATGTAGAAAGGGGAGTG
184778    TTTCTTCCTGCTGGGCAGGCCCCCAATTATACCTAAAAGAAACCCAAGTTAACACAAGGC
          TCTATGTGACCAGCTTTGGGCTGCCAATTTGACCTCCTTTCCCACCCTTTCTCTTCAAAC
          TCACTGTGCCACAATCACACCAGCCTCCTTACTGTTTCTTGAATATGCCAATCATCCTCT
          CACCTCTGGGCCTTTGCTCAGAATGCTCTTCTCCAAATATCCCCATAGCTCAGACACAGG
          CATCACTTCACTCAGGTCCCTAAGCCAAGACCACCTCCTTGCGGAGGCTCATCCTCATCA
          [C,T]
          TCCTTCCAAAGCATGACACTGCCCCTCCCCATCCTCTTACCTCACTTTATCCTTCATGGG
          GCTCATTGCTACCGCAGAGTATACTATCCCAGATTATACTATACTATGCTGCATATTTAC
          TTGTTCATTTATTGTCTGTCTTCCCCACTAGAATATAAGCTCCATAAGGGAAGAAACTTG
          CTTTATTCACTATTAGAATAGTGCACTATGACTTTTCAAAAATGTTTGTTGAAATGATTA
          ATCAGTGAATAAGTGAGTGAGTGACTGAGTGAACCAATGCCTAACAGAGGCCCTTAGTTC

185666    GGCCTCATGGAGTGGTGAAAATTTACCCTGTTGTATGGAAAAGAGCACAGGGTGAGGATG
          GAGACTGGGATCAGAACTCGGCCTCTTCCACAGACTTGCTGGTGTCCTTGGGTAACTCAT
          AGGAGCTTGCCCAGTGAAATTCAGATTCCTCTTCTCTCAAAATGGTTGCGTATTGGGATG
          GTAGACGAGATTATTCCCTCCTTAGAGGTTTCTACCTTGTACTATATATCTGCATCATCA
          TAATAATCACAGCCACTATTTATTGATCACTTGGTCTGCCCCATGCACTTGACATGTGTC
          [A,G]
          TTGCATTGTATGTTTACCCCAACAACCAGACCTCCATTATTCAGACAAGAAAACTGTCAA
          GTAACTTAGTTAATAGTGGTATAACTACTGGCTTATGCATAGCAGCGCCAGCACTCCAAA
          CTAGGCATACTGGCTCCTGAGCTGTGCTAATTTTGTGCACAAACTAAGTAATAATCAAGT
          TCAAAGGAAAGGAGGCCTAACTGTCTCTCCATTGAGTAGGTTTCATCTGGTGGAACTGAA
          TGGAAAATCCTGTGGTTTTGGAACAGGTTAAGTTGATTTATCCAGGCAGCATGTTCTAAC

185832    TGGGTATTGGGATGGTAGACGAGATTATTCCCTCCTTAGAGGTTTCTACCTTGTACTATA
          TATCTGCATCATCATAATAATCACAGCCACTATTTATTGATCACTTGGTCTGCCCCATGC
          ACTTGACATGTGTCATTGCATTGTATGTTTACCCCAACAACCAGACCTCCATTATTCAGA
          CAAGAAAACTGTCAAGTAACTTAGTTAATAGTGGTATAACTACTGGCTTATGCATAGCAG
          CGCCAGCACTCCAAACTAGGCATACTGGCTCCTGAGCTGTGCTAATTTTGTGCACAAACT
          [A,-]
          AGTAATAATCAAGTTCAAAGGAAAGGAGGCCTAACTGTCTCTCCATTGAGTAGGTTTCAT
          CTGGTGGAACTGAATGGAAAATCCTGTGGTTTTGGAACAGGTTAAGTTGATTTATCCAGG
          CAGCATGTTCTAACTTCTCCCTCCTCCCCCTCTCACAGGGCTTCATGGACATTGACTTAA
          ACAAATTCAAGGAGAGTGGCGCCAATGTGACAGGTTTCCAGCTGGTGAACTACACAGACA
          CTATTCCGGCCAAGATCATGCAGCAGTGGAAGAATAGTGATGCTCGAGACCACACACGGG

187287    CTGAAGTCAAACCAGATAGCTTGACAGTGGCCCATATGGAACCCTGTGTTGAGAAGGATAC
          TAAGGCCAAGTTTGTTTATCTGGACAAACAGTGAATCTTTGACAGACTTTCTCTTGCCAC
          TCAATCCATTTCTTTTTATAAATGGCAAACCGTATAACGGAGATACTTCTTATCCCACTA
          TTCAAACTGATTTAACTCTTCAATAATGAAGACTTATTTCAATATGATCTTAAGCAAACA
          AAATCGCAAATATGCTTTCAAGCAATGAGAAAACTACATAGGAATTAATTAAGTAATGTG
          [C,T]
          AATGATTGCACTCCAATTTCCAAAAGACTGAGCAGATGACAAAAATAACCAAATGTAATT
          TAATTTTTTTTTTTTTTTTGAGATGGAGTCTGGCTCTGTTGCCCAGGCTGGAGTGCAGTG
          GCATGATCTCGGCTCACTGCAAGCTCCACCTCCCGAGTTCACGCCATTCTCCTGCCTCAG
          CCTCCCAAGTAGCTGGGACTACAGGCACCCGCCACCACGTCTGGCTAATTTTTTGTATTT
          TTTAGTAGAGATGGGGTTTCACCGTGTTAGCCAGGATGGTCTTGATCTCCTGACCTTGTG

187351    GCCAAGTTTGTTTATCTGGACAAACAGTGAATCTTTGACAGACTTTCTCTTGCCACTCAA
          TCCATTTCTTTTTATAAATGGCAAACCGTATAACGGAGATACTTCTTATCCCACTATTCA
          AACTGATTTAACTCTTCAATAATGAAGACTTATTTCAATATGATCTTAAGCAAACAAAAT
          CGCAAATATGCTTTCAAGCAATGAGAAAACTACATAGGAATTAATTAAGTAATGTGCAAT
          GATTGCACTCCAATTTCCAAAAGACTGAGCAGATGACAAAAATAACCAAATGTAATTTAA
          [T,-]
          TTTTTTTTTTTTTTGAGATGGAGTCTGGCTCTGTTGCCCAGGCTGGAGTGCAGTGGCAT
          GATCTCGGCTCACTGCAAGCTCCACCTCCCGAGTTCACGCCATTCTCCTGCCTCAGCCTC
          CCAAGTAGCTGGGACTACAGGCACCCGCCACCACGTCTGGCTAATTTTTTGTATTTTTTA
          GTAGAGATGGGGTTTCACCGTGTTAGCCAGGATGGTCTTGATCTCCTGACCTTGTGATCC
          ACCCATCTCAGCCTCCCAAAGTGCTGGGATTACAGGCGTGAGCCACTGCGCCCGGCATGT

187706    TCGGCATGATCTCGGCTCACTGCAAGCTCCACCTCCCGAGTTCACGCCATTCTCCTGCCTC
          AGCCTCCCAAGTAGCTGGGACTACAGGCACCCGCCACCACGTCTGGCTAATTTTTTGTAT
          TTTTTAGTAGAGATGGGGTTTCACCGTGTTAGCCAGGATGGTCTTGATCTCCTGACCTTG
          TGATCCACCCATCTCAGCCTCCCAAAGTGCTGGGATTACAGGCGTGAGCCACTGCGCCCG
          GCATGTAATTTAACTTTTTAAAAAAGAAGTGAGAGAATTAAATTTAAAAAATTAGAAAAA
          [C,T]
          ACCCATTCATTCGTTCTTCAATTCTCTATTGTGAACTTGGAGTGTGCTAGGCAACATAAT
          AAGTATTAGGAACAAATTAGTGAAGAAAACAGACATAGGTTCCAAAGCCAGGATATATTT
          TCCTGGACTGCTCTCCTGATTTTGTTTCATCCACATCCTAGTCCCCTTTTTGTCAGGAGA
```

FIGURE 3, page 114 of 122

```
         GGGTATAATTGATAGTTGTTGTGAGAAAGAATGAGGGGAAAGTTTACAGGATATAAACTT
         ACCACTTAGGTAAGCCATATGTGGAAAAAATTAGGAGCTCACCCTTCTTTCATTTTCTTT

188282   AGCTCACCCTTCTTTCATTTTCTTTTTGCTTTTACTTTTACAAGAGATGAAAGAGTTAAT
         CGTTCCTCTTGGTTTCCAGCTGATGACTGTAATGCCGGGATAAACCAGCTGATTTTTCAT
         GAACTGTATCCAGCCTGCAGATGTGTTATATGTAATCTATGCATTTTTTCCCAAATGAAC
         CAACATTTTAAAAATTGCAAGATTGCACACAGAAACCTAGAATCCTGGCTTCTCTTCAAA
         AATTATAACTGGCAGTACTGAACTCACAGTTCAAGGAGGTCAGCATTGACTAGCATGGTC
         [A,G]
         AGCAGCAGCACCCATCTGCTTGAATATTTATGCTTCTCAGGGACACCATCCCTGATTCAC
         CACTGTCTGCCCCACGTATACCATGCATCTGGCCCACTGCACACCCTTCTCATCACCAGA
         AAACACATTCCCAAATACAGCACCCAAACCTGCCTTCCTGTCAGCTCTCTTTGATACCTA
         ACTGTCTCCATTCCTCCCACTAGTACACCTCTGCGCTCACCTACGATGGGGTGAAGGTGA
         TGGCTGAGGCTTTCCAGAGCCTGCGGAGGCAGAGAATTGATATATCTCGCCGGGGGAATG

190074   ACTTTCACAACCAGGAGAAAGAGATGCTGAAGGAACCTCACCAGCTGTTCCTCAGCCCTG
         ATGAGTGCCTTTCTGTAGAGAAGAATATGTAGGTCTGTCCTTTGAAATGAAGCTAAGCAG
         GATTTCTACTAGCTACATGAGGAACATGCTAAGGAGGACCTCCAGCTGCCATTTCTGCCC
         TCCCCTGGTCCCTGTGCAGGGTGGCTCCCAAGTCACTAGGCAGCAACAACAGACACCAGG
         CAGCTTGCAGGGGAAAATTGCCAAATGGACAGTGCCTGCGCCTCCCTTTCTACCCCCACC
         [C,T]
         CAGCTTATTTAAAATGCTCTTCCAGACTCCACAGTCGAGACAGATTCTGTTTGCAATGTG
         AGGCTGGTTTCAAAAGGTCCCAGAGATTTGTCCTCAGCTTCACAACCCTTCCAACTCCCT
         TGCCTCTCCCATCTTAATGACGTCCTGAAAGGATAGTCTGATGCCACCATGACAGTGATG
         AAGCCTGGGAGGCAGTTCAGGGTGGCAGGAAGGACTCTGTACTGGGAGGCAGGAGAGCTG
         GACTCCACGTCCAGCTGGGCCCCTGGCTCTCTGGATGACCTTGAAACATTCACTTAGCTC

193266   TGGATGGGGATGTCAATGATACCCAGCAAGAGACGAGGTAGGGTGAGGGTACAAGAAAGG
         ACTTGCACATGTCACATTGGCCTGTTAAGGAATTAGGGATAGAAGAGCTGGGTTCCAACC
         GTGGCTCCACGCAGAACTATCTGGGGGATCTTGGACTAATTGCTTGCCTTTTCCAGATCT
         GGATTTTTCCTGTCTGCTAAACAGACATAATCCTCCTAGTGCTGCCTCCCTGACTGGCTT
         GTCACAGGGCTCAGAATTTTAAGAAAGCATCGTGCTTGTGGGCCAAGCATCGTGGTTCAT
         [A,G]
         CCTGTAATCCCAGCACTTTGGGAGGCTGAGGTGGGCAGATCACGAGGTAAGGAGTTTGAG
         ACCAACCTGGCCAACATAGTGAAACCCTGTCTCTACTAAAAATACAAAAAGTTAGCGGGA
         TGTGTAGCAGGCACCTGTAATTCCAGCTACCTGGGAGGCTGAGACAGGAGAATCACTTGA
         ACGCAGGAGGCAGAGGTTACAGTGAGCCGAGGTTGTGCCACTGCATACCACACCAGCCTG
         GGTGACAGTGTGAGACTATGTCAAAAAAAAAAAAAAAAGCATCATGCATGTGTTTCTTTGA

193763   TTACAGTGAGCCGAGGTTGTGCCACTGCATACCACACCAGCCTGGGTGACAGTGTGAGAC
         TATGTCAAAAAAAAAAAAAAAGCATCATGCATGTGTTTCTTTGAACTTCAGGGAAGCTGC
         ATGAGACAGTCAGAGCCAAGATTATTCTTCCCATGACTCAGGTAGGAAAGTGAAGCTTAG
         GAGGGTTCTGAGATTTGCTCTGGCCAGAGTACCTAGAATGTGACCCAGCAAGGACCTAGT
         CTACAGGCCTCACAGCCAGTGAGCATCCAGGAGGAAGGATCCACCTGAGGGCAACTGCAA
         [G,A]
         GGGGATACAGGAGCCCTGCGTCCAGTTTGACTGCTCGGCTGTCTCCTTCAGGACTGCCTT
         TCAGGATCCAATGAGGGCAGGGGAGAGCAGTCACTGTTGACACCTGACAAAGATTCTTTG
         CTTGACCAAACTTTAGTCAGGCTTCTGAACCTTCTCCTAGGCCCATCTGTGCAATTCTTG
         TGAAATCCAGTTTTGGCAAAGAACTTGCTAAGTCGGTTTAGCAAGAACCCTGTCCACCAC
         GTCCACCCTCTTTGCCATGATCATCTTCTTCAGCCCCCACCATCCCCCAGATTATGTCGG

193782   TGCCACTGCATACCACACCAGCCTGGGTGACAGTGTGAGACTATGTCAAAAAAAAAAAAA
         AAGCATCATGCATGTGTTTCTTTGAACTTCAGGGAAGCTGCATGAGACAGTCAGAGCCAA
         GATTATTCTTCCCATGACTCAGGTAGGAAAGTGAAGCTTAGGAGGGTTCTGAGATTTGCT
         CTGGCCAGAGTACCTAGAATGTGACCCAGCAAGGACCTAGTCTACAGGCCTCACAGCCAG
         TGAGCATCCAGGAGGAAGGATCCACCTGAGGGCAACTGCAAGGGGGATACAGGAGCCCTG
         [C,T]
         GTCCAGTTTGACTGCTCGGCTGTCTCCTTCAGGACTGCCTTTCAGGATCCAATGAGGGCA
         GGGGAGAGCAGTCACTGTTGACACCTGACAAAGATTCTTTGCTTGACCAAACTTTAGTCA
         GGCTTCTGAACCTTCTCCTAGGCCCATCTGTGCAATTCTTGTGAAATCCAGTTTTGGCAA
         AGAACTTGCTAAGTCGGTTTAGCAAGAACCCTGTCCACCACGTCCACCCTCTTTGCCATG
         ATCATCTTCTTCAGCCCCCACCATCCCCCAGATTATGTCGGATCATCCTCGTCCATCTTC

194094   CTGCTCGGCTGTCTCCTTCAGGACTGCCTTTCAGGATCCAATGAGGGCAGGGGAGAGCAG
         TCACTGTTGACACCTGACAAAGATTCTTTGCTTGACCAAACTTTAGTCAGGCTTCTGAAC
         CTTCTCCTAGGCCCATCTGTGCAATTCTTGTGAAATCCAGTTTTGGCAAAGAACTTGCTA
         AGTCGGTTTAGCAAGAACCCTGTCCACCACGTCCACCCTCTTTGCCATGATCATCTTCTT
         CAGCCCCCACCATCCCCCAGATTATGTCGGATCATCCTCGTCCATCTTCAGCAAGAATCC
         [T,C]
         CTTAGGCCATTTTAGCCAGAATTCCTCTTAACCCCGATGCTTGCTGTTAGCAATTTCCTA
         TCCACTGACCCCCACCCTGCTCCTTGGCTATATATTCCCACGGGCCCATGCTCTATTCAG
```

FIGURE 3, page 115 of 122

```
         AGTTGAGCCCAATCTCTCTCCACCTCTGCAAGACCCATTGCAGGGGTCTCTATACCTATT
         GCTACGATTCTGAATAAAGTCTTCTTCACTGTGCTTTAACAAGTCTGCTGATTAATTTTT
         TCTTTAACACAGCTGAAGTAATAGAGACATTAACCCGCATTCTCTCAGCACCAAGCAGGA

194499   CCCATGCTCTATTCAGAGTTGAGCCCAATCTCTCTCCACCTCTGCAAGACCCATTGCAGG
         GGTCTCTATACCTATTGCTACGATTCTGAATAAAGTCTTCTTCACTGTGCTTTAACAAGT
         GTGCTGATTAATTTTTTCTTTAACACAGCTGAAGTAATAGAGACATTAACCCGCATTCTC
         TCAGCACCAAGCAGGAAAGGAAATATATGCTTCAGCCTCCCATCAGCAGCAGACTCTGAG
         CTGGCACCCAGTACCCTTTACAGGAAGCCCAAGGTTAATTCTCCATCTTTCATGGAGGGA
         [G,A]
         TTGAGGGCGCCAGGATGGCGACAGAAGTTCCGGGAGCAGGAACCAAGAAGAAGTGCCTGG
         GCTCCATCAATCTGACCTCAGACACCCTGGGATGGGGGGAGAGAGGGATAAGTGCCCAGA
         TCCCAGAGCTCAGACCTGATGGATGGGGACAGTGGTTTCAAGATACACATTTCTGAGAAG
         CTTCTTCCTCTGTCTCTGAGTCCTGACTCTCCTTGATAAATGGTTTGGGGCTGAGCCATT.
         CTCTTGAACTCTCCTTGCTCTGCCATCATGGAATGGTGTTTCTGGGATGTCTCTTTCGCA

195249   TGTGAAACAGGCAAAATAACGTCTGCTCTGGCTACTCACTGGGTTTCTGTGAACATGAAA
         TAAGCAGCTTCTTGTGAGATCACCGTGACAGTGCAAGGGGTCCTTGGGTCACTAGAACTG
         TGCAGGTAGGACCCTTGACCTTATTGGAAACTGAGGAAGGCAGTAAAAGTGTCAGTGACA
         TGATCCTTCTTTCTTCTGAAAGAGTCCCCTTGTCTTAGACAACCTACCAGCCCCAAGGCC
         TCAATTTTAGATTTTATTTTTCATAACTTTTACCCACTCTACACAGCACAGTAGTAGTAG
         [T,C]
         CGTCATTATCATCATTATTATCATCTAAATAATATAAACTATGCATTGAAAACTTATGTC
         CCAGACAATGTGCTAAGTACTTCTTGGAGGAGGAAACTAAGAAGCAGATAGTTTGAGCAA
         GGAACCTATGGTCATACAGTTAGAATGAGCAGAGCACAACCTGGGAAATGCCCAGCAGCA
         ATAGCAGAAAGCAGGTAGAAAACACTACATTGCACATTTTTGTGTTGTCCTCCTGAAGCC
         TAGCACAATAGCACTGGCCTGTGTTTCGGCGAACACTTGGTACCTTAAGTGAAGATACCA

197371   TTAAGATAAAAAAAGGGCAGAGATTTTTGGAAACTGAAGGCTTAGAGAGCTAAATTGCCT
         GAGGGCACTTGGCTATTAAGGATTAAGCTGGGGTTAAATCCAAGTCTTTCAATTGCCAAG
         TATTTTATTCCCTGGACTCAGGAATAAAGAAGAAATTCTTAAAGGAATTAAGAAGCCATC
         TCCAAGCATAGCTTAAGGCTTCATTCATAAAGCTGGCTTCTTGTCCTGGGTCTTCTGACT
         CATTAGTGATGGTGCACCATTTTCTTTCCTTTGCAGGCCCCCCATACTTTCTTCATCTTC
         [A,G]
         GATGTGTATCTGAGAAGGGCAGTGGTCATAGTGGTTGTGTGATGGGAGGTGTTTGGTTAG
         GGATGGTGCAGACATTTCACATTAGTATGCACTCTGACCCATTGTTAGTATTTGCCTAAA
         GAAATAGGTAAAAACAATTGTCAGGATGAATCCCAATTTAGGGAAAAGAGATCTGTAATG
         CATCCCTTGCCTGTGGCAAGGGAGTGAAGAGTTTTAGCATTCAGGATACTCCAAGACATC
         ATTCCATGGAACACTCTTGGGTTCTGAATTTCTACTTCAGTGGAAAAAGCAAACACACAT

198021   CGATTTGAAGGTTTAACAGGAAACGTGCAGTTTAATGAGAAAGGACGCCGGACCAACTAC
         ACGCTCCACGTGATTGAAATGAAACATGACGGCATCCGAAAGGTAAGGTCCCCCTTTACT
         TCTGTTCTGCAGAGAGAAGAGGCTGAGCAGGGACTCTGGCCAGAGCTGAGGGCCTGTGAG
         TCCACCTTTTCTGGACTGGATCTTTGAAGAAACTCAGACAACACAGATTCTAGACTTGGC
         TCTGCCACTAACCAGCTGGGACATTGGGCAAGTCTCGTTCTTCCTCTGAGAATCCATTCA
         [T,C]
         TCATTTGCAAAATTAAGTTTAAAAAAATCTCTACATTTGTCCCAGGATGCTTGTGAAAAT
         CCAAGGTAGAGGAAAGCACTTCTAAAACATAAAGTAATTGATGTGTATAAAATGCCACTC
         CCATTCCTGAGGGTTTCTAAACTAAGAACTTGAGAATGATGATTATTGATGAGGTTAACT
         ATCTCTTCCTAATCGATAGTTGGTCATATCCACTCTATTATTTATACAAAAGTAAGGGTG
         AAAATATATATGTTTACATATATGTATAATGTATAATATGTTTGCATATGAAAATTCTTA

198039   GGAAACGTGCAGTTTAATGAGAAAGGACGCCGGACCAACTACACGCTCCACGTGATTGAA
         ATGAAACATGACGGCATCCGAAAGGTAAGGTCCCCCTTTACTTCTGTTCTGCAGAGAGAA
         GAGGCTGAGCAGGGACTCTGGCCAGAGCTGAGGGCCTGTGAGTCCACCTTTTCTGGACTG
         GATCTTTGAAGAAACTCAGACAACACAGATTCTAGACTTGGCTCTGCCACTAACCAGCTG
         GGACATTGGGCAAGTCTCGTTCTTCCTCTGAGAATCCATTCATTCATTTGCAAAATTAAG
         [T,A]
         TTAAAAAAATCTCTACATTTGTCCCAGGATGCTTGTGAAAATCCAAGGTAGAGGAAAGCA
         CTTCTAAAACATAAAGTAATTGATGTGTATAAAATGCCACTCCCATTCCTGAGGGTTTCT
         AAACTAAGAACTTGAGAATGATGATTATTGATGAGGTTAACTATCTCTTCCTAATCGATA
         GTTGGTCATATCCACTCTATTATTTATACAAAAGTAAGGGTGAAAATATATATGTTTACA
         TATATGTATAATGTATAATATGTTTGCATATGAAAATTCTTAGAATAGCATTCAAATCCT

198143   TGTTCTGCAGAGAGAAGAGGCTGAGCAGGGACTCTGGCCAGAGCTGAGGGCCTGTGAGTC
         CACCTTTTCTGGACTGGATCTTTGAAGAAACTCAGACAACACAGATTCTAGACTTGGCTC
         TGCCACTAACCAGCTGGGACATTGGGCAAGTCTCGTTCTTCCTCTGAGAATCCATTCATT
         CATTTGCAAAATTAAGTTTAAAAAAATCTCTACATTTGTCCCAGGATGCTTGTGAAAATC
         CAAGGTAGAGGAAAGCACTTCTAAAACATAAAGTAATTGATGTGTATAAAATGCCACTCC
         [C,T]
         ATTCCTGAGGGTTTCTAAACTAAGAACTTGAGAATGATGATTATTGATGAGGTTAACTAT
```

FIGURE 3, page 116 of 122

```
         CTCTTCCTAATCGATAGTTGGTCATATCCACTCTATTATTTATACAAAAGTAAGGGTGAA
         AATATATATGTTTACATATATGTATAATGTATAATATGTTTGCATATGAAAATTCTTAGA
         ATAGCATTCAAATCCTTGGAATAACATTTCGAATTCTACCAGAACCTATGTGCCCGGGCC
         TCTGCCGATTTCTTCACCCTTAACCCTTGATACTTCCTTCATCTCTCCACTCCAGTCATT

198458   CTAAACTAAGAACTTGAGAATGATGATTATTGATGAGGTTAACTATCTCTTCCTAATCGA
         TAGTTGGTCATATCCACTCTATTATTTATACAAAAGTAAGGGTGAAAATATATGTTTA
         CATATATGTATAATGTATAATATGTTTGCATATGAAAATTCTTAGAATAGCATTCAAATC
         CTTGGAATAACATTTCGAATTCTACCAGAACCTATGTGCCCGGGCCTCTGCCGATTTCTT
         CACCCTTAACCCTTGATACTTCCTTCATCTCTCCACTCCAGTCATTCTGTTTGTCTTTCA
         [C,T]
         CTCCCTGAATACACCATGTTCTTTCTCATCATTGAGCCTTCATACATGTTTCCTCTGCCT
         GGGACTTCCTCCCCCCATCTCCCTCCTCTTGCCTGCCAATCCCTCCTCAGCCTTCCACAC
         TCAAAGTAAATGTCATTCCCCAGCGAAGCCTTCTCTGGCCTTTCTTATTATGCTTCATGG
         AAGCCTCTACTTCTCTGCTCATGGCCTTCATCACATTGCTAATTCCATTTGGTGGCGTAG
         CATAATGACTGGGAGGCATTGTACAGCATGGCGTAGAGCTGGTAGGGTGCCATGGATCAG

199076   CCTCAACACTGAATCCTGGCTTCACCACTTACTAGTCTGGGGTTCCGGATAATTTATTTG
         AGCTCTTTGTTCCITAATTCTCTTATCTAGTAAGTGGGGATCACCTTAACCATGCCAACC
         TCATAGGGTCATTGAGAGGATTAAATGATCTAAGAGTGTGCAGAAGTTCTAAGTACTGGA
         ACTGGCCCATTGAAAGTTGGGTCTTAATCTCTCAGACTTAATGCTCTCTATGCCTGTGCT
         GTCAGATAACCTTGCCACTAGCCGTATGTGGCTGTTTAGGTTGAATTTTAAATAAATTCC
         [C,A]
         ATTTAAAAATCAGTTCTTCAGTTGCACTATCTACATGTCAAGTGCTCAGTAGCCACATGT
         GGCTAGTGGCTACCACATCAGGCAGCACAGATGTAGAACATTTACATCACTGCAGAAAGT
         TCTACTTTAAAGTTCTCTTTGTCCACTCTCCGTCCTCACCTCCCTTAAACCTGTCTTCTC
         TGCTCTTATGTCTAGAACCGCATCTTCTACCTCACAGCCAATCTTATCTCATTCATTAAG
         GCTATGTCAGTTGTCTATTGCTGCTGTACAAATTACCACAAACAGTGACTTAAAACAACA

199527   CGTCCTCACCTCCCTTAAACCTGTCTTCTCTGCTCTTATGTCTAGAACCGCATCTTCTAC
         CTCACAGCCAATCTTATCTCATTCATTAAGGCTATGTCAGTTGTCTATTGCTGCTGTACA
         AATTACCACAAACAGTGACTTAAAACAACACAGATTTATCATCTCACAATTCTGTAGGTC
         AGAAGTCTGACTTGAGTTTCACTGGACTAAAATCAAAGTGTTGGCAAGGTCATGTTTCTT
         CCTGGAGGCTCCAGAGTTAAGTTTGTTTCTTTGCCTTTTCCAGTTTCTTAAAGGCCACCT
         [A,G]
         TATTCCTTGGCTCCCATGTTACCAAGCTTTCTCCATATTCAAAACCAGCAATGTTACCTC
         TCTCTGACCCTTCTTCTATCATCACATCTTCTCGCTAACCACAGCCTTCCAGAGCCCATC
         TCCCATCTCTGACTGGGAGATCTCCTCCTTCAGGAATCAGCTACAGTAACCTGCCTTGAC
         TTACAGCAGGTACCAAATAAGGGCACCCTATTTGGCTATGAATGTAGCCACTGGGAACGT
         ATCCACTTCTTCAGCAAACTTTTGGCATGTTGATTGTACACAGACACTCTTTCTGGGCTC

199584   TACCTCACAGCCAATCTTATCTCATTCATTAAGGCTATGTCAGTTGTCTATTGCTGCTGT
         ACAAATTACCACAAACAGTGACTTAAAACAACACAGATTTATCATCTCACAATTCTGTAG
         GTCAGAAGTCTGACTTGAGTTTCACTGGACTAAAATCAAAGTGTTGGCAAGGTCATGTTT
         CTTCCTGGAGGCTCCAGAGTTAAGTTTGTTTCTTTGCCTTTTCCAGTTTCTTAAAGGCCA
         CCTATATTCCTTGGCTCCCATGTTACCAAGCTTTCTCCATATTCAAAACCAGCAATGTTA
         [C,G]
         CTCTCTCTGACCCTTCTTCTATCATCACATCTTCTCGCTAACCACAGCCTTCCAGAGCCC
         ATCTCCCATCTCTGACTGGGAGATCTCCTCCTTCAGGAATCAGCTACAGTAACCTGCCTT
         GACTTACAGCAGGTACCAAATAAGGGCACCCTATTTGGCTATGAATGTAGCCACTGGGAA
         CGTATCCACTTCTTCAGCAAACTTTTGGCATGTTGATTGTACACAGACACTCTTTCTGGG
         CTCAAAAACCCTTGAGAATGACATTTATCCAGAAATAGTCCAAGTCTGAGTTCATTTTTG

200070   CCACTTCTTCAGCAAACTTTTGGCATGTTGATTGTACACAGACACTCTTTCTGGGCTCAA
         AAACCCTTGAGAATGACATTTATCCAGAAATAGTCCAAGTCTGAGTTCATTTTTGTTGTC
         CCATGGTCTTCTGATTTTTGCTGCTGGAGAAGACATTTGCTAGGTCACTTAGCTCTTATA
         ACTTTCAATTTCCACATCTGTAAAACGGGCACAGATCATGTCTGCATTAGCGCCTGATCA
         CTGTTCAGTGAATGTTACCTGTGTTAGTGGTTATTAATAGCTATAGTAAATGTTGAAGAG
         [T,G]
         TAGCACACGGCTGAAATCTGGAAAACACTGAGGTGGCTTGTTTATTTCTTTCAAAGCATT
         TAGCAGCTACTGTTAAGAGTACTGCCTCTGGAAGGGACACCAAATATGTGACCATCTCCC
         CAAGGCCATCTTCCTTTCAGATTCTTTTTTTGTTTTTTTGGAGACAGAGCCTTGCTCTGT
         CGCTCAGACTGGAGTGCAATGGCATGGTCTCGGCTCACTGCAACCTCCACCTCCCGGATT
         CAAGTGATTCTCCTGCCTCAGCCTCCCGAGTGGTTGGGATTATAGGTGCCCATCACCACA

200429   TTTAGCAGCTACTGTTAAGAGTACTGCCTCTGGAAGGGACACCAAATATGTGACCATCTC
         CCCAAGGCCATCTTCCTTTCAGATTCTTTTTTTGTTTTTTTGGAGACAGAGCCTTGCTCT
         GTCGCTCAGACTGGAGTGCAATGGCATGGTCTCGGCTCACTGCAACCTCCACCTCCCGGA
         TTCAAGTGATTCTCCTGCCTCAGCCTCCCGAGTGGTTGGGATTATAGGTGCCCATCACCA
         CACCTGGCTAATTTTTGTATTTTGGGTAGACACGGGGTTTCTCACGACGTTGGCCAGACT
         [A,G]
```

FIGURE 3, page 117 of 122

```
         GTCTCAAACTCCTGACCGTGTGATCCATTCACCTCCGCCTCCCAAAGTGCTGAGATTACA
         GGTATGAGCCACCACCCCCAGGCTTTTTTTCTTTCTTTCTTTCTTTTTTGAGGCAGGGT
         CTCGCTCTCTTGCCCAGGCTGGAGTGCAGTGGTACTATCATAGCTCACTATAACCTCAAA
         CTCCTGGGCTCAAGTGATCCACCCACCTCGGCCTCCCAAAGTGCTGGGATTACAAGCATG
         AGCCACTGTCCCCAGCCCCTTTCTTTCAGATTCTGACAACTGCTCGTATCACCTCCTGCC

200676   CTAATTTTTGTATTTTGGGTAGACACGGGGTTTCTCACGACGTTGGCCAGACTAGTCTCA
         AACTCCTGACCGTGTGATCCATTCACCTCCGCCTCCCAAAGTGCTGAGATTACAGGTATG
         AGCCACCACCCCCAGGCTTTTTTTTCTTTCTTTCTTTCTTTTTTGAGGCAGGGTCTCGCT
         CTCTTGCCCAGGCTGGAGTGCAGTGGTACTATCATAGCTCACTATAACCTCAAACTCCTG
         GGCTCAAGTGATCCACCCACCTCGGCCTCCCAAAGTGCTGGGATTACAAGCATGAGCCAC
         [A,G,T]
         GTCCCCAGCCCCTTTCTTTCAGATTCTGAGAACTGCTGGTATCACCTCCTGCCTTGACAA
         TGAAAACATAGATGCAGCATTTTTGTGTAAGGCCCAAGCAGGCAAGCCTATTGCTCCTAG
         ATAGAAAATTGTTGACCATAGACCTGGGCTTTTCCTCAGAATCCTCAGAATGGCCTTTTG
         CTCTCAGGGAAAAAGAATATTGCTATTTCCTGGATAGAACAAATTGGCATTTCTACATT
         GTATATGAGTAGTTATGTGTTTGCCATAATTAAAATATGGATGTCGAACTGTTTTCCCCA

202325   GGAAAAGTAGCTCCTGGCACGTAGCGGACATTCAGCCCACATTTGTTTACTTGTTTGTAC
         TTTTAAACTCCCTTCTATAGGCCACAGGGATTTTATATCAGCATTGCATTTGGGGGAGTC
         AGGCTGTGTAAGCCTGTGGAATGGATAAATCAGCAAAGAGAAATAACAGAGTACCTTAAA
         ATCCATGAGCAAATGGTTGTGCTTTAGTTTTCAGATCCCAGGGCTGTTTTTAAACTTACC
         TTCCAATGGCCAAATCCTTTCTTAGAATGTGGGCTTAAACGTCCTTTGTTTATGGGGGAT
         [T,C]
         TGCCTTTCAGAAAATCAATTCCTCACATCTGTGGCTTCAGGCTTTTTACTCAATCAGCCT
         CCTAACAAAGTAATTTTTCTGATTTTCAAGGGTGACCTAGTTGTACTGGTTTCAGTGAGC
         ATTACATGGCCTTACCTGATTGTGTATAGTAAAAAGGAGCTGTTTCTTCCAGATTTGGAG
         CCTCAGAGAAACTCTCCTGATCTTCAGGCCTATTTCCTGTTCACCCATGTGCCAATATAC
         CCTCTAGGTACCTGGATACAATTTGACATCCCACTGAAATGTGGGTGTTCTAAGCATCCA

202550   GTTTTTAAACTTACCTTCCAATGGCCAAATCCTTTCTTAGAATGTGGGCTTAAACGTCCT
         TTGTTTATGGGGGATTTGCCTTTCAGAAAATCAATTCCTCACATCTGTGGCTTCAGGCTT
         TTTACTCAATCAGCCTCCTAACAAAGTAATTTTTCTGATTTTCAAGGGTGACCTAGTTGT
         ACTGGTTTCAGTGAGCATTACATGGCCTTACCTGATTGTGTATAGTAAAAAGGAGCTGTT
         TCTTCCAGATTTGGAGCCTCAGAGAAACTCTCCTGATCTTCAGGCCTATTTCCTGTTCAC
         [C,T]
         CATGTGCCAATATACCCTCTAGGTACCTGGATACAATTTGACATCCCACTGAAATGTGGG
         TGTTCTAAGCATCCATTCATCATAAAGTTTAGGGGCTTCAGATACCAGGATGGGTACTTG
         CTCTACTAAAATGGGATCCTTAGGAAATCCCGTTCAAGGATACCACTTCACTATGGGGTA
         CTGATTTAGGGTCTCTCTCTGAATAAAATATCTTGTCAAAATCTGGTAGAATCACAAATT
         CTGATAAATGGCTGCCCAATGGAGAAGTTTAGGGAAAATTATCTTACATTTTTCATCGAA

202609   TTTGTTTATGGGGGATTTGCCTTTCAGAAAATCAATTCCTCACATCTGTGGCTTCAGGCT
         TTTTACTCAATCAGCCTCCTAACAAAGTAATTTTTCTGATTTTCAAGGGTGACCTAGTTG
         TACTGGTTTCAGTGAGCATTACATGGCCTTACCTGATTGTGTATAGTAAAAAGGAGCTGT
         TTCTTCCAGATTTGGAGCCTCAGAGAAACTCTCCTGATCTTCAGGCCTATTTCCTGTTCA
         CCCATGTGCCAATATACCCTCTAGGTACCTGGATACAATTTGACATCCCACTGAAATGTG
         [G,C]
         GTGTTCTAAGCATCCATTCATCATAAAGTTTAGGGGCTTCAGATACCAGGATGGGTACTT
         GCTCTACTAAAATGGGATCCTTAGGAAATCCCGTTCAAGGATACCACTTCACTATGGGGT
         ACTGATTTAGGGTCTCTCTCTGAATAAAATATCTTGTCAAAATCTGGTAGAATCACAAAT
         TCTGATAAATGGCTGCCCAATGGAGAAGTTTAGGGAAAATTATCTTACATTTTTCATCGA
         AGAACTGGTATTGTTGATTTAACCGTCTTTTCCCATCACCATTGTTCCTATAGCAATTTT

202714   AGGGTGACCTAGTTGTACTGGTTTCAGTGAGCATTACATGGCCTTACCTGATTGTGTATA
         GTAAAAAGGAGCTGTTTCTTCCAGATTTGGAGCCTCAGAGAAACTCTCCTGATCTTCAGG
         CCTATTTCCTGTTCACCCATGTGCCAATATACCCTCTAGGTACCTGGATACAATTTGACA
         TCCCACTGAAATGTGGGTGTTCTAAGCATCCATTCATCATAAAGTTTAGGGGCTTCAGAT
         ACCAGGATGGGTACTTGCTCTACTAAAATGGGATCCTTAGGAAATCCCGTTCAAGGATAC
         [C,T]
         ACTTCACTATGGGGTACTGATTTAGGGTCTCTCTCTGAATAAAATATCTTGTCAAAATCT
         GGTAGAATCACAAATTCTGATAAATGGCTGCCCAATGGAGAAGTTTAGGGAAAATTATCT
         TACATTTTTCATCGAAGAACTGGTATTGTTGATTTAACCGTCTTTTCCCATCACCATTGT
         TCCTATAGCAATTTTTAGACTGGGTGGAGGAATCTACTTCTCATTTCAATTCGATTTGAG
         TGGCCCTGCCCTGCCCCAAGTTTATTATCCCCACTTCTGACCCTGTGTATAACTAGAATG

202809   CAGAGAAACTCTCCTGATCTTCAGGCCTATTTCCTGTTCACCCATGTGCCAATATACCCT
         CTAGGTACCTGGATACAATTTGACATCCCACTGAAATGTGGGTGTTCTAAGCATCCATTC
         ATCATAAAGTTTAGGGGCTTCAGATACCAGGATGGGTACTTGCTCTACTAAAATGGGATC
         CTTAGGAAATCCCGTTCAAGGATACCACTTCACTATGGGGTACTGATTTAGGGTCTCTCT
         CTGAATAAAATATCTTGTCAAAATCTGGTAGAATCACAAATTCTGATAAATGGCTGCCCA
```

FIGURE 3, page 118 of 122

```
            [A,G]
            TGGAGAAGTTTAGGGAAAATTATCTTACATTTTTCATCGAAGAACTGGTATTGTTGATTT
            AACCGTCTTTTCCCATCACCATTGTTCCTATAGCAATTTTTAGACTGGGTGGAGGAATCT
            ACTTCTCATTTCAATTCGATTTGAGTGGCCCTGCCCTGCCCCAAGTTTATTATCCCCACT
            TCTGACCCTGTGTATAACTAGAATGAAAAGACTGGGCAGGAAACAAGACTAAAGGGACAC
            AAAGTCCTGCTGATATCAAAAGTAATCTTCTAAAGTCCCAAAGAATTTATAGCTTGCCAT

203159      ATTGTTGATTTAACCGTCTTTTCCCATCACCATTGTTCCTATAGCAATTTTTAGACTGGG
            TGGAGGAATCTACTTCTCATTTCAATTCGATTTGAGTGGCCCTGCCCTGCCCCAAGTTTA
            TTATCCCCACTTCTGACCCTGTGTATAACTAGAATGAAAAGACTGGGCAGGAAACAAGAC
            TAAAGGGACACAAAGTCCTGCTGATATCAAAAGTAATCTTCTAAAGTCCCAAAGAATTTA
            TAGCTTGCCATTCCATATGCTTTTTGGAAGTTTTGCTTTAAATCCTTGTTACCCAATTTT
            [G,C]
            ACCATACTGAATCATGTTATAGCATCAGATATAGACATAGCATCTCAGATATAGCCTAAA
            CCTCACCACCTCTCTCCATTTCTACTGCTGAGCCCAGAGCCCAGGCCATCTTCCACACAC
            CACACAGTAGCCTCCTTACCAGTCACGAGTCCTGCTATGTTCTTGCCCCTCTACAAGGCT
            ACTTTTCCACCACAAGACGAGGACAATAATTTTCAAATATATATCAGGTTATATGGCTCC
            TTTCCTTAAAACTTTTACCACTTTCCTGTTGCCAGTAAATATACAACATGGCCCTCAGAG

203168      TTAACCGTCTTTTCCCATCACCATTGTTCCTATAGCAATTTTTAGACTGGGTGGAGGAAT
            CTACTTCTCATTTCAATTCGATTTGAGTGGCCCTGCCCTGCCCCAAGTTTATTATCCCCA
            CTTCTGACCCTGTGTATAACTAGAATGAAAAGACTGGGCAGGAAACAAGACTAAAGGGAC
            ACAAAGTCCTGCTGATATCAAAAGTAATCTTCTAAAGTCCCAAAGAATTTATAGCTTGCC
            ATTCCATATGCTTTTTGGAAGTTTTGCTTTAAATCCTTGTTACCCAATTTTGACCATACT
            [G,A]
            AATCATGTTATAGCATCAGATATAGACATAGCATCTCAGATATAGCCTAAACCTCACCAC
            CTCTCTCCATTTCTACTGCTGAGCCCAGAGCCCAGGCCATCTTCCACACACCACACAGTA
            GCCTCCTTACCAGTCACGAGTCCTGCTATGTTCTTGCCCCTCTACAAGGCTACTTTTCCA
            CCACAAGACGAGGACAATAATTTTCAAATATATATCAGGTTATATGGCTCCTTTCCTTAA
            AACTTTTACCACTTTCCTGTTGCCAGTAAATATACAACATGGCCCTCAGAGCCCTCAATG

203704      CTTAAAACTTTTACCACTTTCCTGTTGCCAGTAAATATACAACATGGCCCTCAGAGCCCT
            CAATGCTGCTTCCCTGTGGCATCAGCTCTCACTCCTCTTTCTCTAGCTCATTTCTCTGCA
            GTTACACTGGCATCTTTGCATTCCTTGAGCACAGCCTCGCACTTTCCTCAAGTCACTTGC
            ATATGCTATTCCTTTACCTGGCATTTTCTATCACTAGAGTTTCATGTGCTGTGTGCCTCC
            TTGTCATTCAGGTCTCAGTCCAAGTGAAGCCACCTTGGAAACGACATCCTTGACCAAGCA
            [C,T]
            TTTTAAAGTCACTCCCACTCACCCAGCTCACAGTCACAATTTCCTTTTTATTTGTACTTT
            TCATGGTGCTTATTCCTTCTGATATATTTTTATTGGTTGATTGATCTAGATTGAGGTTGG
            CAAACTTCTGCCTACTGGCCAAATTCATCCCACCACCTATTTTTGTACAGCCCATGAGCT
            AATGGTTACATGTACATTTTTAAATGGTTGTAATAAATCAAAAGAAGACCATTTTGTGAC
            ATGTGAAAATTATGAGAGATTAAAATTTCAGTGCCCATAAAGTTTTTCTGGAACATAGCT

204111      TAGATTGAGGTTGGCAAACTTCTGCCTACTGGCCAAATTCATCCCACCACCTATTTTTGT
            ACAGCCCATGAGCTAATGGTTACATGTACATTTTTAAATGGTTGTAATAAATCAAAAGAA
            GACCATTTTGTGACATGTGAAAATTATGAGAGATTAAAATTTCAGTGCCCATAAAGTTTT
            TCTGGAACATAGCTATGCTCATTGTTTATATATTATCTATATCTGCCTCTGCATGACAA
            CAACAGAGATAAGTAGTGGCAACACAGACTATATGATCCACAAAGCCAAAGATATCTACC
            [G,A]
            TCTGGCCCTTTAGGATAAAGCTTGTCAACCCCTGGTCTGGATATGTATTTTCTTCATACT
            TCTCTACCTCCTAAATGTTCTAAAACACCAACTCTTTAAAAGCAAGGACCATATTTGTAT
            TTTTATTATATTCACAGTGCCTAGAATATACTGAAACAGAGTAAGCACATACATATAAAA
            GGTTGTTTATTACATCACTGGGAAGTTTATCAAATGTTTCTGTGCAATCAGAGAGCACAC
            TATGCTAGCCCATATTTCAAAAGATCTGCCAATAAGTAAGGGAAAAAAATGCCTGCAAAT

204132      CTGCCTACTGGCCAAATTCATCCCACCACCTATTTTTGTACAGCCCATGAGCTAATGGTT
            ACATGTACATTTTTAAATGGTTGTAATAAATCAAAAGAAGACCATTTTGTGACATGTGAA
            AATTATGAGAGATTAAAATTTCAGTGCCCATAAAGTTTTTCTGGAACATAGCTATGCTCA
            TTTGTTTATATATTATCTATATCTGCCTCTGCATGACAACAACAGAGATAAGTAGTGGCA
            ACACAGACTATATGATCCACAAAGCCAAAGATATCTACCGTCTGGCCCTTTAGGATAAAG
            [C,T]
            TTGTCAACCCCTGGTCTGGATATGTATTTTCTTCATACTTCTCTACCTCCTAAATGTTCT
            AAAACACCAACTCTTTAAAAGCAAGGACCATATTTGTATTTTTATTATATTCACAGTGCC
            TAGAATATACTGAAACAGAGTAAGCACATACATATAAAAGGTTGTTTATTACATCACTGG
            GAAGTTTATCAAATGTTTCTGTGCAATCAGAGAGCACACTATGCTAGCCCATATTTCAAA
            AGATCTGCCAATAAGTAAGGGAAAAAAATGCCTGCAAATTTAATAAAATAACACCTCAAG

204285      AGTTTTTCTGGAACATAGCTATGCTCATTTGTTTATATATTATCTATATCTGCCTCTGCA
            TGACAACAACAGAGATAAGTAGTGGCAACACAGACTATATGATCCACAAAGCCAAAGATA
            TCTACCGTCTGGCCCTTTAGGATAAAGCTTGTCAACCCCTGGTCTGGATATGTATTTTCT
            TCATACTTCTCTACCTCCTAAATGTTCTAAAACACCAACTCTTTAAAAGCAAGGACCATA
```

FIGURE 3, page 119 of 122

TTTGTATTTTTATTATATTCACAGTGCCTAGAATATACTGAAACAGAGTAAGCACATACA
[T,A]
ATAAAAGGTTGTTTATTACATCACTGGGAAGTTTATCAAATGTTTCTGTGCAATCAGAGA
GCACACTATGCTAGCCCATATTTCAAAAGATCTGCCAATAAGTAAGGGAAAAAAATGCCT
GCAAATTTAATAAAATAACACCTCAAGCAGAACTCAGATAAAGTTACACATAAACTTATT
AACTTCAAATCTTTTAAGTGTGTTAATTTAGATAATCCTAGGTGCTGTAACAGATAAACT
CTGAAATCTCAGCTGTTTAATGCAAAAGAAGCTTTTTTTTGTTCACTCAGTGACCACTTT

204334 CTGCCTCTGCATGACAACAACAGAGATAAGTAGTGGCAACACAGACTATATGATCCACAA
AGCCAAAGATATCTACCGTCTGGCCCTTTAGGATAAAGCTTGTCAACCCCTGGTCTGGAT
ATGTATTTTCTTCATACTTCTCTACCTCCTAAATGTTCTAAAACACCAACTCTTTAAAAG
CAAGGACCATATTTGTATTTTTATTATATTCACAGTGCCTAGAATATACTGAAACAGAGT
AAGCACATACATATAAAAGGTTGTTTATTACATCACTGGGAAGTTTATCAAATGTTTCTG
[T,G]
GCAATCAGAGAGCACACTATGCTAGCCCATATTTCAAAAGATCTGCCAATAAGTAAGGGA
AAAAAATGCCTGCAAATTTAATAAAATAACACCTCAAGCAGAACTCAGATAAAGTTACAC
ATAAACTTATTAACTTCAAATCTTTTAAGTGTGTTAATTTAGATAATCCTAGGTGCTGTA
ACAGATAAACTCTGAAATCTCAGCTGTTTAATGCAAAAGAAGCTTTTTTTTGTTCACTCA
GTGACCACTTTTTTGGCTGAGGGTTCTGGCTAAGACTCAGGCTCATGGACCCTCCACTGT

205015 GGGCATCAGCCTAGAAGAGATGCACATCACTTCTGTTGTATTCCGTTGGCCAGAACCCAG
TTACTTGGCTCAATCAGAGGTAAAACAAGCTGGGAAATGTCATTGCTGGCCAGGTAGCCA
CTCTCCACCAACATCTCTACACCATGGAAGGAAAATAAGAATGCTTGGGAGTCAGCTAAT
TATCTTGGCCACAATAGACAACTTAGTCTTTAAAAATTGATACTAAAGGATCTTATTTTT
TGAGGTAAGGGGCTGTGGTCTCAGAGGCAGCCTGGAGATACCAATTTCTGAATTTGATTT
[G,T]
ATGACTGTGCAATATAGATCAATTGAATTTTCAGTTCTATGATCATCTCCTTTTAAGACT
TTCTCCACTTAAAAAATCTGATCTGTCATCTAGATTCATTTTCTACATTCAAAGAATCTT
TAGAGGTAGATGGAAAACACGGAGATCAAAAATTATAACTGGCCCCAGGAGAAGACCTCT
CACTGTCAGAATTGTTTAAATCCTCTCCTGACTGGTAGGCCCCAATCTTTACCAACTACT
AACTCTGATTTACTTTTAGAAAGAATCAAAATTCCTGCATATCCTCAGTAGAGAATCAAA

205155 ACCATGGAAGGAAAATAAGAATGCTTGGGAGTCAGCTAATTATCTTGGCCACAATAGACA
ACTTAGTCTTTAAAAATTGATACTAAAGGATCTTATTTTTGAGGTAAGGGGCTGTGGTC
TCAGAGGCAGCCTGGAGATACCAATTTCTGAATTTGATTTGATGACTGTGCAATATAGAT
CAATTGAATTTTCAGTTCTATGATCATCTCCTTTTAAGACTTTCTCCACTTAAAAAATCT
GATCTGTCATCTAGATTCATTTTCTACATTCAAAGAATCTTTAGAGGTAGATGGAAAACA
[C,A]
GGAGATCAAAAATTATAACTGGCCCCAGGAGAAGACCTCTCACTGTCAGAATTGTTTAAA
TCCTCTCCTGACTGGTAGGCCCCAATCTTTACCAACTACTAACTCTGATTTACTTTTAGA
AAGAATCAAAATTCCTGCATATCCTCAGTAGAGAATCAAAGTGCTGTATTATAATCCAAC
CATTTCCCAAAGAAAGGAAAATTTGCTCTAATCTCCAAAGTGCAATGTCTGTTCAAAAAT
CTTTGCCAGCTTTCTTTTCATCAAACTGTGGAACCAGATTTCTCAGTCTACTAGTTTACA

205510 TTTAAATCCTCTCCTGACTGGTAGGCCCCAATCTTTACCAACTACTAACTCTGATTTACT
TTTAGAAAGAATCAAAATTCCTGCATATCCTCAGTAGAGAATCAAAGTGCTGTATTATAA
TCCAACCATTTCCCAAAGAAAGGAAAATTTGCTCTAATCTCCAAAGTGCAATGTCTGTTC
AAAAATCTTTGCCAGCTTTCTTTTCATCAAACTGTGGAACCAGATTTCTCAGTCTACTAG
TTTACATGAGGCATAGGCATGAGGCTGAGTATCACTCAGCCCACTGACCCTGGCAATATT
[T,A]
TGTTTTATCTCCCTACAAAAGAGTTAGAAATAAAATAGGTTTGTTTACAATTTCTAACTA
TTCTACTAGCTTTTGATATGAAAGTACCTAGCATATAAGCCAAGCTATACCACATTTTTT
TAGAGATCCCAATTTAACAATAGTGCTAAAATTAATAAGTAGTGCTAGCTTTGAAGGACA
ACTATCCTTAAAAATTAAGGTGTCTTTCTAAGCCATATACATCTGGCTTACACAGATTCA
TCTTGCTTTTTTTTCCTATCTTGTATGAAAACCTTGGGATTTTACGGCAGTTTTATAATT

205712 TTCATCAAACTGTGGAACCAGATTTCTCAGTCTACTAGTTTACATGAGGCATAGGCATGA
GGCTGAGTATCACTCAGCCCACTGACCCTGGCAATATTTTGTTTTATCTCCCTACAAAAG
AGTTAGAAATAAAATAGGTTTGTTTACAATTTCTAACTATTCTACTAGCTTTTGATATGA
AAGTACCTAGCATATAAGCCAAGCTATACCACATTTTTTTAGAGATCCCAATTTAACAAT
AGTGCTAAAATTAATAAGTAGTGCTAGCTTTGAAGGACAACTATCCTTAAAAATTAAGGT
[G,A]
TCTTTCTAAGCCATATACATCTGGCTTACACAGATTCATCTTGCTTTTTTTTCCTATCTT
GTATGAAAACCTTGGGATTTTACGGCAGTTTTATAATTTTTAAACCACATACCCTGAACA
TTCTATACATAAAGAAGGGTTATATTGTCAAGTGAATTTCAAAATGCTCTATAATGCATG
CTTCTTTTGCAGATAATGTTCAACAGCAAATTGAAAACAGAAATGTCTTGTAGTATAGAA
ACCTGTTAACCTTCAACTAGGCACTACCCTAATGAATATCATTTTTTAGCTTACTGACAA

206028 TACATCTGGCTTACACAGATTCATCTTGCTTTTTTTTCCTATCTTGTATGAAAACCTTGG
GATTTTACGGCAGTTTTATAATTTTTAAACCACATACCCTGAACATTCTATACATAAAGA
AGGGTTATATTGTCAAGTGAATTTCAAAATGCTCTATAATGCATGCTTCTTTTGCAGATA

FIGURE 3, page 120 of 122

ATGTTCAACAGCAAATTGAAAACAGAAATGTCTTGTAGTATAGAAACCTGTTAACCTTCA
ACTAGGCACTACCCTAATGAATATCATTTTTAGCTTACTGACAATATGAACCATACACT
[G,A]
TGCTAATTGTTTTACATGCATTAACTAATGTAGTTCTCATAGCAGCCCATGAGGCAGGTA
CCATTGTTACATCCACTCTACAGATCAGGGACTGAGGACCACAGAGGTCAGGTAACTTGC
TCAAGCTGATAGTTGGTAATTAGGAAAGCCTAGCTTTTAAACCAGGTCTGGCCTGAGGCC
AGAGACCAAGATCTTGACCACTGGGCTCCCTCTTTTTTAAAATAATACATCTTAATACTC
AGTGGCTTTTAGAGGAATTGGTTGCATGTCAAAGGAAGCAACTTCCTTTCTACTGATGGT

206073 GTATGAAAACCTTGGGATTTTACGGCAGTTTTATAATTTTTAAACCACATACCCTGAACA
TTCTATACATAAAGAAGGGTTATATTGTCAAGTGAATTTCAAAATGCTCTATAATGCATG
CTTCTTTTGCAGATAATGTTCAACAGCAAATTGAAAACAGAAATGTCTTGTAGTATAGAA
ACCTGTTAACCTTCAACTAGGCACTACCCTAATGAATATCATTTTTAGCTTACTGACAA
TATGAACCATACACTGTGCTAATTGTTTTACATGCATTAACTAATGTAGTTCTCATAGCA
[G,C]
CCCATGAGGCAGGTACCATTGTTACATCCACTCTACAGATCAGGGACTGAGGACCACAGA
GGTCAGGTAACTTGCTCAAGCTGATAGTTGGTAATTAGGAAAGCCTAGCTTTTAAACCAG
GTCTGGCCTGAGGCCAGAGACCAAGATCTTGACCACTGGGCTCCCTCTTTTTTAAAATAA
TACATCTTAATACTCAGTGGCTTTTAGAGGAATTGGTTGCATGTCAAAGGAAGCAACTTC
CTTTCTACTGATGGTTGTGCAGTTTGAGTAGGAATATTTAAACCTGTGGACTAATTGTGA

206487 AAACCAGGTCTGGCCTGAGGCCAGAGACCAAGATCTTGACCACTGGGCTCCCTCTTTTTT
AAAATAATACATCTTAATACTCAGTGGCTTTTAGAGGAATTGGTTGCATGTCAAAGGAAG
CAACTTCCTTTCTACTGATGGTTGTGCAGTTTGAGTAGGAATATTTAAACCTGTGGACTA
ATTGTGAAGAAGGAAGAAGAAAGACAGGAAGGAAAGCAGGAAGAATAGGAGGAAGGAAGG
GAGAAAGGATGGATGACAGGGAAGAAAATGAACAAGAAGGAGGAGAAAGGGAAAAGAAAA
[-,A]
AAAACCTTAGGACCATCTATGAGGGGATAAATCATATTTGACAGATATTTTCCCAGGTTT
GTATTGATTTTATTAAATAATCTTACCTTTGAGGTCCACAAGACCTGGGTTCTATGTTCT
GCCACTAATCTACTATATAACCTATTGTTTTGTTAGATCATTTAATCTCCCTAAGCCTAA
GTTTTCCTATCTGTAAAGCAGAGAAAATAATCCTAAGCCTGCCTGCACTATCTGCATAGT
GTAAAGATGTTATAAAAGTACTGTGGAGATTTAAAAAACAAAACAATACCAAAGGAGAAA

207036 GTTATAAAAGTACTGTGGAGATTTAAAAAACAAAACAATACCAAAGGAGAAAACTTTACA
TCATAATATACTACCAGAGTGCTTTTAAACATCTATTTTTCAGCTAGAAGGCTCCTTGAG
AAAGGCAACTCTTGCGGGGAATCCCAATAGGTGAAATAGATAAAAAGCAGAGCTGACCAT
TAGAGCAAGGATGAGGAAGCCAGAGCTCTCTCCTCTTCACTGCCCCTCACCACCTTCCAT
GAGCGGTGAAAGGCCCCACAAGTCTCTTAGGGTTCCCTAGAACACAGTCCTTGCAAAAGC
[G,A]
AGGGAACTGAGACCACACTGTCTTGAGCAAATTCTGTGGTCTCTGCGCCTCTGCTTCTCC
CTGTGAAAAAGGAAAAACTTGGACAAAATGATTCTTCAGTCCCCTTCCAGTTCTGACATT
CTAGAAACGTGAGTTTCTGGTTCTTCTGTCATTAGAAAGCAATGTCTCCTTCCACCTTGA
CTAACAGCATCCCTCACAGGGAACATGGTACACATGCCTGCACTGAGGGTAAGCCTCCAT
GCAGTATCCTGAGAGACATGCTCCCCGTCAGACCTCCGAGCTGTCTCAGCATCGATAGGG

209309 TTCAATTAATATTTCTTGAAAGACCTTGGAAAATGAATTAGTATAAATAACCTACTCAAA
TTTGAAAAATTAATATTGTCAACCATAATTTTTAGGCACTCCTATATATTCAATATTGTA
ATAGTTTATACTTGGAGACAGAAGAAATTTTTAAAAATAAAGGATAAACAACCATCATAG
GAAGTTAAATCTAGATGGAAAAATACAGTTAACCTAAAAATAAAGTAAAAGAATGTAATG
TTTAAATCATATGATTCCAACTATAGTTCAGAATGAGTTCACTGAAGTGCAGGGTTAGTA
[G,C]
ACATGGGGGAAAGAGGGGTTTGACCCTGTGAACAACTGCAGGGAATTAAATCCCATGGTC
CTGGCTTGCATTGTACAAAACAGACTGGCTGTGTAAACAGTTAAGCCCTTATCCCTCAGA
GGTGGCAATTTCCAAACTGAACCAATTATTGTGGGGATTTTCCCTGGGAGCAAAATTGGG
GGCACCTGAAAAGCACTGTGCTTCTTATTATTTCTGTTTACCAATATTTTAGAGCTCGGT
ATGTCCAATTCTTCATGAGCTCCTTACTTGCCTGTCTCTGGTATTGACTGGGTGACCCAG

210867 GAGCTGGCGGCAGAGATTGCCAAGCACGTGGGCTACTCCTACCGTCTGGAGATTGTCAGT
GATGGAAAATACGGAGCCCGAGACCCTGACACGAAGGCCTGGAATGGCATGGTGGGAGAG
CTGGTCTATGGAGTAAGTTCACTGCAGGGTGGGAAATTAGAGGGCGGAGGCAGAGGGTTT
GACAGGAAATCATTTGGTGGTTGGGTGGCCCTGCCCACAGATGTCTATGAAACCCTGTAA
TTGAGTGTTGTTGCTGCTGAACAGATGAGTCATCCAAAATCCAATTTCTTCAGACACTCT
[T,G]
TGTTCAGGTTACTGGTCCCAGGTCCCTCAATCCCACTCAGAGTCTTGTGACGTCAGTTGA
TTGTCGTCCAACACAGGTGACAGCATAGCTCCAAGATCAATTTTCTTGAGGCAGACTGCT
GAGTTGTCTATACAAAGTCACTTGTGGCTCTCTCAGTATCAGTTTCTTCTCTGATATTAA
ATGCATCTGGAGCCAACCTAACTTTCTAGTTACTTGCCTCTCTAGTTTCATGCTCTCTCA
TGAAATTTCCAATTCAGTCAAATGCCCCTTAATTACTCTGTTCCCTAGAGTGCTCCCTTC

212386 GAAATAAGTAAGGTGTGAGAGGAGAATGAGAAAACGCATGGTTTTTGTTGAGGACTTGGG
TTGAAGAGTAGTCAGGGATACATATGAGTAAAAAATAGCAAGAGGAAGAGTGTGGATGAT

FIGURE 3, page 121 of 122

TCAGTGGGCATTGGGAGATCACGAAGGTATTTGAGTAGAGAGACAACAAAAGGCAATGGA
AGAAGCCTCCAGCTGCCTTGTGCAGGGAAGGGACCACCACGGCTTCACTCATAGAAACTA
AAACACATGCCAAGCCCCAGGTCAATGTTAAGTGCTCATAAGGACAAGCAGCCACTGAGG
[A,G]
AGATGATAAATCTTGTTTCATATCAGGGCAAGAGGAGCCATGATGGCCCTGAGAGACATA
CAAAGGGAATTCAAAGAAGAAAAAGATGGAATAAAGGAAATCTTCCTCAGGGAGGTAGCT
TTTGAGATGACATGTGAAGGTGGTTATTGAGTTGGGGAATGGGATGTGCTTCTCTCCTTT
CTTATTCCCTTTACCACCTCTCACTTTGGGAAGCTCCATGGACAAAAGGTAGAGACCTGG
ATAGTACATGCTGCATCTGGAGGCTGGTTTCCATGGGAACTCCCATCAAGCTCTTAAGGT

Chromosome mapping:
Chromosome #: 5

ISOLATED HUMAN GLUTAMATE RECEPTOR DNA

FIELD OF THE INVENTION

The present invention is in the field of transporter proteins that are related to the glutamate receptor subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporters

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) Annu. Rev. Physiol. 50:111–122.

Transporters are generally classified by structure and the type of mode of action. In addition, transporters are sometimes classified by the molecule type that is transported, for example, sugar transporters, chlorine channels, potassium channels, etc. There may be many classes of channels for transporting a single type of molecule (a detailed review of channel types can be found at Alexander, S. P. H. and J. A. Peters: Receptor and transporter nomenclature supplement. Trends Pharmacol. Sci., Elsevier, pp. 65–68 (1997).

The following general classification scheme is known in the art and is followed in the present discoveries.

Channel-type transporters. Transmembrane channel proteins of this class are ubiquitously found in the membranes of all types of organisms from bacteria to higher eukaryotes. Transport systems of this type catalyze facilitated diffusion (by an energy-independent process) by passage through a transmembrane aqueous pore or channel without evidence for a carrier-mediated mechanism. These channel proteins usually consist largely of a-helical spanners, although b-strands may also be present and may even comprise the channel. However, outer membrane porin-type channel proteins are excluded from this class and are instead included in class 9.

Carrier-type transporters. Transport systems are included in this class if they utilize a carrier-mediated process to catalyze uniport (a single species is transported by facilitated diffusion), antiport (two or more species are transported in opposite directions in a tightly coupled process, not coupled to a direct form of energy other than chemiosmotic energy) and/or symport (two or more species are transported together in the same direction in a tightly coupled process, not coupled to a direct form of energy other than chemiosmotic energy).

Pyrophosphate bond hydrolysis-driven active transporters. Transport systems are included in this class if they hydrolyze pyrophosphate or the terminal pyrophosphate bond in ATP or another nucleoside triphosphate to drive the active uptake and/or extrusion of a solute or solutes. The transport protein may or may not be transiently phosphorylated, but the substrate is not phosphorylated.

PEP-dependent, phosphoryl transfer-driven group translocators. Transport systems of the bacterial phosphoenolpyruvate:sugar phosphotransferase system are included in this class. The product of the reaction, derived from extracellular sugar, is a cytoplasmic sugar-phosphate.

Decarboxylation-driven active transporters. Transport systems that drive solute (e.g., ion) uptake or extrusion by decarboxylation of a cytoplasmic substrate are included in this class.

Oxidoreduction-driven active transporters. Transport systems that drive transport of a solute (e.g., an ion) energized by the flow of electrons from a reduced substrate to an oxidized substrate are included in this class.

Light-driven active transporters. Transport systems that utilize light energy to drive transport of a solute (e.g., an ion) are included in this class.

Mechanically-driven active transporters. Transport systems are included in this class if they drive movement of a cell or organelle by allowing the flow of ions (or other solutes) through the membrane down their electrochemical gradients.

Outer-membrane porins (of b-structure). These proteins form transmembrane pores or channels that usually allow the energy independent passage of solutes across a membrane. The transmembrane portions of these proteins consist exclusively of b-strands that form a b-barrel. These porin-type proteins are found in the outer membranes of Gram-negative bacteria, mitochondria and eukaryotic plastids.

Methyltransferase-driven active transporters. A single characterized protein currently falls into this category, the Na+-transporting methyltetrahydromethanopterin:coenzyme M methyltransferase.

Non-ribosome-synthesized channel-forming peptides or peptide-like molecules. These molecules, usually chains of L- and D-amino acids as well as other small molecular building blocks such as lactate, form oligomeric transmembrane ion channels. Voltage may induce channel formation by promoting assembly of the transmembrane channel. These peptides are often made by bacteria and fungi as agents of biological warfare.

Non-Proteinaceous Transport Complexes. Ion conducting substances in biological membranes that do not consist of or are not derived from proteins or peptides fall into this category.

Functionally characterized transporters for which sequence data are lacking. Transporters of particular physiological significance will be included in this category even though a family assignment cannot be made.

Putative transporters in which no family member is an established transporter. Putative transport protein families are grouped under this number and will either be classified elsewhere when the transport function of a member becomes established, or will be eliminated from the TC classification system if the proposed transport function is disproven. These families include a member or members for which a transport function has been suggested, but evidence for such a function is not yet compelling.

Auxiliary transport proteins. Proteins that in some way facilitate transport across one or more biological membranes but do not themselves participate directly in transport are included in this class. These proteins always function in conjunction with one or more transport proteins. They may provide a function connected with energy coupling to transport, play a structural role in complex formation or serve a regulatory function.

Transporters of unknown classification. Transport protein families of unknown classification are grouped under this number and will be classified elsewhere when the transport process and energy coupling mechanism are characterized. These families include at least one member for which a transport function has been established, but either the mode of transport or the energy coupling mechanism is not known.

Ion Channels

An important type of transporter is the ion channel. Ion channels regulate many different cell proliferation, differentiation, and signaling processes by regulating the flow of ions into and out of cells. Ion channels are found in the plasma membranes of virtually every cell in eukaryotic organisms. Ion channels mediate a variety of cellular functions including regulation of membrane potentials and absorption and secretion of ion across epithelial membranes. When present in intracellular membranes of the Golgi apparatus and endocytic vesicles, ion channels, such as chloride channels, also regulate organelle pH. For a review, see Greger, R. (1988) Annu. Rev. Physiol. 50:111–122.

Ion channels are generally classified by structure and the type of mode of action. For example, extracellular ligand gated channels (ELGs) are comprised of five polypeptide subunits, with each subunit having 4 membrane spanning domains, and are activated by the binding of an extracellular ligand to the channel. In addition, channels are sometimes classified by the ion type that is transported, for example, chlorine channels, potassium channels, etc. There may be many classes of channels for transporting a single type of ion (a detailed review of channel types can be found at Alexander, S. P. H. and J. A. Peters (1997). Receptor and ion channel nomenclature supplement. Trends Pharmacol. Sci., Elsevier, pp. 65–68 and http://www-biology.ucsd.edu/~msaier/transport/toc.html.

There are many types of ion channels based on structure. For example, many ion channels fall within one of the following groups: extracellular ligand-gated channels (ELG), intracellular ligand-gated channels (ILG), inward rectifying channels (NR), intercellular (gap junction) channels, and voltage gated channels (VIC). There are additionally recognized other channel families based on ion-type transported, cellular location and drug sensitivity. Detailed information on each of these, their activity, ligand type, ion type, disease association, drugability, and other information pertinent to the present invention, is well known in the art.

Extracellular ligand-gated channels, ELGs, are generally comprised of five polypeptide subunits, Unwin, N. (1993), Cell 72: 31–41; Unwin, N. (1995), Nature 373: 37–43; Hucho, F., et al., (1996) J. Neurochem. 66: 1781–1792; Hucho, F., et al., (1996) Eur. J. Biochem. 239: 539–557; Alexander, S. P. H. and J. A. Peters (1997), Trends Pharmacol. Sci., Elsevier, pp.4–6; 36–40; 42–44; and Xue, H. (1998) J. Mol. Evol. 47: 323–333. Each subunit has 4 membrane spanning regions: this serves as a means of identifying other members of the ELG family of proteins. ELG bind a ligand and in response modulate the flow of ions. Examples of ELG include most members of the neurotransmitter-receptor family of proteins, e.g., GABAI receptors. Other members of this family of ion channels include glycine receptors, ryandyne receptors, and ligand gated calcium channels.

The Voltage-gated Ion Channel (VIC) Superfamily

Proteins of the VIC family are ion-selective channel proteins found in a wide range of bacteria, archaea and eukaryotes Hille, B. (1992), Chapter 9: Structure of channel proteins; Chapter 20: Evolution and diversity. In: Ionic Channels of Excitable Membranes, 2nd Ed., Sinaur Assoc. Inc., Pubs., Sunderland, Massachusetts; Sigworth, F. J. (1993), Quart. Rev. Biophys. 27: 1–40; Salkoff, L; and T. Jegla (1995), Neuron 15: 489–492; Alexander, S. P. H. et al., (1997), Trends Pharmacol. Sci., Elsevier, pp. 76–84; Jan, L. Y. et al., (1997), Annu. Rev. Neurosci. 20: 91–123; Doyle, D. A, et al., (1998) Science 280: 69–77; Terlau, H. and W. Stühmer (1998), Naturwissenschaften 85: 437–444. They are often homo- or heterooligomeric structures with several dissimilar subunits (e.g., a1-a2-d-b $Ca^{2+}$ channels, $ab_1b_2$ $Na^+$ channels or $(a)_4$-b $K^+$ channels), but the channel and the primary receptor is usually associated with the a (or a1) subunit Functionally characterized members are specific for $K^+$, $Na^+$ or $Ca^{2+}$. The $K^+$ channels usually consist of homotetrameric structures with each a-subunit possessing six transmembrane spanners (TMSs). The a1 and a subunits of the $Ca^{2+}$ and $Na^+$ channels, respectively, are about four times as large and possess 4 units, each with 6 TMSs separated by a hydrophilic loop, for a total of 24 TMSs. These large channel proteins form heterotetra-unit structures equivalent to the homotetrameric structures of most $K^+$ channels. All four units of the $Ca^{2+}$ and $Na^+$ channels are homologous to the single unit in the homotetrameric $K^+$ channels. Ion flux via the eukaryotic channels is generally controlled by the transmembrane electrical potential (hence the designation, voltage-sensitive) although some are controlled by ligand or receptor binding.

Several putative $K^+$-selective channel proteins of the VIC family have been identified in prokaryotes. The structure of one of them, the KcsA $K^+$ channel of *Streptomyces lividans,* has been solved to 3.2 Å resolution. The protein possesses four identical subunits, each with two transmembrane helices, arranged in the shape of an inverted teepee or cone. The cone cradles the "selectivity filter" P domain in its outer end. The narrow selectivity filter is only 12 Å long, whereas the remainder of the channel is wider and lined with hydrophobic residues. A large water-filled cavity and helix dipoles stabilize $K^+$ in the pore. The selectivity filter has two bound $K^+$ ions about 7.5 Å apart from each other. Ion conduction is proposed to result from a balance of electrostatic attractive and repulsive forces.

In eukaryotes, each VIC family channel type has several subtypes based on pharmacological and electrophysiological data. Thus, there are five types of $Ca^{2+}$ channels (L, N, P, Q and T). There are at least ten types of $K^+$ channels, each responding in different ways to different stimuli: voltage-sensitive [Ka, Kv, Kvr, Kvs and Ksr], $Ca^{2+}$-sensitive [$BK_{Ca}$, $IK_{Ca}$ and $SK_{Ca}$] and receptor-coupled [$K_M$ and $K_{ACh}$]. There are at least six types of $Na^+$ channels (I, II, III, $\mu$1, H1 and PN3). Tetrameric channels from both prokaryotic and eukaryotic organisms are known in which each a-subunit possesses 2 TMSs rather than 6, and these two TMSs are homologous to TMSs 5 and 6 of the six TMS unit found in the voltage-sensitive channel proteins. KcsA of *S. lividans* is an example of such a 2 TMS channel protein. These channels may include the KNa ($Na^+$-activated) and $K_{Vol}$ (cell volume-sensitive) $K^+$ channels, as well as distantly related channels such as the Tok1 $K^+$ channel of yeast, the TWIK-1 inward rectifier $K^+$ channel of the mouse and the TREK-1 $K^+$ channel of the mouse. Because of insufficient sequence similarity with proteins of the VIC family, inward rectifier $K^+$ IRK channels (ATP-regulated; G-protein-activated)

which possess a P domain and two flanking TMSs are placed in a distinct family. However, substantial sequence similarity in the P region suggests that they are homologous. The b, g and d subunits of VIC family members, when present, frequently play regulatory roles in channel activation/deactivation.

The Epithelial $Na^+$ Channel (ENaC) Family

The ENaC family consists of over twenty-four sequenced proteins (Canessa, C. M., et al., (1994), Nature 367: 463–467, Le, T. and M. H. Saier, Jr. (1996), Mol. Membr. Biol. 13: 149–157; Garty, H. and L. G. Palmer (1997), Physiol. Rev. 77: 359–396; Waldmann, R., et al., (1997), Nature 386: 173–177; Darboux, I., et al., (1998), J. Biol. Chem. 273: 9424–9429; Firsov, D., et al., (1998), EMBO J. 17: 344–352; Horisberger, J.-D. (1998). Curr. Opin. Struc. Biol. 10: 443–449). All are from animals with no recognizable homologues in other eukaryotes or bacteria. The vertebrate ENaC proteins from epithelial cells cluster tightly together on the phylogenetic tree: voltage-insensitive ENaC homologues are also found in the brain. Eleven sequenced *C. elegans* proteins, including the degenerins, are distantly related to the vertebrate proteins as well as to each other. At least some of these proteins form part of a mechano-transducing complex for touch sensitivity. The homologous *Helix aspersa* (FMRF-amide)-activated $Na^+$ channel is the fist peptide neurotransmitter-gated ionotropic receptor to be sequenced.

Protein members of this family all exhibit the same apparent topology, each with N- and C-termini on the inside of the cell, two amphipathic transmembrane spanning segments, and a large extracellular loop. The extracellular domains contain numerous highly conserved cysteine residues. They are proposed to serve a receptor function.

Mammalian ENaC is important for the maintenance of $Na^+$ balance and the regulation of blood pressure. Three homologous ENaC subunits, alpha, beta, and gamma, have been shown to assemble to form the highly $Na^+$-selective channel. The stoichiometry of the three subunits is $alpha_2$, beta1, gamma1 in a heterotetrameric architecture.

The Glutamate-gated Ion Channel (GIC) Family of Neurotransmitter Receptors

Members of the GIC family are heteropentameric complexes in which each of the 5 subunits is of 800–1000 amino acyl residues in length (Nakanishi, N., et al, (1990), Neuron 5: 569–581; Unwin, N. (1993), Cell 72: 31–41; Alexander, S. P. H. and J. A. Peters (1997) Trends Pharmacol. Sci., Elsevier, pp. 36–40). These subunits may span the membrane three or five times as putative a-helices with the N-termini (the glutamate-binding domains) localized extracellularly and the C-termini localized cytoplasmically. They may be distantly related to the ligand-gated ion channels, and if so, they may possess substantial b-structure in their transmembrane regions. However, homology between these two families cannot be established on the basis of sequence comparisons alone. The subunits fall into six subfamilies: a, b, g, d, e and z.

At The GIC channels are divided into three types: (1) a-amino-3-hydroxy-5-methyl-4-isoxazole propionate (AMPA)-, (2) kainate- and (3) N-methyl-D-aspartate (NMDA)-selective glutamate receptors. Subunits of the AMPA and kainate classes exhibit 35–40% identity with each other while subunits of the NMDA receptors exhibit 22–24% identity with the former subunits. They possess large N-terminal, estracellular glutamate-binding domains that are homologous to the periplasmic glutamine and glutamate receptors of ABC-type uptake permeases of Gram-negative bacteria. All known members of the GIC family are from animals. The different channel (receptor) types exhibit distinct ion selectivities and conductance properties. The NMDA-selective large conductance channels are highly permeable to monovalent cations and $Ca^{2+}$. The AMPA- and kainate-selective ion channels are permeable primarily to monovalent cations with only low permeability to $Ca^{2+}$.

The Chloride Channel (CIC) Family

The CIC family is a large family consisting of dozens of sequenced proteins derived from Gram-negative and Gram-positive bacteria, cyanobacteria, archaea, yeast, plants and animals (Steinmeyer, K., et al., (1991), Nature 354: 301–304; Uchida, S., et al., (1993), J. Biol. Chem. 268: 3821–3824; Huang, M.-E., et al., (1994), J. Mol. Biol. 242: 595–598; Kawasaki, M., et al., (1994), Neuron 12: 597–604; Fisher, W. E., et al., (1995), Genomics. 29:598–606; and Foskett, J. K. (1998), Annu. Rev. Physiol. 60: 689–717). These proteins are essentially ubiquitous, although they are not encoded within genomes of *Haemophilus influenzae, Mycoplasma genitalium,* and *Mycoplasma pneumoniae.* Sequenced proteins vary in size from 395 amino acyl residues (*M. jannaschii*) to 988 residues (man). Several organisms contain multiple CIC family paralogues. For example, *Synechocystis* has two paralogues, one of 451 residues in length and the other of 899 residues. *Arabidopsis thaliana* has at least four sequenced paralogues, (775–792 residues), humans also have at least five paralogues (820–988 residues), and *C. elegans* also has at least five (810–950 residues). There are nine known members in mammals, and mutations in three of the corresponding genes cause human diseases. *E. coli, Methanococcusjannaschii* and *Saccharomyces cerevisiae* only have one CIC family member each. With the exception of the larger *Synechocystis* paralogue, all bacterial proteins are small (395–492 residues) while all eukaryotic proteins are larger (687–988 residues). These proteins exhibit 10–12 putative transmembrane a-helical spanners (TMSs) and appear to be present in the membrane as homodimers. While one member of the family, Torpedo CIC-O, has been reported to have two channels, one per subunit, others are believed to have just one.

All functionally characterized members of the CIC family transport chloride, some in a voltage-regulated process. These channels serve a variety of physiological functions (cell volume regulation; membrane potential stabilization; signal transduction; transepithelial transport, etc.). Different homologues in humans exhibit differing anion selectivities, i.e., CIC4 and CIC5 share a $NO_3^- > Cl^- > Br^- > I^-$ conductance sequence, while ClC3 has an $I^- > Cl^-$ selectivity. The ClC4 and ClC5 channels and others exhibit outward rectifying currents with currents only at voltages more positive than +20 mV.

Animal Inward Rectifier $K^+$ Channel (IRK-C) Family

IRK channels possess the “minimal channel-forming structure” with only a P domain, characteristic of the channel proteins of the VIC family, and two flanking transmembrane spanners (Shuck, M. E., et al., (1994), J. Biol. Chem. 269: 24261–24270; Ashen, M. D., et al., (1995), Am. J. Physiol. 268: H506–H511; Salkoff, L. and T. Jegla (1995), Neuron 15: 489–492; Aguilar-Bryan, L., et al., (1998), Physiol. Rev. 78: 227–245; Ruknudin, A., et al., (1998), J. Biol. Chem. 273: 14165–14171). They may exist in the membrane as homo- or heterooligomers. They have a greater tendency to let $K^+$ flow into the cell than out. Voltage-dependence may be regulated by external $K^+$, by internal $Mg^{2+}$, by internal ATP and/or by G-proteins. The P domains of IRK channels exhibit limited sequence similarity to those of the VIC family, but this sequence similarity is insufficient to establish homology. Inward rectifiers play a role in setting cellular membrane potentials, and the closing of these channels upon depolarization permits the occurrence of long duration action potentials with a plateau phase. Inward rectifiers lack the intrinsic voltage sensing helices found in VIC family channels. In a few cases, those of Kir1.1a and Kir6.2, for example, direct interaction with a member of the ABC superfamily has been proposed to confer unique functional and regulatory properties to the heteromeric complex, including sensitivity to ATP. The SUR1 sulfonylurea receptor (spQ09428) is the ABC protein that regulates the Kir6.2 channel in response to ATP, and CFTR may regulate Kir1.1a Mutations in SUR1 are the cause of familial persistent hyperinsulinemic hypoglycemia in infancy (PHHI), an autosomal recessive disorder characterized by unregulated insulin secretion in the pancreas.

ATP-gated Cation Channel (ACC) Family

Members of the ACC family (also called P2X receptors) respond to ATP, a functional neurotransmitter released by exocytosis from many types of neurons (North, R. A. (1996), Curr. Opin. Cell Biol. 8: 474–483; Soto, F., M. Garcia-Guzman and W. Stühmer (1997), J. Membr. Biol. 160: 91–100). They have been placed into seven groups ($P2X_1$–$P2X_7$) based on their pharmacological properties. These channels, which function at neuron-neuron and neuron-smooth muscle junctions, may play roles in the control of blood pressure and pain sensation. They may also function in lymphocyte and platelet physiology. They are found only in animals.

The proteins of the ACC family are quite similar in sequence (>35% identity), but they possess 380–1000 amino acyl residues per subunit with variability in length localized primarily to the C-terminal domains. They possess two transmembrane spanners, one about 30–50 residues from their N-termini, the other near residues 320–340. The extraccllular receptor domains between these two spanners (of about 270 residues) are well conserved with numerous conserved glycyl and cysteyl residues. The hydrophilic C-termini vary in length from 25 to 240 residues. They resemble the topologically similar epithelial $Na^+$ channel (ENaC) proteins in possessing (a) N- and C-termini localized intracellularly, (b) two putative transmembrane spanners, (c) a large extracellular loop domain, and (d) many conserved extracellular cysteyl residues. ACC family members are, however, not demonstrably homologous with them. ACC channels are probably hetero- or homomultimers and transport small monovalent cations ($Me^+$). Some also transport $Ca^{2+}$; a few also transport small metabolites.

The Ryanodine-Inositol 1,4,5-triphosphate Receptor $Ca^{2+}$ Channel (RIR-CaC) Family Ryanodine (Ry)-sensitive and inositol 1,4,5-triphosphate (IP3)-sensitive $Ca^{2+}$+-release channels function in the release of $Ca^{2+}$ from intracellular storage sites in animal cells and thereby regulate various $Ca^{2+}$ dependent physiological processes (Hasan, G. et al., (1992) Development 116: 967–975; Michikawa, T., et al., (1994), J. Biol. Chem. 269: 9184–9189; Tunwell, R. E. A., (1996), Biochem. J. 318: 477–487; Lee, A. G. (1996) *Biomembranes,* Vol. 6, Transmembrane Receptors and Channels (A. G. Lee, ed.), JAI Press, Denver, Colo., pp 291–326; Mikoshiba, K., et al., (1996) J. Biochem. Biomem. 6: 273–289). Ry receptors occur primarily in muscle cell sarcoplasmic reticular (SR) membranes, and IP3 receptors occur primarily in brain cell endoplasmic reticular (ER) membranes where they effect release of $Ca^{2+}$ into the cytoplasm upon activation (opening) of the channel.

The Ry receptors are activated as a result of the activity of dihydropyrdine-sensitive $Ca^{2+}$ channels. The latter are members of the voltage-sensitive ion channel (VIC) family. Dihydropyridine-sensitive channels are present in the T-tubular systems of muscle tissues.

Ry receptors are homotetrameric complexes with each subunit exhibiting a molecular size of over 500,000 daltons (about 5,000 amino acyl residues). They possess C-terminal domains with six putative transmembrane a-helical spanners (TMSs). Putative pore-forming sequences occur between the fifth and sixth TMSs as suggested for members of the VIC family. The large N-terminal hydrophilic domains and the small C-terminal hydrophilic domains are localized to the cytoplasm. Low resolution 3-dimensional structural data are available. Mammals possess at least the isoforms that probably arose by gene duplication and divergence before divergence of the mammalian species. Homologues are present in humans and *Caenorabditis elegans.*

$IP_3$ receptors resemble Ry receptors in many respects. (1) They are homotetrameric complexes with each subunit exhibiting a molecular size of over 300,000 daltons (about 2,700 amino acyl residues). (2) They possess C-terminal channel domains that are homologous to those of the Ry receptors. (3) The channel domains possess six putative TMSs and a putative channel lining region between TMSs 5 and 6. (4) Both the large N-terminal domains and the smaller C-terminal tails face the cytoplasm. (5) They possess covalently linked carbohydrate on extracytoplasmic loops of the channel domains. (6) They have three currently recognized isoforms (types 1, 2, and 3) in mammals which are subject to differential regulation and have different tissue distributions.

$IP_3$ receptors possess three domains: N-terminal $IP_3$-binding domains, central coupling or regulatory domains and C-terminal channel domains. Channels are activated by $IP_3$ binding, and like the Ry receptors, the activities of the $IP_3$ receptor channels are regulated by phosphorylation of the regulatory domains, catalyzed by various protein kinases. They predominate in the endoplasmic reticular membranes of various cell types in the brain but have also been found in the plasma membranes of some nerve cells derived from a variety of tissues.

The channel domains of the Ry and $IP_3$ receptors comprise a coherent family that in spite of apparent structural similarities, do not show appreciable sequence similarity of the proteins of the VIC family. The Ry receptors and the $IP_3$ receptors cluster separately on the RIR-CaC family tree. They both have homologues in *Drosophila.* Based on the phylogenetic tree for the family, the family probably evolved in the following sequence: (1) A gene duplication event occurred that gave rise to Ry and $IP_3$ receptors in invertebrates. (2) Vertebrates evolved from invertebrates. (3) The three isoforms of each receptor arose as a result of two distinct gene duplication events. (4) These isoforms were transmitted to mammals before divergence of the mammalian species.

The Organellar Chloride Channel (O—CIC) Family

Proteins of the O—CIC family are voltage-sensitive chloride channels found in intracellular membranes but not the plasma membranes of animal cells (Landry, D, et al., (993), J. Biol. Chem. 268: 14948–14955; Valenzuela, S et al., (1997), J. Biol. Chem. 272: 12575–12582; and Duncan, R. R., et al., (1997), J. Biol. Chem. 272: 23880–23886).

They are found in human nuclear membranes, and the bovine protein targets to the microsomes, but not the plasma membrane, when expressed in *Xenopus laevis* oocytes. These proteins are thought to function in the regulation of the membrane potential and in transepithelial ion absorption and secretion in the kidney. They possess two putative transmembrane a-helical spanners (TMSs) with cytoplasmic N- and C-termini and a large luminal loop that may be glycosylated. The bovine protein is 437 amino acyl residues in length and has the two putative TMSs at positions 223–239 and 367–385. The human nuclear protein is much smaller (241 residues). A *C. elegans* homologue is 260 residues long.

Glutamate Receptor

Glutamate receptors are the predominant excitatory neurotransmitter receptors in the mammalian brain and are activated in a variety of normal neurophysiologic processes. The classification of glutamate receptors is based on their activation by different pharmacologic agonists. Thus, glutamate receptors have been named according to their respective agonists, the N-methyl-D-aspartate, quisqualic acid (QUIS), kainate (KA), and 2-amino4-phosphonobutyrate (AP4) receptors.

The present invention has substantial similarity to a human glutamate receptor (GLUH1). Puckett et al. (1991) isolated and sequenced a human glutamate receptor cDNA. The sequence of GLUH1 was predicted to encode a 907-amino acid protein that had 97% identity to one of the rodent kainate receptor subunits. GLUR1 mRNA is widely expressed in human brain. The human gene encoding the GluHI subunit is located at 5q33. While the GluII gene is not located near a chromosomal region associated with any human neurogenetic disorders, the homologous region on mouse chromosome 11 contains the sites of five neurologic mutations.

Zamanillo et al. (1999) generated mice lacking the AMPA receptor subunit GluRA, also known as GluR1, by homologous recombination. Homozygous knockout mice exhibited normal development, life expectancy, and fine structure of neuronal dendrites and synapses. They were smaller than their littermates during the first postnatal weeks, but after weaning their size was normal. In hippocampal CA1 pyramidal neurons, GluRA–/– mice showed a reduction in functional AMPA receptors, with the remaining receptors preferentially targeted to synapses. Thus, the CA1 soma-patch currents were strongly reduced but glutamatergic synaptic currents were unaltered; evoked dendritic and spinous calcium currents, calcium-dependent gene activation, and hippocampal field potentials were as in wildtype. In adult GluRA–/– mice, associative long-term potentiation was absent in CA3 to CA1 synapses, but spatial learning in the water maze was not impaired. The results suggested to Zamanillo et al. (1999) that CA1 hippocampal long-term potentiation is controlled by the number or subunit composition of AMPA receptors and show a dichotomy between long-term potentiation in CA1 and acquisition of spatial memory. For a review related to the present invention, see Puckett et al., Proc. Natl. Acad. Sci. U.S.A. 88 (17), 7557–7561 (1991); Gregor et al., Proc. Nat. Acad. Sci. 90: 3053–3057, 1993; Lee et al., Nature 405: 955–959, 2000; Shi et al., Science 284: 1811–1816, 1999; Sun et al., Proc. Nat. Acad. Sci. 89: 1443–1447, 1992; Warrington et al., Genomics 13: 803–808, 1992; Zamanillo et al., Science 284: 1805–1811, 1999.

Transporter proteins, particularly members of the glutamate receptor subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter peptides and proteins that are related to the glutamate receptor subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter activity in cells and tissues that express the transporter. Experimental data as provided in FIG. 1 indicates expression in humans in the placenta, nervous system, brain and hippocampus.

DESCRIPTION OF THE FIGURE SHEETS

FIG. 1 provides the nucleotide sequence of a cDNA molecule sequence that encodes the transporter protein of the present invention. (SEQ ID NO: 1) In addition structure and functional information is provided, such as ATG start, stop and tissue distribution, where available, that allows one to readily determine specific uses of inventions based on this molecular sequence. Experimental data as provided in FIG. 1, indicates expression in humans in the placenta, nervous system, brain and hippocampus.

FIG. 2 provides the predicted amino acid sequence of the transporter of the present invention. (SEQ ID NO: 2) In addition structure and functional information such as protein family, function, and modification sites is provided where available, allowing one to readily determine specific uses of inventions based on this molecular sequence.

FIG. 3 provides genomic sequences that span the gene encoding the transporter protein of the present invention. (SEQ ID NO: 3) In addition structure and functional information, such as intron/exon structure, promoter location, etc., is provided where available, allowing one to readily determine specific uses of inventions based on this molecular sequence. 331 SNPs, including 27 indels, have been identified in the gene encoding the receptor protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter protein or part of a transporter protein and are related to the glutamate receptor subfamily. Utilizing these sequences, additional genomic sequences were assembled and transcript and/or cDNA sequences were isolated and characterized. Based on this analysis, the present invention provides amino acid sequences of human transporter peptides and proteins that are related to the glutamate receptor subfamily, nucleic acid sequences in the form of transcript sequences, cDNA sequences and/or genomic sequences that encode these transporter peptides and proteins, nucleic acid variation (allelic information), tissue distribution of expression, and information about the closest art known protein/peptide/domain that has structural or sequence homology to the transporter of the present invention.

In addition to being previously unknown, the peptides that are provided in the present invention are selected based on their ability to be used for the development of commercially important products and services. Specifically, the present peptides are selected based on homology and/or structural relatedness to known transporter proteins of the glutamate receptor subfamily and the expression pattern observed. Experimental data as provided in FIG. 1 indicates expression in humans in the placenta, nervous system, brain and hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known glutamate receptor family or subfamily of transporter proteins.

Specific Embodiments

Peptide Molecules

The present invention provides nucleic acid sequences that encode protein molecules that have been identified as being members of the transporter family of proteins and are related to the glutamate receptor subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the transporter peptides of the present invention, transporter peptides, or peptides/proteins of the present invention.

The present invention provides isolated peptide and protein molecules that consist of, consist essentially of, or comprising the amino acid sequences of the transporter peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be “isolated” or “purified” when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, “substantially free of cellular material” includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language “substantially free of chemical precursors or other chemicals” includes preparations of the peptide in which it is separated from chemical precursors or other chemicals that are involved in its synthesis. In one embodiment, the language “substantially free of chemical precursors or other chemicals” includes preparations of the transporter peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter peptide can be purified from cells that naturally express it, purified from cells that have been altered to express it (recombinant), or synthesized using known protein synthesis methods. Experimental data as provided in FIG. 1 indicates expression in humans in the placenta, nervous system, brain and hippocampus. For example, a nucleic acid molecule encoding the transporter peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter peptides of the present invention are the naturally occurring mature proteins. A brief description of how various types of these proteins can be made/isolated is provided below.

The transporter peptides of the present invention can be attached to heterologous sequences to form chimeric or fusion proteins. Such chimeric and fusion proteins comprise a transporter peptide operatively linked to a heterologous protein having an amino acid sequence not substantially homologous to the transporter peptide. “Operatively linked” indicates that the transporter peptide and the heterologous protein are fused in-frame. The heterologous protein can be fused to the N-terminus or C-terminus of the transporter peptide.

In some uses, the fusion protein does not affect the activity of the transporter peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A transporter peptide-encoding nucleic acid can be cloned into such an expression vector such that the fusion moiety is linked in-frame to the transporter peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter peptides of the present invention as well as being encoded by the same genetic locus as the transporter peptide provided herein. As indicated by the data presented in FIG. 3, the map position was determined to be on chromosome 5 by ePCR.

Allelic variants of a transporter peptide can readily be identified as being a human protein having a high degree (significant) of sequence homology/identity to at least a portion of the transporter peptide as well as being encoded by the same genetic locus as the transporter peptide provided herein. Genetic locus can readily be determined based on the genomic information provided in FIG. 3, such as the genomic sequence mapped to the reference human. As indicated by the data presented in FIG. 3, the map position was determined to be on chromosome 5 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter peptide encoding nucleic acid molecule under stringent conditions as more fully described below.

FIG. 3 provides information on SNPs that have been identified in a gene encoding the transporter protein of the present invention. 331 SNP variants were found, including 27 indels (indicated by a "-") and 1 SNP in exons. SNPs, identified at different nucleotide positions in introns and regions 5' and 3' of the ORF, may affect control/regulatory elements.

Paralogs of a transporter peptide can readily be identified as having some degree of significant sequence homology/identity to at least a portion of the transporter peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter peptide encoding nucleic acid molecule under moderate to stringent conditions as more fully described below.

Orthologs of a transporter peptide can readily be identified as having some degree of significant sequence homology/identity to at least a portion of the transporter peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter peptide encoding nucleic acid molecule under moderate to stringent conditions, as more fully described below, depending on the degree of relatedness of the two organisms yielding the proteins.

Non-naturally occurring variants of the transporter peptides of the present invention can readily be generated using recombinant techniques. Such variants include, but are not limited to deletions, additions and substitutions in the amino acid sequence of the transporter peptide. For example, one class of substitutions are conserved amino acid substitution. Such substitutions are those that substitute a given amino acid in a transporter peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as transporter activity or in assays such as an in vitro proliferative activity. Sites that are critical for binding partner/substrate binding can also be determined by structural analysis such as crystallization, nuclear magnetic resonance or photoaffinity labeling (Smith et at., *J. Mol. Biol.* 224:899–904 (1992); de Vos et al. *Science* 255:306–312 (1992)).

The present invention further provides fragments of the transporter peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter peptide. Such fragments can be chosen based on the ability to retain one or more of the biological activities of the transporter peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth Enzynol.* 182: 626–646 (1990)) and Rattan et al. (*Ann N.Y. Acad. Sci.* 663:48–62 (1992)).

Accordingly, the transporter peptides of the present invention also encompass derivatives or analogs in which a substituted amino acid residue is not one encoded by the genetic code, in which a substituent group is included, in which the mature transporter peptide is fused with another compound, such as a compound to increase the half-life of the transporter peptide (for example, polyethylene glycol), or in which the additional amino acids are fused to the mature transporter peptide, such as a leader or secretory sequence or a sequence for purification of the mature transporter peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter-effector protein interaction or transporter-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, transporters isolated from humans and their human/mammalian orthologs serve as targets for identifying agents for use in mammalian therapeutic applications, e.g. a human drug, particularly in modulating a biological or pathological response in a cell or tissue that expresses the transporter. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus. A large percentage of pharmaceutical agents are being developed that modulate the activity of transporter proteins, particularly members of the glutamate receptor subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the placenta, nervous system, brain and hippocampus. Such uses can readily be determined using the information provided herein, that known in the art and routine experimentation.

The proteins of the present invention (including variants and fragments that may have been disclosed prior to the present invention) are useful for biological assays related to transporters that are related to members of the glutamate receptor subfamily. Such assays involve any of the known transporter functions or activities or properties useful for diagnosis and treatment of transporter-related conditions that are specific for the subfamily of transporters that the one of the present invention belongs to, particularly in cells and tissues that express the transporter. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus. The proteins of the present invention are also useful in drug screening assays, in cell-based or cell-free systems ((Hodgson, Bio/technology, 1992, September 10(9);973–80). Cell-based systems can be native, i.e., cells that normally express the transporter, as a biopsy or expanded in cell culture. Experimental data as provided in FIG. 1 indicates expression in humans in the placenta, nervous system, brain and hippocampus. In an alternate embodiment, cell-based assays involve recombinant host cells expressing the transporter protein.

The polypeptides can be used to identify compounds that modulate transporter activity of the protein in its natural state or an altered form that causes a specific disease or pathology associated with the transporter. Both the transporters of the present invention and appropriate variants and fragments can be used in high-throughput screens to assay candidate compounds for the ability to bind to the transporter. These compounds can be further screened against a functional transporter to determine the effect of the compound on the transporter activity. Further, these compounds can be tested in animal or invertebrate systems to determine activity/effectiveness. Compounds can be identified that activate (agonist) or inactivate (antagonist) the transporter to a desired degree.

Further, the proteins of the present invention can be used to screen a compound for the ability to stimulate or inhibit interaction between the transporter protein and a molecule that normally interacts with the transporter protein, e.g. a substrate or a component of the signal pathway that the transporter protein normally interacts (for example, another transporter). Such assays typically include the steps of combining the transporter protein with a candidate compound under conditions that allow the transporter protein, or fragment, to interact with the target molecule, and to detect the formation of a complex between the protein and the target or to detect the biochemical consequence of the interaction with the transporter protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab'$_2$), Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporters or appropriate fragments containing mutations that affect transporter function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter activity. The assays typically involve an assay of events in the signal transduction pathway that indicate transporter activity. Thus, the transport of a ligand, change in cell membrane potential, activation of a protein, a change in the expression of genes that are up- or down-regulated in response to the transporter protein dependent signal cascade can be assayed.

Any of the biological or biochemical functions mediated by the transporter can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter can be assayed. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus.

Binding and/or activating compounds can also be screened by using chimeric transporter proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter. Accordingly, a different set of signal transduction components is available as an end-point assay for activation. This allows for assays to be performed in other than the specific host cell from which the transporter is derived.

The proteins of the present invention are also useful in competition binding assays in methods designed to discover compounds that interact with the tansporter (e.g. binding partners and/or ligands). Thus, a compound is exposed to a transporter polypeptide under conditions that allow the compound to bind or to otherwise interact with the polypeptide. Soluble transporter polypeptide is also added to the mixture. If the test compound interacts with the soluble transporter polypeptide, it decreases the amount of complex formed or activity from the transporter target. This type of assay is particularly useful in cases in which compounds are sought that interact with specific regions of the transporter. Thus, the soluble polypeptide that competes with the target transporter region is designed to contain peptide sequences corresponding to the region of interest.

To perform cell free drug screening assays, it is sometimes desirable to immobilize either the transporter protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter-binding protein and a candidate compound are incubated in the transporter protein-presenting wells and the amount of complex trapped in the well can be quantitated. Methods for detecting such complexes, in addition to those described above for the GST-immobilized complexes, include immunodetection of complexes using antibodies reactive with the transporter protein target molecule, or which are reactive with transporter protein and compete with the target molecule, as well as enzyme-linked assays which rely on detecting an enzymatic activity associated with the target molecule.

Agents that modulate one of the transporters of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of transporter protein activity identified according to these drug screening assays can be used to treat a subject with a disorder mediated by the transporter pathway, by treating cells or tissues that express the transporter. Experimental data as provided in FIG. 1 indicates expression in humans in the placenta, nervous system, brain and hippocampus. These methods of treatment include the steps of administering a modulator of transporter activity in a pharmaceutical composition to a subject in need of such treatment, the modulator being identified as described herein.

In yet another aspect of the invention, the transporter proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the transporter and are involved in transporter activity. Such transporter-binding proteins are also likely to be involved in the propagation of signals by the transporter proteins or transporter targets as, for example, downstream elements of a transporter-mediated signaling pathway. Alternatively, such transporter-binding proteins are likely to be transporter inhibitors.

The two-hybrid system is based on the modular nature of most transcription factors, which consist of separable DNA-binding and activation domains. Briefly, the assay utilizes two different DNA constructs. In one construct, the gene that codes for a transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter protein.

This invention further pertains to novel agents identified by the above-described screening assays. Accordingly, it is within the scope of this invention to further use an agent identified as described herein in an appropriate animal model. For example, an agent identified as described herein (e.g., a transporter-modulating agent, an antisense transporter nucleic acid molecule, a transporter-specific antibody, or a transporter-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the placenta, nervous system, brain and hippocampus. The method involves contacting a biological sample with a compound capable of interacting with the transporter protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter protein in which one or more of the transporter functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the placenta, nervous system, brain and hippocampus. Accordingly, methods for treatment include the use of the transporter protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter proteins. Antibodies can be prepared from any region of the peptide as described herein. However, preferred regions will include those involved in function/activity and/or transporter/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the placenta, nervous system, brain and hippocanpus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the placenta, nervous system, brain and hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the placenta, nervous system, brain and hippocampus. Thus, where a specific protein has been correlated with expression in a specific tissue, antibodies that are specific for this protein can be used to identify a tissue type.

The antibodies are also useful for inhibiting protein function, for example, blocking the binding of the transporter peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter peptide or protein of the present invention (cDNA, transcript and genomic sequence). Such nucleic acid molecules will consist of, consist essentially of, or comprise a nucleotide sequence that encodes one of the transporter peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomnic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the transporter proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred noncoding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 5 by ePCR.

FIG. 3 provides information on SNPs that have been identified in a gene encoding the transporter protein of the present invention. 331 SNP variants were found, including 27 indels (indicated by a "-") and 1 SNP in exons. SNPs, identified at different nucleotide positions in introns and regions 5' and 3' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 1×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 331 SNPs, including 27 indels, have been identified in the gene encoding the receptor protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 5 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter protein, such as by measuring a level of a transporter-encoding nucleic acid in a sample of cells from a subject e.g., mRNA or genomic DNA, or determining if a transporter gene has been mutated. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus.

Nucleic acid expression assays are useful for drug screening to identify compounds that modulate transporter nucleic acid expression.

The invention thus provides a method for identifying a compound that can be used to treat a disorder associated with nucleic acid expression of the transporter gene, particularly biological and pathological processes that are mediated by the transporter in cells and tissues that express it. Experimental data as provided in FIG. 1 indicates expression in humans in the placenta, nervous system, brain and hippocampus. The method typically includes assaying the ability of the compound to modulate the expression of the transporter nucleic acid and thus identifying a compound that can be used to treat a disorder characterized by undesired transporter nucleic acid expression. The assays can be performed in cell-based and cell-free systems. Cell-based assays include cells naturally expressing the transporter nucleic acid or recombinant cells genetically engineered to express specific nucleic acid sequences.

The assay for transporter nucleic acid expression can involve direct assay of nucleic acid levels, such as mRNA levels, or on collateral compounds involved in the signal pathway. Further, the expression of genes that are up or down-regulated in response to the transporter protein signal pathway can also be assayed. In this embodiment the regulatory regions of these genes can be operably linked to a reporter gene such as luciferase.

Thus, modulators of transporter gene expression can be identified in a method wherein a cell is contacted with a candidate compound and the expression of mRNA determined. The level of expression of transporter mRNA in the presence of the candidate compound is compared to the level of expression of transporter mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter nucleic acid expression in cells and tissues that express the transporter. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus. Modulation includes both up-regulation (i.e. activation or agonization) or down-regulation (suppression or antagonization) or nucleic acid expression.

Alternatively, a modulator for transporter nucleic acid expression can be a small molecule or drug identified using the screening assays described herein as long as the drug or small molecule inhibits the transporter nucleic acid expression in the cells and tissues that express the protein. Experimental data as provided in FIG. 1 indicates expression in humans in the placenta, nervous system, brain and hippocampus.

The nucleic acid molecules are also useful for monitoring the effectiveness of modulating compounds on the expression or activity of the transporter gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter nucleic acid expression, and particularly in qualitative changes that lead to pathology. The nucleic acid molecules can be used to detect mutations in transporter genes and gene expression products such as mRNA. The nucleic acid molecules can be used as hybridization probes to detect naturally occurring genetic mutations in the transporter gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter gene associated with a dysfunction provides a diagnostic tool for an active disease or susceptibility to disease when the disease results from overexpression, underexpression, or altered expression of a transporter protein.

Individuals carrying mutations in the transporter gene can be detected at the nucleic acid level by a variety of techniques. FIG. 3 provides information on SNPs that have been identified in a gene encoding the transporter protein of the present invention. 331 SNP variants were found, including 27 indels (indicated by a "-") and 1 SNP in exons. SNPs, identified at different nucleotide positions in introns and regions 5' and 3' of the ORF, may affect control/regulatory elements. As indicated by the data presented in FIG. 3, the map position was determined to be on chromosome 5 by ePCR Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159(1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al, *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter gene in an individual in order to select an appropriate compound or dosage regimen for treatment. FIG. 3 provides information on SNPs that have been identified in a gene encoding the transporter protein of the present invention. 331 SNP variants were found, including 27 indels (indicated by a "-") and 1 SNP in exons. SNPs, identified at different nucleotide positions in introns and regions 5' and 3' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter gene expression in cells, tissues, and organisms. A DNA antisense nucleic acid molecule is designed to be complementary to a region of the gene involved in transcription, preventing transcription and hence production of transporter protein. An antisense RNA or DNA nucleic acid molecule would hybridize to the mRNA and thus block translation of mRNA into transporter protein.

Alternatively, a class of antisense molecules can be used to inactivate mRNA in order to decrease expression of transporter nucleic acid. Accordingly, these molecules can treat a disorder characterized by abnormal or undesired transporter nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter protein, such as ligand binding.

The nucleic acid molecules also provide vectors for gene therapy in patients containing cells that are aberrant in transporter gene expression. Thus, recombinant cells, which include the patient's cells that have been engineered ex vivo and returned to the patient, are introduced into an individual where the cells produce the desired transporter protein to treat the individual.

The invention also encompasses kits for detecting the presence of a transporter nucleic acid in a biological sample. Experimental data as provided in FIG. 1 indicates that the transporter proteins of the present invention are expressed in humans in the placenta, nervous system and brain detected by a virtual northern blot. In addition, PCR-based tissue screening panels indicate expression in hippocampus. For example, the kit can comprise reagents such as a labeled or labelable nucleic acid or agent capable of detecting transporter nucleic acid in a biological sample; means for determining the amount of transporter nucleic acid in the sample; and means for comparing the amount of transporter nucleic acid in the sample with a standard. The compound or agent can be packaged in a suitable container. The kit can further comprise instructions for using the kit to detect transporter protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter gene of the present invention. FIG. 3 provides information on SNPs that have been identified in a gene encoding the transporter protein of the present invention. 331 SNP variants were found, including 27 indels (indicated by a "–") and 1 SNP in exons. SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed,* Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.,* Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporters, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter protein or peptide that can be further purified to produce desired amounts of transporter protein or fragments. Thus, host cells containing expression vectors are useful for peptide production.

Host cells are also useful for conducting cell-based assays involving the transporter protein or transporter protein fragments, such as those described above as well as other formats known in the art. Thus, a recombinant host cell expressing a native transporter protein is useful for assaying compounds that stimulate or inhibit transporter protein function.

Host cells are also useful for identifying transporter protein mutants in which these functions are affected. If the mutants naturally occur and give rise to a pathology, host cells containing the mutations are useful to assay compounds that have a desired effect on the mutant transporter protein (for example, stimulating or inhibiting function) which may not be indicated by their effect on the native transporter protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter protein and identifying and evaluating modulators of transporter protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the transporter protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgene. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter protein activation, and signal transduction, may not be evident from in vitro cell-free or cell-based assays. Accordingly, it is useful to provide non-human transgenic animals to assay in vivo transporter protein function, including ligand interaction, the effect of specific mutant transporter proteins on transporter protein function and ligand interaction, and the effect of chimeric transporter proteins. It is also possible to assess the effect of null mutations, that is mutations that substantially or completely eliminate one or more transporter protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO:2;

(b) a nucleic acid sequence consisting of the nucleic acid sequence of SEQ ID No: 1;

(c) a nucleic acid sequence consisting of the nucleic acid sequence of SEQ ID No: 3; and (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO: 2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2434
<212> TYPE: DNA
<213> ORGANISM: Human

<400> SEQUENCE: 1

| | | | | | |
|---|---|---|---|---|---|
| tgcagtttaa | gtgttcggat | tccaagggaa | acagacaaac | ctcacgaaag | gaaggaagca | 60 |
| agcaagcaag | gaaggaactg | caggaggaaa | agaacaggca | gaacagcgag | aagaataaag | 120 |
| ggaaaggggg | ggaaacacca | aatctatgat | tggacctggg | cttcttttttc | gccaatgcaa | 180 |
| aaaggaatat | gcagcacatt | tttgccttct | tctgcaccgg | tttcctaggc | gcggtagtag | 240 |
| gtgccaattt | ccccaacaat | atccagatcg | ggggattatt | tccaaaccag | cagtcacagg | 300 |
| aacatgctgc | ttttagattt | gctttgtcgc | aactcacaga | gcccccgaag | ctgctccccc | 360 |
| agattgatat | tgtgaacatc | agcgacagct | ttgagatgac | ctatagattc | tgttcccagt | 420 |
| tctccaaagg | agtctatgcc | atctttgggt | tttatgaacg | taggactgtc | aacatgctga | 480 |
| cctccttttg | tggggccctc | cacgtctgct | tcattacgcc | gagctttccc | gttgatacat | 540 |
| ccaatcagtt | tgtccttcag | ctgcgccctg | aactgcagga | tgccctcatc | agcatcattg | 600 |
| accattacaa | gtggcagaaa | tttgtctaca | tttatgatgc | cgaccggggc | ttatccgtcc | 660 |
| tgcagaaagt | cctggataca | gctgctgaga | agaactggca | ggtgacagca | gtcaacattt | 720 |
| tgacaaccac | agaggaggga | taccggatgc | tctttcagga | cctggagaag | aaaaaggagc | 780 |
| ggctggtggt | ggtggactgt | gaatcagaac | gcctcaatgc | tatcttgggc | cagattataa | 840 |
| agctagagaa | gaatggcatc | ggctaccact | acattcttgc | aaatctgggc | ttcatggaca | 900 |
| ttgacttaaa | caaattcaag | gagagtggcg | ccaatgtgac | aggtttccag | ctggtgaact | 960 |
| acacagacac | tattccggcc | aagatcatgc | agcagtggaa | gaatagtgat | gctcgagacc | 1020 |
| acacacgggt | ggactggaag | agacccaagt | acacctctgc | gctcacctac | gatggggtga | 1080 |
| aggtgatggc | tgaggctttc | cagagcctgc | ggaggcagag | aattgatata | tctcgccggg | 1140 |
| ggaatgctgg | ggattgtctg | gctaacccag | ctgttccctg | gggccaaggg | atcgacatcc | 1200 |
| agagagctct | gcagcaggtg | cgatttgaag | gtttaacagg | aaacgtgcag | tttaatgaga | 1260 |
| aaggacgccg | gaccaactac | acgctccacg | tgattgaaat | gaaacatgac | ggcatccgaa | 1320 |
| agattggtta | ctggaatgaa | gatgataagt | ttgtccctgc | agccaccgat | gcccaagctg | 1380 |

-continued

```
ggggcgataa ttcaagtgtt cagaacagaa catacatcgt cacaacaatc ctagaagatc   1440

cttatgtgat gctcaagaag aacgccaatc agtttgaggg caatgaccgt tacgagggct   1500

actgtgtaga gctggcggca gagattgcca agcacgtggg ctactcctac cgtctggaga   1560

ttgtcagtga tggaaaatac ggagcccgag accctgacac gaaggcctgg aatggcatgg   1620

tgggagagct ggtctatgga gtaagttcac tgcagggtgg gaaattagag ggcggaggca   1680

gagggtttga caggaaatca tttggtggtt gggtggccct gcccacagat gtctatgaaa   1740

ccctgtaatt gagtgttgtt gctgctgaac agatgagtca tccaaaatcc aatttcttca   1800

gacactcttt gttcaggtta ctggtcccag gtccctcaat cccactcaga gtcttgtgac   1860

gtcagttgat tgtcgtccaa cacaggtgac agcatagctc caagatcaat ttcttgagg    1920

cagactgctg agttgtctat acaaagtcac ttgtggctct ctcagtatca gtttcttctc   1980

tgatattaaa tgcatctgga gccaacctaa ctttctagtt acttgcctct ctagtttcat   2040

gctctctcat gaaatttcca attcagtcaa atgcccctta attactctgt tccctagagt   2100

gctcccttcc actctccacc cctaagatac tactccttca aaacctatat caaataatac   2160

ttttttcagg gtgtgtttct ttctttcttc tcataatagg tatgaatgtg ccttttaatt   2220

gttctcgcct tcccctatag aatttagttg ctggtttttt ttaatggttt accctgcctt   2280

atataacggt tacctgtgta acaggggtag gactattcta tctttatagt gctcaccaca   2340

cttgaaataa ctccatgcac aattgctata aaatcttcaa taaattacag cagttttgaa   2400

aaaaaaaaaa aaaaaaaaaa aaaaaaaaaa aaaa                               2434
```

```
<210> SEQ ID NO 2
<211> LENGTH: 519
<212> TYPE: PRT
<213> ORGANISM: Human

<400> SEQUENCE: 2

Met Gln His Ile Phe Ala Phe Phe Cys Thr Gly Phe Leu Gly Ala Val
 1               5                  10                  15

Val Gly Ala Asn Phe Pro Asn Asn Ile Gln Ile Gly Gly Leu Phe Pro
            20                  25                  30

Asn Gln Gln Ser Gln Glu His Ala Ala Phe Arg Phe Ala Leu Ser Gln
        35                  40                  45

Leu Thr Glu Pro Pro Lys Leu Leu Pro Gln Ile Asp Ile Val Asn Ile
    50                  55                  60

Ser Asp Ser Phe Glu Met Thr Tyr Arg Phe Cys Ser Gln Phe Ser Lys
65                  70                  75                  80

Gly Val Tyr Ala Ile Phe Gly Phe Tyr Glu Arg Arg Thr Val Asn Met
                85                  90                  95

Leu Thr Ser Phe Cys Gly Ala Leu His Val Cys Phe Ile Thr Pro Ser
            100                 105                 110

Phe Pro Val Asp Thr Ser Asn Gln Phe Val Leu Gln Leu Arg Pro Glu
        115                 120                 125

Leu Gln Asp Ala Leu Ile Ser Ile Ile Asp His Tyr Lys Trp Gln Lys
    130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
            180                 185                 190
```

-continued

```
Glu Lys Lys Lys Glu Arg Leu Val Val Val Asp Cys Glu Ser Glu Arg
        195                 200                 205

Leu Asn Ala Ile Leu Gly Gln Ile Ile Lys Leu Glu Lys Asn Gly Ile
    210                 215                 220

Gly Tyr His Tyr Ile Leu Ala Asn Leu Gly Phe Met Asp Ile Asp Leu
225                 230                 235                 240

Asn Lys Phe Lys Glu Ser Gly Ala Asn Val Thr Gly Phe Gln Leu Val
                245                 250                 255

Asn Tyr Thr Asp Thr Ile Pro Ala Lys Ile Met Gln Gln Trp Lys Asn
            260                 265                 270

Ser Asp Ala Arg Asp His Thr Arg Val Asp Trp Lys Arg Pro Lys Tyr
        275                 280                 285

Thr Ser Ala Leu Thr Tyr Asp Gly Val Lys Val Met Ala Glu Ala Phe
    290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
                325                 330                 335

Ile Gln Arg Ala Leu Gln Gln Val Arg Phe Glu Gly Leu Thr Gly Asn
            340                 345                 350

Val Gln Phe Asn Glu Lys Gly Arg Arg Thr Asn Tyr Thr Leu His Val
        355                 360                 365

Ile Glu Met Lys His Asp Gly Ile Arg Lys Ile Gly Tyr Trp Asn Glu
    370                 375                 380

Asp Asp Lys Phe Val Pro Ala Ala Thr Asp Ala Gln Ala Gly Gly Asp
385                 390                 395                 400

Asn Ser Ser Val Gln Asn Arg Thr Tyr Ile Val Thr Thr Ile Leu Glu
                405                 410                 415

Asp Pro Tyr Val Met Leu Lys Lys Asn Ala Asn Gln Phe Glu Gly Asn
            420                 425                 430

Asp Arg Tyr Glu Gly Tyr Cys Val Glu Leu Ala Ala Glu Ile Ala Lys
        435                 440                 445

His Val Gly Tyr Ser Tyr Arg Leu Glu Ile Val Ser Asp Gly Lys Tyr
    450                 455                 460

Gly Ala Arg Asp Pro Asp Thr Lys Ala Trp Asn Gly Met Val Gly Glu
465                 470                 475                 480

Leu Val Tyr Gly Val Ser Ser Leu Gln Gly Gly Lys Leu Glu Gly Gly
                485                 490                 495

Gly Arg Gly Phe Asp Arg Lys Ser Phe Gly Gly Trp Val Ala Leu Pro
            500                 505                 510

Thr Asp Val Tyr Glu Thr Leu
        515


<210> SEQ ID NO 3
<211> LENGTH: 213456
<212> TYPE: DNA
<213> ORGANISM: Human
<220> FEATURE:
<221> NAME/KEY: misc_feature
<222> LOCATION: (1)...(213456)
<223> OTHER INFORMATION: n = A,T,C or G

<400> SEQUENCE: 3

ttcaaagtag taagatacaa aaactgaaaa tggagaaatt aaaagatgga atcattaaat 60

cagagactct taatgttggc agagacctta gaagtgatct ttcctgattc tgttctctca 120
```

-continued tcttcctatg ctgatgctta ttcttccttt agaaggttcc tacccagtgc ttgctgttat 180
tagagcctaa gagttaagag ctggggcctg atggtggcat ttactgtgtt taaatgccca 240
atctctttca ttagcagtga aaacttgggg tgagttttta gacctctgtt tcttcatcta 300
taaaatgggc atgaggctac ctacacaggt attgtacaaa taaatgatgc aggtgcattt 360
cttagcatgg tacctggcac attcaaaata gtgaataaac attagcctta aaaattattt 420
tagctaatta attaatatat gtgaaagtgc ataggaaatc acaaagcatt tgacctccaa 480
gttgttccta ttttggggct tcattgtaca tggtcagata ttttttacaa atcccagtcc 540
ttgtagctgt cactcaagtc cacatgatat acagtcctgg tgagggaagt gaagagtctg 600
tggataaaat ggcctattca tatggcaaag caaaatggag tccaaagtct attatttctt 660
tcttactaaa gacaaagttg actttccttt tcctggatca tctcctgttg gacaggagtc 720
ctggccaggg cagtaagtca actggtaacg gccaaagcac tcaagtttgt aggttgtact 780
gtacatctta gtaggtctgt gtctttatga cttaatccca gaagtcttat ctttttcatc 840
tgtaaaacag ggctcatggc cactttacag gtttggagtg aagatagatg gataaaaatc 900
tgtaaagttc cttcaaaaac tgtattctgt ggcggctagt ggctgctgct ttgcatttaa 960
cactactatc ctgaacacag ctgatctctc tacaggttat ttcagcagaa gccctggtct 1020
aggagagtct atgaagttcc agcttacacc agacatgacc agcatccaga aagacctgaa 1080
agaagcttga atcctctcac tagaatccct gcaaaatgac tcatgtaatt gctctgtgta 1140
agtatcctta gtctttattg tacacccaca cgattctgat gctatagact cctgtggaat 1200
gcagggaaag agagaagggg gcccatttta aatgcctagg attgaaaaga gaccaccgtt 1260
tcacttgtaa aggtagacag ggactgtcaa atacctggtc aaaatacctg ccagtcactc 1320
cagatcctcc cttgtttgtc tatctgtcat tccttccatt aggagagaga aagctttttt 1380 tttttttcc tttaaatttc ctaggaggga tttctagggt ctttccctca ggaattagtt 1440
gtaggaataa ttgggccagt ggagtgcagg agatatatcc agcgcagccc atgcactcct 1500
agaaaaagtg acctagatca agcagctggt ggattgagga ctattgtggg gacccccctgc 1560 cacctactga cttacagctg aacccacatt cccagcagct tcagcctggg ggctggggga 1620
gcgggcagac cgagctcaga aaggcagggg agggtaaaga ggactgtggg gttgcccctt 1680
tcaggaccaa gtgccacgtg tcacacaccc ccacctccac ctttctgcac acacagaaag 1740
gaggataagg tgaggatggg aggaaggggg aacaggtagg gaggtcggct gtggaactcc 1800
aagctagctc ggtgggtatt agcatagagc ttgctgcctg tgtgagtgtg agggggagag 1860
cgagagagag caagggaggg agagagaggc aggctgcgag gggagaggag agggagtggg 1920
ggagccagcg ctccagctag catgaggacg ggcttctttt cccgtgctca gttaatctgg 1980
ctgtcagttg gtgttaacgc tgcagtttaa gtgttcggat tccaagggaa acagacaaac 2040
ctcacgaaag gaaggaagca agcaagcaag gaaggaactg caggaggaaa agaacaggca 2100
gaacagcgag aagaataaag ggaaaggggg ggaaacacca aatctatgat tggacctggg 2160
cttctttttc gccaatgcaa aaaggaatat gcagcacatt tttgccttct tctgcaccgg 2220
tttcctaggc gcggtagtag gtgccaattt ccccaacaat atccagatcg gtgagtgagg 2280
gggcagcctg gggagggact ttctgggtct ggccagggat ttttttgggg ataggggttg 2340 tgtacccccct ccccggtact gactgttttg cttggctccc taaagctgtg ctgcggtaac 2400
agaagggaga cttgggctta cagccagagg agggggcttc tcctgatcgg atgaggggca 2460
gaggggaagt gttcacacac gcacacatac cctactcgca ctccaggcaa gagcatgtga 2520

-continued

```
aatggaggaa ccatcgcttt ggaggaaaaa aaaaatcagg ctggaaaggg tggtgggtgt 2580
ttaaggagtt aactctattg cttggtagat ggtgcttgat tccattttta atgtaagtat 2640
gtatggtgtg tgtgttttca cgtgtgtgat tatatattac atatgcacat atatatgtaa 2700
ttgaaggagg cagtgctttc tctgctgggg gacagaaaag agaccctcga gaagaaggag 2760
tgaggggtgc tgggtatatt gcagccactg aaataatgcc agaaggcccc cactccaagg 2820
cgggtaggct ccctctcctg ttctggactc ctccagctgc cttctctttg ctgtctgcca 2880
tgctgcgctg gtggtctcca ctcccccgat cctggaactt cctcgcctgc cttttctccg 2940
ttccttcctt gccccctcct cttagatttc ctatccacag aggtctacct tttacacaca 3000
caaacacaca cacgtacaca tgctcctttc tcctcctgtt ggctctccat tatccttgtt 3060
actgggctcc atcctctcaa cttggaggca ggtttcaaca tgctgcatgc ttttttttgtt 3120
ccccatttcc ccttcttagt tgttacactt ctcaaaggcc ccgccaccct ccctgtattt 3180
ctgaggggac tgacagatat tgctactcct gataatcatg agggaaagca aaacaaacag 3240
aagcaataac accaatcaca aagcatgtcc acaagggctt ggggcttccg tgtgaccagc 3300
atgtcagtgt cgtttgtgtc ccggaatgaa gcaagctgct gtgtttggaa gcatcttcgt 3360
tggtttggtt tctagtctct ctcccctggt agggagatag ctccactagg gaaagttcgc 3420
attgctggga gtttgtgctc ttttgtgagt gtgtgtttga ggggggatgt ggtgcaattg 3480
atattttgtc gggcatacat gtgctgcagt acccatctct ttcagcctct ccagctagct 3540
ggcggcttgg agtggccatg gagtaacttg ctttgtttcc tgacacctgt taagctacat 3600
cctgaagtgt gtacgtatct gtgtgttagt gcctaacacg caaaacttcc tgccttcagg 3660
ggagacactt cccttgtagc ccagcccgta gccttctact cctcaacctc ccatcctttc 3720
tctttcattc attgcagagg aggagaaagg ggacagggaa gtgtttgggg tgtggtcatc 3780
tggggggaag ggggagcatc ataatcaaga atttttttttg ttttcattct ttaaaatggg 3840
agcacttgta catgtggaaa tcactggctc ttacatgtgg cattgtttac atttgtgctt 3900
atatactacc tatcctttgt ggcttggaag tgtttgtcta gtatatttgt gtatatagta 3960
aatggtataa atgcatgagg atgtttcatg tatgtgctat gttttctcat gtatctctgc 4020
atatttttaa aattatattt agccctaact tggttgttca actgataaag ccattgctac 4080
tgttttcaaa aaaaaaagag attgaagcat taaattgtag aacaaaatgc tgaaaatatc 4140
actgccatca ggtagtactt gattctattt gtgtgatctg taacaaaagg cttgcaatcc 4200
atttattggt tcttaaaaac agacacccac tctacaagaa gttagaagtg cattatgttt 4260
ggactgtgat tactgtcaga tttgagataa acttctatgt aaacatcatt atagttcagt 4320
ctctagaaat ggctgatttt aattcacaga aatgtaattg atttacatgt tgacagtaaa 4380
tacaaaggta agccatggac tcttgtttct cggaacaggc atcccatcag gcacctttac 4440
tataccttttt actagaatag aatgtttgta tcctcttgag atgcctaaga tcccacatct 4500
ttgaagcaca aggttccacc atgcaaacac acaatggcaa tcccttatgt aacaagtcat 4560
tcctaggtaa ctgggatcat gtgtggtgaa agagtaagca aaacattgtt tgcagaaaag 4620
caagagtttt tagagaaaat gaataataaa ccttaggggc aatagaatag ttaaattgca 4680
tgcaggtctt gctaggccaa agactaaaaa ctgtccatgt aaacagttat agtagtggag 4740
aagcccacag ggtcccagag ctagatttca atcaccctgc agcactgatt agtacctact 4800
tcccgtaagg ctctctggtg agagatgagg ctgatgtaag aaaaattaga catgactaga 4860
gggtgagggg gcttatgtgt atgtttatat aagagaatag cagctcctag gtggtttgca 4920
```

-continued

```
caagggagga agaagagaaa tggcacaagt ctcctgtttt ctctgacttt agctgagttg 4980
aggggtacac aatcaaatgt ttgagcaaag taatagatat tagaggccca tgtcacaaaa 5040
aagctcatct gtaggagttt aagtttcagt gtccagttaa gcctatttga actctcatct 5100
ctaccactca aggctacagc tagtgagttt ggcatgggga gaagaaaagg actcatctgg 5160
agtgagtcgt gaggaactaa aacctgtctc tagcccatat accatgttgc attttctttt 5220
ctcatagggg gattatttcc aaaccagcag tcacaggaac atgctgcttt tagatttgct 5280
ttgtcgcaac tcacagagcc cccgaagctg ctcccccaga ttgatattgt gaacatcagc 5340
gacagctttg agatgaccta tagatgtaag taattgcttc tatttctgag atgtctttct 5400
gcgctagacc aatgaaagga gggcctgtgg gtaggtggtg gtgttgcaaa aatgacttca 5460
gttgccattc gtctttgtaa gagaaagccc tccaagaaaa atttctagag gcttctgagt 5520
gattccagca gttggcattt tagcccctgc aatgcttcat gtaatggatt tgctttttca 5580
ctgtcagcta actttaatgc cagcacgatg ggtgcttggg ttgactgcat cttccctacc 5640
ttgcagaggt tttctggcac agctgagaga gttttacaca tacgaatctt ctgagaggca 5700
tagaattaag ggtcctgagt ttgtgaaaat gtggtttaaa gtgcttaagg catttcctat 5760
ctacatgtta aatggacaga atgtagcttg ataagaaata atagctgaga agttgtacac 5820
atctggttct tcattttcgg aagtgaccaa taattaaaac ttggtgcctt ggtcatttta 5880
aaaatagctt gaggaaattg gttgtttaag gcacagtttg taggatggtc attgagcatc 5940
aaacagaaca aaggtggcct caagaagaag ggatagataa atctctgaca tctgaattga 6000
atgcattgta aaatgtgggc aacaaacacc attctgagtt ttcctggcaa ctaggaatga 6060
aaaggaagcc tgtgctcaca tgattggctt ttcatgacag atgaaagcat aaaaattaat 6120
caggaaacat attttccctt cagggattaa gctcaagtaa aaatttatgg cagggaaatg 6180
tgagctgaat tcacaagaac aatttgagac cccaaactgg attgaattgg cacgatagtc 6240
ttggtgtgtc actattgact tggtgacttc tgctgagctg tctctggtgg aagtcatgga 6300
ccatatttcc tttgtgtctt tctcatagtc ccactggtga gttctcaatg atttgaatag 6360
gctatgcttt gaagtctcaa aatgagaagt cagaattctt tctatcccaa agaccactcc 6420
taaaataatg ttgttacaaa ttccaagaac tataattata gcagatttca tttattgaga 6480
acttactgtg catcagaact atgataaata ctttatagtc atttatagtc acattcatta 6540
ccatgtatta agcactgact acagcccatg taatgcacta attgcttttt atgtgttagc 6600
tcatttaatc ctcacaggag ctttgcagag tactagacat tatcttcctt ttagagatga 6660
gaaaactgag gctacaacag attatataac ttgcccaagg ttactcagga agcaaatggt 6720
ggttttgaga cctgaaggtc catgttcctg gatactgtga cagatacact gattcttatg 6780
gtaccctaat caactagtgg gattacccaa gaaatgaaag ggaattttca gggtcttgta 6840
aggcagaggt ctaataaagt acctaaggag aaaaacttac agtgtttcaa actgtagcta 6900
tgatttgcac aggactggtc cattgaataa ataaaatagc aattcttcat tttggtaatg 6960
ctgaggttga aaatcttatc tactgtgtta ctcactaccc ttaaaaaaat agctgaagtt 7020
taattgctga attttagttc tatgaaacta tctttctggg aatctagaat aatactgagt 7080
agctattttg ctattagata acctttcttt actttttaat gtggctttga ttagggtctt 7140
tggaaggggc atttggttgg gggcatcagt gtacctataa atgtttaaac gcatatacat 7200
gtgctaattt atttcctgga gcagggctcc atagcttttg tcatacttta tagcttttgt 7260
attacttgca tagagaatca agaataaata gctggtgtgt gtattcactc atgctgctga 7320
```

-continued

```
gaaatatcta cagcaggttt tggttgaaag agatgtgaac tgctctccta gtagtgtcaa 7380
gatgttgact ggcacagcaa gaaaataaaa gacaaaaata ggagaaaagg ttctaaggca 7440
aaaggtggtg cttctgtctt gttatctcag caacctaaga cttgatctct aatagggtta 7500
atgactgttt attagggaga cagaaatatg atacagacaa tgttgttcat tttggtcaac 7560
aggcctggag tggatgaatc tgagttcttg aacttgatgc tgccatccat gaactagtgt 7620
acaggtttcc atgaattcct gtcttgttcg ttcagttaat tctttaagtg tttcttcaaa 7680
gctataaact gaaatagata ttggaaatac agagatgata aaatgccctt gctctcaggt 7740
agcttacagt ctagtgggaa acattgttat ggggattatc tgagaagcaa taatcttatt 7800
ttgtgcttag actttgtgtt tcttttcttt agctcccaga tcccaaaggg ggtactgggc 7860
aagttaggtg gaaatggtgg cctggctgga ggagcctctc ttaaatttca tgtaaggcta 7920
ggaatacttt agggctgtgt tcactgtggt ccattggttt gggaaaactt tacatctgtc 7980
ccaattttaa ttgagtaaaa aatgtcagtg ggagcaaagc agttttagga agaatgtact 8040
cattactgat acatggaaaa gcaagaaaag catcttattc agactaattt tctgtgctgt 8100
gtttttgaa atctgaatta gtagttgcct taaattaact gcccaataag tcttagatct 8160
agaaaatgac caaattttat ttgttttttt ttcataattt ttgctgtcat ttgatttttt 8220
ccctttgcat tttgctattc attgtccctc caccagaggg tggagaaggg aagggagagg 8280
aagtgtaatg ggacctgttc atgctagaca tgttagcagc aggggactaa aaatgaggag 8340
aggtggttat atggtaggga aggtggggaa gatagaagag gactatggct actactactg 8400
gccaaggtga gagtttggtg ccttcttcgt gttcaatctt tcttgcttcc ctggtctgcc 8460
attgttaaag agtaaagcca ttgaatcagc aacccaatgc cttgggatct cctttaagca 8520
cttttccaag cttacagggg tagagtttgg ggagattgtg catagagaag atatttactg 8580
atcagctacc cagcttattt tggtgccttt gtggtaagtg taaataaagg aataaatgaa 8640
atgctgattg agattattac tattagaggt ctgagtagca tagttgcagc ttaattctta 8700
ccttttaatt tattcaccta tttattcatt cattcattca gcaagtatat actgaatgcc 8760
tacttcatgc caaacactgg gccagacgct aggaatatag gggccaggaa agaaggcaca 8820
gcctctttcc ttgtggagct aacagtttag cccagaggtt cacaaacttc agtgcactta 8880
aaattcactc agggagcttg tttaaagcaa gactcatgat gaacttttta cttcttgaat 8940
caagatattc aagagtaggc cctggaggaa ttctatagca attattatgg ggattacact 9000
ttaagaatct ctttaatcta aaaagtcttc catcccttta gtaagcattt ttgagccctc 9060
aaccaaacct aggcatgaca taaagtgcta caaatgcaga caacagtaag ttgcattccc 9120
caccctggag tactttatcc atagtaagac attttctatc ctgtaaagag aaaattaaaa 9180
tgtaatgttg taagtgctat agcagcaatt tgtatggagt attgaagatt ccttgaagag 9240
tggagttttt ctctaggagg tggtgattga attgagcctc aacgataaat agggttatct 9300
atctgcagaa ggggtcacca aatatagcca tccacaagcc agttccagca cagagactga 9360
gttctgggcc catacactgt gtaagaacca tggaatttca cattagaact tggacatctt 9420
gtcttgacta atatttttaa atattaaaat atctggcaac actagggccc aggtctatgc 9480
agcctcaatt tgctgagatg ggacagagta aaccccatct acatggcctc tttcccaatc 9540
agcccattct tcccattttc tttacctgct ggctttggca agcattgagt ttgcaagccc 9600
tgattgatag cactgcaatg ttgtctgtgt tgtgtcttta taggttagct tcaccaccag 9660
aatataaact gctgtcagaa agaccatgta tatctatagt ttagtgttga gaacacttgg 9720
```

-continued

```
aaatgcctct aatacaaatg aataaatgtc tgtaggagtc agggaattac acagcataaa 9780
aatgttcaga gcctcaatga caataggtga aaggtagcaa ccctaactac agtgggatgc 9840
cctctgtcat ggacctactg gggaagccca ggggcttcct aacaagacat taggcactgg 9900
caacagagag atggccttag ctcttgcctg aacatggctc atcaacttca gagttgcaac 9960
acagatttgt ttttcttgac ctacacaatg ctttttcata tttggcataa aaatccagat 10020
ttctggcatc tttaaaaaaa aaacttaggg cattaagcaa ccctaggccc acattcctgc 10080
ttaacttcta ttttctagag ctgagaagtg ctgccctttt taaatacata aactcccaag 10140
ttaaccaaag tttccattac ttcctgtttg attgctagag taatcaaatt atgttgtttg 10200
ggcaggcctg taagtaggcc aatctactca tacctgattt atatcgtcag cattcatcat 10260
tttattattt tgttctaata atatctatta cttaccctgt caaaaataat aaaagacaca 10320
aaagatgtat aactcctact ctcaaaaaaa gtagtgtgta tacagtaatg aagagaatgg 10380
tggctgatgg tgggataaac aagaattatt ttgaagacct actatgtgcc aaatactttg 10440
caggtgttgt cttaagtttt ataactgtct tgaaaggtga ttatccccat ttcattgatg 10500
atggtactga gactgagaga gattgtgtct tctttatatt atgcaacaaa taaaaaccta 10560
agctagtatt taaagccagt ttgggggggct ccaaaactca atgagcattc tccttttaaa 10620
gatctatgaa tatggccagg ggcagtggct cacacttgta atcccagcac tttggaaggc 10680
cgaggtgggc agatcatgag gtcaggagat tgacaccatc ctggctaata cagtgaaacc 10740
ccatctctac taaaaataca aaaacttagc tgggcgtggt ggcacgcacc tgtagtccca 10800
gctactcagg aggctgaggc aggagaattg cttgaactca ggaggcagag gttgcattga 10860
gccaagatca cgccactgca ctccagcctg gcaacagagc gagaatttgt ctcaaaaaaa 10920
aaaaaaaaaa aaaaaaaaaa cctatgaata tatggacaga gaaaagtacc atagcagtga 10980
aatagcccaa cggtagaagt gtcacagtgg aatttatgat tcaagcttaa gagctaagtc 11040
ttccaaggca gaagctatga ctgtggatga tgaaaacttc ttggggaagg tggaacttta 11100
gcaggcatta aagggtggag cagattttgg ttgtggagtg ggaggagggt attttgagtg 11160
ggtaaagtca caatattcct cctcgcctcc cctcaaccac tgctgcatat gcttgttacc 11220
atgtggtgga gatttgggag tttgcctcct gcaccacact atgttctcag ctccatggca 11280
gatgtctaca tttctctggt taatgttaca gtctgaagtt ggctcctcaa tcttcacccg 11340
tgcccttaca ttaaggcaca caagtgttga catttgtctg tggttgactc ttggctctta 11400
ttataatatt gataatcatc agcttttatg gatagaaaaa tccttgtaaa catttctttc 11460
cctgactagt ttgaagatcc tgctgggatg agtgagctta ctgctctcct ctcagccact 11520
caggataaag tgatcatata gcacatttgg aaaactggta agcttcatgt atttgttcat 11580
tcattcattc atccgaaacc cttttattat caccttctat ggggatatgt actgtcactg 11640
ccccactcca tacctttgta gacagcatta gttgattaca gaattttttc ccactgaatc 11700
tacacgtggc ctcaaattgg tgacagctga tgcaagagat gaaatccatt tttcattaca 11760
aggcattgca ctagaaattg agaaaaataa aatgcattag gcattgattt tcctcttaag 11820
gggctcaggt tcttataaag gaaataggca taaaccaaat ctgcctctct ttctctctct 11880
ctctctctct ctctctcccc ctcttacata cacacacaca cacacacaca cacacacaca 11940
cacacacaca cattcagagg aaggaaggaa aacctttagt tggagggatt taggtttcat 12000
aaaacaagga catttgagtt gaatttggaa agataggtag gatgtagatg ggaaaatata 12060
tatgtatata tttgtataca cacacacaca ccccacacac cttcctgtaa tggcaggttt 12120
```

-continued

```
gatgcagtaa atagcatact gagttgagat ttgaagacat ggattcaaat gctggactac 12180
cttcttgaat cgtttaggta taaccttgga gaaacatccc ctcccccaag cttatttata 12240
aaatgaagct catggtctct gagagtcctt ctggggctgt atttctatgc tggcagcata 12300
tggaaaacac cagagatata tgattaatag aagttctcta cctttggcta gcaagaggat 12360
ccctaaacaa gctaagtgtc taaggaaagc tctagacttc ccttccacca acttgcacat 12420
tcagggcgca ttctgtatgc aaatgctgaa gcattatgcc tactttgggg cctcagatga 12480
attcattcaa tatttaacaa atatttatgg agtgcttact attgtgaaca aaactagaaa 12540
gcagccctgt gctcatggag ctcaccagct aataaaggag gctgccatta gatgatcaca 12600
tgaatgagtg tataggttgt aataaacaat ctgaaagaaa gggccatgat tctatgaaag 12660
catatacaaa ggaaccagct cgtgcaggag gatgaatagg tgcttgagct gaggactgaa 12720
ggctttggtg atgcagtgat gggaacagga ggagtgtttg agaagcttcc tgggcagagg 12780
cctggccagg ccttgtaggc tctgttatgg attttgatct ttagctcaaa cactaaagaa 12840
cccatggaag ggttttaagc agagaagtgc cgtgtttaga tttctgtttt ctcatcagaa 12900
atcagatgct tgatagtact ttgccaaatt cacatttgct gaagacgtct ggcttgtgtt 12960
tcaatggcct tgtttcttta cttccatctc cagtttggga tggagtctgg cagatgggca 13020
ggaggatggg gacagaggcc aggggaaagg gaagctgatg acttggttta ggggtgcgtt 13080
gtcatggtat gtggctctct gtgtgcccat gggcattcct ggagattgga ggctgatcca 13140
gtgcagtgcc tggagaactg gtgaggctgt gtggaggcag ggattcattc agagtcctca 13200
tttattttaa caaggaagac atacatagca ctgaagctca gcctctgttc caatcagaca 13260
actcagtggt cttcaaattc acactgccat ttccttcact tacacttaca aactgctcct 13320
tccatactgc tctgctgaaa ttctgtcctt ctggtcagcc ctagctctta ttttaccttc 13380
ttcactgagc ctttttctc tttcatattc acatgctctt ctgcccttca gctgtttta 13440
ccatctccct agcaatggtc acgcttatcc ccaggtttta ctcaccttgt cacttgaaca 13500
cgtgtcttac ctgcccaact ggactaagca atgtgaggtc aatgaccttg tttactttag 13560
cttcccatca cagtctccac cacagtatag tgttcagtgg tgctagatga atgaaagaat 13620
agatggcagt gacaagaata agcctgaatc attgctgctt agggtaatgc ttttgatatt 13680
atgagttttg agagttccaa caggctgtgc tgtaaatacc tatggatggt tattactgtg 13740
tagctccaaa gttatggggg tgaaaatcag gtgtaagtcc aattgaaagc tcattttagc 13800
tcccgctgga ctattgtcat gaggggtcct aaataaggta taaggttcca tcttctaaat 13860
aaagaatttc tgattcaagc cctgggtttg ccattgatgt atgagccttg tatgcatctt 13920
acgactttgg tgtgtcccag cctgctgtcc agaaagcaca ggggagccca gggccatggg 13980
aggtccaggt tgaggaggca ggcaaaactg gggcaaatga ggcagttgga ggctaatgaa 14040
attgataccc tatggttagg cgtgtttcca tgtgttcatt gtttggaacc tctaggatga 14100
aaataaagtt tgagaatagc ctttagtttg tctacaaaag taatatatac attacagaaa 14160
gctataggaa cagagacagc aaacacaata aaacttgtat aattatagta ctaaggatac 14220
attttccatc ctttttgaa cctaacaatt taaacattaa tagatttatc ttactgtctt 14280
ataacatgat tttttgcata ttacaacctt taggctactt ttattattgc acattcattt 14340
ttaatggttt cataaaagcc cactgtacat atgtacccta atttatttaa gctgtctcct 14400
tttatgggat atctagttta tttcccttttt tttcttaaaa acagtgctgt gatatttctc 14460
tcaataaaat tttaatcatt tgtacatatt ttgttgtgat tttaagggaa ctataaaccc 14520
```

-continued agtagaacaa tttccaatga aattgaataa aatttctagt atgtgcagaa cttgagataa 14580
cttgtttaat gtgagttctg acattgactt gctgtgtaac cttgaaaagc ttttatatcc 14640
agtttagttt ccagatgtat aatatggggt gctaatacct gattctcaaa cttattagaa 14700
caggcaagtg ccattatttg tatgaaagag ctttgaaaaa tcaaacatgc taggcaaacg 14760
cagggtaata taattaacca ggcttcttat ctattagcat aaatgcacat aagtaaaatg 14820
taactaatta atttttagtg ttttcctagg aaggtgttca ttacccataa atgaatctat 14880
tttatggata gggaaaattg aaatcttaag gctaagttta tccaagatct aaatatatag 14940
ctatgctaag tctgaaagca tttcttttca tttatgattc aatccatgaa aatggacgaa 15000
atatgtggat cataagagtt tctttggctt aagaaattat tgtttataga aataaggggg 15060
aaagcccatt tgagcagtaa gcagtcagga ctgtttgtgg caagtgacag aaacccaact 15120
aactggatag ttttaacttc aggtatagcc aaattcaagg gcttgattga tgtcatcagg 15180
actgagacat gccctctaga tttttatgct tagcttttct ctaaactggc tttactctca 15240
ggcatagata tgtcatatat cagatcccag cactggcagc cttcacctgc ccagctacaa 15300
gtccagtgga aaggaaactt ctcttttctc atcagttcca caaaagtcct gggcctgatg 15360
tcattggata aaacttagga cacatgctca tttctgaata tgacacagtg gccaggatat 15420
tgtagtcttt tgcttgacat gggcctagtg aaatcatcat ttttagagct tggggtagtg 15480
agaagaacca aaagattgtg gatttaagcc agcccaccaa aaccatacgg acatggggga 15540
ggaataattc cctcaaaggg aatcaggatg ctattaccaa aagaatggag attgaatgct 15600
tgagaggcaa aatagatata tatatatatt tttgtctatt aagcatatat atatatacac 15660
tatctatata tagatgtaaa tgtatttatt gtctatttta tgtatttatt gtaaataaat 15720
acatttactc tctctatata tatattctat ctatatatag atgtccccca ttgcacatct 15780
tttcagaaaa gaaaattcag acaggctgga gctgaaccaa tgcagacaaa aagtcaacat 15840
gctaaagtca gaagagccac caatgagaca agcacataca agggattctg gtgggtaagt 15900
caagatcaga agtcaggaca ggcaaaaggt ctgaaattca ggcttctgag ttaatcaaag 15960
ctgtaggggt ctttggtaat ccttgtccag ccacgagcaa acctgtgttc acagaacagt 16020
tagaaagtgc tagccattca cccacataga agcgactggg aggtggtctc tccaggccac 16080
tctgataata agttgaggtt gtcggctgta aaatgtttgg tgatcctgag gcaccaatac 16140
tctgtcccag tgaccaggac atttcctgct ctactcaaac actcaagcta ttgtgcacaa 16200
actctttaac agtcccagtt ggaatcttgg ctgcaaatct gatgagccca caccaccaga 16260
tggtaggttc tcctaattgg ttccatcccc tctagttttt ggcaggaacg aaaccttccc 16320
tatacctgaa gaggggacag ggagagccag gatcaaatga aggaggcttt aacctctgtt 16380
aaacaagcag agatctcaag ctggctcctg tccaaggcaa acagggcagt atggttcttt 16440
tacataggtc atggatttac aggggactga tatcctaaga ctaacactga tgaggcacaa 16500
gactgtaatg attgaaaagt ggtttagcta caaaggtcaa ctgatttggg ggaaggtgca 16560
cttgtttatt caataattga tatttgtgga gcatcgtggt agatgagatt attatttggc 16620
aattatttct ctctccctca aactccttgg gaaaaaaata taacttcctg cttcattaat 16680
gtcacatttg gtcatttgac atgctctggc aacttagata ttagtagata tgtttgaagc 16740
agagattatg agaagaacat gccccagaga gcctgctcgt ctcataggaa aggtaaatac 16800
agtaagtaga agtgtcccag tcaacccaca gcccacagac taaagtttga agcagagcta 16860
tcccagctga cctgaaaatc tgtgagcatt gtaggaaatg ctcaatgtta tataccactg 16920

-continued aaattggaaa tggtttgttt tgcagcaata gctggccaat agaagcaacc agcgtgtgtt 16980
ccacactttg ctaggcactg agggaacatt ggaaatgaca gacatagtcc tggtctccat 17040
ggagcactat tgtagctagg aagatagaca atgaatacat ttacaaataa aatatatata 17100
gagagatcat tactagggtc ataaagaaaa taggatgtag tgacatcacc actatggtag 17160
agaagaacac ctttaaagta agtggtcaaa gaaggcattt caaaggaggt gacttctgag 17220
ctcagatata aaagttggaa gagagccaaa tgagagtaaa ttcccctgtg gaatgtcgaa 17280
atccagcccc atgggcaact tggattgaga atcttggtct aggcagagga gaatgaggtg 17340
ccctggaaaa atctcctgca aactaggtca ctcacttgtc ttagggcaga tactagcttc 17400
tctctaccac atcacatgtg caagtcaagg gctggcagat cacttgctgc caagactaga 17460
tggtctcagg cattggaagc cactgagcat agcaaggcag agagggggag gtatgctagg 17520
gcattcctaa ccatgaggtg atggaattgg ctatacttct tggcttggct ccagaatact 17580
caagagttgt tgcttattag gatggcaaga aggggtgtgt gtgtgtgtgt gtgtgtgtgt 17640
gtgtgtgtgt gtgtgttcat acatatattc attctttcac agaggaggaa aatgaactag 17700
atggcttcta gatccctttc caagtgtgtg attataaaaa ggatgctgag atttaaatta 17760
tgtgtgaagg aaatgttaaa ttgaagaact tcatcttagc tctgtgccaa gctccatttg 17820
ttaattgagg tggttaatta gaaaggagtc tcccttgagc aagcaggata agctccagca 17880
tccctaatct atctggtaaa ggctatagag gtgtcacacc tacaagggag aacaaagaac 17940
atctaatgca agccctctgt ttaatcttca ctccagacac tgaaaagcaa gaatgttggg 18000
ggacaggaag ctcacagcgc ccgcatggaa tttagactcc aagtagttta ttagctttgg 18060
gaaaattatt taacttacac tgcacttact agctcttctt ccttactcca agatcactct 18120
gaatacttta aaatatggtt ggacatggtg gctcacacct gtaatcccag cactttggga 18180
ggccaaggcg ggcagatcac ttgaggccag gagttcgaga tcagtcgggc caacatggca 18240
aaaccctgcc tctactaaaa aatacaaaaa atagctggca tggtggcaca cacctggaat 18300
ctcagctact tgggaggctg aggcacgaga attacttgaa tatgggaggt ggaggttgca 18360
gtgagccaag atcaagccac tgcactccag cctgggagaa agagtgagac tccttctcaa 18420
aaaataataa taataaataa ataaaagatg gtttctatgt tgatgtaatg aaccaagtat 18480
tctagggtta tggaagaatt tctcatcagc aaatccagct acttatgtct ttgtttcttg 18540
cagcctaggg ctgatggaag tcttcacacc ccttccaaga acccccacaa acattccacc 18600
acccccacat accccctgcaa gaatgaagct ttctggggct atgttctcct caacaccacc 18660
acaggggtcc tctctcactc cttctgctcc ttttttctca ctagcgtcta ccctttcccc 18720
aggattccag cctatacatt ctgagttcaa catatcaaaa ccagaacttg gcatccttcc 18780
tgccaaactc attgctcttt tctcacttta tttctgttca atcattcagc cttaaaatgt 18840
gggtgtctgg tttcaacttc tccatataat caatattatg tgttgatttc accaccacta 18900
tgactcgagt ctatccccat tttcttcttt tcccactgga ttatggcttt tgccttctga 18960
ctgtcatctt catgatataa tccacttaca ggtggcggat caatttattg aagactattt 19020
ctgatcatca agcttcttgt ctcaaaaaaa tatcagtggc ttcccatctt attttaagtt 19080
caaactcaga ctaaaatatg agtctctcca taatgggtct ctgcctgcct tcctttttgag 19140 acttacctaa accctacact ctatgttcca gccaaactag actacctagt gttgccacaa 19200
acatgcctct cagtctttca ctgctttggt catactactg attccatctg aaatagtctc 19260
taccacattg agcacccact ctctactaaa ccctggagat accgcagaaa acaaaaccag 19320

-continued caaactccct gtacccttgg ggtttacgtc ctgggaaaca aatacatata atgatttcaa 19380
atactagtta aatgatacaa acatagccaa atagagtcat gggacagaga gtgagctgta 19440
gtgctacatt agatgggtgg tcagggagga caggcatcac ctgaagagat gatattttaa 19500
ctgagccttg ttgcaatcca tagaactttc tgcagtgttg ggagacattc tatatctgtg 19560
ctgtctaata tgtaggcact agcaacatct gcccctatta cacattagaa atgtagtgag 19620
catgactgag gaaccaaatc tttcatgtaa tttaattttt attaattgta atttaaaaag 19680
tcacatgtgg ctagtgactg tcatattaga cagtgctaat ctagattcta gaatatttca 19740
gacaagaaaa aaaaaacagt aagcataaag gctttaaatg agagtgagtg tatattcaaa 19800
gaacagaaag aaggccagtg gagctaaagc atgctgagga aagagacagg gtattttgta 19860
agtcatgata aggaattgac atggagttta aatgcaataa aatcactaat ggattttaag 19920
cttgggagtg tagtgatctg atttaatttt caaaagatta ctgtggctcc tctgtggagg 19980
aaggagaagt gataaattga catgaaaaca gtatgtgtca gtcagttttt gctgcataac 20040
aaataacatc aaaatctcag tggtttataa caaaagcttt tttaaaaaac aatcacatct 20100
gcaggttgca ggctgcagtc tgtaggtcaa ccatgattct gattacactg taggataggt 20160
taggctaaac tccaggaggg ttcaggtctg cccgatgtgt ctttgtttgg gtattgaggg 20220
tcaaggggca gcagctacaa aaagacctgc tctccttttc caggagcaca agaggctaag 20280
ctttatcatg caaatatatt taaagcttct gctcatgtca tgttctctaa tattccattg 20340
gttcaagcaa ggtatgcagc taaacctaat gctcatgggg cagaaaacac actctgtctt 20400
ctaaaaggaa ttacaaagtc atatgacaaa aggcatagat gtgtaatttt ataacaatat 20460
ccaatgtaac acagagggga ctggggaggt tcctacaata gtctggatga cagatggtgg 20520
tggcttggaa aaggtgttag tagaagagat gaaagaggta agattcataa agtattttga 20580
agaaagtatg cacaggattt agtgagagaa tgaaagtaaa gtatggggta aagaaaacag 20640
accattttcc aaagtgcttc tcagatgcta ccacagccct gtgaagctgc ttctccctcc 20700
ctcaattgca gctgatttcc ttttctctta tctcactggc tctctttttt gtgctgcttt 20760
tattggccca tttcaacttt ctaccttctg ttcttgagag gttttatcta ttgttaagac 20820
tctgaggttt tgagggcaag agaataaaat tatttgtatt tgcaacccaa ctgcctaggg 20880
aataggctca ataaatattt ccagggcaat acaatggtta agagcaagga ctttggagat 20940
atcatcctca ttttggatct tgtgtgatct ttataattga cttaacctct caaagccttg 21000
gtttttattt ataaagtggc agtaatcata cactcctttt acagttgtgc agattgaagg 21060
agatcaactt ggaaagtgct tagcataagg cctggcatag agtaagtacc cgataaatga 21120
gagctattat tgtttgttca atttaattgt ttgtgatgac aagcttcttt ggaaatgccc 21180
tccagagtct tcatcagaaa attcaatgtt cttgttgaaa tgaggggcac agagaataaa 21240
aacactctgg atgggatttt gtaatttagt aaggagatct ctagatctaa agtctctttg 21300
atctgaaaat gacagcaaca acaaaacccc aaaatagagc cactttgcta cttgtttcct 21360
tttaccatct gccaagatgg ttctttttag ttctcgaggt cttgcttgga gtcagctgcc 21420
ttaaaataat aaaataaaat ttaaatctgg tcctgcactt atttgggagc gagaagacaa 21480
actgctttaa ctaaatatat agctagttgc tgctggagtg aaatataggg caatgttgac 21540
taaagtgttt gaggaatgaa ctgctctggg aaagtgaatt ttaggataaa actgaggatt 21600
aatcagaacc tgactttttt tttggtaaca tttgtaattg agacagtttc cgacatgtac 21660
ttttcaagct ttcttgcctt agtgagatga ctttgttgat cctagtttaa agttgccttg 21720

-continued atcataagta tcctgtaaat ccagcgggca ttgtgaacag agattgtctg cgattgcaga 21780
tgagaacaga aaggttgggg gtgaaatcgc tgaaaaagag tgcatgaaag aggtgaaaag 21840
ttaacatgat gagtttggat atctgcagga gggtttctcc ggagctctgc aagatacatt 21900
tggaaaaata ggctgggttc agactagaga aggctttgaa ggtcaggaat aagtatttga 21960
gagacaaaat aatatgttta agttgcattg ttgatattcc aaaggtcttg tttataagca 22020
aataaaggat gattttattt agcaagtact agaataatcc tcagcaaaca taaagttacc 22080
tgacatcaaa tgatgcagaa tatccacatt tctacacaat gaactctaca gggttcattt 22140
ttaaagtgtt ttaggagctc atttagtcag tgcttcccat tagaactgtg atgttctgag 22200
gatattaata ggttatttgg ggagcattgg gggtgatgag ggaaggttgc atggttataa 22260
atttagtcat gctgattaag caaagtataa ggggtgctgt gttttaggat tttgaagacc 22320
ctttaaaatg ctaatgtgtc ttgttaattt ctaaaaaaga ggatacagta tgtattttcc 22380
aaacttagtc cctctgtagc ccacagaaca ggcgggtctg attgcttggt gagtgacaga 22440
tcaatgacca caaccaagga gtattttaaa aagggatttt attacttgca acaagtaagg 22500
atggctgaca ctgagcatag ttcccaaagc agtgcctccc caaataaagg tgaacccagg 22560
gcttttattg acctggttgg ctgaatcatt gtatgtagag gtgaagtaaa ggcagtgcag 22620
gtgcaggtgc agtcacagat catgctttta tacttgtggc atgtatagga aatgttgaat 22680
aagctcatct ctggatgggg attttagtac gttaataaag ggagttcacc aaagttcatc 22740
tccaactcag gcatctcaac cagtttttgt tttttgggct tcttcctgga attttttttg 22800
aaacaagaac tcaaggtgca acagttacaa gtgtgtaatt tctcattgtg tgtacccaac 22860
aatctgggga ccctgagtta taactctttt tgctgaattt gtgaataatg tcttgtgatg 22920
tttaatcctg ttttacatat ggtgaaacta aggctgagag catacacagg gatttatctg 22980
cagtcaggta gcagccaggt cacgatgcta acacagaact tttgaccgtc acccaaggcc 23040
tcctactctt ccaggctccc tgtcaatttt tggagccagt cctctaaaca gttttaccca 23100
gaacaaggaa ttgccggtga tttcagaaag aactggcaga ctcgggggag gcacttgcca 23160
aattggctca ggctggcctt gctgccatgc ttcttttcct cgttcctgca aagccagttc 23220
taggtaacct acctgcagat gtctaccctg aaataacacc cagcctctgt tacactgctg 23280
ttacacacaa acaaacaaag caaatctgct gcaaaaagag gcaggttgaa ataaattatt 23340
tttagtgcaa catataacgt caatgtcaaa aatacgaaag aggcaggttg catagggagg 23400
ctgaggagga gatgctgaga ttcagtgtgg aaggtgacaa gataagagga ggaaagtttg 23460
ccctggccct gaggcagcaa aattaatttt gccccaggcc tttaactgag ggaaccaaat 23520
ctatttatta cagaaattat aaagagattt ggtgactgac cccactttac cttgagtgat 23580
tggactttac acgcaggtaa taggaataat agtgtcatat ttatagagca tgttcaggtg 23640
gttgaggata tggaaagcct ttccagtaag gaatggttgg aggctctgag aaggaaaaac 23700
ttaggcttgg atttcatcat caaacttcta aacaaacata tttggaaagg tactgcattt 23760
tctatggccc aagaggccaa aacacagaca aagtgagtac aacatttggt ctggcagatt 23820
ttgactccac acgacagagc ccattctaag tgtgtggact ggctagcagt ggcgagggtt 23880
ccctttctct agtctgcaaa cctcccaatc aacatggctg ttagaaacct ggtccttttg 23940
cagaattgct ttaccacttc taccttgatg acccagtgcc tgtgatacca ccgttagaaa 24000
gtcatctaat tgcgtttaaa cttgttctct ccagcatccg ttgaatagca aagacaaatc 24060
cttctgacca tagttctaat tctgtgggct ggcactatgg atttaattgt gccctcccaa 24120

-continued

```
aatccgtttg ttaaagccct aacctccagc atgatggtag tgggtttagc tgtcgtcatg 24180
aggatgtcat cctcataatg gattaatact ctataagaga caccagaata cttgctcttt 24240
ctctttttct gtgcacatgc accaaagtaa ggtcatgaga acacacagca agatggcggc 24300
cattggcaag tcaggaagag aacctcacca tagtggcacc atgatctcgc acttccagtt 24360
tccagaactg tgaaaaaaga aatttttgtt gtttaagtca ccattccata gtatttggtt 24420
atggcatcct gagctgacta acaccactgg taattaaggt gtttcttcca tgaaaaatga 24480
aatgatggtc aataggaagc aaacagaagc ttaagcagaa gggcagaaag gagtgcattt 24540
gggaaccaga gggagtccta tagagactag acctgggatt ttgacagttc tgctgagggc 24600
tggccctgtg cccagcctcc ttccacttct cttcatctca ctagaccaag aaaatatgca 24660
catctgttat ccacaaatac tctgaattcc cccgccaacg cagatccccg ggaaaaccta 24720
acacaagcag aacagtggag gagatgcacg gggtatttgg tgtttctcag gaaaaaggct 24780
tgatttttg acaccctcta tcttggtctc ttaatttgtc ctgagtcagt gagccacagt 24840
gaagtccaga gaaaaaaatg gaaataggag aatcgggctt aaacctcagt tttgtcgctg 24900
attaacctgt gatcttgggc aacccactga tctgttcttt gtttcagttt ccctccatga 24960
ccctgagtac tttaatagcc tctattctcc catgtatctc tgttgaacag atcataaaga 25020
gtagtgatta tgaatccaga ctttactgtt actgtcaaat atcacattaa tttcctcagc 25080
cactttacac ctgtgcaacc tgaggcaaaa ttttgtaata tctctgtttc agtttttata 25140
gctgtcaaat ggggttaata acaatcccta tcacaagcag tctttacagg catggaatga 25200
aaaattgctt gtgaaatgct gagtgtaagg cctattatat tcagtaacta ttacctctat 25260
tttggttcaa caccattttg cagtctcccc caaacaccct gctgcaacac acctctaagc 25320
cttggctatg ctggcctaaa aaacttctag acacccttga tgacccaaat gaaaatcttc 25380
tgaacccaag gaatgctttc ctggctgtgt aggtggcaag catcacactc tcaagggagt 25440
aaaactgtgc ctttctgcaa ccattattgc ccataaccca tcatgttgtg atgcgttttt 25500
tacaagattg tcttttgttg tctatgcttt tggggttata tgcaagaaat cattatccag 25560
accaatgtca catggttttt cccctatgtt tttctccagt cgttttacaa tttcaggact 25620
tacatttaag tatttaattc attttgagtt gattcttgtg taagggatga gaaaacggtc 25680
caattcaatt cttctgcatg tgaatagcca gcttttccgg caccatttat tgaagagact 25740
atccttttcc ccttgtgtgc tcttggcacc tttgtagaaa atcagttgat catagacttg 25800
taggtttatt tctcagctgt ctatcctatt ccattggtct acatatctgc ttttatgcta 25860
gtaccatgct gttttgatta gtatagcttt gcaatatatt ttgaaatcag atcatgtgat 25920
gcctgcagct ttgtttttgc ttaaaattgc tttggctgtt tgggattttt ttgtagttcc 25980
atacaaattt tgggattttt ttctatttct gtgaagaatg atgttggaat tttgacagag 26040
attgcattta acaagaaaat taataaccct attaaaaatg ggcaaaagac ttgaatggac 26100
attcctcaaa agaaagcata caataatgga caacagatat ataaaaaaat gttccacatc 26160
attaatcatc aggaaaatgc aaattaaaac cacagcataa tatcacctca gacctcttag 26220
aatggtatta tcaaaaagat gaaaaaaagc aaatgctggt aaggatgtga aaagaaaagg 26280
aaacccttgt atactgttgg aaatcatgta aattattgcc ctcagtttac aaaacaatat 26340
gaaggtttct caaaaaatta aaagcagaat tatcatgatt caaccaattg aatcatggta 26400
aacatctaaa gttctgggta tatatctaaa gaaattgaaa taaatatgtc aaagaaatat 26460
ctgcactctc atgttcattg cagcattatt tacaatagtt aagatatgga aacaacctaa 26520
```

-continued atgcccatca acagatgcta ggataaaaaa atgtggtatt gctacataat gaaatactac 26580
tgagacttta aaaaaagaag aaaattctgt tatctgtgac aacatgaata taactagagg 26640
acatcatgct aagttaaata atccaaccac agaatgacaa atattgcatg atctcattca 26700
tatgtgaaat ctaaaagcat caaactcgta gaagtaaaga gtagaatggt ggttgcagag 26760
gctggggact tggggcatat gttggtcaaa gggcacaagg tttcagttag acagaaggaa 26820
taagttctgg tgagatattg cacaacaaag tgactgtagt taataatata ttatgtattt 26880
caaaatttct aaaagactgg attttaaatg ttctcaccac aaagaaatga caagtatgtg 26940
aggttatgaa tacgttaatt agcctgattt gttcatgcca caatgtatat gtctatcaaa 27000
agatcacact gtaacacaga aatagatatt atttgtcaat taaaaacaaa ttttttaaaa 27060
aggctatttt tcttgctgaa tcccacatgt ctctggggct agggtagatg tcttttttaa 27120
ccagattgtg tccagcttag tccggtgttc aataagcatt aagtgtctga agggtggtca 27180
atggacaaac agatgaaggg ttgcatagat taatagaagt ctaccatatc taggctggga 27240
gtggtggctc acacctgtaa tcccagcact ttgggaggcc aaggtgggcg gatcatgagg 27300
tcaggagatt gagaccatcc tggctaacac ggtgaaaccc tgtctctact aaaaatacaa 27360
aaaatcagcc tgacgtggtg gcgggcgcct gtaatcccag ctgctcagaa ggctaaggca 27420
ggagaatcac ttgaacctgg gaggcagaga tttcagtgag ccaagatcac accactgcac 27480
tccagcctgg gcaaccgagt gagactctgt ctcaaaaaaa taaaaataag aaatctacca 27540
tatctacttc tcaggcataa atatgataac tatttccttt aatttcccat tggataaata 27600
actgtttata aacatctagt tgccagaccc atgcttggag tctcagggct aaaagaaatg 27660
ctccccattt gctctatgtg ctagtcacat caatccccact tgatccccac agcacccttt 27720
gggggaaaga gagtagttga taatctgatt ttaccaatga acaaaggctc agaaaagact 27780
agttgatcct aaaaacacca cacagcattc taatgttgta aaaatacctg gatttgagtc 27840
ccctgtacac tgatgccttg tggtgtggca ttggctcaga tgcttccctc ctctgggatg 27900
tggactggcc tctgaggtct ctttaacctc tggaatcatg tgagctggag cacctgttgg 27960
ctggggagac aaaaggctgc tgcgtccaga tctcccttca cgaggaagaa atgtgtctgc 28020
acttttcata tcaaagcact tgggcagcat gggggcgtat tgtgatgagg ctgatggatc 28080
ctccctgaac tggtgcctca gcgttcccat gccaactgag ggaaggaaaa gaaaaaaagg 28140
aaaaacaaaa atcaaacacg aaaactgagc ttgatctaga gctgaagaaa aatattctac 28200
tgatggcaac attcatggcc gtattatgaa gaaaaacaaa ttcataaaaa cctcagcttg 28260
gccttaatgg ttggatctta agatgagtga caaatgacga aatattgggt atgagagaga 28320
ggcaggaggt gggaggagag caggccctgc aatcagaatc acttatttgt aacatccatt 28380
cacgaataca ttgccctcag ccacgcagga aacccacaca ggcctagagg atgctctctg 28440
ctttttttcgt ggtcctgcca ttcccaccag tacccagagg cccgaaccag cgaggagaaa 28500
acattcactc tttctctgaa tattcaattg aacttgtttt cagtttcctg acagcatcca 28560
gatccccaga gtgcctgcat ggctttattt tttcatccac cgcctgctga ctggtccctc 28620
tcttaatacc cctcctcccc cagggcttgc ttcttcctgt tttgtgggga gcagaacatt 28680
tgagcttcca ggggtagtaa ccactagtgc tggtaagcac agctttggaa atcaggggag 28740
ggaccctcaa agaaccatgg aaagtcccct gggccctcag aaagggaggg atcaaattaa 28800
gtaagggaaa cagacatgag atatgggcag atgggaagct aagtagctgt ggcagctcct 28860
tataaagaga tcacagctgg agatgcgttc actaatccca cagaataatc ctctgtttct 28920

-continued ctttcctgaa cccccacatc tagttcatca gcaagtctgt cagtgctagt tacaaaatat 28980
attttgaatc cacacacttt tttcaaaaaa aatctctacc ataaccccgt atccctcaca 29040
ctgtgatctt tttcccatat cactacatta acctcctaac ctgtcttctt gcctccttcc 29100
agacaatgtt ccacctggag gctaaagtga ctttttaaac ctattgagct gaacattcca 29160
ttcctctgct taagtaaatg tagactccct tccttggcct acaaggccct ccatgaacct 29220
gtccctccct aaccttacct cttgcccctc tctcatgtaa ctggatttca gccttccagg 29280
ccttccttca gttccttaaa caggccaagc tgccagggcc tttgcactgg ctgttccctt 29340
tgcctgggat gccgttaaat ctcatcatgg ctggctctag ttcactattc aggtcccaat 29400
tcccacgtta ctttctcaga gagtgttccc tgaacactta atctaaagta aatttctaat 29460
tgccctctct tccagcactt caacatcctt caaagcattt tttttaaata gcccacaggt 29520
gctactaaac tttgaagctt ttttttata attagtaccc attttgccta cttacttgta 29580
ttatctgatg tcttttttta cctgctcagt gtaagcgcca caagaaaagg atctgcttct 29640
tgttccttgt atcctgtgtc tagtctgggg ttagcacaga ctaagtgctt agtagacatt 29700
tatcaagtaa ccacataaat gaatgaattt ctgaagtggc tatttctttc tacctggatt 29760
tgagctcagc cctggggata cagacatgaa aaatacacag ccactactct gaagctgctc 29820
atggcctaat gagggaaact gagaagtcag tagtttcagg attaaaagcc agtagtttca 29880
ggattaaaag tatgataatg tatattatta atcatgtgta tacatgtaca ataatagtaa 29940
tagtggccaa acttgagcca ttatgtgctc agcactgtac aaatattatg caagtatttt 30000
ttttcatata attgccacaa taaacttatg agttagtatt atcacattta aactacataa 30060
aaatgcattt ggcagatgca gaaatggaga tactgcgagg ttcaaataac tgggccatgg 30120
ggacagttag taagtggctg agtgaattca gcctggcatc gtgctccatg tcagagccag 30180
tgctctgaag cactagatca gtgattctca aaagatgacc gtcctggact ggtagagtca 30240
gcatcacatg gcagcctgtt agaaatgcca gttcaaggcc aggcacggtg gcttacgcct 30300
gtaatcccag cactttggga ggccgaggtg ggcagatcac aaggtcagga gatcgagacc 30360
atcctggcta acaccgtgaa accccgtctc taccaaaaat acaaaaaatt agccgggcat 30420
gatggcacgc acctgtagtc cagctcctca ggaggctgag gcaggagaat cgctggaatc 30480
gggaggtggc agctgcagtg agccaagatc acgccactgc actccagcct ggacgacaga 30540
gcgagactcc atctcaaaaa aaaaggaaag aaaagaaatg ccaattcgag ggtctcaggc 30600
cggacctcct gaatcagaaa ctttggagtt ggggctcagc actctgtttt aacaggcccc 30660
gcagatgatt ctgaagatgc tcaccaaagt ttgacaacca ctacctattg aatgacttaa 30720
ttttatggga tactagatca gactagatca gagtctgaag tttttctgta actcagttct 30780
catcttaacg ctgtgagtgt agattgctct caatccacgg ctgaagaagc cagattgtga 30840
ctgaataaag ccagttaccc tgcctgaccc tggctccagg acctgcagca tgtaaaacat 30900
catccaggag tgcagcccct gtgaagacag ctgacctgaa gggcatggag tctgtgaccc 30960
catccacctt gagaagcatg cttcaaccag caaaggaaag acagtcctag acaaggaaac 31020
atcatcaagt ctctctgtag gaatacttca tatcagacca tattgccatg tgttgaagat 31080
tattatataa tgataataat tagtacaata gtaataccat acattttgat tacatttttg 31140
acattttcaa ggcatgttta tattctaata atctattttc cctcttgata attttatttt 31200
ctcccttaaa aatctctcca gttacacaaa gtagagtagg agtgaaagga ttgttaatct 31260

-continued gttaatctgc ctgtccaggg gagaggcaaa gtaaagagat gtatctgtga tttcatggcc 31320
tgttaggttc gtagtaacaa tagctaatgt gtgttaggga gcttaagtgg gccaggctct 31380
ttgctagata tgtcagtgct tattaattta ataaaacctc tagatccaag gcttccagac 31440
tcccaactgg tctccttcag caagcagcgt ttcttttctt tcacctcact ctgaattctt 31500
cagactctct agtcattcat ttattttatt cattcaactt ttatttagct tatacatcct 31560
acagagaagg tgaagggcac agaggtgaat gtgctggccc acaaattgct agctctctca 31620
ggggaatcca gaacaatgca gtgccaccca cagtggagcc ttgaaggaca aaggcaaatt 31680
atttaccaaa tcaaaagttg ccagattcaa gattctctgc agttctttga ggtttgagct 31740
tggtgcataa gaagaaaggg ggattttgtt ctaatgaaag acaggacaca agggcctacc 31800
tacaaaaatt gctgcaataa atgaggacat cattaaaatt gtctttgtgg gggcccatgg 31860
atatggaagt gagtagggaa gatgtataca agcaatggaa ggaataaaag acagaagact 31920
tcctagatct agtgctagag gctccatagt tctgttcctt acaaatgctg taactttggg 31980
ccagcctccc aacctattca accttctgct tccttctcca tgaaataaga acctggattt 32040
cttactcacc tgattcacag ggaacctctg aaaatcaaac gtaagaatta gtaatagtaa 32100
taataacaat ataaatagct aacatctatt gagcaattat atttcttact ttcactggct 32160
tatttcattt aatcatgaaa gcatttccat gaagcagata atgttttagg ccccagttta 32220
tagattataa aaacagaggt ttagtaaatt actaagttca cccaccctta acaagcagtg 32280
gaacaaggat ttgaattcag atctgtctga tctttgaacc tattactatt aaatcactac 32340
cccagaattc aaaaacaaat gaggaaaact ctgcgagtca tgctgatgaa atgagcggaa 32400
tcaaaagagg gaacaaaagt gagggcctgg ggtcagaggc tgttagcttg gcatgaagga 32460
tggaaagcat ttccagatac catgtcctga gtgagcacaa tgcttaggct atgcagcaga 32520
ccctggacag tggaccaagg tttaagagtc agtgtgaact ttcaggaaga agagtttatg 32580
cagagtaaca catgccataa acagaagaaa gtatcaggga ccagagaaac agagtaagag 32640
gcagagctgg agtcaggcag ctgcagattc caatggcctc tgactttctg ctgtagctgc 32700
aaaggtacat tttatttaac tccatgccca gccctgtggc agtctgggag ccctttgaca 32760
gaactacagc ttccacatct ggctcagtgg ggaaggagaa atagatcttc ccgggcaaaa 32820
agaagcagct cagtcttgct gccttccctt gagtctggac agaaccatcc tcggtggtga 32880
gcttcccaga gccttttggg agtggctcag gggaccaatt tgcttccttg aagaattttg 32940
aatagcttca gatgtagctc tggtggttga agctaaggac aataatgaaa ataatatgat 33000
agctgacatt cattgaactc taatcagggg cttgttttaa ggcatatttt aggctctatg 33060
cactgttgtg tgtcttgctg ctctcattac accaaagata ttatagcaca cccacatctc 33120
acattgaatc tgatttatgt gtgagttgag tggcattgct gcacactagt tggtgcaatg 33180
acatgtttta tagatattta aatatttatt aatttgattt tacagtttgc ttttaatatt 33240
tcagagtcaa tatatttatt tttctggtca gacatacttt ttaggcccac ccttcaaaag 33300
actgtaggac ccagacactg agttttctca tgccacctgg agaaagtgat cctgtaatta 33360
ttgtgttggg agctgagtgc tcccacacat tgcctgtgga taagtgtaag actctggaat 33420
taaactgcct taggtttgaa tcctgaaccc actactttct agctgtgtaa tctttggcaa 33480
gtgccatatc ctatttgtgc ctcagttttc tcatttgcaa gatggttatt gtaaggactg 33540
aatcagagaa cacataaaca gtttaaaata ctacctgtaa cctgtatcat ggcatgtaaa 33600
gttgttatta ttgatattta aaatgtccca gtgaggtagc cactatagtt attcccattt 33660

-continued

```
tgaaaatgaa gtcaatttga tgaatggtgg agagggacat tgaactcagg tggtctgacc 33720
gtagagctca tattcataat gagtaagagt ttgtatcagt caagttaggc caggttatac 33780
cacagtaaca aatgaccccc aaacttccat gggctaatat aacatgagtt tatttcttgg 33840
tcatgctgca agtccaacac aaaatggtgg gggagtgggg agaggcattg ctcctcatgc 33900
ttccttaggg acccaagctg aaagagggac catcctaaca tgatcacagt gtcaaaggaa 33960
cttatgtaat aagccacacc ctggctctaa agccttattc ccaaggtcac ggacatcatt 34020
tccacacaca gttcattgga tcaagcaagt tgatggccag gcttaacttt aaaggaggta 34080
gaaaagtgaa atcttaccat gtaactgcaa aattgggaat agccaaatgt tatctcagag 34140
gaaggttttg aggatcaaat taattaatct atgaaattat caaaaatagg gcctagaaca 34200
tagaaaaatc ttctttaatg ttaggtatga attcttatta attaatgaat tgcctcttgt 34260
agcagctctc ctgtataaat atcttccacc tgattctctt gttcctgata tctctctctc 34320
tctctctctc tctctctctc tcaatgatcc atcttgcaga cctgatccat tttattatta 34380
gacctctctc ttatcatgtc atctctcttg ttctcccttg tctgattggg taagttcaga 34440
gtcctaagca agatatctga gggcaatccg taattcactt ctaacctact ctggaatttt 34500
ttctcccact tttctctaag gctgtgttct aactggaagg actcattcac tgttcccaaa 34560
ttagactggc acattcctac cccatccctt gatattcttc attcttattg tataatctcc 34620
cttctcaaat gcctcttgcc tttctgcaat tttatatccc tcattatgca gtttaccact 34680
tcctccaaga agcctcattt ttcaccacag cctgaaatga tttcattcag ggctgaactt 34740
ccacagtact actcatttgg ctgaacttta ctactcattt gaccctgaac tcagactgct 34800
ttgaacattt ttttttttat ttatgcttat gttgttactg ttgtggaaag aacacagagc 34860
acagcatcag actcatattg atctaaattt caggtctgtc attgactggc cttgacaccc 34920
tgtgcaggtc agccatgttc tcgagctcct tgcccctttc ctgtgacatg aaagtgatta 34980
tacctatttc ataagaatgc tgcgaggata gaattgaaaa caagttatag tgacctacat 35040
ataggagatg actgtcctca tcatagctgt gtccctagta tcaagaacag tacctggcaa 35100
ataatagtca gctcaatgac tatttgttga ctgaatgaat tattagtaat caccagccac 35160
tcttactgca tgctagtttt ctccaaaagc tgtaagttcc ttgaagacag ctttgaaaag 35220
taaagttctt tggagtctta ggcaacggtt ctcaagctta attatacagg agaagcaagg 35280
aatgttattg aaatgctagt agttggaatc tggatgtact gaatcagaat tcctggcaca 35340
gggccaggcg cagtggctca cgcctgtaat cccagcactt tgggacgctg aggcaggcag 35400
atcacaaggt caagacatag agatcagcct gaccaacatg gtgaaatccc tgtctccact 35460
aaaaatacaa aaattagctg ggcgtggtgg ggctcacctg tagtcccagc tactcaggag 35520
gctgaggcag gagaattgct tgaaccttgg aggcggaggt tgcagtgagc caaggtcacg 35580
ccactgcact ccagcctgga aacagagtga gactcagttt aaaaaaacaa aaagaattct 35640
tggcacagag tctaaacatc tgtatgataa caaacttccc aaatgataga gtctgaagat 35700
tatgctttga gaaatcttat tttggaagag ctcctcttga ctggatacaa atcttttcct 35760
ggtagggctt tgtaagacaa ctcatctata aggatgaata aactttctat ccttctggac 35820
tagctttcct gcatagctaa ctcatttaat tccaggctag atcacttcta aaaaatcaat 35880
gcattagaat tgaattaatt tgtgttcact taattgatat agtgtgtgct tttctaaatg 35940
gcactaggtt tgaaagtgaa gctggtcaca ctttttttaca gtaggcttct ctaataacac 36000
ttgattctgt ctttgtaccc agtgtcttct gtatagtatt agctcaggga tttgtacgtt 36060
```

-continued gttggccaac aaactttgtt gatgcattga aaaatacagt ttcctaattg caactccagt 36120
gaacctgtaa tatagtaaga tcctacaggt ctctgtagga aatattgcta ctgaaagtca 36180
aagatcactc attaagtcca tctcatagtt gattgtagtc cagtggaaat atttgctata 36240
tttggcagaa ctgtctttgt ataaatagtg aacagataca ttccatctta gcactgccag 36300
cttaggatct cttaaggatt cgactattta cttaactgag gtacagccca tgggacacac 36360
atcacctatt gaattccagg tcttagcagt ttattagaag tgtaaacaat gcttccattc 36420
aaaaaagtca actcatccaa ttgttaagac gatttatctt ttttctttca tttcagccta 36480
gtgcagtgat tctcagctgg gagtgatttt gccccttttcc cttcctgggg gacatgtggc 36540
aatgtctgga gacactttta agtgtcacaa ctcaggactg gagaactact attgacattt 36600
aggtaaaagc aatggatgtg ctaaccatcc tgtaatgcac agaacaaacc cctacaacaa 36660
ataattatct gggctaaaat gtcaataatg ctgaggttaa gaaacctcat tctatttttt 36720
gtactcatta actatccccc tcaaaacatc tcatgtaccc cataaatata tatacctact 36780
atgtaccaca aaattaaaaa taaaaaagag tataaaatta aaaaaaaaaa ccacctagtc 36840
tagttctttt tttggccaag tgctgggcac tggttccctc tgctatttca ttgtgtggaa 36900
cctggatggg ctactcagag tgttccttgt tcagaatcaa cttcagctgg cttactctta 36960
gtgggaaggc aaaacttggg agataagggt catctcaatt tctcctttct ttaagcacta 37020
gtggttagcc ctgtagctgg aatacaaacc acaaccctct ctcctgattc actataagaa 37080
cctggcttgg acttctcaag atagttttcc ctcctcattt ccctggcttg gttggaacac 37140
actccactca gtaagttgga gagtctctgt gggtatacaa ctggcacttt gattgccgca 37200
actttgttat ctgtgatcat ggtatataat aatcaggatg aaagtcaagt ttcctattag 37260
taatttagca acagtcactc aacactgtaa aagaaaacta ctcctgtgga aattaaacag 37320
agtcattttc ttgtggtgaa aaggtcctgg gtttgcctca gtgggtctag atttcagcct 37380
tggctactaa acttgctcat gggcctctgt ttctttatct gtatgatggg aataataatt 37440
tctgccctga ttacattaat gatggagagg atctataaga tggctcctaa gttctgtaaa 37500
atgtaccgca gttgctcccc aaaagtgaaa cttgggattg ggaaaacttc tacacaatcc 37560
cagtctatga attaacactt aggaatcact gcattattat ttgaagaagt atatttataa 37620
ctgcagcata tcagcaaaat gaggccaata tagtaaagca aaatgtatat tttaaaggac 37680
tcatattcta agcttatact cttttttttgt tcaaataccct tttctattat gcaatgttat 37740
ggtgatagat tgcagaatgt ttggttgtgt tttaaaacaa cttacatgaa aatatcaaac 37800
attaacaacc tgtatcagtc ccagaaatgt ctttaaatat ttttctgatc tttgaaactg 37860
aatccaaagg aactctgcaa agtctcctca gcaggaatgt tatcatggat gatacattgt 37920
gaataaagtt gtgtgaatgt aaactggatg catttggtat gttaaaaata ctgttcacat 37980
gctttattaa ttcatgcaca atcatctgca ggaggcagat cctatttgcc cgggatcaca 38040
ctgaaacaca aagagggtga atatgtgcac agggcagcaa agcaaaaaga tcagcagctt 38100
tggactcagg caaagctgat gtccctgctg agctcagcca cttatcagct tcatgactct 38160
atgctaaatt ttaagagcct cagtttcttc atctgcaaaa atggaaatag taatactacc 38220
ccacagggtt gtttgtgtga ctaagtgagc caatataggg aagaggctag atagagagac 38280
tagcacttgg tgggtgctca gggttgtttg tttcattcat ttaaattatt tccagtatcc 38340
cctagtgtgt aaatagtgaa tctgtgacat ggaggctctt ccaaatttaa tccagtgcca 38400
tatgccttcg tgatgctgat cataatcttg agaacacaat cctgaactcc gcaatcttga 38460

-continued

```
atactgaaat cgcaaaaatt caaaatccct aaagtctaaa atttccaata gctaaattcc 38520
tgaaaaacac aattttgaaa gattaaaatt gcaaatcttg aaatcttgca aatcaaatcc 38580
tggggaaggg attagtgtat ttttggttgt acacaggata ggtgcatcgt gttagttaca 38640
tcatattagg cagaactctt atcctgttat tgtcttcatt tggaaattaa ttatggttta 38700
aggagatgca tattggagct gacaaggggc agacatgtgg gcttaatttt aggtgtacac 38760
ttgactggat taaggaatat ctaaaacctg gtaaaacatt acttttggtg tgtctgtgag 38820
tgtgtttcca gaggagtgtg tgacctaagt ggattaggcg gggaagatct gccctcagtg 38880
gtggcaggca cccttcaatc agcagagggc acaggaagaa caaatacaga agtcaaattg 38940
gtctctctgg cagctggctg gcttttcttc tactgcactg gacatcagaa atattccaaa 39000
aagtgtagtt tcacaatgtt cactttctcc ataagcatca tgtgtgtaca tgaaaacatg 39060
gaaacttcct taataaatgt agagatgtct ttttgtatat cttcgttggt gaaatggaac 39120
atttcttgag atctcagttc tgtgagcaat tgcaagtgtg gtgatgaccc attgcagttc 39180
ttgatcaatt tcgtcaaaag atttaggttg tccatcatgt atttcagatg attgcagtag 39240
taaagcttag tgcacacaat taccaaccat agttatatac atttgtaaat tttacttttt 39300
gacttattac tttatgagta cagttcattt gcacatcttt gttgtaacca tgaaactgcc 39360
attagtacac ctgagtgttt atgcttgcga aaatgtgtat gttattattg aatattttat 39420
tgtatagagt ggactatgtg tgttctttgc atttttattt ttctcaaaac atatagacat 39480
tattttatgt ttctcaaata aaagaaacat tgccctttta aaatgtgaat aaatgtcttt 39540
taaattttct ttttattatt ttttccagaa tatgtttttg ggtttttgat cttttgagat 39600
ttcaacattt gggattatgg tgtttgggat tgtgtctttc aggattatag ccaaacccat 39660
ttcttctctg cctctgaaca tctgcaaacc cactattcta gtcctcactt ttaagggtac 39720
aggctcagag gactaaactg aggttctcaa gcttttatgt gcatcagact cacctggaaa 39780
acttgttaaa acacagcttg caaggccaac cccagaattt ctgatttggg aggtctggtg 39840
tgaggacaag aatttacatt tctaccaagt tccaggtgat gctgatgctg ctggtccagg 39900
gaccaccttt tgagaatcac tgagctaaat gtttctttct cttttcagca acatttcact 39960
cctgtggttc ctgactgttg ttggcagttt tcccacaatt ttccaaaact ggtcttcatc 40020
cagtgtctcc tctcatagta gacatcacat tcatccagaa aataaggcat tctcctatat 40080
gccttcttct ctcttcctcc acgttccttc tgtcttcagg cattgtctca ctggtccctg 40140
gcccagtctg tcaatcagct gacatcactg cccccacttg ctttgaatca tgcctcctcc 40200
cttaatgtct atgtgtcctt gcataggttg gttaccagag tagatataca aagaatgaat 40260
gagtctcccc atctttccga cctcaagaac ttgattagtg gtatcctgac tggaacaatg 40320
gaatatggcc ttttgtctgc aaacagaaac aattatagca ggttttctca ctagggtcat 40380
gtttgcctat tttatgttaa taagagctgt tgtattgact tagctgtctt tattctagtc 40440
acttctgctt cacaataaga ggctatctgt gcttgcgttc caggggggtga gttactgtct 40500
tatattgtct gacagggctg tcccttgagg aatatctttc cccaatgcca gttcttgtag 40560
aggggccagg aggtcagaac ttaagctaac aaatgattat ctttctcagc agaattacca 40620
gaggacctca gactcctggg ttcctcctta agggactcag gttcagatct ttggcccaga 40680
acacactgta acctctgagt tcaggcttta gatgaggcac ctgtcaattc ctatgggacc 40740
tcaacccagt ctcaaatact tggtcaaaag gtgagttgaa acttaaaaca gtaccagccc 40800
ctggacagta taagttggtc tcatcacatc gaagtattca tgatgagcat cataaaatct 40860
```

-continued tctgagagtt ggttttgatg aacagataag gaagaatacc aacaccctaa aagttgaggg 40920
caattcaagt ccagatgaga agaaacgtgc aggattgcag acttggaatc ccaaagaggc 40980
acttagtaat ggttataaac tctgagggtt attcgtaact gatgcctggc cttggggtaa 41040
atggatatcc tgaggctttg ggcagaacag ttgcaaactc cccaaccttc tgcttttctt 41100
ggaggtgatg tttgtatgaa aagagcagtt ttctggaatt cacacaataa aatgagccct 41160
ctcatttcag gccctctgct gggtaatctt gggcaatatg cttcccctct ctgagcctta 41220
ttaccctgtt ccctcatttt cgaagcagat tctaacctcc gatctgcttc tgtggtggcc 41280
tcactgggat attctgaagc tcaagtgctg ctgctgctaa taataataat accaattact 41340
atagcaacag caacaactct aactgtgagc acttgtgctg tgcccagctc tgcggatggt 41400
ctcatgtgtt ccatcagccc gttcttacag aagttctggt aggtagttac tatcattata 41460
cccatcccat aggcaaaaaa actcagccac agaaaggtta aatagcttgt ctcaggtcac 41520
atagctaata gtggtagagt ctgtactgga acccagcact gtcctgcatt taactgctat 41580
ggtacactgc tctgtagatg ttaaaattac ttttggtgaa ctttaagtaa ctatcaatgg 41640
aagatgattt ctttgccatg cgacagtttg ctctccaagc tttaagcgga tcaccaagga 41700
gtctaactcc tctggccctg actgcctcca tcttggtttc ttgccctgca tgggttcatc 41760
ttttctttgt ttcccctctc tggcattatg aaaatgagaa gcagctgtga gccctgcaga 41820
ttgcaaatgg gattgtgagt gttgctatct ctctaacaac taattcatta cccagtggca 41880
gatagtttcc gctgtgctgt tacaatctat ttgacttcca ggtgccacat ggaataaaaa 41940
acaatttgtt caacagttgg gcctgggtgt ttgcattcag acaggcatgc tttacctccc 42000
tatgtccttg agggctgccc tctctggtaa ggagccttct ttctgggcag gaaaagctca 42060
ctgcacaggt gatagacact gaaggatatg tctggacttg gaagtaactt gatctaacca 42120
gccatacctt tcagaaaata ttccaaaaat agttactgaa cacctatgat gtgccagtta 42180
ctgtgccagg agctggctat gcagtgacag taagatagac gcaagctctg ctcttaaaat 42240
aagcacatct gcagataact aatagcagta acttcagata ataataaagg tcagggggaa 42300
aataagactg ggtgatgtga cagagagctg ttggtctgga cagggacaga gagggatggt 42360
tgaagaagag atacatgagc taagatgaga atggtaagtg agagttggct gtgggataat 42420
agtggggaaa aatattctag gcagagggaa cttcaagtac aaaagttttt aggtgggtac 42480
aagttgagat ggttcaagta atagaaagga agcccacatg gggggttggga ggtggtgagc 42540 cctagaggta gagtgctagg agaggtggtt gtagggtcag tcagggacaa atgatgcagg 42600
gccttctaga ccatgggcct tcctggggat cttctctttc agccctctac gggcccagcc 42660
aaccaaggca ggaactgcct tctgtgtatt catcatatct ctgaagtcca accccaaacc 42720
tctccaaggc caagtctgtg tctttttctt tctaaatatc ctcacccaaa tcttacacag 42780
ttcttgacac atagcagatt ctcaggatag cctgatgact tcaaggtata agttaaggaa 42840
gatattgcag accacagata tattttattt ataaccaagg aagagcttat atttagcaaa 42900
agtctgcact tcctcagtag gtactaagct ccctgttact agaggtacat aagcagaaga 42960
tggaagatca gttggtggga atgtattgaa tagaggtagt agtcatggtg ttttgcaata 43020
gagatagcag tagtggtcac aatgataaaa atagtaatat tcctatgtat taaacagtca 43080
atatatgcca gaccctagat gtatattatc tcatttaagc ttcctaaaac aacctcataa 43140
ggaaatacca ttattatttc cacttccagt cacagagact gaaacctctc acatttaagg 43200
actgtgcacc tggggtcagg tagtgagtaa gtggtagggt ccacttgaaa acccatactt 43260

-continued

```
ccagtccata cttgaaaacc ctctctaggg aaacttaatg attggagtcc atattttgac 43320
ttcatgtatc ttggcttttt atttctatcc agagctttat tgcagggtgt agggggtgtc 43380
actcttttac agcctttaca gcccttttac atatattagg taataatata gaattgaatt 43440
ctaaaatagc tgaaagtatg tttttttcctc cagcaaaatc attccccaaa gatcatcccc 43500
aaactgatga gtatcttgtt cctgtgagca ttactgtact gatctttctc ccgtcatgta 43560
gtactttgtt atttgagtca tttcagctct tcagggtact caagagtagg tgctgttgcc 43620
ttacactgtt taagcattct catagacctc tgaatttctt cagacctcac actcactcct 43680
tgttgtgatt taatatctgt cttcccaaca gggactcaag ctatatcccc agtacctagc 43740
aaatggcaag tggcagacac ccaatagaca ggctgaatga atgaatgcta agttctgtct 43800
atcatcttca taccatggct gctcccattt agttggaacg tgtgctcttc agtttccaca 43860
aaccccacag cagtgtcttg gactcctcaa cattgaggat gtcatgtatg tgtcatttat 43920
tattatcctt gcttttgtga cacccaccag gctcactgga tcacattgtc accctagccc 43980
ctgtgggcat ctggatttgg gaaccttaac ctgaggatct tggtaaaacc tcctggtgtt 44040
tccggtttgg gaagtaggct gtagagtcaa tacctgcggt caaacatcag ccctacatcc 44100
tcactaattg tgtgaccttg agcaagcccc tttacttcat ctagctaata aaaaataaat 44160
aaataaataa aacagtcacc tctgcatagg tgtatggcaa ggactgagtc aagaaatttt 44220
taagaacact tagcccagga cctagaagat tctagtaagg gtttagtaaa tgttaattat 44280
ggttgttagt aacatcatca aatttttaaa atattatcac actgactttt tgtgaatcta 44340
gacttgctag ctctggtgtg catccaatga tacaaacccc catattcaac attcctcttt 44400
gaaaggtttc acagaatgtt gtctgagctg accttaaaga taccttgcag ctccaaagtt 44460
ctgtgacttt caccaggagt ctcaaggcaa atgcacagaa gggtcaggca agtatcgtga 44520
atggaggctg gaccagggag cccatgcatt cttccaaagg catttcaatt cagtcttgtt 44580
aaagcactga gttgcacaaa agaaacgtca ctgttggcca gcctcggttc ttcggctagc 44640
tccttcaacc caagtgtatc atctaggatg gaggaggctt ctgagggact gagggaggac 44700
aaatcttgga aagagaggta caaggaagag atgggatttg gataaggcaa ggaagagcca 44760
ggaggctttg gatgaactga cctctagata cattcatttt tatgccaaaa gtccatttcc 44820
cactctttaa accccttcac ctcttctcaa gaaacttgtg tctcagcttc agagagccat 44880
ggcctcattt aaaatgttgt gaaagaaggt gatggaagca tcaggttcct aggctggtga 44940
atttttattt ttatttctcc attgacacag tttaaccttt gcttttggca gctagcatat 45000
tgctcaaata aagtgaagag aagggtgtgg gggagaaggc aagagatatt tggctagaag 45060
gttatgagaa tcacaatagc tgtcatatga gtgccgagca ttcttctaag cacatcccat 45120
gcataatctc atttaatgct cacaatagtc ctctgaagtc taatgtctat ttagaaaagg 45180
gaagcttatc tgaggtttag catagaataa ctcacccatg gtcacctatg tgaaaaaagt 45240
gcagagctaa gaatggaatt gaaatctgtc aaactccaga gtgtagagac tgaccaagta 45300
gaccccccac ttccaggcca atgcatttcg gcacttgatt tgtggcaagg agtcctctca 45360
gggttttggg gctatgctgg tgcttgctat gctgcctcgg aaatgtcacc taacctagaa 45420
atagtgttta ttctgttaca aagcaagttg gaagaaaaga aaacactcct tttttctttt 45480
ttctgtgcct cctctcctta ctttcccctg aaacttaagt tccaaggagt gcaattagca 45540
ggtcagcttg tcttgctgaa cagtcaggtt actttccctc agtatttgat gccaagtgaa 45600
tgttgagctg aaaggctggc tgataaatgc cctctgggg agaaggaact gtgaaatagc 45660
```

-continued ctggatctat tggcagatac tagggccaaa aagtccttag aaactcaacc tgaaaaaaat 45720
gtctagggaa agcaaaacgg ccaactaagg tagtaaacac ttcagaaaac cttgataata 45780
gcaatttgga aaatcttgca tgtacagttt catttcataa acccctccag tcatgggatg 45840
gatacagatg tcttgcctga aaatgtaact ggtaaattta cagataataa tgtattggta 45900
gttgctcaca gaaagacagt atcacgttgt ggagtaagtg cttgactgag actaaaaggt 45960
cttggtatga gcctcagggt catcattacc agctgtgtga ccctgaagaa gtcaggcatt 46020
ttcttggcca tctatgaagt tggattttaa ctccccaacc ctaatccacc agccattctt 46080
aatcaaggag tcagataaat gtctggcccc tgtgggattc atttcactgt cttcagagaa 46140
aagggcatat ttgaaaaagt gtattctaca cggtaacctt ctagagaggc acaggccttt 46200
ttttgttttg ttttgttttg ttttgttttg ttttattttt gaggtggagt ctctgttgcc 46260
ccaggctgga gtgcagtggc acaatcttgg ttcattataa cttttacctc ctgggttcaa 46320
gcaattctcc tgccacagcc tcctgagtag ctcggattac aggcatgcat caccatgcct 46380
ggcaaagttc tgtatcttta gtagagacag ggcttcccca tgttggccag gctggtcttg 46440
aactcctgac ctcaagcgat ctgcccgtct cggcctccca aaatgctggg attgcaggca 46500
tgagccaccg cacccagccc aacacaggcc atttttaatg ggttgttagg ataaggtggg 46560
taaatagatg tgaacgtgcc atgtaaattt agaatgtcaa acacgtacag actaatgcta 46620
tttacccacc atccaccacc attgtttatc cagttgttta ttcaattgca aatggcttct 46680
tagcctgttg gagaaatgat ctgaggtggt cagaggtatg gcccatatct gtcaaataaa 46740
gcaacctcct ggcacatatg ataggccaaa accctatcac ttgggatttg tgaacaacat 46800
tctccagtca gctgaacaag caggtgctag aaaagagtgt aaataattca acttgtttca 46860
ggacatgtgt ttaggtgagt aacgtgaatg tgaacagttt ttatctttta tttcttggtc 46920
tcaagttggc actattaggc atccattcct aacataaaat agtgtctatg aatggcagct 46980
ggtcattaga tgtacatatc caaatccaag atcagtacaa ttttcacctc caccttgtct 47040
tacctcttgc actccctaac tcagtggcag tgccacaatc cacctaatca cccagaaaga 47100
gaccaagaga cttttgattc tttttccctt atccatgtct ttgatctgcc accaagttct 47160
ggagctgtta cctctactgt ctccctctaa tctgtcacgc tgtcaatggt ggcaggaaat 47220
accgacagca gctcctaact ggcttctgcc accactgctt acccactgcc aaatccatcc 47280
caattcttgc tgtcagaatc gtccttttaa aacaaatcat ctactgtggc actccttgtt 47340
ccacacctgg ggaaatccag cctccgtagt gtgatattga aggctcagca gactctgacc 47400
ctgtcccatc tcaattgtcc ttccacaccc ctcccctaaa ttatgccaca aattcttgtc 47460
tgtgttctaa acaatagcca gatttccctc atttccctcc tgtttctgcc ctctgaccaa 47520
actcaatttg ccagcaatgc tctctggttt ttttctttct tcatccctgt ctcctctcaa 47580
gacttttaat cgtccctcag ggccaagttt agatctaacc cctaccaata agctttcctc 47640
aatctcccac ccctacctcc acaagaatta gccttccccc attatatccc ttatcattct 47700
gccgtacatt agcaagattt gtatgcatga ctgttagact gacagctccc tttgggggaa 47760
agggccttct tgtgctcatc tgtccatctc ctttctctct tcttcctctt gcctcctccc 47820
tcctaacctc ctccagccca gcatctaagt gcagtacatt tcacataaga gacaccccag 47880
caaagtgtgt tgaatagaat ccattaattt gcattccatt tctttggaaa tagcttttgg 47940
gatccattgg gcagatagtg aaaatttcaa ctaacatgat ggtggagaaa aaccttaact 48000
tttgtgctca tgttaaattt agaaacattt tgtttcattc tatcacctct gctaacctct 48060

-continued taactaactt gaggttatgg agaaagggca gaagacttat ttttctactt ctttaatatt 48120
tccggtcaat tctctcttct ccatcagtat tgccagtgcc ttcgttgaga caggtcatct 48180
ttgtggttaa agtttgaagt ccctgagata agactatctg ggttttaata ctagttatgc 48240
taacagacag accttgggtg agttagttac tctttctggg cctcagtttc ctcaacccata 48300 aaatgaaaat attaatgcta cccattttgt agagagagat tccacaggcc tagttggtgg 48360
ccagggaacc ctgggataat aaaagcaatc ggacatcttg ggaaccaggt aatctcctaa 48420
cattccaaag atacctgctg tcccctctca acgccataca gtgtgtgcca gtagattata 48480
aactgcataa ggaaagagat gatgtctgct ctcctccata tccctggctc ctgacacata 48540
agaggatcat aaacgcactt tgcaaagcaa atgccagctc tggaattctg cagcagcctg 48600
gagaccagac cctgcacatc aaggcccagt ggaaaactaa tgatttctcc cccgcagacc 48660
tgcctagcga agggccccgt ggagcttggc tggtgagagc attcttcatt ctccgcatgt 48720
ccctggctct ccctctctct ccccacctcc gcagcctccc agtcaagcta ttgtgcatct 48780
cctgctctct gtgtctcgct gcctgggtcc ctttctgcgc tgctgcctaa gcattgtctg 48840
tgatgtcttt agtgtgaaag gtgattcaca gaaataaatt gcattgtgtt ttaggtccat 48900
agcaatctac ctctgtaatc atgtctgtaa gggacttcat aatagtgtga gggccttggt 48960
gtcagaacca gggtctccag tggcttcaag atagataagt gctgcaacca aatgcacatt 49020
cagccagtga agttgcaagt tagaggtgaa gatggaggtg ctgctgctat gaagcaacca 49080
tactctcagc ccttttatct gcaggttgat aaaaatcaat caaaacatga gatgtggttt 49140
tttgtttgtt tttaataacc actggaaaac taagacttgt ttaatagagt ctcagccaac 49200
agcttgtgct cttaccagcc ctgtgattag acgaaaggga aagttcaaag tgtcacctag 49260
aagggggagg caccaaagaa gaagaggcag ggaggtgata cagtgaaagg caaggaggag 49320
ctgggctgga atctgagaaa cctgagactg atttgttcta atcatcatcc tatgtgatgg 49380
tggaagataa gaaccacaga ttctggaagg aaattgatgg catagactca acaacagtgg 49440
gatgaatatt tatacacaat aaaagggggg caagctggtt ctcccaaaat atttagaaat 49500
gatgggaagt agggggaatt gtgctccctt gatcacatta ttcagaagtg actgcattct 49560
tatggcattt ttaacagttt attgagatat aatttatatg ccatagagtt tacttattta 49620
aagtgtatat ctcatgacat tttaaggtga tatattgtta agtctatgac aaaaagattt 49680
aaaggaagca atgtgaaaca aagaccacaa gatgagtaga gaggctgtca aaggtggagg 49740
ggtgtttttt taatgtgtct gcttccccag caactggtag atctgccctc atcccacctc 49800
ccaccaccca aggtctggct atgcctgcag gttcactaca tgaagtaaga ataggtggct 49860
cttagtcagc tcacaggaca ctcacacagc taaatgctag gaatccctct gggaggtcta 49920
ctgcaatctt ggaggtttag aatttgttcc gcttgaactt tcagattatg agtcccactg 49980
cacagccacc cacccaccct ttttgtgtga cacttgcgtt agcacaacat gtccctattt 50040
ctccctctaa ttaggtcttt accaattgat ttagaggcca tgttcagttt ccataagcaa 50100
tcaggtacat cctacaggtg cgttcatatg gtatcatttg tcctcattcc tctggatggt 50160
tatgatcctc aaaactacct tacctgtaac ctatactaaa atatcttaat cctagcatgt 50220
gtaattccaa tgaagtcctt cctcttgaaa actactcttg gttctgttct tgaattattt 50280
tctgtcaata tcttccttgg aatgacactg gctgggtttg tgaactaatc aaacctcatg 50340
aaggggtaac tagctggcca gggctgagag aatgattaaa ttaggtcact gtttcctaaa 50400
cacaaccctt ctcctatctt catgtattta tcatatctgt gcatttactt atattttcct 50460

-continued ttaacaaaca tattttaatt aaagttattt aaaaaggaaa catatcaact attgcaaata 50520
gaaaaaccag tatcactatt aataggtaga agctataaaa ttaaaacaaa gcattgttat 50580
tatattctag ccatatgcca ttgcattcat agcgttctga gcctgattct tgcctctttt 50640
tgtttaaaat aaaagggaaa tggcaaggta tggagataaa taatttacca aacagatttt 50700
ctttttcact taatagcagg aataaaagga aatttaaaat gaatgtgcat acgcattgtg 50760
agtctgttgt ttaatgccat tctcacattg ggaaattcca ctcaccatac ctgggttcta 50820
gtctttactg agcaattaaa ttgctatatg gctagctcac cttcttgtac ctcaatttgt 50880
acatatgtag aatgaggttg gtgagttgaa atacagaatt cctttaaacc caagtttctc 50940
aatgttgctc acgggcaagc tgcacctgaa ttttctgtgt aggtatactt gttgaaaaat 51000
gttaatttct aagctccatc caagatattc tgaaaaagaa tttctggaaa tttttcctgt 51060
ttttatcatt tgtccagttg accatgggat attataagat tcaaaccatc accttaaagc 51120
ctgtatgata aactgaagag tagaactgaa ctgtgaatag gaatcaagag gtctccgttt 51180
cagcagcaac ttacagtgta agcttgcgct cagctaacca ctctcatttc tccatttgag 51240
cagtcaggtc acattcggaa ggctccaagt cccttccaat tctacaaata cagtgttggg 51300
ttgctttgtt caaagttttc tctgaaaatc tgtgctgagg ccaggtgctt ggtaaggttg 51360
aaggtagaga tggccaaatg acagctgtgg tctgtggggt gcattgtccc ctctggaaag 51420
ccagccagtg cacgtggaga cgagccagag ctgcctctgc ctgccttgcc ttaacagcat 51480
atatcctcca gcagggccag ccagatcggg caagcatctg cagaaaggct tagcgagatc 51540
tcttgcaaag tcagcttagg ccctgctgga gagacaagaa ggaagacttc tatgaatgct 51600
aagtgggtag aaaggaaact acagcagggt ctggcttgga ttaactcttc atatcctgga 51660
tgccctggat tgagatctga gtctatgaca tgtgtgtctt tttcaaactg cctcctaatg 51720
aaacacatat atccatcatc cagagactaa aaactaagtc tcaacctgaa cttcatggcc 51780
ccccagagca ctcctagcct gtcctctctg cctcaactcc catggttggc caactggttc 51840
attgatcaac tgattaattc atccaccaat tatttttgag acaaccactc tgggccagac 51900
cctatgttag ttactgagaa tatacttgtg accaagatga acaaggtctc ttttctcatg 51960
aaatttaagg gaaaaaataa acaaataaac gggacaatcg cagatggggg aaagtgcttt 52020
agagggaaag aataaggtaa agcgataaag actagcaaag gggaggcctg tcaaaagagg 52080
ggacatatga gacccaaaaa aggagaaaaa cccagtccta caaatattgt ggtaatgttc 52140
caggcaaagg gaagaatcta tacaagcctc tgaggcaaca aaaggcttga gtagctttgg 52200
gaattgaatg aacgttggtg tggctggagc taagtaagat aaagtaagaa tgatatgaga 52260
tgatgtagga gaggcaggca gtacccaaaa cctgcaggac ccgggaggtc acaattccca 52320
tttccaggct cttctcttca gcctaactgc aatacatttt ttcttgagca tacctctact 52380
ttcccactgc cttcattttg catgtgccta atgcttttgt ctggcataac ttggccccta 52440
atcacagtat aagcaaattc ttcctccatt ctttcgtacc cagctcaaac attacctcct 52500
tcacagagct tgtcctaaat accacattta tgctgagtag acatgagctt ttccttcttc 52560
tgaccactca acttcccctg agcttcattt actctttctc ttttgttctc attcccaaga 52620
ttaactttca gtctaaaagt tccttgtggg aagaggaaag gacctaatat ttgaaggaca 52680
ctatttgtgc caggtgacat gctaggagct tcatatatcc catttcattc atgactatag 52740
tcttgtaaat taggtgttat tagcctcatt ttagaggtaa gaaaccagtg ttaaattact 52800
tgaactacag cacaaaacta catgatgcag gtattaactc taaattccct cagtatacct 52860

-continued agcattgccc cttgctcatc attagtacta atttctcgaa gtgactatac actctggcaa 52920
cttctaatcc tcatttaaga ccaagaaaag gccggacact gtggctcacg cctgtaatcc 52980
cagcactttg ggaggtcaaa gcaggcggat caagaggtca agagattgag accatcctgg 53040
ccaacatagt gaaaccccat ctctactaaa aatacaaaaa ttagctggac atggtggccc 53100
acacctgtag tctcagctgc ttgagaggct gaggcaggag aatcgcttga acatgggagg 53160
tggaggttgc agtgagctga gatcacgcca ctgcacacca gccgggtgac agaacgagat 53220
cctgtttcaa aaaaaaaaaa aaaaaaaaaa caagaaaagt gttgccaggt atggggcaca 53280
tacctagaac tgtggccatt catcctgcaa cttgaacttt gggcatcacc ttgatccctg 53340
atacctactt ctcttcatcc caatctgctc tgtccttctg ggccagcctg ttcttcctga 53400
tgataaataa gtattgaacc tgagcctatt ataccccagg cctcagctga agtgtctatc 53460
ccaaagtgct tgatgttcag agagtagctc taaccaaact ttccccatcc agaaggatat 53520
ccaaagacaa actcattgtc tataacacca agagatagaa cccctataag tcaaacttct 53580
atgcctcccc tacattctcc actttgtaga gagatattca aatcctctct tttcctgtta 53640
attactgagc agctgtggaa tcagcatgga tcacaattct gccttccttt tgaaggaata 53700
acatgcaagc aggagttgcc acattgtgat catggactta cttcagatgt ataataaatg 53760
acatcccatg agaatggctt gacagcagct gatggcactt ggcaaagcat tctttatttg 53820
ccataggatg aaattatcac tttactaaga gtaagtgttt acaagcaact ggagatcagg 53880
aactagagaa aataattcca tgtcccagat tgaaggttta cagcagatat acagtggagt 53940
gaactagcaa tcacagagtc tagtctttgc tctgccattt gctagctatg aagccttggc 54000
taacttcatt tcattttcta tgattcatct catggtacct cctcctagaa gatttcctta 54060
accacttcct cttctcccag tctggccagg tggccctcct atgtccttcc atagtgcctt 54120 ttttttttcat ttatcacatt atattataat agttatataa acactttcgt ctctcactaa 54180
attatgtgag taaagtatag tgattaagaa caagaatgtt ataatcagac agatatgggt 54240
tggaaccagg gtttggctgt catctagcta tctgataaaa atacacttct tagagcattg 54300
ttataaggat taagcataca taaagcaatt agcatagagt atgggtcata actagtaaat 54360
gttttgcctt ttatttttgc ctttatagcc acagtggcta acgcaatacc tagcacacat 54420
ggtaggaggg ttggtgatgg tgatggagat gtgatggagg tggtggtgat cctggtgata 54480
cctgagtgga ggtaatggtg gcaatgttgg aatggtgaca atgttgtaat cccagtggta 54540
atattataat ggtggcagtt gtggtggtgg tggtgatgat gatgatagta acaaatgagg 54600
atgataagaa tcaacagcta acatttgtag agagtttact attgtatata caaggcatgg 54660
tactaagtac ttgcatatat ctaatttcat ccttttgact tcttttagat atggccagta 54720
ctccacatct ttcaagtggg tgaactgagg tttcagaagt tgagtaattt cctgagagcc 54780
tacatttagt aaactaagac aaagtcagaa tttgatacag gccatatgat gtcatcatat 54840
atatgtaaag tgctcaactg ttggttactt gaatgaggaa ggaaagaagg aagaaagaga 54900
aggagtgagg gagggaggaa tttacttgtt ttctaatctt aagattcctt ttctgaaaat 54960
agagataatt ctagcattta tggaaatcaa atgagattaa aaaaagtcaa agctctttga 55020
aaactgtcaa gtcttctcta tgtacgaggg ctaaaccatc agaggcagct tcataattac 55080
tcattcattc attcaataga tatttggttt tctgttttag gcactagaat atagtgggca 55140
aaacaaacta aagtgcctgc cctcagtgag ctttcagtcg agtctagtga cagacaagca 55200
aatgccaggt gaaatatata gtcctgtggg aaaaaataaa gcatggaggg ggtgagggaa 55260

-continued tatgtgtgta tgttgggggt ggggtcactc tttaaatagg gtggtgaggg aaggcctctg 55320
ataaggtgat atctgagcag ggcctgaaaa aggtaagcca gggagtcaca cagaatctgg 55380
gaaaaaagtg ttttatatcc cacaggggag tttaaaagtc aaatgaggaa tgatatcact 55440
gtgataagaa tgctaggaat gggattatgc aggaacccca aggcctgctg ccagtgacta 55500
tgcagtcaag tcagtctttt ccttggtaac ctcctctggt ggggtctctg aaggctcagt 55560
caaggtgtga tgtcccaggg gagatactat tatctgaaag catggttcct ctggcaacag 55620
gcaatgggtc tgagggagat atcttctatt ctccattcaa ccatccatga gcatgatgac 55680
actaggcagg tcatctgtgc tcatggcatc accccttcca gctgggaaag acaaaggaaa 55740
gtcagggagg ttctccccac atcaaatgga aaagtcctgc tccaccaggg tctataatga 55800
aatggtttat ttaagtctat aatgacctaa gataaagtta atttacttta ttcagattta 55860
cagacattac caaattacat aggattgcaa acacaggaga agataaaata aattaccaac 55920
cagattgaag agcttagaga aataggtaaa tagtcatggg aagagattta atttagataa 55980
accaaaggca ggatatctgg aaaatgccaa ggtcagggaa aagccgagag gaaaagatag 56040
ctagtaagat ggaagagaca tggaaaggat tcagaaaatg acgttggtga tagtgagtgt 56100
ggccagtatt atgataaaga tagaggaaat gggaaagata ttactgaaaa atatggcttc 56160
tccttagaat cccaaaataa atgaggtaat ttgtggaaag cagtgccaga ctggattctg 56220
tggtcttagt tccaagtctg ctaggaactg cctctgcaac ttgggaaagc tttttgattt 56280
ttttctaacc tttagcttcc tcttctgtta tgacatacaa tacggttcta agtctaaatg 56340
tttctagttc tcttgtgttt aaggaaggcg ccatgtgctc tgaggagacc ctgaatccat 56400
ccctggtcct cctggctgac cttaatagaa acattgaaag atggagattc atgacaagta 56460
gtcaaacgga aaggcattca ttttggagat ggatcaaggg tccaggctca tcggagacac 56520
tgaaaaagtt gaaaggttgc aaaattgagg gagaacgaca gttatgatag ttcagtataa 56580
ctgggttttg ccagaggttg tagaaaaaag ttaaagattg atttgaaatg gttgaggggt 56640
atgtacaatg cagaaggagg ggtgagttaa ataagacaat ttataggctg gatgtcttca 56700
gggactgggg ggaagtttgg gtatctttaa gatggcatgg cagtctgaca tacaggaata 56760
gttgtatcca ctgcaaatca taaccttcta tgcatttcag ggtcggctta aggatatttg 56820
caaagaacat actggaggga gaacatcaga cttgtcctag ttgcttgggt cccgggttag 56880
ttcaccacta cagcaatgtg ggagctaact gcatgctaag cttggcatgc agggattggc 56940
aaaccttttc tgtaaaaacc cagatagtaa atgttttaga ttttgtgagc catacggtct 57000
ctgtcacaat tactcaactt tgctgctgga gagtgaaggc agcaactgat tggtccctct 57060
tataattgaa gctcctgaga tggcattctc ctgaatgata atatttaaat gaaggccata 57120
gctgtattcc aataaaactt tatttacaaa cagatagctg aatttggccc acacaccata 57180
gtcggccaac ccctgtttaa ggcatgatgg ccctgcctat tagcaaatat gtcctcatca 57240
gtgtcctgaa acatgttcaa ttttatgtgt aactcctccc tattgggaac aaagtgaggg 57300
ccaacaattc ttttccagta ggtggtccaa agaatataat tactgaggcg tgtgtcactg 57360
gaaatgcatt ccaatataac aaacatctta ggtacttaac ttgttcattg atgtttgagg 57420
atgaatttgt aggggaacat tagatgttcg tatgattgac ctatgttgaa aggagactta 57480
ctaaggtaga ggcaggtttt cactttctcc aagaaggaag agttgaagaa gtcccttcaa 57540
tctagaggaa tcatcattgt gcaaacatca gggaagagat ggagcaaagt taaatggctg 57600
gaagtcacag ggagctctgt tatggctagt tgtaacacag attatgcacc tggagcttta 57660

-continued cattttataa aattttttgg aagtgctttg ttaccttact tatcagaaga tgctaaagtc 57720
attcccatag gttctccatg aatgaaggaa ttcaataatt attaccgatg atgataattt 57780
atgcttatta taatgtaatg gtcattagca cagcagcagc cattcactga ggcactgtgc 57840
ccagggctcc acaagcatca tctcaagttg ttccaacagt catgggaagc aggtatgggg 57900
aacgtcttac agatgaagaa attgagagtc aggtttgata attggcccaa ggaaacacag 57960
tttattataa gtgccaaagt caggcctcaa actcagctct gctcccacag ctgacactcc 58020
taaccaacac attgtcctat tgcacaactg cagcattctt tcattagtgg gtatgttaat 58080
gtgaagaacc agcacttgga ccagtgcctt ataaggatcc tttgaaacca agattttatt 58140
gtggttgaag ggcagagagc taaatcacca aaatgtgtaa gtagagacag accagaatgt 58200
aatctccatg aaagcaatgt ccttctctgt tttttaattt tttcaccatg ttatccctag 58260
cacttagttg tgtctgataa atatttgaat aaatgcatca gtatgtgaac attatttgga 58320
attatttttt ctttttaata tcaaaaatct cataaccacc taggccaagc ttaacccgtg 58380
ggcctcaggc cgcatgcagc ccaacacggc tttgaatgag gcccaataca aatttgtaaa 58440
gtttcttaaa acattttgag actttttgtg tgattttttt tttagctcat cagctattgt 58500
tagtgttagt gtatgtgatg tgtggtccaa gacaatgctt cttctttcaa tgcagcccag 58560
agaagccaaa agattggaca cccctgatct agcctgtctc aatgtctagg ctttgagaca 58620
cccctgatct aggctataga aatgtctcct atttctctct cttttaacca catagttcaa 58680
taccctggac acagtaggca cttaaggaat atttgctaag gatggggcat gatagctgac 58740
ccttaataaa taaagtgcta cattgctaca gtaatcaaca accttctacc cttcctagct 58800
cctgtgacag atgcaactac ttcttattcc ccatgtggga gttgtaactc aacacttctc 58860
tcccctattt atggatgcag attggaaaat acattagaaa gggagaagcc aaaatatcct 58920
ctgatttata atcagtactt tggttgaaac tttcatgact atattagtaa tagctagtta 58980
cctgtaacac agtttagagc cattaataaa atacctcgtg gaacttttat gtggctccat 59040
gtagcagagc tcagacctgt ggaagaacct ggagtaatta gctggaagga tgttatcaca 59100
gttagcacca tccaaagagt gaatccactg cagagtgaac taatgagccc tggtctgaga 59160
gacactgaat cagaggtgac caggagtcag gtatagaggg gctatactag gtataggtca 59220
gatataatta tcactaaagc ccctttaaaa tataaacgtc ctagattttt gacatacccc 59280
atgtctccat ttattgtgac attgtctttt ggtaaatgaa ccccttctca taaaaaaaat 59340
ttttgttgaa atataatata catcacttgc atgaattttt actcctgctt gagcaggctg 59400
agcctggttg gtaatgttag caggatctca gtctatggca gacatactga ctcttccttt 59460
gcttttaagg tggtgtgatt tcaactaaca gaattcatgt tgtattagac cacataagct 59520
catgtcctgg aaagagagcc accttgccaa ccagttcata aaaattagct cagcactttc 59580
tcgtgagctc cgcatggtcc tgggatggcc tgaggtgggt cccagcaata tgtatttttt 59640
aaaaatcttc tcaattgtga aacacagttc tgaaatagaa cttcatcatt tggggtctgc 59700
aaggcgaatg gtgttgtacc attgtattca caagtaaact gagacccaga gactaaatgt 59760
ccctgttgtc agaggtacag cagtagttag gggcatattt gggactaaaa ttcatattag 59820
ttttctctag atacagaaat atttcagtca ggccaatttt tatacaaaac taacttcagg 59880
actgatggtt tagccagttg ttggtcagtt atatgtgtag gtttgtgtgt tattgttata 59940
aaaagcagta tcctttcaaa ttatatgagg gatacatgtt tatcatggga aactataaaa 60000
tgtgagaaaa aggggaatag aatcaaagta tctatcattg cacaactctg agataaccct 60060

-continued cttattatgt tgctatatgt ccctttagac ctgctattca tatgttgggt tttttattat 60120
tttctaagac tgggattatg gtgtatgcac agtttttcat tcttcactgt tattatatta 60180
tgagcatctt tcatgttaat aaataggcat tcacactagc tcttaaatag ctatgtcgaa 60240
ttccttgatg taatatatca taatgtgttc aacagagtct ttattggatg tttaggatgt 60300
ctgtgtattt taaaaacaac aaacttgaat aaatactata caacttctaa agctcagaag 60360
tgagatattt aggtagcaaa cagctctgat gaacttaaag agttaacaat cagctaacca 60420
gaaaatgagc tccccctcct ttcaaccagg ttaaaacctg gttctttcaa ccaggctgga 60480
taattgagat ggtacacatt aatgatccct gttctcatca ttgttcagtg ccaggcatgg 60540
ccaacacttt gaaatattag taatcaggct cactgagttt cttttcaggt ttgaaacaga 60600
gctctgcaca atacattatt acttgtggat ccttgagact tctctgccac ctccaagagc 60660
agaagcaggg tcttccgagg ttaacagtca ccactgggtt ttaatcagga aaaagaaaga 60720
aagccataaa tttaaactct gaaaaactca gtacccaccc agaaacagca acaaaatcag 60780
attggagtct ggaagaaagg tcctctagac ttgagaaagt tcagggtgaa attgggttta 60840
ttgtgggtct gagatcagaa agtaaaattc taaagagctc aaggcaacaa catccaaaaa 60900
gtgggcaaaa atggccaaag aatggactgt ggtattttct gggaaagaaa acgatttccc 60960 ctccctttc aaaaatttc caggaaacta attgtcaggc aacccacttg tagaatggaa 61020
gcatctctca aagtgatcta gaaattccaa gaagattttt tttctactgt tatgatgccc 61080
aggggagata gaagggtggc ttgcaaagtg gactcaggtc tgcattccaa aactgccttc 61140
attcccttta tgtgggacta agaaaattat attatccatc taggcatttg tcctccatcc 61200
attaaataag aagtagagag gcgttacagt actcatcaag aattccagtt ctatcgctta 61260
ctatcggtat gaaattggat catctcttta atctctttga gtctcaattt ccagtcttta 61320
aaatagagac aaaaatatgt tccttagaag attgcattga atattaaaat acaatgagct 61380
atagagaaag cttaggctag gatctgtgac atggttggtg tttaataatt acaggattca 61440
gcaggtgttt tatttttttt tcctttccag ctccaaatta ttctatgtca ggtgttaggg 61500
gtatatagat atgctaagat atgttcattt cccaccaggg agtcgagtcc actgtggggt 61560
aaagacgtgt acacacagct gtcctagaag atcaagaagt agagagctgt gtcatgaagg 61620
ctctccaggg gtgaatggga gaggctaaca gtagaggcag gcattggggt gggctttaaa 61680
agatgaaaaa aaaaattaag gcagggtagg agcagaagca ctcagataag gaaaaaatgg 61740
cacaactggt tggatgaatt gttactatta ttgcttgaat ggcacaactg gttggatgaa 61800
ttgttactat tattgtacct attctaatag gtacaattgt taaggtaaag gaaaaaacca 61860
tatttgcaac tagaaccaaa tcaactactg ctagaaaatt taaaatcttc cttcaatatc 61920
aaggtagaaa aagcttagca tcttcatttt gctactaaca ttctgacctt ggacaaataa 61980
ctttacctgt tcctcagcta aaatgaggat gtaaatccta acctgtctat cttaatagga 62040
tgttgtaaga attaactgaa ataatgtaca gtctgcctca caatcatctg gacggcttga 62100
gaaagcacag attgccagat cccaccccca gaggttctaa ttcagtaggt ctggggttgg 62160
acccaagaat ttatattctt ttttattatg atgatgatta ttatacttta agttttaggg 62220
tacatgtgca caatgtgcag gttagttaca tatgtataca atgaatttat attcttaaca 62280
agctctcaag tgatgctgat atagctggtc tggggattac agtaagaaaa ccactgcttt 62340
aggtcaatgc agtttttttt aaaagctatt attcataact ggctcaagag tcatgtaagt 62400
gttgattatg ttttattatg tgtctagacc cttaatagac tactcaggat atgcacaaat 62460

-continued agaagatgta atattttctg tagcattccc tacaccaaat cggccttgct cggtcatgca 62520
tagttaatgt atgtgttgat tttatttgtc ttcgtgtggc ttctagtctc actagaaaga 62580
catacattta tttgaatgtt gtagaatgat attattcatt ggaataaaat cggatctttt 62640
tacagttttt tttgtttgtt tgtttcttaa tgagcaggcc tatgattcct aaaggacttt 62700
ttattttatt tcatttgaac ctttgataga aactgcatct ttcatgtgac cactctccat 62760
ttttctgctc atatgaccac atttcccagt agtctttaaa ggctccagtt tggatgggat 62820
ttcgattaat ggaagagaac agatagctct gtaaatagag ccagatgtct cttgcaatat 62880
ctgaaatgaa ctgtctcaac catcagaact gtaaatcacc ttcagaaggc tccttctccc 62940
aggagtagtc tttgcattat tcatagccct tttgctgtag tacattcttg tctcatgaag 63000
attacagcca atcactatgc tttcatagcc catcctcctc cctgaacccc tgctttcatg 63060
ctgtgtcata gccttggcac tctgttcttt gaacttcttt gaggagtagt gttttccagg 63120
acctagcttc agttatgcca agagtgtttc ctttctgtga tcatgataca ttgtaaagta 63180
tgtggttcct ttttcaaagg gaaaatacta tagtcaccct aattccttca agaaagaagg 63240
cagagaaagc ccccccctcat cctctccgaa gcagtcacat gctctattca gaatgaatca 63300
tcactttgga attgtctgcc agtgttttgt ggggtgaggc tcagactctt tctatgggta 63360
gatctgtagg cctgttttct ctgcaccaga ggtcccaaac tggtgttcta tggattgcat 63420
ccagtgattt tatgtgtagc ataacttttt aagaggaaga gagaagaaaa ttgactttgc 63480
gatcaacatt acaaaaaaac atcatgagac tttgaataga aatttggatt ttcagcaaaa 63540
aaaaagaaaa aaaaaaagaa gaaggtttgg cagtactgga ctcccatctt taagggtaac 63600
agccgaatgc tggccacgtc ctgtaagaac ccacactctc cagtttgctg ctgtccatac 63660
cagcttgtgt gactccttta cattacctgc ttgactccta aaggtatttc aattagtggc 63720
ctgtttttgc tctttttggc aagttcacag acttacagag tttgaaagct aaaggagtcc 63780
ctgagaacaa ggattttcta atgttacttc acatcaaaat cacctatacc ctataaccag 63840
gctgcatcca gtaccaatta aataagaatc tctggggagg accaagctgt caggattttt 63900
ttttttaatt ccccagatga ttccagtata cagatcagtt catctaagaa ccagtacctt 63960
ggaagaatac tactcagaat ttattgtgca tacaaatcac ctggagattt gttaaaatgc 64020
agattctgtg ggggcagggt ctaaggttta gcatttctta caagccaatg cttctggtcc 64080
cccaatcata ttttgcatag caaagcctaa gagatcttct ggtctgtcct ttttcataag 64140
ttcaaagaga tgtcaaaatg aagctttcct tgttaagtat ctaagcttag gatgaattat 64200
ttatttattt ctccagcttt tcttttccaa acaacctttt tctgtagaaa cagggtcttg 64260
ctatgttgcc ctggctggtt tcaaactctt ggcctcaagc aatactccca ccttagcctc 64320
ccaaagtgcc aggattacag gcatgagtca ctgcatctag ccagagtttg cttttaaaag 64380
cataaatgac agtggtgtca aggatattcc tgtggaaagt agtttttcct cttatttact 64440
tacattccaa cattccttct taactaaaag agaaagaagt gggtcttcag ccaaaagaac 64500
attatttcac cctggtgatg ctcatgggat tcccatttta tgatggtaga tgtgttactg 64560
gtggtgaatc catacaggtc tgcagcaacc tcaattcttg cctcctcaaa agaaagaatt 64620
cgaatgagag gcataagaca gagtgaaaga ctgaggcagg tttcagagca ggagtgaatg 64680
tttattaaaa agctttagaa caggaatgaa agaaagtaaa gtacacttgg aagagggtta 64740
acggggagac ttgagagacc aagtgcatgg tttgacctct gacttggggt tttatgtgct 64800
ggtgtgcttc gggggtctta cattacttct ccactgattc ttccattggg atggactgtc 64860

-continued catatgcaca gtggcctgtt agtgcttgtg aggagccgca tgcacagtgt gtttactgaa 64920
gttgtatcca tgctcacgtg aggcattctt cccttaccag tattcgtaga accatatgcc 64980
agttaaactc caccattttg cctcttagtg tgcatgcttg agctcattca cccagtttct 65040
gagatattgg gaaaatgcga tcaccagttt caggtttttc tatccattgg gaaactgcct 65100
ttccctggca ctggctgcaa ccaattatta ttttagagag acagtttaat aatcgcctat 65160
catctgatgg ttgcctgaca tttcttgtgg tggcagcagg ggggaccctc tcctgtcctg 65220
ctcgtgtctg actagctacc tactgtaata aatggggtgc agattagaaa acaggtcctt 65280
accctccccc ttccccaccc agttattgct caagatcaca taattatgaa atagaagagc 65340
tgatacatag agaaaaatag ttccagttgt ctttataagt ggttcaaaac tctgtgagct 65400
tctttgatgg gttgagttgt aagttatgtg gcagcctctc ctttcaggtg agaatgaagc 65460
agtcagccag gtctaattgc ctagttatat gagtgtactg agtaggtaac tctctcaata 65520
gtttaatttg aggtctgcaa ttggagagtt gatgctgaaa catttctcag gaccagaaat 65580
ttcctttcag gctagccact tctctgagct gaaaatgctg tcatggtgaa ttcattcttc 65640
tagatccatg ttttttaagt atattatcaa aggactatgt gtatcggaat cccttgagac 65700
tctagttaat gactgtccac gtcccactcc cagagattcc gagtcagtaa atctggggtg 65760
gggctcagga agtggttttt tgttgttgtt gctgctttgt tttgtttttg agatggagtt 65820
ttactctgtt gcccaggctg gaatgcagtg gcgtgatctt ggctcactgc aacctctgcc 65880
tcccaggttc aagcgattct cctgcctcag cctcccaagt agctgggatt acaggtgccc 65940
accagcatgc caggctaatt tttatatttt tagtagagac ggggttcccc catgttggcc 66000
aggctggtca caaactgctg acctcacatg atctgcccac ctcagcctcc caaagtgctg 66060
gaattacagg catgagccac tgcacctggc caggaagtgg catttttcag aaaactcatc 66120
caagtgattt tgatgcaggt agtaggccag atgcagagaa atatgatata aaggtaaatg 66180
tcctttcttc cctgtctact agtatagtga ccattttctc ctgaatcaaa tactgcagcc 66240
ttgaaactag ttaaaaccag ggttgtgcca tacttctact cagctcagaa ggaggctctc 66300
catttgagaa cacatgggtt ccttttgcta ccaggacatg cagcttggaa cctctgattc 66360
tcagtgatgt aggcattttc ttagcataca gcagcctgga atttatcata atgtacatgt 66420
cacaggagga tatgaaatag agtaaacacc ttttttatag actttagatt ttgaggtctc 66480
actacagcag cgttttgcaa ctttttaaaa aagaaccaat aatgatctct ttggatgttc 66540
ataaaagcct cacactctgc tgtcccatac tagattctga tatacctaac tttgaaggat 66600
gtccaccatt gagtgtcact acatacaggg agcaaattcc atttcatttt tcgcgcattc 66660
ctaccaacga agagaaattt gaggcacatt attttaggaa atttgtacca taaaaacaat 66720
aggtatacat caatgtttta tcatttataa tgtttcaacc ttaatatgtt tttgacactg 66780
ctcctgctgc actggaggaa tgttgtaata gattgttaca taaccacttc tcctggcagg 66840
tattttcccc cttccttatt ccactaagac tcacttgcaa cgcaaagacc agggcctcat 66900
ggaagaaggc agctgggcac aagcctgttg ccatggaaag cttagggcgg gaagcgattg 66960
attggtctct gcatacagag actgatctag aaggcttcag tgtgtctgaa tggacctgtc 67020
tgggctggaa tttcagtcag tctgacagac tgctaaagga gactcaggtg tacacttcag 67080
caacttgata actcttcccc agctgaaagt cgaatcattt gatccaacgg gaaagaagct 67140
aaaattgtcc tgacagctaa agagcgatct gacctttgtg atcaggagga gaatttcttg 67200
tgatacagaa agtgaaagta gaaactggaa tgatggtatt gatgatgaag gcatttagag 67260

-continued

```
cagcaggcac tgccattcat taaaagattg cactgtgtca ggcacatgct ttatcctatt 67320
gaaccatcat gccaaacttg ggacacttag gtatcattgt ttttcatttt ccattaagaa 67380
cttgaggatt aaagctgtta atctatctgt tcatggtgaa atgagtagta tgtggcctgg 67440
gtttgaacct ttgttatagc tgcaattttt tcagagcttt taattgttga actacacggt 67500
gtttctgggg ctattcttga tctttgcaca gtgtgggggc gaaagttggt ccttttagga 67560
attcaactat tctctcattt agttatggcc aagaaaggag aggctcagag atcagttggt 67620
gcctcaaaag gtcgctcttc cctgcagccg acttaatatg tctcctagct cccagtccag 67680
tgctccagca agatccggaa gctaaatatt ccctgaagcc tttataatct attgagaata 67740
cacaacagag ttgctgggag tttttccaag gcagtaagtc tcatttttct tattagtttg 67800
gatcccctga acccttaagg tagtatctca aatgcagtta agtgttcaac caatatttgt 67860
tgcaagaata aacattacta gtaagaaatg tgatcttgga gacaatattt tatgttccta 67920
gtctctagtt ttcctatttt tgaaataagc aggtgtgttc tagatatttc gaaaggccct 67980
tccactttaa aacttattta actctagagc aaggatctct cacctgaagt ctgaagattg 68040
gtctatgtac tctctgtaac cctacatgaa atgctttaaa acttcattta cagttatgtg 68100
tccattaaca attggaatac attcagagaa atgtgtcagt ggacaatttc accattgctt 68160
gaatatcaca gagtgttact tacacaaatc taaatggtgt agcctactac acacctaggc 68220
tatattgtat gatacagatt atagctccta gactacaaac ctgtgcagca tgttactgta 68280
ctgaatactg aggcaagtgt aacacaatgg taagtatttg tgtatctaaa tatatctaaa 68340
catagtaaag gtacagttaa aatataatat aaaagatgaa aactagtaca cctgtataag 68400
gcacttacca tgaatggagc ttgcagaact ggacgttgct ctggtgagtc agtgagtgaa 68460
tgatgaatga atgtgaaggc ctaggacatt actatgcact actatagagt ttataaacac 68520
tccacggtta ggctacacta aatttattta gaagtctatt tttatttcat tttgtttttg 68580
aaatggagtc tcactcttgt cacccaggct agagtgcaat ggcaagatct tggctcactg 68640
caacctccac ctcccaggtt caagcgattc tcctgcctca gcttcccaag tagctgggat 68700
tacaggcacc tgcccccatg tctggctaat ttctttaaca ataaagtgaa cttggcttac 68760
tgtaattttt tactgtacaa acttttaaat gttttaactt tttgactctt ttgtagtaac 68820
agcttaaaac acaaacacat tgtacaacta tacaactttt ttttccttat atccctatgc 68880
tataagcttt tctttttcta tttctaactt tttgttactt tttaaacttt ttggttagaa 68940
aatgtttaaa gggtaaagac acaaactaga gaatttatat ctttaaactt taaatgttta 69000
agaagtaaag atattaagac acaaacacat gcattagcct aggcctacac tgggtcagga 69060
tcatcaacat cactgtcttt cttccacctc cacagcttgt ccggctgaaa ggtcttcagt 69120
ggcaatagca cgcatggagc tgtcatcacc tataatactg ccttcttctg gaatacctcc 69180
tgaaggactt gcctgaggct attttacagc taccttttt tataagtaga aagagtgcac 69240
tgtaaaataa caacatatat agtaaatgta taaaccagtt acataactgc ttattatcaa 69300
gtattatgta ctgtacatga ctgtatgtgt tatactttta tatacaacca cagcacagta 69360
ggtttgttta agccagcatc accacaaaca cattagtaat gcattgtgct acattactat 69420
ggccaagata tcactaaaca ataggaattt ttcagcccca ttataatctt atgggaccac 69480
cgtcatataa gcaggtcatt gttaaccaaa acatcattat gtggtgcgtt actatatttt 69540
ggtataattt acatatagta aaattcactc cttttataca gttctatgaa ttttgacaaa 69600
cctatatagt catttaacca ccattataat caatatataa aatattttaa ttatcccaaa 69660
```

-continued aaggtttttt aagcacattt ataggcaatt ttctcccctg caaccccagc ctctggaacc 69720
actgatttgt tttctgtttc tataattttt ttcttttcca gaatgtcatc tacatggaat 69780
tctgcaggat gtagcctttg cattctggct tctttcactt agattcattt tgagatccgt 69840
tcacattgtt gtgtgtatta gtagcttgtt ccttttttatt gctgagcaaa tttttcattg 69900
tatgtctgta ccataatttg tttattcatt ccccagctga tgaacattta gtctgtattc 69960
aatttggggc atttataatg aagctgttat aaatattcat acatagtttt ttatgtgaac 70020
atattgctta atttctcttg tgtaaatatt atggggagtg ggcttatgga gaattgagaa 70080
atatacatta atgtatctat aattttttttt ctgggaagat agtacacagc ttttgtcgga 70140
ttcccaaaac gggccagggc tcacaaaagg ttaggcccca ctgaccttgc tgcttcctct 70200
ggtttgtgtt gggttcttta agctctgtgg tctggctttc aagtggagca tcaaactgag 70260
aggcagcctg gcttaggaaa acaggcattg ggttaggatt gaagtgcttc ccaccttagt 70320
ctagtctttc actgtgtgac attgccagcc ttctttccct ttccgggacc ttggaaaccc 70380
tgtccattgg taaccagttt gatggctaag ctccattttt ccatcatgtt tcctagacaa 70440
cgccatgcaa gcttctgctc cagcccctttt ggagctctga ttcagacact aatctcaggc 70500
cctccaagga agcatcattc agaccttccc tgcttcctgc agaggcacat gtagtacagt 70560
acgtgaggct ttctatggag ctgctctcat ttttgttcat taacttctct ccctgggagg 70620
aggcatgcca gggagggcgt ttatcaagat gaggcacatg acaataggag caccagattt 70680
ccagtccctg ttttgttatc agaagttcgc tttccagact tgggcaaatc actttaatgt 70740
ctcttgctta aaaccttgac tagcttttca atgtttttgg ggacaaggac tcaaggcctt 70800
agagatcttg tgatctctct acatgtgtaa taaatatata aaccataata tagctgctta 70860
ttatcaagta tcatgcactg tacatgactg tatgtgctat acttttatat gcaactggca 70920
gcacagtagg tttctttaaa ccagcatcaa cacaaacaca ttagtaatgc attgtgttac 70980
aacattacca tggcagagat attactagac aataggaatt tttcagctct attataatct 71040
tatgggacca ccatcatata agcaggtcat tgttaaccaa aacatcatta catggtacat 71100
gactatattt tggtataatt ttatacaaaa aaaaattgcc tgacttttgc ctacctaccc 71160
agctcctact tccttgagtt cactcctttg tgcactccaa ccccactcac ctatctgtta 71220
tccttctgac acaccctatt gcctccttcc atttggcttt atcctacaaa gtttgctgtt 71280
tacaaagttt actctgaaat agaggtcatc attttgaaga ctagaaaacc aaggcacaga 71340
gacttacatg ccttgcccaa gtttgcatag tttgtaaatg gaaaagctgg ggaaaatcca 71400
cggaaacttg gctctggatt ccatgctatt gaccaactcc tgacttcctg ccctgctaga 71460
ccttagtggg tggtcatgaa ataaaggatg taggaacagt gtgccaagag ttctgttgga 71520
ttattttagc tgaaatctca taatggcttt ttatagaata ttaatgactt acagagctct 71580
ttgctctggg ttatggactt aggtttctaa attgtcatct ccttctagat aacttttcag 71640
gaacttatca gcacccacac aggactggat gtgcttttgg aaggtaccat ggaggctgat 71700
atggtgtggc tatatcaaat ctcatcttga attgtagctc ccataacccc cacgtgtcaa 71760
gggagggacc aggtgggagg taattaaatc atgggtgtgt gtttttccgt gctgtcctcg 71820
tgacagtgaa taagtctcat gagatctgat ggttttataa agggcagttc cccctgcacat 71880
gctttcttgc ctgccaccat gtaagaagtg cctttgctct tctaccatga ttgtgaggcc 71940
tccctagctg tgtgcaactg tgagtctact taacctcttt ttctttataa actactcagt 72000
cttgggtgtg cttttattag cagcatgaca acagactagt ctaatacaga ggctttgggc 72060

-continued ataagctatg ggcctttggt tttgaggttc tccaatattc agctgggaaa ttatgtacca 72120
ctaagatgag ttttggagaa gcctccttga gagtaattaa accagagcag caaaacaata 72180
gactcctacc tgtatggaaa ggacagagtc acaagtcaaa gcttcaggct gaacctttct 72240
tagcaaagtg agaagggtag atctgagaca aaggagcagg gatttttttt aggttgattc 72300
ctgtatttat gtaacttctt tctcctcaac agtacaggtt tcttcatgat acatgtcttc 72360
aagacagcat tggagtaaag gattctcagt ggccttgttt tattcaatgg catttagtaa 72420
acgtggggaa gggatcaaga gtccacatca gatcctggcc ctggagcagc ttttctagtc 72480
gggggtcatg atagctacag tctctctagt atcttctctg tgccatttaa ataaataaat 72540
cagagaattg gactcagaat ctgattctct gattccgctg agtcagttct tggccagggt 72600
catgaaactg gtaacttgta cagcctggac ccgtactcaa ggatgtgaga cttggagtgg 72660
gggttgagag gaggacagtt catgacaagc ctgacccaac atagtgctgt gcccaattag 72720
ctagctacac agataagcaa actgaggcta ccactgggtc agttcttggc aagggtcagg 72780
aagctgtaac ttgtagagcc tggacaagtg tctgtgatgt caaaccccgt ccatgtaact 72840
gctagttact atatgggaac tcaagtttat tacttaactg tattaagctt ccatttctc 72900
taagaaatgg gggaaaaaaa gcttttacct tggcttaaag cagttgcaag aattaaaaag 72960
ttaattcatg ttgtttattt atcagaatgc ctagcacatt ataagtctca gtataggaga 73020
attgtattat tcttaccatc atcaccatca ccaccattat ttgccaagag agaggtatat 73080
gcaaagtgct atagtggttc aaaggagggg gcaatcgctt ccaccaggaa gacagtggag 73140
ggtagtgtga ggataaatgt aaaacctgaa aatttaaact tgaacttgaa aggagactgt 73200
gtatgtggga attttggatc aaaaggggat tccaatagaa gaaacagctg agttaaagca 73260
aagcgataga acactgataa cgactatgaa tggtgaatag agcattttgg ctgattgctg 73320
tgtacctaaa tggagatgag ggtggaaaga tgcattgggg ggtaagactt tgagaaccaa 73380
gttcatttga gaaccaagtt catttgagaa caactacgaa tggtgaatag agcattttgg 73440
ctgattgctg tgtacctaaa tggaggtgag ggtggaaaga tgcattgggg gataactatg 73500
agaaccaagt taagggaagt gtcatgagca gagctatgct ccaaaaagat ttagcaggcc 73560
atctataccc attatgtctg gggtgcatat gagggagtta caggatgtga gacttggagt 73620
gggggtggag ggagggcagt tcatgacaag cctgacccaa cacactgttg tgtccaatta 73680
gcacgaccta ttttggcttt gaatggggaa ggagaatctg tgacctctga gtcagccttt 73740
atggaatgct caagacttaa caggtcttgc aagatgcatt ctctatcagt catagtactt 73800
taataatggt tccttactca gcttcattca ttcattggaa attcatgcat gtctttgtag 73860
tccataggat tctcagaata accttgtgac tagacgagag aaatattgac tgtgcgatta 73920
ctgaaggcaa agactgtttg tgatgcttga ttacttgatt tttgcatatc caacaagtga 73980
atgagtgagt aagtgagtga gtgagtgaat gattgaatct ccacttgact cctgaggcaa 74040
ctgagatgag gagatattaa aatatctcaa ggtgtcatta ttggacacac atatgactag 74100
gacttttgtt actttcatac ttctccattt acaatttctt aaaagagtac tttccaaagt 74160
atatacaatt taatgatttg aaatcctgct tgcggccagg cacggtggct catgcctgta 74220
atcccagcac tttgggaggc tgaggcgtgt ggatcacgag atcaagagat tgagaccatc 74280
ccggccaaca tggtgaaacc ccgtctctac taaaaataga aaaattagct gggcatggtg 74340
gcaggtgcct gtaatcccag ctacttggga ggctgaggca gaagaatcac ttgaacctgg 74400
gaggcagagg ttgtagtgag ccaaagactg tgccactgca ccccagattg gcgacagagc 74460

-continued gagactctgt ctcaaaaaaa aaaaaaaaaa ccttcttgct tttgttgctg ttttcttcct 74520
aaaagtggag ctttgccttt tcccttttaa gtcagtcact gagacagtat ttggttttgt 74580
gccctctgag agttattttc cagcccacga gccccacgtt ctgattctga tgtgagataa 74640
tggagcttag ccctcagaga tatggaagac accaattgtt tcgttctcta agtgttcaga 74700
aacaactgtt cttttctttt cttccttttt tacttcccct tacaagactt tcttttcttt 74760
gcctcaaaga gggtaaagga tggaagatag aaggaggaac tcaggttagt ctatggctca 74820
gaggccttga atagtttggg aaaaaaatta aacaacatga aactataact tctcattgtt 74880
ctctgctgct tccacctccc actgacagtg tatgctttcc atcaaatatg tgtaatattg 74940
gttgtggagc agatcaaaaa catctatttt ctctggaatg tacagtcagt caatcttgaa 75000
gaaggagcat cgtatcaaag aggtctgttg tcaaatacct acttcccccct ttctgtcctt 75060 tctcttcccc ttcaagggaa acaaatgtct gggttgcaga aaggcccttt catctcaaat 75120
tgttctcttt tcattagtgt cttggtttgg gcagggggta tggaggcagt ctactatgag 75180
tagtattgtt gaggacatga aatgttaaat aataagattt tacatttgta aagtgccatg 75240
ttccttgctt ttacagacag aaacttaggc tgctgggttt tgaacaatta agttgaggag 75300
ctatttggga tatgttgtat aaatcataac cgcttgttga agggtgtgct gaaatcaagg 75360
tgtgacctct gcacaattca gggacctcct cttgggcaag tctagagtcc cagccttgcc 75420
aatgcttcag aaatgattag attcaaggtg ccaacatcag gccaactgaa cccttgagag 75480
attgccctat aaactgttat tggagcagca tctgtttgcc agggtaaata ttcagtcata 75540
tggactgggc cctggagtct tcagatggtg cagcccttcc cagagggaag acttcatggg 75600
ggtccaaatg ctggtaagaa gtttttgttt gtctgtgtct gccatcacag catagagatt 75660
aagaacctgg tatttggaat cagacagatt tttgtgtatt atttacctgt tgctgcataa 75720
caaattgccc ccaaactcgg tgactttcta caacaatctt tgtttattat ctcttatgga 75780
tccctgggcc aagaattcac atggagcaca atggagaagg atggaagacc tgaaaactaa 75840
actgaaatca tctaaagact tatttactca tgtgagctgt gttggagctg tcagctgcaa 75900
cacttacaca aggcctctgc attgggcctg aacttcctca caacatggtg actgggtctt 75960
aaggattggc ctagataaag tcatggcaga gaccactcat ggaaagctat gtcaacaatg 76020
gaagatgaat ggccaggatg aagacagaga gagagagagt aaagaattcc aaaggttgcc 76080
atgtttgtct aaccctgctt cacagaacca acagacaaaa tctgtagcct cctctccttg 76140
tcagatctgt gtattttgta tgggaatgaa tatgtcagaa agtagtagct tagtgataaa 76200
ttatgcaaca gcctcttctt cattctaggt tcaccagtac tgccaaatta acattacctg 76260
agcacctcct ttgcccaaga atttttacaa gtgtaatttc atttaattct cacaacaacc 76320
caaagttata attttaattt tccccccttt ggattagaac ttagaggata tggaaacctc 76380
tcagtcaccc atatatgtaa actactgcta aaaaggttta ttttaaagaa gtggagctgt 76440
tatttactct catacattca cctattttag tttcagggag tacttctatg gcggacttat 76500
gtaatacctg tgatcgtata agaaagtctt ttggttcagg tattcttatc acattatcta 76560
acatatctgt gagacttacc tttgatctcc catgtcgtta tacttccaaa gccaccttca 76620
actaaaatct acactaaaca aagaaaagtg cttcaataaa tctgtgtttc taagcaattg 76680
tcacctttcc caaaaaagta aaatagcaat ttctatagct gttttttctt ttaatggctt 76740
tattgagatg tgtcacatac catatcattc acccatttaa agtgttcagt tcagtatttt 76800
ttagtatatt cacagatata tacattcatc gccataatct aattttaaaa catttctctc 76860

-continued ttgcaaaagt agcccagtac ccattagctg tcattcccca gcaccctccc accatcaggt 76920
tctaagcaac catgaatcta ccttctattt ctgtagattt gcctattctg accattttct 76980
atatatgaaa tcatactatt tgtggtcctt tgtgactggc ctctttcact tagcataatg 77040
ttttcaaggt tcattcatgt cttagcatgt atcagtgctt catcccttta tggtatatcc 77100
ataaaatgaa atattatagg actatagtat ttcattttat ggatatacca tattttgttt 77160
atccatttat tagttgatag acatttgagt tgtttttact ttttgactac tatgactaat 77220
gctgctatgg aaattctttt acaagttgtc atgtggccat atgttttcat ttttcttgag 77280
tgtgtaccta gtggtgaaat tgctgtgtta tgtagtaact ctatgtttag ccttttgagg 77340
aactgccaaa ctgttttcca aagtgattgc accagtttac attctcacca gcaatatatg 77400
agggtttcaa tttctccaca tccttaccaa cacttgttat tgtctgtctt tttcattata 77460
gtcattctgt gggtatgaag tggtatctca ttgtggtttt gatttacatt ttgtaacgac 77520
tgatgggtgt tgaacatctt ttttatttcc tattggttat tttgtatatc ttctttggag 77580
aaatagctct ccaattccct gccttttttt tttttttttt ttttttccag agacagagtc 77640
tcactcttgt cacccaggct gcagtggagt ggtgcgatct tggctcactg caacctccgc 77700
ctcctgggtt caagcgattc ccttgcctta gactcccaag tagctgggat tacaggcatc 77760
caccatgcca agctaatttt tttgcatttt tagtagagat ggggtttcac catgttggcc 77820
aggttggtct cgaactcctg acctcaggtg atctgcctgc ctcgacctcc caaagtgctg 77880
ggattacaga tgtgaaccac catgcccagc ctcttgtcca ttttttaatt tggttgtttg 77940
tcttatatta ttgaattgta agaatgtttt aacgtattct agttataagc tgcttatcag 78000
atatacattt gcaaatattg tctttttttt tttttttttt tttgagacgg agttttgctc 78060
ttgtcgccca ggttggagtg caatggcaca atctcggctc actgcaacct ccgcctcctg 78120
ggttcaagcg attctcctgc ctcagcctcc tgagtagctg ggattacagg tgtgcaccac 78180
cacgcccagc taatttttgt atttttgata gagacggggc ttcaccatat tggccaggct 78240
ggtctcaaac tcctgacctc gggtgatcca cccgcctcgg cctcccaaag tgctgggatt 78300
acaggcatga gccaccgtgc ctggccacaa atattgtctt ttattctatg ggttacctat 78360
tagccttctt tatggtatca tttgcagcac agttttagat cttttttgtt gttgttgttt 78420
agcttgttta tttgtttcat tttatgtgca gtactcactt ctgctttcat tcatttatgc 78480
cttgagtgtc cattatgtgt caggaacttt tctagacact ggtgatatgt cagtgaatag 78540
gatagaacaa tgtccttgct ctcctgaaac taatattcca ctcaagaaag gcagatgata 78600
aacaaataaa tcaaagattt cagacaatga taaatatgtt taagaaaatg aagtgagata 78660
atgaagtgga aaatttttat gaggcgtgtg tccagggtgg ggaggcagct ttaggtagat 78720
tcacactgtt ggcatttggg gccagataat tctttgttgt gttgtagctg tcctgtgcaa 78780
atatcctaca atgcaaggac agctgcctgt gtaaggatat ctgtagcagg atctctgacc 78840
tctacccact aggtaccatt agtacctccc tcacttgcta taatcgtaca aaatatctac 78900
agacactgcc aaatgttcct cagagagaaa aatcactctc aattgagaac cactcagatt 78960
aatagttgag aaaggcatct ccgagtgatg acctgaagac agagtccacc ttatgggaag 79020
cagtggagca aaagcattca agatagatgg taaataagtg cagaagcaag gtggggatgc 79080
acttgatgtg tttgagaata gaaacaaggc tttagagtga cagtgtggtg aataagggaa 79140
agaatagtag gagataaaaa tagagaggta ggctggggtc agattatgaa ggatctagta 79200
gacagtaata agaaatttgg aattattccg agtacagtat aattggaagc cagtaagtca 79260

-continued gggataaatg ggtgctctca aatataggaa ataagctgta gatttggggt tttgtcccac 79320
tttattttat tttgagtttt tgtgggtttt tgttgttgtt tttgctcaag gatccacaat 79380
cagagagtga tagagctagg actaaaaccc aagtctccag gctagtaagc tataggtctt 79440
tctattaaac acgggtgacg aagcagtcta catttattaa ctgtaggatt gcaattggcc 79500
gttactctaa ctgacctttc cctgaatcca ccttgtttaa gaattcctaa tatagtactt 79560
agcatttggc atgaaaatca aagaagatga actttagcaa gaagctaatc caaatctgct 79620
tcacagacca gcagcatcag catcacctgg aaacttgtta gaaatgcaga atctcaggcc 79680
cacctcaaac ctactgaatt aaaatctgtg ccttgatagt ccctagttaa ttagtatgca 79740
tgttaaagct tgagaagcac tgatctagtt tatcaaaata tcatcagaaa cagtcgagtg 79800
attcaaatgg tttttttaa tgggctttta ctgagtcaga agactaatga tggtgtcatc 79860
attaagctct cattataaca tctttttat tcctttcttt ctttggctca cagcaattct 79920
tcactcacaa agtcctatgt agtcttcctt aataacagca tacattcttt cctttcattt 79980
ctgcagccac cacctttgtc tttaccctca ctaatttgta cctagcttat tatagccata 80040
tcaaaattta tgccttcctc ccttcatgcc cttcattgcc tagagctctc cgaatctcaa 80100
acttcatatg gctttttctt gtcttcagag taaaattcac atttccaact ctgactttga 80160
aggccttcta tatcaaaact ccaaacacgt ttcccagaga atctgttgtg tgtatgtctt 80220
taagtccatg tctttgttca caccctggaa tgccctttcc catcctttct actgccttca 80280
aggctctgct gaaatcccac ttccatcagt gatgtcaaat ctacccagtt gcctacccag 80340
gttctacggc acttgttgcc tgtaccaatt attttttggt ggggggtct gatagcatta 80400
taatttcagg cacaagcaca ggtcttcata actaaattgt agttcatgga gaacagaggc 80460
cacatctttg tctgctccca ctctaatgct tagtaaggca ctaagcatgt agtaggtaat 80520
cagtaaatat tttgcctttg aatctgaagt tgtggagtaa tgcccagatt tacaagcact 80580
tcgtttctac taatttattt tctctaaggg tctatgctac agttcagcaa ttgtgtaaac 80640
agcattgttt ataaagccag ccatgggtaa gcagtctcag atcagctggg tggtaggcaa 80700
tggatgcagt ccagaatttc aggccaaata aaattgtgaa tctttatttc aagaaccact 80760
gtattctgtg ggaccaagct ctgttccggg tgtcagaaca ataggtatcc ctccctgctg 80820
ctgagcagct gtatggggca aaaagccccg attgagcctg gcccgcctga acctgggata 80880
gcccagatat aaaatgataa taacattgac ctgaattctg tattttgtta catttttgtg 80940
tttgcttagt acttctttct taaggttgtt ggcaagagca tctgctggta acttggctca 81000
gtgtgttgta ggtttttgta tatggtttgg gtttcctatt cctgggcatt gaactattaa 81060
gattcctgca gataggcata actacttaca gccttttctg tgtatatatt agctcttacg 81120
gacctcataa acctaaagag gtgcagagga aaagtgccat cattctcatt ttacaactgg 81180
ggaagcagag gcccagaaaa gtgatctaac tttcccaagt tcacaaatgt gttattagag 81240
ctgcaaccag agctaaggtt gaggctttat gaaccttagg ttactattcg gttaataggc 81300
tcagtgcagc cttaccttac taattattaa aaatagacaa cattaggatt taaaccagat 81360
ggtcttttcc tgttgttcac actcttaccc actgtcagca atggcccatc agataatcca 81420
cactgattca tgaaaaggca aatattttct gtttctgttc taagctaggc ttgccaaaac 81480
cgagagcaat attctctatc cccgagatgc attgcttcaa gcacctatct actttctctg 81540
caaagttatc cctttggcaa tggttcttca attctgatta tatctgggag agaaataata 81600
aacctattta gatgctaatt ggctttaaca tctcagtgag tcaacaggct catgtatgtc 81660

-continued ctacaagaag tctctcaaac ctggatcata cagctatcaa acagtgttgc tcagccacca 81720
acttcaaaat ggctcaatcc atttgagttt acaaagcatt ccattttata gcaaaggaca 81780
tctgtgctaa ggatagtgtc ttaaaggcta ggcttttgag gtggcaatta ttttcttgct 81840
gaggtttcag aatagacaat tttttttcct acattaaaac agagaaatga agagtctgag 81900
tattctagga agttcatggc ataatggtaa gcagataaat ttctgatatc cttctgaaaa 81960
ttaacttagt agctttgtga cctctggcgc cttatcttct ccaagcctcg gttttctcat 82020
ctgtaaaatg gaagtcataa tggtacttac aaggccaaaa tgatgactaa atgagaggat 82080
aaatttaaaa tatttagctc aatgcctggc acatagtaag tgcttcataa caattgagta 82140
ctagtattac tattatttat taataattcc tatagtcaaa tagaataagg agtccccctt 82200
gttcactata gatattcaga atgtccttct ctcaggcctg aatgagtaat tccttctgga 82260
ttactaatat caaaagtcca tttgtatctg attgagatga ggaaagaaat gcaggatgga 82320
gcagggaacc agtcctcaca ctacatggtt tactccagcg attctcaacg ttagcactac 82380
ctatgttttg cacagggtta gtctttgttt tggggggctg tcctgcacaa tggaggatgt 82440
tcatcagtat ccttggcctc tatccattat aagatgccag cagcaaacca acctcctcca 82500
agttctgatg accaaaacta tatccagata tttgccgact gggggcactt gcccccagtt 82560
gagagtcact aattacacag tacatttgtc catgatgggg acatgtaggc tcacggggta 82620
gccagtgaca ggcaggcaga caggagtggg gaattttttt tctgtaaagg ccccaagtag 82680
caaatatttt aggcactgtc tgtcccaact actaaactct gccatgtagc ttgaaagcag 82740
ccaaagacaa cacataaatg aacatgttcc agcaaaacta tttatgggcc ctgaaatttg 82800
aatttcatat aattttcatg tgtcactaag taatcttttt aaaattttta ttcaaccacc 82860
taaaaatgtt aaaactatac atgagtcgta caaaatcagg tggtgggcta gacttggccc 82920
atgagccata gttttctgac ctttggacta agaaatacat gaagccgtaa cttcatattt 82980
atccctaaga taaacatggg ataaatatga tacttctcct aacaccatca aatttacata 83040
taaattttag agaaagcata ttattttatt aaaatgagca ttgctatatt ttggaatagg 83100
acccaagcca aaatgaattt tagagataaa acattatatt ccaaagttat atcttgcttc 83160
ccatgggctg ttgacccatg cctcaggtcc ccagaggcct tcatttcctg ccttcatttt 83220
cccttgcttt taggctacct tggtaggaaa acttaagaag ttgccatgcc attttaagtg 83280
agaaactaag tcatataaga gccttttaga cttcccataa ctggttaccc ttagatagtg 83340
tccaataagg cacctcaaaa tattctaagt gctctagtgg ttgtctaata tatttcatca 83400
gagaatggtt gtgtaatata cgattgttta atccaaggtg gctcctataa atcctttttg 83460
aaatgttcaa gtatctctgt cacacacttg gggtatgagg tttattcact tccattgtca 83520
actaagcagc atgtgtaccc cacagcttga tgagtaccca gaaaatcagc aaatggtgtg 83580
ggccctactc tcaggaagct ggaatctgat ggtgatatta ggacctgctc atatgagatg 83640
acccgcaaag agtacaccat caagaaaggt gttgtggcag aaggagaagt ggagtggcaa 83700
gcgggaggca cattttctag cacctcctgt gcattcatcc tgaaggagag agttacttta 83760
cctttagata agtttttctc ttctgcccag agtgcttttt tgagacagat tctgagacat 83820
catccaagtt cagctgggaa gaatgccaca attgattaga gctgtcagcc gtggatggga 83880
gatcagggat tggctggcaa aagtgccagg gtgttgacag gcatagtctc agtcatctcc 83940
acagttcttc ctggctggaa atgcctctgg ctatattacc cttattgcat gatttcatgg 84000
tactgatcag atccaaagaa ggaggatgat tgtgagatgc aaagctcagg ggacgactac 84060

-continued gcggtgaagg tgagagaatg cccagagctt tgaagaggct gcttcttctt caaagctgtg 84120
ttccagcaga gcacattttg tgcatacttg aattttggtt ggctctaggc tgagcgcatt 84180
ctattgtggc gttggcatgg gaagagggag gcatgcgaga aatattgcat ctctgctatt 84240
ctcctgggcc cttgtgaatg ggaatgtctt cttaatgagc ctatcccaga gagtctggcc 84300
tttcagataa acaaataagc atcagcagga gatgctcaca aaaggactgg gcaaaatagg 84360
gccacgttga gtgacaaccc aaataaagga gtcctaagag gtctgaagct ggtggctaat 84420
gagcacatct cctcatttgt gatttcttgg ccaggacatg tattgttgag ggtgccagga 84480
aagtctgtct tattttatac aggaagaagc ctttctggcc tttgtcctgg tactggcttt 84540
tatattttat gttgggctag gggcctgcct ggaggacatt tacaaggtga ggagaaatct 84600
caagctgatt ttaacctaac acaattttct tatctttcta gtgatatata tcagttttct 84660
cacttgggaa atgggaataa aaatacaact cacctactag aattgttggg atgattaagt 84720
cggatgattc tcagaaagca cttcccacag tttccaatat gtagtcagca tctgatacat 84780
gttggctgca atcattatta gtaacagtat tatcatcatc attttcatat gtggaaagat 84840
accaaaagga gtgtccaggg gtgagggatc tagttccaat tctgctacca gctggctgtg 84900
agattttagg caagtcatct ctcatgtcaa ctgagagtgc tggacgggag tttttattca 84960
ttttgtaaac atatttggag gacctactaa gtgccaggct ctatttccag ggagcaaata 85020
tataaaggtg aataagacac attttctgta ctcaagagat cccaaaggta atggaggaga 85080
caggtaacac atgtgaccac atagcatgag aattgctctt actgtgtggc tgcatgccaa 85140
atgctcgtga ggcctggcac ggaattagca agactaaagg ctctgtccca gtccaacctt 85200
ctgtgagtct ataactgaag catccaaagt ataagctggg tgattagggg aagaagaagt 85260
cacctagctg gcaaggggcc taaaactcaa gtcccctcct tctaggacca gagtactcac 85320
caactaccaa gctgccttaa aataaaaaca ttcaagaaca agtgatgtgc agagaggcaa 85380
cacagtgata agtaactggg gtctggaaat gggagacttc aacttcaatt tcagcactgt 85440
tattttggta gtttaatgat ttagagtcag ttgtttaatc tcttagagac tcagttactt 85500
catcagcaag ggtgttacta tagtaatacc tgctagacat tattattata tggagagaga 85560
gagcttggta agctgtgaca tatacattct agttggtggt tgtttctgtt gttattatta 85620
atagtaacaa caataaatat cctgttgttt attttttga agtgttcagt ggctggtaac 85680
tgaattagag tgcctggaga tataggtaag ggttttttgt tttaataatc attatctttg 85740
ttcaagagaa taggaaaaat ataagcctct ttttaacttt aatgcaaaaa agtctttata 85800
gcttgtgtgt gaaaaacaag aggaagggag gaaggggagg aaagagattg tctatttcta 85860
cttaaagcta attagagaag taattttagg taagagtatt atgacctgat ttctgattaa 85920
tttaagtatt attatactgt tgtaatagaa atccctgaag tgctttattg attatctgtt 85980
ggtagaatga aagggtaagc agctgtagta aataaaattt ttgtctgagg caaagcaaag 86040
gagaagtaat ataggagaaa ttattataat aaagatggga gtgagagaag aaacctgggt 86100
tctagttctt tcagataggt gaccttgaac aaatctcttc cctatacttg gcctcggttt 86160
ccccatcgga acaacctagg gcatactcta gataatccct aaggtccctt tcagccttga 86220
caaactatga gatttctacc tgtacaatac tgaaacagtg attaagaggg agagacaccc 86280
acaaagaaag aaatagtttg tgctgtgctc aaatgcctga ctgataaaaa agagaacaga 86340
ctcataaaac ccactaattc aaattaaatg gataattctt gttgattttg agctggcaat 86400
ctcaggcttc taaatcacaa ggaaactcca tttgatcctg caatggtctc ttggtctctt 86460

-continued

```
tcttagctca gtagtgctaa gcacagaggt ttcatggaaa tcaagagaga aagagagaga 86520
gagagagaga gagagagaga gctgtttaaa aaaagaagaa caatatactt ggatgaacta 86580
aagagtggtc ctcatgaaag cctcataatg tccattgcct acctgtttaa ccctttgtgg 86640
cctgattttt ggtcctcaac tgaaatcaaa ttaggtagtc ttatgtaggg aaatgaataa 86700
cttgtacact gttgttgttt gccatcttta ggaccaccaa agggtaacga attcagcaga 86760
cccacaatcc ggcacttcag gtttttgaaa tttactcatg aaaatttagg aagtcctaaa 86820
ggctgtgaaa aatcattgaa cttcattggc aggcaggacc ttgctttcaa aactctatga 86880
ggctacaaat cagagattga aacctaaaga gggaacaggg ctttcccaga gtcacctgcc 86940
ttcccaggca gaactgggac tcgaagtcac agctagacta gaactccact gattccaaat 87000
ccagtataac caagtctcct gtggcctttc ccatgatctg gacccaaaga ctttctgatg 87060
ttccccaaaa gagttgtagg tgcactctgt tctctggttc tttgcagtgt aatggcagaa 87120
ctgaggttag aattctcctt ggatgtaagg atcaccagcc caccaggctg gcagttagac 87180
aagggagtga tggatttggg atgctttgtg tgaccttgta tacaacaggt tcttagacac 87240
aaccctagga catggaaaag aattacattc atcctgagcc ccagctactg ttaccaattc 87300
aaattaggac aacatattga ttaagataca ggtagttatg ctaccctaag aactggaatc 87360
tgaataccta ctttttattt ctacttctac cgcttgttag taacctattc ttgatccacc 87420
atttaacttc tgtgagcctc agtttctcca tctttaagac agtgatgata atgacagtat 87480
ctgtagaaca gcttaacttg aactaaatga gaaaaactaa acaaaacaca tagaattaag 87540
tatgaatttc tgaggttagt ttatacatgt tttaagagct tagagaaaag gaaaaaacat 87600
aagtatccta aggagattag gaaatgtttc cttggggagg ttggaaagca gctaagcctt 87660
gaagaatagg atgtattttg aacactggga gaagagatga gaaggtagtg aagtggaggc 87720
aatagcctgc actatccaga gacagtttct gattgtccta atgctatggg ctctctactt 87780
cagtttaaga aatattccaa tctttgatac cttcattcaa cagtcctttc tatttttcta 87840
atttcatttc ctgaattgtt tccctgcgga ggagtgggcc tacttgttga aataaatcac 87900
atcacagata cctcttttct tctcttttgt taaaagttct gttaaaatat atatattgtt 87960
aaaaaattaa aggttatctc cagataattc cccaaatgag taggcttagg ctttaatcat 88020
attatgttcc cttccttctt gctcttcact tgccaagtta tactaatgat cataatctct 88080
tctatgtgtt ttggacttta cagtgtgtga aggttttatt gccactgttg gccctctcag 88140
tgagctgatg caataattta ggttataatt gttggactct ttatacgaat gagttgctag 88200
agctttagag atgttgcctg acacgtagca ggctctcaat aaatattgga tggatggatg 88260
gatggatgga tggatggatg gatggatgga tggatggatg gtcctctccc ccctcgcttt 88320
cttgtgtgtt ggtgcccgcc tcgccgtttg tgcggtgtcc gttggttccg gctcctctct 88380
ttcgttcttc gttngtttcg tcctctcttc ttcgtgcgtg ccttctcttc cctcgcctct 88440
cgtccgttgt ctctttctcg cgtctcgctc ttctcttcgt cgcatctggg ttcgctgtcc 88500
ccttgtgcgg taccgtctct gttccttgcc tctttcgttt gtctcgagcg tcnctcattg 88560
cgccgtcctt cctagccatc gatatcgttc gtctggttct cgcgtcctct cgtgtcctct 88620
ctcgtgtcgt cgcgcatcag atctcgtgcg cgccccctcg ccgcttttct ctcttgtctg 88680
ctcacgcgat tgcgttgcgc tcgctttccc gcccgttgcc gttcgcgctc cgtcctcttg 88740
ccccatgcct ccccccagat aaatcannnn nnnnnnnnnn nnnnnnnnnn nnnnnnnnnn 88800
nnnnnnnnnn nnnnnntaac tccagcttca gcagagatcc caaggcacag aaagcaggca 88860
```

-continued

```
taccctgcaa tcatttatct ctgggatgcc ctggagcctg tcaaatggag atagggacca 88920
agatggtatg ttgtaatttt gtgatataga aaatctggtc aatttccatg aagcaaggcc 88980
ctcaccccta tggctgcttg tataagatac tgtccccttt tgtaccctgt gtagataatg 89040
tgtttggagt tcctccttta gttgagaaaa atagaatcct tgctcacttc catcccaaag 89100
tctggatttg agagggatca atgcttggtt tgcagggaga atatgcagaa caaaggaagg 89160
accagaaaac tagaagtcag aagacctaag ttcaagaccc aagttcaaaa cttataaact 89220
taacttattt attcattgat tatgtattga ttccttactc tgaggcaggc tttgccagac 89280
agtgagaaca cagtagtgag taagggggac aagacacctg acttcatgga ccttagttca 89340
agtggggtaa gagagaaaaa ttaaataaat caactgaata agcaagataa ttgtaagata 89400
aagattcccc aggcacagtg gctcgcgcct gtaatcccag cacttcggaa ggccaaggca 89460
ggcagatcac ctaaggtcag gagttcgaga ctagcctggc caacatgaca aaacccagtc 89520
tctactaaaa atacaacaaa ttagctgagc atcatggtgc gtgcctgtaa ttctagctac 89580
tcgggaggct gaggacatga aaatcgcttg aacctaggag gcagaggttg cagtgagcca 89640
agatcacacc attgcgcccc agcctgagca gcagagagag actctgtcaa aaaaaaaaaa 89700
aaaaaaaaaa aatgaaagta aagaagaaag aaagaaaaga aaaggagaaa gaaaacacga 89760
ttctctgaag aaaaaagcaa tacactgaga gaaggaaaca tgaaggtatt cgtttaaata 89820
gtgggtcagt gaatgccctt actgagtaaa agtgacattt aagcctagat ttcaatgctg 89880
gatggtattc atgctacaaa acaatttgga gaatattcta gccaaaaggg aataatttgt 89940
gcaatgattt gaaaaatgga aggacaacca gggtagctgg aatgtttatg gcaagggaga 90000
gagtgataga agattaaatc aggaaaacag agaaagtaac agatgaggca gtgcttgaca 90060
ggccatgaaa agaagagtga cttttatttt aagtgcatga gaagccactg gaaggtcaca 90120
agtagaaagg gatgtggtct catctgtttt aagaatttgg tccagtcggc tggccgcggt 90180
ggctcatgcc tgtaatccca gcactttggg agcccaaggc gggtggatca cgaggtcagg 90240
aattcgagac cagcctggcc agcatggtga aaccccgtct ttactaaaaa tacaaaaaat 90300
tagctgggca tggtggcgtg cacctgtagt cctagctact tgggaggctg aggcaggaga 90360
attgcttgaa cccgccaggt ggagattgca gtgagccgag atagcaccat tgcactccag 90420
cctgggtgac agagggagac tccatctcaa aaataaataa ataaataaat aaaagaattt 90480
cgcccagtca ctgaacttct ttgtgactcc cttttctctc ctgaaaacaa ggattaaact 90540
actgattgtc cttccaagag gttgtctgag tgtcagatca tgttcattat aatactttgc 90600
tccaagttgt gcttgataaa ttttgaactg aattgtttca taacaatatg aaaatgcttt 90660
ataaactgta aagggccatg caagtataaa gtattaccaa taaccatcat ttccccaaag 90720
ctctgactcc tttccaggag tttgtgtgga acaggtaaga taactggcca taaaatgctt 90780
tgaaaaccct atgctaataa aagatacttt atatttatgt tcatttgttt attgaagttt 90840
gcatttggtt cctttattcc atagcaccaa tgtattctct atttttgggc taggaaacaa 90900
caagcagact caagtgtgtt atttaacctc aagaaataaa aatatccaga gataatatga 90960
tgagtgaggc tgagagtcaa gtcagcaagt ctttggttag aactgggcac ttcttcactc 91020
tcttacctga gtagatggga gcttgtcctc attagtcata ggccccccgt tacttataaa 91080
gaagttgtga aaaataatac tgacaatgat gataatttga atgacacatg tttagtaatg 91140
catatagata tatactcatg ggtatgtata tacagtccct tgctactttt ctcaaagcat 91200
gtttttctca tctattgttt taatttagct cacactcaca tgcagaggta gagtaggagt 91260
```

-continued attccaattg gagaaatggc catgaagtgc ttaagtggtt tgcttcaagg tcacactgtg 91320
agtgatagag gagttgaaac caagtcacag agctccctag tcctgtgcca gcactctgta 91380
tcaagacccc tcagctcctg cggggccttg tgaaaaaaca aaaacaaaca aacaaacaaa 91440
caaaaaaaaa caggatcctg agcctcacat taaacaatta ggaactggag cattttcaca 91500
ctttagaaaa tatttgatcc atgtagccta gccctcttcc ctcatgtcac atacagggaa 91560
acagaggacc acaagtagga gcccacttgg gcaggtgagt tttctgccaa ctgctcaagc 91620
acctactgat gcttcagctc tctgtctttt aacctcatat gtagctggtg actaaggtgg 91680
atggagataa tgcagtagaa gtcaaggtgg tcccctctga ggaccatctt accagagagg 91740
gaatcacagt aggaagagaa ctcttcagtt aattgataat tttttctttg caatggaagg 91800
gaggtctctg tgaccttggg tctgacctcg agcctgacat gcctttttcc ctagccctct 91860
cttgctctcc cttcagggat ttgggcaagg taaatcttca agttcattta ccttctttaa 91920
aattgggcag ctttacacat tatcttggcc aatttgagcc taaaaagtga tgtagctcag 91980
aagcagtcaa gtttagttgg atgaacatga gtattaggct gggaagctca tgcccaagtg 92040
tgaaccttgt agccttaatc aagtgtctgc cttagagcta agcttctctc ttggtgaaat 92100
ggtttaaaat acccatccag tacatgtcct aaaatggaca tgaggttcct ctgggataaa 92160
ggatgagaag atactttgta ttttgtaaca ttctactcag atgcaggatg ttcatctcat 92220
taatattaca ctctggtgcc agtttctggg gggtcagctg cagagaagct agttcaggct 92280
gcaacatctc attagaagct gaaatttgga ttcaggaaga ggagcatgga gtgggtgaga 92340
gccactgtct gctgctcaag ttcctgctgc tatctgtatt cagagaggca tcctggtacc 92400
ttagcagtgc tgctcagtgg gacgtctctg actttgatgt tgcacgtgtc aacattctaa 92460
tagggcagca gccgagatgg ggtatgagtt tggaaagaca tcttatgaca gctttttcct 92520
aaagatgttt caagagataa ccctttagaa ataacgaagg tagtttatgc atttcatagg 92580
aaacccagcg gcttacgtag cagctcactt cgaagtctgg catgcggacg gcttcctact 92640
gtcccgtttt tgccctccct gcacatctgt gagaaatcat cacttgtcac agtaacacag 92700
tattgtattt agttacattg acagcaatgg tgaaaggact ataagcctat ttccttctaa 92760
actgttcaca tcaaatgaac cttaaacatt tactcctctc ttaaaatgta aatcagatca 92820
cctcagccta ctgtttaaac attctatcat ggctttccat catgaataga atccaaatgc 92880
ctaacacaag ctggatggta gcctgatctg acctttgctg acctctctga cctcccctca 92940
cacacagctc cccttgctca ctgtgcttga gccacactgg tcttcatttg tgctcaaata 93000
tgccaagttt tctcctacct taggagctac tattaaaata cctaactaaa gctctaaagc 93060
tcttcatgcc tgcaccactc ttttctaaga tatttcctgc ctgcctcctt cacatcgagt 93120
ctcagcccag ctcagccatc tcttcagtca gtacttcgct gaccttcccc tttggcccca 93180
ctcctacccc tctgtacatc tccattacat tgcctttggt aatgtcttct tagcacatat 93240
cgatttgttt acctattaat tccatgccat gagaggagag attctttctt ttctcttttt 93300
tttttttttt agaagggtgt tgttctgtca cccaggatgg tgtgcagtgg catgatctcc 93360
gctcactgca atctctgctc cctgcctcca aggttcaacc tattctcctg cctcagcctc 93420
ccaagtagct gagactacag gcacatgtca ccacgcccgg ctaatttttg tattttaagt 93480
agagatgggg tttcaccatg ttggccaggc tggtctcaaa ctcctggtct catgtgatct 93540
acgtgcctca acctcccaaa gtgctgggat cacaggcgta agccaccaca ctcagcctga 93600
gatcctttct ttcttatggt ctcctgaatc tctagcatgg aagaataaag gtgccgtagc 93660

-continued acagaataga tctattatcc aatgaatatt tgttggagga atgaatcaat cctctctttt 93720
tacagaggga gaagttagga ccagagaaga gtagacatca ttgtgtttct gaaggtttta 93780
tgttagcacc tttgggccat gctgggacct tggcaaatta tagcattcaa gggttttagg 93840
gtaatgttca tggatcccta gaaagtcagc aaatggggat cagggtgtct tgagccctgt 93900
gaaagtgttg gcatatttct ggggagaaga ttcatagctt ttattagtac ttcaaataga 93960
tatttgatcc attggtagca cccatcaatt tttcctttta attagcttag tttggggaat 94020
gtggagcgag cctaaaagag gatagatgtc tcagcaccac cttgaagacc tttcttcttt 94080
ttcactgaca gcatggttcc atcgttctgc ccctgaatac ggggacagct cctctttttc 94140
tattaccaga gcatatcttt cttaaattca ctatttccat gatgaatcta cagtgccaga 94200
agctagagtc tggaatcaaa gaattccaga gttgggagag cacttaattc agtgttcata 94260
aaccaaagtg tacagcagaa ttttctgggg agctttttac aactatgcgt ttcccactcc 94320
ttcccctgac ttttatttgt ttgtttattt ttgttagaga taagatctta ctctgtcacc 94380
caggctggag ttcagtggca cgatcacagc tcactatagc cttgaactcc tgggcacagc 94440
aatcatccac ctgagcctcc caagtaacca ggactacagg gggtgtgcca ccatgcccag 94500
ctaatttttg tatttttggt agagacgggg tttcatcatg ttgcccagcc tcatctcaaa 94560
ctcctgacct caagcaattc tcccacctca gcctcccaaa gtgctgggat tacaggcatg 94620
agccaccaca cttagctaat tgtagtattt ttggtacaga tggggcttcg ccatgttgcc 94680
cagactcatt ttgaactcct gggctcaagt gatccgtctg cctcagcctc ccaaagtgct 94740
gggactgcaa gtgtgagcct ctgcacccgg gtcccctgac ttttagaagt ggagtatatt 94800
aggttcctag tgtttctgta acaaaattcc acaagcagga tggcttaaaa caacagaaac 94860
tcatggtctc atagttctga aggatagaag tctgaaatga aagtgttgct agggctgtgc 94920
tctctctaaa acctgtaagt gagaatcctt ccttgactct tcctagcttc tggtggttgc 94980
catcaatcct gggtgatcct tgacttgaaa ctgtcaaaga actcctgcac tttaatttcc 95040
tcctctgtca ccacatggct ctttcccctc gtgtgtctgt gtgtcttttc ttcttataag 95100
gacaccaatc aaattgtatt aaggtccacc ctactccagt atgaccacat cctaactttt 95160
tatgtctaca atgaccctat ttccaaataa ggtcacattc tgaggtactg taagttgaaa 95220
ctttgttttc aggagatacc caaaacatga catgacatgg ggtatgggaa tctgtatttt 95280
ttaaaaaaac tccaccagtg attgtgttga gacacattgc tcttatacac atgcccttca 95340
ctgaaaaggt gagagaaact gagggctggg aaagggacaa gctcagagtc actcagagtc 95400
tcaatgaccc agactggggc accaagtatc atgattcccc caacattctt tctaatgtgc 95460
caagctgcct tttggagtct ggacctggtg atgctctcac tggtctccaa ggaccagcat 95520
ttaagtgaat atttccagtg gtccatgtct gccccaaggg gctacttact actccagtgt 95580
aactagaggg gcattagtgg atcttttggt caaatcaact gcctccatcc caaaggatat 95640
ggttttgggg caagttggac tactccagca gtcatggaca ggcaccccag cttcctccaa 95700
gttgtactca tgttgcccca aattactgtg gcggatggct ggtactatga tgaaattctg 95760
tgttatatgt gtgagaagac ttccttcctc atccatcact tacccagaac actaacatgt 95820
ggtatatatt aacacgatcc tctcttgggt tagcatgtgg gtgggttctt aggaaaataa 95880
attaacatct ggaaagacaa cccaagcctt gcccacagtg tttgagatgt tactcagtgg 95940
aaatattggt tgtcgtgccc aatttgtgtc ccctcccatt gtgtttttat gctggaagtc 96000
tgcacaatct gttgatcccc gtctcaactg gctccctcac agcagatgca tttaaagtca 96060

-continued cagatctcaa agtaagcaaa tctaaagtgt ttaatctatt attaatcagc tagttgccca 96120
aatgatagag ctctagggga ccctgaggaa gacatcaata tttatggcct ccttagggag 96180
tgcatatttt tctctctctc ctttattccc acctttcttg ccttcagatg agaatggaaa 96240
tatgaagcct gttatgtttt atgccattgt acaaggcagg aatgtcatgt tttgaaatga 96300
gatgactaca atgtggtatt ttatgtttgt ttgagaatat tagctgttag ggctgtggta 96360
acctctacca gattgggtta aacaaaagca gtctgcagtc catgataata caatggaaaa 96420
gcatagggaa cacaagaaac ctgggtgaac tttttcacaa acaattcatt tttctaatga 96480
ggcaactaaa gctcagaaaa ggaaagggtc ttccttgtga tcatacattc attttatcat 96540
tcaacaaacc ttaactgaat acctcctatt caacagtgca cgagctgcca ggaacaatga 96600
agtaagtatt aacagaaatg cctaacattt actgagcact tcttaggtgc tgggtacaca 96660
ctaagtcctt caagtagtct ctcctgctga aagtgctatt ccaagtgcaa gttggaacag 96720
caggtgcctt ggcaccaaag ctctatgtga ccgacctttc tgacctggcc tcacttcctt 96780
ccccctcccc tcatttctct ctcttctctc cctttatttt tcttttcttt ctctctctct 96840 ttttttttt ttttttttt tttttgagac agactcttgc tctgtcgccc aggctggagt 96900
acactgtcgc gatctcagct cactgcaacc tccacctccc gggtccaagc aattttcctg 96960
tctcaccctc ccaagtagct gggactacag gcacccacaa ccatgcccag ctaatttttg 97020
tgtttttagt agagacaggg tttcaccata ttggtcaggc tggtcgtgaa atcctgacct 97080
caggtgatcc gccctcctcg gcctcccaaa gtgctgggat tacaggtgtg agccactgtg 97140
cccggcccct gtcctcattt cttatgctcc agcctcagtg gctttcattg ttactgtttt 97200
tggaatataa atcaggctta ttgccccttt ggacctttga atcacctgtc catgctgact 97260
agattcctct tcccatcctc atttctggct actcatattt caggtcttag cacaaaatct 97320
ttttcagcaa tttcttgaaa gtgagtcacc ccattctcac ccattaagag atagtgacta 97380
tcgctatcat aagatagtca ctatctctta acaaacctgt tttagtgtca tcctacacag 97440
tgatgtgctg tcaaatcctt aacacctgag tctgatgggg tggtggtgag gagggggagt 97500
gtggtgagga gggggagtgt gctgatttca agcatttgcc aattttcatg atgtaaagac 97560
ctttactatg gctgattcaa tagttcaagc tatcagcatg atgtcactga atgagaagtt 97620
gggaagagat atacacagtc cactcttgtg agccactatg caccagctct gacatacttc 97680
ttgttgtctg aaattatcat atttatttgt ttagttgtaa ttcttttacc ctcctatgca 97740
atgtaagctc caaaggaaga ggaaccttat ttgttctggt tatggttgta tttctagcat 97800
ctggaacagg gccaagaata tgatagtaac ttaataaata actgtggaat gaattatgaa 97860
tgaatgaatg agaattctca caataactcg gttaggtagg tgctactatt atcctcattc 97920
accgagtaag gagactaaaa tgtggctaga gattaaataa cttgtccaag ctcacacagt 97980
cagtgcatgg gattgccagg atttgaatca aggcaatttt tctccagagt ctcttctcta 98040
aatcccaagt tatatgaatt taacaaagtc actcctcttg aagagctcaa agtctagaga 98100
agaaatagac acttgaacaa aaggggaata atgcacccat gacaatgaca aatatgtacg 98160
taatatacac tcagagacct cggtgagtga gaaccaggag agtggcatgg tgattaagta 98220
aggtaatatt tgatggagtc ttggaggata tcattggagt gctttttcca ccatgccaaa 98280
gttgcttccc acctggaaaa actgacatta tgaaatcttt cttggataag gaagagaaat 98340
caggctttac tcaaatgtaa agaaaagcac agaagcatta ttgagatggt ttgagggtca 98400
gccggatatt tcagtacaca agaaaactga tagtccactt gaggcacgtt tccagacagg 98460

-continued gtcttaactt ctcctcactg ctgatcttgt gacatgttct ctgatgaagg gctttttttaa 98520 gctctaggtt gaattgctca cccatttctg cttctgattc tttgcctcct gcatcaaaat 98580
ttcaggtggc tactcacctg ggatggtagt gtgatatagt ttggatgttt gctcccaccc 98640
aaatctcatg ttgaattgta atccccaatg ctgaaggtgg ggcctagtgg gaggtgtgtg 98700
ggtcatgggg gcagatccct cagggcttgg tgctgttctt ccaataggga ctgacttctc 98760
ataagatcta gttgttataa aatgtggcac ctcccccacc accctctctc actcttgttt 98820
ttgccatgtg acatgcttgc tcccacttca ctacccacca tgattataag cttccagagg 98880
cctccccaga agcagatgct ggtgctatgc ttcctgtact gcctgcagaa ctgtgagcca 98940
attaaacctc ttaaataaat tatccagtct caggtatttc tttacagcag tgcaagaaca 99000
gcctaacaca tagtgagtgg acagagtact attgcagtct ctgattgttc tagtagccag 99060
gcttgagaaa ccacagagtc atcactgaca actgccttgg cactccctgc ctcttcttct 99120
cccctcccca atcccaaata gctactaggt tcctttgtca ggtcttgcat catacctttc 99180
ccttcatctc cacagctatc attctggtcc aagatatggg tctattcatc cactcattca 99240
ttcaacatac gctgagttgt tgtctgctct gtcccaggca atgtggtagg ctcagggaat 99300
acaatgataa ccaaaagcag acatgactcc tacactcaca gatcctattt ccaggggggc 99360
atattctagt ggggcaagca gttgtaaatc aaataaccac ctgcataaat ggataatgcc 99420
actgtgatga aaattaccaa ggggagaagg acatggtgct gggggagtct ctaacagggc 99480
atttgacata atcaggaaca ccagggaagt agtcacattt ataccaaaat cttaggttct 99540
aaaaaatgag aaagcattaa ggtatcgaat ggaggaaagg tcattcctgc caattgaaaa 99600
gacatgtaca aatattcttc aatggaagga ccttagctcc tgccaggata gtgaaaagca 99660
ggttggtttg gatggggaca gagaacacag gcagagaatg atgtgggatc aggctgaata 99720
aatacggcag tgttagcctc tgtgtctaga tatttgaggg aatcaatttt tgcactccct 99780
ctataatacc tagtctcccc ttctggctca ttttgtgcac cctttgccaa attcctcttt 99840
ctaaagcact gggtttgtgt gtatgtgtat gcacgcactt cccccaaccc ccatgcctcc 99900
attactcctc tactccaaaa aatgtcagtt gtttttctag tgcctgcaat gtaaggccta 99960
agcccactgg catcaaagac ttctgtaatt tagcatcaac taaactttca gctgtcactt 100020
cccactgttg ggaaaccata taacatgatg ttagaacata gtgacagaag gagctttgga 100080
gtcaaatagc tgatgtaaat cttgtttctt ccattttctg cctttgtgac ctaggataga 100140
ttgcttaatc ctgctgagcc tatggtttta tacttttaaa ttgaaattat agtgtaaagt 100200
ttaaatcaga taattaaata aagccttgag cataatccat gatgtactga aagtaatgat 100260
taaataatag tctattagac tatacagcct actcactatc tctcattctt atctagtatt 100320
tactagctag ttaggcacta tttctattgc ttagaacaac ttctttcgca tctatccaaa 100380
atgtataacc ctttggtcac cagatcaata tcttcagctc cttcctttca ggtactatat 100440
attgcatttg cttcataaca cctaatacaa tgcatgaagc atgcttttaa taaacattcc 100500
ttggatggat gaataaataa atgaataaag aaatgaagta aaagaaagtc aatttttata 100560
ttattctaag tgagggaaaa aagagaaacg aatcaaaata tcttggaaat aaaattctgt 100620
tcctctctga gcttttgatt tgtttataag ctggggagca tgttgcttac catttattta 100680
gtctcacaag tatgttaaca tcatcaacat aaggtttatg aagtacttta tactgcctgg 100740
aggaaggatg gtatagaaat ttaaaatatt atatatgatc cttccaggaa gaaaaaaaga 100800
agcaatatct attctgtgag gtgcatcaat tttggatcac tctaatggaa gtgccccgag 100860

-continued cagttggttt atttcttcaa atgtgaatta atttatacat ttcaaagctc ctgatggata 100920
cttttcattt taattaagta catttttgcc aaatttcaac tttaaaaact caacaaattt 100980
gttcccacac ttgctttgta gaatttgcaa tattagatat aaatttatta taaaagggta 101040
tgttagaaac ttctcatact gaaatcggcc acccagcaac tttttcttag gattcaagtg 101100
ctctaacatg tgcttgcttg tttgtctgtg tgattcggtg gttttatttt gattttcata 101160
gaaaataata aatatgtctt gaaatgatca tttcattact gagtattgcc agaggttcag 101220
agtccttgtg tgcatctgca tttactctca ggttggcact ataaactgct actgcaattg 101280
tgataaacta tcgagaacag aaaaaagaaa atttgataca gaaataatgc atagtaaaat 101340
aatgctgggt gagggctcac tgacataata atgtactgta tggaaaaaga gggaagatgc 101400
tgttgaagaa actgaatatt cacgcagcgc acagtagttc aggtgtgctg agctcacaga 101460
atcaatgtga ttgcacagta ctatattgct gtcacaaatg gtgttttgga gtaaacaaat 101520
accattgttt ctaacattaa attaatattg gtgattcaaa atgtactgaa attataattt 101580
gtgtttgtct catttgtaaa tttcctttgg ttttatagtt ttaagatagc tataaataaa 101640
ggattgatct ctgacttcat gtttgtacat tttcaagtat cattatagta aatataattt 101700
gtcaacattg tggattcaga agaacagttt ccttcaaaaa gcgttcataa attacatcag 101760
ttcgaaaaaa ttgcattagt agatgatagt aaaagcctcc aagaaagtgt tgcattatgg 101820
ccaagcttta ttataccaag ttcacaaaac ataaagggag gaatcagaaa tgcagagaat 101880
ggcagatatg gaaacagcag ctttgcaggt aagagtaaaa tactgaagtt ctaagaggtt 101940
tttagggttg gataaaatgg aaaaatcaag actgagagac cgccagagtc ctgtgagtat 102000
tgttgatgaa ctcttaaaat gtgcaaactc aacaagctat tgaaatgtgt gtgtgtgtgt 102060
gtgtgttaca atatatgtat ctcttcttca atgctttgga gatctttttc ctacaggact 102120
acttctctaa tttaccaata acaggctttg tggaaatgat accaatttta aagaaattta 102180
ctttacacct atattttcct aaaaaaaaat ttgtgaaaca agggcatcct tattttacct 102240
cttcaaaact gttatctata ccaagttatc ataaaagcag taaacctgca tttgttagtt 102300
tttaaacttt attttcaact tcctatgtct ataaatgttt gttcttgttt aggatgtgta 102360
ctgtgcttgt tagaagaata ccaccttttt ttcttaccct tttaaagttg agaagattat 102420
ttgtaagagt gtgaaatggt ctaagcattg ccccttttaaa tgggggtatt gtgttaattg 102480
taagcactgc aaagtgggtt gctatattgt ggctgttgta ctcagtgtca aaagatttag 102540
ttccttcttg acccagtcct agttattcaa gagtcatcaa acagagatac acaattttaa 102600
attgtttttc agaatgaatc tgaagagagc gaagagttga gtggagaagt cagctagatc 102660
atccttgtct atctatgcag actccttccc ataatttttc cccaatctag tttatgccta 102720
attttatacc aggaatttct tcctgacctt ttaattgcct gtccttaggg catgaaaatt 102780
atgagtgtaa ttttacagac cattcttaac ttttcaaaac cattccaacg atattcatct 102840
aagaaatggc cagtgtttgt ggagcactaa tttgtcacgc agcattgtgc tagacattca 102900
agatatccca ttgagtatcg cacgaaaacc ctgaccaaca catccctata ccaactaggt 102960
cagatcctca ttcacaggta ttcataatac ataaaattcc cctgcatagc actaggtcac 103020
atgtaggcaa taattattta tcttgtatat gccttttcac tcaactgtga gctcctagag 103080
gacataggta aaatctgttt tgttcactgc tgaattccta gaacccaaca tagtatctag 103140
caccaagaag cactcaatag aagttggatg aactaaagaa gaaatggttg gtctaggaag 103200
gggttgggac cataagaagc atactgttat ttaagaagca aggaaggcat ttaaaaagca 103260

-continued cagaattgaa taaaggcaga ttcctgcagc aagaatgcca cacaagtcag aaagtaggcc 103320
agattattaa ctacaaacta aggaagtaga ataacctttt gtgattgcaa catgaaagca 103380
aaagtccaaa ccaagaatca tctcaaaaga tagaaagtat attaggaaaa catgctttaa 103440
ctgtacccgg aagaaaaaga agtgggctac ccccttttagt gtgtgaggag ggaaagcaaa 103500
tgactgattt caaaaggcaa aaacatctcg ggctttattc ttttgcccca ccttagtttt 103560
tctttcccag agtaaaggca gtgatattat aaaagcacac agcatccaga ggggttgggg 103620
aggagtatgg ccatgaaact aagggctgat gaaagatgat tttagaagtt ggttcttttc 103680
atagcaagag gctgtattcc ttgaactgtc caagccatgg cctgttgttt ttcagaactc 103740
acagaaggtg gtaaaggtca gagagtgtcc ctgaaactag tagatggctc tagattccat 103800
tgaattcctg ccaaggggcc tgacagcata gatgaattct actacttcca gcttcctcta 103860
gagttagcag agtccaggtt tgggagtcag gagacccaga ttctagtcct gtctgtgccg 103920
tggtctcttt gtggttttga gcatatcact ttatctcttg tatcctcagt ttcctcttgt 103980
gtaaaaagga gatttttctc atcactagtt ggtaggacaa ggacattttt aatttatttt 104040
ttctccctaa ataatgcatg cataacttac aaaatcaaat gttacttcaa gtcataagac 104100
aaaattcaac attctcttcc ctcctccctt tctatcttgg attccagctc tcatagggga 104160
tcactttagg ctctcttagc tgtttcttct gatattttac ctttgtatct cttgtattgc 104220
ctgttctggt ttgggctgct ataacaaata ctatagactg ggtggcttaa acaaaagatg 104280
tttatttctc agttctggag gctgggaagt acaagatcaa tgtgaggcca atttgggtct 104340
tggcaaagac ctgcttccta gtttacagat ggccaccttc ttgctgcatc tttgcatgaa 104400
agagagagga gagacagaga gaaattgagt ctctttctct tcttagagtc tcatcatggg 104460
gctccaccct cgtgacctct tctaaatctg attaactgcc aggcgcagtg gctcacacct 104520
gtgatcccag cactttggga ggccgaggtg ggtggattgc tcaaggtcag gagttggaga 104580
ccaacctggc caagatggca aaaccctgtc tttactaaaa atacaaaaaa ttagcctggc 104640
ttggtaacac atgcccgtag tcgcagccac tcgggaggct gaggcatgag aatcacttga 104700
gcctggaagg tggaggatgc agtaagctga catcacgcca ctgccctccc acctgggtga 104760
cagagtaaaa ttccatctca aaaaaataaa aaataataat aaatctgatt accccccaaa 104820
gactccatct tctaatccta tcccactaga gattagggtt tcaacttatg aatttgtgta 104880
gggggcacaa acatggagtc catagcaatg ccgtttcctg atttttcaat tttagatatt 104940
agtttttgac tgtactatgg cagatgcaga atattaaatt aatattcagt atttacgtta 105000
tgatgactaa ataaatacct tcacaaccaa gccaaatagc acactcttaa actttttgtg 105060
tttctgcttt attgtttttt gtttgtttgc ttgcttgctt gctttgttta ttttattctg 105120
catattttat cattgactca gatccaaaat ttctgagcaa accacagaat tcctcccagt 105180
tacaatcagg agtgtgagat gatctctcag ttgcatggtt ttcccagaga ccttcctctg 105240
ggagccccat tcagctgaag cctgacctgg ttgctgctgt gacctgcagg agagctatct 105300
tcctgggacc aacacttttc gctagttcag gctctcctat tctctatatc tcattcttcc 105360
tcattaccag ttatgctctc attttggcag aatgcatttt cccgtagttt cttaagaaag 105420
acaacatgag ggtaaatttt tagatcttgc atatttgaaa tagtttttat tccactctta 105480
aacttcattg attggagatg aaatgcaagc ttggaaataa tttttattca gaattttgca 105540
cacattattt cattatcttc ttttttccat tgtggctgat taaaaagtcc aatgttattc 105600
tgcatgctcc ttctttgttt gggatttatt gtcccttctc ctcctccaga agctgttacg 105660

-continued attatctttt tgtctctaaa gttctaactt caagacgatc gccttttttta attcacaggt 105720
cattcatggg gctagaaaga cattctgtaa gctttttcca cctgaagact cagacccttc 105780
agttttaaga gattttcttt tgtaatttat ttgatatcat ccttgccttc atttctgctc 105840
tttcatttgc agttccatat gttaggcttc caagattcta tttctttgac ttttatttta 105900
ttttttgggt gataccttca acttcgtctt tcagtatttt tgtcaactaa tatatttatc 105960
tactgcatta acttcctaga gttctttttt gctttttgat ttttccttca ttatagcatt 106020
ctattcatac tctagaatga gtgtatgttt ttttaatgtg ttcttttggt ccctaaattg 106080
tgcttgtttc ccatgattta ttttcattca tttgcttgtt aattttaatt tctccctctc 106140
cctcctccat atttagaggc ccttgactat ctgctcttat aagtaccaca aagccaatgg 106200
gctcttctgc atgcaagtag gaagatggcc agtaagtgtc ctctccctta ttctcagcta 106260
tacctggtga tcctaaccta gagtctaaat actttgtctt cttcagagtc cacccccagt 106320
cttctgcttg gctgaaaaag agggattacc tggctgcata ggctagggca ggggctctgg 106380
ggctttccac caggttttac cccatcccat acctcagact tcaaagtatc cagtgcttca 106440
tatttttaca cctttcttgt gatctgtggt tttatggctt tcttcttatt gactctactc 106500
acttcctctt cacagatggt tatttcagct ttcttcacct tgctaagtca gttaccttca 106560
tccactctcc atccttcaga tgttgtactt cctttgtctt ctcttccctc ttttaagttt 106620
ctctttgatc tgtatattca cacctatttt attattttgc tgtgatttat gtgagtttgg 106680
gggagatagc aaagataagc atgtatgttc cacatcacat gcatcagaca cagtgttgtg 106740
aaactgtaat ttttaaaata aacttttatt gtagttttag atttacagaa agttcacaag 106800
gttagttcag agagttccca aatactctgt gctccatttt tctcccctat gattaaaatc 106860
ttacattagt gtggtgcatt tgtcacagtt aatgaaccaa tactaatact aatacattat 106920
tattaactaa cactaaatac ttgtttagct agctctttgg aaagaagtca ctatgtccag 106980
tctacattta agaagtgatg agttacactc tacctctttg agggcagagt gtctatgtaa 107040
attatttcaa attattctga ctgggaaatt tgtttcttct cactatttat ttacatatcc 107100
agtcatttat ttatatcaat atggattcaa ggatatctat tttatacttt gggttataat 107160
tcaataccat ttcatttatt ttattgctca cattgtgaaa tgctttttaa ttgtaaacct 107220
ttatctaaaa agcaagatat gagttaaata atataatata atatatatat aattaatata 107280
tataatataa tgtaaatacg gtctacatct tagaaatagt tctttagtcc tttactaact 107340
aacaaagtgc tagacacaga atgctgggca ggcacatagg attggaacac taaatacttc 107400
tttggctaac ttagtgcttt taaatatata ttcagtcatt tctaaattcc cagtgtcatg 107460
ttccatgaga ggtcacatag atgcataaaa gctccctcaa ggactgtaac cttattaggg 107520
aaatacacat atatagacaa taaaaaaaaa aacaggtcaa cactgtcact aagtagcaaa 107580
ttatgtcatt ttcatagttt aagagtgaca gatttcatgg cctgagtgat caatttggat 107640
gcatccatca tggctggcat cccagaaaag gctgggaatg atttagacag agtgaaatga 107700
gagagtcttt taaccacaca gggtataaca agtatgcatc tattcttttt ggaatgttta 107760
aaaattatca aatcagaagc atcttaaaat tcacttttct ttgaaaaatg tatgcaagat 107820
ccagccactt tatttttgtt catatttggt tttcggctct gtccacatgt acatttcaaa 107880
atccaacaaa caattccatt gtttatacat tgtggcttcc agctgacaaa acccctttat 107940
acactggctc actgatcccc acagcaggcc tgtgaaagag gcagttacaa caggtattac 108000
atagagctcc attttgcaga tggggaaatg gaggcccctg attttcagga ggttgcacag 108060

-continued gtacaaatgg gagaggtgga tctagaactc agcactcctg actccaaatc caaggctctg 108120
ttcatcaact tggagcccct gttctgacgc tggaaaagct gggtggagga gaggcaggag 108180
agatggagac tctaaaaact cagtgttgtg gtttgttagg tctctggtgt ccttactctc 108240
ccttctcaaa tgaaatgtaa tatctcagcc ttagagatta aaatgggttg ccagttattc 108300
tccttccttt tccaggaaga ggggattctg caccactaat ctttgctagt tgaacaagtt 108360
gtttaatgaa aaatcatatt tgtttgctaa agctggtccc accggcaagc cggtgctagt 108420
gccactcagc tgtcatacag gctgatgggt caggcaagag gtggacgtag ggtctctggg 108480
aatggtctga gctcacccgg tcccgtggcc tccccaggca ttctgcacac ttggctgtct 108540
gcagcctcct ctgctaggaa tgaagcagag agagcaagca aacaccacca ggaaagcttc 108600
tttaaggtcc tttgaagggt tcactctgcg ggagactgac ggttttgaac atttcagctc 108660
tgcagagcct taagccctgt tttgaagggg cgctttggtc aatagaaatt tggtccttag 108720
aactcacttt ccctcttttc ctttgtatac ttcaactctt agtacgttca gggactacct 108780
gaatatgaat tggttattga gactttcaga ggcaggatct ctgaaggtct gtgccatgga 108840
tcctgcaccc cattttgcaa ttttgcatgt tattcttctt tctaggtttg tggcccaatt 108900
aggggatcac caaatctttt tcaagaactc aggttctata ggcagactgc cagggtttgt 108960
attctggttg cttcatttca catctatgtg gcctcagacc agttatttaa agcctaggag 109020
cctcactttt ctcatctaaa aagaagcaat gagttcttgc ttcagaggat gattgagtat 109080
tcagtgagat aatgcaatgg tccctagtac atagaagcac tcttaaaata ttaacattag 109140
ttttacctat tattgaataa actttgctat ttctgagtgc caaaggaaat accaagatgg 109200
ctaaaaaacc atacttgccc tcaagaaaat cacagtctag ctgggtccag tggcttatgc 109260
ctgtaattcc agcactttgg gagataaatg caggagaatt acttacacct aggagttcaa 109320
gacaaggctg ggcaacatgg caagaccccg tctctaaaaa aaaaaaaaaa attaattagc 109380
ctggtgctgt ggcatgtacc tgtagtccca tctactcagg aggctgagtt gggaggattg 109440
cttgagccta ggaggtcaag gctgcagtaa gccatgttca tgccactaca ttccagcctg 109500
ggtgacaagg tgaaactcag tctcaaaaag aagaagatca cagtttagaa gcagatctag 109560
agaatgacat gtaaataaca gattacatat ataatgacca ttgtataaat gtgattttat 109620
atgtataatg attatatata gtggatattt tatataataa tatactatca catgttatta 109680
tatattatgg caattatata tataatcaaa tatactaagt cttgtcaaag tagtatactc 109740
aaactacttg ggggagggag aatgcaagaa taggaagagc acatcctgtc agtgctgtta 109800
cctttgattt gattctgatg gtttcagaaa ggaagcacct gactgggttc agttaaatta 109860
tgggttgagt ttagtaccta ttagaggaaa gggaaaaata aaagcaaaga gactagcacc 109920
aaattaaaag tatattttag gaacaccaga caatccattt gcagttacac aggggaaaaa 109980
gtaagaaaaa tataatagat aaggtggaaa agcagtttat gcttagaatc tggaaagcct 110040
tgaatgccaa gcagcagagg tgagggaagg actcagatcc taaggtggtc tcgtggagaa 110100
ctgagtttga caatcttact tattagcctc ccttaactgc cttccttaac tgcctttgga 110160
tctgtatttc cttcttagga atttcttgtt tcttcctttc cttatagcca atatttattg 110220
ggctcttgag tttatgatat ggtccactga aaatctacaa tctatctgtc caatgatact 110280
ttaacagaat aaaatgaagg ttaaaccacg gcagcttttc tcactaacat tcaataattt 110340
aggtttaata aagcttccgt ggagtggggc tattttgttt aggtttttta ttgtatttta 110400
ttttatttga gacagaatct ctctgtgtca cccaggctgg agtacagtgg cacaatctcg 110460

-continued gctcaccgca agctccacct cccaggttca tgccattctc ctgcctcagc ctcccgagca 110520
gctggaactg caggcgcccg ccaccacgcc tggctagttt ttttgtattt ttagtagaga 110580
tggggtttca ccctgttagc caggatggtc tcgatctcct gacctcatga tccacccacc 110640
tcagcctgcc aaagtgctgg gattacaggc atgagccact gtacccggcc agggctgttg 110700
attttatata atttccttcc tttttggctg attgaagtcc attgctaatt ctagtttgac 110760
actttttatt acctcaacta gattattttg tccagaaagt ttactgagca tcttctaggc 110820
taagcacttt agaaagtatg aaagaagttt aattcacaat acttatccta aaagatcaca 110880
atcttgctga tggcacttag acagtacagc aatcccttga tatccacagg ggtttggtac 110940
caggactcct acagatacca acatctaggt atgtttaagt cctttatata acatggcgtg 111000
gtgtttgcac ataacctagg cacatcctct cacatacttt aaatcatctc tatattactt 111060
ataataccta atacaatgta aatactatgt aaatagctgc cacactttat tattttgatt 111120
gttatgttgt taattttatt tttaatattt tcaatctgca gttgtgaatc tgcaaacgta 111180
gaacccacag atacagaggg gcaactgtac tcaaattatt tgagagtggt gcaagcccgc 111240
cagtgagttt gtcaccagtt gagaagactt aaacgactaa ctctataata tagagattta 111300
ttctgggtgg tcaggaaggg ccaagatcat agatagttaa agatccagag aaaatgggac 111360
tttgaagtaa atgaagggag gggaaaagaa aaatgtgcct gagaaatagc ataagtaaaa 111420
gtcctgaggt acatggtgga gtcacagggg aaaggaagaa ggctgtcggc ttgactaaag 111480
tgtgtgcagg gagatgaagc cagctagata aggtggacac ggaggcactg cgcaccttgt 111540
tgccaaatag cgccggtcgt cagagagtct acagtgagag ccatctcttc ctgtttgtaa 111600
tagaagtatg gagtctggac ccggcgcggt ggctcacgct tgtaatccca gcactttcgg 111660
aggccgaggc gggtggatcg cgaggtcaga agattgagac catcctggct aacatggtga 111720
aacactgtct ctactaaaaa tacaaaaaaa ctagctgggc gtggtggcgg gcgcctgtag 111780
tcccagatac tcgggaggct gaggcagcag aatggcgtga acccaggagg cggagtttgc 111840
agtgagccga gatcgcgccg ctgcactcca gcctgggcga cagagcgaga ctccatctca 111900
aaaaaaaaaa aaaaaaaaaa aaaagtatgg agtttgtaag gataggtttt caatcagtag 111960
aaaaagagaa atgccctcaa atccagaatt tatttaggaa agaaatagcg cttttccacc 112020
caggtttttg actgtggaaa gtcaaaggag gcacctgaaa tttcagacca ctatacccaa 112080
agcacctaca tacatagaaa atggtgatct caagcctcag agtgaaaaat gaacatccca 112140
gggagaccaa agaggagaag tgcctgtctg tttcttgcca ggctgggggg ccaaagggaa 112200
actgggagaa gaagcagaga cacgtctacc accatggaac cttgctgcta aaaattgatt 112260
tcagagtttc cttatgtctc acagcctggg aacttgaatt aaatgagctt tgcacagaga 112320
ttgccaaccc aaaagacctg ggaggtgaag ccttctgttt atttcaagtt taactgtagc 112380
ttcagctgtc agagcagcat cacatcttgg gatcccacct ggagcatcct agcctcgggg 112440
cacttcttta tctcatgagg aaggtggaag tctgagctga tcagatgctt gatgatgaag 112500
tggattcctc ctgaggtaga aacttcctct cactggaagt tttcaagtag aggaccactt 112560
tgcagggaca ttgtcaagaa aattcattca ttcgctggat gaacagaatg atgataaaca 112620
gctaacaccg actgagcaca tgctggtgcc agaccctgtg tttagcactt taagtatttt 112680
gcttcctatg tctccatgag ataagagatg ctgttatccc cattttacaa gcaagaagcc 112740
aaaacctcaa agagtttgga atcttaccta agatctcata actcataagt ggtaaatatt 112800
taaaccaagt ctgtctgatt ctgtgatcca tattcttact ttttaacttc ttatttccag 112860

-continued aaaagtgcac taaagcccac atacttcaca aagagacttt ttttaatatc ttacagccct 112920
gctgttttat aatctcactg ctaaagatga aggcattttt ggtttctgac cttttgctgg 112980
gacatgaagg tcttgggatt aaggttcata tactctcaca tgtgtgagtt tcatgtcctc 113040
agtgcccatg tctaaaagca aaagtgaaaa ttaaatcaga gcggaaaaca cctctctatt 113100
caacaccaga ttgttagggc tgagctgaaa agctcctaag taaactagtt catggccaag 113160
tggccagaga acaaattcta ggagcctgaa atgtgagatg ggagagccag tttgcaaccc 113220
caccttgttc acaggatgat ttcaggcagg ttccttagat gactgaagtt tttgaattgt 113280
aagggacctt agagagtcct aatgcagatt gttatcaatt atgctgtaca gaattataga 113340
gttcacaact tattctgcaa atattcattg tgaacttgct atgtgcctag tattggccag 113400
gagatgcctc cagggctgct agaaaggaga aggaggaaca ataggacaaa gttgttctct 113460
catcctcact tctttagctg tgccctccat tgtctgtgtc atgtcagcat tgcagttaag 113520
acttattttg aaaaggacac tatataccaa aggactataa atcatgctgc tataaagaca 113580
catgcacact tatgtttatt gcagcactat tcacaatagc aaagacttgg aaccaaccca 113640
aatgtccaac aatgatagac tggattaaga aaatgtggca catatacacc atggaatact 113700
atgcagcctt aaaaaatgat gagttcatgt cctttgtaga gacatggatg aaattggaaa 113760
tcatcattct cagtaaacta tcgcaaggac aaaaaaccaa acactgcatg ttctcactca 113820
taggtgggaa ttgaacaatg agaacacatg gacacaggaa ggggaacatc acacactggg 113880
gcctgttgtg gggtgggggg agtggggagg gataagcatt aggagatata cctaatgcta 113940
aatgacgagt taatgggtgc agcacaccag catggcacat gtatacatat gtaactaacc 114000
tgcacattgt gcacatgtac cctataactt aaagtataat aataataaaa taaaagaaaa 114060
taaaataaga aaaagacact atatagcttg aattgctctt agacagcaat gttctattct 114120
aacactccca tttgatagat gatgaagcca aaaaagataa agtaatttgc ccaaagtcca 114180
gccatcgttg ctagctagtt gccactttac cccagtacct cctacagccc tgggctacag 114240
ttcccacatc tctacgatgg aggaagggga acagactctc tctagcagtc ttttccaagg 114300
ccaaagtgtt ttcattttct gaatttcttg aacatccact gtttggccag tattgtcctt 114360
agctatctaa tagtcacaac ccttaagttc ttttctttct gtccctcgtg ccctttgtct 114420
tcaggctggt aaactgtcat agatattgat ctgagctttg tttaatcatg ctaagcttat 114480
accatgggtc ccagggaaac taggaagatg aacagtatat aacaattaca attaacttgt 114540
catttagcat taggtatatc tcctaatgct atccctcccc tgtcccccca ccccacaaca 114600
gtccccagag tgtgatgttc cccttcctgt gtccatgtgt tctcattgtt caattcccac 114660
ctatgagtga gaacatgcag tgtttggttt tttgtctttg tgatagttta ctgagaatga 114720
tgatttccaa tttcatccat gtccctacaa aggacatgaa ctcatcattt tttaaggctg 114780
catagtattc catggtgtat atgtgccaca ttttcttaat ccagtctatc attgttggac 114840
atttgggttg gttccaagtc tttgctattg tgaatagtgc cacaataaac ataacgtgtg 114900
catgtgtctt tatagcagca tgatttatag ccctttggct atatacccag taatgggatg 114960
gctgggtcaa atggtatttc tagttctaga tccctgagga atcgccacat gtgccctaaa 115020
acttaaagta taataataat taaaaaaaaa cagttaccag tatttattga gtgcctaagg 115080
tagtaaaggc ttgagaagct ggagcctatt ttcataccga atatgtaaat atcgacatct 115140
ctgctctaga agatctagga cactctggaa aagtgtctgt atatcttata ttaggagtag 115200
tggcctcacc aatgtggtgt catggttagt aaaggacagg ctgagtgaac aagaagggac 115260

-continued tgatcatgtc tttgccagtt gccaccgcct agctacgttc ttgggcatgg gacctaattt 115320
gtccagcctc aactttcatc tgtgtgacag gtccaataat tccccatacc acagggatgt 115380
tgtgatgatt aaatgataag cagagatttt agtacaggat tggatatata gtaagctctc 115440
cataaatggt aatactatta ctatacatat acatgtattt tacataccta tatatattta 115500
catacattta tgatctagtt tataatctcc aatatgcctt ggaagcttca gaatgagtct 115560
tatttcattt ttgtaatgtt actatcatac acagcaataa cagaaacaag ttctaaaatt 115620
tctccctgga gctttacttc aggagtttgc taccaattag aggggtgggg ggaagaggaa 115680
gagatgggag aaagagaatt tcacctgttt tagtctctat atacaaataa agtgggtgac 115740
ccctaacttt gccaagctct tgcctcagaa tgaaaccaca cccagtgcct gtaacttcct 115800
aatcaaacac gtgagttacc ttcaagggtt acaaaatcat agttcatgga tgaaatatgt 115860
gtggcccaaa cagaattcta atttgttaaa aaaaacagtt gctaaccttt caaaatacaa 115920
gaatttcatt tgaaaatcta ggtttctgtc ttctcactta cttttaactt tcttaatctg 115980
acctacatac tcaaggcaaa actatatagc acactgtttt atcacaaagg taacactcag 116040
ccaagtcaag aattgtagcg ttgtcagccc ccaggaatgc tcttgtgccc atccctagct 116100
ctatacactg tctctccaaa cagaacctct atcgggattc atcataacat ccttgttttt 116160
ctttagaact ttaccaccta agcatgcatt tctaaatgtt agagtttaat tttgtctaca 116220
ttttggaatt cagaatatac tcctgacctc acggtaggaa aaatcttctt aaacaaaata 116280
taaaaccatc cataaggaag aaactgataa attgaactgt attaaagtta acagtttctg 116340
tcctataaag caggagatac cattaagaga gtgaaaatgc aagctacaga aaggaacact 116400
cacatttaga atacctaaaa tcagtttaaa aagaggagag acaaccaagt agaaaaacag 116460
gcaaaaggtg gccaggcgca gtggtcagga atttgagacc agcctgacca acacggcaaa 116520
accccgtctc tactaaatat acaaaaatta gccaggcctg gtggtgcaca cctgtaatcc 116580
cagctactag ggaggctgag acaggagaat cgcttgagcc caggatgtgg aggttgcagt 116640
gagccaagat tgcaccactg cactccagcc tgggtgacag agtgagactc tgtctcaaaa 116700
aaaaaaaaaa gagatgagct attaacactt aaaaaggcac atcaacattt caataagcat 116760
ccagtatgta tttatgtgtg tatctgttta cgtttgctta atataacact cataggattc 116820
atcctcatga ttgtagatag gtgtagttta ctcattttca ttcctgtata ggattctatt 116880
gtatgagtat gccaaaattt attcatccat aattctactc ttgatggaca tttgggccgt 116940
ttacactttt gaataatgag tctataaata ttcttgtata tgtgtctggg tgcacatgtg 117000
cacatatttt ttgttggata taaacctggg agtgttatgt gaatgttcag ctttaataga 117060
tactgccaaa tagtttttca aagtagctgt accaatttac actcccacca tcaatatgtg 117120
acaattccca ttgctccaaa ttctctcaaa cacttgggat tgtaagtcat tttaatttta 117180
gccctcctgg tgggggtgta gtgataactc attgtgattt taatttgtat ttctcttgat 117240
tatttgtgag ttttaacttc atttcatgtg cttattgaaa tgctgatatg ctttttttaag 117300 tgataacagt taatacctttt tttaaaaatt gattttaggt attctaaatg tgagccttca 117360
gtcaaatgtg tatgttgcaa atatcttctt cctttccata gcttgcattt tcactctctt 117420
aatggtatct cttgctgtgc aggacagaaa ctgttaactt gaatgcagtc caatttatca 117480
gtttcttcct tatggatggt tttatatttt gtttaggaaa acttttccta ccctgagatc 117540
aggaatatat tcttctatat taacttttgg tggccttatg tttttccact taaattaatg 117600
atccatctgg tactgatttt tatttagggt atagtatagg ggtctagaat caatttttct 117660

-continued acatagatat ccagttgtca gcatcattta ttgaaaagat caccttttct ccactaaact 117720
tcagtggcat cttggtcata aatcaagtga ccaagtatgt ctggttctgc ttctggtctt 117780
tcttttctgt tccactggtt tgtttatttc tcaggtactt agatttaaac tgagcctttg 117840
tatctggaac aggaagcttt tcccctttttt caaaattgtt ttggctatta ttagaccttt 117900
acatttacat acaaatttta gaaccagcat gtcacattcc aaataaaacc tacagaaatt 117960
ctaattggga tataatttaa ttacaatcag tttgggagag ttgatatctt tacaatattg 118020
agtcttcaaa tcccagagca tagtatattg cttcaattat taagatcttc ttttattttt 118080
ttcagtaata ttttgtagtt ttcagtacag atcttttgtt agatttattt tgtaggtatt 118140
caatgttttt tgatattata aaaagtgttc ttaaaatatt atgtcataat tgtttggcgc 118200
tggtaaatgg aaatacaaat gattaatttt atattgattt tatgtctcgt gaccttgcta 118260
aattcacttt tttctacagt ttttctttct gtgaatacag tcatgtcatt tatgggtaat 118320
gagagtatta ttttttcctt gccaacttga ccataatatc tccttattca gtttgttagt 118380
actttaagat gtttttcatc ctgattatga aataataaag tatgtgtaat tttcttttct 118440
tacaataccc ttgttcaatt tggtattcag gttatgctga cctcaggagg aaaataaggc 118500
agtgctccct cttcccattc tttaaaagaa tgatataaac atatcacaaa agatatatat 118560
atatatatat atatatatat aatcacagtt tctttatcca ctcgttgatt gatgggcatt 118620
tgcattggtt tcacattttt gcaattgtaa attgtgccgc tataacatgc atgtgcaagt 118680
atctttttca tataatgact tgttttcctc tgggtagatt tataatctca ccttctatac 118740
tattgacatt ggtggatttt ttgcttggtt gctctcatat tttctctcaa attattgagg 118800
ggttggtttt gactttgttt atcttgtcta ttgtacattt atttcattaa cttctacact 118860
ttatttactt cttcttttct atgtttaatt tgcagggctt tttcctgact tcttaaaatg 118920
gatgcttggt tcattgattt ttttcatatc ttttcttctt ttctaatata tgcatttgta 118980
aagccttgca tttctctcta aagatagact taaccacatc actattttct tggcttgttt 119040
cagatttact aaattttaaa tttttttgac tttttactcc tgtattaatt tgaatattag 119100 gcaccccctta actgttcttc tagtgcttac actgatgatt gcaacattca ttcttggcat 119160
atcaaatgtt attgtaattg ccacttacac ccttttccca gatggtacaa agaccttgaa 119220
tacttagttt tatttattta actgctaatg tacatgttat tattgttgca taatttttat 119280
atttttacag tcgacaatat ggtattattg ttgttgctgc tcttttattc agtcagcatt 119340
atttatattt acccatatat ttataatttt tattaccttt tattctattt gttatctcaa 119400
agtttccatc tggaataatt ttccttcttt gtgaataata tcattctgta tttccattag 119460
tgtgggtctg ttgttgacaa ttttttttct ttttctttgc atcaaaatgt ctttatttta 119520
cattctctat ggaaaaaagt ttttgttgga tatgtagtct acatcacagt tattctctgt 119580
cagcacttta aagatgtaat ttagttgttt cttgtgaagg gtcagctgtc tgctttattg 119640
ttgatctttt gacagtaatc tgtctgcctt tgccccactt ccaggtacag agttactgtc 119700
tttggttttc agcaattttg caatattctg gttagttgcg attctttttt ttaatttaac 119760
atcatttggg tacattggac ttctcaaatt tgtgtcttga tgtcttttgt caggtttgga 119820
gagcttttgg caattaattc ttcagacatc atttatgtgt ccttcttttt tcactttatg 119880
aaatttcatt tacaatgatg ttaaggtgtt tcactgtaac ccacattctt ttccatattt 119940
tctatcattt tctctttata tgtttcaatc ctgttatatt cttctgatct atcttgatgt 120000
ttgctaattc tctttttggc tgcacctaat ctgccattgt tcctgtctat tgaattttag 120060

-continued atgccagtca ttatactgtt caattttgga aaatttttcg tggttctttc acatggtttt 120120
cagtcctctg ataaaattat caatccttca tttaatctcc tgggagatag taagcatagt 120180
tgattatgaa atttatgtct gtaatgtctg attactctat tatcttgagc ccctgtgggt 120240
ctattcctat tttctctgct tttctgttca ttttaattta tgttgtctta tcttcctgta 120300
taacagtttt tttttactgc gttctggaca ttgaatttgc aaaatttctt tgcagaaata 120360
atttgaggcc taagctgatg ttatcttttt ccctagtaga tatatgtttg cttgctgcac 120420
tagtactcca ttatcaggtc aatccaattt cagggattga gatgatttga agctacactg 120480
caacccttac tagtacctgt ctatttccag ttcagcctta ctcctattgg gcagcccttc 120540
tgagtcccag cctaaagttg ggtttaacaa gcttccccca ctgcaatcac catattttgg 120600
tcctggactc caaatttcat ctttctattt ctggcaagct cttaaatgag cttcctctta 120660
gttgtttagt tgcttactct agaattagta aatatcccca aggtgcaagc agctccaaac 120720
acaaaggtta cctcccgggc ttcctccatc cttagatccc agccctgcta ttctttgctc 120780
ttttgttagc tctcctacat cttcaagtag atttgtaaat attttgccca gcttttcttg 120840
ttgttctcat tgggagtatt cgtccaaatt acatagtctt tcattaacac aagaggaagt 120900
cctgttcctg atcttgaaaa aaatgataga tatgtccaca ataggctgaa acaaggcagt 120960
gatttctccc ttcatatgag gaatacattc tcccacaatg tccagctagc ctccttctca 121020
ttcaccttag cccagtgact ttggcatttg ggattcagac tcttttcctt tttttttttt 121080
tttttttttt tgagatggag tcttgctctg tcacccaggc tggagtgcag tggagcaatc 121140
ttggctcact gcaggctcca ccttccgggt tcaggtcatt ctcctgcctc agccttccga 121200
gtagctggga ttacatggcc caccaccaca cccagctaat ttttgtattt ttagtagaga 121260
cgaggtttca ccatgttagc caggatggtc tcgatctcct gaccttgtga tctgccggcc 121320
tcggcctccc aaagtgctgg gattacaggc atgagccacc gagcccagcc cagactcttt 121380
tcttaaatat tccaataagg tacaatttga tcatcctagg tttctttcct ctaagtctgg 121440
catgatatgg ttggtaaatg gaggttaact attttattat tttgctagag aagaactcct 121500
aaagccccta tggggttggc atcattctac tgtctgcatg cctggaagat ctaaaatatt 121560
tagtgggccc agaactcctc tatgaggaca gattgccaga ctgctttgca ctgcagagcc 121620
tttcaatgga aaactggatt tctagcctca gttgtgatgt gagaccagga cagtgttgaa 121680
tggagactaa aaatagggtg acttacaaac agatagtgtg tatctcccag ggagtgtgaa 121740
gtccactttc caaagcaact gccagcataa ggagtgttaa tgccctctgg gatccaagta 121800
ggatgaaaac aaaccacaga aaatgaggta ggatgttcaa ctctcccttt cagtgatcag 121860
gaaatctaca tgctcataga ctggattatt cagaatagac cttgttgaaa gttactggaa 121920
tggaggaaaa ccctacaaag atttccagat tccctgggga agacaaaagt atttggtctt 121980
tgttgttatc gttgttgttg tttaaagtga actcctgtcc tttgctctaa ttcaaggaag 122040
aatttctgag tatagctact ctatgcaaaa taatctctgc ctttagggct tcccctaatt 122100
gtggtcgaga gtgtagtctc cagagtcaag atgcctagat ttcaatcctt attctactat 122160
ttattagcat tgtaaccttg ggcaagttat ctaatttctc tatgttgcaa tttccccatt 122220
tataaaatgg aagtaaaagt gctactttat ctccaagggt ttttgtgagg attttaaaaa 122280
gtcatgcata taaagtatct agaacagtgt ctggcacatg gaaaaactca aataaaaata 122340
gctatttata attaattttg ttttagtatt ataattgtat agtaatgctc aacacgttta 122400
tcgtgtgtct ctcaaagccc tggatttctt atctcagttc tgcactcttt catttaaagt 122460

-continued tctgaacagg ctgtcttcaa cctggtggat ggttcaaaca ggctgtccaa ctttcttagt 122520
tggatatggg gatttccaaa tcttgctgct catttcagaa agctttttga aaatatagac 122580
tcctaggatt tgcccacaga gattctgatt tagtagattt ggagtgaggc ctaggaagct 122640
atattttaaa aagcttgcca ctacgtataa tatgcaacca atttggaatg actgaactat 122700
gatgacctgg taccaattat taaatatatg gagccaatta ttaaatattc ataaattttg 122760
caaactgatt gttaaaccat tagtagttat tagctatggt aggaatattt acaccatgga 122820
aactggcaaa tcctacattc tttttttcct ggaaagctgg tttactgtcc caccactggc 122880
acaatcttct tagcccctgg gatctggagt atctctgtct gaatctcctt tggttagaac 122940
tttacatctc catgattttc tgttctctaa ttgaggtttt gatctgccag gcagtagata 123000
ttcctgtgac tgaaagggct tccagctaga tatctctgca gccataatca agctctccat 123060
cattgctttg ttttgaggca gaggtggaaa actggtggtc agtggtgatt ctggttcaca 123120
gatgcataat tgttggctct cacgaagact taaaattaaa gtcggaggca gctttttaaa 123180
aaattataag atggcatata aaaatccaga ttctcacctt ctctttcaaa aaacaaacaa 123240
acaaacaaaa actaagttga aagaagatct ggacctgctt ttcagtggac aaagttcagc 123300
caaagctacg tgagcactgg caggggaaag gtgttctctc accggctcat ttgttcattt 123360
atgttttccg cctggccttg agcttgcagc tcctctggga agcagtgtgt tctgttggaa 123420
aaggtgccag actgggtctt tggagatgta ggtttgtaat catgactctg ttttttaatt 123480
tatcgtgtga ccttggtcaa gtcattctcc ctaacagagc ctcagtttct cacctgcaaa 123540
ctagggagaa tgcttgcttt gtctgcctct ccaaatgtga gatggggaaa tgtgagtcct 123600
tgaccaccag ctgtagaaaa gtaaggaatt attgctaaat attgattcct atttcctgcc 123660
attggcacct aggtgggaat gaataatccc agaacaggtt ctgataggag aaaatatttg 123720
aatagatagg agtgctgaga agggataagg agagagtgcc tataatgaga aaagtgcaca 123780
aaacagaaat actagtgaat atgctgaatc tacagtcttc ttaagggaaa tttgggaaca 123840
tgagaatttg aagttgatac tattaaccaa cctcatgtca catataagaa aatatgggct 123900
tggaaatcaa atctgcacat aaattccaga aggctatgcc tttgtgcaag ttaacttatc 123960
tgagcctctg tttcctcatg tatacaaggt ggatattaga atctatcttg caatgcattg 124020
tgaagattca gtgggataat gcatattaag tgcctgagat attttgtgaa tgtccaataa 124080
atggcaactg ctgttatcag ctcaaatcag gcatatgcaa attgaactac tggcaaatag 124140
ggaagtagtt aggagaatat gatgtattgt tagtggatat ttccttatca gaaaagaact 124200
ttgcataatc cgtaagggac ttcttctact tcccattcca ctgaagaact tcaatttagt 124260
attttaccca gcatttgctg caagcttcgt aggataccca gccacacata cccatatcag 124320
cagcaagttc tgagagccag cggcagtatt agcattataa agtgtttcca gagttggacc 124380
agtgtgtgct tccccttcat aaatccttaa atcttaggct cactcagctg gaaaaaaaaa 124440
aaagaaatct gggtttgaag aacacttatt tatttttgat tttctctgcc ttgtgtgctt 124500
cttttgactg cgcatctgaa tatcaaggca agaagtgctc aagttcctct gggctctgga 124560
aggctggaac caattggtat tcttggagtc ggtccttttt ggactaaagc tcctttttct 124620
tttcctcccc ccaataaaaa tttctgttcc agggagtact ttctcagtca ctcctttcct 124680
aatgtaattc tgtttgattt ccactgaacg gctcctgaaa ggagacactg aaccatgcct 124740
ccacaagcat ttcaattcct caacaccagc tttcaggcag gagcagttcc agatgcattt 124800
ttatatccag taatcatgca tttaaccaaa atgattgatg cagcattttt tcccctctct 124860

-continued atcatttcca gtccattagt cttatttgtt ttccatggtt tgggttcctg ccaaatcagt 124920
gaatatacaa atacttgcat aagtcatgca catctacaca cacatacatg taataggtac 124980
tgggtctgta tctgagttga atattcaaca ttttatttcc aggcttcatg tctccactga 125040
agttttagcc gcttctttcc ttctttctta cttccctctc tcccttcttt ttttccctct 125100
cttcctctcc tttatagtct attaagttgg tgcaaaagta attgtgattt tgccattact 125160
tttaatgaca aaccacaatg gcttttgcac caacctaaca cttttcccag aaacagccac 125220
tttttttttt ttgtcagcca tcatagaatc tgatattctt cagcgttaaa ggggcttgag 125280
agaggcattt acataatccg ttcactttag tttcagaaaa tcaacaggcc agaaaggaaa 125340
ccatgtgcca tcccaggctt tccttggccc ttaggcaaac attccagtgc cacgtccccc 125400
atcagccctt gcacgccctg gaccctgccc gctgcatcag ccacctctcc acctcagtct 125460
tcacactgac ctctccactt caatcttcac gctgtagcca cacaggcctt tagtccttgc 125520
cttggggcct tcacacctgc ttctctcgct gctcggacag tttttcatac ataggtgcac 125580
acaccttctt cactgctcca cctcctattt attctttagg tctcagctca aatgacactt 125640
cttagatcac acaccatacc accctctcct gactttccac cctttctctt ctgacactta 125700
ttacgatttg taattttgta tttacttggg tatttagttg tttaatgtat cttcacttat 125760
tagaagacaa gccctataag gacaaagacc atgttttccc cgcccctcaa ttgtttcctc 125820
agtgccatag acagtgcctt gtgtttgata gtgacaatag ttagcaatca taaagtgaca 125880
gtatctaaca tctgttaaaa acttgctagt tccaggcaca gtgtcctatg atttttatat 125940
gtatttactc atttaatact tacaacaatt atcccgtaaa gtaggtgtga ttattatccc 126000
cgttttgcaa ataaggaaac tggtcaagtc actcacccaa gattatatgg ctggaaagtg 126060
gcagagtttg tttgtaaccc aggcattgac tccaaaacct gaacccacaa ccaggccatg 126120
ctactcctgt taagcacttc attaatattc attgagagaa taagtgaaaa atatacctta 126180
atcaattagt agcaaaactg aaaacctaaa ttgtttgatt gataagccat ttctctttct 126240
atgcaaacag agagcctctc aggtaccacc agaatgcagc agaaagaaag agaagattaa 126300
caaattcatt tattgctgat aagaactatg agagggacgc tgtgatatag atcatgaagt 126360
gaagtggaaa ttattatttt agattcaggc aggacccagt ggcaggtgga aaaaatacag 126420
agtcaattga agaggcctta agataaggaa tcagattctc cagaaacatc aagtgggttt 126480
acagttatta tcattaacaa tttaggcaat tcttatgcta tggataacat tttccaaatg 126540
tgattttaaa gtatgagtaa tcatcagttt tatgaaactg ctgctcagaa ttctaggata 126600
aaaactccaa taatgagcct tgttcagttg ttccatggca tgtggaacag ttcctagcac 126660
atataagcac tcaacagaca tttatttagt aattaatggg aaatgaacat caacaaatcc 126720
atcagcaaat acttactaag tactcgttat taagtctata cagatcaagg cacaacaagg 126780
cacaaaagta aaatgtcaga tttcttttca tggagagctc ataatccagg tagacccaga 126840
aataaccacc acaatgaata aaagctgcta gctgggcatg gtggcacatg cctgtaaccc 126900
caacacattg ggagtctgag atgaaaggac cgcttgagac caggagtatg agaccatact 126960
agtcaacata gtaaggccct gcctctacaa aaaattttta aaaatcagct gagcatggtg 127020
gcctgtgcct gtaattccag cttctcagga gactgaggca ggaggatcac ttgagcccag 127080
gcggtcgagg ctgcagtgag ctatgattgc acctctacat accagcttgg gcaacaaagc 127140
aagatcctgc ctattaaaaa ttgttgataa aataaaaaat aaaagtaaac gccaccatca 127200
ctggggagtt gctttgtcca ggggctctgc catgtccctc tgcatatatt aggtcatctt 127260

-continued

```
tatactcgta acaactttaa gatgatggta cccttcctca tccccatctc tagatgttga 127320
aactgaggtt taaagatgct aatttctgtc ctaaagacac agaaacaaga acttagtgca 127380
gccaggattt gaactcaggt cggtttgagt ctggaaccaa tgatgccaaa tgtcttcatc 127440
cctttatttt gaaagcacta tctgtgggtg aggcatacta gaactacaag actttgcagt 127500
atcagaggat gggagtggct acagagggat caatgaaagc aacattaccc agtctctcca 127560
ggtctgcata tcctgcttac ctgggtatga aacactccat ctctcacctg ccacagtcct 127620
gtcattcagg tcccagattc agtatcactt ctgcatatgc tgcttacttg ggtatgaaat 127680
actccatccc tcacctgcca caatcctatc gttcaagtcc cagattcagt gtcacttctt 127740
cctggaaggc ttttcaaaca tggtacaatt tgattgtttc ttcctttatg ctccttttag 127800
aatccggtgt gtttcctgat tataattctt atctcgcatt ctgattactt gtttcccatt 127860
aactagtctt tgagttcctc taggacaggg gtgaccaatc ttttggcttc cctgagccac 127920
tttggaagaa gaattgtctt gggccacaca taaaatacac caacatcaat gatgagctaa 127980
aaaaaaaaat tcgcaaaaaa aaaatctcat aatgttttaa gaaactttac acatttgtgt 128040
tgggacatat tcaaagccat cctgggctgc atgtggctca caggccacag gttggacaag 128100
cttgctctag gatacaattt tattctccca gggcctagca cagcccctag catatagtaa 128160
gtcatttaat aaataagtgt ggaacgaatg aattttaggt agaaattgtc atcagatggt 128220
tcaactaata tacagcacaa ttccaagaga ggagtgtatt cttgggcatc agggaaaagg 128280
gactttggaa aagttgagtt ggaggccatg tggctattaa gatatctgtc tccacatgcc 128340
tcgactgact gtgtgagcct tggaaagtta ttctctcttc acttcagtgt tttcatcctt 128400
ataattaaga tgataaaaac tgggttgttg ggaagttgaa ataacttaac atgcaggaac 128460
tcagcagagt gtctgttcat tgtaagtact caaatgttgg ccatggctat agctgctgct 128520
gcttgtcttc tctgaattat tattatggaa atttgggtga gtacagcatt tcaggcagca 128580
ggtcacttct gagtaaaagt acagaactat gaagagatct cctacccttg gatataaaaa 128640
caattcacag cattgccaag aaagactgta gatattcagg gatgagagtg agattcctat 128700
gagccagaga atcaaaagct ctgtaaatta gtgagttcgt gatatcatgc tacgctcctg 128760
tttttaagag ctagatatca aaataaatgg tccagtgtat gtgcctgatg gctatgtctt 128820
ttccactgta cacacaagta agattctgca tggtgactat cattttgttt tcaggaagta 128880
gatgaatcag ccgtttggtt ccctgggaat gtgggctgct ggcttttaat tctttttggg 128940
gaagatttct atgtcatcag ccatcttgtt tatctggaaa catgggacaa acgttggctc 129000
tctttctacc tatgtagtcc tttgctaggg ttgtacagct tgagtagaat tgggaaaagt 129060
gatttggatc cttgtgactg ggattaggga gaattggtac atgagtatac agaatctttt 129120
cattgatctc cttgcctctg accttgattt agccacctac tttcagtgga taaggcccta 129180
cagaacaaac caactgaagc atactttagg ataggccaca cctctaatct catatttatt 129240
atgaccaact aaaaactgct tatccttctc tttatgtcta ttatttaact ttcccctcct 129300
ctctaccttc tttcccttaa gtccttctga tacactacat gctcctgcca ttgtgactat 129360
gagtctaaaa agctggtggc attacccacc ttcccctcca ccttcaaaac tcacatgtac 129420
accatgcttt gggcttctct gatttggctc actatttctt caacttagaa cgcccacttt 129480
ctattatgat cattaaaaga tcctggattt atgtgtgggg tggatgtagt aacaactggg 129540
aaatagcata aaattatttg gtttcttgta tgctggtttt cttcccagag gtaacctgtt 129600
tggtttgacg tttggcttaa tgttgttaat ttgacgaagg tggaaatgga tgggctagaa 129660
```

-continued

```
atctttgtgg gactaggata aggcttgaat ggtctaatct agggattcaa actttctagt 129720
taagaatgta caacctgtga ggataatttg cattttattc tacatatatc ccaatttaac 129780
cagctttcag actttaaatc accataagat tttggaaaac ttctactgtc taaatacaga 129840
ataaagtttt ctaagccaga tgaaaaaaat tgcatcattc ttgcaccctg caggcaaatg 129900
catgttgact gcaaagctat ataaatgtgt gttgagtgat ttaacaggtc tggctattga 129960
acttgttaaa aatggatgtc aggaaagaaa aacagcaggt gggtgtagac tggaggagtg 130020
ggcaatgcct gctgacagaa agaggagtga cagctgacaa ggagggaagg cccaatggag 130080
acttcaggct caccacgtat ggagcagtct ggggaccgaa acaaagaaat gaaaacaaac 130140
agagcaccct accacctcaa gaatccctaa gggagttata atatgcacaa atgctcatga 130200
ttattaacta ggaaccagtt attctatgcc tgctatgagc caggattcat tccaggaaat 130260
taaagagaat agaaagaagt ataaaataca gtgcctaggt ctgcaagtat ttattacctg 130320
tgacactact atgttggcca aggagaagtt ctgtatatta tgctcttttt ataaaagcag 130380
aagcatgtat agaaactatt aggatatttt tcttcaaaat gtttaaaatt ctttagctgc 130440
ttacaagaga aatttattta gtactacttt ctcaaagatc ccatttcctg acaatgctaa 130500
taatggaggc atttcaagat aatgacctca taaaattcac acaactgtct gtctgtgcag 130560
acttagatag cacagtcatg acctcactta ggtcagggac agatcttagc ttgatagggc 130620
aatggtcaga aatgcagttt ggtttaaaca gttttttcct cttctctgtt gactcattta 130680
atgaaagaaa gtgtctcatt caacctgcat atttttttca aagattccac aatgatgggg 130740
ccatgtctcc tatgagttat tatacaaaat ggacactgag tcctgaggta cattaggaag 130800
ccccaaactt atccttgtat ttaattcatt tgaacatttt ggatatttta ttttatcaag 130860
ccagtcattt cgagttgaga agtccgaaga tcttactcat tttagaaaga ctaggttagg 130920
gcattttctc tggggaaaga cctcttctgt aagggaactt caagaaaggg agcagatggg 130980
ctctgtgtct actgagagac aggaggataa tcaggcagtg acatagccca tggtactgga 131040
gagaaagaca aatcgctatc cacataatgg aaggcatggg gtagggtgag ccaaatggaa 131100
ggcttataaa ggcagcaagc aatgaggact agccatttat ttaaaatgga aaagggacaa 131160
ggtatcttta tcccacttta tcccactgtc caacaaaatt attttaaaaa aaagagagag 131220
agagagagaa gatgaagaaa ttaagagtgg gaaaatacta ctacaaccgt ttggcctttc 131280
tggcctctta aaatctgagg caggtcaggg aaaacatggc aagaacacta aacttaaaga 131340
gtcaggaaat ggatgctcaa gtgttgttgc tgcctctgac tcagccttac tgtgtgacct 131400
tgaggacaat atttccccaa actccacccc agagcactta ccgcttccct gtagataaat 131460
ataaggaagt tagaacaagt ctctacagtt ctttccattc ctgacattct aggcttttat 131520
aatgagctaa aacaagaagc ttgtttttta atgtgtgaca caccatgaaa tgtatacaga 131580
gaagtgacct ataaattctg attaagtgtg aattagatgc aaatacaaaa tgcaagatta 131640
gagtgaaaag cattacccct ctgtaggtca ggaagtataa tgtggtttct ttgcactatg 131700
aataatgaat attgtacatg ccgaaatgag cactggaaaa catagaagga actagatgct 131760
cttctagaat gggctttctt ccctttggga tagacttttt ttttttttcc tatttttgca 131820
cccatgctta gagaggacac aaacatctct gagattctac ttgagacaat gcgacaagca 131880
cttaaaggaa caccaaatca tttgagtgca caggcaatga caccatctgt agacttatct 131940
gatccagaga acctgaggtg gagcctatag cctctggtca gttggaagcg gtggggaaat 132000
ctcaagaaca cttgtcctga gagaaagaaa actttatctg cttgttacac atgagcctga 132060
```

-continued gctgaggaaa tagacctgga tccagggaat tcgtgtttac tgggtgccac aacttgtgtt 132120
agcacttgac atgatttctt ctatttaaat attagactaa aaacactcta tcagactagg 132180
gttttaaaat actatttcat ttttttggta cctatttata aaatggggaa actgagtctt 132240
gggggatatt aaggtcttat agactgtaaa tggtataatc caaggttgaa aggtttcctg 132300
actctaatgc tggttctctt tcacaatacc tcattgcctt ctggaagttg tagttcctac 132360
cctagttctg cctttatttg gctgtggtaa tcaaaacaaa tcacttaagt tcttgaatct 132420
cattttgttc ttctgttaaa tatcacaaaa ccaaccaacc aaccaaaaca gtgagaatat 132480
agctttgtta tgcttccatg atttgtggat ggtcttcaca ggcaacaatt aattcatgag 132540
gaatgatgcc cactgctgtc atgcaacata gtggccctgg attttaagga atccatgtat 132600
taatacatgc aacctgaaat cacatatgta aattgtatta tatacttgca tatctatatt 132660
gttttagaga agaggctaaa gctttcttga gaggctttct gtggcatcta tatccccaaa 132720
ttcctaaaaa tcattaggtt cttggcagct cattaagtga ttagtaggtc tccttatgat 132780
gtgttataac tcaaaacatc agtaaccatc tgaaagaaat taaggtttag gacaggcatg 132840
gtggtacaca cctgtaatcc cagcatttgg ggaggtaaag atggcagtat cgcttgaggc 132900
caagagttta agaacagcct gagcaacaca gtgagaccct atctttacaa aaaatttaaa 132960
attgttatta aaagaaatta aagtttagta catgaaagca gctgaaactc agaactgacc 133020
cttacatcag aaaccatgtg gtatcatgga aagaaatctg gcaaagaatc aaagattctg 133080
ggtcctactt tactctgctg tgaacccact ccatgaatct gggcacatac ttgggccccc 133140
attagtttgt cattcaaaaa gagatgctaa gttccagcct gcctctccca aagcactttt 133200
taaaagaatc aaatgtgata atatggatga aggcactttg gcaaaatatg aagtaccctg 133260
caaaagtctg atattaacca tgagatatta aagtatcaag tcatttcact agttgtcaac 133320
tgagaaaaag ggaaaattgc aagttccatc agcaaaattt agaagccttg ctttttcatt 133380
ccttcagcaa ggtcctacag ctgatattta tgcataaatt ttcttgactt taatgagaat 133440
tggttgcaaa tacaccttac aggattcaaa tggagatcat caccattcta ggagctgcta 133500
aacagaacat gtggcttctt ctctagccaa gagttctcct cttttatcac ctttatttta 133560
tgatcagtgg ttctcaagga atggtcaagc accagcagcg tgagcatctt ctgggaatat 133620
gttagaaatg aaaattctcg agccccatcc cagacctact aaatcagaaa tcctggaggt 133680
ggagcccagc aggctgtgtt ttaacaaacc cttaagagga ttctgatgcc ctgcacactt 133740
aagtgtgaga accactgcca taagtgagta tccttggaga gacctacttt ggtcctgggt 133800
actttaagga aaatcgtggg gccccagtaa tccaaaagag tacctcatct aagtctctga 133860
agggctgatg ttagagcaaa ggttgggcta gtgaatgtca atgttagcaa acatggtggg 133920
tgtgacccaa aacataatca aataggcctc ttaggttaaa gtcctgatgt taggtttgct 133980
ggttgagaag gaatacaaat gtatctcaag gaatgcagtt ctctcaagat tcagaaagta 134040
tggatacctt tgccatgcct ggcagcttga aagaaatagc aatgtaaagt taaaccacgc 134100
ctatgtgaaa gttagctcca tagcaggctt tcttctctga gatttgaatt tatggaacat 134160
gataacaaat atgaaaatag ataattttta ttgaatatca tatcactacc actattttaa 134220
gtgatttgta tgtattaatg gctaaccttt tttcaggtag ttactccacc aagctctttg 134280
ctgggccctg aaaatgtaac agtgaacaag aaaaaaatct ctttcctcaa ggaactcaca 134340
cttcaatgaa gggaaattag aagaaattag cctattactg ttcaagttca gggtgtttgc 134400
agaggcctag atgcggcacc tacactcagt cttatgtaaa tagaggtttc tcaaaggaag 134460

-continued aaatgtataa atttagacct ctgtagagtg agaggagttg atcactttag agtggagaaa 134520
cagatttagg ataactatac tctagatcac acagcaagta agtgatagtg ttgggatttg 134580
aactcaggtt ggtttcatcc aaagccattg ctttcaacca ttaaggcaag ggcagaaaat 134640
gggttttatc aagcctgtca attctgacaa attaataatg gcttccaaga atgtggatgg 134700
tgaatactcg gtgagcactg ggctcaattg gaaaaaaaaa tgccatgatt aattaataat 134760
gtcttccctg ggttcagaga ggagggtgta tgtgtcatgc atttgcctac cctgcagtac 134820
agagtactgc ctccaggact tagcacgaga ggatgaaatc tgcggttgtt tcttattcat 134880
gtaagagtgt ctatgacttc aaggaacctt agagctcaat ggcatcagca ggggcttatt 134940
atatgttagc aaaggtagca agtgacagcc caggatggag cattcagtaa aaaagagaat 135000
aaagtttcct gtcaaaagag aagacactaa ttaagtttaa cagtgaaaaa caaacaacaa 135060
agcaattggt cttactaaga gactaaactt caaaatttgt aagccaattt cattttcatc 135120
ttttacctct gttagttcta tcaacatgga cggcgttaat atgacagaat atttgtttgg 135180
aaataatggg atccatatgt attgagtcag cttcatcacg cccaggggaa acttaaattt 135240
taaaatgcca cccaaaatat atgcattcaa catgcataat ggctcatctg ttgaatagtt 135300
gggaagtgat atcaatcaga aggattaaga agatggctgt ttaaggcaat gatgataata 135360
aattagtgcc agtttgcttc aatatgtttt atggcgtcag taagatggta ggtgagctct 135420
ttgaagtctc gttgaatatg gttgtttctg cagcacattt gttaaaccca tatatggatt 135480
gaaatcatac taatgacaat aactgctcct atgactcaaa agggaaacaa atggatactg 135540
tcaagttagt cagtgcttgg aaatggcttc tggatgaatt tcctttgcaa aaagtctctt 135600
tcactttccc cagctcacct tcacatttaa ccgtaataag cactctttac tctagacatt 135660
taacagatgt ttttaaataa ctcagttatt gggtatataa aaagaagaag atgacctccc 135720
caaaagtccc aaggtcagag ctatttgcca tctgagcaat tgtccccagg aagaatgttg 135780
tgaatgatca cttctctcta accgtgactc agcacagcac accaacctgc acccattttc 135840
agaggctcac cttgggttga gggtgacttt gagtatatgg gcctcagcag tcaccgccca 135900
agggctgtgc ctgcttgtca tgcttctcta tcaccccacc cacctgcagc catcagagag 135960
gaccagtttc tcactgatcc tcctccccctg atgcatttac atgagagatg ggggaggagc 136020
tttccccctt gagacttgtt caccttgttt tactttggaa gacaagattt tacagtacca 136080
ggaatcaaaa catttctctg atcacgtcat gctgaccagt gctaaattat ctctgattca 136140
ttgtacattt tacaggttat ttgaaacctc aacagggggg aaaaaaattg atagtattct 136200
gtgtagaaga ggctctggcc acagaccgaa aaggacttta tctttactca tccctaccag 136260
attagataat cacgtggaaa actgtaagaa acatcttcaa catacaagaa acatgcatct 136320
ttagtatctt ctgtatgcag attccaacat ggagaaagtg ttctagagcc taaggtttga 136380
ggactccagg tttgagtcca tgttaaatgg aaggaggaag agaaccattt aaaggtttgc 136440
atttaatgct tttaatacat tcaggactca gtaacgtctc ctgtgcagag ctcctgatcc 136500
attcacggca gcagagacat accaagtcag cacagagaag atgccttggc tatacaattc 136560
attcatgtgc cgcagccctg gttggctgct gaatataagt ccctagtaca tctctatttt 136620
ttttttagca atattgctgc tgaagcttag ctgtgtgctc tcgtgtgtcc catcctgctc 136680
tttctgcctc aggtgtgtgg tctagttaat cctccattcc atgggagaaa catagcccag 136740
gaatgctggt tgtgaggaga tttgatttct actcctactt ctgccattaa ctgtatgact 136800
ttgggcaagg ctctttcctg gtcccagccc agccccagct attcagcatc catttaggat 136860

-continued aggttggtct ctaaggagcc tttctagccc cagcattcaa ggacttagtg gaaactagaa 136920
ttctgggttc agttgagttc agtgccaccg gcatttgccg actgacttcc tctttgtcat 136980
caagcaccat acggggcact gcaggggata tgtttatatc agagctctct ctgataccac 137040
ggcactcacg ggcaaaggga gagtgggatg agaaaaacaa gtgtattgat ataccagtgc 137100
agagcagact atgttgtatg ctggaagcaa agtacaaatg attatagggt ccaaaggaag 137160
cagaaatttc atttatttat gaaaagtcag aataaaactt catggcattt cagatcagcc 137220
ttgaaagaga aaattcaaac aggatccagt gaagtttcta tagcaacatt tactgagcaa 137280
atattatgtg ccagccaatg ttctgagcac tttgcacaca gtaacttatt tattcctctc 137340
agtcttttga gattaagact ctggttatct gattctgtat atgaggaaac tgaggcatag 137400
actggctaag gaataggctt aggctcatgc cacaaacaag cacaagcaca aggattcaaa 137460
gcttagcgat ctggtgccta cgcccgtcac ttagtgtgga gagtcaactg actgtcacat 137520
aaacaaggcc accgaacctg gagggaggga gacctgactc tgcagatgag ctttgtgtcc 137580
ctgggaaagt cttttcagcc tctgaccttc acgtttctta actctgaaat gcgaatgaaa 137640
aatagtttcc tcgttgggtt atgatgattc agcaaaatgg caggaataag aatagatttt 137700
aaatgattaa aagttctaga tgattttaaa taggagagaa aagcagagga gctgattgag 137760
caaatgctga gaggaggtaa agtgtgggac atatttaggg cagagtgatt attcagtatt 137820
agggtctctt ctccacagtt tgagaggttc ccacctgaag tcttgttcca tctcatctct 137880
tccagctatg ccaggccttg actctgctct ctctatgtgg agaatgacaa atctagtctc 137940
tgtgtgtgtg tgtctgtgtg tgtgtgtgtg tgtgtgtgtg tgtgtgtgtg tgtgtgtatg 138000
tgttgtgctg ttgaagctga atgccagcac aattctcatc agcatttgag ttcattggca 138060
gcatttgaaa gaaagtatag acccttagct ctcagtgcta atatagacat tggcacatta 138120
gtttcagctg aattaactca tgtaggactg acgctaaggg acagttagag tggagtggaa 138180
acttctctgc atacagaaat aacatctcag cactgtctgt gtagcaagat gtattatcat 138240
catcttattg gtactggaca aagcaggatc ttcagatggt gcccagcgac tatagggact 138300
aatgggaaag cagaagggat gcagcgtggt taaatccaaa aaaagagcag cagctcaaga 138360
gacagtagga aatacgatgg acaagggtca ggagaccagg atttgagccc cagcttaggt 138420
gattggtcct ggaaatgtca tttctataaa ttagcacaac tgataaagat gctctctaaa 138480
gcaccttcgg ttctgatagc ctaaaaatgc atgagttatt tttaagcaga aacttaacta 138540
cagctattct tagtctctca actagaagct acatgtgatt ctgcatttct tattaactga 138600
gaggtacaat tttccactgc atgttgctct tatctttctt agtggccaga taatgttatt 138660
tataaaacaa taacaatata gcctcagata actgcagcaa cagaaacaat agtagtcatt 138720
tacagggcca ggaactgtgc aaaaacacgt tttacatgca tttgattctc agagcagcac 138780
cattgggtgg gtactattat ttccataata cagatgagca agcaaaggtt tcagagttac 138840
taattaactt gcccaaggga cgaagcaccg ttttgaatct ggcttgtcca ccatcaaacc 138900
ctttatcctt aaccactcag gtgtctagcc cagagtagac acaggcacgt gagcccaagt 138960
gttccaggtg gcctttcagc cccagaaatc tcccctcact tgaaaaataa tctagaacaa 139020 ttttttttcag aggaatcagt ctttcttccc cagtcagaat gaagtcacta actccagagt 139080
aaaagaatgg ggcaagcgat gctctctgta aagtgaattc taatgaggta aaagtgggca 139140
ggtctctact ggaggagaga ggacagcagc gaggagagtg gcatgggaag tggagagagc 139200
tgcatatgcc cccacctccc cagttctctg agagatattc cacacaggaa ttcctgaccc 139260

-continued ttgcccagca attgttcaat gactctgacc atggaaagca tacgagaaaa agtacgccag 139320
aaaagttgta tcatggtcgg tagaccagag acaacagaga aactggctgc aagtctcagc 139380
atcactcaga aagcctttgt tcccaaggca ctattaagta tcaggcagac agagagattc 139440
ctgagacaca gctcctgtcc tcacaggaag gactcactgg ataagatggg aggcaaaccc 139500
aggcaggcta gcattgatgc aagatgctga gtgccataac aaacgtctaa gcagcttgct 139560
ttaggtgtag tgtgaaggga ggatcagaca tagttaattc taacacgagg taggaagtgt 139620
taagtgtgct aatagcaata caagccaaga actatgagag cccagcgaag gatggattaa 139680
ttctgactgg gactctcaca gaagaggtgg tgtctaagtg ggaccttgaa ggattggaat 139740
gagagataga gcagtgatga gattctgctc atcacagggg agttggtgta aagaggaaag 139800
tctatttgcc tgtgcttgct tttccgaagg caggacggct acaagcatgg agctgaagtt 139860
cagactgacc tggctttgat ttctgtgtct gtcatttctg tgtgcccttg aactttcata 139920
ttttcctctg taaatggaga ttctagtacc ttcttcatgg cattgtgatt gggaacaatt 139980
acattacaac atgtttagta atgcaagtgt ttaagtacat gttcaataaa tgatagtttt 140040
tattgtctgt gctatgacta tttcagtgaa cattatctca gtcttctggg tagcatctga 140100
ggctaattgg ccactgttag gcaattttaa aagttaacga aatgcaccta caacttcatc 140160
tgcatttgtc ctctcttcag atccttgtat atgagcatct ttgcctattc ttggatcata 140220
gtcttgcttt tttgtttttg atttgtttgt gggttttttt tctatacaat agagcaaatt 140280
attgattcct ttttataatt tcctcttcct gttctaaagt cctaccttgg atggtccact 140340
ctttgttgtg tgttcagatc cagtagtgag tgcagaagga cagttaccat agtcagcctc 140400
tcagttagaa ttctgtcgtg tctacagacc agctttgttc ctctcctagt caccactatg 140460
ctgctgagaa tcatcataga atatgggaac tgcaggcaac tgcagccaaa tcttttgttt 140520
taccaatgag aacctccagc ccagggacag gaagaaaatt gtcaagtttg tacagagaga 140580
caggcagggg tgggcctgtg tactagtcct caagtgtgct gactcacagg ccagtgccct 140640
ggatggtttg catgcccttt ctgcttttct tccgcagact taggctgtga ggagggcaaa 140700
aatgcctttc ctcctcctca tttcctcttc cctcccccctt cctccctgct ttgggtaaag 140760
ctgaaacatg cagctcgtgc ttccacaagg catcctcagc atgcttttca cagcaccctc 140820
tgctgactcc ggggccttca cagcttgcag cccagttgac agccagtgaa gtgagaagat 140880
tggaaacact ttaaactgtc tcagcattga agaaagtgag aagaaggcag gtgggaaacg 140940
tctgtgatga gcgacattgt agagagttaa caaaaactgg gagactttca gggtttcctt 141000
ctcctgctcc cctgaaacca aggattataa atactttcaa tcttacagga caactctagc 141060
tgtgcagtgg tgactaggtt gaagaggatt tggaagcggt acttgggctc cgtgtacaca 141120
cacttgggaa cacatgcaca cacgcattta tgcatttgca ctatgtagta ggcatttctg 141180
ccttggactt ttaaaaacat gcttgccctt taggatcctc atcttggaaa tctgccctct 141240
tctccctctt taagggattg cccttccctc tgaatgtgca gaacatgctg ttcttctact 141300
gcagaattta tttcattttc tcatgcaatt tttattagtg gctcataagt gtgtctttca 141360
tcgcattgga atgaccctct tagaggcaag ggtcttgact gttgttttcc ccatactata 141420
ccacatacac tatgttgaat tgataaattt acttattcag tgaatgtttt ggtattataa 141480
tagacatgtt gcaaggtagt ttagcaaagt gataaggact catgtggaat cagacataca 141540
ggggtttgaa ttgtagctcc actattatca gttctgtgac ccctgcctac ctatgtttta 141600
gtccctcttt tgttaaatgg caataataat aaagtacacc ctcttaagct gttacagaga 141660

-continued ttaaaagaat tgatgaaagt aaaatgtgta gtctattttc tagcattaaa gtgctcagta 141720
tatgcaagca cctattagta attaatgtta gaaataataa tgataattat catcatcatc 141780
atcatcatca tcatcatttg ttgccactgt ggctgtgcca ggttctccag atcctcaatg 141840
atcccctttc ttttcttaga tatgtgaggg agataagcaa aggaatatat tgaagagaaa 141900
aagcccaatg tttattactg cgtggctgtt gctatgctgt gggcttctat gagctggagg 141960
acccaagaaa gctactttcc ctgtggccct cacctattct tggctgtctg gatctcagca 142020
ctatggggat cagaagaggc caccccaaaa caataggaaa taaaaaggaa tttttgccca 142080
atgctttgaa caaggcaggt ccaagcttcc cacctcagat cttcagagtg aagtcccctc 142140
cctcccatgc tcaaagcagc tctagacctg cacagcaccc tcaaagaagc aaatccagca 142200
gagattttat ggctttagca ccatctggcc ttatctcctt agctgtcttg aaggagacaa 142260
tagagggtgg aggagaagta atcatcctaa aaccaacagg tggccccagt tgtaggctat 142320
gtagcagcat ggctgtggtg gtggtggttg cttggtgtat gtgtggaagt gcaagggaag 142380
tctataatgc agtgttctga gtgtgtgcag aacctatgga ggaaatcaga acttgagata 142440
gagaaacaag tcctgttaat ggtaacgcca tttggatctg gaaataactg tgtttgcata 142500
gtccatgtct gttctcttac agatgaggaa acaaaagctc ttcatttaag gagagaaata 142560
gtccactctc ttgtttactc ttttacttga cattgattga acctctcaat ggcaaagact 142620
gtgttgtgca ttagatagat atgctgagaa atgagaaaga ggctgtgccc tcaaaaattt 142680
gtcctaaaag gggaacatct agataatcaa tgagctaata aatgattaga tacagtgttg 142740
tcccttcaac catctctttg gattcaccac attctccaca ctctctctaa agactcccac 142800
tcatgcccct ggtgagtcaa aagctcctgg ccagtagcct cttctctgat caactcatat 142860
atttctgctc atatcacctt tgctggtggc ataccagaat caagaatcaa ttctgtttgt 142920
tttcaaacct gtttatattt ctgtgttttt attatacttg gacaatttaa ttaaaatgat 142980
gtgaactagt gaaatatgag tgcaaaagaa agtctttttt ctgaaactaa atacttttga 143040
aaggctatcg gatgaatcac taaaatcatt gtaatattag gtatcagaga gacgactcta 143100
aggttgggga aaagcatgga agaaaatcta aacttatatt tattttataa gtgccttcaa 143160
gttcctgata tcaaaatatt gatcaataca tgtgcttcac agtgttttaa gttttttttgg 143220
tatatttttt aaataatcta attgccatcc acgttgcatc agttaagagg gcttcaactg 143280
taattaagac tttgagtaaa gttctgtgaa ggatacaaac taaatgttgt gaccgagaac 143340
agcaggatga cctgcttaag gtggtccttg caagataaca agaagccagc caagcaaaag 143400
taggggagaa gagttttggg cagtgagaac cgcatcgggg gaggtgtggt atgttgcaga 143460
agcagcagat gagggaaagg gaaatgataa ggtttttcag gtcaacagcg cttagacagt 143520
gcagattctc aaaggtcatg caaaggagtt gggactttat tcaaagcatg atgagaaagc 143580
atgaggggct tgaggggatc tgtttgacag gatgtgattt ccattttcaa aagagcttcc 143640
tggctgctag atgaaggatg gatgagaacg gaaaaaggga aagtgggcaa ggtggaggca 143700
gggatgaatt aaagtgacaa aggcaagtga taaagtgcaa taagtctaca gtgacaggtg 143760
agcagtggca gagccctagg ccagggtgag aatggagatg taaagtgggc attgtaaata 143820
catttgtgac atctttagag ggacgtgcat ccatattttc tttagtcaat ctgcatgacc 143880
aaacttacag ctaatttttg aaggcatagg tgatctgatg ggggagaaaa tcctaccaaa 143940
agtcaggcag ctgggtttct ttttctagtt tgatatttat tggctgtgct actcagagca 144000
agcaacttaa ctcttggaag ctcatctaga aaaggacaat aataatatcc tgtgcagccc 144060

-continued acctcatatt tgggttatgc agtttaaata aatagatggc ttacatgtat ctaggacttt 144120
ggtaagctta ttccttcact tgatcctcac ggcgcataag gcagatacta tggtcctcac 144180
gtcacaggtg agcagaccag tacctgttca ataaaccgtt attgaacatc tactatgtca 144240
gggtcaggga caggccctga gacttttgaa atagattaga cccagccctg tcctacagaa 144300
gttcacagtc tgatgaagaa gacagatatg aaaatgtgaa attatagaat atcaagatac 144360
atgctaagac agaaagtaca ttagaacctt agaggaggaa gaaatgaatt ttttctggaa 144420
ggagtgaaaa gctttccact ggagtcaaca tctggctggg gtcttgaagg atgtgtagaa 144480
gttttccagg tatggagggt catttttgag aaggatatgc aaaagtatgc aggcctggaa 144540
ggaaatggtt catatgcatc tatgtgggtg gggcctcagg tgattggcaa actgttagga 144600
atgaggctgg agagtgaatc aggggcaggg aggctcctgc tcatggatct gtgagtgagt 144660
gagttatgca aaagcaggaa aactagtaca tttgcttcat tttcattctt tcctcaaatg 144720
cttcccccag tttcatagta tacatgttcc tgtgccttat actcccttct tccttgctta 144780
ctgtttcctc cagaattaat ttgaatctca gcctttttcc tggaactctt aattttagca 144840
gggatataca aagggaacac tccaggatag tgagaaatgc ctttttttct ccaaatgtct 144900
tccggaattc tgttacttag caggagttgt ttcctgccat gttttgagaa actttgaaaa 144960
gcgattcaaa cgttggtgca aagggaacta aatacttggt agtgaggagc atcttggcag 145020
agaaggcagc tgagcttttg ctaaagtctc agtggttgaa attgtccagg aggcctgagt 145080
tttggtccct gggctgggca gcatgtgctc ttggttgtca tgcctccatt cctccttctg 145140
gaaaatagta aagaagaaaa tgtataagtt agagaggtga aagagtgtta gagctaatta 145200
aatctcactt attttactta tgaggaaata actcccaaag aggagaaatg actaagttca 145260
tataaagaac ctgcagctaa cttggtcatt tagtcatata aagaacctgc agcttacttg 145320
gtcatttatg catttattcc attcagcaga catgtttcag tgcctcccat gtgccaggca 145380
ctgtggtaga tgctaggaca atagtgataa gtaaataaac atgattcttg ccctaatcag 145440
ggagatgaaa ttaaacaaat aaaccaaaag ttaaacaaaa taattaaaga tagagataag 145500
gtatgatgga aagaaacaag gtaccgcaat agagaataaa gagtagggac cgggcacggt 145560
ggctcactcc tgtaatccca gcattttggg aggccgaggc gggtggatca caaggtcagg 145620
acatcgagac catcctggct aacacggtga aaccccatct ctactaaaaa tacaaaaaaa 145680
attagccagt cgtgatggca ggcacctgta gtcccagcta ctcgggaggc tgaggcagga 145740
gaatggcgtg aacccgggag gtggagcttg cagtgagccg agatcgcgcc actgcaatcc 145800
agtctgggca acagagtgag actccatctc aaaaaaaaaa aagaaaaaaa aaaagagtag 145860
gatgagtatt ttagagaagg cctctatgaa gagagaacat tttaagctga gatctgaaga 145920
atgcgaaggg gtcagccact taaagagggt tggaagagct ttctaggaga taacagcttg 145980
tgtaaaacct caaggcaaga aagtcgggac tgtcctgaaa ggtaagagaa agaccagcat 146040
gaagcccagg cagaggtgtc atggcctgga agcagatgtg gtgggagaga taggcagggc 146100
cagaactcag agcctcagag ttcaaagtgc ccttattggc agactcttga ttgatctcac 146160
acccctgcgg aaaaggaaag gcaagtatac gtgcattgca agactctatt ggccgagcat 146220
ttgtttcaaa tgtcgttttc gcagcatgct ttgctgagac catagattac aaaaacagaa 146280
ataaaaatga ttcagctttt cttctgtgtc tacccctcaa cttaattagt gctcacagct 146340
ccagaaatca gttgagggca ggggtcagga gtgaattcag atatagatga agtgggactt 146400
agtttctggt gttgccactt ggttttaaag atgcagaact tcttatcttc catagcttta 146460

-continued

```
ttttatcctt catttttgtc ctttcacttc ctcagtggat aaatcctagc tagaagatga 146520
attttgctga tttagggcac cctcgggctg tcctctgtag ctttcagtaa agctttgtct 146580
tgattgacag atgctgatca agttcatggg tatgcattac agtgtacgtt tgctggttgg 146640
cctaggaaaa cccatttgca cgtatgactt tcataggaaa agaatggcaa ataagaaaca 146700
aaagattttt tttctgccac tcacccaagg aacagaaatt aagacagcca aaggaagagt 146760
ctgccttcat ttaacggatg atttacctgg tgttccttgc ggtagtggtt cattcgtgaa 146820
ccagcagaag gtattttgtg actatgggga ttgcggagat gactgggcca ggaggggaag 146880
ctgtaaagct aatctctccc acaacccact tctctttggc taatggcttt gcttttgttt 146940
gttctgcttt ggctggttca tgtgctagtt cccaaaggct gcacaaaggc agagctaggt 147000
agatgtactc cctaccaggg ctctttagtg aatcccacct cctagcccca gatgaggctg 147060
agtgaacact cactccagcc ttggactgta gcctttactg tggcccctga acctaaccca 147120
agaatgagac ttgttgaccc aaggctcaga ccccaagtct cagatccctt atttcaaaga 147180
gagctcctca ccccagctcc agactgagcc cctggcccag cattcctggc tgagtcccca 147240
cacgtggtag agccttggcc tcaaagggtc catccacaat gttgtgagtc ccttggtaca 147300
tattcacttt ttgaatgaac ctctgaggac ccctgccctc tcaagactgg cgtctcctct 147360
gccatctcat cagagtggct tttagccatg gagcagtgtc atagcctcct ctagtccaaa 147420
gctggccggt gctaagaaga ggaagcctgg aactcagaac ctctgtcctt gtgccaacat 147480
gttagttgca gtctatctgt gagcttcaca gtcccattga ctcttgtaca gaaatcagca 147540
agcagtggtc ttcagtcaaa ctgggacctc aacaatcgac tttggtcctg tcagggttcc 147600
tttcccttac tcttcttaag agcacccaga gtcaccatga aagaaccaca agtggaaaag 147660
gaatacgtgg gctcagacgt gtgtccatcc ttgcatgacc cttggctcct catctgttca 147720
tgggtttaaa ggtcatcctt cctgccctgc ctaccttatt gagtattcac aacagaaaat 147780
gaatgtagga gattgaaaat tgtataatgc actctaagtt attattacct ctcccaaatt 147840
gtcagcattt catccttgct atctagcagc agaatagtgt agggtaggag tttacaaact 147900
acagcccaca ggccaaagcc agcccaaggc cagattttct aaataaagtt ttattgaaac 147960
acagcaatgt aaatatgtaa actcatttgt ttacatattg tctttggctg ccttcatgct 148020
ataaaagtag cactgagtag tgcagcagag accacatggc ccgcaaaacc taagatattt 148080
actatttggc tttttgcaga aaaagtttgc ctatacctgg catagaggag caaagtgagg 148140
actctgaagt tggaatgcct gtgtttggat tctgaatctt ctacttaatg gctatatgac 148200
cttgtgcaag ttaattagct tcacttttct ctctatgaaa taaaaataaa cattgtatcc 148260
ccaccctgtg ctatcaaatt agcattaaat gagtaattca tgtaaggcac ttagcttagt 148320
atttggcaca tagtgagtgc tcagtgttgg ctgttattat tatccaaaga atgaaagctc 148380
tggtttgtgt tgatggactc tcaggggatg gagtagcatg gtttatggca caggccatgg 148440
agtaggacag aacattattt atatcccagc tctgccactc accacatgaa tgactcggag 148500
aagattaatt aatctccctg aacttcagct tcctcatgca tgaaatagga aaaagaaatt 148560
aaagagttat tgtgaagagt aagtgataaa atgcatgtga agtgccaaga atagaatttg 148620
gaacatagta aacactcaat aggtgatata aatacaataa taaataagaa gaagaatggt 148680
acttttctaa gtagtactag cttctcagaa caaatagaca gttggtagtg actactatgc 148740
aaacatcatg tgaggtagga ggttctactt atcattaata atgctctgga caccaggttt 148800
tgcatattcc aggcacatgt aaattaaata cactttaaaa tggagttgtt tagacagctg 148860
```

-continued tctaggcttt tatctaggcc aatagtcctt caagaccagg tacctttctg tactaacaat 148920
ccatgactct atgactgttc ttaggtgaag tgataggtca aggagaacag catacacgtt 148980
gagtcactct atggaccatc ccggaaagat cctcttctca taataacacg tgggtacaca 149040
gtgatgctaa ggagtttgcc atatggggtg aaaatgctct cattttgaac ccattcaaca 149100
tcttcagggt tgagttctgt aatgggatgt aaatcttctt tcctggggag aaacggctga 149160
ggagactggg tgttgtaggt ggaatacatt aaggctggtg gggtttgagt gccagcccaa 149220
gagcacagct ctcattctca gttggcctaa gctaacaggg agtgatcaag ttcagtggac 149280
tgaagcacag gggagtatta cgtatcttcc agacctgtgg atgctagatg ggcaacctaa 149340
tttagaggaa tatgaaacaa gtaacagcac cgtgcaattt tcgttattcc ctacctagct 149400
ctttatgagt tattgttcat tatattagca gaaaaatgag gatttggaga gcctcttcct 149460 tcaaggggc ttacatctca attgcaggtg aaaaggcata aatacacaaa aagttacttg 149520
ataatataaa ataaaataat caattcattc agtgcaagac atgtcatgaa agaaagatgg 149580
gtcaacttag tatccagaga ttaaaatagg taaatgactt gcattcattc atttattctc 149640
atattcattc atgtccaaaa atattgtgta gtcattatgg gaacccttca aagggatatg 149700
aataataata taagctttat gagggcaaag gcatcatctg tcttatttac cactctattc 149760
cacagtgtct agcccataga ggaaagacaa ggactgagtt agacatagat ccttatttaa 149820
tactcagtgt ttagatgtat gtagttccta acacatttgt ggacatttat ggagctccta 149880
acatgatttt gggctctaat ttatgaaata ctgcaatcag acatttagta gacatctgtt 149940
ggtttgatat gcccagcatg catctcctct ctgttcacag caccttaatt ttcctctggc 150000
tggtagctta gtaacgtgga tagttgttct gcttcccttg acccaggggc ggcccatgcc 150060
caagcaaggc taatcttgaa ctgtgtaaac agttatcaca aatggctgga gcaatggtga 150120
gaccctaaag agactgtcca tgaaatgctg acatctagat ttctagagct gctgcaattt 150180
ctgtcttata tgaggcactt tttcagctgg ggcttcctca tatccttcca aaattctgtt 150240
cttacaaatt acagaaccta aactaataaa gcatgggtgt tagataaaaa attgataaga 150300
cgcacacatt tttatgtaca tttaaaagat gggtggagac tttcagttta tagctaggag 150360
tagggaggtg taagggtctt tatgaaggag atggcatttg agcttaactt ttaaagaatg 150420
gaaaggatct gcaaagatcc ttaaagaaag aaagcaggag gcaggaggcc tgtgcaggct 150480
ggagcagggg catgagtgta ggcccagagc ctacggccga gaaacaactg aaaaacagcc 150540
acgtctgtgc tggaactcag tgaactcact gagcatccca tgtctgtcgt gccattacac 150600
ttaagtcaga tgttcctgtt cccattttct agcttatcct actgagtcac aacaaccttc 150660
ccctccattg tctctcatcc atggactgga cttgagctat gggatgttag agaggaaagg 150720
tcttgtgaga ccagctagga ctgaccctct taggccaaag tgatgctaga gccctccagg 150780
cacccatgcc acacatgaag tgccggatac cttagaagag ctcagtttta ctcagagagc 150840
tatgtgatct ctttctcctc acctgcatct ctactgcttt cctcctttcc ccctatactg 150900
tgtccacatg ggccttctgt ttctcaagct cttcagtctt gttcctgagc ctcattcaga 150960
gcctctgttc cattccttct gcctgagact gcttctttag cctttagcct ggctggctcc 151020
ttcttagggt tcatttctca gctccaatgc tagtgacaca gagaggtctc cctgaccatc 151080
ctgtctaaaa tagtcctgcc agtcactctc acatcatccc gttttatttt ctttgtaata 151140
ttcgcagcat ccaaaatggc cttgtttatt cacatgtcat ctctctccct ctctagagcc 151200
taagctccaa gagagcagag acttatcttt ttatccagtg atgtataccc ctagcaccag 151260

-continued

```
cttgctgcct agcatacact acacattcag gaaacttgtt ggatgggtga atgattaggc 151320
agaagaaaga tggagagaag aaacagaaaa tttcaatctg taggacctca catccccagt 151380
gagtacaaaa gttctattac aggtacttca ccaaaacaaa aaaagtttga gaaacactga 151440
tttagtttaa actctgttat ccagagagga aaaatgcagc ccagagagga gaaggggctt 151500
gttcacagac gtgcttcttt gcatttactt ctccacaatc atgtcaggca cctgaagatt 151560
tttataaggg aagctccagt tgatcagtct gtttgccctg gccccctgcc cttggttaca 151620
tatgtcagcc cacagggtga gtctaaattc caggaccagt gagcccagcc ctgttctaat 151680
tcttagcctc gtatgcagta ccacatctca ttggctttca atgcctagta attaagaccc 151740
atgcttaata ataaatacac aaatatgacc tgggaggatg gcttttcttc cacatctcct 151800
tttgcagcca tcttccaact gggcatcagg gcctggatga agaaagttct tgtgagtctc 151860
aaatgaatcc aaaaccaaag tgaaatgcta cattgacaca tgacacaatg acctaacttc 151920
tccagcccgg gcaaggccct tggcaaccta gtccccaccc atctccaact ctgtgccata 151980
ccccgacccc agtcatactg gtgtttctgg agtttttctg ttgtgccctt ctcttttatc 152040
ttggtgcttt ggataaagtg gtccctctat ctagacacag gaacaaggtg cttaacactg 152100
tgcccggcct ctgctaaagg acccagttaa cactgactat aatagcagtt atgatcattt 152160
atcctgtggc tgatcccttt attactctct caaatcaccc tttattttcc ttaatgtaaa 152220
actcactgaa cacttgctta agctctgtga aggtagaaaa catgtctgtc ttgtgtaatt 152280
gtggtacccc aattttctgg caatattagt ttctggtgcc aataaatatc tgttgaattt 152340
actaaataaa tgataacatt gtatctagta aatgacagac accctggatg tgtctcagaa 152400
tcctaagtaa atgtgatatt gtttaagggc tttgggatga tttatatcta ttatggtaat 152460
tctttgcatg tcagcattat atctacgata caagagaata taaaaaggga tggacaggca 152520
ctcttattgt cctctgagtg atggaaatga agcacatccc ttgatgttac aacgttagag 152580
taagatgatg aagaatgtga ttcccaccaa taaggataga attattccag gaggggaatg 152640
agtgcctgaa agtcccccca ttcacacata cttttgatct ccctccccta aaatgaagct 152700
gtcctgtcac ctcattatct gctatttaca atgaggctgc cacattccca gggacaggag 152760
ccaaggagaa atgtcggtgt gagaggcctt aaatgaagtg acaataaaaa aggagttgtt 152820
aatgccagga gttccctccc tgggagacag ctgtcagggc cagtacccag ggctgggaga 152880
tttattgata ctaagtggat ggtgccctaa ccaggagtga ttatcaaaga ggtttgagtg 152940
aggtgaggat agaattggac agcccacgcc atgcagtgtg tgggttttcc tgctctcact 153000
ggttcctgcc ctcctgcttc cccaagaggg aattcctggc ctcgtttttt acttactctg 153060
attgttggac acgctctgct acagagtttc ttggaggcag ggccctcaga atctgacact 153120
ctggcagggc tccctgaatg ctctctctat ctctgccagg cctttgctgt tgctcttcct 153180
tctacccata tacagtactc tttatgcaca tgtaactgta ccaaaacctc tctcctggct 153240
gattcctcct tatctttcag tgtcaaagct ggcacttcct cttggaagct ttctttgagg 153300
tccccaaagg atggggttag gtgtccctgc ctgctgaact catccttaac atagcatgta 153360
gactgaattg ctattgccta catagttgtc agtctctccc attgtcaaag tgacaatccc 153420
aaagtggttg gggatgggct ggtttaccac tgtatctcca ttgcctaaca tagtgtcttc 153480
acaagtgcca gatactgggt gtcgaatggt gggtggatgg atagatggac caaagaatag 153540
gtgtgtatgt gtatagactt cccagggatg agacaggaat acatcaaaca taccactcaa 153600
ttttatttgc ttatatttca atagattcta atgtagtaat gcctctttat ctggcatcag 153660
```

-continued gggaagacag tgtgctacat gagaggattt tccagaaact gaagctgacc catgtcccaa 153720
gactatttca aacatccatg acatatcaca gacattaagg actcaagctc tgtcgtcaga 153780
ctggtagagg tcatctctca acttgccttg tgctgtttct agacctcact tctccaattt 153840
gaaacccacc tcagggaatg aaaggagtta atgtagagaa atgtctttgg cacagtgtct 153900
ggcacttggc aggtgttgaa gtatcagctc ttaattatta ctatcagaaa gcattacagg 153960
ccagtcacag tggctcacac ctgtaatccc agcactttaa gaggctgagg tgggaggatc 154020
gcttgagacc agcagttcaa gaccagcttg cgcaacataa tgagatccca actctacagt 154080
ttggagctgc agtgagccat gatggcacca ctgcactcca gcccaggtga cggagccaga 154140
ccctgtttca gaaaaaaaaa aaaacaaaga agaagaagag gaagaaagag aacaccatat 154200
tcaagtgctt tctaaatggc aaatactgcg tttcatccca gcaacatgat ggaagtctgt 154260
gcattaaccc agtacacaca gagttctgat tctgaaaaat gccccatctc ttctctccta 154320
cttgtcatat ctgacaatgt agtctccatc tctggctccc tttctagtct gcctcctttc 154380
atctctctac tgggtaactt attcacatag caggttaaaa gttgtgtctt aacacttaag 154440
actccaaatg catctattca gaagtcacaa aggtaaatct gttcaggaaa gtgagatatg 154500
ggctgaggca caactcctgc agagtagtga tctttgcaaa gaggtaagaa aagcaggctg 154560
caggcaggag ggggacagtg caggatccca ggattttgtt acaagggaat ccaagaactc 154620
agagacttac ctgcttactg gatttgaaaa agtgcactgg gggttgctag aatttgacta 154680
aataactaaa atattgtcga atcagtaaac attttccaat caattagact agactctaga 154740
atgtcagagt ctgaaagggc attaagcatt atagagatca aacaatcatt tcacagatgg 154800
gaaagctgag gcctaggaga gcgtgggatt tacttaaagt catacaagta ctctgtaatg 154860
ataaaaccaa aaagagaatc gtccaggtct tctgacagct agcctagtac tttgtctaca 154920
gaaccatgtt atctcttctg attgaatatt ggttgtgaca gattcaaagt agatataata 154980
cctcacaact actaattata tttatcaaca tttaaccaat gactgccttc tcccacaggc 155040
cttgggccta tagggtctgt ctgtctgttt ctgtctctct ctctttcttt tacttcctct 155100
ctctctgctg ttgcttaggt ttggctgaag tgtagaaatg gtctgacagt caggcactga 155160
gcaactctgg gagccagggt tcactcaagt aaatccaggc caggctacct ccaagccatg 155220
ctcttttagg gagtagtgcg taaatgcacc ctcttagcct tagaggagaa agcactctgt 155280
ttaaggtaag agatgtttgc agaaggggaa aatgaggaga taatttgaag gggaaaatgt 155340
cctggcctcc tgtgtgtcta aggatttgtt gtgtctgcct gctcccattt cgtccacccc 155400
catctcaccc tttcctactt cacttctaaa gtcctagcaa gaaacaccat ccatgagggc 155460
cccagaggcc caactaaatg tgtgaaacca agtaggtgac atgagggaat agatctggat 155520
cataagattt atatcctgta ggataatatt ttattgcagc aaggggagag aagagatcct 155580
aaaaatactg tagagagtat attataatat tttaatgagg tttatgtgct ccccatatac 155640
acttcaccct ggatgatgga ttgtgcattt tgacaaatct atatttaaca ttgggagaat 155700
aatatgtgat gtatgcttcc tggtagagaa atcatattta tggaaatctt tattctagtt 155760
attataatag acatttaaag acagtgccta ttgtgggctg tggatagata gagtgtcctc 155820
attagggtgg aggagaaaat agtgtgagtg gcagaggata aatggctacc ttagaagaca 155880
gcaacccagg caggggagca actagttcag ggtgacccaa cagtcacatc tctgtttggg 155940
ttcagctcct cctcagcccc tgctgcaggt catatgccct catcaagcac tcatcattca 156000
tttatttatc aaatatttat taagcatcta ccatgtccca gacactctgc tggcttttgg 156060

-continued gcacaaagaa gcatgtccta attttcaggg aattcacatt gactaaaaca gccacacata 156120
tatacaaata aacaaagaaa attattttag attaattaaa gaatgggaaa taagacagag 156180
tgatgtgata cagactgatg aggggtcact atttagaaga ggtgatgaag caagatctat 156240
acagagaggt gagatttggg ctgaggcaca actgctacaa aggagtgatg tttgcaaaga 156300
ggtaagggaa gagcattgca ggaaggaggg gaacagctgg tgcagagtct cccatgcaga 156360
atgagcttgg agcccagagg aagagagtga aagccagtgt ggctacagca ggcagcaagg 156420
agaagacggt tgtaagttag gtgaagtcag aggagcaggc tattcatgct ctgtgtgatg 156480
gtcagatgtt gagacttttc ctgtgtgcaa tgggaaaact ttgagtggat ttgcacaagg 156540
agaaagaaca atgtgttttg tttgttttgt ctttgttgtt taaataagat ctctctggct 156600
tctgggtaga gaagtgattt tgtcactgaa aaccaaatgt cctaaagctc aaggccatga 156660
acaccacctt cagataccag gagggctata gagtgggtca agagcaagaa ttgtgtgaaa 156720
ccagaatctc agtaactaga agtatgcaag cagatgttaa tgatcacctg ccaggtttcc 156780
tgcagatggt atgctggttt tcagtgggag taggacagat gggttatatg gttcagctgc 156840
aatctttaag agattatgac ctttaaagcc cattttctct agggactaac agaaaacgga 156900
gactcacagt agacaattag gtaccactgg ttaattgcat tctttattgc agcatgggcc 156960
aaaagatttt caataacatt tcaaaagtat tcaccaaaaa aaggtcttgg aggcaaatag 157020
atttgacaaa atctgggata aaaatgggta gaattcctca caatctttta tgcagctaat 157080
gtgaagtatg aaactctaaa acagggacaa agtatgcacc atttcccaaa tgtatttgac 157140
caaagaagac ttattttta aggagcatct tgtggggcta tagtttcatg aaaccttctg 157200
ggcaatggtc gcatactgta atttgagatc ccatacacag tggcaatgtg gggttctgga 157260
aacaggtgat atggtaaaaa gagtaaagga tctaagagca ttaacttttt tatcttaaaa 157320
gaaaaaaata ataataccta agtcacaagg atgtgatgag gactaaatag cctaatatat 157380
gtaanaagga ccacaaagca ctctaaaata ctgttttcat gacaaggatg aatgactttc 157440
ctcaccatcc accttggaag ggcaattttt aggcattgaa gatggccttg ggttggtct 157500
cactggggca aagattatga actctcatcc tatatcatat agtaaaacaa agtttaggag 157560
ctgactgact tggagtttaa tcccatgacc ttggtcttat tagcatcgta ttttaattag 157620
aagtataatc aaccacaaac caggattggc aactgcattg ggattctaca gaatcggtcc 157680
tgtgggtatg ttctcacagc taagctatta ctatggctga tacactgggg ggtctgaaaa 157740
tcagctagca agatgtacaa gcacaaagtg aacattagca gacaaatgaa cactgagagt 157800
taagggctag actgggaaaa tcgacacttg ttttcttaaa cgtgtattag cagcaatagc 157860
tggattcttc ctgtagcacc tttttatgct ttgcctttaa ttgatagaca atgtgagggg 157920
aagatcgtta gattaagagt caagaatatc tgcccaagtc atatgtccta gctgtgctac 157980
cttgaatatg ttcattaaat ttctgagcct tggtttctcc cctttaaaaa aatgacccag 158040
tcatcccttt ctagcctcaa tagggtcatt gtagagacca agtaaggtaa tagatgaaag 158100
tgtcttatat acatggctac tgtaattaat aaccatgaca acttctggct tctaatagat 158160
atctaataaa attggattta cacagatgaa tgaggcatcg aacaggtgaa tgtgtgagtg 158220
gggtagttag atgggtagga tggatggaca gttggataga ctggtgtgtc gaaaggatga 158280
atggatggat tggtttgttg gatgggtaga tggatagatg acagttgggt ggataattga 158340
tgggttggat ggatgaacta gtggatggat tcattttgga gtcatctgac cactttttgc 158400
agtcttctat tcattaatcc ttctcttctc ttgtagtctg ttcccagttc tccaaaggag 158460

-continued tctatgccat ctttgggttt tatgaacgta ggactgtcaa catgctgacc tccttttgtg 158520
gggccctcca cgtctgcttc attacgccga gctttcccgt tgatacatcc aatcagtttg 158580
tccttcagct gcgccctgaa ctgcaggatg ccctcatcag catcattgac cattacaagt 158640
ggcagaaatt tgtctacatt tatgatgccg accggggtaa gccaagggtt aggggaggga 158700
gacttttgag ggatggagag aaaattacca gcagaaagga gaatgatgcc tcactgcttc 158760
cctgaaaaat atgggaaaat tatccaaaat gctttatttc tgagaaatct gactgattta 158820
tcagtagctg acctctaatt cagtttggaa acgcattctg agaataattc tcttaatgca 158880
ccatgtcact ctacagctca ctaagctttc atggctcctg agtccaaact caatgcaaaa 158940
ggacctcaga ctttggagtc aggcagatct ggatctgaaa cctaggttct gtcctctcca 159000
gctgtttgac tttggacaaa ctctctctgc ctcaatttca gcacttatat aatggggata 159060
aaattctcta tgccttcatt ttctcatgtc tataatgagg ataaaaacaa tgtctatctt 159120
ataaaggttt tgtgaaactg aatgagatga ctatgaagtg ttcagtgcct gcaacatagt 159180
aaaaactcaa aattctttct ctgttttaga tgttatcatc atcatcatcc tcctcatcat 159240
aatcttcatc cttctctggg ctttctaatt cttcctcctt tgaatttaac atcacatttt 159300
ccaaatgttt tctatacttt ttcttctcta tgtctttact catgttattc cagttttctg 159360
gaatgcactt cccttctcca atttacatct gtaaatcctt ctcctctttt gcaggatgtc 159420
cctattcccc aattctgtgg atgggagcac tctctccaac tcccatgatg tttgtcttgt 159480
actgtcctac cttctcattg tatactaaat agtcttgtaa taatttattc actactggtg 159540
taaacaaata aatgggtcac gcaagacctg aaaggtgaga cagaggagta cagtactgat 159600
gtggttgcct gcagggagtc ttagaaaact tttgagttgg agagaggttt gtgaaagtga 159660
tttttcaggc agttaggcag gcgtcgttca gatgggaagg agccaacaga agaaaccagg 159720
aacaccctat tttctttgat tttctcttca ctgtccccac tttgatgact tcccttctca 159780
gactgcgact attgcagggg tcacctggaa gtctatttca ggacagcttt gcagcataat 159840
gtagctggag gcctggaagt aataaagcca gaaaaatgta cctttgcttg tgggagatca 159900
tctctggggt cagcagaagc acccacactc tcaaaagagc tccacctacc tcagaactca 159960
gagctcagag ccctgccgtt tgtcagctgt gtgaccttgg actaatgact aaatctctct 160020
aagcctcaat ttccacacta taaaataggg ataataatag tatctacctt gaaagattaa 160080
gtggattaaa accagtagaa cagtgccaga cacacagtac attttcagta aatgttggtc 160140
tcaaactcac caaacaactt gcactgaaaa ggaaacaaag ataggaaggc atagcagaac 160200
caatctgcag atgattcttg aggccagata ccatattggt cactgtggaa gaggttaact 160260
gtgttactga aagtcagaaa tgacatacat acaaaaaatt aatccatgca agatcaaaat 160320
aatatctgtg aataattaat aatgacaccc cccccccaag atgttcatgt tgcaatctct 160380
agaacctgca aatatgtcta tgttacatgg caaaggaaaa tgaaggctgc agttgggatt 160440
aaggttgcta aactattgac ctttaatagg gtaattatcc tggattatgt tgggggggaca 160500 caatgtaatc acaaggtcct taaatgtggg aagttggagt cagaagagtc agtgtcagag 160560
tggtgcaatg tgagaaagac gaccaccatt actggccttg aagatggaag gggccatatg 160620
ccaagaaatg caggtagcct ctagaagttg gaaaggcaag agagtggatt cttccctaga 160680
acctttagac accaacacag ccctgctgac accttgattt tagcctggga cacctatctc 160740
atgcatctta cctcaagaac tgtaagatag tacatttgtg ttgttttaag ccagtaagtg 160800
tgtgataact tgttacagca gcagtaggaa actaatacac catctaattc tccaagaaga 160860

-continued aacaaagcag cattgagtaa tggcctctct actcatttag ctatagatca gaagagagta 160920
gtttaattca ggacacattt tatttattta tttatttatt tagttagtta gttagttgag 160980
acagagtttc actcttgtca cccaggctgg agtgcaatgg cacgatgtgg gctcactgca 161040
acctctgcct cccaggttca agcaattctc ctgcctcagc ctaccaggta gctgggatta 161100
caggtacctg ccaccatgcc tggctaattt ttgtaatttt ttttagtaga gatggggttt 161160
catcatgttt gccaggctgg tctcaaactc ctgacctcag gtgatccacc cacctcgacc 161220
tcccaaagtg ctgggattac aggcgtgagc cactgggcct ggcctgccag gacacatatt 161280
aaacacctac tgtgtgagag acaaagtatt aggtattaaa gatactatat tgaacattca 161340
caaatttgat cagcagttat taggtgacca tttagatgct aggttggcac atttaataag 161400
cagttactga gtgccgaata aaactaacag ctaatattta taaaaccctt gcaggtgtca 161460
ggctctgcta tgtatcaaac attctcactt aatcctcata atgacattat gaggtgagca 161520
ttatttacac cacactttac ctttgaagaa actaaagttt gaagaggcta atgagcctgc 161580
acaaggccat ttagccatat gttggatttg agcctcagat tgttttttaa tcactagttc 161640
taccatctat gttcagaaac acagtgtctg atctcacaga gttcagagtt ttgcagccag 161700
agaaaactag aactgagttt ggcagaagag tgggtttggg ggtagccagg ggaggtaggt 161760
gcctgatggg agtgggtggt gcccacaaat cctgactgtc atttctcttc tactcatctg 161820
aactttaggc ttatccgtcc tgcagaaagt cctggataca gctgctgaga agaactggca 161880
ggtgacagca gtcaacatct tgacaaccac agaggaggga taccggatgc tctttcagga 161940
cctggagaag aaaaaggagc ggctggtggt ggtggactgt gaatcagaac gcctcaatgc 162000
tatcttgggc caggtagtga aagcagcaag ggctcagggt gggtgcggga ggtgattcag 162060
gaatagccag acacactttt gccttgggtg ttataaagag ggttataaag agggttcttg 162120
actaggtgag actaaaagac ctctatctca ttttctataa ttcacaaaat ttaattctga 162180
aatagcacaa acaatgggag ccttgacata gggcttcaaa tggttctcag acctgttaac 162240
tccaatgtat ccctctattg tttaaaaaaa aaaaatgctg gatgcagtgg ctcaggcctg 162300
taatctcagc actttgggag actgaggcag gcggatcacc tgaggtcagg agttcaagac 162360
cagcctagcc aacatggtga aaccctgtct ccactaaaaa aaaaaaaaaa aaaaaaaaat 162420
ttagcttggt gtcgtggcat gtacccataa tcccagctac tcaggagggt gagacagtga 162480
ggcaggagaa tcccttgaac ctgggaggtg gaggttgcag tgagccaaga ttgtgctact 162540
gcactccagc ctaggcaaca gagcaagact ccatctcgaa aaataataaa aaataataat 162600
gataaattac attccatttt agagtttatg aaatgttatc atattaggaa cacagcttat 162660
agggccaaat ttctgggttc gactctggac tctgtcactc atgatccagg gtttggcatc 162720
tcattccttt caccttctta actgttttga aaggctaagg aagcagcagc cacctttatt 162780
tccattgttt ccctgaacat gcccttccct ttgagaaatc aattgacagt acattcttct 162840
ataaacaggc attgtaactt caacagtctt gagctagatc tctctaaact gtgcttcccc 162900
tggtctcaaa acaaaagccc atgcccacca cagaattagg attttttgta gattccttat 162960
ctttttaaac tacatttatg tattcagatt cagagctagc aaggtagcag acgttgcaat 163020
aacttttgaa caatgtcata caataaaatt gatagtttta ggtacttgac aacatgacaa 163080
agtttgttaa tggccttcaa gacccctggg gccctcacag agaatcttgg tactaggaca 163140
gctattactc agaggcctca gcaatagaac acagacagag tttgaatgtt atggattctt 163200
taaggcacta actgttctac tttatgaagt acaaatttgg ccttccctct tggaaagaga 163260

-continued aacccagcaa aacttgttcc attgagatgg aagttctctg ggccggagtc agggatttga 163320
attgcagttt tcaattcagg caggataaga taatagttaa gagcagagat aaaaccagac 163380
tggctagggt tcaaatccca gctctagtat ttactggctt tgtgaccttg accaggtttt 163440
taatctttct acatctcaag ttcttgatct gtaaaatggg catcatcatc ataataatag 163500
ccacttttag agggctcttg tgagaattaa aagaatcaat atatgtgaag cacttagaac 163560
agagtctgcc ccacagtaag tggtacaagc aagcatttgc ctatttttgc tattcctagt 163620
gcctactagg accagcttct tgagtcactt tcttccttgg gcataagtga atccgtctgt 163680
aaaatgtgaa tgaaggcctc tgttctataa aactgataaa aaggcaagat aacatagtcg 163740
atggaaaaag tgccaaatga taatgacata ttaatagaca gatgacctat tgtatattgt 163800
tctatggtac agacagtagc tattactact atttttttag tgtgtatggt ataccagata 163860
ctatgccaag accttcccat gcataatcct acttcattcc cacatcaact ttgtaaaaca 163920
gctttttca attcccctat tttatagatg aagaaaagag agattatact tgcccaacat 163980
ctcacagcta gcatatgata aaagcaggaa gtcaaaccta tcttggtctg gccaaagaac 164040
ctagcttctt aaaaatgcaa cttttctgct tctgctatct ataattaact cctctctcaa 164100
agggcaaact tgcgttttgt aaagaagtga cccgtttgta tgggtatttt agattgtagc 164160
atattgacat tttttaaaat tgtttcattc atctattttg aaaagtaaga ccaaagagtt 164220
gaaaggattt tacagatcac ttgattcttt gcttatgctt acattttata gatagaatga 164280
ctgacagtca aattgattaa gttatttgcc ttagacaaat aatgaatgac agtaatgagc 164340
ctacaactta tatctctgac ttacaatctc acacttagca tcatcctgga ctatctcaca 164400
ttcagtaact gggaacgtac ctgggataca gttacattca gtaactgcat acagtctaac 164460
acaaaatttt ccacctaatc tgaggaaaaa aacagtgact caaaattcca aatagggaat 164520
taactgcctg tgtctgtctc cagcccccac ccaactaaaa tctaagctcg acgatgccag 164580
ggatttttgt tttattttct tccctgctga gtccacaatg ccttggatag tgcttgacac 164640
caaataaagt attcaataca ttcttttcag tgaattaaaa gaataaggaa tcaatgaagc 164700
ctctaagaaa gttcttaaat gtaagataaa tctggatttc tatagatagc cattggctgg 164760
ataagagcct ttaagatgga ggaaaaggca tgtcaggagg cccagagggc atgtgagggc 164820
tgggtttcat actgcagttt tgcaggctga gtgatggatg ctgagcgtcc actggagagg 164880
atggcaggaa gataaacaca caatcaagaa tatccttgga aaccattaga aagagtttag 164940
ggtttattct gtaaacaatg gggagtcagt gaaggtttgt gagcaaggaa caggattatt 165000
agaatataat actttatcaa tatatgatgc caaagcatat aaaacagtca ttaagcacaa 165060
aattagttag aagtgagaat agaccaggac ctgttgaggt tatccatcac atccccctat 165120
gttattgtct tcatggtgct tgtacctgct gaaatcttgt tcatttatct atttatatat 165180
tgaccatctg gcaccctact aaaatgttaa ctcaactcaa tgagggcaca gagaccttgc 165240
ctcacttgct caatgctgtt tccccagcac atagcatagt gcttggcata taatttatgt 165300
taaataaatg tttgttgaat ggattaatta gttaatcata gagggtttta cagaggagtt 165360
gagattggag ctcagccatt aaggatacga acaatcagag agaatgggag aggccattca 165420
gacacaaata ttgtgaatga aggcaatgca ttgggaatga gctttgaagt aatgggggtc 165480
agtgaggtga tggacccctt gtgaaattgc ttcttacatt tataacacct ttctcagttt 165540
gttaccctgt atatatttat ccgttcacct atttattatg gatctcctct caatgaagtg 165600
taacctccaa gagggcaagc accatgcttc tttcaccttt ccactgtgtt gccaatagtg 165660

-continued

```
cttcacccat agcaagctct taatacatat ttgtgaaagg aaggtattag aggagggaag 165720
gtcaatgtat aggttgggga atagatagat gggaaggttg gtatcaggtt ggatcatatg 165780
aaattgccag tttttataag tcaaaagtca tcagttatca gctgtttcct ttgtttcaat 165840
ttgtactttc atcttgtggg gacaatattt ctccattgcc tgaatgtggt tggttttaaa 165900
atatcatgtc tttgctgttt tgtgtttatt agaagctgaa taggttcttg ataaaggtgt 165960
ctcattgttg aaaaggcagc aaaccatttg acaagcagat gaaaaagtaa tgaagaatta 166020
ttaataaaac tatcatccca atagtatttg agctccgtgg tctggaattt cacaatctaa 166080
ccactatttc aaagaattca ttgtgtgtgc ttgcatttaa ttattcccca cataaaaaaa 166140
catgagtcac tatgcacata catccaatta agtagatgtc tgaatgtgga ttttaataac 166200
cttgaaaatt tattcagtta gagaagaagc ccaagtgctt atcatctgtt atatgtctcc 166260
ttgcaacagt gcagggagag agacaccgag cagagtacac taaccccaat ttgatgatta 166320
aaaaaaatag ggaattagat ctagttaatc tgcaggctga gctagatcta aaaccaaggt 166380
ctgtagtctt aaccattcat tattaggtgt gtctcctgcc caagcaaact tctgggcagt 166440
tctttccaca aatatttttt ctacctgtga tgattaggga tagtctgcat tttgggataa 166500
aagggtattc attgacactg gttcttaatg attaaccata atcaaacatc aaatggaaaa 166560
gttcacagga gtcaggtccc tgtcctgata ctgccaccag gctactatca gatctgggca 166620
aaacattttc cctctgtggg tcttgacttc ctatctgtac agtgagagtt tggaccagat 166680
gatcctaact ttcccttcca gcttctaagt tgggcaatcc attaatgtct gagtacctaa 166740
ctgattcggg gaggaaggca caaaattcag aaaaagaaag aagagcatct atatatggtt 166800
catgcaagga attgaaggtg aagtcatcca catacccatc tgaccattca tccaccatcc 166860
atctattaac tcatctgttt ttccaatcag cgaatattgt catgacagat ttcatgcaac 166920
ataaaattcc cacctaaaga agaatctcca catacaagga aggtttatga aagaaagaac 166980
gcagtgagca tttcagatgg gtccttgggg ttacagtaac accactctac ccttggaatc 167040
agacaaaact gatttcaaat tctgtatctg ccacttagta gctgtaagat tacaacttac 167100
agaggttata taataggcag tccatgccta ttccttattt gtaaaataag gatgctaaca 167160
atgccaccat cattggatgg ttgggatatt gtagttctag tacttagggt agggcacatt 167220
gtaagcactc gatatcagct gccgttatta ctgttgttgt cgtggcttta actgttagta 167280
tgattaatga gtctccacct attatgtttt gtagattata aagctagaga agaatggcat 167340
cggctaccac tacattcttg caaatctggt gagtagagca ctgcaggctc tcagctcaag 167400
tcctttccag gtttggggcc ctaccttgct tctgttgtcc ctggctgatg tgaactgagt 167460
gggtggaagg ggcaattcag ggctgtaata atgagtcttg gcaatactac atttttatct 167520
tctccacatc ccactcatca aaccacaaca cactattcat gaacctctaa ccttccttgg 167580
aagagagcat actggtgggc acggctttat catcttcaca attccagctt taattggctc 167640
tgccccttgg caatagggac aaaatcacca catctttgaa ttaatgcaag atgtcttgat 167700
cttactggtt tgggtcctcc atttgaccc cagtgatagt tttacttctt ataaatacat 167760
ttacatcata attacactag tattgacaaa attttaacca gaaacaactt cccagcatga 167820
acaatattat gtccatttag tttatattca cttttctata tggcatagat aagtttgttt 167880
taaaatatat atatatatat atttgtttta atgtactaca gatcattgta ttgagtgcta 167940
ctgtttttta tattacaaag aaaacaactc atcaaatcat tttttgtata tattaaattt 168000
tacctagtag cacatactat tatgagtttt cttttgtaac cattatttct gtcaagtcta 168060
```

-continued tttttctgg gtcatgtttt gtacctccac cttttttgtc atgaagttta attcttctag 168120
cttttctatc caaagccaaa tgtattttta tttggtgttt agccccattt ttaaaggctt 168180
tattgagaca tattttataa agcacacaat tcatccattt aaagtgtaca attaaatggt 168240
tttcaatata ttcacaaagt tatgaaacca tcaccacagt cttattttaa aattcttcat 168300
cactgctagg agaaatccct tacctattag caatgactcc ttatcatccc ctaagctcct 168360
ccagccctag gcaaccatta atttactttc tatccgtatg tatttgcctg tttggagcat 168420
gtcatatatg tgaaatcata caatatgtgg tcatttgtaa ttgacttctt tcacttagca 168480
taacattttc aagtttcacc catgttgcag catgtatcag tacttgattc ctttttattg 168540
ccaaacaata tttcattatg agcatatacc acattttctt tatccatttt tcagttcatg 168600
cacatttggg ttgttttcac tttttgacta ttatgaataa tgctgctata aaatattagt 168660
gtacaagatt ttcactttaa tatataccta ggcatggaat tactgggtta tatgataact 168720
ctatgtttaa cattttgagg aactccaaaa ttattttcca aagtggctgc atcacccatc 168780
aaattttaat caataacaaa tttttccatg tgacagtttg aatgatggca agtgtctctt 168840
aatgataact atttctacag tttattatcc tgttctgtct ttgcaatttt ccatgtttcc 168900
attaagaagt ggtttctagc tttttatcta taacgaattt tcaggtttta acttacttaa 168960
ctgaacatat aactggcttc agttttaacc atgttatttt gtgttgatta tctctatgag 169020
caatagtaat tgaacaaagg attaatattt gttactcatt tctggagtaa agtctgttag 169080
tagaaataag gcacagggtg catgaatcta aaaatgtgac caaagcatcc tgcctaatcc 169140
ataaattctg tccttctttc tgacctggta tccagcctta gatagatccc tgccttactc 169200
ttctttcccc ttcttcaact aacttgtctt ggcaatattt cggagtgagg acttgaaata 169260
agaagggctt agagaagtag gttaatttag gcccagctgt taatggctaa atatattacc 169320
tttctcagag gtatttgcat tttaaatgag ggtggctctc cagacacttt tggggaacga 169380
agagtctcac cctccaaaga ccatttgcaa aaatggaatt tttgacttcg gagtgaggaa 169440
agcccttaac atcccttgac tcccagatcc ttagtgctag agcggactta ggaagtcaac 169500
tccacttaaa cctcacttgt ttatagggaa acaaccagca aaggggtgtg acttggccaa 169560
ggtcacacag tgaggcagca ctagagctag gcctgtcacc aagggtagca ggcagtattc 169620
aggccttttc tataactcca ggtcatctct cagtgaaact ttgtaggcac cctgctgctt 169680
aagaatacac agaacaatac atagaacaag aatacacaga acaagggtgg ggataggcat 169740
aattacctct ctggggtgag atagaaattg catgccagtg gccttagaga cactgaaaga 169800
ccccaggtaa ttacattgcc agcctccatc tgttgccaag taacccctca gtcacagcat 169860
caccaagtca gcctcttggg ttgttgtatc cttctgatct gcatttttct tcttctgact 169920
taatgacctc tcaaatgctt acaactgcca gctaatagga tgaaaattgc atataccatc 169980
caaataaaaa agacttgcat gtttcgatag attagttgat aattaggctt caaattacta 170040
attaattcag tttgaaacat agtcgcagta tgtggtgtgt tttcttcccc cttcagagga 170100
ataatgcaat tcataagacg ataattttta gaatttctgc cacataatta gcctactgct 170160
gcatagaact gacccactcc ttcggaatgt ttgtgattag ggtgtaatta tagagttaga 170220
gaccaaggaa ggctttgaaa gatttaacaa aaggagggag ctacactttt attttacagt 170280
tctttctgtc cctgtcggaa tgcatgagct tcaaagtagc cagcagcatt cttttagcag 170340
atcacttcgg aggaatgctt ctggggttca aatagccacc tttgaagggc tgccggaaga 170400
gaggagggga ggagattgta ggttagagaa gacaacttat aggcaaggag tcaaaacaaa 170460

-continued

```
acaaaacaaa acaaaaacaa acaaacaaaa aaaaaaaaac cttgtttttt gtccagatgc 170520
ccctttagc tggctctgta ttcttggaca actctccaat cctcagtttc ctcatctgtc 170580
aattgagaac aataattcct actctaccta ctcatagtgt cactggggag accaaatatg 170640
ttgccaaatg caccatgctt taaaaagtta aaagtgttct gcacaaatgg aaaattctta 170700
cttcacatat taaatccgcc catctgtaca tattcacata tggtgtgtat gtacatatgc 170760
atatatatgc ttgcatatat atccatattt tataggagag atatgtatgt ttatttccat 170820
agcattggtg tgggcataag atgaacttga accatgcaga aattggaaag ctatgccact 170880
atctctcaca gatgtgcctg ggtcctggaa cacacaagtg ctgagcctgg ctgccagtgg 170940
tcctccaaac cctaacactg actgtgcatt cactccctgc tctgagactg tggggagtgc 171000
agacatctgg cagccagagt ccttcagagt tgtagttctt atctttgtga ctcaccagaa 171060
gcaaatctta gaccaaatga gtgtttctca aaacagagga cctgtggacc tctgtagtgt 171120
ttctgtagag ccagtttgga aaatgtggca ccaacaagcg aatgcttcag tgccactgca 171180
attgccaata tgagtaccta aaccatggag taaatggtca gattgttata ctggtattta 171240
gaattttact ggaatgaaag cacatatttt aaaattctca tagagaacta gaagattggg 171300
agaatttaca cagggttcag cagactcctg tctgaaaaat attgaatttg ttggacaaca 171360
ttgaccagtg tgaacaatat ggtgccttct agaggagtaa taacaatagt aatatcaaca 171420
atctctctca tttttatacc atattatagt ttatgtgata tttctgtatg aatcatacta 171480
ccgggttttg gatgtcataa tactcctatg aagtaaacaa ggtggaattc atcatcccca 171540
ttttacagat gtgggaactg aggctgagac attacatgac tgagctgcag aggagaaaga 171600
caggaaccta attaatggag tttggctgtc aggaatatga caaaaaccaa gagatgtggg 171660
cataagaata agatgatcag gctaacctga tgctgagaca cttgagtcac tgaattagaa 171720
ttccttaaac ccctaataaa ttacaacaat aataacaatg gcaataactt ccacaattga 171780
ctgattgcta cattctagac actatgataa acacttaaat gcatgtcaat taaaccttcc 171840
caatagccct tgaggttgat attatcctca gatgaagaaa cagagcttca gaaaggttga 171900
cttttccaca gtcacaaaac atataaagtg atggagctgc acttctcctc aagggccatg 171960
gaatcccaaa atttgtgttc ttattaccgt gccatgtgag tgctgggcag ggagagttgg 172020
ggaaagagtc aggaaagaga gggggttgtc ctggacaaga cagcttgagt ttaaatcttg 172080
tctacagtag cagcaataga tctgacattc caacccaggc tctcaaattc ccattggaca 172140
tctgtctcac catttactcc atggtttagg tactcatatt ggcaatcgca gtggcactga 172200
agcattcact tgttagtgcc gcattttcca aactggctct acagacacac cacagaggtc 172260
cacaggtcct ctgttttgag aaacactcat ttggtctaag atttgcttct ggtgagtcac 172320
aaaggtaaga actacaacta cattgatgga attttattaa aattattatt tctagtgtga 172380
cagaagctga ggaagagatg acggagttag cccattccag gtcttatcgg ggtacttggg 172440
aaccaggaca gttggccatt tctgccatgt gcttgcagat taactcctgt agaatgttag 172500
attggaagtt ttagtctatt tggcagctat tccaagcccc cagccccatg ctgctgctcc 172560
tctgcgggat cagccctgag cagaaactgt tctttagtct ccttgctccc ctgtggtgat 172620
aaatctgtca gctccttctg caaagctgag ctcatccact ttcttcagtg cctctcttcc 172680
tgttggctcc gtacctcaca gttatgttta gtttctgcag cttctggtta ggcaggtggt 172740
atagtagttg ggaagggtgg ctttggagcc agttctgggt ttgaattctg acttttatac 172800
ttattagcta tgtaacatta gtcaatttat ctacctttc tgagtttttg ttgccttatc 172860
```

-continued tttaaaaaag agaatgatat tatgtacatt cttatagggt tttatgagaa ctaagtgaga 172920
tccctcaacg ctctcggaaa tgaaatcaca tctacctgtt ttatgctgcc atagccccag 172980
atattttttc acttactata cttgagatta gataactgat tctctattat ttcatgtctt 173040
cttccctgtt tatctacaag ctcctagagg aaggattgtg tgtgacttat tctctgttga 173100
attcccaggg cctggcgaag tgagttgcac ataacaggtg tgctttaaaa agtcaatgaa 173160
tgaatgaatg aatgaatgaa taaatgaatt cctagaaaat aatgtctgca cctacatatc 173220
aaatgtactt aaaggcaaaa tcttttagca cctatgctag aagaagtaga ggtagtagga 173280
atatgaattt agttatgaat atgcaaataa gtagttaaag acaggcctaa gaggccttct 173340
aacccacttc atgtagagag ccagaatctc ctctacaacg tccccaacag aaactcagcc 173400
atcaggttca tgcttgaata atacccagtg atggaaaagt cctacctctg agacagcccc 173460
ttttcttctc aaagggctca gacagtttct gcactcttcc tggaacaggg cacgacctgt 173520
gtgctgctca ccctgtgtca ctctctcatc acttctgact ctaatgccct ctggctcttg 173580
caaaacttac ctgtgccttc ccacaaagca gcctttgagt atttgaaaat ggctaccttg 173640
cttactcttt ggtgtttgca ccttcagtct ggacacaccc ctgttccccc agtgccttct 173700
ctcaggatgt ggttcttaca gctgtccaga caaccaccaa acatggacca ggcctgtccg 173760
tatgcctgat actgcactgg gctcatgcaa gaaggactaa gaagcatgag gctgaacttt 173820
gtcccagaag caacctgacc ttttcttcca gctagattag aacatgtaaa ataacattct 173880
caaaagaatg ccagagaaaa atcacagcct gtgaaaatat ctaagcctca tagatggcca 173940
cctaccctgt cacagtgtgg tgatcagagg ccagggaggc cgcctcagct gtggggtgtc 174000
tgggaaggct cgtgaggctg catctacaag gccagcagtc atgtagagtg tgccctcccc 174060
cttgtttgaa gaatccagcg gagtgagagc tgaagggtac ctatgaaact catctcaccc 174120
ggcgcctcat tttataaaat agacactcaa gaatgagaga aaggaggtga tctgtctgaa 174180
ttcacccaga agttaaacag caaagctggg ctaggatttg gagtattcac ttgctccttc 174240
tttgtggctt cttttctcca aactgccttt tcacaatgtg cccatatgcc tctgtgttga 174300
gggtggggca ggagcagaga cagagacaga gacagagagg gagctcagaa gtgcttccta 174360
ctccccactg tgcccctctc aaggactctc tttgctgatg aagcttattc cagtttcctc 174420
ttcttcctcc cacacagcct tccctctccc gctctgctct cacctcactg ttcggtaaca 174480
gacactgtgt gatctccaga gctgacactg cccagagcct ttggaaggaa aaggagagtg 174540
ggtggataga aagacaaacc ccagatgcca aaggatgctg tcttccaagg tgatccaagc 174600
atcccagtct aggttactct ttgtattcac ccccatcctc tgagagaatt caccccagag 174660
acctctgaga ttttctgcct ccctccaaga aaagtaagat tctggtccca ttttataagg 174720
agaaaaatga agttcaagtt gttgaaaaac cttttgtaaa gtcatttgac taaaactgga 174780
attcaaactt aaaacctttc ccattctaag gattaggctt gttctccatt gggccacact 174840
gcccaaactg gggaaacctt tgcaattctt aggactggta ttataattga gcaaagccaa 174900
gaaataaact cctttcttcc ttaaactgcc tgggtttgaa atctggctca gctacttact 174960
agctgtttgt ccattgcaag tcacttctcc tctttgtacc tcagctgtct cacctatgag 175020
tgggaatatt aatgtggatc tcataagata aagataaaat gagttaatgt atgtaaagtt 175080
ttagaacaca gagtgcaaca gaagcccagg gtctcatcct aactctgtca cttactcatg 175140
accatttatg caaatcatat ttttctgtaa gatctcaatt tgttctagaa ttggcataat 175200
gttttcaaaa ggaaaaaaat cagcaaaaca atcttcctgc ctgtgtgatt tagggttcta 175260

-continued gttttcctga ttgtcttcag ttcagaggta tcaaaaaata tctctcatag ccacactggc 175320
tcccttaagc ttaaggaaga ggctgttcta ttaatctcaa gcacttggtg tgtgtatctt 175380
tcgatcttgc aaaccatgca cacctaggct gatttggaat ggcctttttc atgctgggtc 175440
agcatccttt ggaccatttc agatatgtaa gacagtgact atgattgctc tgacagagca 175500
tggaaactca ctgtcaccag cagccttcaa gcaagagggg cccccttagca ctaattttgg 175560
cagatggttg gtgagctatg taactagaag agtctggtcc ttgtttcctt acctatccct 175620
ctttttaaga cagaaaaata gagaatacaa tgggagggaa atggagctcc aggagacaca 175680
ggattttagg taaatactta ctatgtgcca agcactgttc tctaagaatc tgacaggtaa 175740
catagttaat cctcacaaca gctatgagaa ataccataat aatccttatg ttgcagcaaa 175800
ggttactgag gcactaaaag gttgagtagc cctcctgagg ttgcacagct aggaggtggt 175860
ggagctaaga tttgaatcta ggctgacatg cacaggcagt ttctgtgaca gagggcagta 175920
accctctgtg gctctgactc tgaacctcaa tacatgcata ttttctgctt ggtgttccca 175980
gccctcttca cccaaccaaa ggcacttttt ttttttcagg cttcatgctt ttgctgcaag 176040
accttccctg agctccaaga tcaagtttgg gtccactcat tttgctctat aattacttgt 176100
gtaatattgg cctttctcac tagaccttag gtaacttgaa agcaaggacc acacctgtct 176160
tcttctctgc tacatttcta tgtatagcat gggcctgaca gtgttaagca ctcatgagtg 176220
aatgagtaaa tggacaaata aatgatttac tacaatattt cttacctggt tcccagtagc 176280
tttcatattt atcatgtttg gactttcatt cttcttttta tcaaacattc aatgggcacc 176340
tactatatgg gaggcctgtg aaggtgtaaa ccggcttttc atcaaaagat gggcatgcta 176400
tgagtatttg cttggccttt tctagatagg aaggttttga tcatgtaaag ggtagatgca 176460
attggtttta agtccactgg gaactgtagc cataagggcc cacctcatac caggaaattt 176520
gctcttgctc tgaaatggcc ttggccaggt gtcattcctg accacaacag ttggggcaga 176580
gtaaagatga agggactctc tggaagacca actattccca ggccaggtag tacacccatg 176640
cagccttgca ctcaatagcc caacctggag tccctgacct tctgccagaa agtgccagca 176700
ttttatccta aatcccaggg ctgagagaaa ttagtttgtg agaccctgac tgacatttac 176760
aatgctttgt caatactgga tacttgtatg aggtatgtct gttggtgtgt ttgcagatat 176820
ccaagtgtgc ctccctggtt ccaaatgtaa ctggataagt caacacgaat gctttttttct 176880
tctcaatatt tatggtgttt tcactgattt aagcacagct acaatacctt gtttaattag 176940
aggaaaccag actaccctct gtgttaccag agattatata gggagaggac accttaaagg 177000
tttggttggt taaagtggct aaaataggaa aatgtgaaga cttttatgca gagacatggg 177060
tatttgagga cacaattaag tcttcagccc aggagtattc cacaaattca cacatatcca 177120
tattcatgcg cacatacctg tgtgatcata gaattgtaga tcaaagctgg aagagccctt 177180
aagagagaaa tcaagtggct cagaagtttc caaacttttt agtttgaggc tctattttca 177240
aatggaatct tgggggagaa ctctcatata taaaacagat aaaaagcaga gctactatgg 177300
tggaaaagag agggtgggat ttaggaccac atctttctgc cttttcccta acctaatatg 177360
gtaacttcta aaatgcctgc aaccaggaac atagcttata agatcattga tgtagccaaa 177420
gttcttattt tgcagatcaa tcaactaatg gctatacagg ttgagataat tgcccaagga 177480
caaacaactc atgagattca aagacaggat ttatgtggtt ctccctaaaa ctcttttcct 177540
gacacttctt atttatgacc tggttcacaa tagactacac aaaaaagtca ataagaagac 177600
ctctttgatc cacaagacaa aagctgaggc tgagtggtga caggattgaa gcttataaaa 177660

-continued aaatcatgag agggtgagaa gaaactttct gttccttcat tcctccacat gtattgagca 177720
tgcaccctga tccaggtact gcttgtggac gctgtggggg ccaacgtccc tgccctccag 177780
gagctcacag tctcacaggg aagatgagaa gggcccctgc acgttcaaag agaaagctag 177840
gagaggccta gagagatagg aataaagtgc tgtgtggttc acatttcaag taccagcaca 177900
cattaaagga gctaagggaa atgccctgat ctcatggaag cctgatactt ccttcttggt 177960
ataaaaatgt gtgctgctct gagtgcttca ttgcaggaca ggacataaat gaatagattg 178020
gcctcactag tggttgggag gcttgatgta cagtggttag aaaacaagtc ctagagtctt 178080
tttacttgtt ggtctctgtc cctcactagc tatactgtac tgagcaggag ctactccatt 178140
aacttaagcc tcaatttttt aaatttctaa tttgctaatg ggaatgataa tagtacccac 178200
tttacaggat tgctatgagg attaaatgag ataacacaaa taaagtactt agcacagttt 178260
ctactacaca gtacaggttt gatacgtgtt aggtacttgt aattattgtt ttagccaaag 178320
tctgccttct atgacatttg ccctttcatt ggctctggcc tgcgttccag agcctcagag 178380
aacaaatcat ccatctcttc cccatgacaa cccttctggg actcaaatac atccttcact 178440
tactttcttg gtcttctata cttttttagg ctgataattc ccacttttaa aaaaatactt 178500
ctaatataag acttttcaaa ccacagtttc ctataactac tctctcaatg gagctgtcat 178560
ctaagatttt atctgacaat ttggggaaac ttggcatgtt caacctgtgc cattcagagt 178620
atacagtaca agttctttga tttttctctc aacttacctc ctgtggatct caaggggatg 178680
ggatggagga agtgctcttt ccagtgtccc aggatttgtt taataaacct tacttgcccg 178740
tttccttgaa caatgttaga tgctccttct tccttctgac tggtgtggtg tcagcacagg 178800
caggatgatg agggctgaac agctcgtatg tgacccccttg aaagaatccc agagcaaagg 178860
aaatccagct ttgaagataa agcctttcat ccttcgatag ctatgttcct atacacctgc 178920
ttcatgttct ctcaggcttc ttgcctgacc cagtccctgt atttgaagca gttctaacac 178980
ctaacctctt ttgacccaat gataatgata atggtgaatg tgatgatcat aataatagct 179040
aacattcatt aagcacttac tatgtgccag acatggtact aagtgcttag ttttattaat 179100
tcttttaaac cgttcaccaa tcctgtgatg taggtgctat atctgcattt tgaagaccag 179160
agaactgagc ctcagagagg ttaagtaacc agtagacaca tataatcagt tcttttcttt 179220
ccaattgcac gtgataatta atagtcataa tgatggccca gagcctcttc aagattctta 179280
aagcattctc caaatcttca cagcaagatg aaagcatgtc caatgtagtt gtagtgttaa 179340
acacctcttt aggatatcat aattacttga aatgcctttt cattctaatc ctttgaaaat 179400
tataattggc atatgataga tggagtgact atattaacta gtttacttaa ttgagcgcat 179460
ttactcccca tcattgtact caaatgcctt ttcaacattg tgttacctcc tacagtggat 179520
atacagagga gacagattct gttctcaact aatcctctca ccagccatat aaccttaagc 179580
cactattccc ctctttgggc ctcagtttcc ctatctgaac aatatgaggg gtttgtttta 179640
cctcctacag tggatataga gaggagacag attctattct caaccaatcc tctaactggc 179700
catataacct taagccacta ttcccatctc tgggcctcag tttccctatc tgtacaatat 179760
gaagggtttg gtcttctctc caaaatcttt gctcctgtat aggtcaaaag tcagcaaact 179820
atggtccctg tgtcaaatcc agccatcacc tgattttata tggctcatga gctaagaatg 179880
attttttaca ttttttaatt gttgggaaaa aaatcaaaag aatgatattt tataatatgt 179940
ggaactatat gacattaaat taccatgccc aaaaatattg ggacagccat gctcttccaa 180000
ttactatatg ctaaatagta atagtaaatt actattttct atatatggct actttcatgc 180060

-continued tgcaatggca gagctgacta gttgtgacaa gaaccatatg gtttgcaaag cctaaaatat 180120
ttataatctg gccctttaca taaaaagttt gctgacccct tgcatagatg tggaataggg 180180
ggacactaat aggcttcaga taaactagac actttggaag catctaaaga cccttaggag 180240
gttagtgtca aggagaggaa cctagcgcag tcccacaaat attcgttcaa gaaagacagc 180300
tacatttgaa ggcccctgct ctggcagggt gacatattct ggctattaac tgtgccagcc 180360
acagtctgag gttcattgtc cctctttgtc tggagcaatc ttgacacacc atcctaaagc 180420
taaagtcata tgtttctcca ctggtggagc agtagaacac atttgtgaag aagacagatt 180480
ttatagttgg accacagttt gaattcttgc ttgctgtgtg atctcaggga aatttccaaa 180540
ggtctcttaa ccatagctcc ttaacagaaa attaggatgg atactcactc actcatttat 180600
gcaaataagt attgggtgtc tactgtgcac atttacctct tggaattgtt taagtaatta 180660
aaggattatg tatataaagc atttaacaga atgcctgact caggaataga gcttggaaaa 180720
tgtttaaaat acatctcaaa caattattat tcttttgttt ttaaattaca gtaacctcaa 180780
aactcttaaa aagctgtttg aataaagtta tataatgcat acaaaggggc atttttagcc 180840
attattgtca tttttgttct tataagcaat gcttctgaag ccgttttcag tggagcactt 180900
aacagcacca gtgtgcttta atttcaggcc aggagataaa aaattaagca gggctctctt 180960
aaaagaccat aacaaagctt caacaaatgc aacaacttct ctcccctgtc ttgccactgc 181020
tactctgtcc cccactttcc agtgactaat ggatgatatc taagatacat tagagctatc 181080
tgaggatcga tttttatttt ttaatagtat taaaaataca atatattcac atgataaaac 181140
agatattaca gaagggtata aagtaaaaga taaatgccca ttctttccaa ttctatactt 181200
catagaagta actattttaa acccttttcc tgcatttggt tatttaatgg tttcctttac 181260
acttctacat catatattta tgtttctttt tcttgcttta tcaactttaa ctccatatct 181320
gacttcccat tagaaagatg acaaatcagc tcatattaca cccccaacat ccccttctca 181380
atgtttgtta gcctatatgc tattatttgg aattcttctg atgattacct tgtatttttt 181440
acatagtgaa ccttgatttt tgattcacca gcattagagc tttgtcaaaa tacagatatc 181500
cagtttcctc tttagggcta ctgaatgata atccttgggg atggttattt tgcaaaagtg 181560
cctcaaggta ttctgatacg tccctcagaa ccactttctg agagcttaca gtttattggt 181620
caatttcttt gcatttaata atgacagtag acacagcatt ctttctcacc gatttattag 181680
tcacacatgg ggcaatgtga aatgctacat aggtgcagaa gaagcagaca agaacacagt 181740
gacctaatag ccctaggaac tcactcatca ccaagcttca ctttaggtga gaaacagtca 181800
ctcaaagaga agcatctggt accagtgctg ggaggtcagt ggaaggagag tgggtttaga 181860
cctgcattct tgtgctgaat agctggaaaa acacttgact aacctgaaaa acaagtactc 181920
tgtagattaa tttcattttt tttttgtcag tagtaacagt atatagagca atggtcccag 181980
catttgggaa catgttgtaa ataggcaaag tggctcaaag agagtagtaa tcaaacttcg 182040
tagttaaaat ttttaataga atataattag caatgtagta tttttatata atactatata 182100
attaatagca caaataaagc acataaagaa aaatgttcta attaccaaat attaccctct 182160
aaggtttttt ttaataaaat ggcaaagaaa attagaaaat tatttaatta aaccttattt 182220
aatgagagtt cccaggggaa cagaatgagt gaattgaatt ttcccataaa ccagtgggca 182280
aagagttaac acctttattt ccccccttctt agtcaagaac acagttgtgc aggttcattt 182340
tcttgaatta tggagaaatt tagtctagta actataatag agtcatttct tagtgattaa 182400
aagcattgta gagatgcaag attattattc ccagcatgaa atctgaaata ggagggaaga 182460

-continued tgtcagctat tagatgagaa tatagttcat gaccacaagt tatttcctaa ttttgtttct 182520
tttacttaac atcatagcta tgagcttgtt ttatcattct ctgtccattt tttcttagga 182580
ggggatgggg gttcagttgg ggagtcttat tagtttgatc ataagtaatt aaggtttggc 182640
tgcactaacc ttgttgtcag acattctggt gacaagattg agtggcattt atgttgagca 182700
gttgaggaaa ctcggccatt tcctttggcc tccattatgt ctgagatgga agcagtcagt 182760
atgaaatgcc caggaccttg ttacagattt tcaagagaca gaatttgact gcaggagata 182820
ctttccattt caatctccca gtagttactt tatgaacatg ttctttttaa agtctctaag 182880
aactatgaga aatctttcaa ctgtgctcta gcttttaacc agtgctgggg taagtgctct 182940
cttagatggt ataacgtctt ggaatgcata ttgggtacag gaacctagtt ctgatttcac 183000
ctttactaat ggcttgctag aaccattgtg caaatcagct acatctgtga aactgtaaac 183060
tgtggctgtg gaacacgtta aactcaaaag gtattttcaa cctgaatttc tcttttcaac 183120
caattacaat cacccactgg tatttgctgc ctgctggtca tatttctcct ggataattgg 183180
ctttctttct tgaggaaagt ctctggcttt tatttgttca ctcaacaaat atatactgtg 183240
cacctactct gtgccaagca ttgctctagg agcaggttct aggacacatc agtgaccaag 183300
acaaaaaagg ttcctgctct taggaaactg acatttcaat aggaggaaag aggctatggg 183360
aacacatgag taaacaagat aatctcaaat ggtgataaaa actctggaga agctctaaca 183420
gggcactgag atagagcaga ctggataggg tgctgggggt aactctacta tgttcttcca 183480
gaagcagttc cctgaaacaa ggattcaagt acaaggggct tcttgggtgc caatcctaaa 183540
aaaccaggga agggaggcag agaagggaag tctgcctaca aagtttcata aacaagatgc 183600
ctacactgca ggctactgaa ggagaacagt ccctgagggg atcccaacat gtcagtgtag 183660
aactcacctc agggtcatgc catgcagggg agaggattct ggggcactta tctactgact 183720
cttcatctgt cattgattga aagctgcttc tgggcatatt aactccttaa catgtctaac 183780
ttagcctgca ggtaggcgga gtagccaggt gtttgcagtt ggtacgtaaa gtagaatacc 183840
catgtagaaa ggggagtgga agcgaacagg atgctgagat tgtctacaac agggcaagaa 183900
ctagttcttt agataagaag tcaggaaaca cctctctgag agatggcagt ctagctgaga 183960
tccaaaaaat ggaaaggagc cagacaggga aatcacattt ccaggcagag agaatatcaa 184020
ggacaaaagc tctgagtgtg actaagcttg ctttgtttat aaaaatagaa acaataaaaa 184080
atcgcagaac tttagaggca taggggtggg ggagggttgt ttttgaatca taaagtctat 184140
tcttttagat agaaaaatca gagaaagcca atgagaaatt cagaaacata gacggtatcc 184200
taggatccca agagggagct gggaccgctg ctctaattcc ttggctccca gttcagaact 184260
tctccatcga ccatggatcc cctgctcatt ttcccatttc attcattgga atttggtggt 184320
ttcccccaag ccatggagct gaaagggaat tgcctgtatg atcccactca aattccttgg 184380
gcagttttcc aagatacgat caatggcata tgagtggaag atctgcatgt gacttctgaa 184440
aaaagttctt catgaagaag ttgtgcattc catttttttt cttcctgctg ggcaggcccc 184500
caattatacc taaaagaaac ccaagttaac acaaggctct atgtgaccag ctttgggctg 184560
ccaatttgac ctcctttccc accctttctc ttcaaactca ctgtgccaca atcacaccag 184620
cctccttact gtttcttgaa tatgccaatc atcctctcac ctctgggcct ttgctcagaa 184680
tgctcttctc caaatatccc catagctcag acacaggcat cacttcactc aggtccctaa 184740
gccaagacca cctccttgcg gaggctcatc ctcatcactc cttccaaagc atgacactgc 184800
ccctccccat cctcttacct cactttatcc ttcatggggc tcattgctac cgcagagtat 184860

-continued actatcccag attatactat actatgctgc atatttactt gttcatttat tgtctgtctt 184920
ccccactaga atataagctc cataagggaa gaaacttgct ttattcacta ttagaatagt 184980
gcactatgac ttttcaaaaa tgtttgttga aatgattaat cagtgaataa gtgagtgagt 185040
gactgagtga accaatgcct aacagaggcc cttagttctg gtgctctctc tgttactaac 185100
tccctaaatg acgcctctgc aagttgattc ttctactctg cctcagtttc tttatctggc 185160
aaatagacat ataatgttta ccttaaaaaa ggataaactg aaatgaggcc atagatatga 185220
aagtactgca cattattgaa tatattatac aaatgtaaga tttcctttta cagtcgaagc 185280
cttcttgagt tttagtaaac ttcaccaaat ggggtggaaa gtgtcattat aataaacaat 185340
ccttcatggt tgctggaatt gatcaggcct catggagtgg tgaaaattta ccctgttgta 185400
tggaaaagag cacagggtga ggatggagac tgggatcaga actcggcctc ttccacagac 185460
ttgctggtgt ccttgggtaa ctcataggag cttgcccagt gaaattcaga ttcctcttct 185520
ctcaaaatgg ttgggtattg ggatggtaga cgagattatt ccctccttag aggtttctac 185580
cttgtactat atatctgcat catcataata atcacagcca ctatttattg atcacttggt 185640
ctgccccatg cacttgacat gtgtcattgc attgtatgtt taccccaaca accagacctc 185700
cattattcag acaagaaaac tgtcaagtaa cttagttaat agtggtataa ctactggctt 185760
atgcatagca gcgccagcac tccaaactag gcatactggc tcctgagctg tgctaatttt 185820
gtgcacaaac taagtaataa tcaagttcaa aggaaaggag gcctaactgt ctctccattg 185880
agtaggtttc atctggtgga actgaatgga aaatcctgtg gttttggaac aggttaagtt 185940
gatttatcca ggcagcatgt tctaacttct ccctcctccc cctctcacag ggcttcatgg 186000
acattgactt aaacaaattc aaggagagtg gcgccaatgt gacaggtttc cagctggtga 186060
actacacaga cactattccg gccaagatca tgcagcagtg gaagaatagt gatgctcgag 186120
accacacacg ggtggactgg aagagaccca aggtgagtgg atgggcagcc agcagcaaag 186180
ggccagcctg gtccctttgc ctgccccaga tttctgagct gcattagtct ttacaaagga 186240
atcagttttc taaagcaaac aaattcaggg aaatatattt gtaaagatta ttaggtacaa 186300
ggtgcagggg tcagacaacc caaaatgaca tggttttaag gagggagaca ttttatttat 186360
ctctcctgtg aacaaaactt aggagtcagc agtcccagac ttgtaaaatg gctccacagt 186420
tatcaaatac ccaggcttct tgtaccttct tgctctgctg tcatccacat acggctgctg 186480
cctaatagta caagagggct gcttaaacta cagccattgc ctcagcattc tacccagtag 186540
gaagaaaaaa aaacatgcaa tgcacaactt cttcatgaag aactgttttc agaagtcaca 186600
agcagatctt ccattcatat gctattgatc gtatcttgga aaactacccc cagttggctg 186660
caagggaagc tggaaaatgg tggttctatt ctgggcagag ccaccatgtt gcccagctca 186720
ggaggatgct catttcattg tagattgagc ttctttgtgt agtgaggtgg cccttattct 186780
gctcagccat gtgcccagct aaaaatcagg gcaacctaac taaggaatat ccagcagatc 186840
tctacctggg agagtccact ctcagtaatc aggcagactc tctgcttctc acttcccagc 186900
aacacagctc taaatactgc caccaaaatc tattttgttt gttatttgag aatgcttggg 186960
aataaggata gcgaatgatt ctttttctga agtcaaacca gatagcttga cagtggccat 187020
atggaaccct gtgttgagaa ggatactaag gccaagtttg tttatctgga caaacagtga 187080
atctttgaca gactttctct tgccactcaa tccatttctt tttataaatg gcaaaccgta 187140
taacggagat acttcttatc ccactattca aactgattta actcttcaat aatgaagact 187200
tatttcaata tgatcttaag caaacaaaat cgcaaatatg ctttcaagca atgagaaaac 187260

-continued tacataggaa ttaattaagt aatgtgcaat gattgcactc caatttccaa aagactgagc 187320
agatgacaaa aataaccaaa tgtaatttaa tttttttttt ttttttgaga tggagtctgg 187380
ctctgttgcc caggctggag tgcagtggca tgatctcggc tcactgcaag ctccacctcc 187440
cgagttcacg ccattctcct gcctcagcct cccaagtagc tgggactaca ggcacccgcc 187500
accacgtctg gctaattttt tgtatttttt agtagagatg gggtttcacc gtgttagcca 187560
ggatggtctt gatctcctga ccttgtgatc cacccatctc agcctcccaa agtgctggga 187620
ttacaggcgt gagccactgc gcccggcatg taatttaact ttttaaaaaa gaagtgagag 187680
aattaaattt aaaaaattag aaaaataccc attcattcgt tcttcaattc tctattgtga 187740
acttggagtg tgctaggcaa cataataagt attaggaaca aattagtgaa gaaaacagac 187800
ataggttcca aagccaggat atattttcct ggactgctct cctgattttg tttcatccac 187860
atcctagtcc ccttttttgtc aggagagggt ataattgata gttgttgtga gaaagaatga 187920
ggggaaagtt tacaggatat aaacttacca cttaggtaag ccatatgtgg aaaaaattag 187980
gagctcaccc ttctttcatt ttctttttgc ttttactttt acaagagatg aaagagttaa 188040
tcgttcctct tggtttccag ctgatgactg taatgccggg ataaaccagc tgatttttca 188100
tgaactgtat ccagcctgca gatgtgttat atgtaatcta tgcatttttt cccaaatgaa 188160
ccaacatttt aaaaattgca agattgcaca cagaaaccta gaatcctggc ttctcttcaa 188220
aaattataac tggcagtact gaactcacag ttcaaggagg tcagcattga ctagcatggt 188280
caagcagcag cacccatctg cttgaatatt tatgcttctc agggacacca tccctgattc 188340
accactgtct gccccacgta taccatgcat ctggcccact gcacaccctt ctcatcacca 188400
gaaaacacat tcccaaatac agcacccaaa cctgccttcc tgtcagctct ctttgatacc 188460
taactgtctc cattcctccc actagtacac ctctgcgctc acctacgatg gggtgaaggt 188520
gatggctgag gctttccaga gcctgcggag gcagagaatt gatatatctc gccgggggaa 188580
tgctggggat tgtctggcta acccagctgt tccctggggc caagggatcg acatccagag 188640
agctctgcag caggtaagac caccaatgtt tgccccatct cataggagcc tactggggga 188700
tttcagcatc aaattccaat aaaacacagc tattctaaag aaaaggaaga aaatgcctga 188760
agttcagaac aaccactgca ttgttggtgt tggtggttct tagcatacat tgaagctcat 188820
ataaaaaaaa aatgatatgg aacagtcatt tcttgtagtg taaaagctgt attttctcct 188880
tagcaatttt gctgaaaaag gagagctggt gattttctgt gtatgggaaa gggacttgaa 188940
atacacaagg atgaaactga accatgttaa tggtctcctg gaaacactcc cctcttgccc 189000
tgattttctg gatttcttcc tttgctctct gcacacattg tatgagagcc tggggtatgt 189060
ggaccctaaa aatgtttctc agtacttctg atactacctt cttgcttctc agcatttcat 189120
tcatcaatta tgtttgcact taagaatagt taaagggcag ggatagaaaa tggccacgcc 189180
aactccaatc aattggctat acaaaagctt ctgaggctga atccagatac aacagagaga 189240
agcataaata ttcaattagt gatatgtctg ctgtggaagc agcatgagac agtggtacat 189300
gtgggtgtat atttaacatg cctggtttag aagattttgg ggacttgccc tcagctttat 189360
tgctcttggg gctcctgtag atctctaaag cacctcaagc ccaggctatg attctcaaac 189420
tgccaaggaa tagcactata tttttgttct gatgcctcct gctagagaag ctgtatttcc 189480
gaagggacag ggagaggatg gccgtgcttg ctgcaaagga ataacaaagc attggccaca 189540
atgacaaacc agcacagcaa gattatttgg cacaaatgtc cctcaggacc caccctcccc 189600
aacaaatgga gttgcctgcc taagaccagc tttactttta agacgacatt cagcagaaga 189660

-continued tgaatttggg ctccttgggg agaagaggag catttctgaa tgagagagaa atgtacagca 189720
aaatgtacaa ctattcccac ttgtttgcca accacacgtg cacagctcta gcaactttca 189780
caaccaggag aaagagatgc tgaaggaacc tcaccagctg ttcctcagcc ctgatgagtg 189840
cctttctgta gagaagaata tgtaggtctg tcctttgaaa tgaagctaag caggatttct 189900
actagctaca tgaggaacat gctaaggagg acctccagct gccatttctg ccctcccctg 189960
gtccctgtgc agggtggctc ccaagtcact aggcagcaac aacagacacc aggcagcttg 190020
caggggaaaa ttgccaaatg gacagtgcct gcgcctccct ttctacccc accccagctt 190080 atttaaaatg ctcttccaga ctccacagtc gagacagatt ctgtttgcaa tgtgaggctg 190140
gtttcaaaag gtcccagaga tttgtcctca gcttcacaac ccttccaact cccttgcctc 190200
tcccatctta atgacgtcct gaaaggatag tctgatgcca ccatgacagt gatgaagcct 190260
gggaggcagt tcagggtggc aggaaggact ctgtactggg aggcaggaga gctggactcc 190320
acgtccagct gggcccctgg ctctctggat gaccttgaaa cattcactta gctctcctgc 190380
tgccttccct ttccttcccc atgaaaatga agggggtgga gagaggacct caagtctcaa 190440
ctggctctga aaattcaaac agtctaattt tttttcttat ggtctaaccc atgtccttct 190500
ggttgtagtg tatacttagc acactgcttc tgccctcagt agggtttgaa aggaagcagt 190560
ttccatagtc aaaagaacaa tgacctcttt tattttgtct tggagccaag atatgtgtgt 190620
gcctgccctt catcagctgt tctttgagga tctatggtgt gccctggctt ggagccaagc 190680
actgaggaca ataaaagaaa gcaaggcctg cgctcaagga actcctggca gtgtctatgg 190740
agaaaaagag aggaacaact atcccaaata aataaataaa taaacaaaca aacaaacaaa 190800
ccagaacatt ctgaccttaa gatcagaggt tcaaatcgat tcattttcca atctttgtta 190860
agcacctaga atgaaaaaga ttttgttgaa agacacctta gagattactg actcttcttt 190920
tccctcactt tataatgaaa cagcaaatcc agagtgggca gtgactcacc cagggtcaca 190980
cagcagctta gtggcggagg ctggaccaga tcccagtcca gggctcctct tcccccagtt 191040
aggtctgtgc tatgggccca ggggcccttg cttataagca ttgacctctg gagccttcca 191100
tccatagtca ggactactct tcagcaatgg ctttttctag acccatctct tgaaatagcc 191160
atgccaccag ggagctgggt aaatcctgat ggtatccagt cttagaaacc tgaggcttgg 191220
aggctcaggt ctctactgcc ttcacctctg gccttcaggt cacatagtgg gagagaacct 191280
gtggtttagc ttgtgttaga cctgggttgt ctataagtta ggccaagagg tccagcacag 191340
cctacctgga gggcaagcat gctagggagt taaattctga aaataatatg tatggtgtgt 191400
taaaggctta gtatacacaa agctctaaac atttacacat attatatcat tggatctttg 191460
atataacacc ttgaggtagg tagttttatt aaccgtggtt tgtaaatgga gaagccgagc 191520
ttcagacagg ttataaaact tcccaaagtt atacagctag ctagtggtaa agttgggact 191580
ccaaaccaca tttagatgat gcctccctct gtatgcttca ctgctctgaa acctcaaggg 191640
cacggccaaa cagggaagac acaagagcta tggcccagcc cccagcagca catggccttg 191700
ggtaatatct gtgcaccccc tccccttca ctccgctgta atttccctag cagcagaatg 191760
aagataatca gctgcctgcc tgccccctgc ttgccatcta gggagtcatt cagaatatta 191820
atgaacccac atcctggagg ccctcagcac tccaggaagg atgctcatat gtcgccttct 191880
ggacggtgga gaagactcaa ctccccaagt cgggttctta acatagggga ggtaataggc 191940
atttgagaat atgatttttt aaaagaaatc tgtagattct tttgcttaga aaaatgcata 192000
tgtgtacata cataatttct gcatgaccag gagtagagag aacatacata ctcctagaat 192060

-continued ccatcccagg gcctcaaatt tagaatacct cccctaaata gtaatcatcc ctcttggtct 192120
ttgtttttgc aacctgccag ccaacaatca agcatatgga agtgaaggta tgctcagaac 192180
tttgctagat ggggtctggg gttgggtggg caatggagtt taagacgcag tcctgccttt 192240
aagggctaac acaggtgggc ttatggtgct gtggatgatc agagcagaat gccatcactg 192300
aggaatgcag acatcagcaa ggctttctgt aggaatgtga ctggcctttc aataggatga 192360
ccactttatt atccaaaatc tatcatccaa acgggaacac ttaggagtga aaggaaaaac 192420
tactatcaat tattccagaa caagagtacc agaactctcc tgcgttagtc catgtgcatt 192480
gttataaaga aatacctgaa actggataat gtataaagaa aaaggtttca ttttagctaa 192540
tagttttgta ggctgcacac gaagtacact gccagcatct atttttggtg agggcctcag 192600
gaagcttcca atcatggcag agtgtaaagg aagagacagt atgtcacgta gtaagagaag 192660
gagcgtgata gataagggag gaagtgacag gctcttttac acaaccagct ctcatgagaa 192720
ctgagtaaga acttattcat taccatgggg agggcgccaa gccattcagg aaagttccgc 192780
ccccatgatg caaaaacctc ccaccaggca ccacctccaa cgtccagggt catattttaa 192840
catgagactt ggaagggaca aatatccaaa ctatatcacg tcccaggcaa actgagatgg 192900
gtggtaatgg aaccgttaaa tgtatggtaa atttgaacat ggagtaaatt gggttttgga 192960
ggttctggat ggggatgtca atgataccca gcaagagacg aggtagggtg agggtacaag 193020
aaaggacttg cacatgtcac attggcctgt taaggaatta gggatagaag agctgggttc 193080
caaccgtggc tccacgcaga actatctggg ggatcttgga ctaattgctt gccttttcca 193140
gatctggatt tttcctgtct gctaaacaga cataatcctc ctagtgctgc ctccctgact 193200
ggcttgtcac agggctcaga attttaagaa agcatcgtgc ttgtgggcca agcatcgtgg 193260
ttcatacctg taatcccagc actttgggag gctgaggtgg gcagatcacg aggtaaggag 193320
tttgagacca acctggccaa catagtgaaa ccctgtctct actaaaaata caaaaagtta 193380
gcgggatgtg tagcaggcac ctgtaattcc agctacctgg gaggctgaga caggagaatc 193440
acttgaacgc aggaggcaga ggttacagtg agccgaggtt gtgccactgc ataccacacc 193500
agcctgggtg acagtgtgag actatgtcaa aaaaaaaaaa aaagcatcat gcatgtgttt 193560
ctttgaactt cagggaagct gcatgagaca gtcagagcca agattattct tcccatgact 193620
caggtaggaa agtgaagctt aggagggttc tgagatttgc tctggccaga gtacctagaa 193680
tgtgacccag caaggaccta gtctacaggc ctcacagcca gtgagcatcc aggaggaagg 193740
atccacctga gggcaactgc aagggggata caggagccct gcgtccagtt tgactgctcg 193800
gctgtctcct tcaggactgc ctttcaggat ccaatgaggg caggggagag cagtcactgt 193860
tgacacctga caaagattct ttgcttgacc aaactttagt caggcttctg aaccttctcc 193920
taggcccatc tgtgcaattc ttgtgaaatc cagttttggc aaagaacttg ctaagtcggt 193980
ttagcaagaa ccctgtccac cacgtccacc ctctttgcca tgatcatctt cttcagcccc 194040
caccatcccc cagattatgt cggatcatcc tcgtccatct tcagcaagaa tcctcttagg 194100
ccattttagc cagaattcct cttaaccccg atgcttgctg ttagcaattt cctatccact 194160
gacccccacc ctgctccttg gctatatatt cccacgggcc catgctctat tcagagttga 194220
gcccaatctc tctccacctc tgcaagaccc attgcagggg tctctatacc tattgctacg 194280
attctgaata aagtcttctt cactgtgctt taacaagtgt gctgattaat tttttcttta 194340
acacagctga agtaatagag acattaaccc gcattctctc agcaccaagc aggaaaggaa 194400
atatatgctt cagcctccca tcagcagcag actctgagct ggcacccagt accctttaca 194460

-continued ggaagcccaa ggttaattct ccatctttca tggagggagt tgagggcgcc aggatggcga 194520
cagaagttcc gggagcagga accaagaaga agtgcctggg ctccatcaat ctgacctcag 194580
acaccctggg atggggggag agagggataa gtgcccagat cccagagctc agacctgatg 194640
gatggggaca gtggtttcaa gatacacatt tctgagaagc ttcttcctct gtctctgagt 194700
cctgactctc cttgataaat ggtttggggc tgagccattc tcttgaactc tccttgctct 194760
gccatcatgg aatggtgttt ctgggatgtc tctttcgcat tctctgatac tttgttttat 194820
ctcagtgcaa gtaagacttg gcttccccaa ctagatacta agagccttca gttacccttg 194880
acctctcaat gacttactgt gaatcctgga gtcaagcgcc atcagctctg agtctcaata 194940
atctcatctg tgaaacaggc aaaataacgt ctgctctggc tactcactgg gtttctgtga 195000
acatgaaata agcagcttct tgtgagatca ccgtgacagt gcaaggggtc cttgggtcac 195060
tagaactgtg caggtaggac ccttgacctt attggaaact gaggaaggca gtaaaagtgt 195120
cagtgacatg atccttcttt cttctgaaag agtccccttg tcttagacaa cctaccagcc 195180
ccaaggcctc aattttagat tttatttttc ataactttta cccactctac acagcacagt 195240
agtagtagtc gtcattatca tcattattat catctaaata atataaacta tgcattgaaa 195300
acttatgtcc cagacaatgt gctaagtact tcttggagga ggaaactaag aagcagatag 195360
tttgagcaag gaacctatgg tcatacagtt agaatgagca gagcacaacc tgggaaatgc 195420
ccagcagcaa tagcagaaag caggtagaaa acactacatt gcacattttt gtgttgtcct 195480
cctgaagcct agcacaatag cactggcctg tgtttcggcg aacacttggt accttaagtg 195540
aagataccag aagttaccag aagctccaga ttttagacct gcctctgcca ctggttagtc 195600
ataagacttg agcagatcac tttacttccc agaatttggc atctcccatg taaataaaga 195660
tcataatctc taaatggcat acttcagggg gttcctgtga ctagagatga aataatatgt 195720
gtgcaagtgt gtcataaaca tgaagttttt agaaagtaat attagtatta agtatcacca 195780
ttaacaacaa taataataac agctggcatt ttttgaatac tcatcatgca ccaagcattg 195840
atcaaaaaat atctctttta atccttagaa caaccttaag acatagttaa ctctaattgg 195900
ttccattaaa caaatgagaa acttagtcat agagagatta tgtactctgc catactaata 195960
tgccatgctg attattagta tgaaaattga gactggggct gaaaagtaga tgcctgtttg 196020
gataattaat gacactttca gtttgggcaa atcagtctac cagtctacca tctgcacatc 196080
tatccaagtc tgtttctttg gaatgagtca cttacatggt acccaccaaa ctaacactat 196140
cttgaactgg aaataaggga acactaaaga ttggcaagag attactgagg tgataagaag 196200
gtgaagctgc tgatggactg gaattgctcc tttcttttat tctttgtagt agaatctgta 196260
ctttgttttc tctctgaaaa gcaaagatag cccagacatt tatggagctg gggatttctc 196320
ctgatttcat ctaagaaagt aaagagcatg ttgtaaaatt tgctcagtgc tctgggcctg 196380
ttgtgacctc ctcactgaga cttcaaacca gaaggtgaca agagggtcaa cctcgaaaca 196440
ggaacacaca cacatgcaca cacacacgca ttctctctct cactctcaaa cacacacaac 196500
ccccaactct tcttatacgt tctaacaaca gaggagctag ccactgtcag aaaaaaatat 196560
aaaactctgc aaagcttcct tttaagccat ttgaaggagg gaaataaaca gtgctgggtc 196620
acagggttgg atttgtattt gtaacaagta gacacctcac ctcactggcc ttaggcaaga 196680
gggatctgag gacacatggt ggatcactat tagggaatgt ggttgcttgt acctgagctg 196740
atgatacaca gctagactca gactcagttt gagagtggtc ttggatgaca tttatcagtc 196800
acctacagag cagcaagctc aacccttaaat atcttggatc tccatggtca ccatttgact 196860

-continued tttgatatga atttgaagat agaaggccat gaaagtttga ttttgcccat ttgtggagaa 196920
gtctcacgcg gcatatttga gggttccaat acaattttat tttagccaac tgagatttct 196980
ttaacacctt gcattctctt atctgaacac aatgggttct ccctaggtgc tttgaagttt 197040
tcacaccact ttcacattag cagttatcat ttaagataaa aaaagggcag agatttttgg 197100
aaactgaagg cttagagagc taaattgcct gagggcactt ggctattaag gattaagctg 197160
gggttaaatc caagtctttc aattgccaag tattttattc cctggactca ggaataaaga 197220
agaaattctt aaaggaatta agaagccatc tccaagcata gcttaaggct tcattcataa 197280
agctggcttc ttgtcctggg tcttctgact cattagtgat ggtgcaccat tttctttcct 197340
ttgcaggccc cccatacttt cttcatcttc agatgtgtat ctgagaaggg cagtggtcat 197400
agtggttgtg tgatgggagg tgtttggtta gggatggtgc agacatttca cattagtatg 197460
cactctgacc cattgttagt atttgcctaa agaaataggt aaaaacaatt gtcaggatga 197520
atcccaattt agggaaaaga gatctgtaat gcatcccttg cctgtggcaa gggagtgaag 197580
agttttagca ttcaggatac tccaagacat cattccatgg aacactcttg ggttctgaat 197640
ttctacttca gtggaaaaag caaacacaca taaagtacat ctgagttcac tgcccaccac 197700
ttggttttgt tttccaggtg cgatttgaag gtttaacagg aaacgtgcag tttaatgaga 197760
aaggacgccg gaccaactac acgctccacg tgattgaaat gaaacatgac ggcatccgaa 197820
aggtaaggtc cccctttact tctgttctgc agagagaaga ggctgagcag ggactctggc 197880
cagagctgag ggcctgtgag tccacctttt ctggactgga tctttgaaga aactcagaca 197940
acacagattc tagacttggc tctgccacta accagctggg acattgggca agtctcgttc 198000
ttcctctgag aatccattca ttcatttgca aaattaagtt taaaaaaatc tctacatttg 198060
tcccaggatg cttgtgaaaa tccaaggtag aggaaagcac ttctaaaaca taaagtaatt 198120
gatgtgtata aaatgccact cccattcctg agggtttcta aactaagaac ttgagaatga 198180
tgattattga tgaggttaac tatctcttcc taatcgatag ttggtcatat ccactctatt 198240
atttatacaa aagtaagggt gaaaatatat atgtttacat atatgtataa tgtataaatat 198300
gtttgcatat gaaaattctt agaatagcat tcaaatcctt ggaataacat ttcgaattct 198360
accagaacct atgtgcccgg gcctctgccg atttcttcac ccttaaccct tgatacttcc 198420
ttcatctctc cactccagtc attctgtttg tctttcacct ccctgaatac accatgttct 198480
ttctcatcat tgagccttca tacatgtttc ctctgcctgg gacttcctcc ccccatctcc 198540
ctcctcttgc ctgccaatcc ctcctcagcc ttccacactc aaagtaaatg tcattcccca 198600
gcgaagcctt ctctggcctt tcttattatg cttcatggaa gcctctactt ctctgctcat 198660
ggccttcatc acattgctaa ttccatttgg tggcgtagca taatgactgg gaggcattgt 198720
acagcatggc gtagagctgg tagggtgcca tggatcagaa tgctggctct ggaatcctca 198780
acactgaatc ctggcttcac cacttactag tctggggttc cggataattt atttgagctc 198840
tttgttcctt aattctctta tctagtaagt ggggatcacc ttaaccatgc caacctcata 198900
gggtcattga gaggattaaa tgatctaaga gtgtgcagaa gttctaagta ctggaactgg 198960
cccattgaaa gttgggtctt aatctctcag acttaatgct ctctatgcct gtgctgtcag 199020
ataaccttgc cactagccgt atgtggctgt ttaggttgaa ttttaaataa attcccattt 199080
aaaaatcagt tcttcagttg cactatctac atgtcaagtg ctcagtagcc acatgtggct 199140
agtggctacc acatcaggca gcacagatgt agaacattta catcactgca gaaagttcta 199200
ctttaaagtt ctctttgtcc actctccgtc ctcacctccc ttaaacctgt cttctctgct 199260

-continued cttatgtcta gaaccgcatc ttctacctca cagccaatct tatctcattc attaaggcta 199320
tgtcagttgt ctattgctgc tgtacaaatt accacaaaca gtgacttaaa acaacacaga 199380
tttatcatct cacaattctg taggtcagaa gtctgacttg agtttcactg gactaaaatc 199440
aaagtgttgg caaggtcatg tttcttcctg gaggctccag agttaagttt gtttctttgc 199500
cttttccagt ttcttaaagg ccacctatat tccttggctc ccatgttacc aagctttctc 199560
catattcaaa accagcaatg ttacctctct ctgacccttc ttctatcatc acatcttctc 199620
gctaaccaca gccttccaga gcccatctcc catctctgac tgggagatct cctccttcag 199680
gaatcagcta cagtaacctg ccttgactta cagcaggtac caaataaggg caccctattt 199740
ggctatgaat gtagccactg ggaacgtatc cacttcttca gcaaactttt ggcatgttga 199800
ttgtacacag acactctttc tgggctcaaa aacccttgag aatgacattt atccagaaat 199860
agtccaagtc tgagttcatt tttgttgtcc catggtcttc tgatttttgc tgctggagaa 199920
gacatttgct aggtcactta gctcttataa ctttcaattt ccacatctgt aaaacgggca 199980
cagatcatgt ctgcattagc gcctgatcac tgttcagtga atgttacctg tgttagtggt 200040
tattaatagc tatagtaaat gttgaagagt tagcacacgg ctgaaatctg gaaaacactg 200100
aggtggcttg tttatttctt tcaaagcatt tagcagctac tgttaagagt actgcctctg 200160
gaagggacac caaatatgtg accatctccc caaggccatc ttcctttcag attctttttt 200220
tgtttttttg gagacagagc cttgctctgt cgctcagact ggagtgcaat ggcatggtct 200280
cggctcactg caacctccac ctcccggatt caagtgattc tcctgcctca gcctcccgag 200340
tggttgggat tataggtgcc catcaccaca cctggctaat ttttgtattt tgggtagaca 200400
cggggtttct cacgacgttg gccagactag tctcaaactc ctgaccgtgt gatccattca 200460
cctccgcctc ccaaagtgct gagattacag gtatgagcca ccacccccag gctttttttt 200520
ctttctttct ttcttttttg aggcagggtc tcgctctctt gcccaggctg gagtgcagtg 200580
gtactatcat agctcactat aacctcaaac tcctgggctc aagtgatcca cccacctcgg 200640
cctcccaaag tgctgggatt acaagcatga gccactgtcc ccagcccctt tctttcagat 200700
tctgagaact gctggtatca cctcctgcct tgacaatgaa aacatagatg cagcattttt 200760
gtgtaaggcc caagcaggca agcctattgc tcctagatag aaaattgttg accatagacc 200820
tgggcttttc ctcagaatcc tcagaatggc cttttgctct cagggaaaaa agaatattgc 200880
tatttcctgg atagaacaaa ttggcatttc tacattgtat atgagtagtt atgtgtttgc 200940
cataattaaa atatggatgt cgaactgttt tccccaactc tggagtagtg gattagctta 201000
aaatatagcc agattatttt ctacacgtta gtggtcactg ggtatattgg ggatatactg 201060
aaggtgcaac aagtaagaat agaagccaga gacttctatg ccatttctgc catcatccag 201120
ctgtgtggcc ttcagcatgt ctcatagtct ctctgggtct ctaaaataag tgagagacat 201180
tgggctgtgc aaaccttaat tcctctcagc tctgacacct tggatgtcag tgccatctgc 201240
tgcattttta ccatcctctc cctactcaca ttgttcctct cctggctgga cttcggcttc 201300
ctctgtgaaa gtagaatttc cactggggcc ttcatcaatt gacaaactgt cctttggtat 201360
gaaattcccc agttgttact cccagaacca gaggccccag ccctttgagt tgaccctaac 201420
tattgcccag agactgttgg gaggcttttt atctcttcaa gacttgctct tcatcaagaa 201480
cttctcagaa gtggaggcac tgtagcaaga ttaatggttc tcaagcctca gcaaatagaa 201540
gaattactgg gaggccttat ttaaaacgca gattcctggg tcccagcccc tgggtactct 201600
gcttctggag aacagagatg aagcctagga atctgcacct tcttgaatcc tcctctccaa 201660

-continued cccacagatt ttctggttgg tgcgtaaaga gtttgataag aatcactggc aactactaag 201720
gaaagaagat ggaagtaaaa ggaatacaaa taatataata taatataata taatttataa 201780
tataatttac aaaaaaagaa acactgacag ggtggctaag agcttgggct ttagaggcag 201840
acagaccagg attttaagtc tgctttagtc tttactaggc acatgacctt gaacacatta 201900
tttagcctcc ctgcaagtca ttacatcatc tctaaaaggg tggtaatact ctttgcctcc 201960
caggatcact gtcaggattg aataagacaa tgcctgttac accactgctt gtagtaaggg 202020
attcggaaaa gtagctcctg gcacgtagcg gacattcagc ccacatttgt ttacttgttt 202080
gtacttttaa actcccttct ataggccaca gggattttat atcagcattg catttggggg 202140
agtcaggctg tgtaagcctg tggaatggat aaatcagcaa agagaaataa cagagtacct 202200
taaaatccat gagcaaatgg ttgtgcttta gttttcagat cccagggctg tttttaaact 202260
taccttccaa tggccaaatc ctttcttaga atgtgggctt aaacgtcctt tgtttatggg 202320
ggatttgcct ttcagaaaat caattcctca catctgtggc ttcaggcttt ttactcaatc 202380
agcctcctaa caaagtaatt tttctgattt tcaagggtga cctagttgta ctggtttcag 202440
tgagcattac atggccttac ctgattgtgt atagtaaaaa ggagctgttt cttccagatt 202500
tggagcctca gagaaactct cctgatcttc aggcctattt cctgttcacc catgtgccaa 202560
tataccctct aggtacctgg atacaatttg acatcccact gaaatgtggg tgttctaagc 202620
atccattcat cataaagttt aggggcttca gataccagga tgggtacttg ctctactaaa 202680
atgggatcct taggaaatcc cgttcaagga taccacttca ctatggggta ctgatttagg 202740
gtctctctct gaataaaata tcttgtcaaa atctggtaga atcacaaatt ctgataaatg 202800
gctgcccaat ggagaagttt agggaaaatt atcttacatt tttcatcgaa gaactggtat 202860
tgttgattta accgtctttt cccatcacca ttgttcctat agcaattttt agactgggtg 202920
gaggaatcta cttctcattt caattcgatt tgagtggccc tgccctgccc caagtttatt 202980
atccccactt ctgaccctgt gtataactag aatgaaaaga ctgggcagga aacaagacta 203040
aagggacaca aagtcctgct gatatcaaaa gtaatcttct aaagtcccaa agaatttata 203100
gcttgccatt ccatatgctt tttggaagtt ttgctttaaa tccttgttac ccaattttga 203160
ccatactgaa tcatgttata gcatcagata tagacatagc atctcagata tagcctaaac 203220
ctcaccacct ctctccattt ctactgctga gcccagagcc caggccatct tccacacacc 203280
acacagtagc ctccttacca gtcacgagtc ctgctatgtt cttgcccctc tacaaggcta 203340
cttttccacc acaagacgag gacaataatt ttcaaatata tatcaggtta tatggctcct 203400
ttccttaaaa cttttaccac tttcctgttg ccagtaaata tacaacatgg ccctcagagc 203460
cctcaatgct gcttccctgt ggcatcagct ctcactcctc tttctctagc tcatttctct 203520
gcagttacac tggcatcttt gcattccttg agcacagcct cgcactttcc tcaagtcact 203580
tgcatatgct attcctttac ctggcatttt ctatcactag agtttcatgt gctgtgtgcc 203640
tccttgtcat tcaggtctca gtccaagtga agccaccttg gaaacgacat ccttgaccaa 203700
gcacttttaa agtcactccc actcacccag ctcacagtca caatttcctt tttatttgta 203760
cttttcatgg tgcttattcc ttctgatata tttttattgg ttgattgatc tagattgagg 203820
ttggcaaact tctgcctact ggccaaattc atcccaccac ctatttttgt acagcccatg 203880
agctaatggt tacatgtaca tttttaaatg gttgtaataa atcaaaagaa gaccattttg 203940
tgacatgtga aaattatgag agattaaaat ttcagtgccc ataaagtttt tctggaacat 204000
agctatgctc atttgtttat atattatcta tatctgcctc tgcatgacaa caacagagat 204060

-continued aagtagtggc aacacagact atatgatcca caaagccaaa gatatctacc gtctggccct 204120
ttaggataaa gcttgtcaac ccctggtctg gatatgtatt ttcttcatac ttctctacct 204180
cctaaatgtt ctaaaacacc aactctttaa aagcaaggac catatttgta tttttattat 204240
attcacagtg cctagaatat actgaaacag agtaagcaca tacatataaa aggttgttta 204300
ttacatcact gggaagttta tcaaatgttt ctgtgcaatc agagagcaca ctatgctagc 204360
ccatatttca aaagatctgc caataagtaa gggaaaaaaa tgcctgcaaa tttaataaaa 204420
taacacctca agcagaactc agataaagtt acacataaac ttattaactt caaatctttt 204480
aagtgtgtta atttagataa tcctaggtgc tgtaacagat aaactctgaa atctcagctg 204540
tttaatgcaa aagaagcttt tttttgttca ctcagtgacc actttttttgg ctgagggttc 204600 tggctaagac tcaggctcat ggaccctcca ctgtctactt gggtctttct ggatttcaac 204660
atccagctaa cagataggaa tgaaagaaaa tggcaactct gctggagatt tttggggcat 204720
cagcctagaa gagatgcaca tcacttctgt tgtattccgt tggccagaac ccagttactt 204780
ggctcaatca gaggtaaaac aagctgggaa atgtcattgc tggccaggta gccactctcc 204840
accaacatct ctacaccatg gaaggaaaat aagaatgctt gggagtcagc taattatctt 204900
ggccacaata gacaacttag tctttaaaaa ttgatactaa aggatcttat tttttgaggt 204960
aaggggctgt ggtctcagag gcagcctgga gataccaatt tctgaatttg atttgatgac 205020
tgtgcaatat agatcaattg aattttcagt tctatgatca tctcctttta agactttctc 205080
cacttaaaaa atctgatctg tcatctagat tcattttcta cattcaaaga atctttagag 205140
gtagatggaa aacacggaga tcaaaaatta taactggccc caggagaaga cctctcactg 205200
tcagaattgt ttaaatcctc tcctgactgg taggccccaa tctttaccaa ctactaactc 205260
tgatttactt ttagaaagaa tcaaaattcc tgcatatcct cagtagagaa tcaaagtgct 205320
gtattataat ccaaccattt cccaaagaaa ggaaaatttg ctctaatctc caaagtgcaa 205380
tgtctgttca aaaatctttg ccagctttct tttcatcaaa ctgtggaacc agatttctca 205440
gtctactagt ttacatgagg cataggcatg aggctgagta tcactcagcc cactgaccct 205500
ggcaatattt tgttttatct ccctacaaaa gagttagaaa taaaataggt ttgtttacaa 205560
tttctaacta ttctactagc ttttgatatg aaagtaccta gcatataagc caagctatac 205620
cacatttttt tagagatccc aatttaacaa tagtgctaaa attaataagt agtgctagct 205680
ttgaaggaca actatcctta aaaattaagg tgtctttcta agccatatac atctggctta 205740
cacagattca tcttgctttt ttttcctatc ttgtatgaaa accttgggat tttacggcag 205800
ttttataatt tttaaaccac ataccctgaa cattctatac ataaagaagg gttatattgt 205860
caagtgaatt tcaaaatgct ctataatgca tgcttctttt gcagataatg ttcaacagca 205920
aattgaaaac agaaatgtct tgtagtatag aaacctgtta accttcaact aggcactacc 205980
ctaatgaata tcatttttta gcttactgac aatatgaacc atacactgtg ctaattgttt 206040
tacatgcatt aactaatgta gttctcatag cagcccatga ggcaggtacc attgttacat 206100
ccactctaca gatcagggac tgaggaccac agaggtcagg taacttgctc aagctgatag 206160
ttggtaatta ggaaagccta gcttttaaac caggtctggc ctgaggccag agaccaagat 206220
cttgaccact gggctccctc ttttttaaaa taatacatct taatactcag tggcttttag 206280
aggaattggt tgcatgtcaa aggaagcaac ttcctttcta ctgatggttg tgcagtttga 206340
gtaggaatat ttaaacctgt ggactaattg tgaagaagga agaagaaaga caggaaggaa 206400
aggaggaaga ataggaggaa ggaagggaga aaggatggat gacagggaag aaaatgaaca 206460

-continued agaaggagga gaaagggaaa agaaaaaaaa accttaggac catctatgag gggataaatc 206520
atatttgaca gatattttcc caggtttgta ttgattttat taaataatct tacctttgag 206580
gtccacaaga cctgggttct atgttctgcc actaatctac tatataacct attgttttgt 206640
tagatcattt aatctcccta agcctaagtt ttcctatctg taaagcagag aaaataatcc 206700
taagcctgcc tgcactatct gcatagtgta aagatgttat aaaagtactg tggagattta 206760
aaaaacaaaa caataccaaa ggagaaaact ttacatcata atatactacc agagtgcttt 206820
taaacatcta tttttcagct agaaggctcc ttgagaaagg caactcttgc ggggaatccc 206880
aataggtgaa atagataaaa agcagagctg accattagag caaggatgag gaagccagag 206940
ctctctcctc ttcactgccc ctcaccacct tccatgagcg gtgaaaggcc ccacaagtct 207000
cttagggttc cctagaacac agtccttgca aaagcgaggg aactgagacc acactgtctt 207060
gagcaaattc tgtggtctct gcgcctctgc ttctccctgt gaaaaaggaa aaagttggac 207120
aaaatgattc ttcagtcccc ttccagttct gacattctag aaacgtgagt ttctggttct 207180
tctgtcatta gaaagcaatg tctccttcca ccttgactaa cagcatccct cacagggaac 207240
atggtacaca tgcctgcact gagggtaagc ctccatgcag tatcctgaga gacatgctcc 207300
ccgtcagacc tccgagctgt ctcagcatcg atagggtgca ccatgtccat gctgggtcac 207360
tgctgcctgg atgcattcat tctgtccaca aacatttcct gagctgcttc tctgggaaaa 207420
gatgttctag actaagacag gaactctgga acaagtatgt ttatttcagt cttgtccatg 207480
agaaactcat agcaccatgg agagatgggg acagacacac aaacagctag acccagtgtt 207540
ctaatgggaa cgtacacaag gtactcaggg ttgtgtctgg catgcagggg gcacggccct 207600
ggagttggtc tccctggctc atatcctggc tccacggcta ccctgtggcc ttgggaaagt 207660
tacttcactt tccacgtctc gctttctgca tacttaaaat tgaaaggata attaactacc 207720
cacttcgcag gttttgtgag gatgaaagga gttaaaacat aaaaagcact ttaaaaagtc 207780
cctgaaatgc aagcattcag taaatgataa ctaatatgat ttcaagtcca gagcccaatc 207840
ccttcttagg aagaacagca tagtggctaa atgcagcctc tggagagaga ttgtcagggt 207900
tccaggacaa gctcaaccac tttgcagcta cttcacctcg ggcaagttaa cacactccca 207960
caggccagac gaaatggcat gaaaactgtt gaacacttag cctctgacat agcaagagca 208020
tcattagtgc tggcaattat tgttgttaat ggctgcgaga ttacaggaaa aactatttcc 208080
aactgaagga actgggaaag acatgaaggt gaaggtgaca tttcagctga ccatttggca 208140
aatgcctcag tttttgtgag cctatgctga gttctggctg ttgatagacc tgttcatccc 208200
aatgcatatg cacttctagn nnnnnnnnnn nnnnnnnnnn nnnnnnnnnn nnnnnnnnnn 208260
nnnnnnnnnn nnnnnnnnnn nnnnnnnnnn nnnnnnnnnn nnnnnnnnnn nnnnnnnnnn 208320
nnnnnnnnnn nnnnnnnnnn nnnnnnnnnn nnnnnnnnnn nnnnnnnnnn nnnnnnnnnn 208380
nnnnnnnnnn nnnnnnnnnn nnnnnnnnnn nnnnnnnnnn nnnnnnnnnn nnnnnnnnnn 208440
nnnnnnnnnn nnnnnnnnnn nnnnnnnnnn nnnnnnnnnn nnnnnnnnnn nnnnnnnnnn 208500
nnnnnnnnnn nnnnnnnnnn nnnnnnnnnn nnnnnnnnnn nnnnnnnnnn nnnnnnnnnn 208560
nnnnnnnnnn nnnnnnnnnn nnnnnnnnnn nnnnnnnnnn nnnnnnnnnn nnnnnnnnnn 208620
nnnnctactg cccttttggg ctaactctat cttccaccca ggacccacag aacttaaaca 208680
tctgggcaga ttcctgtctt catatcttgg ctcatattct ccctaacctg aaaggttttg 208740
gtccagacca ttcatctctc atgatcataa gccctgattc ctcctgttgc atttttccct 208800
gtgtaagatc ccacacttgg cttttgcttc tctgaactcc ttaggcccac tcacttgtca 208860

-continued cttctgcggc catgtcatgt cttcccatgg tagaccagag gcgttctcag agcaagccct 208920
atctctcaga cttctttgca tctcgtcaac cctgcctgac aacaagcaac actaatgttt 208980
tagctcagag ccttgtgcac aatagcagtt caattaatat ttcttgaaag accttggaaa 209040
atgaattagt ataaataacc tactcaaatt tgaaaaatta atattgtcaa ccataatttt 209100
taggcactcc tatatattca atattgtaat agtttatact tggagacaga agaaattttt 209160
aaaaataaag gataaacaac catcatagga agttaaatct agatggaaaa atacagttaa 209220
cctaaaaata aagtaaaaga atgtaatgtt taaatcatat gattccaact atagttcaga 209280
atgagttcac tgaagtgcag ggttagtaga catgggggaa agaggggttt gaccctgtga 209340
acaactgcag ggaattaaat cccatggtcc tggcttgcat tgtacaaaac agactggctg 209400
tgtaaacagt taagccctta tccctcagag gtggcaattt ccaaactgaa ccaattattg 209460
tggggatttt ccctgggagc aaaattgggg gcacctgaaa agcactgtgc ttcttattat 209520
ttctgtttac caatatttta gagctcggta tgtccaattc ttcatgagct ccttacttgc 209580
ctgtctctgg tattgactgg gtgacccaga gcaggccagt tcagaggagg ctggcccacc 209640
tgacacctcc actctcttct cattaacaga ttggttactg gaatgaagat gataagtttg 209700
tccctgcagc caccgatgcc caagctgggg gcgataattc aagtgttcag aacagaacat 209760
acatcgtcac aacaatccta gtgagtactc agtccttcat caaggttact tgggattcaa 209820
gctaggccag cacaagggtt ttccaccagg actgaaagct ggcctttctt cttgccaaaa 209880
ctgtgtaata gataaaagca gcaagtcgaa aagggaatgc cctgaaaatg agaggctctg 209940
agttttcact ctgtatctct tagtttcact gtctcatcct ttgtaccctt gggtaactta 210000
cttactttct cttgagccag ctttcccata tttaaaacat aagaatgaca ctaaattgtg 210060
ctggttttca tctgtcctcc ctcagtagaa gctattttca aagaaagtcc aatacataaa 210120
gtagctgtaa gtgaagatgc tgtaattttc agtgactgat catgagaaac ctggagcctg 210180
tttagggtct atttctcctt caagatgacc ccagaggtat ttccaaaaaa atacaaaata 210240
tcctggaaca taatttgaaa agctgtatgc catatctcag tgataaaaca ttcttatttt 210300
aacaaagttt gcttccttaa cacaagaagc ttgtaatggg gtagggagtg aagacattta 210360
ggaagtgaat tgaggggcta gagagccttc cccagtgtta accaaacatg atattatgct 210420
atgccaaagt cctccctacc catgggtgaa cccataaccc acattctgct atctccccat 210480
ttctcttcca ggaagatcct tatgtgatgc tcaagaagaa cgccaatcag tttgagggca 210540
atgaccgtta cgagggctac tgtgtagagc tggcggcaga gattgccaag cacgtgggct 210600
actcctaccg tctggagatt gtcagtgatg gaaaatacgg agcccgagac cctgacacga 210660
aggcctggaa tggcatggtg ggagagctgg tctatggagt aagttcactg cagggtggga 210720
aattagaggg cggaggcaga gggtttgaca ggaaatcatt tggtggttgg gtggccctgc 210780
ccacagatgt ctatgaaacc ctgtaattga gtgttgttgc tgctgaacag atgagtcatc 210840
caaaatccaa tttcttcaga cactctttgt tcaggttact ggtcccaggt ccctcaatcc 210900
cactcagagt cttgtgacgt cagttgattg tcgtccaaca caggtgacag catagctcca 210960
agatcaattt tcttgaggca gactgctgag ttgtctatac aaagtcactt gtggctctct 211020
cagtatcagt ttcttctctg atattaaatg catctggagc caacctaact ttctagttac 211080
ttgcctctct agtttcatgc tctctcatga aatttccaat tcagtcaaat gccccttaat 211140
tactctgttc cctagagtgc tcccttccac tctccacccc taagatacta ctccttcaaa 211200
acctatatca aataatactt ttttcagggt gtgtttcttt ctttcttctc ataataggta 211260

-continued

```
tgaatgtgcc ttttaattgt tctcgccttc ccctatagaa tttagttgct ggtttttttt 211320
aatggtttac cctgccttat ataacggtta cctgtgtaac aggggtagga ctattctatc 211380
tttatagtgc tcaccacact tgaaataact ccatgcacaa ttgctataaa atcttcaata 211440
aattacagca gttttgaaaa gctgctgaat gtcccacatt gttttaagca tttggggaat 211500
tattgagaag caaaagattt gatcttttgc ttaatacttt atgaggtaga aaagacccca 211560
tcttttaaca ttttatgggg tagaaaagac aatgtgagaa aatagtaaaa ggtagtatag 211620
aataaggagt ctatattgta tggctcagct aagggctaac tagagtttgt ctagccctca 211680
gtggggatgt gaaacttgaa aaatgaccat atttaaacag accgagaggc cgggcacagt 211740
ggctcacgcc tataatccca gcaccttggg aggccgaggc aggtggatca cctgaggtca 211800
ggaatttgag actagcctgg ccaacatggt gaaaccccat ctctaccaaa aatacaaaaa 211860
ttagctgcac atggtggcgg gcacctgtaa tcccagctcc ttgggaggct gaggcaggag 211920
aatcacttga accaaggaga tagaggttgc agtgagccaa gaccatgcca tcgcactcca 211980
gcctgggaga caagagcgaa actctgtctc aaaaatgata ataaaaaaca tatgagagaa 212040
aagcagccca ggaattttta aagtataaac aataggatgg tggtggaaat aagtaaggtg 212100
tgagaggaga atgagaaaac gcatggtttt tgttgaggac ttgggttgaa gagtagtcag 212160
ggatacatat gagtaaaaaa tagcaagagg aagagtgtgg atgattcagt gggcattggg 212220
agatcacgaa ggtatttgag tagagagaca acaaaaggca atggaagaag cctccagctg 212280
ccttgtgcag ggaagggacc accacggctt cactcataga aactaaaaca catgccaagc 212340
cccaggtcaa tgttaagtgc tcataaggac aagcagccac tgaggaagat gataaatctt 212400
gtttcatatc agggcaagag gagccatgat ggccctgaga gacatacaaa gggaattcaa 212460
agaagaaaaa gatggaataa aggaaatctt cctcagggag gtagcttttg agatgacatg 212520
tgaaggtggt tattgagttg gggaatggga tgtgcttctc tcctttctta ttccctttac 212580
cacctctcac tttgggaagc tccatggaca aaaggtagag acctggatag tacatgctgc 212640
atctggaggc tggtttccat gggaactccc atcaagctct taaggtcatc cccatggcaa 212700
ctgctgtgca cttttcacct tctctagcat ttatcttcac cttcacctca tgtaatgtgg 212760
tttgcttggt taaaagtctg cagtgtgggc agaacaatgc caggatcatc cccagtagcc 212820
aacacagctg gtggtgagtc actggcacag cagggctcag gccagctgga gttacctatg 212880
ggtgcctcag cagccaggcc tgcctcagta gcctcctcct tatcaggcct attcctctgc 212940
ccagtaaaaa ctgttctgac caggtgcggt ggctcatgcc tgtaatccca gcactttggg 213000
aggctgaggc gggtggatca cgaggtcagg agatctagac catcctggct aacacagtga 213060
aaccccatct ctactaagaa tacaaaaaat tagccgggca tggtagtggg cgcctgtagt 213120
cctaggaatt cgggagctga gtagttaagg caggagaatg gcgtgaactg ggaggcggag 213180
cttgcaatga gccaagatgg tgnnnnnnnn nnnnnnnnnn nnnnnnnnnn nnnnnnnnnn 213240
nnnnnnnnnn nnnnnnnnnn nnnnnnnnnn nnnnnnnnnn nnnnnnnnnn nnnnnnnnnn 213300
nnnnnnnnnn nnnnnnnnnn nnnnnnnnnn nnnnnnnnnn nnnnnnnnnn nnnnnnnnnn 213360
nnnnnnnnnn nnnnnnnnnn nnnnnnnnnn nnnnnnnnnn nnnnnnnnnn nnnnnnnnnn 213420
nnnnnnnnnn nnnnnnnnnn nnnnnnnnnn nnnnnn                           213456
```

<210> SEQ ID NO 4
<211> LENGTH: 484
<212> TYPE: PRT
<213> ORGANISM: Human

-continued

<400> SEQUENCE: 4

Met Gln His Ile Phe Ala Phe Phe Cys Thr Gly Phe Leu Gly Ala Val
1 5 10 15

Val Gly Ala Asn Phe Pro Asn Asn Ile Gln Ile Gly Gly Leu Phe Pro
20 25 30

Asn Gln Gln Ser Gln Glu His Ala Ala Phe Arg Phe Ala Leu Ser Gln
35 40 45

Leu Thr Glu Pro Pro Lys Leu Leu Pro Gln Ile Asp Ile Val Asn Ile
50 55 60

Ser Asp Ser Phe Glu Met Thr Tyr Arg Phe Cys Ser Gln Phe Ser Lys
65 70 75 80

Gly Val Tyr Ala Ile Phe Gly Phe Tyr Glu Arg Arg Thr Val Asn Met
85 90 95

Leu Thr Ser Phe Cys Gly Ala Leu His Val Cys Phe Ile Thr Pro Ser
100 105 110

Phe Pro Val Asp Thr Ser Asn Gln Phe Val Leu Gln Leu Arg Pro Glu
115 120 125

Leu Gln Asp Ala Leu Ile Ser Ile Ile Asp His Tyr Lys Trp Gln Lys
130 135 140

Phe Val Tyr Ile Tyr Asp Ala Asp Arg Gly Leu Ser Val Leu Gln Lys
145 150 155 160

Val Leu Asp Thr Ala Ala Glu Lys Asn Trp Gln Val Thr Ala Val Asn
165 170 175

Ile Leu Thr Thr Thr Glu Glu Gly Tyr Arg Met Leu Phe Gln Asp Leu
180 185 190

Glu Lys Lys Lys Glu Arg Leu Val Val Val Asp Cys Glu Ser Glu Arg
195 200 205

Leu Asn Ala Ile Leu Gly Gln Ile Ile Lys Leu Glu Lys Asn Gly Ile
210 215 220

Gly Tyr His Tyr Ile Leu Ala Asn Leu Gly Phe Met Asp Ile Asp Leu
225 230 235 240

Asn Lys Phe Lys Glu Ser Gly Ala Asn Val Thr Gly Phe Gln Leu Val
245 250 255

Asn Tyr Thr Asp Thr Ile Pro Ala Lys Ile Met Gln Gln Trp Lys Asn
260 265 270

Ser Asp Ala Arg Asp His Thr Arg Val Asp Trp Lys Arg Pro Lys Tyr
275 280 285

Thr Ser Ala Leu Thr Tyr Asp Gly Val Lys Val Met Ala Glu Ala Phe
290 295 300

Gln Ser Leu Arg Arg Gln Arg Ile Asp Ile Ser Arg Arg Gly Asn Ala
305 310 315 320

Gly Asp Cys Leu Ala Asn Pro Ala Val Pro Trp Gly Gln Gly Ile Asp
325 330 335

Ile Gln Arg Ala Leu Gln Gln Val Arg Phe Glu Gly Leu Thr Gly Asn
340 345 350

Val Gln Phe Asn Glu Lys Gly Arg Arg Thr Asn Tyr Thr Leu His Val
355 360 365

Ile Glu Met Lys His Asp Gly Ile Arg Lys Ile Gly Tyr Trp Asn Glu
370 375 380

Asp Asp Lys Phe Val Pro Ala Ala Thr Asp Ala Gln Ala Gly Gly Asp
385 390 395 400

Asn Ser Ser Val Gln Asn Arg Thr Tyr Ile Val Thr Thr Ile Leu Glu
405 410 415

-continued

```
Asp Pro Tyr Val Met Leu Lys Lys Asn Ala Asn Gln Phe Glu Gly Asn
            420                 425                 430

Asp Arg Tyr Glu Gly Tyr Cys Val Glu Leu Ala Ala Glu Ile Ala Lys
        435                 440                 445

His Val Gly Tyr Ser Tyr Arg Leu Glu Ile Val Ser Asp Gly Lys Tyr
    450                 455                 460

Gly Ala Arg Asp Pro Asp Thr Lys Ala Trp Asn Gly Met Val Gly Glu
465                 470                 475                 480

Leu Val Tyr Gly
```